United States Patent
Cushing et al.

(10) Patent No.: US 8,940,724 B2
(45) Date of Patent: Jan. 27, 2015

(54) QUINOLINE DERIVITIVES AND THEIR USES

(75) Inventors: Timothy D. Cushing, Pacifica, CA (US); Paul John Dransfield, San Francisco, CA (US); Felix Gonzalez Lopez de Turiso, San Mateo, CA (US); Michael G. Johnson, San Francisco, CA (US); Todd Kohn, San Mateo, CA (US); Vatee Pattaropong, Burlingame, CA (US); Jillian L. Simard, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/823,767

(22) Filed: Jun. 25, 2010

(65) Prior Publication Data

US 2010/0331293 A1   Dec. 30, 2010

Related U.S. Application Data

(60) Provisional application No. 61/220,259, filed on Jun. 25, 2009.

(51) Int. Cl.
*C07D 401/04* (2006.01)
*C07D 215/44* (2006.01)
*C07D 401/12* (2006.01)
*C07D 401/14* (2006.01)
*C07D 407/14* (2006.01)
*C07D 409/12* (2006.01)
*C07D 413/14* (2006.01)
*C07D 417/14* (2006.01)
*C07D 471/14* (2006.01)
*C07D 471/04* (2006.01)

(52) U.S. Cl.
CPC ............ *C07D 401/04* (2013.01); *C07D 215/44* (2013.01); *C07D 401/12* (2013.01); *C07D 401/14* (2013.01); *C07D 407/14* (2013.01); *C07D 409/12* (2013.01); *C07D 413/14* (2013.01); *C07D 417/14* (2013.01); *C07D 471/04* (2013.01)
USPC ............... 514/210.02; 514/232.5; 514/235.2; 514/275; 514/313; 514/228.2; 544/62; 544/80; 544/122; 544/128; 544/58.2; 544/331; 546/162

(58) Field of Classification Search
CPC .. C07D 215/44; C07D 401/04; C07D 401/12; C07D 401/14; C07D 407/14; C07D 409/12; C07D 413/14; C07D 417/14; C07D 471/04
USPC ............ 514/210.02, 232.5, 235.2, 275, 313, 514/228; 546/162; 544/62, 80, 122, 128, 544/331, 58
See application file for complete search history.

(56) References Cited

U.S. PATENT DOCUMENTS

| | | | |
|---|---|---|---|
| 3,655,672 A | 4/1972 | Spietschka | |
| 3,823,147 A * | 7/1974 | Spietschka et al. | ........... 546/154 |
| 5,387,686 A | 2/1995 | Ohyama | |
| 6,355,636 B1 | 3/2002 | Wissner et al. | |
| 6,384,251 B1 | 5/2002 | Frost et al. | |
| 6,638,945 B1 | 10/2003 | Gibson | |

FOREIGN PATENT DOCUMENTS

| | | |
|---|---|---|
| WO | 92/17452 | 10/1992 |
| WO | 00/66583 A1 | 11/2000 |
| WO | 01/68186 A2 | 9/2001 |
| WO | 2004/069250 A1 | 8/2004 |
| WO | 2004/108703 A1 | 12/2004 |
| WO | 2004/108704 A1 | 12/2004 |
| WO | 2004/112710 A2 | 12/2004 |
| WO | 2005/082891 A1 | 9/2005 |
| WO | 2008/056148 A1 | 5/2008 |
| WO | 2008/118455 A1 | 10/2008 |
| WO | 2010/061180 A1 | 6/2010 |

OTHER PUBLICATIONS

Miroshnikova et al. (J. Med. Chem. 2007, 50, 889-896).*
Jordan, V. C. Nature Reviews: Drug Discovery, 2, 2003, p. 205-213).*
Cancer definition in MedicineNet.com-provided herein.*
Leslie, Science vol. 327, 1573 (Mar. 26, 2010).*
DermNet-NZ—(2012)—http://dermnetnz.org/immune/cutaneous-lupus.html.*
The Merck Manual Home Health Handbook—Autoimmune Disorders—revision Jul. 2007—http://www.merckmanuals.com/home/print/immune_disorders/autoimmune_disorders/autoimmune_disorders.html.*

(Continued)

*Primary Examiner* — Kristin Vajda
*Assistant Examiner* — Valerie Rodriguez-Garcia
(74) *Attorney, Agent, or Firm* — Richard V. Person

(57) ABSTRACT

Substituted bicyclic heteroaryls and compositions containing them, for the treatment of general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, including but not restricted to autoimmune diseases such as systemic lupus erythematosis (SLE), myestenia gravis, rheumatoid arthritis, acute disseminated encephalomyelitis, idiopathic thrombocytopenic purpura, multiples sclerosis, Sjogren's syndrome and autoimmune hemolytic anemia, allergic conditions including all forms of hypersensitivity, The present invention also enables methods for treating cancers that are mediated, dependent on or associated with p110δ activity, including but not restricted to leukemias, such as Acute Myeloid leukaemia (AML) Myelo-dysplastic syndrome (MDS) myelo-proliferative diseases (MPD) Chronic Myeloid Leukemia (CML) T-cell Acute Lymphoblastic leukaemia (T-ALL) B-cell Acute Lymphoblastic leukaemia (B-ALL) Non Hodgkins Lymphoma (NHL) B-cell lymphoma and solid tumors, such as breast cancer.

8 Claims, No Drawings

(56) References Cited

OTHER PUBLICATIONS

The American Autoimmune Related Diseases Association (2012)—http://www.aarda.org/research_display.php?ID=47.*
PubMed Health ADAM Medical Encyclopedia—Jun. 12, 2010—http://www.ncbi.nlm.nih.gov/pubmedhealth/PMH0001704/.*
Abdul-Aziz, K and Faizal, AA.(Saudi Med J. Dec. 2005;26(12):1875-81—Abstract).*
Mitch Leslie, Science Now, May 27, 2010—http://news.sciencemag.org/sciencenow/2010/05/ocd-your-immune-system-could-be-.html.*
Corthals, Angelique—The Quarterly Review of Biology, vol. 86 (4) (Dec. 2011.*
Buskila, Dan—IMAJ 2008; vol. 10 :p. 77-78.*
R. Eisenberg; J. Autoimmunity 32 (2009) 223-230.*
A. Tyndall; Best Practice & Research Clinical Haematology (2008) vol. 21 (2); p. 281-289).*
Ashwood—Autoimmunity Reviews 3 (2004) 557-562).*
Lauren Cahoon, Science vol. 322, p. 667-669 (Oct. 31, 2008).*
Bloomfield et al. (J Chem Soc (C), 1970; 2647-2653).*
Zhao et al. (Chemistry & Biodiversity 2005; 2(2); p. 205-214).*
Balkrishen et al. (Indian Journal of Chemistry, vol. 21B, May 1982, pp. 444-448).*
Berndt, et al., "The p110δ structure: Mechanisms for selectivity and potency of new PI(3)K inhibitors" Nature Chemical Biology, Jan. 10, 2010 pp. 1-8.
Berndt, et al., "Supplementary Methods and Results the p110δ structure: Mechanisms for selectivity and potency of new PI(3)K inhibitors" Nature Chemical Biology, Jan. 2010 pp. 1-34.
Domori, et al: Abstract "Aminonaphthyridines" 1972.
Flowers, et al; Abstract "Reaction of aromatic or heterocyclic amines and perfluori-2-methylpent-2-ene to give fused pyridines, ketenimines, or enamines" 1974.
Price, "A Synthesis of Substituted 4-Aminoquinolines" J of Am Chem Soc (1946) pp. 1246-1250, vol. 68.
Boschelli, "Facile preparation of new 4-phenylamino-3-quinolinecarboritrile Src kinase inhibitors via 7-fluoro intermediates: Identification of potent 7-amino analogs", Bioorganic & Medicinal Chem (2008) pp. 405-412, vol. 16 No. 1.
Crespo, "Redesigning kinase inhibitors to enhance specificity", J of Medicinal Chem (2008) pp. 4890-4898, vol. 51, No. 16.
Bernini, et al., Synlett "Polysubstituted Quinolines from 2-Alkynylanilines and a,b-Ynones through a Sequential Conjugate Addition—Cyclization Process" 2009, V-8, pp. 1245-1250.
Yue-Ling Zhao, et al, European J. of Medicinal Chemistry "Synthesis and cytotoxic evaluation of certain 4-anilino-2-phenylquinoline derivatives" 2005, V-40, pp. 792-797.
Yue-Ling Zhao, et al, Chemistry & Biodiversity "Synthesis and Cytotoxic Evaluation of Certain 4-(Phenylamino)furo [2,3-b]quinoline and 2-(Furan-2-yl)-4-(phenylamino)quinoline Derivatives" 2005, V-2, pp. 205-214.
Bloomfield, et al., J. Chemical Society "Cyclic Amidines, Part XXIII. Novel Isomerism of Disubstituted Tricycloquinazolines and Molecular Orientations in Carcinogenesis" 1970, pp. 2647-2653.

\* cited by examiner

QUINOLINE DERIVITIVES AND THEIR USES

This application claims the benefit of U.S. Provisional Application No. 61/220,259, filed Jun. 25, 2009, which is hereby incorporated by reference.

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol Chem, 274: 8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

The levels of phosphatidylinositol-3,4,5-triphosphate (PIP3), the primary product of PI 3-kinase activation, increase upon treatment of cells with a variety of stimuli. This includes signaling through receptors for the majority of growth factors and many inflammatory stimuli, hormones, neurotransmitters and antigens, and thus the activation of PI3Ks represents one, if not the most prevalent, signal transduction events associated with mammalian cell surface receptor activation (Cantley, Science 296:1655-1657 (2002); Vanhaesebroeck et al. Annu Rev. Biochem, 70: 535-602 (2001)). PI 3-kinase activation, therefore, is involved in a wide range of cellular responses including cell growth, migration, differentiation, and apoptosis (Parker et al., Current Biology, 5:577-99 (1995); Yao et al., Science, 267:2003-05 (1995)). Though the downstream targets of phosphorylated lipids generated following PI 3-kinase activation have not been fully characterized, it is known that pleckstrin-homology (PH) domain- and FYVE-finger domain-containing proteins are activated when binding to various phosphatidylinositol lipids (Sternmark et al., J Cell Sci, 112:4175-83 (1999); Lemmon et al., Trends Cell Biol, 7:237-42 (1997)). Two groups of PH-domain containing PI3K effectors have been studied in the context of immune cell signaling, members of the tyrosine kinase TEC family and the serine/threonine kinases of to AGC family. Members of the Tec family containing PH domains with apparent selectivity for PtdIns (3,4,5)P$_3$ include Tec, Btk, Itk and Etk. Binding of PH to PIP$_3$ is critical for tyrosine kinase activity of the Tec family members (Schaeffer and Schwartzberg, Curr. Opin. Immunol. 12: 282-288 (2000)) AGC family members that are regulated by PI3K include the phosphoinositide-dependent kinase (PDK1), AKT (also termed PKB) and certain isoforms of protein kinase C (PKC) and S6 kinase. There are three isoforms of AKT and activation of AKT is strongly associated with PI3K-dependent proliferation and survival signals. Activation of AKT depends on phosphorylation by PDK1, which also has a 3-phosphoinositide-selective PH domain to recruit it to the membrane where it interacts with AKT. Other important PDK1 substrates are PKC and S6 kinase (Deane and Fruman, Annu Rev. Immunol. 22_563-598 (2004)). In vitro, some isoforms of protein kinase C (PKC) are directly activated by PIP3. (Burgering et al., Nature, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are not fully understood.

Cloning of bovine p110α has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol Cell Biol, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., J Biol Chem, 272:19236-41 (1997). It was observed that the human p110δ isoform is expressed in a tissue-restricted fashion. It is expressed at high levels in lymphocytes and lymphoid tissues and has been shown to play a key role in PI 3-kinase-mediated signaling in the immune system (Al-Alwan et al. JI 178: 2328-2335 (2007); Okkenhaug et al JI, 177: 5122-5128 (2006); Lee et al. PNAS, 103: 1289-1294 (2006)). P110δ has also been shown to be expressed at lower levels in breast cells, melanocytes and endothelial cells (Vogt et al. Virology, 344: 131-138 (2006) and has since been implicated in conferring selective migratory properties to breast cancer cells (Sawyer et al. Cancer Res. 63:1667-1675 (2003)). Details concerning the P110δ isoform also can be found in U.S. Pat. Nos. 5,858,753; 5,822,910; and 5,985,589. See also, Vanhaesebroeck et al., Proc Nat. Acad Sci USA, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Five isoforms of p85 have been identified (p85α, p85β, p55γ, p55α and p50α) encoded by three genes. Alternative transcripts of Pik3r1 gene encode the p85α, p55α and p50α proteins (Deane and Fruman, Annu Rev. Immunol. 22: 563-598

(2004)). p85α is ubiquitously expressed while p85β, is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ binds a p101 regulatory subunit that also binds to the βγ subunits of heterotrimeric G proteins. The p101 regulatory subunit for PI3K gamma was originally cloned in swine, and the human ortholog identified subsequently (Krugmann et al., J Biol Chem, 274:17152-8 (1999)). Interaction between the N-terminal region of p101 with the N-terminal region of p110γ is known to activate PI3Kγ through Gβγ. Recently, a p101-homologue has been identified, p84 or p87$^{PIKAP}$ (PI3Kγ adapter protein of 87 kDa) that binds p110γ (Voigt et al. JBC, 281: 9977-9986 (2006), Suire et al. Curr. Biol. 15: 566-570 (2005)). p87$^{PIKAP}$ is homologous to p101 in areas that bind p110γ and Gβγ and also mediates activation of p110γ downstream of G-protein-coupled receptors. Unlike p101, p87$^{PIKAP}$ is highly expressed in the heart and may be crucial to PI3Kγ cardiac function.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol Cell Biol, 14:2675-85 (1994)).

Thus, PI 3-kinases can be defined by their amino acid identity or by their activity. Additional members of this growing gene family include more distantly related lipid and protein kinases including Vps34 TOR1, and TOR2 of Saccharomyces cerevisiae (and their mammalian homologs such as FRAP and mTOR), the ataxia telangiectasia gene product (ATR) and the catalytic subunit of DNA-dependent protein kinase (DNA-PK). See generally, Hunter, Cell, 83:1-4 (1995).

PI 3-kinase is also involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the IC$_{50}$ values of wortmannin against each of the various Class I PI 3-kinases are in the range of 1-10 nM. Similarly, the IC$_{50}$ values for LY294002 against each of these PI 3-kinases is about 1 μM (Froman et al., Ann Rev Biochem, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., Proc Natl Acad Sci USA, 91:4960-64 (1994)). Moreover, it has been shown that wortmannin and LY294002 block neutrophil migration and superoxide release. However, inasmuch as these compounds do not distinguish among the various isoforms of PI3K, it remains unclear from these studies which particular PI3K isoform or isoforms are involved in these phenomena and what functions the different Class I PI3K enzymes perform in both normal and diseased tissues in general. The co-expression of several PI3K isoforms in most tissues has confounded efforts to segregate the activities of each enzyme until recently.

The separation of the activities of the various PI3K isozymes has been advanced recently with the development of genetically manipulated mice that allowed the study of isoform-specific knock-out and kinase dead knock-in mice and the development of more selective inhibitors for some of the different isoforms. P110α and p110β knockout mice have been generated and are both embryonic lethal and little information can be obtained from these mice regarding the expression and function of p110 alpha and beta (Bi et al. Mamm. Genome, 13:169-172 (2002); Bi et al. J. Biol. Chem. 274: 10963-10968 (1999)). More recently, p110α kinase dead knock in mice were generated with a single point mutation in the DFG motif of the ATP binding pocket (p110αD$^{933A}$) that impairs kinase activity but preserves mutant p110α kinase expression. In contrast to knock out mice, the knockin approach preserves signaling complex stoichiometry, scaffold functions and mimics small molecule approaches more realistically than knock out mice. Similar to the p110α KO mice, p110αD$^{933A}$ homozygous mice are embryonic lethal. However, heterozygous mice are viable and fertile but display severely blunted signaling via insulin-receptor substrate (IRS) proteins, key mediators of insulin, insulin-like growth factor-1 and leptin action. Defective responsiveness to these hormones leads to hyperinsulinemia, glucose intolerance, hyperphagia, increase adiposity and reduced overall growth in heterozygotes (Foukas, et al. Nature, 441: 366-370 (2006)). These studies revealed a defined, non-redundant role for p110α as an intermediate in IGF-1, insulin and leptin signaling that is not substituted for by other isoforms. We will have to await the description of the p110β kinase-dead knock in mice to further understand the function of this isoform (mice have been made but not yet published; Vanhaesebroeck).

P110γ knock out and kinase-dead knock in mice have both been generated and overall show similar and mild phenotypes with primary defects in migration of cells of the innate immune system and a defect in thymic development of T cells (Li et al. Science, 287: 1046-1049 (2000), Sasaki et al. Science, 287: 1040-1046 (2000), Patrucco et al. Cell, 118: 375-387 (2004)).

Similar to p110γ, PI3K delta knock out and kinase-dead knock-in mice have been made and are viable with mild and like phenotypes. The p110δ$^{D910A}$ mutant knock in mice demonstrated an important role for delta in B cell development and function, with marginal zone B cells and CD5+ B1 cells nearly undetectable, and B- and T cell antigen receptor signaling (Clayton et al. J. Exp. Med. 196:753-763 (2002); Okkenhaug et al. Science, 297: 1031-1034 (2002)). The p110δ$^{D910A}$ mice have been studied extensively and have elucidated the diverse role that delta plays in the immune system. T cell dependent and T cell independent immune responses are severely attenuated in p110δ$^{D910A}$ and secretion of TH1 (INF-γ) and TH2 cytokine (IL-4, IL-5) are impaired (Okkenhaug et al. J. Immunol. 177: 5122-5128 (2006)). A human patient with a mutation in p110δ has also recently been described. A taiwanese boy with a primary B cell immunodeficiency and a gamma-hypoglobulinemia of previously unknown aetiology presented with a single base-pair substitution, m.3256G to A in codon 1021 in exon 24 of p110δ. This mutation resulted in a mis-sense amino acid substitution (E to K) at codon 1021, which is located in the highly conserved catalytic domain of p110δ protein. The patient has no other identified mutations and his phenotype is consistent with p110δ deficiency in mice as far as studied. (Jou et al. Int. J. Immunogenet. 33: 361-369 (2006)).

Isoform-selective small molecule compounds have been developed with varying success to all Class I PI3 kinase isoforms (Ito et al. J. Pharm. Exp. Therapeut., 321:1-8 (2007)). Inhibitors to alpha are desirable because mutations in p110α have been identified in several solid tumors; for example, an amplification mutation of alpha is associated with 50% of ovarian, cervical, lung and breast cancer and an activation mutation has been described in more than 50% of bowel and 25% of breast cancers (Hennessy et al. Nature Reviews, 4: 988-1004 (2005)). Yamanouchi has developed a compound YM-024 that inhibits alpha and delta equi-potently and is 8- and 28-fold selective over beta and gamma respectively (Ito et al. J. Pharm. Exp. Therapeut., 321:1-8 (2007)).

P110β is involved in thrombus formation (Jackson et al. Nature Med. 11: 507-514 (2005)) and small molecule inhibitors specific for this isoform are thought after for indication involving clotting disorders (TGX-221: 0.007 uM on beta; 14-fold selective over delta, and more than 500-fold selective over gamma and alpha) (Ito et al. J. Pharm. Exp. Therapeut., 321:1-8 (2007)).

Selective compounds to p110γ are being developed by several groups as immunosuppressive agents for autoimmune disease (Rueckle et al. Nature Reviews, 5: 903-918 (2006)). Of note, AS 605240 has been shown to be efficacious in a mouse model of rheumatoid arthritis (Camps et al. Nature Medicine, 11: 936-943 (2005)) and to delay onset of disease in a model of systemic lupus erythematosis (Barber et al. Nature Medicine, 11: 933-935 (205)).

Delta-selective inhibitors have also been described recently. The most selective compounds include the quinazolinone purine inhibitors (PIK39 and IC87114). IC87114 inhibits p110δ in the high nanomolar range (triple digit) and has greater than 100-fold selectivity against p110α, is 52 fold selective against p110β but lacks selectivity against p110γ (approx. 8-fold). It shows no activity against any protein kinases tested (Knight et al. Cell, 125: 733-747 (2006)). Using delta-selective compounds or genetically manipulated mice (p110δ$^{D910A}$) it was shown that in addition to playing a key role in B and T cell activation, delta is also partially involved in neutrophil migration and primed neutrophil respiratory burst and leads to a partial block of antigen-IgE mediated mast cell degranulation (Condliffe et al. Blood, 106: 1432-1440 (2005); Ali et al. Nature, 431: 1007-1011 (2002)). Hence p110δ is emerging as an important mediator of many key inflammatory responses that are also known to participate in aberrant inflammatory conditions, including but not limited to autoimmune disease and allergy. To support this notion, there is a growing body of p110δ target validation data derived from studies using both genetic tools and pharmacologic agents. Thus, using the delta-selective compound IC 87114 and the p110δ$^{D910A}$ mice, Ali et al. (Nature, 431: 1007-1011 (2002)) have demonstrated that delta plays a critical role in a murine model of allergic disease. In the absence of functional delta, passive cutaneous anaphylaxis (PCA) is significantly reduced and can be attributed to a reduction in allergen-IgE induced mast cell activation and degranulation. In addition, inhibition of delta with IC 87114 has been shown to significantly ameliorate inflammation and disease in a murine model of asthma using ovalbumin-induced airway inflammation (Lee et al. FASEB, 20: 455-465 (2006). These data utilizing compound were corroborated in p110δ$^{D910A}$ mutant mice using the same model of allergic airway inflammation by a different group (Nashed et al. Eur. J. Immunol. 37:416-424 (2007)).

There exists a need for further characterization of PI3Kδ function in inflammatory and auto-immune settings. Furthermore, our understanding of PI3Kδ requires further elaboration of the structural interactions of p110δ, both with its regulatory subunit and with other proteins in the cell. There also remains a need for more potent and selective or specific inhibitors of PI3K delta, in order to avoid potential toxicology associated with activity on isozymes p110 alpha (insulin signaling) and beta (platelet activation). In particular, selective or specific inhibitors of PI3Kδ are desirable for exploring the role of this isozyme further and for development of superior pharmaceuticals to modulate the activity of the isozyme.

SUMMARY

The present invention comprises a new class of compounds having the general formula

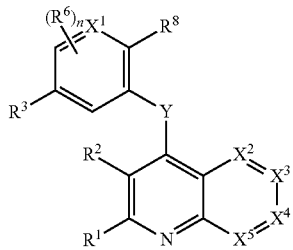

which are useful to inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

DETAILED DESCRIPTION

One aspect of the present invention relates to compounds having the structure:

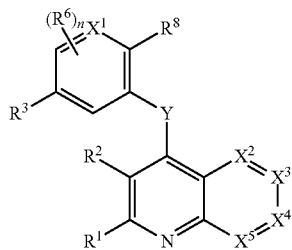

or any pharmaceutically-acceptable salt thereof, wherein:
  $X^1$ is C or N;
  $X^2$ is $C(R^4)$ or N;
  $X^3$ is $C(R^5)$ or N;
  $X^4$ is $C(R^5)$ or N;
  $X^5$ is $C(R^4)$ or N; wherein no more than two of $X^2$, $X^3$, $X^4$ and $X^5$ are N;
  Y is $NR^7$, $CR^aR^a$, S or O;
  n is 0, 1, 2 or 3;
  $R^1$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$, —N$R^aC_{2-6}$alkO$R^a$, —N$R^aC_{2-6}$alkCO$_2R^a$, —N$R^aC_{2-6}$alkSO$_2R^b$, —CH$_2$C(=O)$R^a$, —CH$_2$C(=O)O$R^a$, —CH$_2$C(=O)N$R^aR^a$, —CH$_2$C(=N$R^a$)N$R^aR^a$, —CH$_2$O$R^a$, —CH$_2$C(=O)$R^a$, —CH$_2$C(=O)N$R^aR^a$, —CH$_2$C(=O)N($R^a$)S(=O)$_2R^a$, —CH$_2$OC$_{2-6}$alkN$R^aR^a$, —CH$_2$OC$_{2-6}$alkO$R^a$, —CH$_2$S$R^a$, —CH$_2$S(=O)$R^a$, —CH$_2$S(=O)$_2R^b$, —CH$_2$S(=O)$_2$N$R^aR^a$, —CH$_2$S(=O)$_2$N($R^a$)C(=O)$R^a$, —CH$_2$S(=O)$_2$N($R^a$)C(=O)O$R^a$, —CH$_2$S(=O)$_2$N($R^a$)C(=O)N$R^aR^a$, —CH$_2$N$R^aR^a$, —CH$_2$N($R^a$)C(=O)$R^a$, —CH$_2$N($R^a$)C(=O)O$R^a$, —CH$_2$N($R^a$)C(=O)N$R^aR^a$, ($R^a$)C(=N$R^a$)N$R^aR^a$, —CH$_2$N($R^a$)S(=O)$_2R^a$, —CH$_2$N($R^a$)S(=O)$_2$N$R^aR^a$, —CH$_2$N$R^aC_{2-6}$alkN$R^aR^a$, —CH$_2$N$R^aC_{2-6}$alkO$R^a$, —CH$_2$N$R^aC_{2-6}$alkCO$_2R^a$ and —CH$_2$N$R^aC_{2-6}$alkSO$_2R^b$; or $R^1$ is a direct-bonded, $C_{1-4}$alk-linked, OC$_{1-2}$alk-linked, $C_{1-2}$alkO-linked, N($R^a$)-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1 or 2 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups, and wherein the ring is additionally substituted by 0 or 1 directly bonded, SO$_2$ linked, C(=O) linked or CH$_2$ linked group selected from phenyl, pyridyl, pyrimidyl, morpholino, piperazinyl, piperadinyl, pyrrolidinyl, cyclopentyl, cyclohexyl all of which are further substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^2$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$;

$R^3$ is selected from a saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; or $R^3$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$;

$R^4$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk, C(=O)NH$_2$, C(=O)NHC$_{1-4}$alk, C(=O)N(C$_{1-4}$alk)C$_{1-4}$alk, N(H)C(=O)C$_{1-4}$alk, N(C$_{1-4}$alk)C(=O)C$_{1-4}$alk, C$_{1-4}$haloalk or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —OC$_{1-4}$alk, —NH$_2$, —NHC$_{1-4}$alk, —N(C$_{1-4}$alk)C$_{1-4}$alk;

$R^5$ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk or $C_{1-4}$haloalk;

$R^6$ is selected from halo, cyano, OH, OC$_{1-4}$alk, $C_{1-4}$alk, $C_{1-3}$haloalk, OC$_{1-4}$alk, NH$_2$, NHC$_{1-4}$alk, N(C$_{1-4}$alk)C$_{1-4}$alk, —C(=O)O$R^a$, —C(=O)N($R^a$)$R^a$, —N($R^a$)C(=O)$R^b$ and a 5- or 6-membered saturated or partially saturated heterocyclic ring containing 1, 2 or 3 heteroatoms selected from N, O and S, wherein the ring is substituted by 0, 1, 2 or 3 substituents selected from halo, cyano, OH, oxo, OC$_{1-4}$alk, $C_{1-4}$alk, $C_{1-3}$haloalk, OC$_{1-4}$alk, NH$_2$, NHC$_{1-4}$alk and N(C$_{1-4}$alk)C$_{1-4}$alk;

$R^7$ is H, $C_{1-6}$alk, —C(=O)N($R^a$)$R^a$, —C(=O)$R^b$ or $C_{1-4}$haloalk;

$R^8$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkN$R^a R^a$, —OC$_{2-6}$alkO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkN$R^a R^a$ and —N$R^a$C$_{2-6}$alkO$R^a$; or $R^8$ is selected from H, halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkN$R^a R^a$, —OC$_{2-6}$alkO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkN$R^a R^a$ and —N$R^a$C$_{2-6}$alkO$R^a$;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OC$_{1-4}$alk, —NH$_2$, —NHC$_{1-4}$alk, —N(C$_{1-4}$alk)C$_{1-4}$alk.

Another aspect of the invention is a compound having the structure

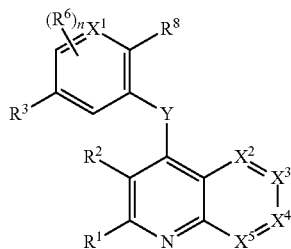

or any pharmaceutically-acceptable salt thereof, wherein:
$X^1$ is C or N;
$X^2$ is C($R^4$) or N;
$X^3$ is C($R^5$) or N;
$X^4$ is C($R^5$) or N;
$X^5$ is C($R^4$) or N; wherein no more than two of $X^2$, $X^3$, $X^4$ and $X^5$ are N;
n is 0, 1, 2 or 3;
$R^1$ is selected from H, halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkN$R^a R^a$, —OC$_{2-6}$alkO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkN$R^a R^a$ and —N$R^a$C$_{2-6}$alkO$R^a$; or $R^1$ is a direct-bonded, $C_{1-4}$alk-linked, OC$_{1-2}$alk-linked, $C_{1-2}$alkO-linked or O-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkN$R^a R^a$, —OC$_{2-6}$alkO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkN$R^a R^a$ and —N$R^a$C$_{2-6}$alkO$R^a$, wherein the available carbon atoms of the ring are additionally substituted by 0, 1 or 2 oxo or thioxo groups;

$R^2$ is selected from halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkN$R^a R^a$, —OC$_{2-6}$alkO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkN$R^a R^a$ and —N$R^a$C$_{2-6}$alkO$R^a$; or $R^1$ and $R^2$ together form a saturated or partially-saturated 2-, 3-, 4- or 5-carbon bridge substituted by 0, 1 or 2 substituents selected from halo, cyano, OH, OC$_{1-4}$alk, $C_{1-4}$alk, $C_{1-3}$haloalk, OC$_{1-4}$alk, NH$_2$, NHC$_{1-4}$alk and N(C$_{1-4}$alk)C$_{1-4}$alk;

$R^3$ is selected from a saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkN$R^a R^a$, —OC$_{2-6}$alkO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkN$R^a R^a$ and —N$R^a$C$_{2-6}$alkO$R^a$; or $R^3$ is selected from halo, $C_{1-6}$alk, $C_{1-4}$haloalk, cyano, nitro, —C(=O)$R^a$, —C(=O)O$R^a$, —C(=O)N$R^a R^a$, —C(=N$R^a$)N$R^a R^a$, —O$R^a$, —OC(=O)$R^a$, —OC(=O)N$R^a R^a$, —OC(=O)N($R^a$)S(=O)$_2 R^a$, —OC$_{2-6}$alkN$R^a R^a$, —OC$_{2-6}$alkO$R^a$, —S$R^a$, —S(=O)$R^a$, —S(=O)$_2 R^a$, —S(=O)$_2$N$R^a R^a$, —S(=O)$_2$N($R^a$)C(=O)$R^a$, —S(=O)$_2$N($R^a$)C(=O)O$R^a$, —S(=O)$_2$N($R^a$)C(=O)N$R^a R^a$, —N$R^a R^a$, —N($R^a$)C(=O)$R^a$, —N($R^a$)C(=O)O$R^a$, —N($R^a$)C(=O)N$R^a R^a$, —N($R^a$)C(=N$R^a$)N$R^a R^a$, —N($R^a$)S(=O)$_2 R^a$, —N($R^a$)S(=O)$_2$N$R^a R^a$, —N$R^a$C$_{2-6}$alkN$R^a R^a$ and —N$R^a$C$_{2-6}$alkO$R^a$;

R$^4$ is, independently, in each instance, H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk, C$_{1-4}$haloalk or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, C$_{1-4}$alk, C$_{1-3}$haloalk, —OC$_{1-4}$alk, —NH$_2$, —NHC$_{1-4}$alk, —N(C$_{1-4}$alk)C$_{1-4}$alk;

R$^5$ is, independently, in each instance, H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk or C$_{1-4}$haloalk;

R$^6$ is selected from halo, cyano, OH, OC$_{1-4}$alk, C$_{1-4}$alk, C$_{1-3}$haloalk, OC$_{1-4}$alk, NH$_2$, NHC$_{1-4}$alk, N(C$_{1-4}$alk)C$_{1-4}$alk;

R$^7$ is H, C$_{1-6}$alk or C$_{1-4}$haloalk;

R$^8$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R$^2$ substituents, and the ring is additionally substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^8$ is selected from H, halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^a$ is independently, at each instance, H or R$^b$; and

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OC$_{1-4}$alk, —NH$_2$, —NHC$_{1-4}$alk, —N(C$_{1-4}$alk)C$_{1-4}$alk.

In another embodiment, in conjunction with any of the above or below embodiments, X$^1$ is N.

In another embodiment, in conjunction with any of the above or below embodiments, X$^1$ is C.

In another embodiment, in conjunction with any of the above or below embodiments,
X$^2$ is C(R$^4$);
X$^3$ is C(R$^5$);
X$^4$ is C(R$^5$); and
X$^5$ is C(R$^4$).

In another embodiment, in conjunction with any of the above or below embodiments,
X$^2$ is N;
X$^3$ is C(R$^5$);
X$^4$ is C(R$^5$); and
X$^5$ is C(R$^4$).

In another embodiment, in conjunction with any of the above or below embodiments,
X$^2$ is C(R$^4$);
X$^3$ is N;
X$^4$ is C(R$^5$); and
X$^5$ is C(R$^4$).

In another embodiment, in conjunction with any of the above or below embodiments,
X$^2$ is C(R$^4$);
X$^3$ is C(R$^5$);
X$^4$ is N; and
X$^5$ is C(R$^4$).

In another embodiment, in conjunction with any of the above or below embodiments,
X$^2$ is C(R$^4$);
X$^3$ is C(R$^5$);
X$^4$ is C(R$^5$); and
X$^5$ is N.

In another embodiment, in conjunction with any of the above or below embodiments, the compounds have the structure

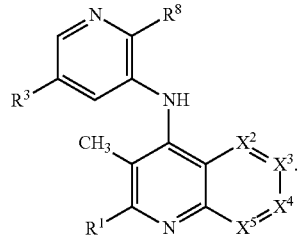

In another embodiment, in conjunction with any of the above or below embodiments, the compounds have the structure

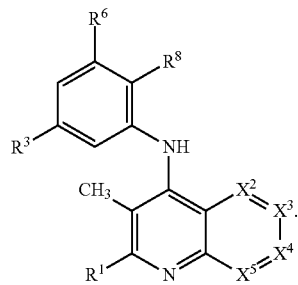

In another embodiment, in conjunction with any of the above or below embodiments, the compounds have the structure

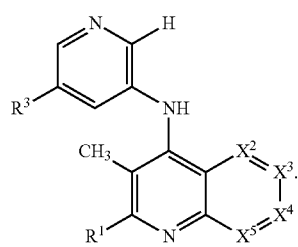

In another embodiment, in conjunction with any of the above or below embodiments, the compounds have the structure

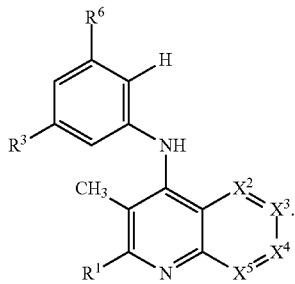

In another embodiment, in conjunction with any of the above or below embodiments, $R^1$ is selected from $C_{1-6}$alk and $C_{1-4}$haloalk.

In another embodiment, in conjunction with any of the above or below embodiments, $R^1$ is a direct-bonded unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^1$ is a direct-bonded unsaturated 5-, 6- or 7-membered monocyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^1$ is phenyl or pyridine, both of which are substituted by 0, 1, 2 or 3 substituents independently selected from halo, $C_{1-6}$alk and $C_{1-4}$haloalk.

In another embodiment, in conjunction with any of the above or below embodiments, $R^1$ is a methylene-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^1$ is an ethylene-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^2$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any of the above or below embodiments, $R^2$ is selected from halo, $C_{1-6}$alk and $C_{1-4}$haloalk.

In another embodiment, in conjunction with any of the above or below embodiments, $R^2$ is H.

In another embodiment, in conjunction with any of the above or below embodiments, $R^1$ and $R^2$ together form a saturated or partially-saturated 2-, 3-, 4- or 5-carbon bridge substituted by 0, 1, 2 or 3 substituents selected from halo, cyano, OH, OC$_{1-4}$alk, C$_{1-4}$alk, C$_{1-3}$haloalk, OC$_{1-4}$alk, NH$_2$, NHC$_{1-4}$alk and N(C$_{1-4}$alk)C$_{1-4}$alk.

In another embodiment, in conjunction with any of the above or below embodiments, $R^3$ is selected from saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C (=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, R$^3$ is selected from saturated 5-, 6- or 7-membered monocyclic ring containing 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, R$^3$ is selected from saturated 5-, 6- or 7-membered monocyclic ring containing 1, 2, 3 or 4 atoms selected from N, O and S, but containing no more than one O or S, wherein the ring is substituted by 0, 1, 2 or 3 substituents independently selected from halo, C$_{1-6}$alk and C$_{1-4}$haloalk.

In another embodiment, in conjunction with any of the above or below embodiments, R$^3$ is selected from saturated 6-membered monocyclic ring containing 1 or 2 atoms selected from N, O and S, but containing no more than one O or S, wherein the ring is substituted by 0, 1, 2 or 3 substituents independently selected from halo, C$_{1-6}$alk and C$_{1-4}$haloalk.

In another embodiment, in conjunction with any of the above or below embodiments, R$^3$ is selected from saturated 6-membered monocyclic ring containing 1 or 2 atoms selected from N, O and S, but containing no more than one O or S.

In another embodiment, in conjunction with any of the above or below embodiments, R$^3$ is selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, R$^8$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R$^2$ substituents, and the ring is additionally substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, R$^8$ is selected from saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, R$^8$ is selected from saturated 5-, 6- or 7-membered monocyclic ring containing 1 or 2 atoms selected from N, O and S, but containing no more than one O or S, wherein the ring is substituted by 0, 1, 2 or 3 substituents independently selected from halo, C$_{1-6}$alk and C$_{1-4}$haloalk.

In another embodiment, in conjunction with any of the above or below embodiments, R$^8$ is selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, R$^8$ is cyano.

Another aspect of the invention relates to a method of treating PI3K-mediated conditions or disorders.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of rheumatoid arthritis, ankylosing spondylitis, osteoarthritis, psoriatic arthritis, psoriasis, inflammatory diseases or autoimmune diseases comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases and autoimmune diseases, inflammatory bowel disorders, inflammatory eye disorders, inflammatory or unstable bladder disorders, skin complaints with inflammatory components, chronic inflammatory conditions, autoimmune diseases, systemic lupus erythematosis (SLE), myestenia gravis, rheumatoid arthritis, acute disseminated encephalomyelitis, idiopathic thrombocytopenic purpura, multiples sclerosis, Sjogren's syndrome and autoimmune hemolytic anemia, allergic conditions and hypersensitivity, comprising the step of administering a compound according to any of the above or below embodiments.

Another aspect of the invention relates to the treatment of cancers that are mediated, dependent on or associated with p110δ activity, comprising the step of administering a compound according to any of the above or below embodiments.

Another aspect of the invention relates to the treatment of cancers are selected from acute myeloid leukaemia, myelodysplastic syndrome, myelo-proliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, and autoimmune diseases.

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alk" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. Examples of $C_{1-6}$alk include, but are not limited to the following:

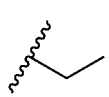 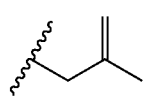 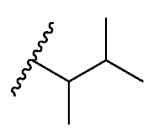

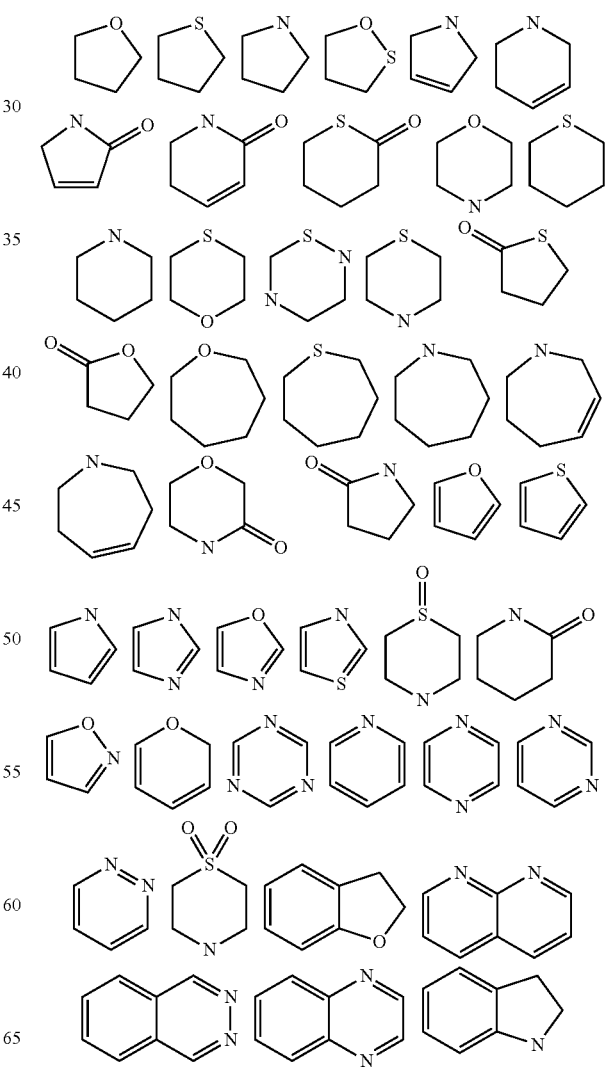

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{V-W}$haloalk" means an alk group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

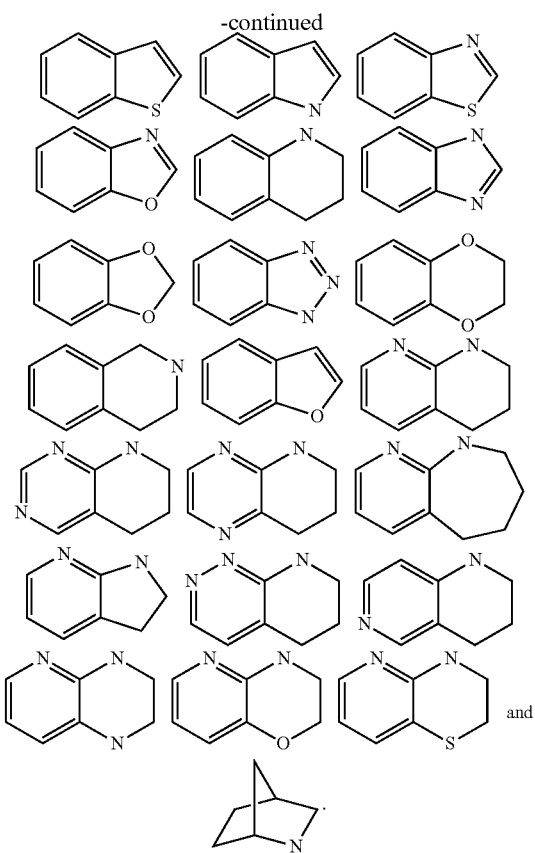

"$C_{\alpha\text{-}\beta}$spiroalk" means a geminally-attached alkyl ring comprising a minimum of α and a maximum of β carbon atoms that is attached to a chain or another ring—such as:

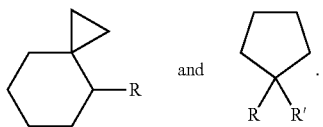

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl. Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art.

Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

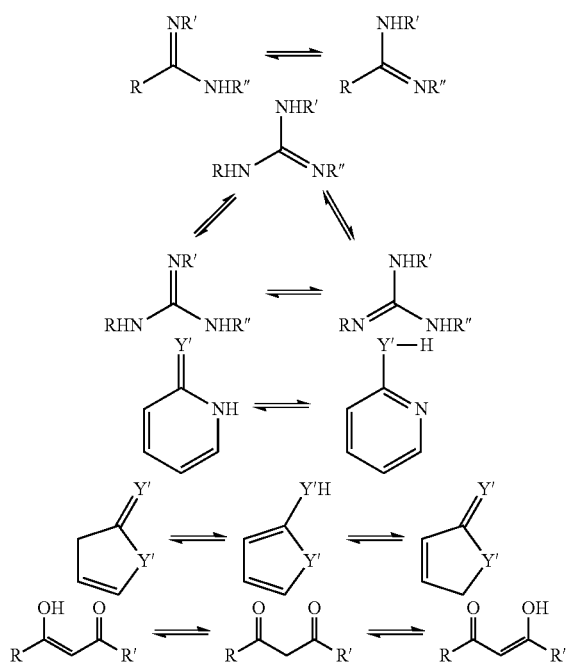

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)).

Hydroxy groups have been masked as esters and ethers. EP 039,051 (Sloan and Little, Apr. 11, 1981) discloses Mannichbase hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

The following abbreviations are used:
aq.—aqueous
BINAP—2,2'-bis(diphenylphosphino)-1,1'-binaphthyl
concd—concentrated
DCM—dichloromethane
DMF—N,N-dimethylformamide
DMSO—dimethylsulfoxide
Et$_2$O—diethyl ether
EtOAc—ethyl acetate
EtOH—ethyl alcohol
h—hour(s)
min—minutes
MeOH—methyl alcohol
NMP—1-methyl-2-pyrrolidinone
rt—room temperature
satd—saturated
TFA—trifluoroacetic acid
THF—tetrahydrofuran
X-Phos—2-dicyclohexylphosphino-2',4',6'-tri-isopropyl-1, 1'-biphenyl
General Reagents and solvents used below can be obtained from commercial sources. $^1$H-NMR spectra were recorded on a Bruker 400 MHz and 500 MHz NMR spectrometer. Significant peaks are tabulated in the order: number of protons, multiplicity (s, singlet; d, doublet; t, triplet; q, quartet; m, multiplet; br s, broad singlet), and coupling constant(s) in Hertz (Hz). Mass spectrometry results are reported as the ratio of mass over charge, followed by the relative abundance of each ion (in parentheses Electrospray ionization (ESI) mass spectrometry analysis was conducted on a Agilent 1100 series LC/MSD electrospray mass spectrometer. All compounds could be analyzed in the positive ESI mode using acetonitrile:water with 0.1% formic acid as the delivery solvent. Reverse phase analytical HPLC was carried out using a Agilent 1200 series on Agilent Eclipse XDB-C18 5 µm column (4.6×150 mm) as the stationary phase and eluting with acetonitrile:H$_2$O with 0.1% TFA. Reverse phase semi-prep HPLC was carried out using a Agilent 1100 Series on a Phenomenex Gemini™ 10 μm C18 column (250×21.20 mm) as the stationary phase and eluting with acetonitrile:H$_2$O with 0.1% TFA.

Procedure A

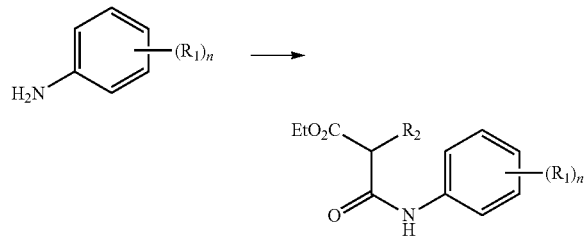

A mixture of the substituted aniline (1 equiv.) in pyridine (2 equiv.) was treated with diethyl alkylmalonate (1.5 equiv.) and the stirred mixture was heated at 130° C. for 24 h. After this time the reaction was treated with diethyl alkylmalonate (0.5 equiv.) and heated at 130° C. for an additional 12 h. After this time the reaction was cooled to rt and evaporated under reduced pressure. The crude product was taken up in DCM, washed with satd aq. bicarbonate and the separated organic layer was dried over magnesium sulfate, filtered and evaporated under reduced pressure. The crude product was dissolved in benzene and evaporated under reduced pressure. The crude product was purified by column chromatography on silica (using a gradient of hexanes:EtOAc, 1:0 to 3:1 as eluant) to provide ethyl substituted phenylamino-oxopropanoates.

Procedure B

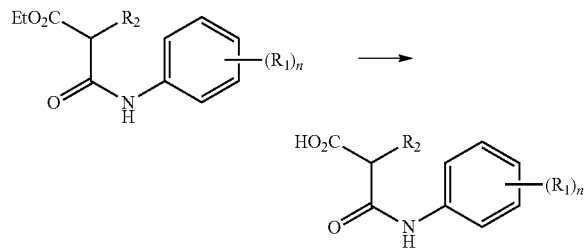

A mixture of the ethyl substituted phenylamino-oxopropanoate (1 equiv.) in THF-water (4:1, 0.878M) was treated with sodium hydroxide (1.2 equiv.) and stirred at rt for 1 h. After this time the reaction was acidified to pH 2 with concd HCl and then it was extracted with EtOAc. The separated organic layer was dried over magnesium sulfate, filtered and evaporated under reduced pressure to give substituted phenylamino-oxopropanoic acids.

Procedure C

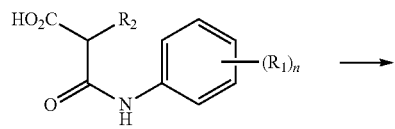

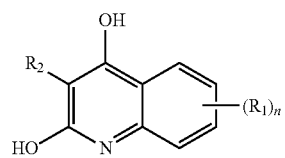

A mixture of phenylamino-oxopropanoic acid in polyphosphoric acid (0.6M) was stirred at 130° C. for 2 h. After this time the reaction was cooled to rt and treated with 2M aq. sodium hydroxide until a precipitate formed. The precipitate was filtered and washed with 1M aq. sodium hydroxide and dried under vacuum to give substituted quinoline diols.

Procedure D

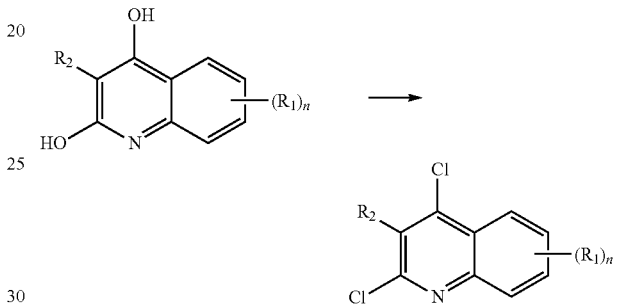

A mixture of the quinoline diol (1 equiv.) and phosphorus oxychloride (10 equiv.) was heated at 100° C. for 2 h. After this time the reaction was cooled to rt and evaporated under reduced pressure. The resulting brown residue was taken up in DCM and washed with water. The separated organic layer was dried over magnesium sulfate, filtered and evaporated under reduced pressure. The product was then purified by column chromatography (using a 9 to 1 mixture of hexanes and EtOAc as eluant) to give the substituted dichloroquinolines.

Procedure E

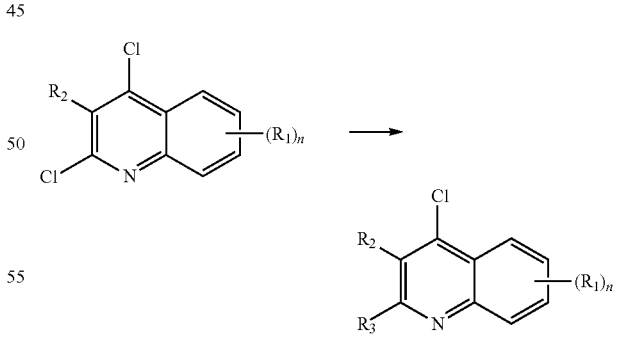

A mixture of the substituted dichloroquinoline (1 equiv.), the Stille reagent (1 equiv.) and tetrakis(triphenylphosphine) palladium (0.1 equiv.) in toluene (0.21M) was heated at reflux overnight. After this time the reaction was cooled to rt and treated with EtOAc and water. The separated organic layer was dried over magnesium sulfate, filtered and evaporated in vacuo. Column chromatography gave the substituted 4-chloro quinolines.

Procedure F

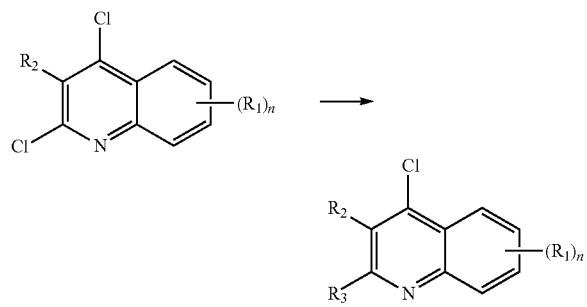

A mixture of the substituted dichloroquinoline (1 equiv.), the boronic acid (1 equiv.), sodium carbonate (2 equiv.) and tetrakis(triphenylphosphine)palladium (0.1 equiv.) in toluene-water (5:2, 0.15M) was heated at reflux overnight. After this time the reaction was cooled to rt and treated with EtOAc and water. The separated organic layer was dried over magnesium sulfate, filtered and evaporated in vacuo. Column chromatography gave the substituted 4-chloro quinolines.

Procedure G

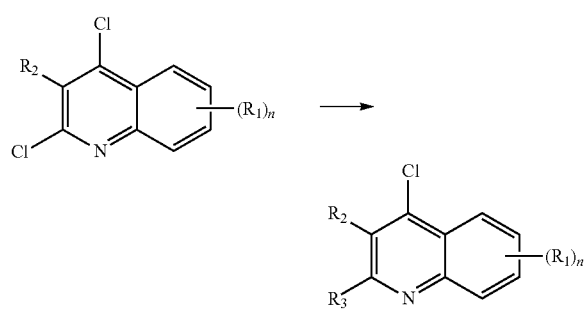

A mixture of the substituted dichloroquinoline (1 equiv.) and the amine ($R_3$—H, 1 equiv.) in isopropanol (0.4M) was heated in a sealed tube overnight at 85° C. The reaction was cooled to rt and concd to dryness under reduced pressure. The residue was then purified by medium pressure chromatography to give the corresponding substituted 4-chloroquinolines.

Procedure H

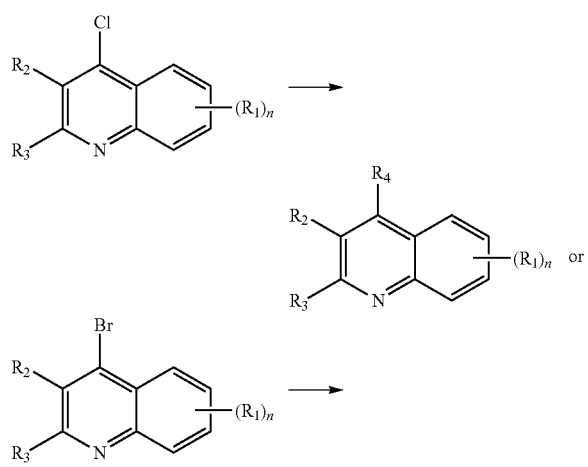

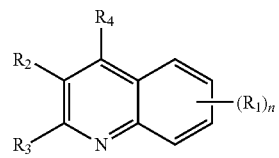

A mixture of the substituted 4-chloroquinoline or 4-bromoquinoline (1 equiv.) and the amine ($R_4$—H, 1.1 equiv.), sodium tert-butoxide (2.5 equiv.), X-Phos (0.16 equiv.) and tris(dibenzylideneacetone)dipalladium(0) (0.04 equiv.) in a suitable solvent (0.5M) was heated in an oil bath or a microwave reactor at 110° C. for 45 min. The reaction was cooled to rt and diluted with water. The mixture was extracted with EtOAc, DCM or a 10% MeOH:DCM mixture. The combined organic layers were dried over magnesium sulfate and filtered. The filtrate was concd under reduced pressure and the residue was then purified by medium pressure chromatography to give the corresponding substituted quinolines.

Procedure I

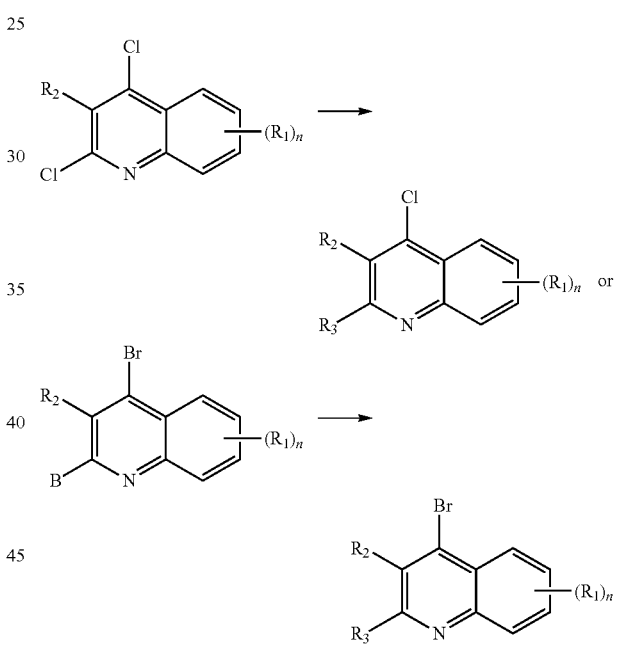

A mixture of the substituted 4-chloroquinoline or 4-bromoquinoline (1 equiv.), the other nitrogen containing reagent ($R_3$—H, 1.1 equiv.), potassium carbonate (2.5 equiv.), di-tert-butyl(2',4',6'-triisopropyl-3,4,5,6-tetramethylbiphenyl-2-yl)-phosphine (0.05 equiv.), activated three angstrom molecular sieves and tris(dibenzylideneacetone)dipalladium(0) (0.02 equiv.) in a suitable solvent (0.5M) was heated in an oil bath or a microwave reactor at 110° C. for 3 h. The reaction was cooled to rt and filtered. To the filtrate was added water and the mixture was extracted with EtOAc, DCM or a 10% MeOH:DCM mixture. The combined organic layers were dried over magnesium sulfate and filtered. The filtrate was concd under reduced pressure and the residue was then purified by medium pressure chromatography to give the corresponding substituted quinolines.

Procedure J

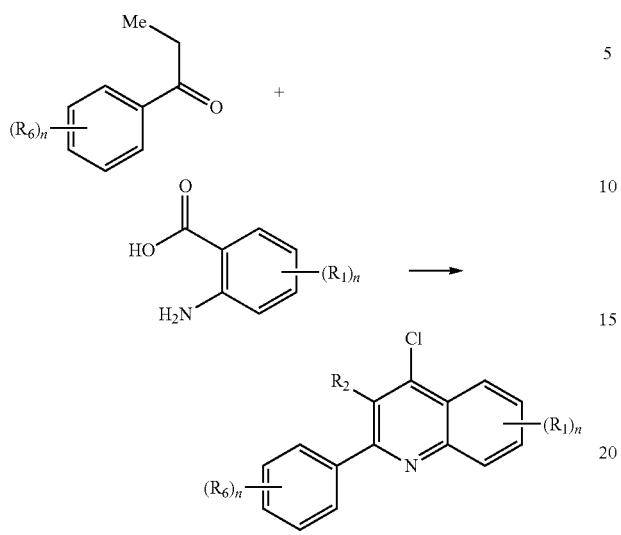

A mixture of the aminobenzoic acid (1.3 equiv.) and the aryl propanone (1.0 equiv.) in phosphorous oxychloride (0.5M) was heated to 90° C. for 2 h then concd under reduced pressure. The concentrate was partitioned between DCM and satd aq. sodium bicarbonate solution, stirring vigorously for 1 h. The organic extract was washed with water then brine, stirred over anhydrous magnesium sulfate, filtered and the filtrate concd under reduced pressure. The product was isolated by column chromatography on silica gel, eluting with EtOAc gradient in hexane.

Procedure K

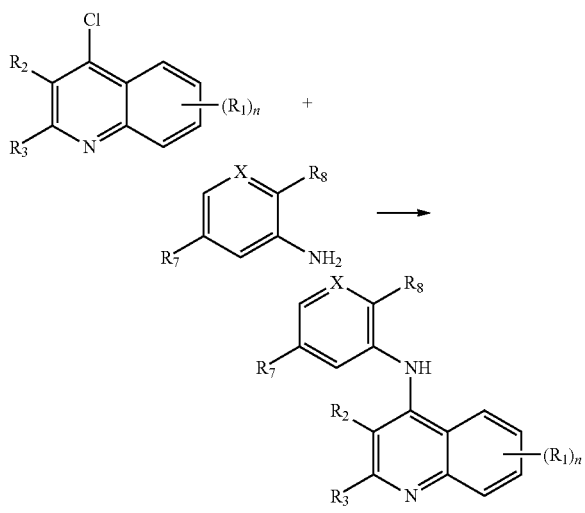

Method 1:

A mixture of the substituted quinoline (1.0 equiv.), the substituted aniline (1.0 equiv.) and 4.0N hydrochloric acid solution in 1,4-dioxane (1.0 equiv.) in MeOH (0.4M) was heated in a microwave at 150° C. for 2 h. The reaction was partitioned between DCM and satd aq. sodium bicarbonate solution. The organic separation was stirred over anhydrous magnesium sulfate, filtered and the filtrate concd under reduced pressure to afford product, which was isolated by column chromatography on silica gel.

Method 2:

A mixture of the substituted quinoline (2.0 equiv.), the substituted aniline (1.0 equiv.) and 4N hydrochloric acid in 1,4-dioxane (0.1 equiv.) in 1-methyl-2-pyrrolidinone (0.8M) was heated in a microwave at 150° C. for 4 h. The reaction was partitioned between EtOAc and satd aq. sodium bicarbonate. The organic separation was washed with water then brine, stirred over anhydrous magnesium sulfate, filtered and the filtrate concd under reduced pressure to afford product, which was isolated by chromatography on silica gel.

Example 1

N-(2,5-di-4-Morpholinylphenyl)-8-fluoro-3-methyl-2-(2-pyridinyl)-4-quinolinamine 4,4'-(2-Nitro-1,4-phenylene)dimorpholine

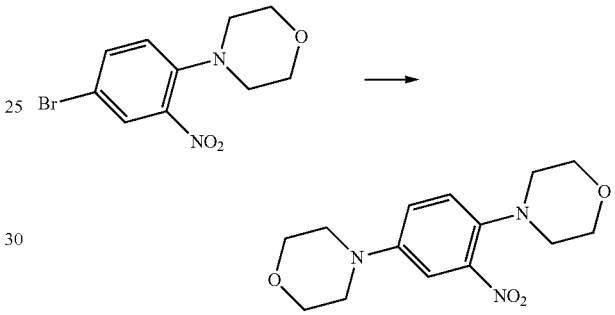

4-(4-Bromo-2-nitrophenyl)morpholine (500 mg, 1.74 mmol), morpholine (0.3 mL, 3.48 mmol), Pd$_2$dba$_3$ (112 mg, 0.12 mmol), X-Phos (125 mg, 261 μmol) and sodium tert-butoxide were suspended in toluene (71.0 mL, 666 mmol) and heated at reflux for 2 h. After this time the reaction was cooled to rt and evaporated in vacuo. The residue was taken up in EtOAc (80 mL) and washed with NaHCO$_3$ (satd aq. solution, 40 mL) and brine (40 mL). The separated organic layer was dried over magnesium sulfate, filtered and evaporated in vacuo. Column chromatography (hexanes:EtOAc, 1:0 to 1:2) gave 4,4'-(2-nitro-1,4-phenylene)dimorpholine. Mass Spectrum (ESI) m/e=294.2 (M+1).

2,5-Dimorpholinoaniline

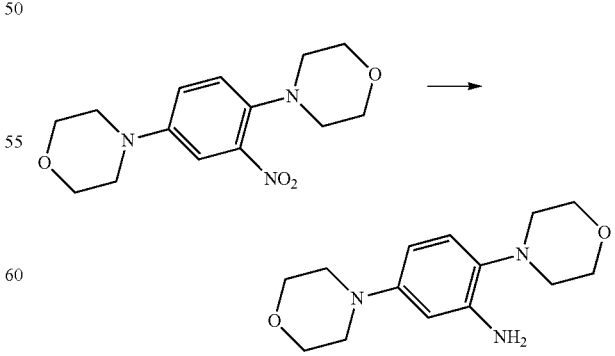

To a stirred solution of 4,4'-(2-nitro-1,4-phenylene)dimorpholine (5.6 g, 19 mmol) in EtOAc (90 mL) was added stannous chloride, dihydrate (18 g, 95 mmol). The reaction was stirred at rt for 10 min and at reflux for 90 min. After this time the reaction was cooled to rt and a precipitate formed. The precipitate was collected and washed with 1N NaOH (40 mL), water (50 mL) and brine (50 mL) and dried under vacuum overnight. After this time the solid was dissolved in EtOAc (200 mL) and washed with 1N NaOH (30 mL) and brine (50 mL), dried over magnesium sulfate, filtered and evaporated in vacuo to give 2,5-dimorpholinoaniline.

Ethyl 3-(2-fluorophenylamino)-2-methyl-3-oxopropanoate

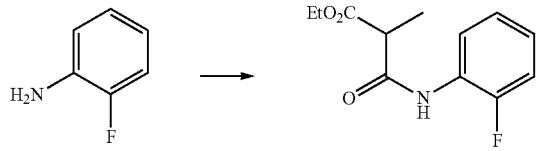 [SMILES: Nc1ccccc1F ; CCOC(=O)C(C)C(=O)Nc1ccccc1F]

Prepared according to general Procedure A using 2-fluoroaniline (17 mL, 180 mmol), pyridine (29 mL, 360 mmol) and diethyl methylmalonate (46 mL, 270 mmol). The crude was purified by column chromatography on silica (using a gradient of hexanes:EtOAc, 1:0 to 4:1 as eluant) to give ethyl 3-(2-fluorophenylamino)-2-methyl-3-oxopropanoate as a light brown solid. Mass Spectrum (ESI) m/e=239.9 (M+1).

3-(2-Fluorophenylamino)-2-methyl-3-oxopropanoic acid

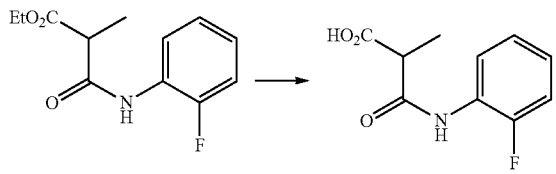 [SMILES: CCOC(=O)C(C)C(=O)Nc1ccccc1F ; CC(C(=O)O)C(=O)Nc1ccccc1F]

Prepared according to general Procedure B using ethyl 3-(2-fluorophenylamino)-2-methyl-3-oxopropanoate (15.0 g, 62.7 mmol) and NaOH (3.26 g, 81.5 mmol) in THF (60 mL) to give 3-(2-fluorophenylamino)-2-methyl-3-oxopropanoic acid as a white solid. Mass Spectrum (ESI) m/e=212.1 (M+1).

8-Fluoro-3-methylquinoline-2,4-diol

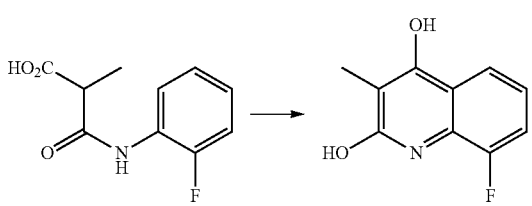

Prepared according to general Procedure C using 3-(2-fluorophenylamino)-2-methyl-3-oxopropanoic acid (11 g, 52 mmol) and polyphosphoric acid (80 mL) to give 8-fluoro-3-methylquinoline-2,4-diol as a white solid. Mass Spectrum (ESI) m/e=193.9 (M+1).

2,4-Dichloro-8-fluoro-3-methylquinoline

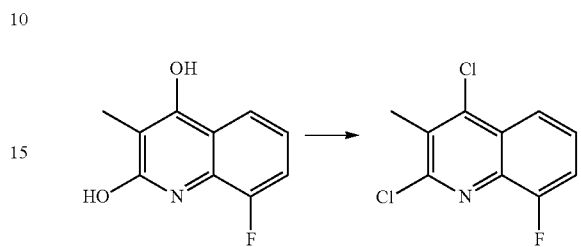

Prepared according to general Procedure D using 8-fluoro-3-methylquinoline-2,4-diol (2.8 g, 14 mmol) and phosphorous oxychloride (14 mL, 145 mmol) to give 2,4-dichloro-8-fluoro-3-methylquinoline as a white solid. Mass Spectrum (ESI) m/e=229.9 (M+1).

4-Chloro-8-fluoro-3-methyl-2-(pyridin-2-yl)quinoline

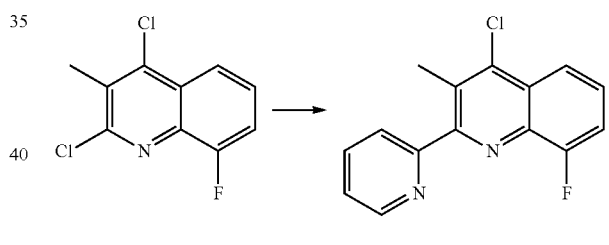

Prepared according to general Procedure E using 2,4-dichloro-8-fluoro-3-methylquinoline (1.0 g, 4.35 mmol), tetrakis(triphenylphosphine)palladium(0) (251 mg, 0.22 mmol) and 2-tributylstannylpyridine (1.6 mL, 4.35 mmol) in toluene (15 mL) to give 4-chloro-8-fluoro-3-methyl-2-(pyridin-2-yl) quinoline as a white solid.

N-(2,5-di-4-Morpholinylphenyl)-8-fluoro-3-methyl-2-(2-pyridinyl)-4-quinolinamine

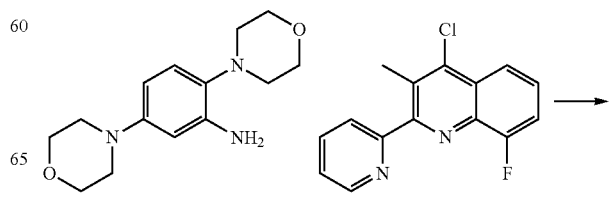

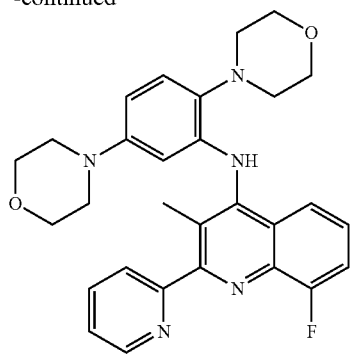

Prepared according to general Procedure K using 4-chloro-8-fluoro-3-methyl-2-(pyridin-2-yl)quinoline (95 mg, 0.348 mmol), 2,5-dimorpholinoaniline (92 mg, 0.348 mmol) and a 4.0M solution of HCl in dioxane (0.09 mL, 0.348 mmol) in MeOH (2.0 mL) and heating in the microwave for 2 h at 150° C. After purification N-(2,5-di-4-morpholinylphenyl)-8-fluoro-3-methyl-2-(2-pyridinyl)-4-quinolinamine was obtained as a yellow film. $^1$H NMR (400 MHz, chloroform-d) δ ppm 8.72 (1H, dd, J=4.7, 1.6 Hz), 7.87-8.00 (2H, m), 7.64-7.71 (1H, m), 7.31-7.45 (4H, m), 7.11 (1H, d, J=8.6 Hz), 6.47 (1H, d, J=7.4 Hz), 6.04 (1H, br. s.), 3.90 (4H, t, J=4.9 Hz), 3.68-3.79 (4H, m), 2.99-3.14 (4H, m), 2.86-2.98 (4H, m), 2.42 (3H, s). Mass Spectrum (ESI) m/e=500.2 (M+1).

Example 2

N-(2,5-di-4-Morpholinylphenyl)-8-fluoro-3-methyl-2-(2-pyridinyl)-4-quinolinamine

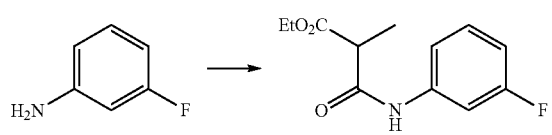 [SMILES: Nc1cccc(F)c1 ; CCOC(=O)C(C)C(=O)Nc1cccc(F)c1]

Prepared according to Procedure A using 3-fluoroaniline (18 mL, 187 mmol), pyridine (31 mL, 374 mmol) and diethyl methylmalonate (48 mL, 281 mmol). The crude was purified by column chromatography on silica (using a gradient of hexanes:EtOAc, 1:0 to 3:1 as eluant) to give ethyl 3-(3-fluorophenylamino)-2-methyl-3-oxopropanoate as a light brown solid. Mass Spectrum (ESI) m/e=240.1 (M+1).

3-(3-Fluorophenylamino)-2-methyl-3-oxopropanoic acid

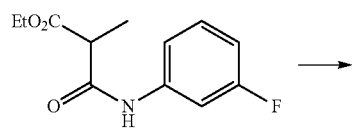

Prepared according to Procedure B using ethyl 3-(3-fluorophenylamino)-2-methyl-3-oxopropanoate (21.0 g, 87.8 mmol) in THF (80 mL) to give 3-(3-fluorophenylamino)-2-methyl-3-oxopropanoic acid as a white solid. Mass Spectrum (ESI) m/e=212.1 (M+1).

7-Fluoro-3-methylquinoline-2,4-diol and 5-fluoro-3-methylquinoline-2,4-diol

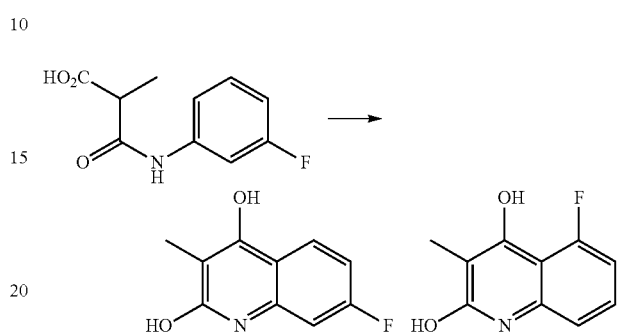

Prepared according to Procedure C using 3-(3-fluorophenylamino)-2-methyl-3-oxopropanoic acid (19 g, 90 mmol) and polyphosphoric acid (150 mL) to give a mixture of 7-fluoro-3-methylquinoline-2,4-diol and 5-fluoro-3-methylquinoline-2,4-diol. Mass Spectrum (ESI) m/e=194.1 (M+1).

2,4-Dichloro-7-fluoro-3-methylquinoline and 2,4-dichloro-5-fluoro-3-methyl quinoline

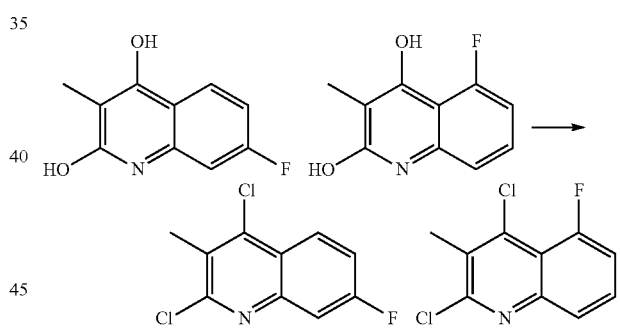

Prepared according to Procedure D using 7-fluoro-3-methylquinoline-2,4-diol and 5-fluoro-3-methylquinoline-2,4-diol (14.0 g, 72 mmol) to give a mixture of 2,4-dichloro-7-fluoro-3-methylquinoline and 2,4-dichloro-5-fluoro-3-methyl quinoline as a white solid. Mass Spectrum (ESI) m/e=230 (M+1).

4-Chloro-5-fluoro-3-methyl-2-(pyridin-2-yl)quinoline and 4-chloro-7-fluoro-3-methyl-2-(pyridin-2-yl)quinoline

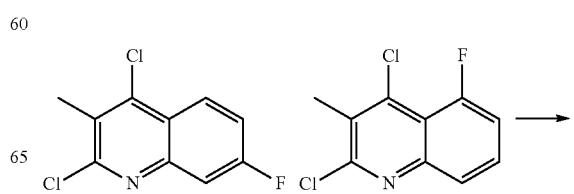

33

-continued

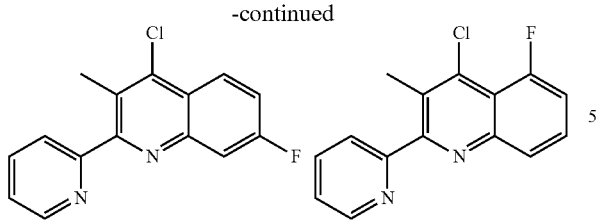

Prepared according to general Procedure E using 2,4-dichloro-7-fluoro-3-methylquinoline and 2,4-dichloro-5-fluoro-3-methyl quinoline (1.5 g, 6.52 mmol), tetrakis(triphenylphosphine)palladium(0) (377 mg, 0.326 mmol) in toluene (20 mL) to give a separable mixture of 4-chloro-7-fluoro-3-methyl-2-(pyridin-2-yl)-quinoline (Mass Spectrum (ESI) m/e=273.0 (M+1)) and 4-chloro-5-fluoro-3-methyl-2-(pyridin-2-yl)quinoline (Mass Spectrum (ESI) m/e=273.0 (M+1)).

N-(2,5-Di-4-morpholinylphenyl)-8-fluoro-3-methyl-2-(2-pyridinyl)-4-quinolinamine

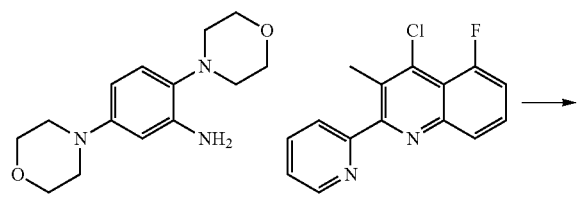

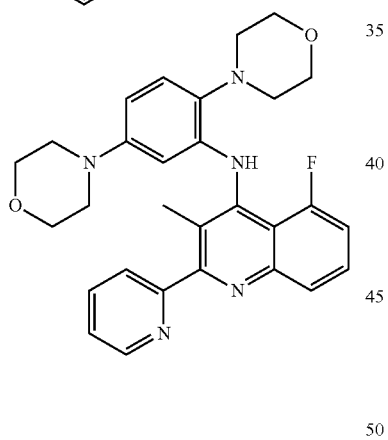

Prepared according to general Procedure K using 4-chloro-5-fluoro-3-methyl-2-(pyridin-2-yl)quinoline (52 mg, 0.191 mmol), 2,5-dimorpholinoaniline (50 mg, 0.191 mmol) and a 4.0M solution of HCl in dioxane (0.048 mL, 0.191 mmol) in MeOH (0.5 mL) and heating in the microwave for 2 h at 150° C. After purification N-(2,5-di-4-morpholinylphenyl)-8-fluoro-3-methyl-2-(2-pyridinyl)-4-quinolinamine was obtained as a yellow film. $^1$H NMR (400 MHz, chloroform-d) δ ppm 8.63-8.75 (1H, m), 8.21 (1H, d, J=11.0 Hz), 7.96 (1H, d, J=8.2 Hz), 7.83-7.92 (2H, m), 7.57 (1H, td, J=8.2, 5.5 Hz), 7.37 (1H, ddd, J=6.7, 4.5, 2.5 Hz), 7.11-7.18 (1H, m), 7.09 (1H, d, J=8.6 Hz), 6.46 (1H, dd, J=8.4, 2.9 Hz), 6.23 (1H, d, J=2.7 Hz), 3.91 (4H, t, J=4.5 Hz), 3.75-3.85 (4H, m), 3.04-3.11 (8H, m), 2.24 (3H, s). Mass Spectrum (ESI) m/e=230 (M+1). Mass Spectrum (ESI) m/e=500 (M+1).

34

Example 3

N-(2,5-Di-4-morpholinylphenyl)-8-fluoro-3-methyl-2-(2-pyridinyl)-4-quinolinamine 4-Chloro-7-fluoro-3-methyl-2-(pyridin-3-yl)quinoline and 4-chloro-5-fluoro-3-methyl-2-(pyridin-3-yl)quinoline

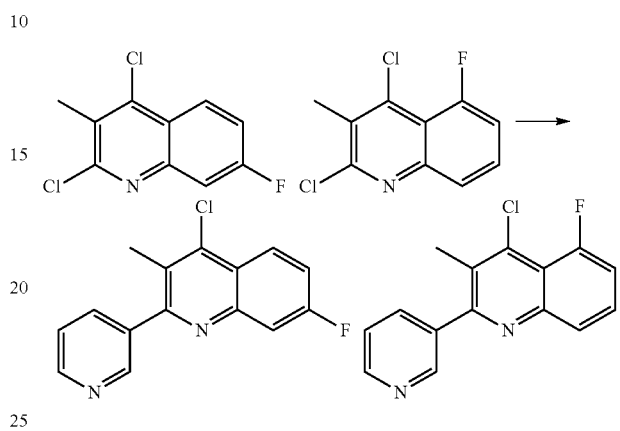

Prepared according to general Procedure E using 2,4-dichloro-7-fluoro-3-methylquinoline and 2,4-dichloro-5-fluoro-3-methyl quinoline (1.0 g, 4.35 mmol), tetrakis(triphenylphosphine)palladium(0) (251 mg, 0.22 mmol) in toluene (15 mL) to give a separable mixture of 4-chloro-7-fluoro-3-methyl-2-(pyridin-3-yl)quinoline and 4-chloro-5-fluoro-3-methyl-2-(pyridin-3-yl)quinoline.

N-(2,5-Di-4-morpholinylphenyl)-8-fluoro-3-methyl-2-(2-pyridinyl)-4-quinolinamine

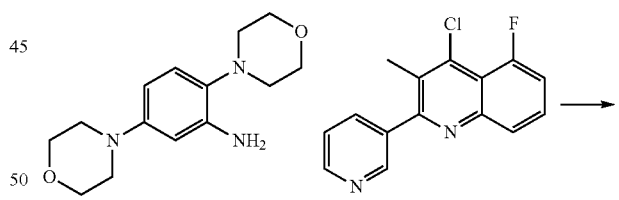

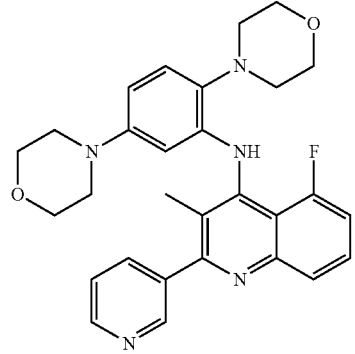

Prepared according to general Procedure K using 4-chloro-5-fluoro-3-methyl-2-(pyridin-3-yl)quinoline (50 mg, 0.183 mmol), 2,5-dimorpholinoaniline (48 mg, 0.183 mmol) and a 4.0M solution of HCl in dioxane (0.046 mL, 0.183 mmol) in MeOH (0.5 mL) and heating in the microwave for 2 h at 150° C. After purification N-(2,5-di-4-morpholinylphenyl)-8-fluoro-3-methyl-2-(2-pyridinyl)-4-quinolinamine was obtained as a yellow film. $^1$H NMR (400 MHz, chloroform-d) δ ppm 8.88 (1H, d, J=2.3 Hz), 8.72 (1H, dd, J=4.9, 1.8 Hz), 8.24 (1H, d, J=11.3 Hz), 7.99 (1H, dt, J=7.8, 2.2 Hz), 7.94 (1H, d, J=8.2 Hz), 7.60 (1H, td, J=8.2, 5.5 Hz), 7.48 (1H, dd, J=7.8, 5.1 Hz), 7.13-7.21 (1H, m), 7.11 (1H, d, J=8.6 Hz), 6.50 (1H, dd, J=8.6, 2.7 Hz), 6.15 (1H, d, J=2.7 Hz), 3.90 (4H, t, J=4.5 Hz), 3.73-3.85 (4H, m), 2.83-3.13 (8H, m), 2.20 (3H, s). Mass Spectrum (ESI) m/e=500.2 (M+1).

Example 4

N-(2,5-Di-4-morpholinylphenyl)-8-fluoro-3-methyl-2-(2-pyridinyl)-4-quinolinamine

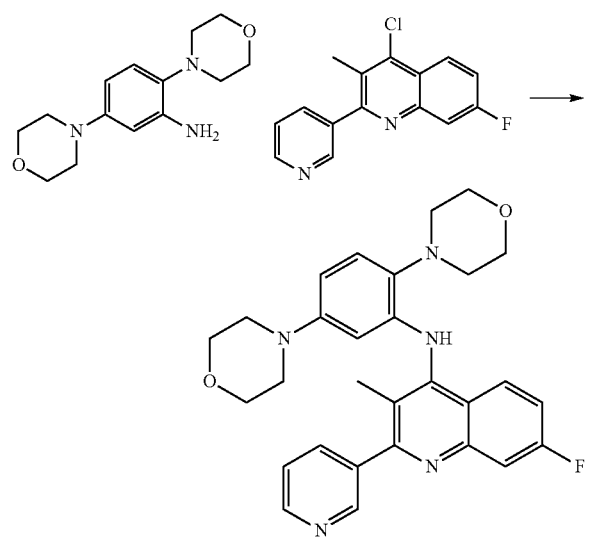

Prepared according to general Procedure K using 4-chloro-7-fluoro-3-methyl-2-(pyridin-3-yl)quinoline (57 mg, 0.209 mmol), 2,5-dimorpholinoaniline (55 mg, 0.209 mmol) and a 4.0M solution of HCl in dioxane (0.052 mL, 0.209 mmol) in MeOH (0.5 mL) and heating in the microwave for 2 h at 150° C. After purification N-(2,5-di-4-morpholinylphenyl)-8-fluoro-3-methyl-2-(2-pyridinyl)-4-quinolinamine was obtained. $^1$H NMR (400 MHz, chloroform-d) δ ppm 8.88 (1H, d, J=2.3 Hz), 8.72 (1H, dd, J=4.9, 1.8 Hz), 7.99 (1H, dt, J=7.8, 2.2 Hz), 7.90 (1H, dd, J=9.2, 6.1 Hz), 7.76 (1H, dd, J=10.0, 2.5 Hz), 7.48 (1H, dd, J=8.0, 4.9 Hz), 7.20-7.31 (2H, m), 7.12 (1H, d, J=8.6 Hz), 6.46 (1H, dd, J=8.6, 2.7 Hz), 6.00 (1H, d, J=2.7 Hz), 3.91 (4H, t, J=4.7 Hz), 3.66-3.79 (4H, m), 2.99-3.14 (4H, m), 2.86-2.99 (4H, m), 2.31 (3H, s). Mass Spectrum (ESI) m/e=500.2 (M+1).

Example 5

N-(2,5-Di-4-morpholinylphenyl)-7-fluoro-3-methyl-2-(1,3-thiazol-2-yl)-4-quinolinamine 2-(4-Chloro-8-fluoro-3-methylquinolin-2-yl)thiazole

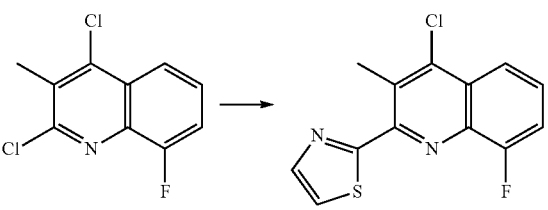 [SMILES: Cc1c(Cl)nc2c(F)cccc2c1Cl ; Cc1c(-c2nccs2)nc2c(F)cccc2c1Cl]

Prepared according to Procedure E using 2,4-dichloro-8-fluoro-3-methylquinoline (250 mg, 1.087 mmol), 2-tributylstannylthiazole (0.34 mL, 1.087 mmol) and tetrakis(triphenylphosphine)palladium(0) (126 mg, 0.109 mmol) in toluene (4 mL) and heating at reflux overnight. After purification 2-(4-chloro-8-fluoro-3-methylquinolin-2-yl)thiazole was obtained.

N-(2,5-Di-4-morpholinylphenyl)-7-fluoro-3-methyl-2-(1,3-thiazol-2-yl)-4-quinolinamine

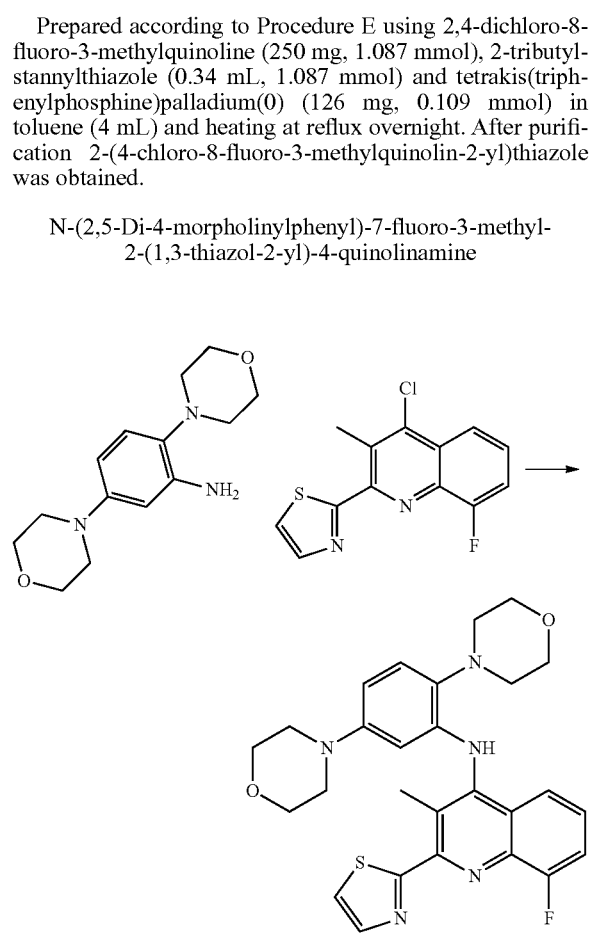

Prepared according to general Procedure K using 2-(4-chloro-8-fluoro-3-methylquinolin-2-yl)thiazole (46 mg, 0.165 mmol), 2,5-dimorpholinoaniline (43 mg, 0.165 mmol) and a 4.0M solution of HCl in dioxane (0.041 mL, 0.165 mmol) in MeOH (0.5 mL) and heating in the microwave for 2 h at 150° C. After purification N-(2,5-di-4-morpholinylphenyl)-7-fluoro-3-methyl-2-(1,3-thiazol-2-yl)-4-quinolinamine was obtained as a yellow film. $^1$H NMR (500 MHz, chloroform-d) δ ppm 7.96-8.05 (1H, m), 7.62 (1H, s), 7.51-7.56 (1H, m), 7.39 (2H, t, J=2.3 Hz), 7.12 (1H, d, J=8.8 Hz), 6.44 (1H, dd, J=8.7, 2.6 Hz), 5.92 (1H, d, J=2.7 Hz), 3.83-3.96 (4H, m), 3.70 (4H, dd, J=5.5, 4.0 Hz), 2.99-3.13 (4H, m), 2.87-2.93 (4H, m), 2.83 (3H, s). Mass Spectrum (ESI) m/e=506.0 (M+1).

Example 6

6-Chloro-N-(2,5-di-4-morpholinylphenyl)-2-(2-fluorophenyl)-3-methyl-4-quinolinamine

4,6-Dichloro-2-(2-fluorophenyl)-3-methylquinoline

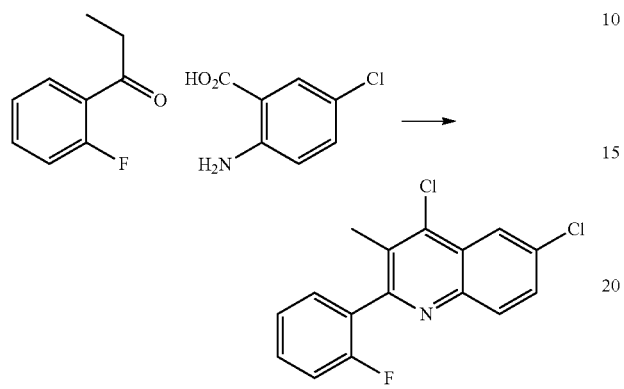

Prepared according to Procedure J using 2-amino-5-chlorobenzoic acid (1.5 equiv.) and 1-(2-fluorophenyl)propan-1-one (1 equiv.) in phosphorous oxychloride to afford 4,6-dichloro-2-(2-fluorophenyl)-3-methylquinoline upon purification by chromatography on silica gel. Mass Spectrum (ESI) m/e=306.0 (M+1).

6-Chloro-N-(2,5-di-4-morpholinylphenyl)-2-(2-fluorophenyl)-3-methyl-4-quinolinamine

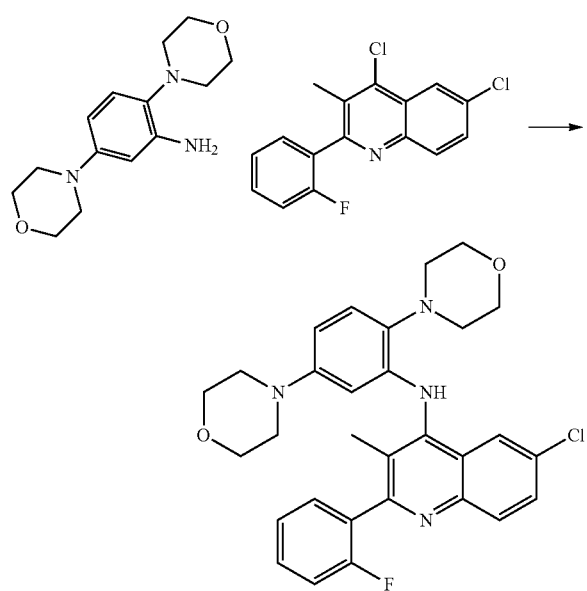

Prepared according to general Procedure K using 4,6-dichloro-2-(2-fluorophenyl)-3-methylquinoline (116 mg, 0.38 mmol), 2,5-dimorpholinoaniline (100 mg, 0.38 mmol) and a 4.0M solution of HCl in dioxane (0.095 mL, 0.38 mmol) in MeOH (1.0 mL) and heating in the microwave for 2 h at 150° C. After purification 6-chloro-N-(2,5-di-4-morpholinylphenyl)-2-(2-fluorophenyl)-3-methyl-4-quinolinamine was obtained as a yellow film. $^1$H NMR (400 MHz, chloroform-d) δ ppm 8.10 (1H, d, J=9.0 Hz), 7.90 (1H, d, J=2.3 Hz), 7.58-7.67 (2H, m), 7.47 (1H, d, J=8.2 Hz), 7.31-7.37 (1H, m), 7.16-7.22 (1H, m), 7.13 (1H, d, J=8.6 Hz), 6.45 (1H, dd, J=8.6, 2.7 Hz), 6.00-6.08 (1H, m), 3.93 (4H, t, J=4.5 Hz), 3.76 (4H, dd, J=5.9, 3.9 Hz), 3.06 (4H, d, J=1.2 Hz), 2.91-3.02 (4H, m), 2.20 (3H, d, J=2.3 Hz). Mass Spectrum (ESI) m/e=533.2 (M+1).

Example 7

N-(2,5-Di-4-morpholinylphenyl)-2-(2-fluorophenyl)-3-methyl-7-(trifluoromethyl)-4-quinolinamine

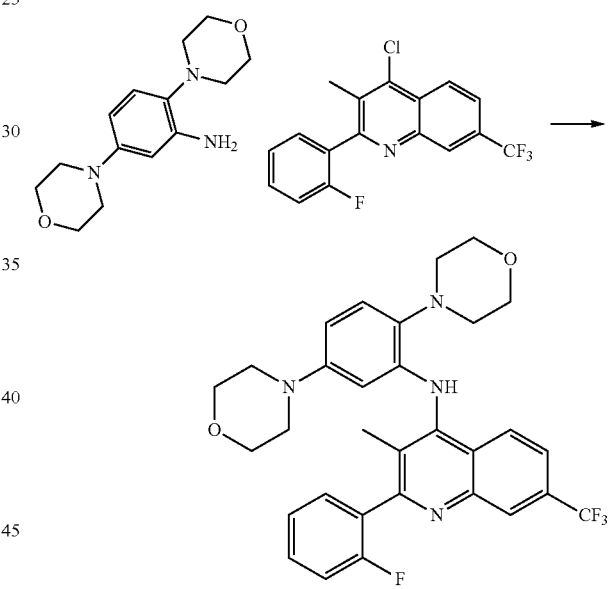

Prepared according to general Procedure K using 4-chloro-2-(2-fluorophenyl)-3-methyl-7-(trifluoromethyl)quinoline (129 mg, 0.38 mmol), 2,5-dimorpholinoaniline (100 mg, 0.38 mmol) and a 4.0M solution of HCl in dioxane (0.095 mL, 0.38 mmol) in MeOH (1.0 mL) and heating in the microwave for 2 h at 150° C. After purification N-(2,5-di-4-morpholinylphenyl)-2-(2-fluorophenyl)-3-methyl-7-(trifluoromethyl)-4-quinolinamine was obtained as a yellow film. $^1$H NMR (400 MHz, chloroform-d) δ ppm 8.49 (1H, s), 8.04 (1H, d, J=8.6 Hz), 7.58-7.72 (2H, m), 7.46-7.54 (1H, m, J=7.9, 7.9, 5.4, 2.0 Hz), 7.30-7.40 (2H, m), 7.17-7.24 (1H, m), 7.13 (1H, d, J=8.6 Hz), 6.47 (1H, dd, J=8.6, 2.7 Hz), 6.04 (1H, d, J=0.8 Hz), 3.92 (4H, t, J=4.7 Hz), 3.69-3.80 (4H, m), 3.06 (4H, br. s.), 2.82-3.00 (4H, m), 2.24 (3H, s). Mass Spectrum (ESI) m/e=567.3 (M+1).

Example 8

N-(2,5-Di-4-morpholinylphenyl)-2-(2-fluorophenyl)-3-methyl-4-quinolinamine

4-Chloro-2-(2-fluorophenyl)-3-methylquinoline

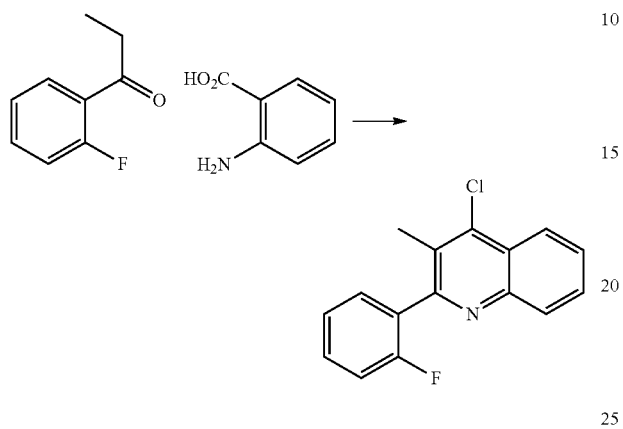

Prepared according to Procedure J using 2-aminobenzoic acid (1.5 equiv.) and 1-(2-fluorophenyl)propan-1-one (1 equiv.) in phosphorous oxychloride to afford 4-chloro-2-(2-fluorophenyl)-3-methylquinoline upon purification by chromatography on silica gel. Mass Spectrum (ESI) m/e=272.0 (M+1).

N-(2,5-Di-4-morpholinylphenyl)-2-(2-fluorophenyl)-3-methyl-4-quinolinamine

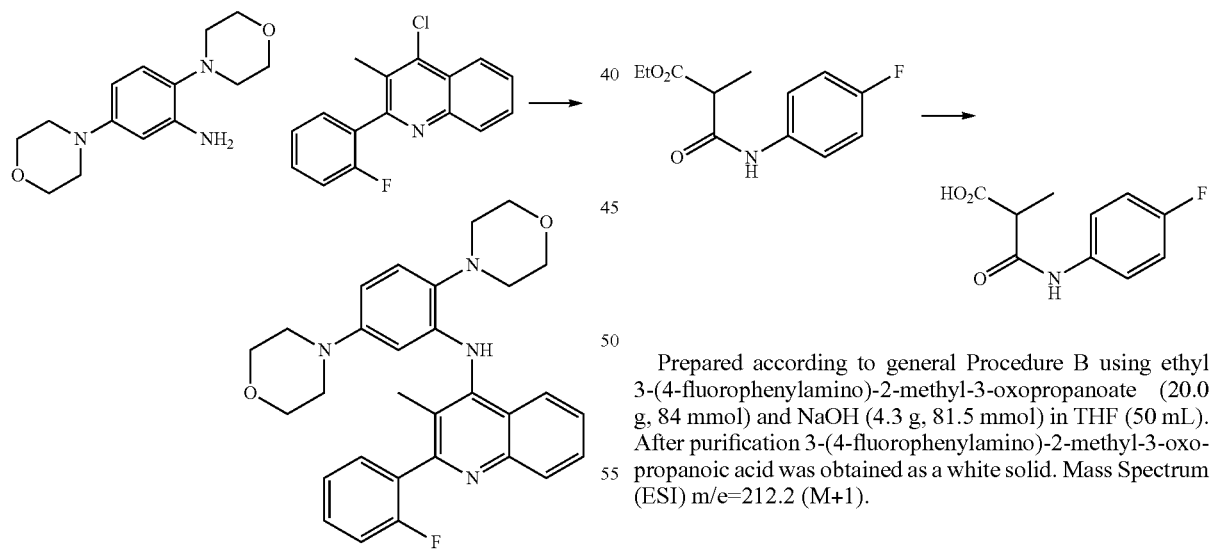

Prepared according to general Procedure K using 4-chloro-2-(2-fluorophenyl)-3-methylquinoline (103 mg, 0.38 mmol), 2,5-dimorpholinoaniline (100 mg, 0.38 mmol) and a 4.0M solution of HCl in dioxane (0.095 mL, 0.38 mmol) in MeOH (1.0 mL) and heating in the microwave for 2 h at 150° C. After purification N-(2,5-di-4-morpholinylphenyl)-2-(2-fluorophenyl)-3-methyl-4-quinolinamine was obtained as a yellow film. $^1$H NMR (400 MHz, chloroform-d) δ ppm 8.29 (1H, d, J=8.6 Hz), 7.93 (1H, d, J=8.2 Hz), 7.68-7.76 (1H, m), 7.65 (1H, td, J=7.4, 1.6 Hz), 7.40-7.55 (3H, m), 7.34 (1H, t, J=7.4 Hz), 7.19 (1H, t, J=9.0 Hz), 7.11 (1H, d, J=8.6 Hz), 6.47 (1H, dd, J=8.8, 2.9 Hz), 6.06-6.20 (1H, m), 3.85-4.00 (4H, m), 3.67-3.80 (4H, m), 3.01-3.17 (4H, m), 2.88-3.00 (4H, m), 2.21 (3H, d, J=2.3 Hz). Mass Spectrum (ESI) m/e=499.2 (M+1).

Example 9

N-(2,5-Di-4-morpholinylphenyl)-6-fluoro-3-methyl-2-(3-pyridinyl)-4-quinolinamine

Ethyl 3-(4-fluorophenylamino)-2-methyl-3-oxopropanoate

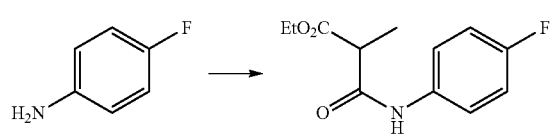 [SMILES: Nc1ccc(F)cc1 ; CCOC(=O)C(C)C(=O)Nc1ccc(F)cc1]

Prepared according to general Procedure A using 4-fluoroaniline (18 g, 162 mmol), pyridine (13 mL, 162 mmol) and diethyl methylmalonate (28 mL, 162 mmol). After purification ethyl 3-(4-fluorophenylamino)-2-methyl-3-oxopropanoate was obtained. Mass Spectrum (ESI) m/e=240.1 (M+1).

3-(4-Fluorophenylamino)-2-methyl-3-oxopropanoic acid

Prepared according to general Procedure B using ethyl 3-(4-fluorophenylamino)-2-methyl-3-oxopropanoate (20.0 g, 84 mmol) and NaOH (4.3 g, 81.5 mmol) in THF (50 mL). After purification 3-(4-fluorophenylamino)-2-methyl-3-oxopropanoic acid was obtained as a white solid. Mass Spectrum (ESI) m/e=212.2 (M+1).

6-Fluoro-3-methylquinoline-2,4-diol

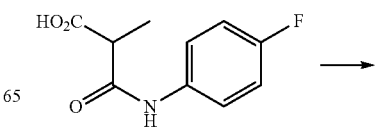

-continued

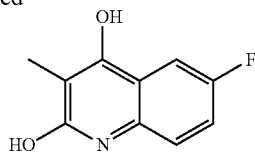

Prepared according to general Procedure C using 3-(4-fluorophenylamino)-2-methyl-3-oxopropanoic acid (15 g, 71 mmol) and polyphosphoric acid (60 mL) and heating at 130° C. for 14 h. After purification 6-fluoro-3-methylquinoline-2,4-diol was obtained as a tan solid. Mass Spectrum (ESI) m/e=194.2 (M+1).

2,4-Dichloro-6-fluoro-3-methylquinoline

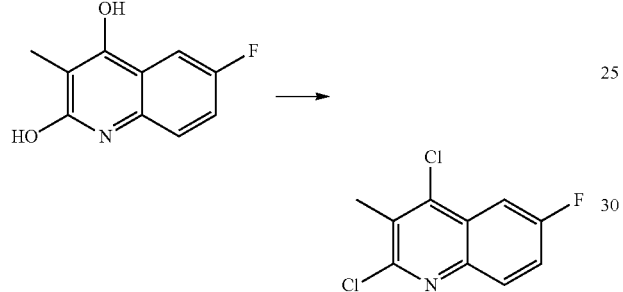

Prepared according to general Procedure D using 6-fluoro-3-methylquinoline-2,4-diol (4.0 g, 21 mmol) and phosphorous oxychloride (19 mL, 207 mmol) to give 2,4-dichloro-6-fluoro-3-methylquinoline as a white solid. Mass Spectrum (ESI) m/e=230.0 (M+1).

4-Chloro-6-fluoro-3-methyl-2-(pyridin-3-yl)quinoline

Prepared according to general Procedure F using 2,4-dichloro-6-fluoro-3-methylquinoline (300 mg, 1.3 mmol), 3-pyridylboronic acid (160 mg, 1.3 mmol), tetrakis(triphenylphosphine)palladium(0), sodium carbonate (242 mg, 2.28 mmol) in toluene:water (5 mL:2 mL) and heating at 130° C. overnight. After purification 4-chloro-6-fluoro-3-methyl-2-(pyridin-3-yl)quinoline was obtained as a white solid.

N-(2,5-Di-4-morpholinylphenyl)-6-fluoro-3-methyl-2-(3-pyridinyl)-4-quinolinamine

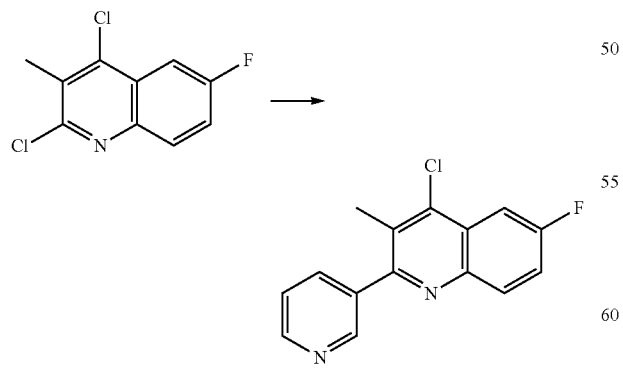

Prepared according to general Procedure K using 4-chloro-6-fluoro-3-methyl-2-(pyridin-3-yl)quinoline (140 mg, 0.51 mmol), 2,5-dimorpholinoaniline (135 mg, 0.51 mmol) and a 4.0M solution of HCl in dioxane (0.13 mL, 0.51 mmol) in MeOH (1.0 mL) and heating in the microwave for 2 h at 150° C. After purification N-(2,5-di-4-morpholinylphenyl)-6-fluoro-3-methyl-2-(3-pyridinyl)-4-quinolinamine was obtained. $^1$H NMR (400 MHz, chloroform-d) δ ppm 8.88 (1H, d, J=2.3 Hz), 8.72 (1H, dd, J=5.1, 2.0 Hz), 8.16 (1H, dd, J=9.0, 5.5 Hz), 7.99 (1H, dt, J=7.8, 2.2 Hz), 7.43-7.57 (3H, m), 7.16-7.20 (1H, m), 7.13 (1H, d, J=8.6 Hz), 6.46 (1H, dd, J=8.6, 2.7 Hz), 5.97 (1H, d, J=2.7 Hz), 3.87-3.99 (4H, m), 3.67-3.80 (4H, m), 3.01-3.13 (4H, m), 2.83-2.98 (4H, m), 2.33 (3H, s). Mass Spectrum (ESI) m/e=500.0 (M+1).

Example 10

N-(2,5-Di-4-morpholinylphenyl)-6-fluoro-2-(5-fluoro-3-pyridinyl)-3-methyl-4-quinolinamine 4-Chloro-6-fluoro-2-(5-fluoropyridin-3-yl)-3-methylquinoline

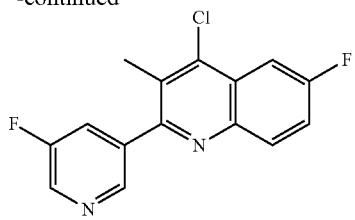

Prepared according to general Procedure F using 2,4-dichloro-6-fluoro-3-methylquinoline (300 mg, 1.3 mmol), 5-fluoropyridin-3-ylboronic acid (160 mg, 1.3 mmol), tetrakis(triphenylphosphine)palladium(0) (151 mg, 0.13 mmol), sodium carbonate (242 mg, 2.28 mmol) in toluene:water (5 mL:2 mL) and heating at 130° C. overnight. After purification 4-chloro-6-fluoro-2-(5-fluoropyridin-3-yl)-3-methylquinoline was obtained as a white solid. Mass Spectrum (ESI) m/e=291.0 (M+1).

N-(2,5-Di-4-morpholinylphenyl)-6-fluoro-2-(5-fluoro-3-pyridinyl)-3-methyl-4-quinolinamine

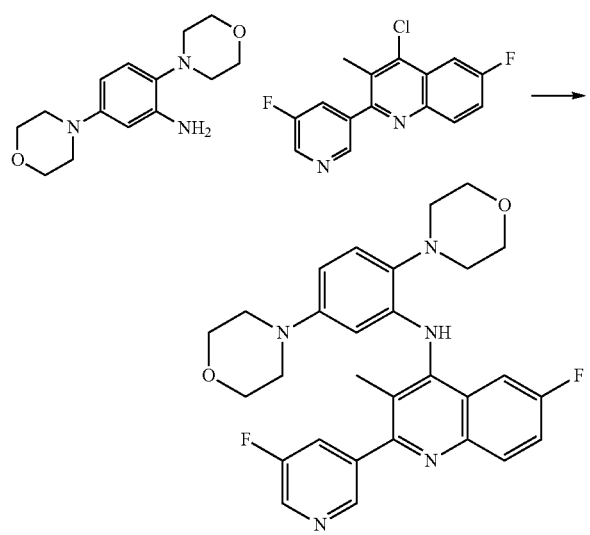

Prepared according to general Procedure K using 4-chloro-6-fluoro-2-(5-fluoropyridin-3-yl)-3-methylquinoline (110 mg, 0.38 mmol), 2,5-dimorpholinoaniline (120 mg, 0.38 mmol) and a 4.0M solution of HCl in dioxane (0.09 mL, 0.38 mmol) in MeOH (1.0 mL) and heating in the microwave for 2 h at 150° C. After purification N-(2,5-di-4-morpholinylphenyl)-6-fluoro-2-(5-fluoro-3-pyridinyl)-3-methyl-4-quinolinamine was obtained. $^1$H NMR (500 MHz, chloroform-d) δ ppm 8.70 (1H, t, J=1.7 Hz), 8.60 (1H, d, J=2.7 Hz), 8.13-8.22 (1H, m), 7.77 (1H, dt, J=8.8, 2.3 Hz), 7.44-7.55 (2H, m), 7.25 (1H, s), 7.15 (1H, d, J=8.6 Hz), 6.51 (1H, dd, J=8.8, 2.7 Hz), 6.01 (1H, dd, J=2.4, 0.5 Hz), 3.91 (4H, t, J=4.6 Hz), 3.69-3.79 (4H, m), 3.06 (4H, t, J=4.6 Hz), 2.90-2.99 (4H, m), 2.34 (3H, s). Mass Spectrum (ESI) m/e=518.1 (M+1).

Example 11

N-(2,5-Di-4-morpholinylphenyl)-6-fluoro-2-(5-fluoro-3-pyridinyl)-3-methyl-4-quinolinamine 4-Chloro-8-fluoro-3-methyl-2-(pyridin-3-yl)quinoline

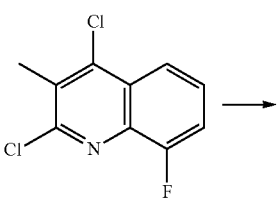

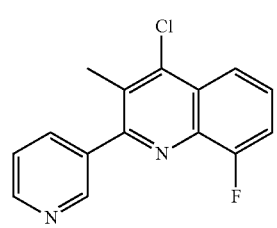

Prepared according to general Procedure F using 2,4-dichloro-8-fluoro-3-methylquinoline (250 mg, 1.1 mmol), 3-pyridylboronic acid (134 mg, 1.1 mmol), tetrakis(triphenylphosphine)palladium(0) (126 mg, 0.11 mmol), sodium carbonate (202 mg, 1.90 mmol) in toluene:water (5 mL:2 mL) and heating at 130° C. overnight. After purification 4-chloro-8-fluoro-3-methyl-2-(pyridin-3-yl)quinoline was obtained as a white solid. Mass Spectrum (ESI) m/e=273.0 (M+1).

N-(2,5-Di-4-morpholinylphenyl)-6-fluoro-2-(5-fluoro-3-pyridinyl)-3-methyl-4-quinolinamine

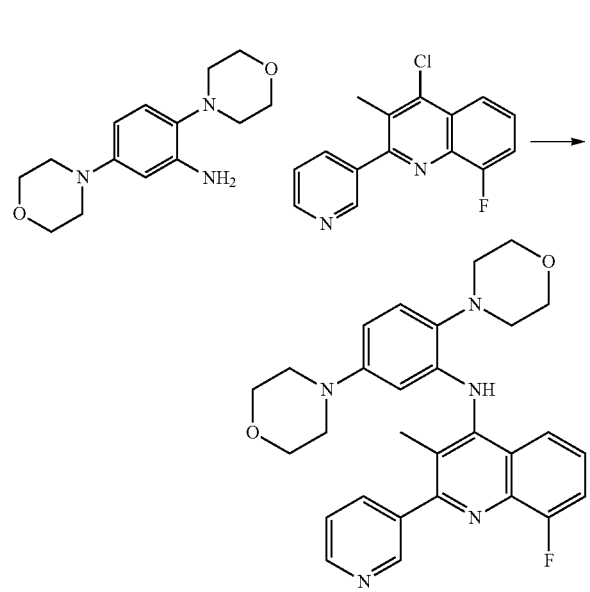

Prepared according to general Procedure K using 4-chloro-8-fluoro-3-methyl-2-(pyridin-3-yl)quinoline (100 mg, 0.37 mmol), 2,5-dimorpholinoaniline (97 mg, 0.37 mmol) and a 4.0M solution of HCl in dioxane (0.09 mL, 0.37 mmol) in MeOH (1.0 mL) and heating in the microwave for 2 h at 150° C. After purification N-(2,5-di-4-morpholinylphenyl)-6-fluoro-2-(5-fluoro-3-pyridinyl)-3-methyl-4-quinolinamine was obtained. ¹H NMR (400 MHz, chloroform-d) δ ppm 8.90 (1H, d, J=2.3 Hz), 8.71 (1H, dd, J=4.9, 1.8 Hz), 8.03 (1H, dt, J=7.8, 2.2 Hz), 7.65-7.75 (1H, m), 7.48 (1H, dd, J=8.0, 4.9 Hz), 7.36-7.45 (2H, m), 7.12 (1H, d, J=8.6 Hz), 6.47 (1H, dd, J=8.6, 2.7 Hz), 6.00 (1H, d, J=2.7 Hz), 3.86-3.99 (4H, m), 3.64-3.80 (4H, m), 3.01-3.13 (4H, m), 2.86-2.99 (4H, m), 2.34 (3H, s). Mass Spectrum (ESI) m/e=500.2 (M+1).

Example 12

N-(2,5-Di-4-morpholinylphenyl)-6-fluoro-3-methyl-2-(2-pyridinyl)-4-quinolinamine 4-Chloro-6-fluoro-3-methyl-2-(pyridin-2-yl)quinoline

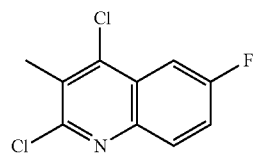

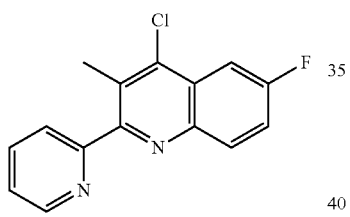

Prepared according to general Procedure E using 2,4-dichloro-6-fluoro-3-methylquinoline (250 mg, 1.1 mmol), 2-(tributylstannyl)pyridine (400 mg, 1.1 mmol), tetrakis(triphenylphosphine)palladium(0) (63 mg, 0.05 mmol) in toluene (5 mL) and heating at 110° C. overnight. After purification 4-chloro-6-fluoro-3-methyl-2-(pyridin-2-yl)quinoline was obtained as a white solid.

N-(2,5-di-4-morpholinylphenyl)-6-fluoro-3-methyl-2-(2-pyridinyl)-4-quinolinamine

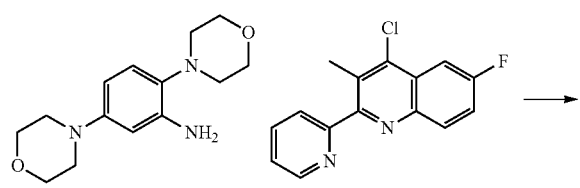

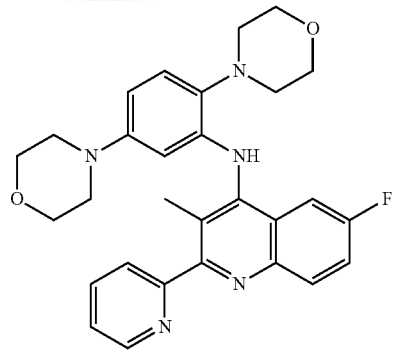

Prepared according to general Procedure K using 4-chloro-6-fluoro-3-methyl-2-(pyridin-2-yl)quinoline (100 mg, 0.37 mmol), 2,5-dimorpholinoaniline (97 mg, 0.37 mmol) and a 4.0M solution of HCl in dioxane (0.09 mL, 0.37 mmol) in MeOH (1.0 mL) and heating in the microwave for 2 h at 150° C. After purification N-(2,5-di-4-morpholinylphenyl)-6-fluoro-3-methyl-2-(2-pyridinyl)-4-quinolinamine was obtained. ¹H NMR (500 MHz, chloroform-d) δ ppm 8.67-8.81 (1H, m), 8.19 (1H, dd, J=9.0, 5.4 Hz), 7.83-7.94 (2H, m), 7.42-7.52 (2H, m), 7.39 (1H, ddd, J=7.3, 4.8, 1.6 Hz), 7.17 (1H, s), 7.12 (1H, d, J=8.6 Hz), 6.45 (1H, dd, J=8.7, 2.8 Hz), 5.99 (1H, d, J=2.7 Hz), 3.84-3.98 (4H, m), 3.65-3.79 (4H, m), 3.06 (4H, dd, J=3.4, 2.0 Hz), 2.83-2.95 (4H, m), 2.39 (3H, s). Mass Spectrum (ESI) m/e=500.2 (M+1).

Example 13

N-(2,5-Di-4-morpholinyl-3-pyridinyl)-7-fluoro-2-(2-fluorophenyl)-3-methyl-4-quinolinamine

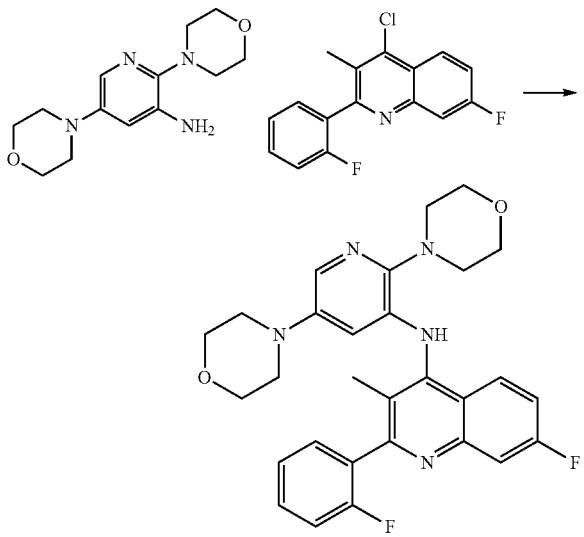

Prepared according to general Procedure K using 4-chloro-7-fluoro-2-(2-fluorophenyl)-3-methylquinoline (100 mg, 0.34 mmol), 2,5-dimorpholinopyridin-3-amine (91 mg, 0.34 mmol) and a 4.0M solution of HCl in dioxane (0.017 mL, 0.069 mmol) in MeOH (1.0 mL) and heating in the microwave for 2 h at 150° C. After purification N-(2,5-di-4-morpholinyl-3-pyridinyl)-7-fluoro-2-(2-fluorophenyl)-3-methyl-4-quinolinamine was obtained as a yellow film. ¹H NMR (500 MHz, chloroform-d) δ ppm δ ppm 7.85 (1H, br. s.), 7.81 (1H, dd, J=9.9, 2.6 Hz), 7.58-7.65 (2H, m), 7.44-7.51 (1H, m), 7.30-7.37 (2H, m), 7.20 (1H, t, J=9.2 Hz), 6.85 (1H, br. s.), 6.27 (1H, br. s.), 3.94 (4H, t, J=4.6 Hz), 3.71-3.80 (4H, m), 3.22 (4H, br. s.), 2.98 (4H, br. s.), 2.18 (3H, s). Mass Spectrum (ESI) m/e=518.2 (M+1).

Example 14

N-(2,5-Di-4-morpholinyl-3-pyridinyl)-5-fluoro-3-methyl-2-(3-pyridinyl)-4-quinolinamine

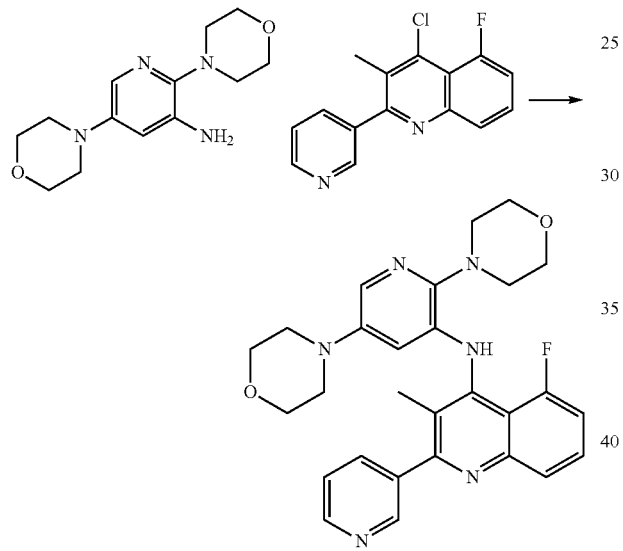

Prepared according to general Procedure K using 4-chloro-5-fluoro-3-methyl-2-(pyridin-3-yl)quinoline (83 mg, 0.30 mmol), 2,5-dimorpholinopyridin-3-amine (80 mg, 0.30 mmol) and a 4.0M solution of HCl in dioxane (0.015 mL, 0.061 mmol) in MeOH (1.0 mL) and heating in the microwave for 2 h at 150° C. After purification N-(2,5-di-4-morpholinyl-3-pyridinyl)-5-fluoro-3-methyl-2-(3-pyridinyl)-4-quinolinamine was obtained as a yellow film. ¹H NMR (400 MHz, chloroform-d) δ ppm 8.87 (1H, d, J=2.3 Hz), 8.73 (1H, dd, J=4.9, 1.8 Hz), 7.93-8.03 (2H, m), 7.84 (1H, d, J=12.1 Hz), 7.66 (1H, d, J=2.7 Hz), 7.59-7.64 (1H, m), 7.49 (1H, dd, J=7.8, 5.1 Hz), 7.16-7.24 (1H, m), 6.37 (1H, d, J=2.7 Hz), 3.87-3.98 (4H, m), 3.75-3.86 (4H, m), 3.22 (4H, br. s.), 2.95-3.07 (4H, m), 2.19 (3H, s). Mass Spectrum (ESI) m/e=501.2 (M+1).

Example 15

2-(7-Fluoro-2-(2-fluorophenyl)-3-methylquinolin-4-ylamino)-4-morpholinobenzonitrile 4-Morpholino-2-nitrobenzonitrile

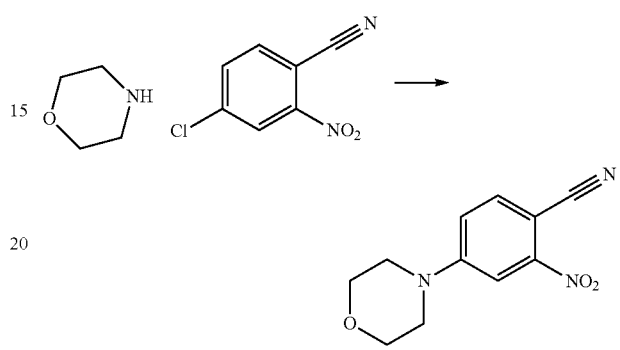

To a stirred solution of 4-chloro-2-nitrobenzonitrile (2.0 g, 11 mmol) in THF (40 mL) was added morpholine (1.0 g, 11 mmol). The reaction was heated at reflux overnight. After this time the reaction was cooled to rt and then it was partitioned between EtOAc (150 mL) and NaHCO₃ (50 mL, satd aq. solution). The separated organic layer was dried over magnesium sulfate, filtered and evaporated in vacuo. Column chromatography (hexanes:EtOAc, 1:0 to 1:1) gave 4-morpholino-2-nitrobenzonitrile.

2-Amino-4-morpholinobenzonitrile

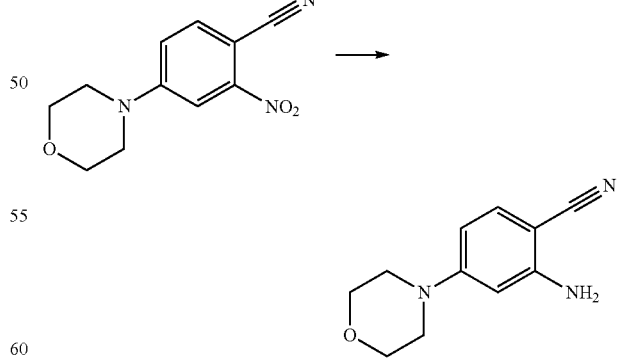

A solution of 4-morpholino-2-nitrobenzonitrile (300 mg, 0.24 mmol) in MeOH (140 mL) was reduced using a continuos flow hydrogenation reactor (flow rate: 1 mL/min, 10% mol Pd/C, temperature 40° C., H₂ pressure: 10 atm) to give 2-amino-4-morpholinobenzonitrile.

2-((7-Fluoro-2-(2-fluorophenyl)-3-methyl-4-quinolinyl)amino)-4-(4-morpholinyl)benzonitrile


Prepared according to general Procedure K using 4-chloro-7-fluoro-2-(2-fluorophenyl)-3-methylquinoline (70 mg, 0.24 mmol), 2-amino-4-morpholinobenzonitrile (49 mg, 0.24 mmol) and a 4.0M solution of HCl in dioxane (0.030 mL, 0.121 mmol) in MeOH (1.0 mL) and heating in the microwave for 2 h at 150° C. After purification 2-((7-fluoro-2-(2-fluorophenyl)-3-methyl-4-quinolinyl)amino)-4-(4-morpholinyl)benzonitrile was obtained as a yellow film. $^1$H NMR (500 MHz, chloroform-d) δ ppm 7.94-8.03 (1H, m), 7.82 (1H, dd, J=9.8, 2.7 Hz), 7.60-7.66 (1H, m), 7.43-7.52 (2H, m), 7.32-7.40 (2H, m), 7.13-7.22 (1H, m), 6.56 (1H, br. s.), 6.41 (1H, dd, J=8.8, 2.2 Hz), 5.81 (1H, d, J=2.7 Hz), 3.68-3.77 (4H, m), 2.98-3.15 (4H, m), 2.12-2.26 (3H, s). Mass Spectrum (ESI) m/e=457.0 (M+1).

Example 16

2-((7-Fluoro-3-methyl-2-(3-pyridinyl)-4-quinolinyl)amino)-4-(4-morpholinyl)benzonitrile

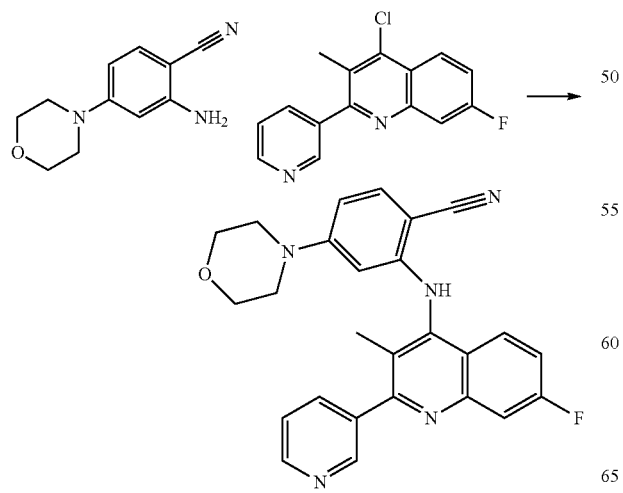

Prepared according to general Procedure K using 4-chloro-7-fluoro-3-methyl-2-(pyridin-3-yl)quinoline (150 mg, 0.55 mmol), 2-amino-4-morpholinobenzonitrile (112 mg, 0.55 mmol) and a 4.0M solution of HCl in dioxane (0.028 mL, 0.11 mmol) in NMP (1.0 mL) and heating in the microwave for 2 h at 150° C. After purification 2-((7-fluoro-3-methyl-2-(3-pyridinyl)-4-quinolinyl)amino)-4-(4-morpholinyl)benzonitrile was obtained as a yellow film. $^1$H NMR (500 MHz, chloroform-d) δ ppm 8.87 (1H, dd, J=2.0, 0.5 Hz), 8.73 (1H, dd, J=4.9, 1.7 Hz), 7.99 (1H, dt, J=7.8, 2.0 Hz), 7.92 (1H, dd, J=9.3, 5.9 Hz), 7.80 (1H, dd, J=9.8, 2.4 Hz), 7.44-7.51 (2H, m), 7.33 (1H, ddd, J=9.2, 8.0, 2.6 Hz), 6.46 (1H, s), 6.43 (1H, dd, J=8.9, 2.3 Hz), 5.72 (1H, d, J=2.2 Hz), 3.63-3.76 (4H, m), 2.95-3.09 (4H, m), 2.35 (3H, s). Mass Spectrum (ESI) m/e=440.0 (M+1).

Example 17

N-(2,5-Di-4-morpholinyl-3-pyridinyl)-7-fluoro-3-methyl-2-(3-pyridinyl)-4-quinolinamine

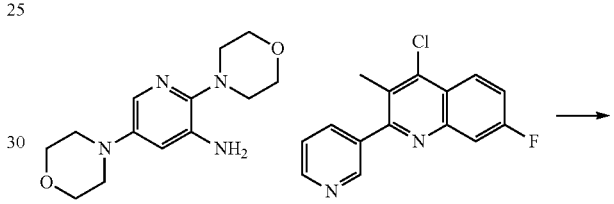

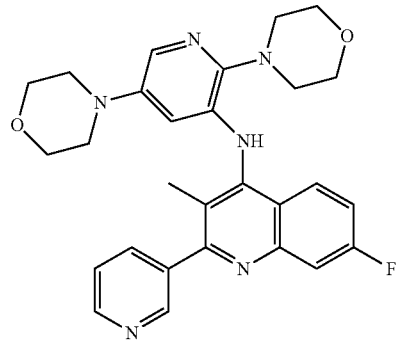

Prepared according to general Procedure K using 4-chloro-7-fluoro-3-methyl-2-(pyridin-3-yl)quinoline (95 mg, 0.35 mmol), 2,5-dimorpholinopyridin-3-amine (92 mg, 0.35 mmol) and a 4.0M solution of HCl in dioxane (0.017 mL, 0.07 mmol) in NMP (1.0 mL) and heating in the microwave for 2 h at 150° C. After purification N-(2,5-di-4-morpholinyl-3- pyridinyl)-7-fluoro-3-methyl-2-(3-pyridinyl)-4-quinolinamine was obtained. ¹H NMR (400 MHz, chloroform-d) δ ppm 8.87 (1H, d, J=2.7 Hz), 8.73 (1H, dd, J=5.1, 2.0 Hz), 7.99 (1H, dt, J=7.8, 2.0 Hz), 7.74-7.89 (2H, m), 7.62 (1H, d, J=2.7 Hz), 7.49 (1H, dd, J=8.0, 4.9 Hz), 7.31 (1H, ddd, J=9.3, 7.9, 2.7 Hz), 6.80 (1H, s), 6.21 (1H, d, J=2.7 Hz), 3.89-3.99 (4H, m), 3.75 (4H, ddd, J=4.3, 2.7, 2.3 Hz), 3.23 (4H, t, J=4.9 Hz), 2.87-3.01 (4H, m), 2.31 (3H, s). Mass Spectrum (ESI) m/e=501.2 (M+1).

Example 18

2-(2-Fluorophenyl)-3-methyl-N-(2-(4-morpholinyl)-5-(3-pyridinyl)phenyl)-4-quinolinamine

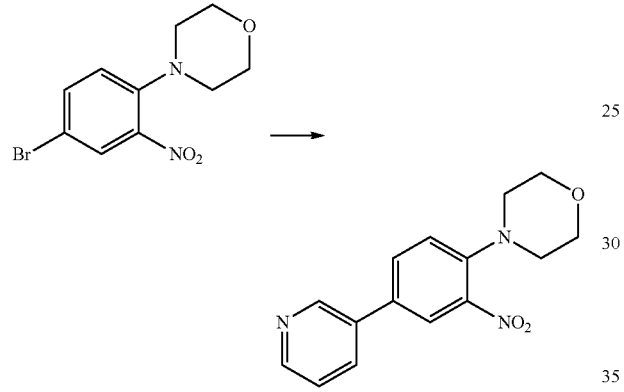

Prepared according to general Procedure F using 4-(4-bromo-2-nitrophenyl)-morpholine (1.0 g, 3.48 mmol), 3-pyridylboronic acid (428 mg, 3.48 mmol), tetrakis(triphenylphosphine)palladium(0) (402 mg, 0.35 mmol), and sodium carbonate (646 mg, 6.1 mmol) in toluene:water (20 mL:4 mL) and heating at reflux for 12 h. After purification 4-(2-nitro-4-(pyridin-3-yl)phenyl)morpholine was obtained.

2-Morpholino-5-(pyridin-3-yl)aniline

A solution of 4-(2-nitro-4-(pyridin-3-yl)phenyl)morpholine (300 mg, 0.24 mmol) in MeOH (140 mL) was reduced using a continuous flow hydrogenation reactor (flow rate: 1 mL/min, 10% mol Pd/C, temperature 40° C., H₂ pressure: 10 bar) to give 2-morpholino-5-(pyridin-3-yl)aniline.

2-(2-Fluorophenyl)-3-methyl-N-(2-(4-morpholinyl)-5-(3-pyridinyl)phenyl)-4-quinolinamine

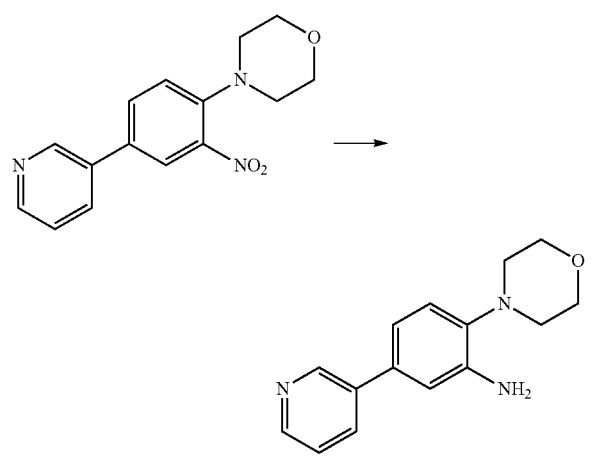

Prepared according to general Procedure K using 4-chloro-2-(2-fluorophenyl)-3-methylquinoline (64 mg, 0.23 mmol), 2-morpholino-5-(pyridin-3-yl)aniline (60 mg, 0.23 mmol) and a 4.0M solution of HCl in dioxane (0.06 mL, 0.23 mmol) in NMP (1.0 mL) and heating in the microwave for 2 h at 150° C. After purification 2-(2-fluorophenyl)-3-methyl-N-(2-(4-morpholinyl)-5-(3-pyridinyl)phenyl)-4-quinolinamine was obtained. ¹H NMR (400 MHz, chloroform-d) δ ppm 8.49 (1H, dd, J=4.7, 1.6 Hz), 8.19 (1H, d, J=8.2 Hz), 7.92 (1H, d, J=8.2 Hz), 7.59-7.76 (4H, m), 7.54 (1H, d, J=7.4 Hz), 7.47 (1H, d, J=8.2 Hz), 7.31-7.36 (1H, m), 7.10-7.24 (4H, m), 6.65 (1H, br. s.), 3.97 (4H, t, J=4.7 Hz), 3.09-3.30 (4H, m), 2.26 (3H, d, J=2.3 Hz). Mass Spectrum (ESI) m/e=491.0 (M+1).

Example 19

N-(5-(2-Amino-6-methyl-4-pyrimidinyl)-2-(4-morpholinyl)-phenyl)-2-(2-fluorophenyl)-3-methyl-4-quinolinamine

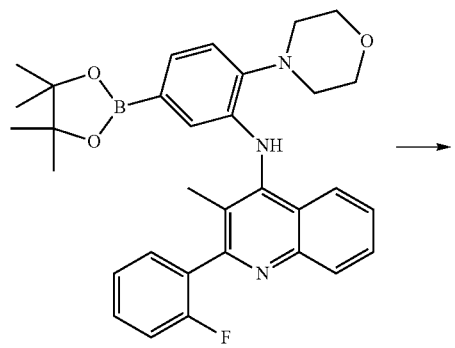

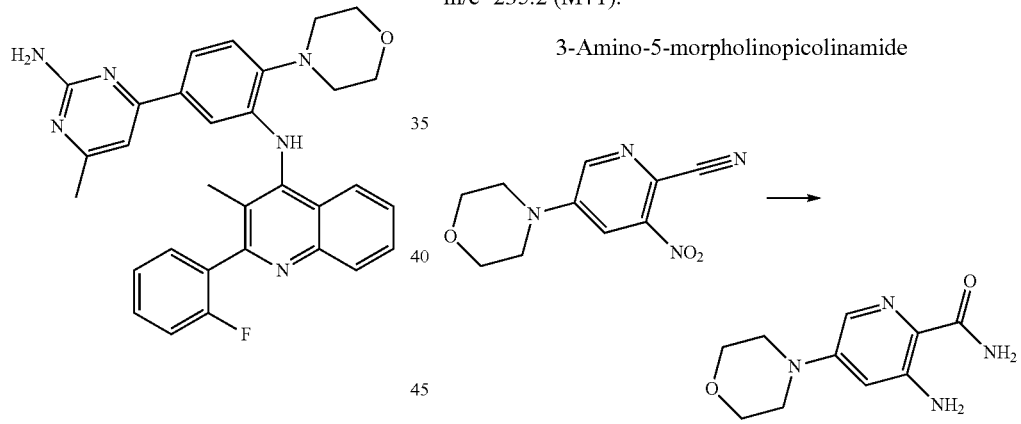

A solution of 2-(2-fluorophenyl)-3-methyl-N-(2-morpholino-5-(4,4,5,5-tetramethyl-1,3,2-dioxaborolan-2-yl)phenyl)quinolin-4-amine (100 mg, 0.185 mmol; described herein), 4-chloro-6-methylpyrimidin-2-amine (26.6 mg, 0.185 mmol), sodium carbonate (58.9 mg, 0.556 mmol), dichlorobis(triphenylphosphine)-palladium(ii) (13.0 mg, 0.019 mmol), 1,4-dioxane (4.0 mL), and water (1.0 mL) was heated in a microwave at 120° C. for 60 min. The mixture was then cooled to rt and partitioned between EtOAc and water. The organic layer was dried (magnesium sulfate) and concd, and chromatography afforded N-(5-(2-amino-6-methyl-4-pyrimidinyl)-2-(4-morpholinyl)phenyl)-2-(2-fluorophenyl)-3-methyl-4-quinolinamine. $^1$H NMR (400 MHz, TFA) δ ppm 8.32 (1H, dd, J=8.8, 2.2 Hz), 7.95-8.17 (5H, m), 7.72 (2H, m), 7.55 (1H, m), 7.40-7.48 (1H, m), 7.24-7.37 (2H, m), 4.30-4.47 (4H, m), 4.07-4.25 (4H, m), 2.60 (3H, s), 2.09 (3H, br. s.). Mass Spectrum (ESI) m/e=521.1 (M+1).

Example 20

3-((7-Fluoro-3-methyl-2-(2-pyridinyl)-4-quinolinyl)amino)-5-(4-morpholinyl)-2-pyridinecarbonitrile 5-Morpholino-3-nitropicolinonitrile

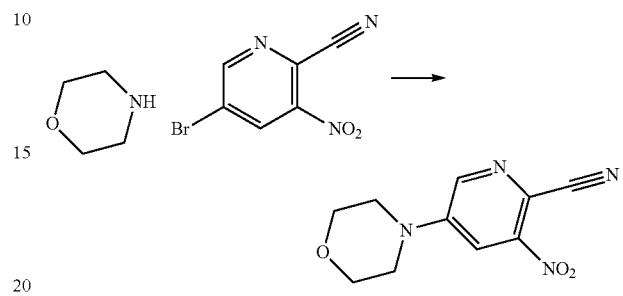

To a stirred solution of 5-bromo-3-nitropicolinonitrile (5.0 g, 22 mmol) in DMSO (30 mL) was added morpholine (3.8 mL, 44 mmol). The reaction was stirred at rt for 2 h. After this time the reaction was diluted with EtOAc (300 mL) and water (100 mL). The separated organic layer was dried over magnesium sulfate, filtered and evaporated in vacuo. The resulting solid was washed with MeOH (15 mL) to give 5-morpholino-3-nitropicolinonitrile. Mass Spectrum (ESI) m/e=235.2 (M+1).

3-Amino-5-morpholinopicolinamide

To a stirred solution of 5-morpholino-3-nitropicolinonitrile (100 mg, 0.43 mmol) in EtOAc (5 mL) was added stannous chloride, dihydrate (0.41 g, 2.13 mmol). The reaction was heated at reflux for 15 min. After this time a white solid precipitates. The suspension was filtered and the resulting solid was washed with 1.0M NaOH (10 mL) and brine (10 mL) and dried under vacuum to give 3-amino-5-morpholinopicolinamide. Mass Spectrum (ESI) m/e=223.2 (M+1).

3-Amino-5-morpholinopicolinonitrile

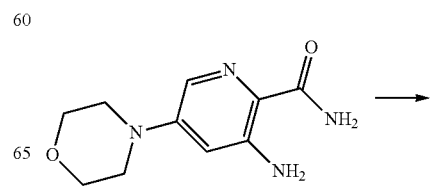

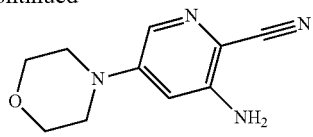

A stirred solution of 3-amino-5-morpholinopicolinamide (0.35 g, 1.57 mmol) in acetonitrile (10 mL) was treated with phosphorus oxychloride (0.29 mL, 3.15 mmol). The reaction was heated at reflux for 1 h. After this time the reaction was cooled to rt and evaporated in vacuo. The residue was dissolved in Et$_2$O (10 mL) and treated with 4.0M HCl in dioxane (0.2 mL). The resulting solid was filtered and dried under vacuum to give 3-amino-5-morpholinopicolinonitrile. Mass Spectrum (ESI) m/e=205.2 (M+1).

3-((7-Fluoro-3-methyl-2-(2-pyridinyl)-4-quinolinyl)amino)-5-(4-morpholinyl)-2-pyridinecarbonitrile

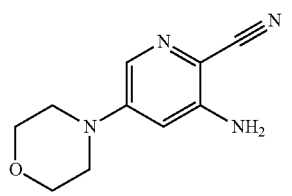

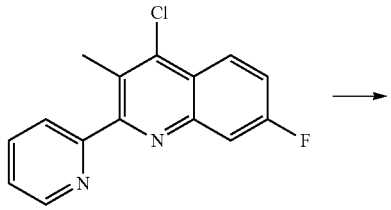

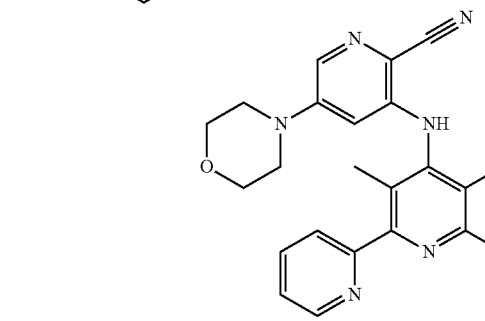

Prepared according to general Procedure K using 4-chloro-7-fluoro-3-methyl-2-(pyridin-2-yl)quinoline (93 mg, 0.34 mmol), 3-amino-5-morpholinopicolinonitrile (70 mg, 0.34 mmol) and a 4.0M solution of HCl in dioxane (0.08 mL, 0.34 mmol) in NMP (1.0 mL) and heating in the microwave for 2 h at 150° C. After purification 3-((7-fluoro-3-methyl-2-(2-pyridinyl)-4-quinolinyl)amino)-5-(4-morpholinyl)-2-pyridinecarbonitrile was obtained. $^1$H NMR (400 MHz, chloroform-d) δ ppm 8.74 (1H, dt, J=3.1, 1.6 Hz), 7.76-8.00 (5H, m), 7.31-7.49 (2H, m), 6.46 (1H, s), 5.92 (1H, d, J=2.3 Hz), 3.68-3.84 (4H, m), 3.00-3.19 (4H, m), 2.42 (3H, s). Mass Spectrum (ESI) m/e=441.0 (M+1).

Example 21

3-((5-Fluoro-3-methyl-2-(2-pyridinyl)-4-quinolinyl)amino)-5-(4-morpholinyl)-2-pyridinecarbonitrile

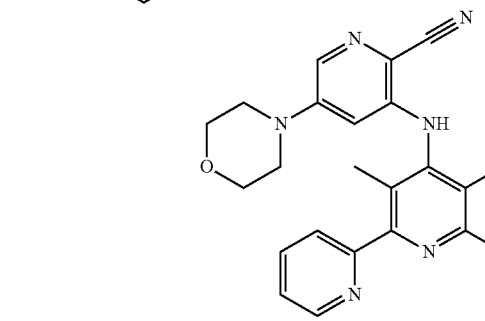

Prepared according to general Procedure K using 4-chloro-5-fluoro-3-methyl-2-(pyridin-2-yl)quinoline (93 mg, 0.34 mmol), 3-amino-5-morpholinopicolinonitrile (70 mg, 0.34 mmol) and a 4.0M solution of HCl in dioxane (0.08 mL, 0.34 mmol) in NMP (1.0 mL) and heating in the microwave for 2 h at 150° C. After purification 3-((5-fluoro-3-methyl-2-(2-pyridinyl)-4-quinolinyl)amino)-5-(4-morpholinyl)-2-pyridinecarbonitrile was obtained. $^1$H NMR (400 MHz, chloroform-d) δ ppm 8.68 (1H, dt, J=3.1, 1.6 Hz), 8.00 (1H, d, J=8.6 Hz), 7.87-7.97 (3H, m), 7.64 (1H, td, J=8.2, 5.5 Hz), 7.39 (1H, ddd, J=7.0, 4.9, 1.8 Hz), 7.17-7.32 (2H, m), 6.23 (1H, d, J=2.3 Hz), 3.75-3.86 (4H, m), 3.17-3.31 (4H, m), 2.29 (3H, s). Mass Spectrum (ESI) m/e=441.1 (M+1).

Example 22

7-Fluoro-3-methyl-N-(2-(4-morpholinyl)-5-(4-thiomorpholinyl)-3-pyridinyl)-2-(2-pyridinyl)-4-quinolinamine 4-(3-Nitro-5-thiomorpholinopyridin-2-yl)morpholine

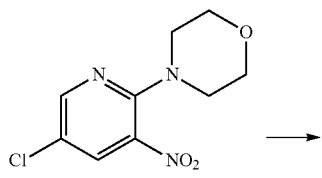

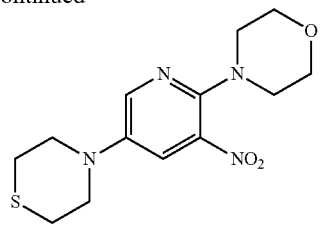

A stirred solution of 4-(5-chloro-3-nitropyridin-2-yl)morpholine (400 mg, 1.64 mmol) in toluene (15.7 mL, 147.7 mmol) was treated with Pd₂dba₃ (75 mg, 0.082 mmol), X-Phos (78 mg, 0.16 mmol), potassium tert butoxide (368 mg, 3.28 mmol) and thiomorpholine (203 mg, 1.97 mmol). The reaction was heated at 115° C. overnight. After this time the reaction was cooled to rt and diluted with EtOAc (100 mL) and water (50 mL). The separated organic layer was washed with NaHCO₃ (satd aq. solution, 40 mL), brine (40 mL) and then dried over magnesium sulfate, filtered and evaporated in vacuo. Column chromatography (hexanes:EtOAc, 1:0 to 1:2) gave 4-(3-nitro-5-thiomorpholinopyridin-2-yl)morpholine as a red oil. Mass Spectrum (ESI) m/e=311.2 (M+1).

2-Morpholino-5-thiomorpholinopyridin-3-amine

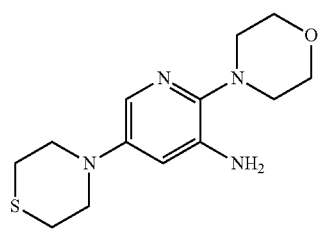

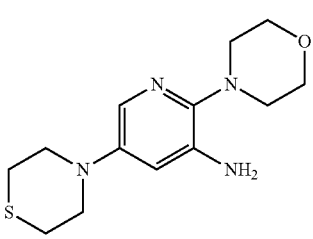

A solution of 4-(3-nitro-5-thiomorpholinopyridin-2-yl)morpholine (140 mg, 0.45 mmol) in MeOH (100 mL) was reduced using a continuous flow hydrogenation reactor (flow rate: 1 mL/min, 10% mol Pd/C, temperature 35° C., H₂ pressure: 10 bar) to give 2-morpholino-5-thiomorpholinopyridin-3-amine.

7-Fluoro-3-methyl-N-(2-(4-morpholinyl)-5-(4-thiomorpholinyl)-3-pyridinyl)-2-(2-pyridinyl)-4-quinolinamine

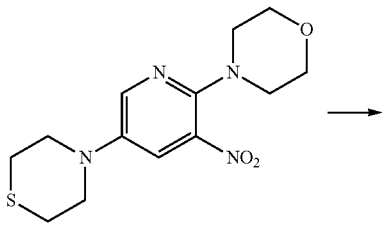

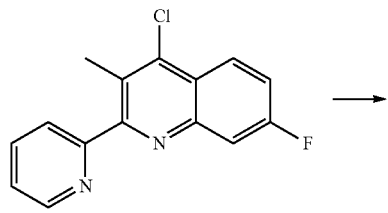

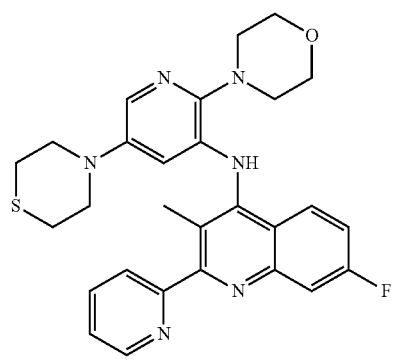

Prepared according to general Procedure K using 4-chloro-7-fluoro-3-methyl-2-(pyridin-2-yl)quinoline (117 mg, 0.43 mmol), 2-morpholino-5-thiomorpholinopyridin-3-amine (120 mg, 0.43 mmol) and a 4.0M solution of HCl in dioxane (0.11 mL, 0.43 mmol) in NMP (1.0 mL) and heating in the microwave for 2 h at 150° C. After purification 7-fluoro-3-methyl-N-(2-(4-morpholinyl)-5-(4-thiomorpholinyl)-3-pyridinyl)-2-(2-pyridinyl)-4-quinolinamine was obtained. $^1$H NMR (400 MHz, chloroform-d) δ ppm 8.74 (1H, dd, J=4.1, 1.0 Hz), 7.85-7.96 (2H, m), 7.75-7.84 (2H, m), 7.58 (1H, d, J=2.7 Hz), 7.40 (1H, ddd, J=7.0, 4.9, 1.8 Hz), 7.28-7.32 (1H, m), 6.74 (1H, s), 6.19 (1H, d, J=2.7 Hz), 3.93 (4H, t, J=4.7 Hz), 3.31 (4H, ddd, J=4.9, 2.7, 2.5 Hz), 3.23 (4H, br. s.), 2.63 (4H, dt, J=5.1, 2.5 Hz), 2.38 (3H, s). Mass Spectrum (ESI) m/e=517.0 (M+1).

Example 23

N-(5-(1,1-Dioxido-4-thiomorpholinyl)-2-(4-morpholinyl)-3-pyridinyl)-7-fluoro-3-methyl-2-(2-pyridinyl)-4-quinolinamine

4-[5-(1,1-Dioxidothiomorpholin-4-yl)-3-nitropyridin-2-yl]morpholine

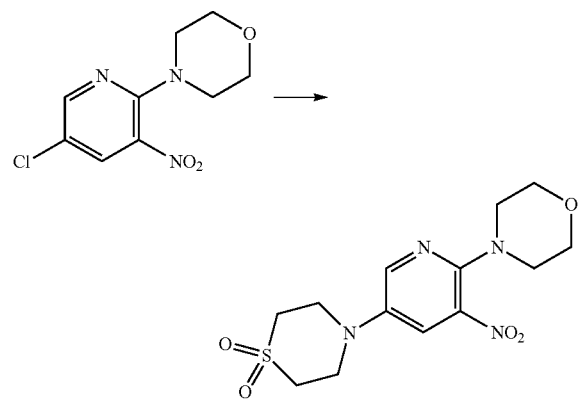

A stirred solution of 4-(5-chloro-3-nitropyridin-2-yl)morpholine (500 mg, 2.05 mmol), thiomorpholine 1,1-dioxide (333 mg, 2.46 mmol), $Pd_2dba_3$ (94 mg, 0.10 mmol), X-Phos (98 mg, 0.20 mmol), sodium tert-butoxide (394 mg, 4.1 mmol) in toluene (19.7 mL, 184.7 mmol) was heated at reflux for 14 h. After this time the reaction was cooled to rt and partitioned between EtOAc (100 mL) and $NaHCO_3$ (satd aq. solution, 50 mL). The separated organic layer was washed with brine (50 mL), dried over magnesium sulfate, filtered and evaporated in vacuo. Column chromatography (hexanes: EtOAc, 1:0 to 1:1) gave 4-[5-(1,1-dioxidothiomorpholin-4-yl)-3-nitropyridin-2-yl]morpholine.

5-(1,1-Dioxidothiomorpholin-4-yl)-2-morpholin-4-ylpyridin-3-amine

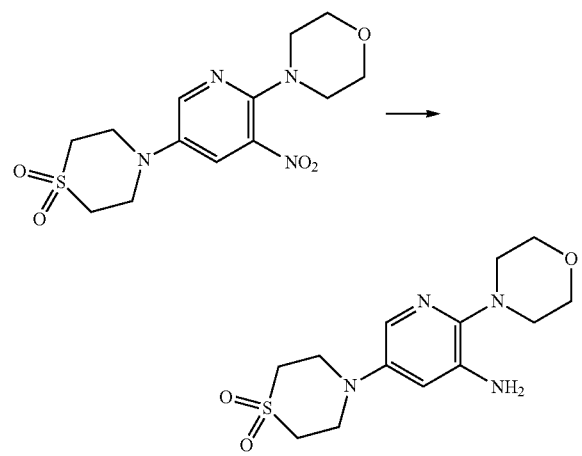

A solution of 4-[5-(1,1-dioxidothiomorpholin-4-yl)-3-nitropyridin-2-yl]morpholine (180 mg, 0.53 mmol) in MeOH (100 mL) was reduced using a continuous flow hydrogenation reactor (flow rate: 1 mL/min, 10% mol Pd/C, temperature 35° C., $H_2$ pressure: 20 bar) to give 5-(1,1-dioxidothiomorpholin-4-yl)-2-morpholin-4-ylpyridin-3-amine.

N-(5-(1,1-Dioxido-4-thiomorpholinyl)-2-(4-morpholinyl)-3-pyridinyl)-7-fluoro-3-methyl-2-(2-pyridinyl)-4-quinolinamine

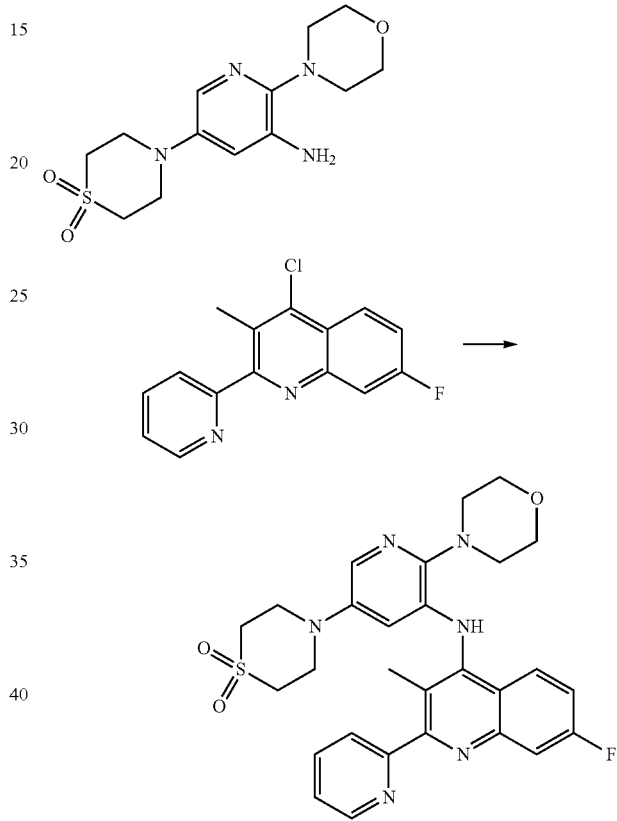

Prepared according to general Procedure K using 4-chloro-7-fluoro-3-methyl-2-(pyridin-2-yl)quinoline (61 mg, 0.22 mmol), 5-(1,1-dioxidothiomorpholin-4-yl)-2-morpholin-4-ylpyridin-3-amine (70 mg, 0.22 mmol) and a 4.0M solution of HCl in dioxane (0.05 mL, 0.22 mmol) in NMP (1.0 mL) and heating in the microwave for 2 h at 150° C. After purification N-(5-(1,1-dioxido-4-thiomorpholinyl)-2-(4-morpholinyl)-3-pyridinyl)-7-fluoro-3-methyl-2-(2-pyridinyl)-4-quinolinamine was obtained. $^1$H NMR (400 MHz, chloroform-d) δ ppm 8.74 (1H, dd, J=3.5, 1.2 Hz), 7.87-7.99 (2H, m), 7.75-7.85 (2H, m), 7.61 (1H, d, J=2.7 Hz), 7.41 (1H, d, J=1.6 Hz), 7.32 (1H, s), 6.76 (1H, s), 6.22 (1H, d, J=2.7 Hz), 3.94 (4H, t, J=4.7 Hz), 3.53-3.67 (4H, m), 3.25 (4H, br. s.), 2.90-3.11 (4H, m), 2.37 (3H, s). Mass Spectrum (ESI) m/e=549.3 (M+1).

Example 24

4-Bromo-2-((7-fluoro-3-methyl-2-(2-pyridinyl)-4-quinolinyl)-oxy)benzonitrile

7-Fluoro-3-methyl-2-(pyridin-2-yl)quinolin-4-ol

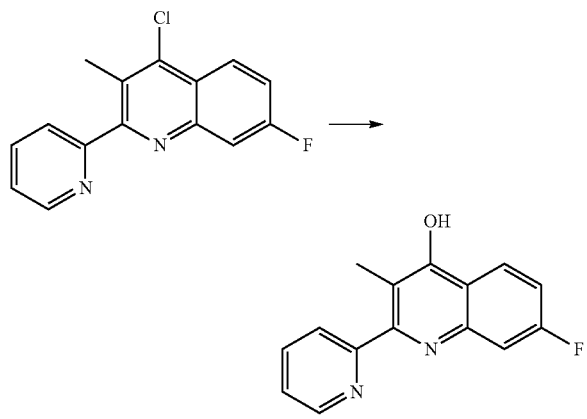

4-Chloro-7-fluoro-3-methyl-2-(pyridin-2-yl)quinoline (200 mg, 0.73 mmol) in NMP (2 mL) and water (0.26 mL, 14.7 mmol) was heated in the microwave at 150° C. for 4 h. After this EtOAc (10 mL) was added. The resulting precipitate was filtered to give 7-fluoro-3-methyl-2-(pyridin-2-yl)quinolin-4-ol. Mass Spectrum (ESI) m/e=255.2 (M+1).

4-Bromo-2-((7-fluoro-3-methyl-2-(2-pyridinyl)-4-quinolinyl)oxy)benzonitrile

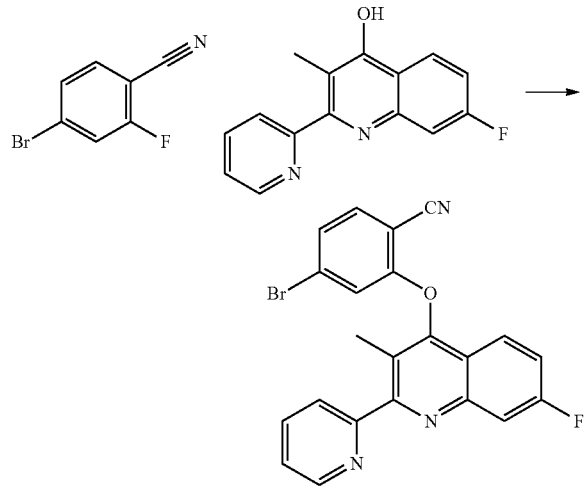

To a stirred solution of 7-fluoro-3-methyl-2-(pyridin-2-yl)quinolin-4-ol (130 mg, 0.51 mmol) in DMF (2.5 mL) was added sodium hydride (18.4 mg, 0.77 mmol). The reaction was stirred at rt for 20 min and then treated with 4-bromo-2-fluorobenzonitrile (102 mg, 0.51 mmol). The reaction was stirred at rt for 20 min and then at 110° C. for 12 h. After this time the reaction was cooled to rt and diluted with EtOAc (100 mL) and LiCl (1M aq. solution, 40 mL). The separated organic layer was dried over magnesium sulfate, filtered and evaporated in vacuo and the residue was purified by flash chromatography (hexanes:EtOAc, 1:0 to 2:1) to give 4-bromo-2-((7-fluoro-3-methyl-2-(2-pyridinyl)-4-quinolinyl)oxy)benzonitrile. $^1$H NMR (400 MHz, chloroform-d) δ ppm 8.75 (1H, d, J=5.1 Hz), 7.90-7.98 (2H, m), 7.77-7.89 (2H, m), 7.62 (1H, d, J=8.2 Hz), 7.29-7.45 (3H, m), 6.64 (1H, d, J=2.0 Hz), 2.41 (3H, s). Mass Spectrum (ESI) m/e=434.0 [(M+1) ($^{79}$Br)] and 435.8 [(M+1) ($^{81}$Br)].

Example 25

2-((7-Fluoro-3-methyl-2-(2-pyridinyl)-4-quinolinyl)oxy)-4-(4-morpholinyl)benzonitrile

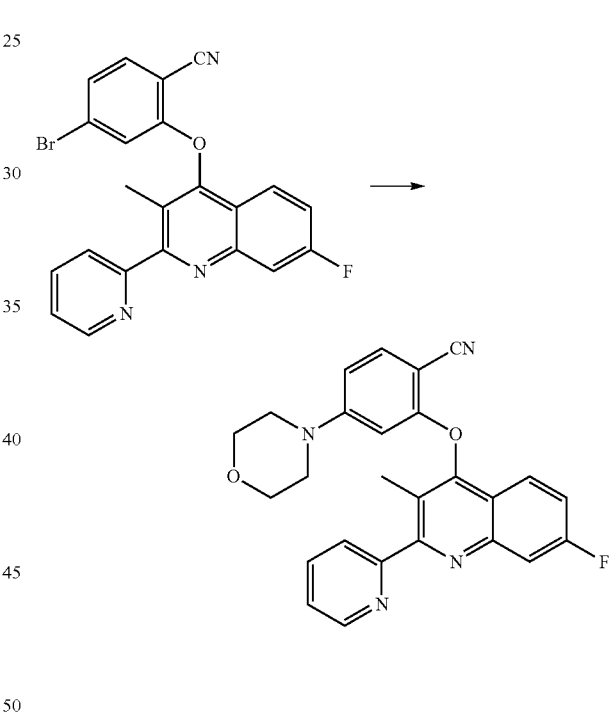

Prepared according to general Procedure H using 4-bromo-2-(7-fluoro-3-methyl-2-(pyridin-2-yl)quinolin-4-yloxy)benzonitrile (70 mg, 0.16 mmol), tris(dibenzylideneacetone)dipalladium(0) (7.4 mg, 0.008 mmol), X-Phos (7.7 mg, 0.016 mmol), morpholine (28 mg, 0.32 mmol) and sodium tert-butoxide (31 mg, 0.32 mmol) in toluene (6.9 mL) and heating at reflux for 2 h. After purification 2-((7-fluoro-3-methyl-2-(2-pyridinyl)-4-quinolinyl)oxy)-4-(4-morpholinyl)benzonitrile was obtained. $^1$H NMR (400 MHz, chloroform-d) δ ppm 8.68-8.78 (1H, m), 7.86-7.95 (3H, m), 7.82 (1H, dd, J=10.0, 2.5 Hz), 7.57 (1H, d, J=8.6 Hz), 7.41 (1H, ddd, J=6.7, 4.6, 2.3 Hz), 7.30-7.36 (1H, m), 6.56 (1H, dd, J=9.0, 2.3 Hz), 5.83 (1H, d, J=2.3 Hz), 3.69 (4H, dd, J=6.1, 3.7 Hz), 2.90-3.10 (4H, m), 2.30-2.46 (3H, s). Mass Spectrum (ESI) m/e=441.0 (M+1).

Example 26

N-(2,5-Di-4-morpholinylphenyl)-7-fluoro-2-(2-fluorophenyl)-3-methyl-4-quinolinamine

4-Chloro-7-fluoro-2-(2-fluorophenyl)-3-methylquinoline

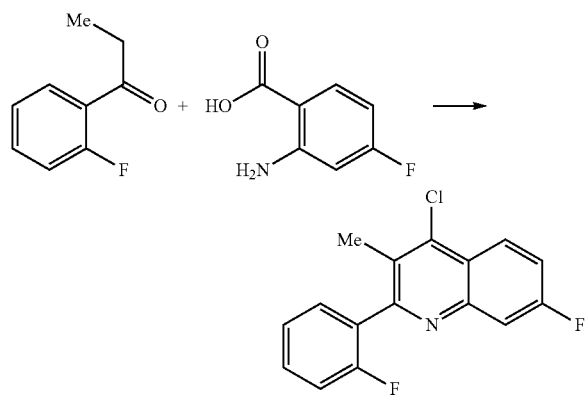

Prepared according to Procedure J using 2-amino-4-fluorobenzoic acid (4.90 g, 31.6 mmol) and 1-(2-fluorophenyl)propan-1-one (3.70 g, 24.3 mmol) in phosphorous oxychloride (45.00 mL, 483 mmol) to afford product as a white solid upon purification by chromatography on silica gel. Mass Spectrum (ESI) m/e=290.0 (M+1).

4-(4-Bromo-2-nitrophenyl)morpholine

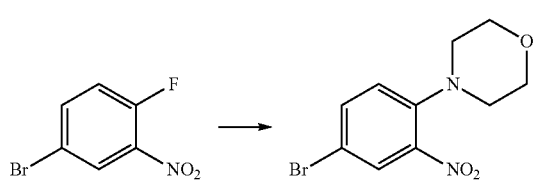 [SMILES: O=[N+]([O-])c1cc(Br)ccc1F ; O=[N+]([O-])c1cc(Br)ccc1N1CCOCC1]

To a solution of 4-bromo-1-fluoro-2-nitrobenzene (10.088 g, 45.9 mmol) in dimethyl sulfoxide (20.00 mL, 282 mmol) was added morpholine (6.00 mL, 68.8 mmol). A vigorous exotherm developed and the solution turned an intense orange-red. After 10 min LC-MS indicated no starting material remained and the desired product predominated. The reaction was poured into 200 mL satd aq. Sodium bicarbonate solution and the aq. Mixture was extracted with 200 mL Et$_2$O. The ether extract was washed with 100 mL water followed by 100 mL brine then stirred over anhydrous magnesium sulfate, filtered and the filtrate concd under reduced pressure to afford an orange oil. Mass Spectrum (ESI) m/e=287.0 & 289.0 (M+1).

5-Bromo-2-morpholinoaniline

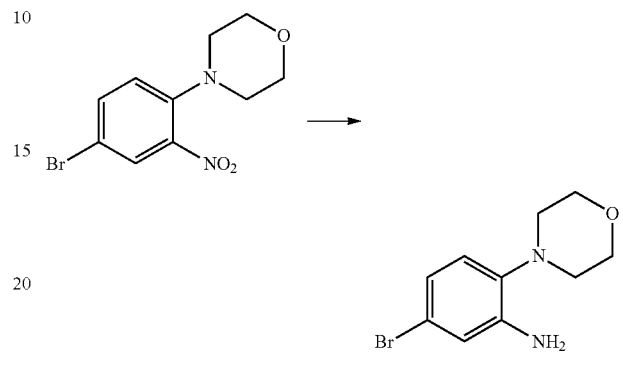

To a solution of 4-(4-bromo-2-nitrophenyl)morpholine (13.2 g, 46 mmol) dissolved in EtOAc (200.00 mL, 2043 mmol) at rt was added all in one portion tin(II) chloride dehydrate (52 g, 230 mmol). An exotherm developed and the orange color faded to a faint yellow. The reaction was stirred at ambient temperature for 15 min then heated to reflux for 45 min. After 60 min TLC indicated no starting material remained and the reaction was equilibrated to rt. The reaction was washed with 200 mL 5N aq. Sodium hydroxide solution followed by 100 mL water and 50 mL brine. The organic separation was stirred over anhydrous magnesium sulfate, filtered and the filtrate concd under reduced pressure to afford a pale yellow solid. Mass Spectrum (ESI) m/e=257.0 & 259.0 (M+1).

N-(5-Bromo-2-morpholinophenyl)-7-fluoro-2-(2-fluorophenyl)-3-methylquinolin-4-amine

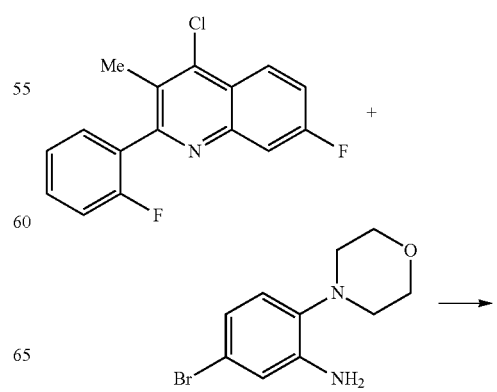

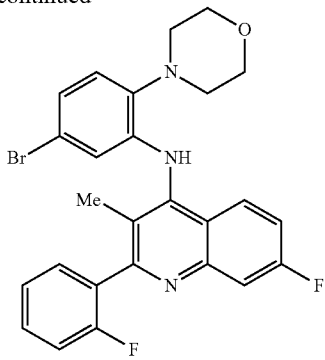

Prepared according to Procedure K, Method 1 using 4-chloro-7-fluoro-2-(2-fluorophenyl)-3-methylquinoline (118 mg, 407 μmol), 5-bromo-2-morpholinobenzenamine (105 mg, 407 μmol) and 4.0N hydrochloric acid (0.10 mL, 407 μmol) in 1,4-dioxane in MeOH (1.00 mL) to afford a yellow solid after purification by chromatography on silica gel, eluting with EtOAc-DCM-hexane solvent mixture. Mass Spectrum (ESI) m/e=510.0 & 512.0 (M+1).

N-(2,5-Di-4-morpholinylphenyl)-7-fluoro-2-(2-fluorophenyl)-3-methyl-4-quinolinamine

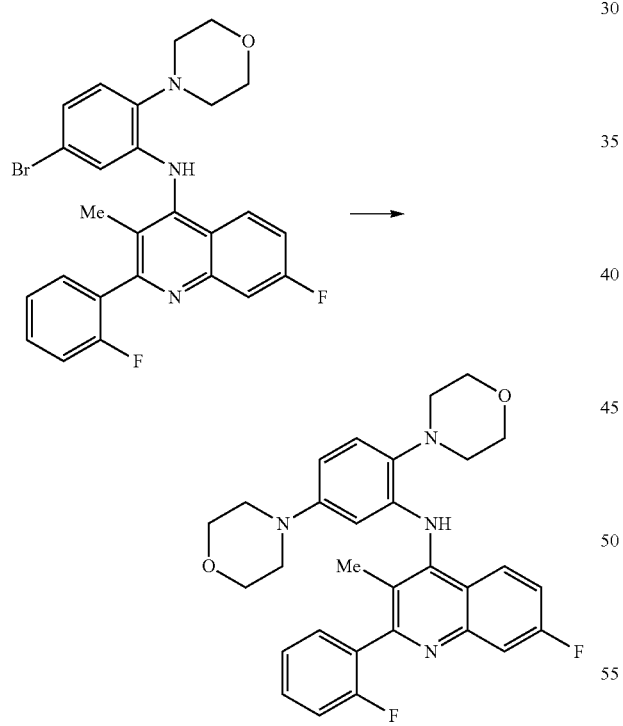

A mixture of N-(5-bromo-2-morpholinophenyl)-7-fluoro-2-(2-fluorophenyl)-3-methylquinolin-4-amine (50 mg, 98 μmol), morpholine (0.017 mL, 196 μmol), tris(dibenzylideneacetone)dipalladium(0) (6.3 mg, 6.9 μmol), X-Phos (7.0 mg, 15 μmol) and sodium tert-butoxide (19 mg, 196 μmol) in toluene (4.00 mL, 37552 μmol) was degassed by evacuation-back fill 3× then heated to reflux in an oil bath for 90 min, after which time LC-MS indicated only desired product predominated. The reaction was equilibrated to rt, concd under reduced pressure and the concentrate partitioned between 25 mL each DCM and water. The organic separation was stirred over anhydrous magnesium sulfate, filtered and the filtrate concd under reduced pressure to afford a yellow-brown solid. The product was isolated by reversed phase HPLC on Phenomenex™ C18 column, eluting with MeCN/water+0.1% TFA. $^1$H NMR (400 MHz, chloroform-d) δ ppm 7.83 (1H, dd, J=9.2, 6.1 Hz), 7.70 (1H, dd, J=10.0, 2.5 Hz), 7.52 (1H, td, J=7.4, 2.0 Hz), 7.33-7.45 (1H, m, J=7.9, 7.9, 5.4, 2.0 Hz), 7.15-7.30 (3H, m), 7.06-7.15 (1H, m), 7.03 (1H, d, J=8.6 Hz), 6.36 (1H, dd, J=8.6, 2.7 Hz), 5.96 (1H, d, J=2.0 Hz), 3.83 (4H, t, J=4.5 Hz), 3.58-3.75 (4H, m), 2.97 (4H, d, J=2.7 Hz), 2.75-2.92 (4H, m), 2.11 (3H, d, J=2.3 Hz). Mass Spectrum (ESI) m/e=517.2 (M+1).

Example 27

N-(2,5-Di-4-morpholinylphenyl)-7-fluoro-2-(2-fluorophenyl)-3-methyl-4-quinolinamine N-(5-Bromo-2-morpholinophenyl)-7-fluoro-3-methyl-2-(pyridin-2-yl)-quinolin-4-amine

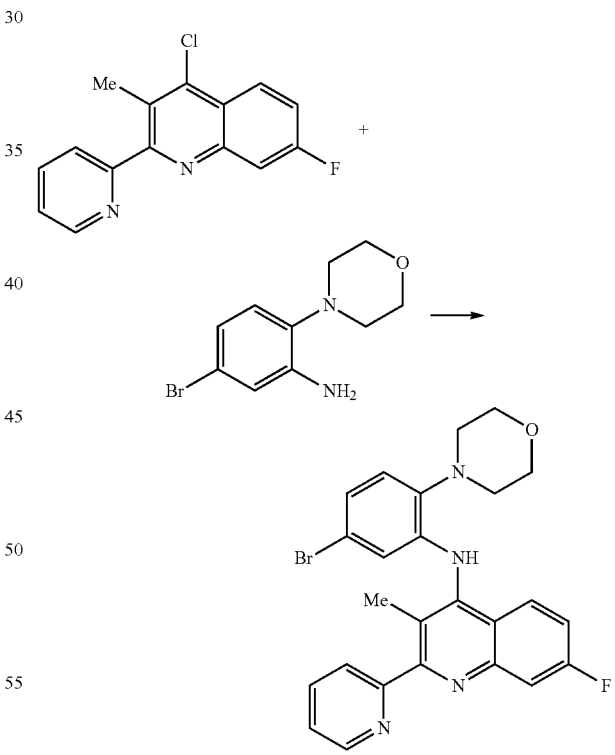

Prepared according to Procedure K, Method 1 using 4-chloro-7-fluoro-3-methyl-2-(pyridin-2-yl)quinoline (131 mg, 480 μmol), 5-bromo-2-morpholinobenzenamine (124 mg, 480 μmol) and 4.0N hydrochloric acid (0.12 mL, 480 μmol) solution in dioxane in MeOH (1.50 mL) to afford a yellow solid after purification by chromatography on silica gel, eluting with EtOAc-hexane solvent mixture. Mass Spectrum (ESI) m/e=493.0 & 495.0 (M+1).

N-(2,5-Di-4-morpholinylphenyl)-7-fluoro-2-(2-fluorophenyl)-3-methyl-4-quinolinamine

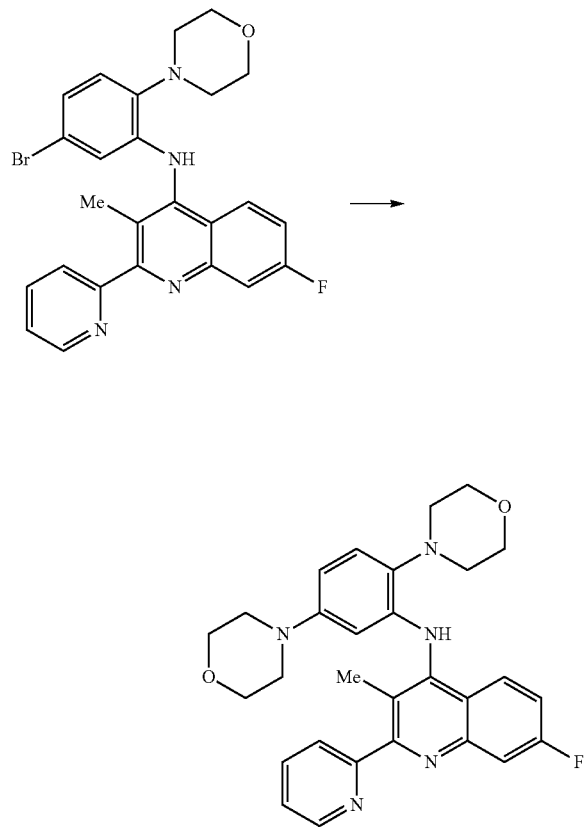

A mixture of N-(5-bromo-2-morpholinophenyl)-7-fluoro-3-methyl-2-(pyridin-2-yl)quinolin-4-amine (40 mg, 81 μmol), morpholine (0.014 mL, 162 μmol), tris(dibenzylideneacetone)dipalladium(0) (5.2 mg, 5.7 μmol), X-Phos (5.8 mg, 12 μmol) and sodium tert-butoxide (16 mg, 162 μmol) in toluene (4.00 mL, 37552 μmol) was heated to 100° C. for 3 h, after which time TLC and LC-MS indicated no starting chloroquinoline remained. The reaction was diluted with 25 mL EtOAc and washed with 25 mL water. The organic separation was stirred over anhydrous magnesium sulfate, filtered and the filtrate concd under reduced pressure to afford an orange, foamy solid. The product was isolated by chromatography on silica gel, eluting with 1-5% MeOH in DCM to afford product as a faint yellow solid. $^1$H NMR (400 MHz, chloroform-d) δ ppm 8.65 (1H, dd, J=3.7, 1.0 Hz), 7.75-7.88 (3H, m), 7.70 (1H, dd, J=10.0, 2.5 Hz), 7.30 (1H, ddd, J=7.0, 5.1, 2.0 Hz), 7.06-7.22 (2H, m), 7.02 (1H, d, J=8.6 Hz), 6.35 (1H, dd, J=8.8, 2.9 Hz), 5.91 (1H, d, J=2.7 Hz), 3.82 (4H, t, J=4.5 Hz), 3.55-3.71 (4H, m), 2.98 (4H, d, J=3.1 Hz), 2.74-2.88 (4H, m), 2.30 (3H, s). Mass Spectrum (ESI) m/e=500.2 (M+1).

Example 28

N-(2,5-Di-4-morpholinylphenyl)-3-methyl-2-phenyl-4-quinolinamine

4-Chloro-3-methyl-2-phenylquinoline

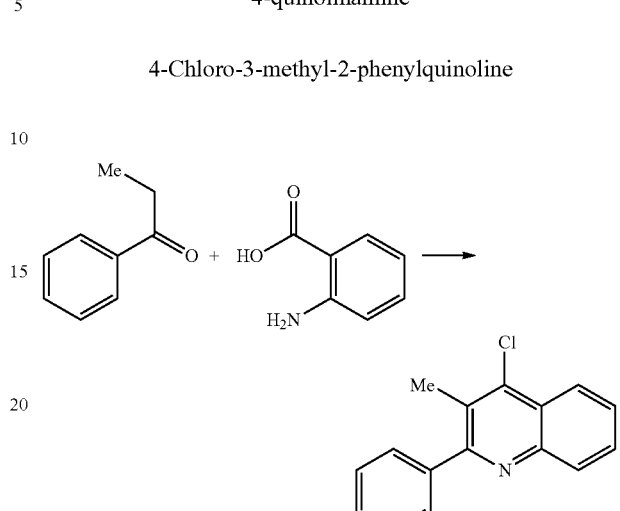

Prepared according to Procedure J using anthranilic acid and propiophenone in phosphorous oxychloride to afford a colorless solid upon purification by chromatography on silica gel. Mass Spectrum (ESI) m/e=254.0 (M+1).

4,4'-(2-Nitro-1,4-phenylene)dimorpholine

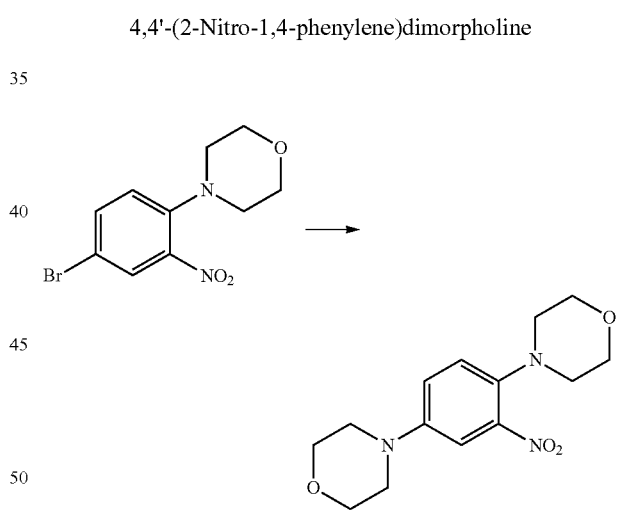

4-(4-Bromo-2-nitrophenyl)morpholine (500 mg, 1741 μmol) and morpholine (303 μL, 3483 μmol) were dissolved in toluene (71047 μL, 666992 μmol). To the stirred mixture was added X-Phos (125 mg, 261 μmol), sodium tert-butoxide (335 mg, 3483 μmol) and tris(dibenzylideneacetone)dipalladium (o) (112 mg, 122 μmol) in one portion. The reaction was heated to reflux for 2 h. After this time TLC and LC/MS show desired product. The reaction was cooled to rt and evaporated in vacuo. The residue was taken up in EtOAc (80 mL) and washed with satd aq. sodium bicarbonate solution (40 mL) and brine (40 mL). The separated organic layer was dried over magnesium sulfate, filtered and evaporated in vacuo. Column chromatography (hexanes:EtOAc, 1:0 to 1:2) gave desired product.

2,5-Dimorpholinoaniline

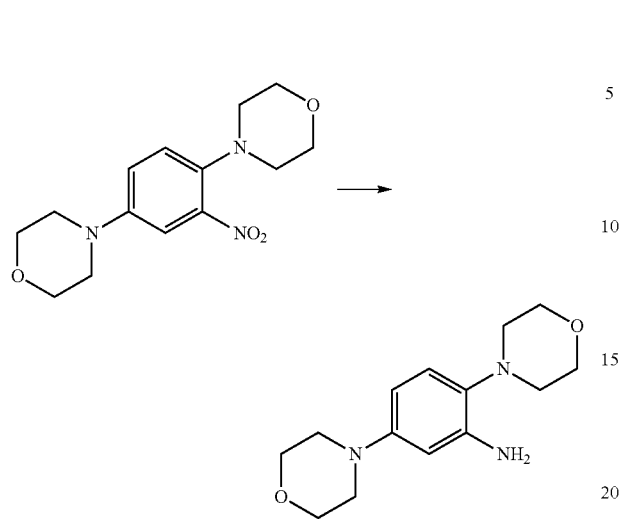

To a stirred solution of 4-(4-morpholino-3-nitrophenyl)morpholine (5600 mg, 19 mmol) in EtOAc was added stannous chloride, dihydrate (18 g, 95 mmol). The reaction was stirred at rt for 10 min and at reflux for 90 min. After this time LC/MS shows desired product. The reaction was cooled to rt and the precipitate was collected and washed with aq. 1N sodium hydroxide solution, water and brine and dried under vacuum overnight. After this time the solid was dissolved in EtOAc and washed with aq. 1N sodium hydroxide solution and brine, dried, filtered and evaporated in vacuo to give desired product. The filtrate was diluted with EtOAc (300 mL) and washed with aq. sodium hydroxide and brine, dried over magnesium sulfate, filtered and evaporated in vacuo to give additional desired product.

N-(2,5-di-4-Morpholinylphenyl)-3-methyl-2-phenyl-4-quinolinamine

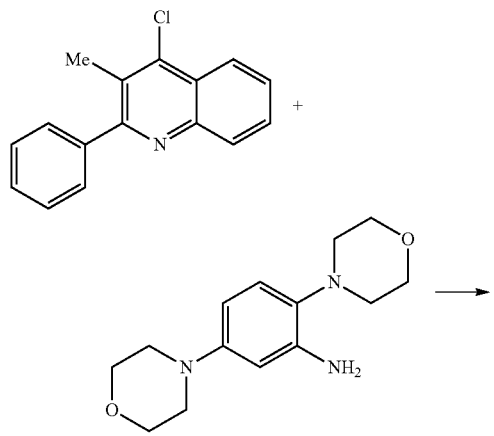

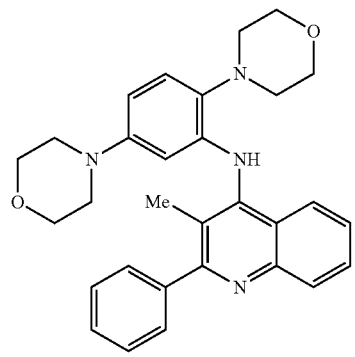

Prepared according to Procedure K, Method 1 using 4-chloro-3-methyl-2-phenylquinoline (150 mg, 591 μmol), 2,5-dimorpholinobenzenamine (156 mg, 591 μmol) and 4N hydrochloric acid solution in dioxane (0.15 mL, 591 μmol) in MeOH (3.00 mL) to afford product as a colorless solid after purification by chromatography on silica gel eluting with MeOH gradient in DCM. $^1$H NMR (400 MHz, chloroform-d) δ ppm 8.18 (1H, d, J=8.2 Hz), 7.90 (1H, dd, J=8.6, 1.2 Hz), 7.69 (1H, td, J=7.6, 1.2 Hz), 7.59-7.66 (2H, m), 7.41-7.57 (4H, m), 7.23 (1H, s), 7.12 (1H, d, J=8.6 Hz), 6.44 (1H, dd, J=8.6, 2.7 Hz), 6.04 (1H, d, J=2.7 Hz), 3.88-4.01 (4H, m), 3.69-3.80 (4H, m), 3.02-3.16 (4H, m), 2.88-3.00 (4H, m), 2.32 (3H, s). Mass Spectrum (ESI) m/e=481.3 (M+1).

Example 29

N-(2,5-Di-4-morpholinylphenyl)-5-fluoro-2-(2-fluorophenyl)-3-methyl-4-quinolinamine 4-Chloro-5-fluoro-2-(2-fluorophenyl)-3-methylquinoline

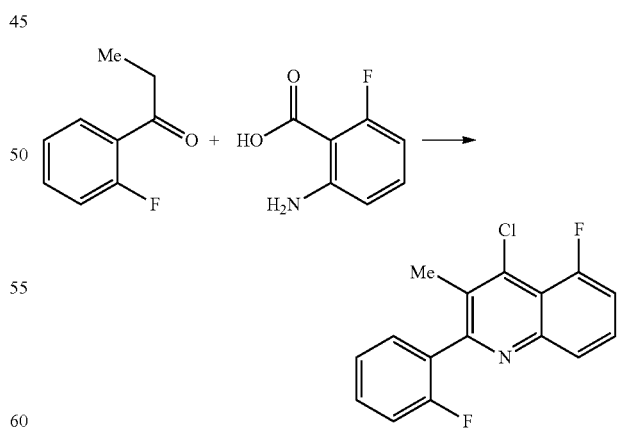

Prepared according to Procedure J using 1-(2-fluorophenyl)propan-1-one and 2-amino-6-fluorobenzoic acid in phosphorous oxychloride to afford a colorless solid upon purification by chromatography on silica gel. Mass Spectrum (ESI) m/e=290.0 (M+1).

71

N-(2,5-Di-4-morpholinylphenyl)-5-fluoro-2-(2-fluorophenyl)-3-methyl-4-quinolinamine

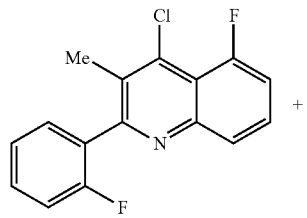

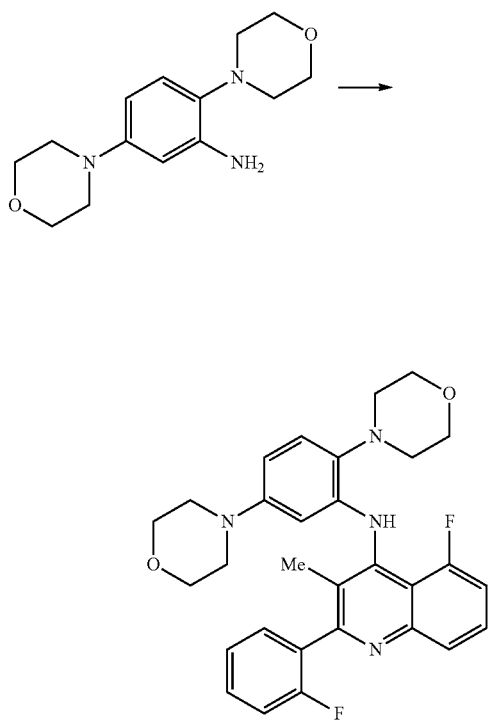

Prepared according to Procedure K, Method 1 using 4-chloro-5-fluoro-2-(2-fluorophenyl)-3-methylquinoline (137 mg, 473 μmol), 2,5-dimorpholinobenzeneamine (125 mg, 473 μmol) and 4N hydrochloric acid solution in dioxane (0.12 mL, 473 μmol) in MeOH (3.00 mL) to afford product as a colorless solid after purification by chromatography on silica gel, eluting with MeOH gradient in DCM. $^1$H NMR (400 MHz, chloroform-d) δ ppm 8.23-8.51 (1H, m), 7.96 (1H, d, J=8.2 Hz), 7.53-7.69 (2H, m), 7.42-7.53 (1H, m, J=7.8, 7.8, 5.5, 2.0 Hz), 7.31-7.40 (1H, m), 7.13-7.26 (2H, m), 7.10 (1H, d, J=8.6 Hz), 6.47 (1H, dd, J=8.4, 2.9 Hz), 6.12-6.27 (1H, m), 3.92 (4H, t, J=4.7 Hz), 3.75-3.87 (4H, m), 3.12-3.21 (2H, m), 3.00-3.12 (4H, m), 2.69-2.98 (2H, m), 2.11 (3H, d, J=2.3 Hz). Mass Spectrum (ESI) m/e=517.3 (M+1).

Example 30

N-(2,5-Di-4-morpholinylphenyl)-6,7-difluoro-2-(2-fluorophenyl)-3-methyl-4-quinolinamine 4-Chloro-6,7-difluoro-2-(2-fluorophenyl)-3-methylquinoline

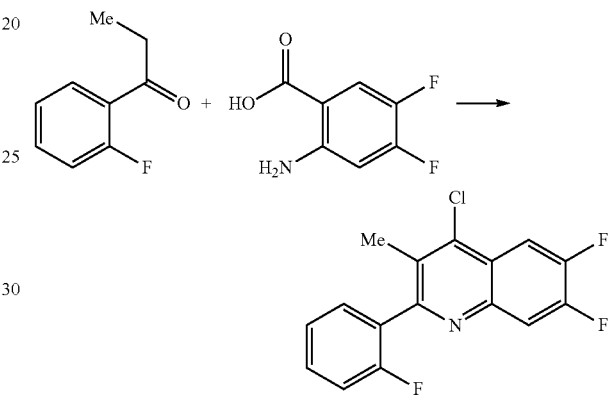

Prepared according to Procedure J using 1-(2-fluorophenyl)propan-1-one and 2-amino-4,5-difluorobenzoic acid in phosphorous oxychloride to afford a colorless solid upon purification by chromatography on silica gel. Mass Spectrum (ESI) m/e=308.0 (M+1).

N-(2,5-Di-4-morpholinylphenyl)-6,7-difluoro-2-(2-fluorophenyl)-3-methyl-4-quinolinamine

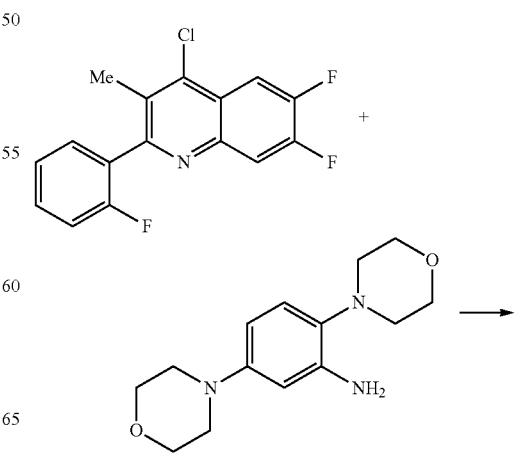

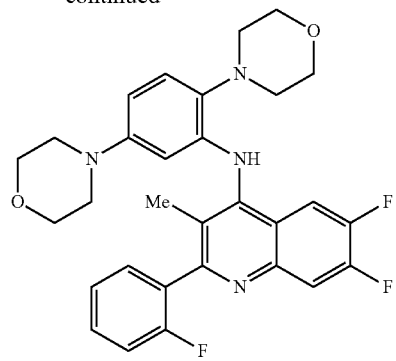

Prepared according to Procedure K, Method 1 using 4-chloro-6,7-difluoro-2-(2-fluorophenyl)-3-methylquinoline (100 mg, 325 µmol), 2,5-dimorpholinobenzenamine (86 mg, 325 µmol) and 4N hydrochloric acid solution in dioxane (0.081 mL, 325 µmol) in MeOH (3.00 mL) to afford product as a colorless solid after purification by chromatography on silica gel eluting with MeOH gradient in DCM. $^1$H NMR (400 MHz, chloroform-d) δ ppm 7.91 (1H, dd, J=11.0, 7.8 Hz), 7.55-7.71 (2H, m), 7.43-7.54 (1H, m, J=7.9, 7.9, 5.4, 2.0 Hz), 7.31-7.40 (1H, m), 7.09-7.25 (3H, m), 6.46 (1H, dd, J=8.6, 2.7 Hz), 6.01 (1H, br. s.), 3.87-4.05 (4H, m), 3.73-3.83 (4H, m), 3.06 (4H, dd, J=2.5, 1.8 Hz), 2.90-3.01 (4H, m), 2.21 (3H, d, J=2.0 Hz). Mass Spectrum (ESI) m/e=535.3 (M+1).

Example 31

N-(2,5-Di-4-morpholinylphenyl)-2-(3-fluorophenyl)-3-methyl-4-quinolinamine

4-Chloro-2-(3-fluorophenyl)-3-methylquinoline

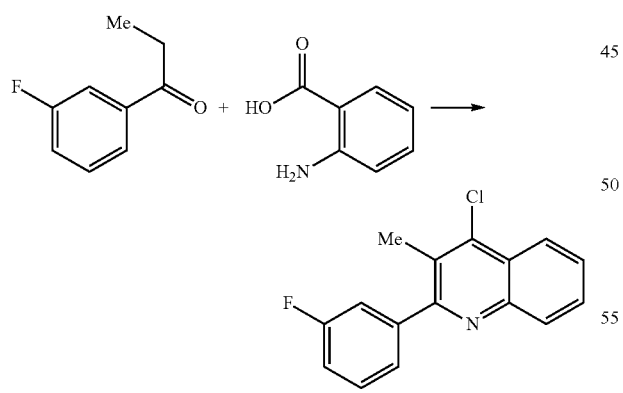

Prepared according to Procedure J using 1-(3-fluorophenyl)propan-1-one and anthranillic acid in phosphorous oxychloride to afford a colorless solid upon purification by chromatography on silica gel. Mass Spectrum (ESI) m/e=272.0 (M+1).

N-(2,5-Di-4-morpholinylphenyl)-2-(3-fluorophenyl)-3-methyl-4-quinolinamine

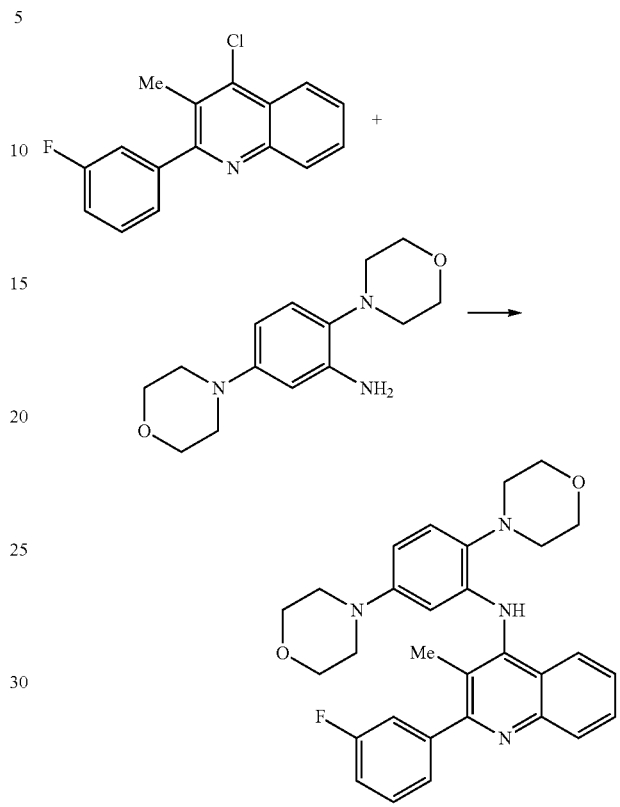

Prepared according to Procedure K, Method 1 using 4-chloro-2-(3-fluorophenyl)-3-methylquinoline (127 mg, 467 µmol), 2,5-dimorpholinobenzenamine (123 mg, 467 µmol) and 4N hydrochloric acid solution in dioxane (0.12 mL, 467 µmol) in MeOH (3.00 mL) to afford product as a colorless solid after purification by chromatography on silica gel, eluting with MeOH gradient in DCM. $^1$H NMR (400 MHz, chloroform-d) δ ppm 8.16 (1H, d, J=8.2 Hz), 7.90 (1H, dd, J=8.0, 1.0 Hz), 7.66-7.75 (1H, m), 7.43-7.56 (2H, m), 7.32-7.43 (2H, m), 7.25 (1H, s), 7.07-7.22 (2H, m), 6.45 (1H, dd, J=8.6, 2.7 Hz), 6.03 (1H, d, J=2.7 Hz), 3.88-3.99 (4H, m), 3.67-3.80 (4H, m), 3.01-3.14 (4H, m), 2.88-2.99 (4H, m), 2.32 (3H, s). Mass Spectrum (ESI) m/e=499.1 (M+1).

Example 32

7-Chloro-N-(2,5-di-4-morpholinylphenyl)-2-(2-fluorophenyl)-3-methyl-4-quinolinamine 4,7-Dichloro-2-(2-fluorophenyl)-3-methylquinoline

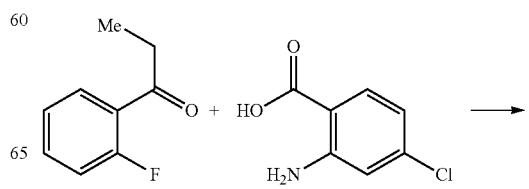

75
-continued

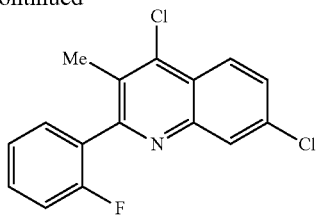

Prepared according to Procedure J using 1-(2-fluorophenyl)propan-1-one and 2-amino-4-chlorobenzoic acid in phosphorous oxychloride to afford a colorless solid upon purification by chromatography on silica gel. Mass Spectrum (ESI) m/e=305.9 (M+1).

7-Chloro-N-(2,5-di-4-morpholinylphenyl)-2-(2-fluorophenyl)-3-methyl-4-quinolinamine

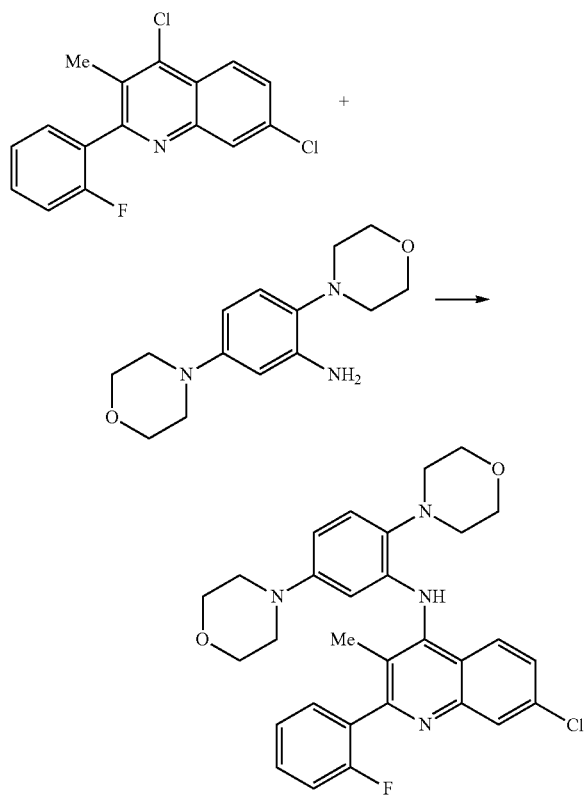

Prepared according to Procedure K, Method 1 using 4,7-dichloro-2-(2-fluorophenyl)-3-methylquinoline (125 mg, 408 µmol), 2,5-dimorpholinobenzenamine (108 mg, 408 µmol) and 4N hydrochloric acid solution in dioxane (0.10 mL, 408 µmol) in MeOH (3.00 mL) to afford product as a colorless solid after purification by chromatography on silica gel, eluting with MeOH gradient in DCM. $^1$H NMR (400 MHz, chloroform-d) δ ppm 8.02 (1H, d, J=2.3 Hz), 7.72 (1H, d, J=9.0 Hz), 7.46 (1H, td, J=7.4, 2.0 Hz), 7.26-7.40 (2H, m), 7.17-7.25 (1H, m), 7.13 (1H, s), 7.02-7.10 (1H, m), 6.98 (1H, d, J=8.6 Hz), 6.31 (1H, dd, J=8.6, 2.7 Hz), 5.91 (1H, br. s.), 3.77 (4H, t, J=4.7 Hz), 3.59-3.68 (4H, m), 2.91 (4H, br. s.), 2.74-2.87 (4H, m), 2.06 (3H, d, J=2.0 Hz). Mass Spectrum (ESI) m/e=533.2 (M+1).

76

Example 33

N-(2,5-Di-4-morpholinylphenyl)-3-methyl-2-(2-pyridinyl)-4-quinolinamine

Ethyl 2-methyl-3-oxo-3-(phenylamino)propanoate

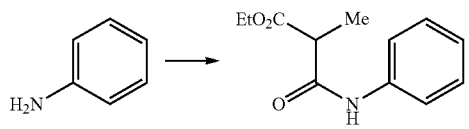 [SMILES: Nc1ccccc1 ; CCOC(=O)C(C)C(=O)Nc1ccccc1]

Prepared according to Procedure A using diethyl 2-methylmalonate (24.485 g, 141 mmol), aniline (9.00 mL, 99 mmol) and pyridine (16 mL) to afford product as a colorless oil after purification by chromatography on silica gel, eluting with EtOAc gradient in hexane. $^1$H NMR (400 MHz, chloroform-d) δ ppm 8.66 (1H, br. s.), 7.55 (2H, d, J=7.8 Hz), 7.33 (2H, t, J=8.0 Hz), 7.13 (1H, t, J=7.4 Hz), 4.20-4.33 (2H, m), 3.46 (1H, q, J=7.2 Hz), 1.56 (3H, d, J=7.4 Hz), 1.26-1.39 (3H, m).

2-Methyl-3-oxo-3-(phenylamino)propanoic acid

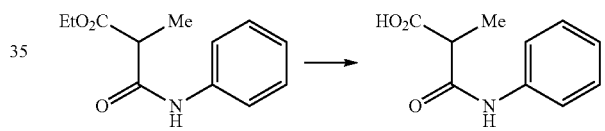

Prepared according to Procedure B using ethyl 2-methyl-3-oxo-3-(phenylamino)-propanoate (8.60 g, 39 mmol) and sodium hydroxide (2.00 g, 50 mmol) in THF (40.00 mL), water (10.00 mL, 555 mmol) and MeOH (10.00 mL) to afford product as a colorless solid, which was used without further purification. Mass Spectrum (ESI) m/e=192.1 [M−1].

4-Hydroxy-3-methylquinolin-2(1H)-one

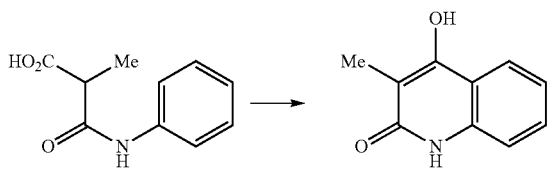 [SMILES: CC(C(=O)O)C(=O)Nc1ccccc1 ; Cc1c(O)c2ccccc2[nH]c1=O]

Prepared according to Procedure C using 2-methyl-3-oxo-3-(phenylamino)propanoic acid (6.51 g, 34 mmol) in 25 mL PPA to afford a colorless solid, which was used without further purification. $^1$H NMR (400 MHz, DMSO-d$_6$) δ ppm 11.32 (1H, br. s.), 7.86 (1H, dd, J=8.2, 1.6 Hz), 7.35-7.54 (1H, m), 7.25 (1H, d, J=7.8 Hz), 7.02-7.20 (1H, m), 2.00 (3H, s).

2,4-Dichloro-3-methylquinoline

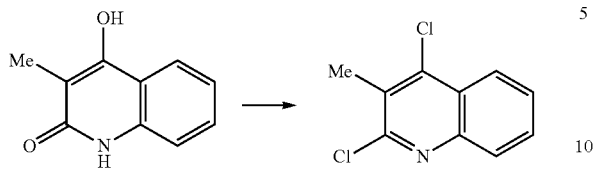

Prepared according to Procedure D using 4-hydroxy-3-methylquinolin-2(1H)-one (4.51 g, 25.7 mmol) in phosphorous oxychloride (20.00 mL) to afford a tan solid, which was used without further purification. $^1$H NMR (400 MHz, DMSO-$d_6$) δ ppm 8.04 (1H, dd, J=8.2, 1.6 Hz), 7.91 (1H, d, J=8.6 Hz), 7.80 (1H, td, J=7.6, 1.6 Hz), 7.64-7.75 (1H, m), 2.51 (3H, s).

4-Chloro-3-methyl-2-(pyridin-2-yl)quinoline

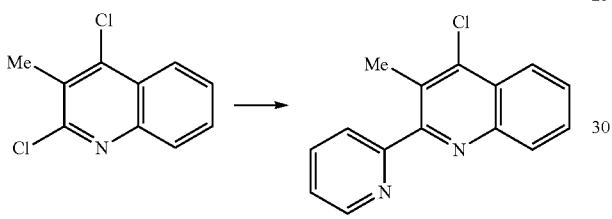

Prepared according to Procedure E using 2,4-dichloro-3-methylquinoline (1.038 g, 4.9 mmol), 2-(tributylstannyl)pyridine (2.0 g, 5.4 mmol) and tetrakis(triphenylphosphine)palladium(0) (0.28 g, 0.24 mmol) in toluene (10.00 mL) to afford product as an off-white solid upon purification by precipitation from EtOAc and chromatography on silica gel, eluting with EtOAc gradient in hexane. Mass Spectrum (ESI) m/e=255.1 (M+1).

N-(2,5-Di-4-morpholinylphenyl)-3-methyl-2-(2-pyridinyl)-4-quinolinamine

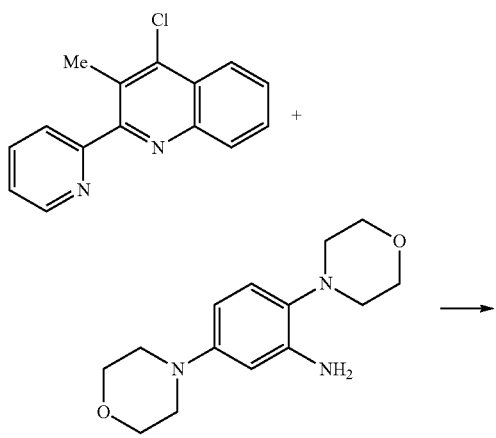

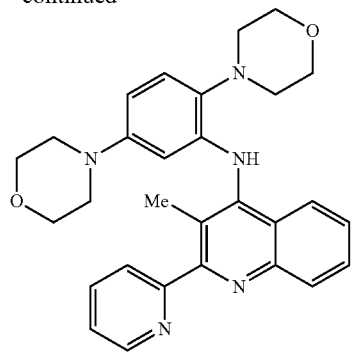

Prepared according to Procedure K, Method 2 using 4-chloro-3-methyl-2-(pyridin-2-yl)quinoline (77 mg, 302 µmol), 2,5-dimorpholinobenzenamine (80 mg, 302 µmol) and 4N hydrochloric acid solution in dioxane (7.6 µL, 30 µmol) in NMP (1 mL) to afford product as a colorless solid upon purification by reversed phase HPLC. $^1$H NMR (400 MHz, chloroform-d) δ ppm 8.58-8.72 (1H, m), 8.13 (1H, d, J=8.6 Hz), 7.74-7.90 (3H, m), 7.54-7.68 (1H, m), 7.39 (1H, td, J=7.6, 1.2 Hz), 7.25-7.35 (1H, m), 7.15 (1H, s), 7.02 (1H, d, J=8.6 Hz), 6.35 (1H, dd, J=8.6, 2.7 Hz), 5.95 (1H, d, J=2.7 Hz), 3.74-3.93 (4H, m), 3.52-3.72 (4H, m), 2.99 (4H, d, J=3.9 Hz), 2.72-2.89 (4H, m), 2.31 (3H, s). Mass Spectrum (ESI) m/e=482.2 (M+1).

Example 34

2-((2-(2-Fluorophenyl)-3-methyl-4-quinolinyl)amino)-4-(4-morpholinyl)benzonitrile

4-Chloro-2-(2-fluorophenyl)-3-methylquinoline

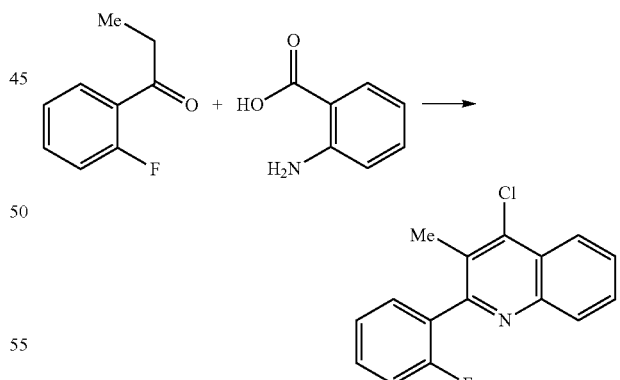

Prepared according to Procedure J, using 2-aminobenzoic acid (14.6 g, 106 mmol) and 1-(2-fluorophenyl)propan-1-one (10.78 g, 70.8 mmol) in phosphorous oxychloride (35.00 mL) to afford product as a colorless solid upon purification by chromatography on silica gel, eluting with EtOAc gradient in hexane. Mass Spectrum (ESI) m/e=272.0 (M+1).

4-Morpholino-2-nitrobenzonitrile

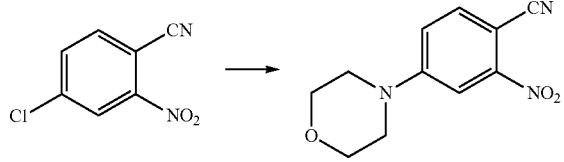 [SMILES: N#Cc1ccc(Cl)cc1[N+](=O)[O-] ; N#Cc1ccc(N2CCOCC2)cc1[N+](=O)[O-]]

A mixture of 4-chloro-2-nitrobenzonitrile (7.828 g, 42.9 mmol) and morpholine (4.49 mL, 51.5 mmol) in DMSO (20.00 mL) was stirred at rt for 1 h, after which time LC-MS indicated a small amount of desired product formed. The reaction was heated to 100° C. After 24 h the reaction was equilibrated to rt and poured into 50 mL ea 1N aq. hydrochloric acid and EtOAc. The resulting orange precipitate was collected by filtration, rinsing with EtOAc, then dried under vacuum. Mass Spectrum (ESI) m/e=234.1 (M+1).

2-Amino-4-morpholinobenzonitrile

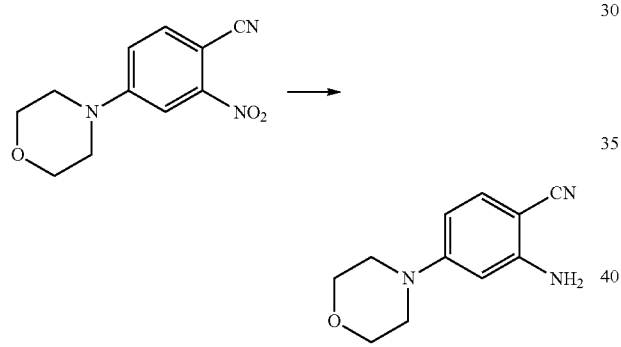

To a mixture of 4-morpholino-2-nitrobenzonitrile (388 mg, 1664 µmol) in acetic acid (6.00 mL, 104809 µmol) at rt was added all at once zinc powder (1632 mg, 24955 µmol). An exotherm developed. The reaction was stirred at ambient temperature for 2 h then filtered, and rinsed with EtOAc. The filtrate was concd under reduced pressure to afford a slightly yellow solid. Mass Spectrum (ESI) m/e=204.1 (M+1).

2-((2-(2-Fluorophenyl)-3-methyl-4-quinolinyl)amino)-4-(4-morpholinyl)-benzonitrile

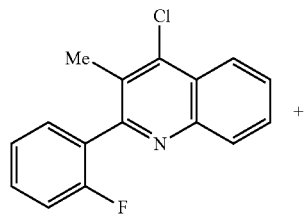

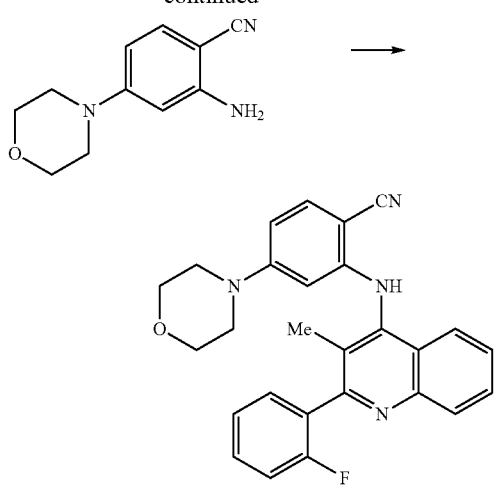

Prepared according to Procedure K, Method 2 using 2-amino-4-morpholinobenzonitrile (82 mg, 405 µmol), 4-chloro-2-(2-fluorophenyl)-3-methylquinoline (110 mg, 405 µmol) and 4N hydrochloric acid solution in dioxane (0.010 mL, 40 µmol) in NMP (0.50 mL) to afford product as a tan solid upon purification by chromatography on silica gel, eluting with EtOAc gradient in DCM. $^1$H NMR (400 MHz, chloroform-d) δ ppm 8.11 (1H, d, J=8.6 Hz), 7.90 (1H, d, J=8.6 Hz), 7.61-7.74 (1H, m), 7.45-7.61 (2H, m), 7.32-7.45 (2H, m), 7.26 (1H, t, J=7.4 Hz), 7.08 (1H, t, J=9.2 Hz), 6.55 (1H, br. s.), 6.31 (1H, dd, J=8.8, 2.5 Hz), 5.76 (1H, br. s.), 3.54-3.73 (4H, m), 2.88-3.11 (4H, m), 2.04-2.23 (3H, m). Mass Spectrum (ESI) m/e=439.1 (M+1).

Example 35

N-(5-(2-Amino-4-pyrimidinyl)-2-(4-morpholinyl)phenyl)-2-(2-fluorophenyl)-3-methyl-4-quinolinamine

N-(5-Bromo-2-morpholinophenyl)-2-(2-fluorophenyl)-3-methylquinolin-4-amine

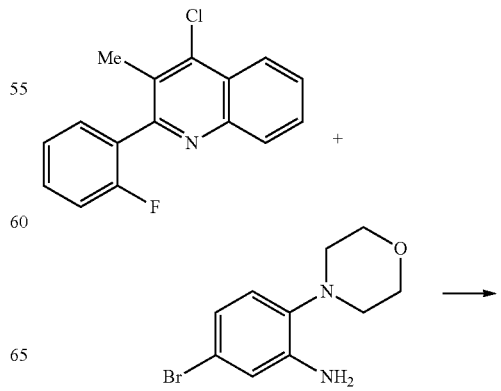

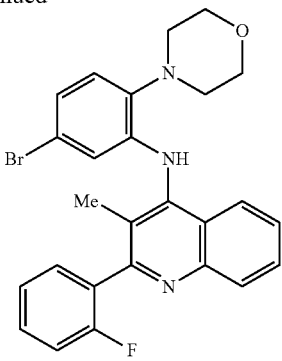

Prepared according to Procedure K, Method 2 using 4-chloro-2-(2-fluorophenyl)-3-methylquinoline (230 mg, 848 μmol), 5-bromo-2-morpholinobenzenamine (109 mg, 424 μmol) and 4N hydrochloric acid solution in dioxane (0.011 mL, 42 μmol) in NMP (0.50 mL) to afford a colorless solid upon purification by chromatography on silica gel, eluting with EtOAc gradient in hexane. Mass Spectrum (ESI) m/e=492.1 & 494.1 (M+1).

N-(4-(3-(2-(2-Fluorophenyl)-3-methylquinolin-4-ylamino)-4-morpholinophenyl)pyrimidin-2-yl)acetamide

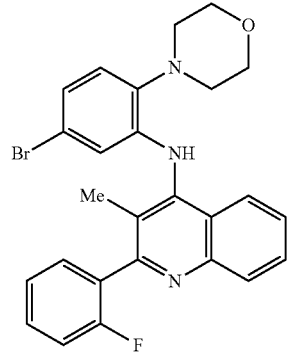

→

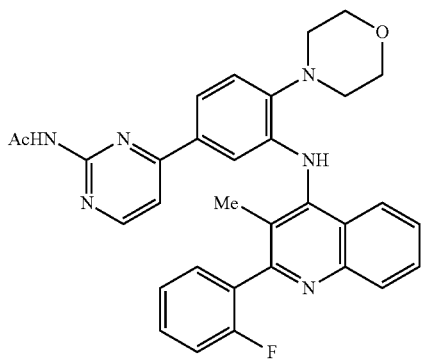

A mixture of N-(5-bromo-2-morpholinophenyl)-2-(2-fluorophenyl)-3-methylquinolin-4-amine (100 mg, 203 μmol), N-(4-(trimethylstannyl)pyrimidin-2-yl)-acetamide (91 mg, 305 μmol) and tetrakis(triphenylphosphine)palladium(0) (23 mg, 20 μmol) in toluene (4.00 mL) was purged with nitrogen and heated to gentle reflux. After 3.5 h LC-MS indicated no starting bromide remained and the reaction was removed from heat and left stirring overnight at rt before concentrating under reduced pressure. The concentrate was dissolved in 3 mL DMF and purified by reversed-phase HPLC. Mass Spectrum (ESI) m/e=549.3 (M+1).

N-(5-(2-Amino-4-pyrimidinyl)-2-(4-morpholinyl)phenyl)-2-(2-fluorophenyl)-3-methyl-4-quinolinamine

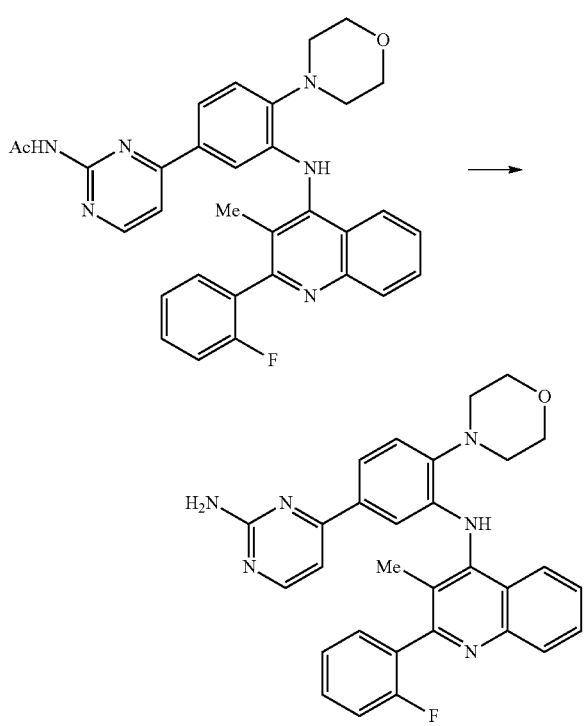

A solution of N-(4-(3-(2-(2-fluorophenyl)-3-methylquinolin-4-ylamino)-4-morpholinophenyl)pyrimidin-2-yl)acetamide (20 mg, 36 μmol) and concentrated aq. hydrochloric acid (1.50 mL, 18.0 mmol) in acetonitrile (4.00 mL, 76.6 mmol) was heated to 90° C. After 18 h the pH was made alkaline by addition of sodium hydroxide. The reaction mixture was partitioned between 30 mL ea EtOAc and water. The organic layer was stirred over anhydrous magnesium sulfate, filtered and the filtrate concentrated under reduced pressure to afford a yellow solid. The product was purified by chromatography on silica gel eluting with 5-10% MeOH in DCM to afford a colorless solid. $^1$H NMR (400 MHz, chloroform-d) δ ppm 8.07-8.27 (2H, m), 7.84 (1H, d, J=8.2 Hz), 7.51-7.67 (3H, m), 7.37-7.49 (2H, m), 7.27 (1H, t, J=7.4 Hz), 7.01-7.23 (5H, m), 6.78 (1H, br. s.), 5.10 (2H, br. s.), 3.87 (4H, t, J=4.5 Hz), 3.11 (4H, br. s.), 2.06-2.21 (3H, m). Mass Spectrum (ESI) m/e=507.2 (M+1).

Example 36

2-(2-Fluorophenyl)-3-methyl-N-(2-(4-morpholinyl)-5-(4-pyridinyl)phenyl)-4-quinolinamine

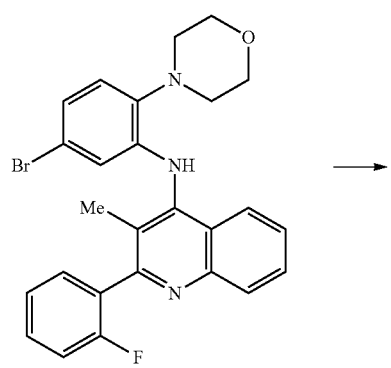

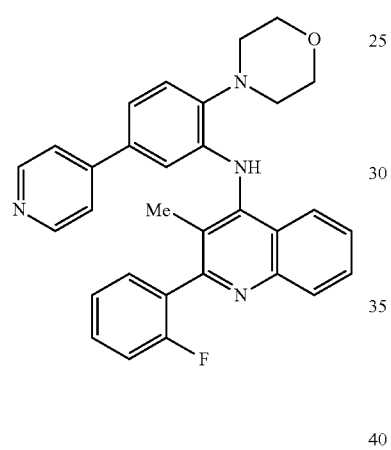

A mixture of sodium carbonate (68 mg, 640 µmol), pyridin-4-ylboronic acid (40 mg, 329 µmol), N-(5-bromo-2-morpholinophenyl)-2-(2-fluorophenyl)-3-methylquinolin-4-amine (90 mg, 183 µmol) and dichlorobis(triphenylphosphine)-palladium(II) (13 mg, 18 µmol) in water (2.00 mL) and 1,4-dioxane (8.00 mL) was purged with nitrogen then heated in a microwave vessel with stirring at 130° C. for 60 min, after which time LC-MS indicated no starting material remained and desired product predominated. The reaction was diluted with 30 mL water and extracted with 3×15 mL EtOAc. The combined organic extracts were stirred over magnesium sulfate, filtered and the filtrate concentrated under reduced pressure to afford a dark brown oil. The desired product was isolated as a colorless solid by chromatography on silica gel eluting with a gradient of 1-5% MeOH in DCM. $^1$H NMR (400 MHz, chloroform-d) δ ppm 8.55 (2H, dd, J=4.3, 1.6 Hz), 8.21 (1H, d, J=8.2 Hz), 7.93 (1H, d, J=8.6 Hz), 7.61-7.79 (3H, m), 7.40-7.61 (3H, m), 7.10-7.40 (7H, m), 6.74 (1H, d, J=0.8 Hz), 3.98 (4H, t, J=4.5 Hz), 3.02-3.29 (4H, m), 2.26 (3H, d, J=2.3 Hz). Mass Spectrum (ESI) m/e=491.2 (M+1).

Example 37

2-(2-Fluorophenyl)-3-methyl-N-(2-(4-morpholinyl)-5-(3-thiophenyl)phenyl)-4-quinolinamine

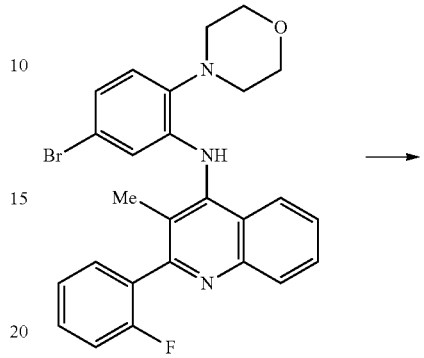

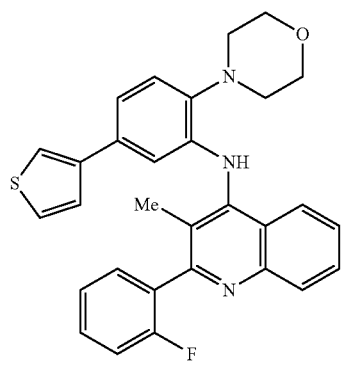

A mixture of dichlorobis(triphenylphosphine)palladium (II) (13 mg, 18 µmol), N-(5-bromo-2-morpholinophenyl)-2-(2-fluorophenyl)-3-methylquinolin-4-amine (88 mg, 179 µmol), thiophen-3-ylboronic acid (34 mg, 268 µmol) and sodium carbonate (57 mg, 536 µmol) in water (0.25 mL) and 1,4-dioxane (1.00 mL) was purged with nitrogen then heated in a microwave vessel to 130° C. for 60 min, after which time TLC indicated no starting material remained and LC-MS indicated only desired product present. The reaction was partitioned between water and EtOAc (30 mL ea). The organic separation was stirred over anhydrous magnesium sulfate, filtered and the filtrate concentrated under reduced pressure to afford a brown film. The desired product was isolated by chromatography on silica gel eluting isocratically with 33% EtOAc in hexane to afford a colorless solid. $^1$H NMR (400 MHz, DMSO-$d_6$) δ ppm 7.99 (2H, dd, J=15.3, 8.2 Hz), 7.79 (1H, s), 7.71 (1H, dd, J=7.0, 7.0 Hz), 7.45-7.63 (5H, m), 7.32-7.45 (2H, m), 7.12-7.29 (3H, m), 6.69 (1H, d, J=1.6 Hz), 3.59 (4H, br. s.), 2.91 (4H, br. s.), 2.06 (3H, d, J=1.6 Hz). Mass Spectrum (ESI) m/e=496.1 (M+1).

Example 38

N-(5-(2-Amino-4-pyridinyl)-2-(4-morpholinyl)phenyl)-2-(2-fluorophenyl)-3-methyl-4-quinolinamine 2-(2-Fluorophenyl)-3-methyl-N-(2-morpholino-5-(4,4,5,5-tetramethyl-1,3,2-dioxaborolan-2-yl)phenyl)quinolin-4-amine

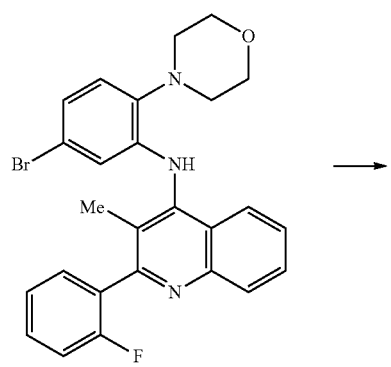

A mixture of N-(5-bromo-2-morpholinophenyl)-2-(2-fluorophenyl)-3-methylquinolin-4-amine (290 mg, 0.589 mmol), 4,4,4',4',5,5,5',5'-octamethyl-2,2'-bi(1,3,2-dioxaborolane) (224 mg, 0.883 mmol), bis(tricyclohexylphosphine)-palladium(o) (39.3 mg, 0.059 mmol) and potassium acetate (69.6 mg, 1.178 mmol) in 1,4-dioxane (4.00 mL) was purged with nitrogen then heated to 100° C. for 90 min, after which time LC-MS indicated no starting material remained. The reaction was diluted with 30 mL Et$_2$O and filtered through a pad of silica gel, rinsing with 30 mL Et$_2$O. The filtrate was concentrated under reduced pressure to afford a brown oily solid. The crude material was purified by chromatography on silica gel eluting with a gradient of 20-30% EtOAc in hexane to afford a tan solid. Mass Spectrum (ESI) m/e=540.3 (M+1).

N-(5-(2-Amino-4-pyridinyl)-2-(4-morpholinyl)phenyl)-2-(2-fluorophenyl)-3-methyl-4-quinolinamine

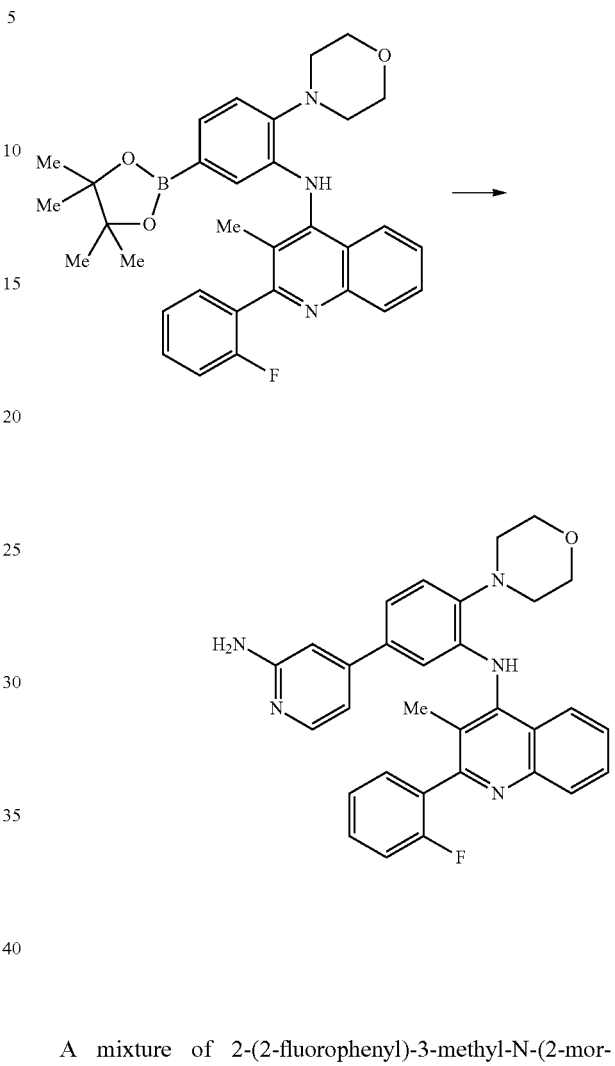

A mixture of 2-(2-fluorophenyl)-3-methyl-N-(2-morpholino-5-(4,4,5,5-tetramethyl-1,3,2-dioxaborolan-2-yl)phenyl)quinolin-4-amine (44.0 mg, 0.082 mmol), 4-bromopyridin-2-amine (14.1 mg, 0.082 mmol), dichlorobis(triphenylphosphine)palladium(II) (5.73 mg, 8.16 μmol) and sodium carbonate (14.68 mg, 0.245 mmol) in 1,4-dioxane (2.00 mL) and water (0.500 mL) in a microwave vessel was purged with nitrogen then heated in a microwave at 120° C. for 60 min, after which time LC-MS indicated no starting material remained and desired product was present. The reaction was partitioned between 30 mL EtOAc and 20 mL water. The organic separation was stirred over anhydrous magnesium sulfate, filtered and the filtrate concentrated under reduced pressure to afford a yellow film. The product was isolated by preparative scale reversed-phase HPLC, affording a colorless solid. $^1$H NMR (400 MHz, chloroform-d) δ ppm 8.11 (1H, d, J=8.2 Hz), 7.92 (1H, d, J=5.5 Hz), 7.84 (1H, d, J=8.6 Hz), 7.60-7.69 (1H, m), 7.56 (1H, td, J=7.4, 2.0 Hz), 7.34-7.51 (2H, m), 7.26 (1H, t, J=7.4 Hz), 6.99-7.21 (5H, m), 6.63 (2H, dd, J=7.4, 2.3 Hz), 6.43 (1H, br. s.), 4.44 (2H, d, J=1.2 Hz), 3.88 (4H, t, J=4.7 Hz), 2.94-3.23 (4H, m), 2.15 (3H, d, J=2.3 Hz). Mass Spectrum (ESI) m/e=506.2 (M+1).

Example 39

8-Chloro-N-(2,5-di-4-morpholinylphenyl)-2,3-dimethyl-4-quinolinamine

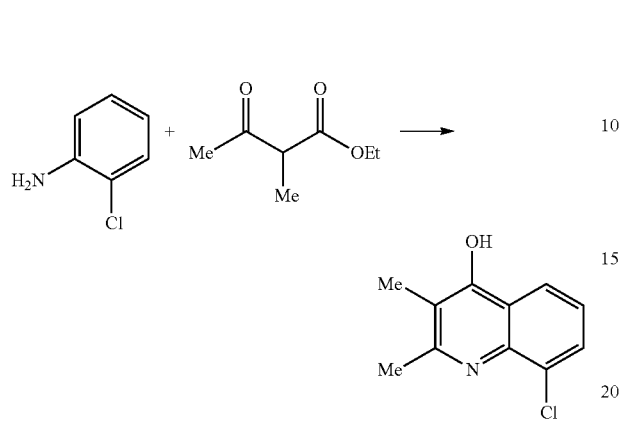

A mixture of 2-chlorobenzenamine (5.342 g, 41.9 mmol) and ethyl 2-methyl-3-oxobutanoate (12.1 mL, 83.7 mmol) in 16 g PPA was heated to 140° C. for 23 h then equilibrated to rt. Approximately 200 mL of 5% aq. sodium hydroxide solution was added and the resulting pink precipitate collected by filtration, rinsing with water. The pink solid was dried in a vacuum dessicator over $P_2O_5$. After several hours, the solid was suspended in hot EtOAc and the solid collected by filtration. The resulting colorless solid was dried under reduced pressure. Mass Spectrum (ESI) m/e=208.0 (M+1).

4,8-Dichloro-2,3-dimethylquinoline

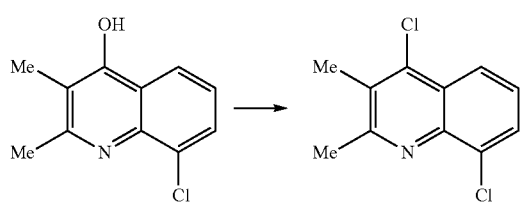 [SMILES: Cc1nc2c(Cl)cccc2c(O)c1C ; Cc1nc2c(Cl)cccc2c(Cl)c1C]

A mixture of 8-chloro-2,3-dimethylquinolin-4-ol (1.83 g, 8.81 mmol) in phosphorous oxychloride (10.00 mL) was heated to reflux for 2 h, after which time LC-MS indicated only product present. The reaction solution was poured into ice and adjusted to pH>10. The aq. mixture was extracted with 2×75 mL DCM. The combined organic extracts were stirred over anhydrous magnesium sulfate, filtered and the filtrate concentrated under reduced pressure to afford a pale yellow solid, which was not further purified. Mass Spectrum (ESI) m/e=226.0 (M+1).

N-(5-Bromo-2-morpholinophenyl)-8-chloro-2,3-dimethylquinolin-4-amine

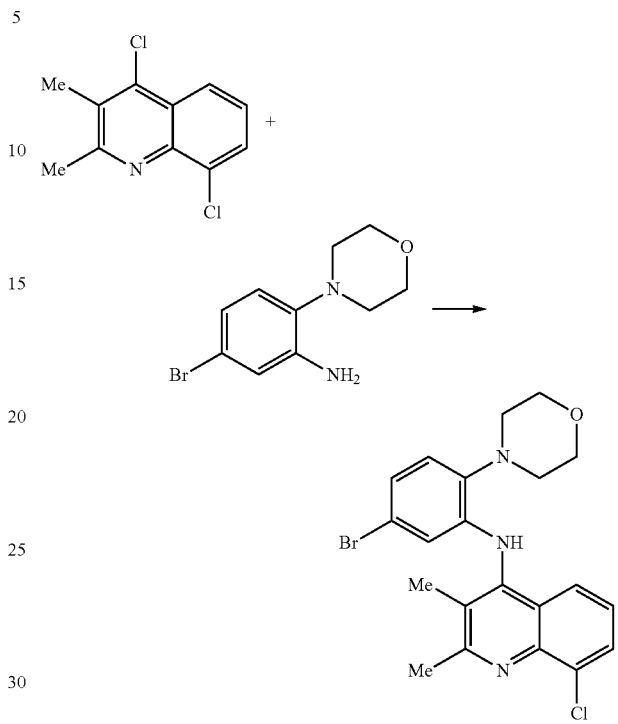

Prepared according to Procedure K, Method 1 using 4,8-dichloro-2,3-dimethylquinoline (104 mg, 460 µmol), 5-bromo-2-morpholinobenzenamine (118 mg, 460 µmol) and 4N hydrochloric acid solution in dioxane (0.050 mL, 200 µmol) in MeOH (1.00 mL) to afford a colorless solid upon purification by chromatography on silica gel, eluting with a $Et_2O$ gradient in toluene. $^1H$ NMR (400 MHz, chloroform-d) δ ppm 7.69 (1H, dd, J=7.4, 1.2 Hz), 7.55-7.63 (1H, m), 7.23-7.30 (1H, m), 6.92-6.98 (1H, m), 6.85-6.92 (1H, m), 6.83 (1H, s), 6.18 (1H, d, J=2.3 Hz), 3.80-3.91 (4H, m), 2.92-3.08 (4H, m), 2.71-2.78 (3H, m), 2.23 (3H, s).

8-Chloro-N-(2,5-di-4-morpholinylphenyl)-2,3-dimethyl-4-quinolinamine

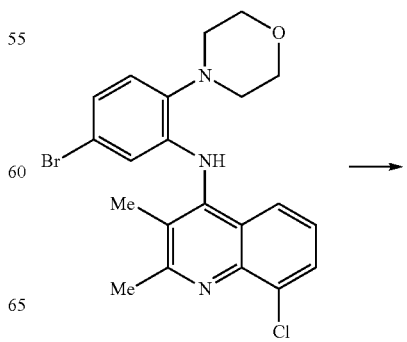

-continued

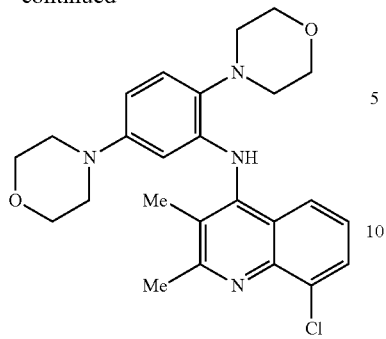

In a teflon-capped vial, a mixture of N-(5-bromo-2-morpholinophenyl)-8-chloro-2,3-dimethylquinolin-4-amine (75 mg, 168 μmol), morpholine (0.02 mL, 252 μmol), Pd₂dba₃ (15 mg, 17 μmol), X-Phos (8 mg, 17 μmol) and cesium carbonate (82 mg, 252 μmol) in 1,4-dioxane (4.00 mL) was purged with nitrogen, capped and heated in a 120° C. oil bath for 72 h. The reaction mixture was partitioned between 25 mL EtOAc and 25 mL water. The organic separation was stirred over anhydrous magnesium sulfate, filtered and the filtrate concentrated under reduced pressure to afford and orange oil. The product was purified by preparative reversed-phase HPLC to afford a yellow oil. ¹H NMR (400 MHz, chloroform-d) δ ppm 7.83 (2H, dd, J=11.7, 7.8 Hz), 7.34-7.44 (1H, m), 7.09-7.18 (2H, m), 6.90 (1H, dd, J=8.8, 2.5 Hz), 6.60 (1H, d, J=2.7 Hz), 3.76 (8H, ddd, J=17.8, 4.7, 4.5 Hz), 2.97-3.16 (8H, m), 2.92 (3H, s), 2.24 (3H, s). Mass Spectrum (ESI) m/e=453.1 (M+1).

Example 40

N-(2,5-Di-4-morpholinylphenyl)-5,7-difluoro-3-methyl-2-(2-pyridinyl)-4-quinolinamine

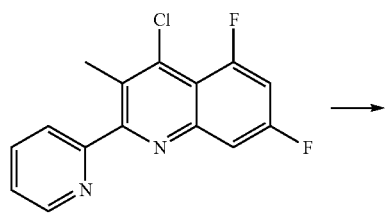

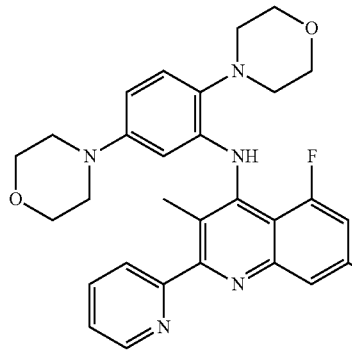

Prepared according to Procedure H using 4-chloro-5,7-difluoro-3-methyl-2-(pyridin-2-yl)quinoline (39.8 mg, 0.137 mmol) and 2,5-dimorpholinoaniline in toluene to give N-(2,5-di-4-morpholinylphenyl)-5,7-difluoro-3-methyl-2-(2-pyridinyl)-4-quinolinamine. ¹H NMR (CDCl₃) δ ppm 8.71 (1H, d, J=4.7 Hz), 8.15 (1H, d, J=10.2 Hz), 7.82-7.97 (2H, m), 7.64 (1H, d, J=9.4 Hz), 7.38 (1H, ddd, J=6.7, 4.7, 2.3 Hz), 7.10 (1H, d, J=8.6 Hz), 6.99 (1H, ddd, J=13.3, 8.6, 2.7 Hz), 6.48 (1H, dd, J=8.4, 2.5 Hz), 6.22 (1H, d, J=2.3 Hz), 3.90 (4H, t, J=4.3 Hz), 3.76-3.85 (4H, m), 3.05-3.19 (4H, m), 2.92 (4H, br. s.), 2.22 (3H, s). Mass Spectrum (ESI) m/e=518.2 (M+1).

Example 41

Preparation of N-(2,5-di-4-morpholinyl-3-pyridinyl)-5,7-difluoro-3-methyl-2-(2-(methylsulfanyl)phenyl)-4-quinolinamine 4-Chloro-5,7-difluoro-3-methyl-2-(2-(methylthio)phenyl)quinoline

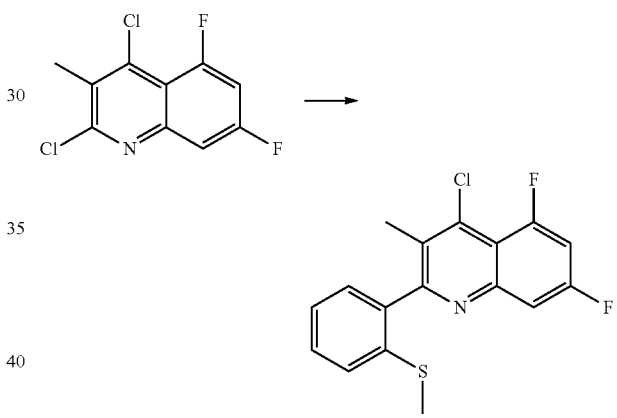

Prepared according to Procedure F using 2,4-dichloro-5,7-difluoro-3-methylquinoline (550 mg, 2.22 mmol) and 2-(methylthio)phenylboronic acid to give 4-chloro-5,7-difluoro-3-methyl-2-(2-(methylthio)phenyl)quinoline. Mass Spectrum (ESI) m/e=336.1 (M+1).

N-(2,5-Di-4-morpholinyl-3-pyridinyl)-5,7-difluoro-3-methyl-2-(2-(methylsulfanyl)phenyl)-4-quinolinamine

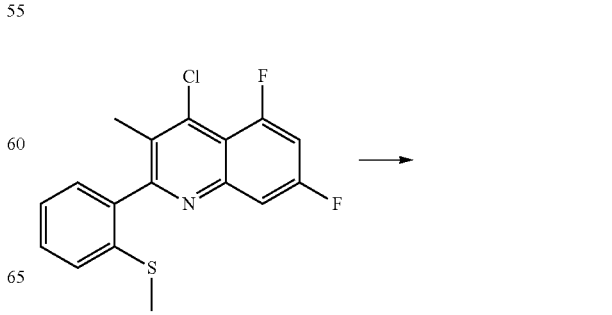

-continued

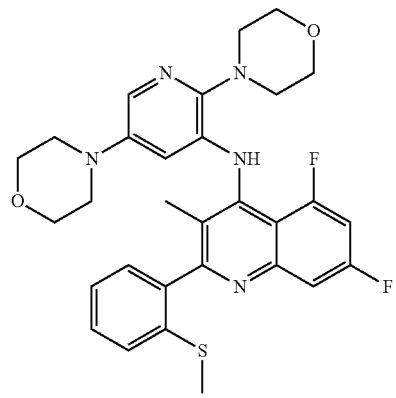

Prepared according to Procedure H using 4-chloro-5,7-difluoro-3-methyl-2-(2-(methylthio)phenyl)quinoline (75.0 mg, 0.22 mmol) and 2,5-dimorpholinopyridin-3-amine in toluene to give N-(2,5-di-4-morpholinyl-3-pyridinyl)-5,7-difluoro-3-methyl-2-(2-(methylsulfanyl)phenyl)-4-quinolinamine. $^1$H NMR (CDCl$_3$) δ ppm 7.83 (1H, d, J=12.1 Hz), 7.64 (1H, d, J=9.0 Hz), 7.61 (1H, d, J=2.7 Hz), 7.64 (1H, d, J=9.4 Hz), 7.43-7.50 (1H, m), 7.37-7.42 (1H, m), 7.34 (1H, td, J=7.2, 1.2 Hz), 7.25-7.30 (1H, m), 7.03 (1H, ddd, J=13.5, 8.5, 2.5 Hz), 6.42 (1H, br. s.), 3.92 (4H, br. s.), 3.73-3.83 (4H, m), 3.39 (2H, br. s.), 3.03-3.12 (4H, m), 2.85-3.03 (2H, m), 2.41 (3H, s), 1.97 (3H, s). Mass Spectrum (ESI) m/e=564.3 (M+1).

Example 42

N-(2,5-Di-4-morpholinyl-3-pyridinyl)-5,7-difluoro-3-methyl-2-(1-piperidinyl)-4-quinolinamine 4-Chloro-5,7-difluoro-3-methyl-2-(piperidin-1-yl)quinoline

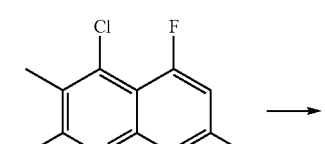

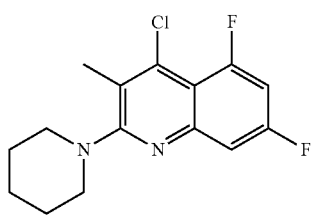

Prepared according to Procedure G using 2,4-dichloro-5,7-difluoro-3-methylquinoline (300 mg, 1.21 mmol) and piperidine in to give 4-chloro-5,7-difluoro-3-methyl-2-(piperidin-1-yl)quinoline. Mass Spectrum (ESI) m/e=297.1 (M+1).

N-(2,5-Di-4-morpholinyl-3-pyridinyl)-5,7-difluoro-3-methyl-2-(1-piperidinyl)-4-quinolinamine

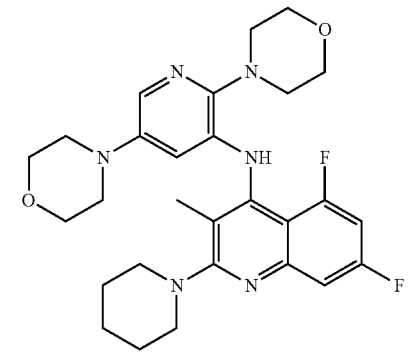

Prepared according to Procedure H using 4-chloro-5,7-difluoro-3-methyl-2-(piperidin-1-yl)quinoline (110 mg, 0.37 mmol) and 2,5-dimorpholinopyridin-3-amine in toluene to give N-(2,5-dimorpholinopyridin-3-yl)-5,7-difluoro-3-methyl-2-(piperidin-1-yl)quinolin-4-amine. $^1$H NMR (CDCl$_3$) δ ppm 7.62 (1H, br. s.), 7.53 (1H, d), 7.37 (1H, br. s.), 6.69-6.84 (1H, m), 6.29 (1H, d, J=2.3 Hz), 3.90 (4H, t, J=4.3 Hz), 3.72-3.84 (4H, m), 3.36 (4H, br. s.), 3.18 (2H, br. s.), 2.91-3.06 (4H, m), 2.09 (3H, s), 1.47-1.90 (8H, m). Mass Spectrum (ESI) m/e=525.3 (M+1).

Example 43

N-(5-(2-Amino-6-methyl-4-pyrimidinyl)-2-(4-morpholinyl)-3-pyridinyl)-5,7-difluoro-3-methyl-2-(2-pyridinyl)-4-quinolinamine N-(5-Bromo-2-morpholinopyridin-3-yl)-5,7-difluoro-3-methyl-2-(pyridin-2-yl)quinolin-4-amine

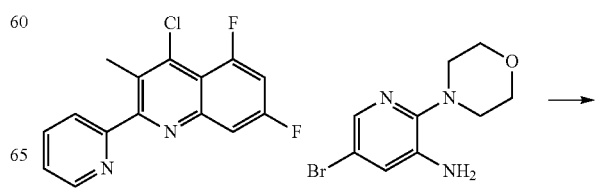

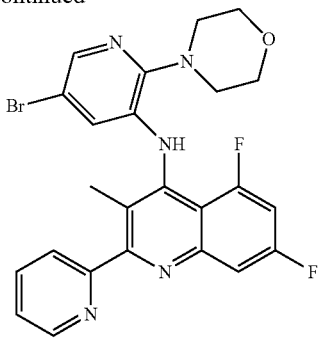

Prepared according to Procedure K, method 2 using 4-chloro-5,7-difluoro-3-methyl-2-(pyridin-2-yl)quinoline (538 mg, 1.85 mmol; described herein), 5-bromo-2-morpholinopyridin-3-amine (478 mg, 1.85 mmol; described herein), 4.0M hydrochloric acid in 1,4-dioxane (0.46 mL, 1.85 mmol), and NMP (1.2 mL). The reaction was then partitioned between EtOAc and water, and a solid that precipitated out of the aq. layer was isolated by filtration and identified as N-(5-bromo-2-morpholinopyridin-3-yl)-5,7-difluoro-3-methyl-2-(pyridin-2-yl)quinolin-4-amine, a yellow solid. Mass Spectrum (ESI) m/e=512.0 (M+1).

5-(5,7-Difluoro-3-methyl-2-(pyridin-2-yl)quinolin-4-ylamino)-6-morpholinopyridin-3-ylboronic acid

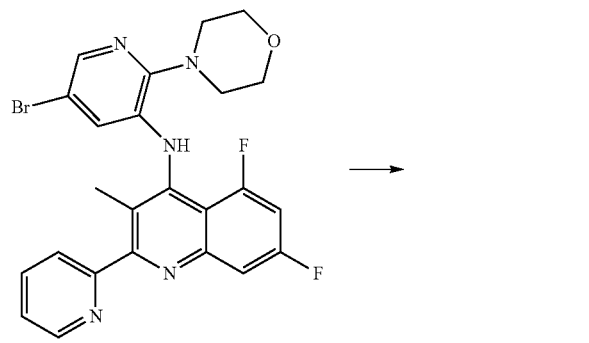

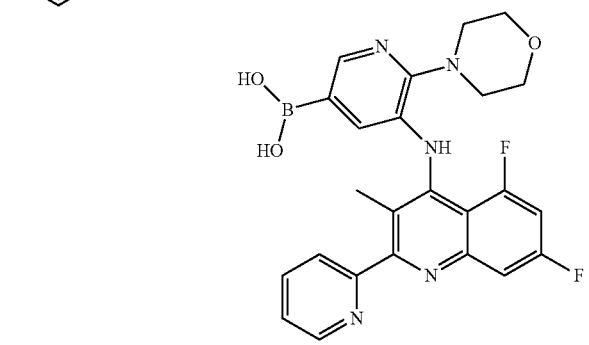

A solution of N-(5-bromo-2-morpholinopyridin-3-yl)-5,7-difluoro-3-methyl-2-(pyridin-2-yl)quinolin-4-amine (395 mg, 0.77 mmol; described herein), 4,4,4',4',5,5,5',5'-octam-ethyl-2,2'-bi(1,3,2-dioxaborolane) (215 mg, 0.85 mmol), bis(tricyclohexylphosphine)palladium(o) (25.7 mg, 0.039 mmol), potassium acetate (113 mg, 1.16 mmol), and 1,4-dioxane (10.6 mL) was stirred at 93° C. for 24 h. The reaction was then cooled to rt and partitioned between EtOAc and water. The organic layer was dried (magnesium sulfate) and concentrated, and chromatography afforded 5-(5,7-difluoro-3-methyl-2-(pyridin-2-yl)quinolin-4-ylamino)-6-morpholinopyridin-3-ylboronic acid as a yellow solid. Mass Spectrum (ESI) m/e=478.1 (M+1).

N-(5-(2-Amino-6-methyl-4-pyrimidinyl)-2-(4-morpholinyl)-3-pyridinyl)-5,7-difluoro-3-methyl-2-(2-pyridinyl)-4-quinolinamine

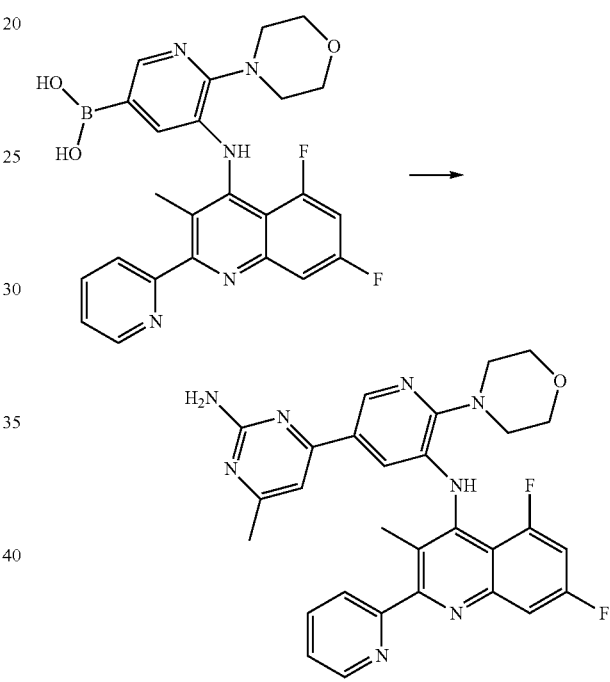

A solution of 5-(5,7-difluoro-3-methyl-2-(pyridin-2-yl)quinolin-4-ylamino)-6-morpholinopyridin-3-ylboronic acid (0.026 mmol, described herein), 4-chloro-6-methylpyrimidin-2-amine (3.7 mg, 0.026 mmol), sodium carbonate (8.18 mg, 0.077 mmol), dichlorobis(triphenylphosphine)palladium(ii) (1.8 mg, 2.57 µmol), 1,4-dioxane (560 µL) and water (140 µL) heated in a microwave at 120° C. for 60 min. The reaction was then cooled to rt and partitioned between EtOAc and water. The organic layer was dried (magnesium sulfate) and concentrated, and chromatography afforded N-(5-(2-amino-6-methyl-4-pyrimidinyl)-2-(4-morpholinyl)-3-pyridinyl)-5,7-difluoro-3-methyl-2-(2-pyridinyl)-4-quinolinamine as a yellow solid. $^1$H NMR (400 MHz, chloroform-d) δ ppm 8.72-8.81 (1H, m), 8.52-8.61 (1H, m), 7.85-7.96 (2H, m), 7.61-7.71 (1H, m), 7.52-7.61 (1H, m), 7.47-7.52 (1H, m), 7.41 (1H, m), 7.03 (1H, m), 6.84-6.93 (1H, m), 5.22 (2H, br. s.), 3.94 (4H, br. s.), 3.45-3.73 (2H, m), 3.00-3.40 (2H, br. s.), 2.33-2.52 (3H, m), 2.15-2.29 (3H, m). Mass Spectrum (ESI) m/e=541.0 (M+1).

Example 44

N-(2,5-Di-4-morpholinyl-3-pyridinyl)-5,7-difluoro-3-methyl-2-(2-(methylsulfonyl)phenyl)-4-quinolinamine 4-Chloro-5,7-difluoro-3-methyl-2-(2-(methylsulfonyl)phenyl)quinoline

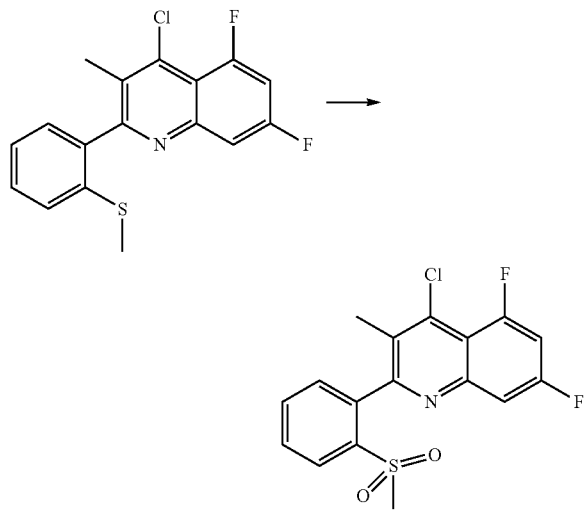

The 4-chloro-5,7-difluoro-3-methyl-2-(2-(methylthio)phenyl)quinoline (300 mg, 0.893 mmol) was dissolved in chloroform (8 mL) and Oxone™ (1.65 g, 2.68 mmol) and wet aluminum(III) oxide (910 mg, 8.90 mmol) was added. The heterogeneous mixture was stirred vigorously at 65° C. and refluxed for five h. Another portion of Oxone™ (1.65 g, 2.68 mmol) and aluminum(III) oxide (910 mg, 8.90 mmol) was added and the reaction was stirred vigorously overnight at 65° C. The reaction was cooled to rt and slurried in DCM and filtered. The filtrate was concentrated and the crude product was purified by medium pressure chromatography (silica gel, 0 to 50% EtOAc:hexanes) to give 4-chloro-5,7-difluoro-3-methyl-2-(2-(methylsulfonyl)phenyl)quinoline. Mass Spectrum (ESI) m/e=368.0 (M+1).

N-(2,5-Di-4-morpholinyl-3-pyridinyl)-5,7-difluoro-3-methyl-2-(2-(methylsulfonyl)phenyl)-4-quinolinamine

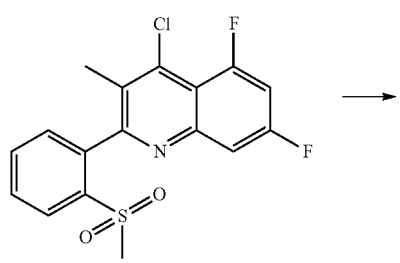

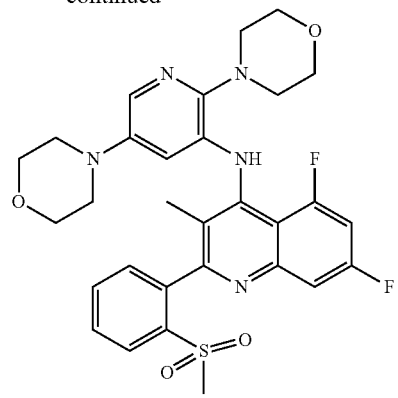

Prepared according to Procedure H using 4-chloro-5,7-difluoro-3-methyl-2-(2-(methylsulfonyl)phenyl)quinoline (70.0 mg, 0.190 mmol) and 2,5-dimorpholinopyridin-3-amine in toluene to give N-(2,5-di-4-morpholinyl-3-pyridinyl)-5,7-difluoro-3-methyl-2-(2-(methylsulfonyl)phenyl)-4-quinolinamine. $^1$H NMR (CDCl$_3$) δ ppm 8.21 (1H, d, J=7.8 Hz), 7.84 (1H, d, J=11.7.0 Hz), 7.80 (1H, td, J=7.5, 1.4 Hz), 7.70 (1H, td, J=7.7, 1.4 Hz), 7.54 (1H, br. s.), 7.50 (1H, d, J=9.4), 7.41 (1H, d, J=7.4 Hz), 7.06 (1H, ddd, J=13.5, 8.6, 2.5 Hz), 6.52 (1H, br. s.), 3.84-4.03 (4H, m), 3.70-3.83 (4H, m), 3.32-3.56 (2H, m), 2.87-3.19 (9H, m), 1.92 (3H, s). Mass Spectrum (ESI) m/e=596.2 (M+1).

Example 45

N-(2,5-Di-4-morpholinyl-3-pyridinyl)-5,8-difluoro-3-methyl-2-(2-pyridinyl)-4-quinolinamine Ethyl 3-(2,5-difluorophenylamino)-2-methyl-3-oxopropanoate

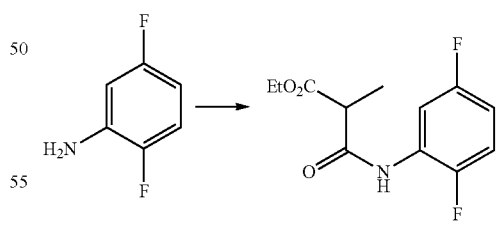

Prepared according to Procedure A using 2,5-difluoroaniline (5.00 g, 38.7 mmol) and diethyl 2-methylmalonate to give ethyl 3-(2,5-difluorophenylamino)-2-methyl-3-oxopropanoate. Mass Spectrum (ESI) m/e=258.1 (M+1).

3-(2,5-Difluorophenylamino)-2-methyl-3-oxopropanoic acid

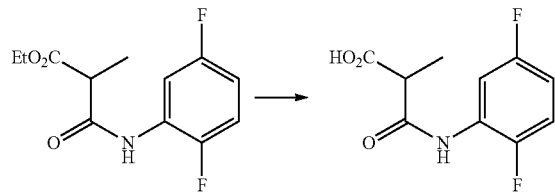 [SMILES: CCOC(=O)C(C)C(=O)Nc1cc(F)ccc1F ; CC(C(=O)O)C(=O)Nc1cc(F)ccc1F]

Prepared according to Procedure B using ethyl 3-(2,5-difluorophenylamino)-2-methyl-3-oxopropanoate (3.32 g, 12.9 mmol) to give 3-(2,5-difluorophenylamino)-2-methyl-3-oxopropanoic acid. Mass Spectrum (ESI) m/e=230.1 (M+1).

5,8-Difluoro-3-methylquinoline-2,4-diol

Prepared according to Procedure C using 3-(2,5-difluorophenylamino)-2-methyl-3-oxopropanoic acid (2.65 g, 11.6 mmol) to give 5,8-difluoro-3-methylquinoline-2,4-diol. Mass Spectrum (ESI) m/e=212.1 (M+1).

2,4-Dichloro-5,8-difluoro-3-methylquinoline

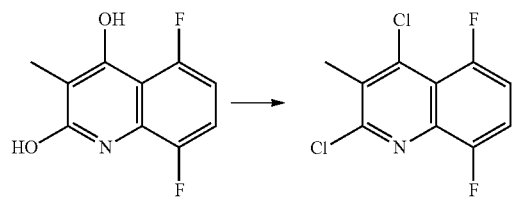

Prepared according to Procedure D using 5,8-difluoro-3-methylquinoline-2,4-diol (2.15 g, 10.2 mmol) to give 2,4-dichloro-5,8-difluoro-3-methylquinoline. Mass Spectrum (ESI) m/e=250.0 (M+1).

4-Chloro-5,8-difluoro-3-methyl-2-(pyridin-2-yl)quinoline

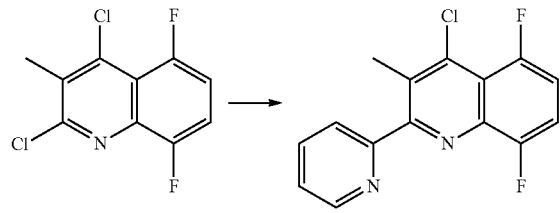 [SMILES: Cc1c(Cl)nc2c(F)ccc(F)c2c1Cl ; Cc1c(-c2ccccn2)nc2c(F)ccc(F)c2c1Cl]

Prepared according to Procedure E using 2,4-dichloro-5,8-difluoro-3-methylquinoline (500 mg, 2.02 mmol) to give 4-chloro-5,8-difluoro-3-methyl-2-(pyridin-2-yl)quinoline. Mass Spectrum (ESI) m/e=291.1 (M+1).

N-(5-Bromo-2-morpholinopyridin-3-yl)-5,8-difluoro-3-methyl-2-(pyridin-2-yl)quinolin-4-amine

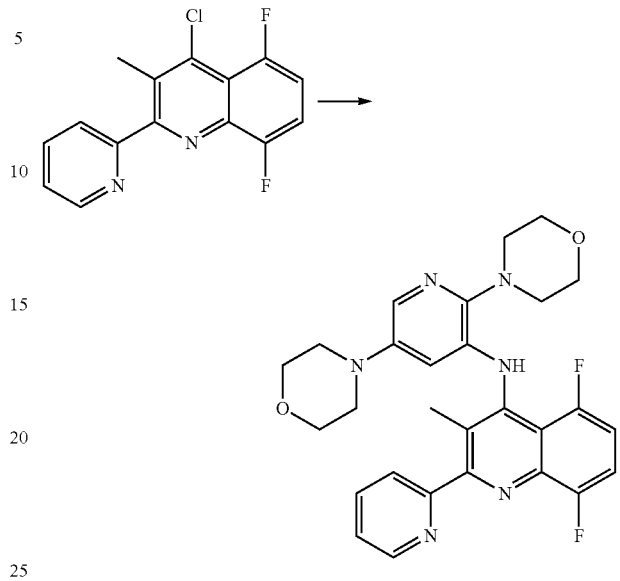

Prepared according to the acid catalyzed Procedure K, Method 2 using 4-chloro-5,8-difluoro-3-methyl-2-(pyridin-2-yl)quinoline (300 mg, 1.03 mmol) and 5-bromo-2-morpholinopyridin-3-amine to give N-(5-bromo-2-morpholinopyridin-3-yl)-5,8-difluoro-3-methyl-2-(pyridin-2-yl)quinolin-4-amine. Mass Spectrum (ESI) m/e=512.0 (M+1).

N-(2,5-Di-4-morpholinyl-3-pyridinyl)-5,8-difluoro-3-methyl-2-(2-pyridinyl)-4-quinolinamine

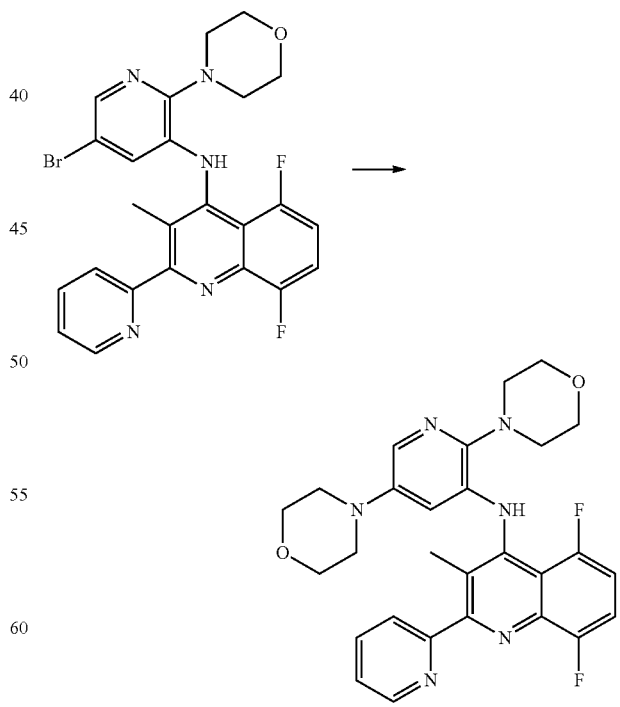

Prepared according to Procedure H using N-(5-bromo-2-morpholinopyridin-3-yl)-5,8-difluoro-3-methyl-2-(pyridin-2-yl)quinolin-4-amine (40.0 mg, 0.131 mmol) and morpholine in toluene to give N-(2,5-di-4-morpholinyl-3-pyridinyl)-5,8-difluoro-3-methyl-2-(2-pyridinyl)-4-quinolinamine. $^1$H NMR (CDCl$_3$) δ ppm 8.68 (1H, d, J=3.9 Hz), 8.00 (1H, d, J=7.8 Hz), 7.78-7.96 (2H, m), 7.63 (1H, d, J=2.3 Hz), 7.34-7.44 (1H, m), 7.28-7.34 (1H, m), 7.11 (1H, ddd, J=12.8, 8.7, 3.9 Hz), 6.47 (1H, d, J=2.3 Hz), 3.87-4.01 (4H, m), 3.76-3.87 (4H, m), 3.15-3.49 (4H, m), 2.98-3.13 (4H, m), 2.26 (3H, s). Mass Spectrum (ESI) m/e=519.2 (M+1).

Example 46

N-(2,5-Di-4-morpholinyl-3-pyridinyl)-3-ethyl-5,7-difluoro-2-(2-pyridinyl)-4-quinolinamine Ethyl 2-(3,5-difluorophenylcarbamoyl)butanoate

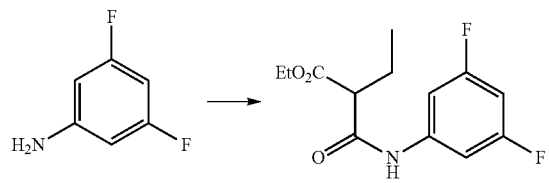 [SMILES: Nc1cc(F)cc(F)c1 ; CCOC(=O)C(CC)C(=O)Nc1cc(F)cc(F)c1]

Prepared according to Procedure A using 3,5-difluoroaniline (5.60 g, 43.4 mmol) and diethyl 2-ethylmalonate to give ethyl 2-(3,5-difluorophenylcarbamoyl)butanoate. Mass Spectrum (ESI) m/e=272.0 (M+1).

2-(3,5-Difluorophenylcarbamoyl)butanoic acid

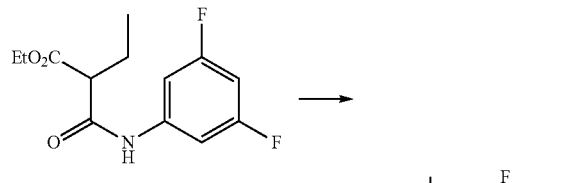

Prepared according to Procedure B using ethyl 2-(3,5-difluorophenyl carbamoyl)-butanoate (5.65 g, 20.8 mmol) to give 2-(3,5-difluorophenylcarbamoyl)butanoic acid. Mass Spectrum (ESI) m/e=244.1 (M+1).

3-Ethyl-5,7-difluoroquinoline-2,4-diol

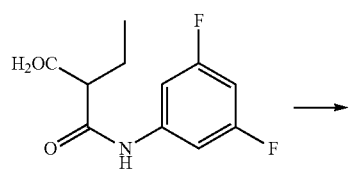

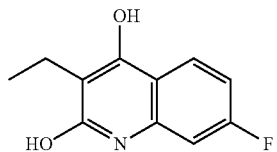

Prepared according to Procedure C using 2-(3,5-difluorophenylcarbamoyl)butanoic acid (5.07 g, 20.9 mmol) to give 3-ethyl-5,7-difluoroquinoline-2,4-diol. Mass Spectrum (ESI) m/e=226.1 (M+1).

2,4-Dichloro-3-ethyl-5,7-difluoroquinoline

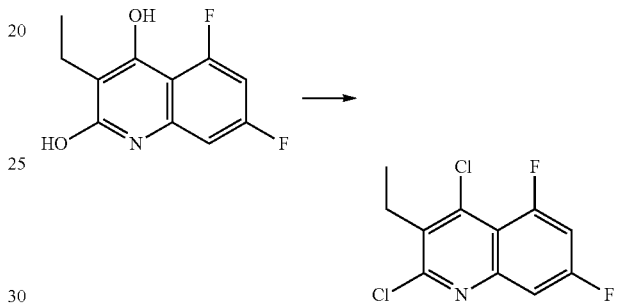

Prepared according to Procedure D using 3-ethyl-5,7-difluoroquinoline-2,4-diol (3.00 g, 13.3 mmol) to give 2,4-dichloro-3-ethyl-5,7-difluoroquinoline. Mass Spectrum (ESI) m/e=262.0 (M+1).

4-Chloro-3-ethyl-5,7-difluoro-2-(pyridin-2-yl)quinoline

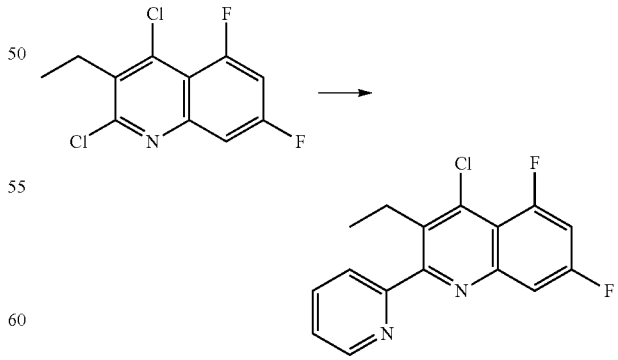

Prepared according to Procedure E using 2,4-dichloro-3-ethyl-5,7-difluoroquinoline (350 mg, 1.34 mmol) to give 4-chloro-3-ethyl-5,7-difluoro-2-(pyridin-2-yl)quinoline. Mass Spectrum (ESI) m/e=305.0 (M+1).

101

N-(2,5-Di-4-morpholinyl-3-pyridinyl)-3-ethyl-5,7-difluoro-2-(2-pyridinyl)-4-quinolinamine

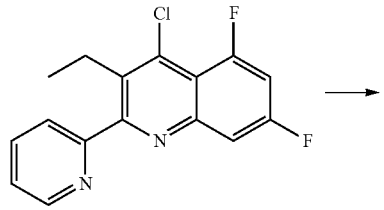

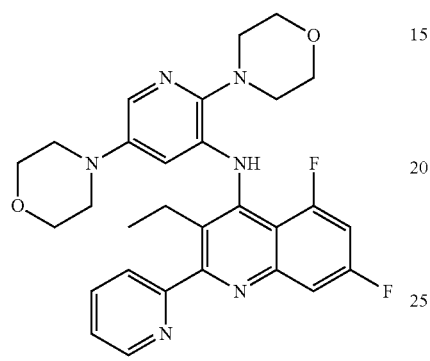

Prepared according to Procedure H using 4-chloro-3-ethyl-5,7-difluoro-2-(pyridin-2-yl)quinoline (40.0 mg, 0.131 mmol) and 2,5-dimorpholinopyridin-3-amine in toluene to give N-(2,5-di-4-morpholinyl-3-pyridinyl)-3-ethyl-5,7-difluoro-2-(2-pyridinyl)-4-quinolinamine. $^1$H NMR (CDCl$_3$) δ ppm 8.70 (1H, td, J=2.4, 1.0 Hz), 7.79-8.00 (2H, m), 7.53-7.66 (2H, m), 7.45 (1H, d, J=6.3 Hz), 7.40 (1H, ddd, J=7.3, 4.8, 1.6 Hz), 6.98 (1H, ddd, J=12.8, 8.7, 2.6 Hz), 6.43 (1H, d, J=2.3 Hz), 3.87-4.07 (4H, m), 3.73-3.82 (4H, m), 3.15-3.35 (4H, m), 2.93-3.03 (4H, m), 2.70 (2H, br. s.), 0.98 (3H, t, J=7.5 Hz). Mass Spectrum (ESI) m/e=533.2 (M+1).

Example 47

N-(2,5-Di-4-morpholinyl-3-pyridinyl)-5,7-difluoro-2-(6-methoxy-2-pyridinyl)-3-methyl-4-quinolinamine 4-Chloro-5,7-difluoro-2-(6-methoxypyridin-2-yl)-3-methylquinoline

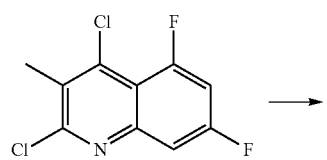

102

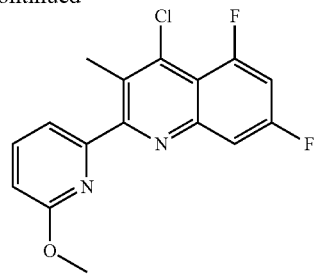

Prepared according to Procedure E using 2,4-dichloro-5,7-difluoro-3-methylquinoline (250 mg, 1.01 mmol) and 2-methoxy-6-(tributylstannyl)pyridine to give 4-chloro-5,7-difluoro-2-(6-methoxypyridin-2-yl)-3-methylquinoline. Mass Spectrum (ESI) m/e=321.1 (M+1).

N-(2,5-Di-4-morpholinyl-3-pyridinyl)-5,7-difluoro-2-(6-methoxy-2-pyridinyl)-3-methyl-4-quinolinamine

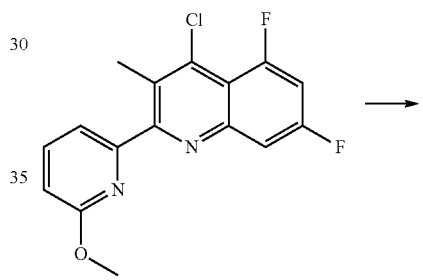

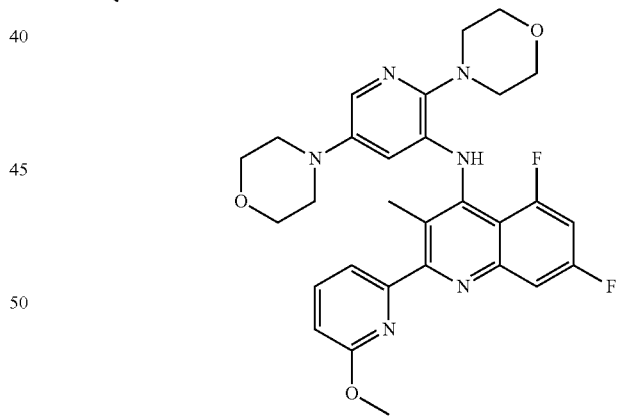

Prepared according to Procedure H using 4-chloro-5,7-difluoro-2-(6-methoxypyridin-2-yl)-3-methylquinoline (40.0 mg, 0.125 mmol) and 2,5-dimorpholinopyridin-3-amine in toluene to give N-(2,5-di-4-morpholinyl-3-pyridinyl)-5,7-difluoro-2-(6-methoxy-2-pyridinyl)-3-methyl-4-quinolinamine. $^1$H NMR (CDCl$_3$) δ ppm 7.78-7.87 (1H, m), 7.77 (1H, dd,), 7.61-7.68 (2H, m), 7.56 (1H, dd, J=7.2, 0.8 Hz), 6.98-7.09 (1H, m), 6.86 (1H, dd, J=8.2, 0.8 Hz), 6.45 (1H, d, J=2.5 Hz), 3.93 (3H, s), 3.86-4.01 (4H, m), 3.71-3.83 (4H, m), 3.09-3.53 (4H, m), 3.02-3.08 (4H, m), 2.26 (3H, s). Mass Spectrum (ESI) m/e=549.3 (M+1).

Example 48

1-(4-((2,5-Di-4-morpholinyl-3-pyridinyl)amino)-5,7-difluoro-3-methyl-2-quinolinyl)-2-piperidinone 1-(4-Chloro-5,7-difluoro-3-methylquinolin-2-yl)piperidin-2-one

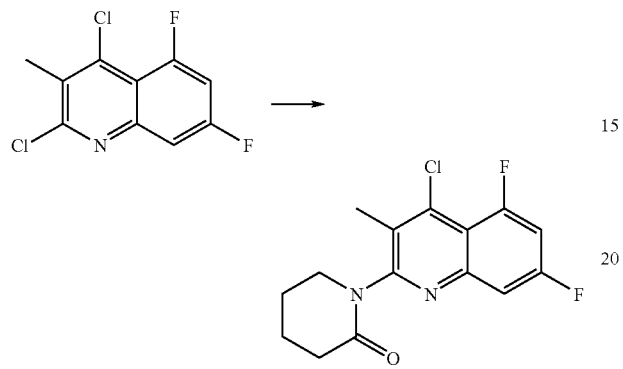

Prepared according to Procedure I using 2,4-dichloro-5,7-difluoro-3-methylquinoline (250 mg, 1.01 mmol) and piperidin-2-one to give 1-(4-chloro-5,7-difluoro-3-methylquinolin-2-yl)piperidin-2-one. Mass Spectrum (ESI) m/e=311.0 (M+1).

1-(4-((2,5-Di-4-morpholinyl-3-pyridinyl)amino)-5,7-difluoro-3-methyl-2-quinolinyl)-2-piperidinone

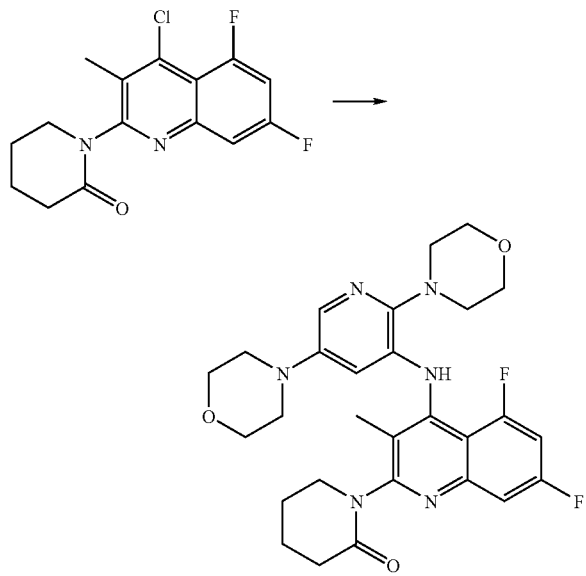

Prepared according to Procedure H using 1-(4-chloro-5,7-difluoro-3-methylquinolin-2-yl)piperidin-2-one (35.0 mg, 0.113 mmol) and 2,5-dimorpholinopyridin-3-amine in toluene to give 1-(4-((2,5-di-4-morpholinyl-3-pyridinyl)amino)-5,7-difluoro-3-methyl-2-quinolinyl)-2-piperidinone. $^1$H NMR (CDCl$_3$) δ ppm 8.01 (1H, br. s.), 7.60 (1H, d, J=2.5 Hz), 7.47 (1H, d, J=9.8 Hz), 6.99 (1H, ddd, J=13.7, 8.6, 2.5 Hz), 6.51 (1H, br. s.), 4.33 (1H, br. s.), 3.83-4.01 (4H, m), 3.77-3.83 (4H, m), 3.48-3.59 (1H, m), 3.41 (2H, br. s.), 3.16 (4H, br. s,), 2.89-3.07 (2H, m), 2.50-2.61 (2H, m), 1.88-2.19 (7H, m). Mass Spectrum (ESI) m/e=539.2 (M+1).

Example 49

N-(2,5-Di-4-morpholinyl-3-pyridinyl)-5,7-difluoro-N,3-dimethyl-2-(2-pyridinyl)-4-quinolinamine N-(5-Bromo-2-morpholinopyridin-3-yl)-5,7-difluoro-N,3-dimethyl-2-(pyridin-2-yl)quinolin-4-amine

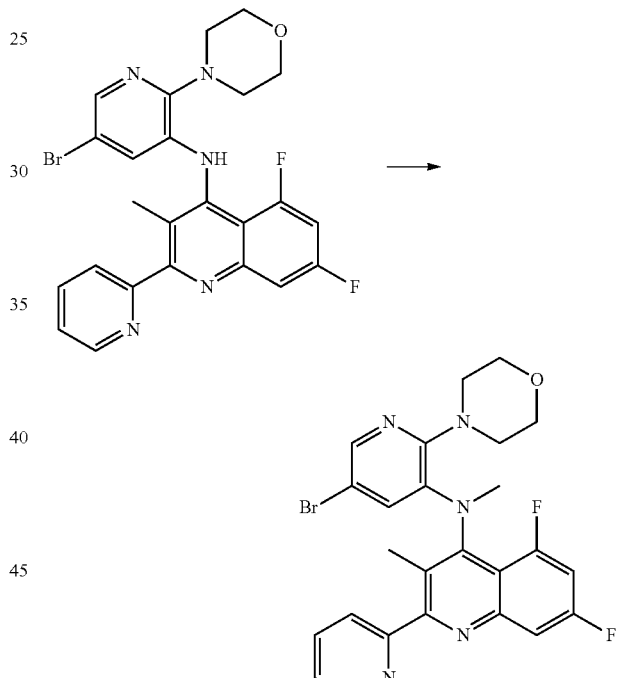

To a stirred solution of N-(5-bromo-2-morpholinopyridin-3-yl)-5,7-difluoro-3-methyl-2-(pyridin-2-yl)quinolin-4-amine (described herein) (18.0 mg, 0.035 mmol) in N,N-dimethylformamide (2 mL) was added 60% sodium hydride (2.11 mg, 0.053 mmol), followed by iodomethane (7.5 mg, 0.053 mmol). Stirring continued for 1.5 h. Water was added to quench the reaction and the resulting mixture was extracted with EtOAc (3×10 mL). The combined organic layers was dried over magnesium sulfate, filtered and concentrated in vacuo. The crude product was purified by column chromatography on silica gel (0-60% EtOAc/hexanes) to give N-(5-bromo-2-morpholinopyridin-3-yl)-5,7-difluoro-N,3-dimethyl-2-(pyridin-2-yl)quinolin-4-amine as a yellow foam. Mass Spectrum (ESI) m/e=526.2, (M+1).

N-(2,5-Di-4-morpholinyl-3-pyridinyl)-5,7-difluoro-N,3-dimethyl-2-(2-pyridinyl)-4-quinolinamine

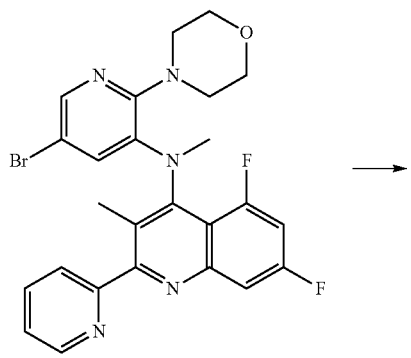

A stirred mixture of N-(5-bromo-2-morpholinopyridin-3-yl)-5,7-difluoro-N,3-dimethyl-2-(pyridin-2-yl)quinolin-4-amine (12.0 mg, 0.023 mmol), tris(dibenzylideneacetone) dipalladium (0) (2.1 mg, 2.280 µmol), 2-dicyclohexylphosphino-2,4,6,-triisopropylbiphenyl (2.2 mg, 4.56 µmol), and sodium tert-butoxide (15 mg, 0.153 mmol) in toluene (2 mL) was purged three times with argon and placed under vacuum three times. Before heating, morpholine (9.93 µL, 0.114 mmol) was added and the mixture was heated to 100° C. Stirring continued for 21 h. After which the reaction was cooled to rt, diluted with water and extracted with EtOAc (3×10 mL). The combined organic layers were dried over magnesium sulfate, filtered and concentrated in vacuo. The crude product was dissolved in MeOH and purified by HPLC (10-90% of 0.1% TFA acetonitrile solution in 0.1% TFA water solution) to yield N-(2,5-di-4-morpholinyl-3-pyridinyl)-5,7-difluoro-N,3-dimethyl-2-(2-pyridinyl)-4-quinolinamine. $^1$H NMR (400 MHz, CD$_3$OD) δ ppm 8.66 (1H, d, J=4.7 Hz), 8.01 (1H, m), 7.78 (1H, d, J=7.8 Hz), 7.61-7.67 (1H, m), 7.60 (1H, d, J=2.7 Hz), 7.51 (1H, m), 7.23 (1H, m), 7.10 (1H, br. s.), 3.82-3.92 (4H, m), 3.35-3.44 (4H, m), 3.31 (4H, m), 3.17-3.28 (4H, m), 2.46 (3H, br. s.), 1.94-2.04 (3H, s); Mass Spectrum (ESI) m/e=533.2 (M+1).

Example 50 & 51

Preparation of N-(2,5-di-4-morpholinylphenyl)-5-fluoro-3,8-dimethyl-2-(2-pyridinyl)-4-quinolinamine (Example 50) and N-(2,5-di-4-morpholinyl-3-pyridinyl)-5-fluoro-3,8-dimethyl-2-(2-pyridinyl)-4-quinolinamine (Example 51)

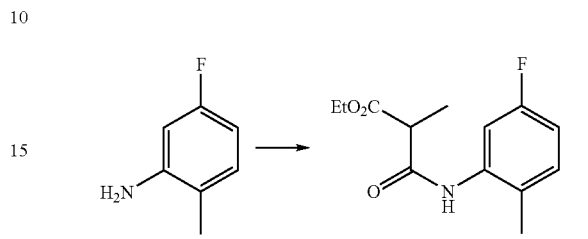

The ester was prepared according to Procedure A using diethyl 2-methylmalonate (6.18 mL, 36.0 mmol), pyridine (3.88 mL, 47.9 mmol) and 5-fluoro-2-methylaniline (3.00 g, 23.97 mmol). Heating continued for 4 days. The residue was purified by column chromatography on silica gel (0-30% EtOAc/hexanes) to give ethyl 3-(5-fluoro-2-methylphenylamino)-2-methyl-3-oxopropanoate as a tan solid. Mass Spectrum (ESI) m/e=254.2, (M+1).

3-(5-Fluoro-2-methylphenylamino)-2-methyl-3-oxopropanoic acid

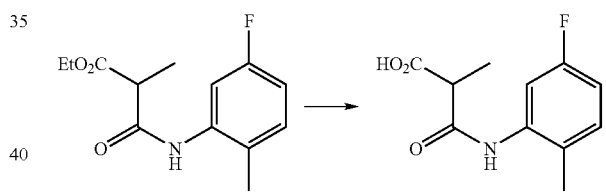

The acid was prepared according to Procedure B using ethyl 3-(5-fluoro-2-methylphenylamino)-2-methyl-3-oxopropanoate (2.45 g, 9.67 mmol) in THF (10.0 mL). The crude product was used without further purification. Mass Spectrum (ESI) m/e=226.0, (M+1).

5-Fluoro-3,8-dimethylquinoline-2,4-diol

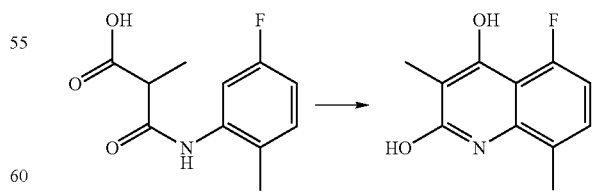

The diol was prepared according to Procedure C using (5-fluoro-2-methylphenylamino)-2-methyl-3-oxopropanoic acid (2.08 g, 9.24 mmol) and polyphosphoric acid (10 mL, 9.24 mmol) to give 5-fluoro-3,8-dimethylquinoline-2,4-diol. Mass Spectrum (ESI) m/e=208.1, (M+1).

2,4-Dichloro-5-fluoro-3,8-dimethylquinoline

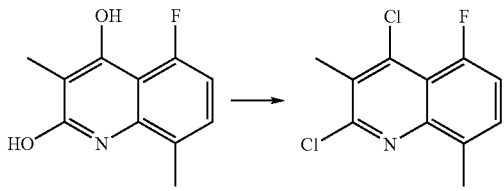

The dichloride was prepared according to Procedure D using 5-fluoro-3,8-dimethylquinoline-2,4-diol (1.9 g, 9.17 mmol) and phosphorus oxychloride (8.55 mL, 92 mmol) to give 2,4-dichloro-5-fluoro-3,8-dimethylquinoline. Mass Spectrum (ESI) m/e=244.1, (M+1).

4-Chloro-5-fluoro-3,8-dimethyl-2-(pyridin-2-yl) quinoline

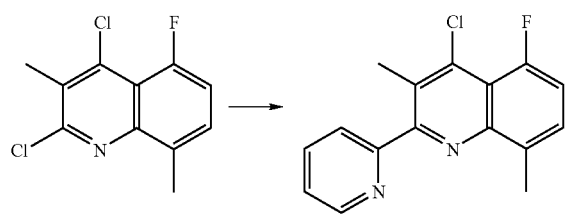 [SMILES: Cc1c(Cl)nc2c(C)ccc(F)c2c1Cl ; Cc1c(-c2ccccn2)nc2c(C)ccc(F)c2c1Cl]

The chloride was prepared according to Procedure E using 2,4,6-trichloro-7-fluoro-3-methylquinoline (0.50 g, 1.9 mmol), 2-(tributylstannyl)pyridine (0.77 mL, 2.08 mmol), palladium tetrakistriphenylphosphine (0.22 g, 0.19 mmol) in toluene (1.9 mL) to give 4-chloro-5-fluoro-3,8-dimethyl-2-(pyridin-2-yl)quinoline as a white solid. Mass Spectrum (ESI) m/e=307.0, (M+1).

N-(2,5-Di-4-morpholinylphenyl)-5-fluoro-3,8-dimethyl-2-(2-pyridinyl)-4-quinolinamine and N-(2,5-di-4-morpholinyl-3-pyridinyl)-5-fluoro-3,8-dimethyl-2-(2-pyridinyl)-4-quinolinamine

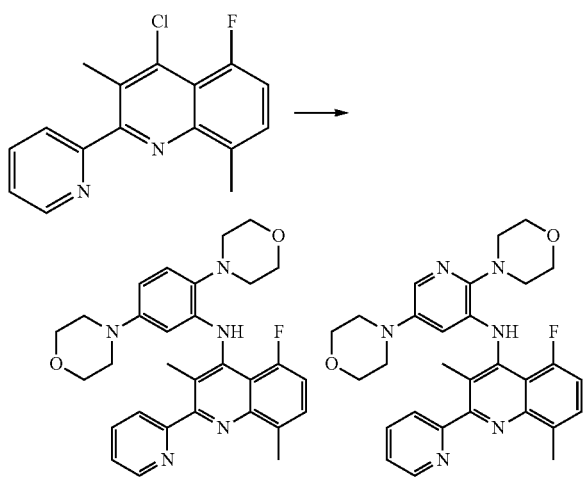

To a stirred solution of dicyclohexyl(2',4',6'-triisopropyl-biphenyl-2-yl)phosphine (27.0 mg, 0.056 mmol), 2,5-dimorpholinopyridin-3-amine (37.0 mg, 0.140 mmol), 2,5-dimorpholinoaniline (55.0 mg, 0.21 mmol), 4-chloro-5-fluoro-3,8-dimethyl-2-(pyridin-2-yl)quinoline (100.0 mg, 0.35 mmol) and $Pd_2dba_3$ (13.0 mg, 0.014 mmol) in toluene (3.5 mL) was added sodium t-butoxide (84.0 mg, 0.87 mmol). The reaction mixture was heated to 120° C. and stirred for 45 min. The reaction was cooled to rt and diluted with water (25 mL). The mixture was extracted with EtOAc (3×10 mL) and DCM (1×10 mL). The organic layers were dried over magnesium sulfate, filtered and concentrated in vacuo. The crude product was purified by column chromatography on silica gel (0 to 100% EtOAc in DCM) to give the desired products N-(2,5-di-4-morpholinylphenyl)-5-fluoro-3,8-dimethyl-2-(2-pyridinyl)-4-quinolinamine. $^1$H NMR (400 MHz, $CDCl_3$) δ ppm 8.69 (1H, br. m.), 8.22 (1H br m), 8.02-8.12 (1H, m), 7.89 (1H, br. m.), 7.40 (2H, m), 7.28 (1H, m), 6.98-7.15 (2H, m), 6.24 (1H, br. s.), 3.87-4.00 (4H, br m), 3.80 (4H, br m), 3.09 (8H, br. m.), 2.77 (3H, s), 2.32 (3H, s); Mass Spectrum (ESI) m/e=514.3 (M+1). Further elution gave N-(2,5-di-4-morpholinyl-3-pyridinyl)-5-fluoro-3,8-dimethyl-2-(2-pyridinyl)-4-quinolinamine. $^1$H NMR (400 MHz, $CDCl_3$) δ ppm 8.68 (1H, ddd, J=4.9, 1.8, 1.0 Hz), 8.08 (1H, d, J=7.8 Hz), 7.90 (1H, m), 7.82 (1H, br d), 7.60 (1H, d, J=2.5 Hz), 7.40-7.48 (1H, m), 7.37 (1H, m), 7.07 (1H, dd, J=13.6, 7.9 Hz), 6.47 (1H, br. s.), 3.88-4.00 (4H, m), 3.75-3.85 (4H, m), 3.23 (4H, br. s.), 3.03-3.13 (4H, m), 2.78 (3H, s), 2.31 (3H, s); Mass Spectrum (ESI) m/e=515.2 (M+1).

Example 52

Preparation of 6-chloro-N-(2,5-di-4-morpholinyl-3-pyridinyl)-5-fluoro-3-methyl-2-(2-pyridinyl)-4-quinolinamine

Ethyl 3-(4-chloro-3-fluorophenylamino)-2-methyl-3-oxopropanoate

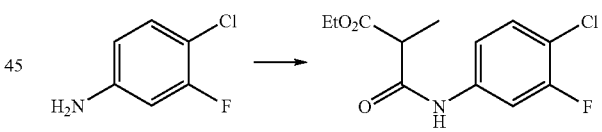

The ester was prepared according to Procedure A using diethyl 2-methylmalonate (5.32 mL, 30.9 mmol), pyridine (3.33 mL, 41.2 mmol) and 4-chloro-3-fluoroaniline (3.00 g, 20.6 mmol). The residue was purified by column chromatography on silica gel (0-30% EtOAc/hexanes) to give ethyl 3-(4-chloro-3-fluorophenylamino)-2-methyl-3-oxopropanoate as a red oil. Mass Spectrum (ESI) m/e=274.1 (M+1).

3-(4-Chloro-3-fluorophenylamino)-2-methyl-3-oxopropanoic acid

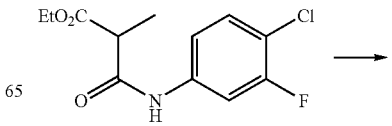

-continued

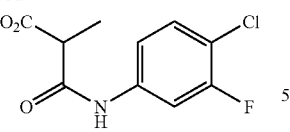

The acid was prepared according to Procedure B using ethyl 3-(4-chloro-3-fluorophenylamino)-2-methyl-3-oxopropanoate (2.75 g, 10.1 mmol) in THF (10.1 mL) to give 3-(4-chloro-3-fluorophenylamino)-2-methyl-3-oxopropanoic acid. Mass Spectrum (ESI) m/e=245.9 (M+1).

6-Chloro-7-fluoro-3-methylquinoline-2,4-diol and 6-chloro-5-fluoro-3-methylquinoline-2,4-diol

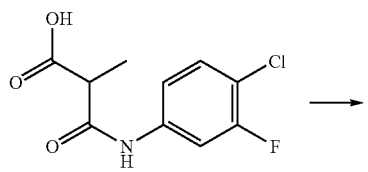

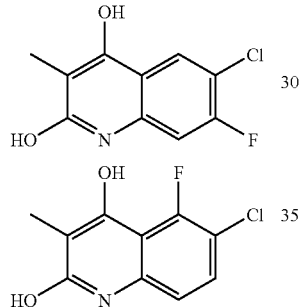

The diols were prepared according to Procedure C using 3-(4-chloro-3-fluorophenylamino)-2-methyl-3-oxopropanoic acid (2.5 g, 10.2 mmol) and polyphosphoric acid (10 mL, 10.2 mmol) to give a mixture of 6-chloro-7-fluoro-3-methylquinoline-2,4-diol and 6-chloro-5-fluoro-3-methylquinoline-2,4-diol. Mass Spectrum (ESI) m/e=228.1 (M+1).

2,4,6-Trichloro-7-fluoro-3-methylquinoline and 2,4,6-trichloro-5-fluoro-3-methylquinoline

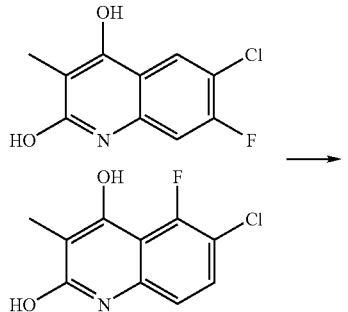

-continued

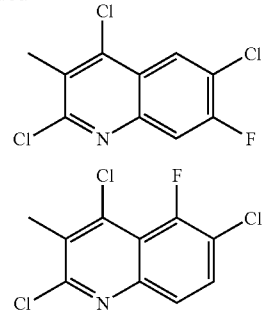

The trichloride was prepared according to Procedure D using a mixture of 6-chloro-7-fluoro-3-methylquinoline-2,4-diol and 6-chloro-5-fluoro-3-methylquinoline-2,4-diol (1.15 g, 5.1 mmol) to give a mixture of 2,4,6-trichloro-7-fluoro-3-methylquinoline and 2,4,6-trichloro-5-fluoro-3-methylquinoline (~4:1, as determined by $^1$H NMR analysis). $^1$H NMR (400 MHz, CDCl$_3$) δ ppm 8.26 (1H, d, J=7.8 Hz), 7.65-7.80 (1.4H, m), 2.65-2.72 (4H, m).

4,6-Dichloro-5-fluoro-3-methyl-2-(pyridin-2-yl) quinoline

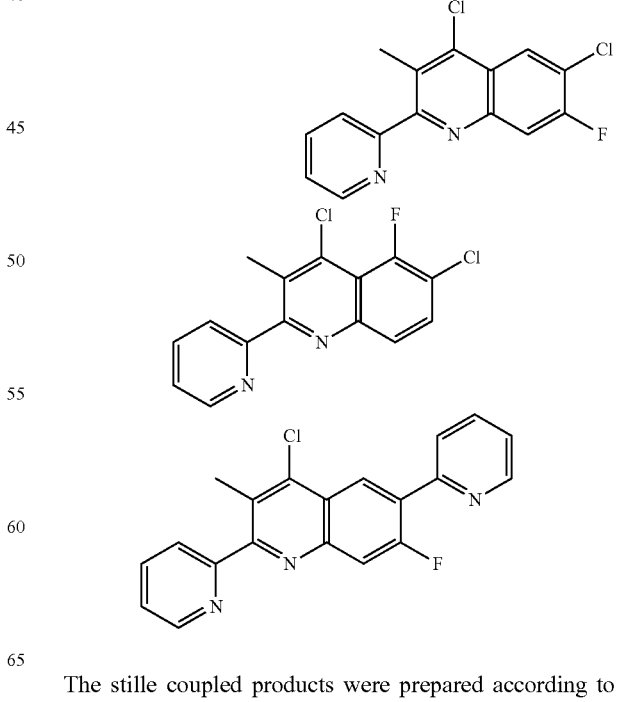

The stille coupled products were prepared according to Procedure E using a mixture of 2,4,6-trichloro-7-fluoro-3- methylquinoline and 2,4,6-trichloro-5-fluoro-3-methylquinoline (0.50 g, 1.90 mmol), 2-(tributylstannyl)pyridine (0.77 mL, 2.08 mmol), palladium tetrakistriphenylphosphine (0.22 g, 0.19 mmol) in toluene (1.90 mL) to give 4,6-dichloro-7-fluoro-3-methyl-2-(pyridin-2-yl)-quinoline as a white solid. Further elution gave 4,6-dichloro-5-fluoro-3-methyl-2-(pyridin-2-yl)quinoline as a white solid. Mass Spectrum (ESI) m/e=307.0 (M+1). Further elution gave 4-chloro-7-fluoro-3-methyl-2,6-di(pyridin-2-yl)-quinoline.

6-Chloro-N-(2,5-di-4-morpholinyl-3-pyridinyl)-5-fluoro-3-methyl-2-(2-pyridinyl)-4-quinolinamine

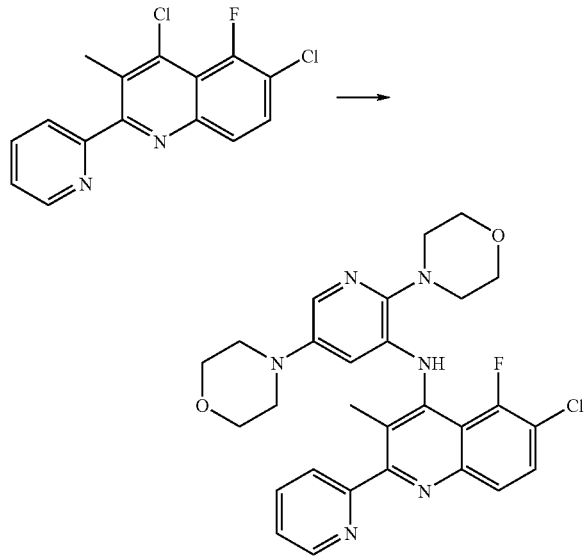

To a stirred solution of dicyclohexyl(2',4',6'-triisopropylbiphenyl-2-yl)phosphine (0.018 g, 0.038 mmol), 2,5-dimorpholinopyridin-3-amine (0.074 g, 0.281 mmol), 4,6-dichloro-5-fluoro-3-methyl-2-(pyridin-2-yl)quinoline (0.072 g, 0.234 mmol) and Pd$_2$dba$_3$ (8.59 mg, 9.38 μmol) in toluene (2.3 mL, 0.23 mmol) was added sodium t-butoxide (0.056 g, 0.59 mmol). The reaction mixture was heated to 120° C. and stirred for 45 min. The reaction was cooled to rt and diluted with water (25 mL). The mixture was extracted with EtOAc (2×10 mL) and DCM (1×10 mL). The organic layers were combined and dried over magnesium sulfate, filtered and concentrated in vacuo. The crude product was purified by column chromatography on silica gel (0 to 100% EtOAc/DCM) to give the desired product 6-chloro-N-(2,5-di-4-morpholinyl-3-pyridinyl)-5-fluoro-3-methyl-2-(2-pyridinyl)-4-quinolinamine. $^1$H NMR (400 MHz, CDCl$_3$) δ ppm 8.70 (1H, dd, J=4.7, 1.2 Hz), 7.90 (3H, m), 7.57-7.73 (3H, m), 7.39 (1H, m), 6.41 (1H, s), 3.94 (4H, br. s.), 3.80 (4H, br m), 3.22 (4H, br. s.), 3.06 (4H, br m), 2.26 (3H, s). Mass Spectrum (ESI) m/e=535.3 (M+1).

Example 53

Preparation of N-(2,5-di-4-morpholinyl-3-pyridinyl)-2-(2-pyridinyl)pyrido[2,3-d]pyrimidin-4-amine 2-(Pyridin-2-yl)pyrido[2,3-d]pyrimidin-4-ol

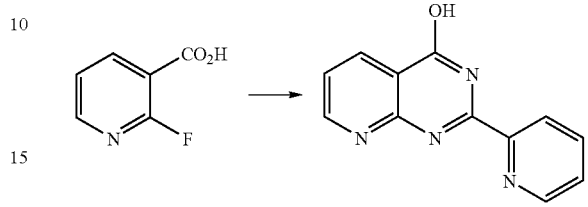

To a stirred solution of 2-fluoro-3-pyridinecarboxylic acid (6.3 g, 44.6 mmol) in DCM (112 mL) was added thionyl chloride (15.0 mL, 205 mmol). The reaction was heated to 40° C. and stirring continued for 3.5 h. After which, the reaction mixture was concentrated in vacuo to provide 2-fluoronicotinoyl chloride as a yellow solid. The product was taken on crude to the next step. To a stirred solution of 2-fluoronicotinoyl chloride (6.3 g, 39.5 mmol) in acetonitrile (197 mL, 39.5 mmol) was added diisopropylethylamine (27.5 mL, 158 mmol) followed by picolinimidamide (5.26 g, 43.4 mmol). The reaction was heated to 90° C. and stirring continued for 27 h. The reaction mixture was filtered and the filtrate was concentrated in vacuo. The residue was placed in Et$_2$O (100 mL) and the mixture was filtered and was further washed with Et$_2$O. The product was dried under vacuum and used crude in the next reaction. Mass Spectrum (ESI) m/e=225.1 (M+1).

4-Methoxy-2-(pyridin-2-yl)pyrido[2,3-d]pyrimidine

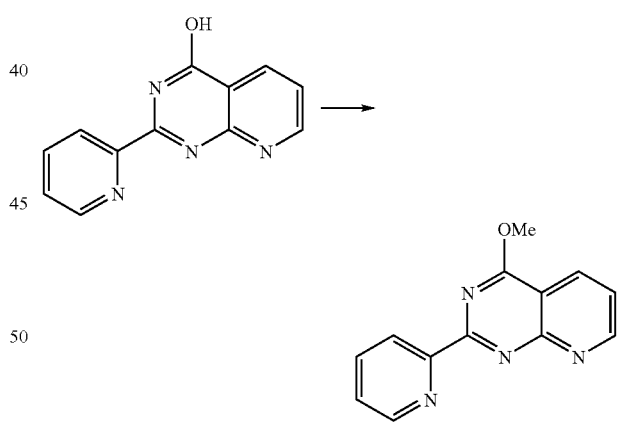

2-(Pyridin-2-yl)pyrido[2,3-d]pyrimidin-4-ol (2.00 g, 8.92 mmol) was slurried in phosphorus oxychloride (8.31 mL, 89 mmol) and heated to 100° C. for 2 h. After which the reaction was cooled to rt and then concentrated under reduced pressure. The residue was taken up with DCM (100 mL) and washed with water (2×100 mL). The organic layer was then dried over magnesium sulfate and the residue was purified by silica gel chromatography (0 to 30% MeOH in DCM) to give 4-methoxy-2-(pyridin-2-yl)pyrido[2,3-d]pyrimidine. $^1$H NMR (400 MHz, CD$_3$OD) δ ppm 9.37 (1H, dd, J=4.7, 2.0 Hz), 9.26 (1H, d, J=8.2 Hz), 9.05-9.11 (1H, m), 8.95-9.02 (1H, m), 8.90 (1H, m), 8.33 (1H, m), 7.95-8.01 (1H, m), 4.52 (3H, s).

113

N-(2,5-Di-4-morpholinyl-3-pyridinyl)-2-(2-pyridinyl)pyrido[2,3-d]pyrimidin-4-amine

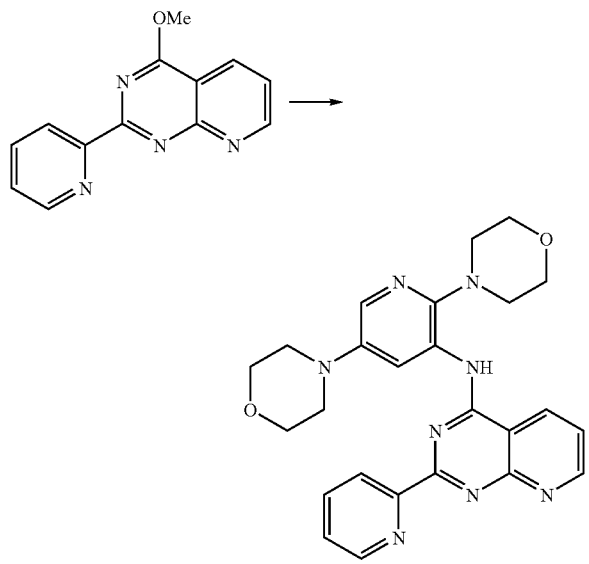

To a stirred solution of 4-methoxy-2-(pyridin-2-yl)pyrido[2,3-d]pyrimidine (0.050 g, 0.21 mmol) and 2,5-dimorpholinopyridin-3-amine (0.061 g, 0.23 mmol) in N,N-dimethylformamide (2.0 mL) was added 60% sodium hydride (9.23 mg, 0.23 mmol). The reaction was heated to 60° C. Stirring continued overnight. The reaction was cooled to rt and water was added to quench. The reaction was extracted with EtOAc (3×10 mL). The combined organic layer were dried over magnesium sulfate, filtered and concentrated in vacuo. The residue was purified by column chromatography on silica gel (0 to 30% MeOH in DCM) to give N-(2,5-di-4-morpholinyl-3-pyridinyl)-2-(2-pyridinyl)pyrido[2,3-d]pyrimidin-4-amine. $^1$H NMR (400 MHz, CDCl$_3$) δ ppm 9.75 (1H, d, J=2.7 Hz), 9.36 (1H, br. s.), 9.23 (1H, dd, J=4.4, 1.7 Hz), 8.87 (1H, d, J=8.0 Hz), 8.70 (1H, m), 8.30 (1H, dd, J=8.2, 1.8 Hz), 7.91 (1H, m), 7.84 (1H, d, J=2.7 Hz), 7.62 (1H, dd, J=8.2, 4.3 Hz), 7.42-7.49 (1H, m), 3.94-4.04 (8H, m), 3.43-3.55 (4H, br m), 3.09 (4H, br. m.). Mass Spectrum (ESI) m/e=471.3 (M+1).

Example 54

Preparation of N-(2,5-di-4-morpholinyl-3-pyridinyl)-N-ethyl-5,7-difluoro-3-methyl-2-(2-pyridinyl)-4-quinolinamine

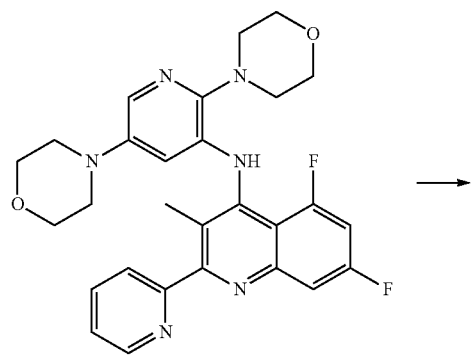

114

-continued

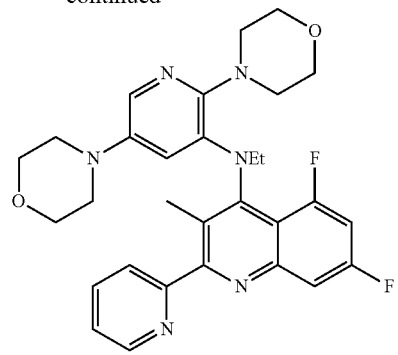

To a stirred solution of N-(2,5-dimorpholinopyridin-3-yl)-5,7-difluoro-3-methyl-2-(pyridin-2-yl)quinolin-4-amine (0.050 g, 0.096 mmol), in N,N-dimethylformamide (1.0 mL) was added iodoethane (0.030 g, 0.193 mmol) followed by 60% sodium hydride (7.71 mg, 0.193 mmol). The reaction was heated to 60° C. and stirring continued for 41 h. Water was added to quench the reaction and the resulting mixture was extracted with EtOAc (3×10 mL). The combined organic layers were dried over magnesium sulfate, filtered and concentrated in vacuo. The crude product was purified by column chromatography on basic alumina (0-50% EtOAc/hexane) to give N-(2,5-di-4-morpholinyl-3-pyridinyl)-N-ethyl-5,7-difluoro-3-methyl-2-(2-pyridinyl)-4-quinolinamine. $^1$H NMR (400 MHz, CDCl$_3$) δ ppm 8.66 (1H, d, J=4.3 Hz), 8.02 (1H, s), 7.83-7.90 (1H, m), 7.77-7.83 (1H, m), 7.61-7.69 (2H, m), 7.35 (1H, ddd, J=7.4, 4.9, 1.4 Hz), 6.86-7.00 (2H, m), 3.77-3.98 (6H, m), 3.21 (4H, br. s.), 2.95 (4H, s), 2.88 (3H, s), 2.48 (4H, br. s.), 2.12 (3H, s). Mass Spectrum (ESI) m/e=547.3 (M+1).

Example 55

Preparation of N-(2,5-di-4-morpholinyl-3-pyridinyl)-3-methyl-2,8-di-2-pyridinyl-4-quinolinamine Ethyl 3-(2-bromophenylamino)-2-methyl-3-oxopropanoate

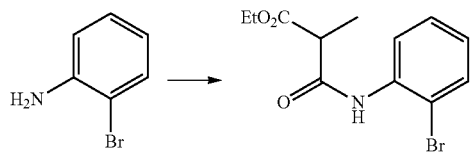

The ester was prepared according to Procedure A using diethyl 2-methylmalonate (6.00 mL, 34.9 mmol), pyridine (3.76 mL, 46.5 mmol) and 2-bromoaniline (4.00 g, 23.3 mmol). The residue was purified by column chromatography on silica gel (0-30% EtOAc/hexane) to give ethyl 3-(2-bromophenylamino)-2-methyl-3-oxopropanoate as a yellow solid. Mass Spectrum (ESI) m/e=300.0 (M+1).

3-(2-Bromophenylamino)-2-methyl-3-oxopropanoic acid

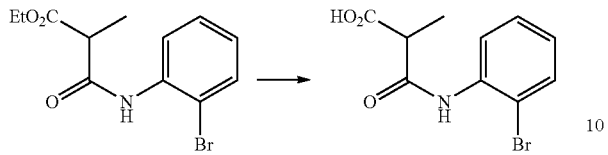

The acid was prepared according to Procedure B using ethyl 3-(2-bromophenylamino)-2-methyl-3-oxopropanoate (2.7 g, 9.00 mmol) in THF (9.00 mL) to give 3-(2-bromophenylamino)-2-methyl-3-oxopropanoic acid. Mass Spectrum (ESI) m/e=272.0 (M+1).

8-Bromo-2,4-dichloro-3-methylquinoline

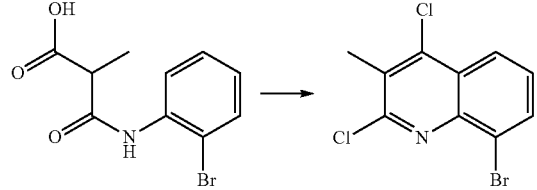

The diol was prepared according to Procedure C using 3-(2-bromophenylamino)-2-methyl-3-oxopropanoic acid (2.5 g, 9.19 mmol) and polyphosphoric acid (10 mL, 9.19 mmol) to give 8-bromo-3-methylquinoline-2,4-diol. The diol was used crude in the next reaction. The dichloride was prepared according to Procedure D using 8-bromo-3-methylquinoline-2,4-diol (2.00 g, 7.87 mmol). Heating continued for 19 h to give 8-bromo-2,4-dichloro-3-methylquinoline. Mass Spectrum (ESI) m/e=289.9 (M+1).

8-Bromo-4-chloro-3-methyl-2-(pyridin-2-yl)quinoline and 4-chloro-3-methyl-2,8-di(pyridin-2-yl)quinoline

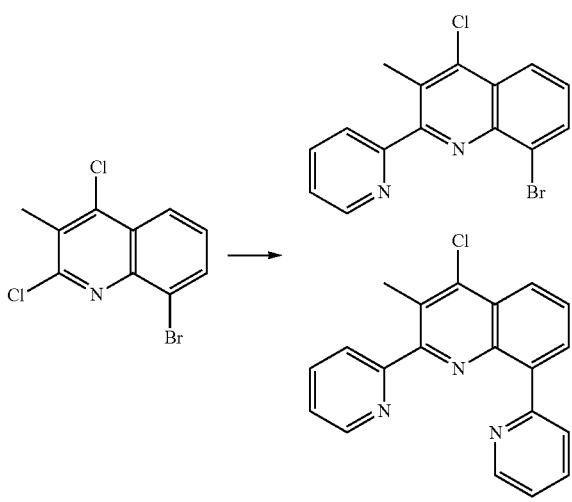 [SMILES: Cc1c(Cl)nc2c(Br)cccc2c1Cl ; Cc1c(-c2ccccn2)nc2c(-c3ccccn3)cccc2c1Cl ; Cc1c(-c2ccccn2)nc2c(Br)cccc2c1Cl]

The chlorides were prepared according to Procedure E using 8-bromo-2,4-dichloro-3-methylquinoline (0.32 g, 1.11 mmol), 2-(tributylstannyl)pyridine (0.45 mL, 1.23 mmol) and palladium tetrakistriphenylphosphine (0.13 g, 0.11 mmol) in toluene (2.2 mL) to give 8-bromo-4-chloro-3-methyl-2-(pyridin-2-yl)quinoline and further elution gave 4-chloro-3-methyl-2,8-di(pyridin-2-yl)quinoline as a white solid. Mass Spectrum (ESI) m/e=332.0 (M+1).

N-(2,5-Di-4-morpholinyl-3-pyridinyl)-3-methyl-2,8-di-2-pyridinyl-4-quinolinamine

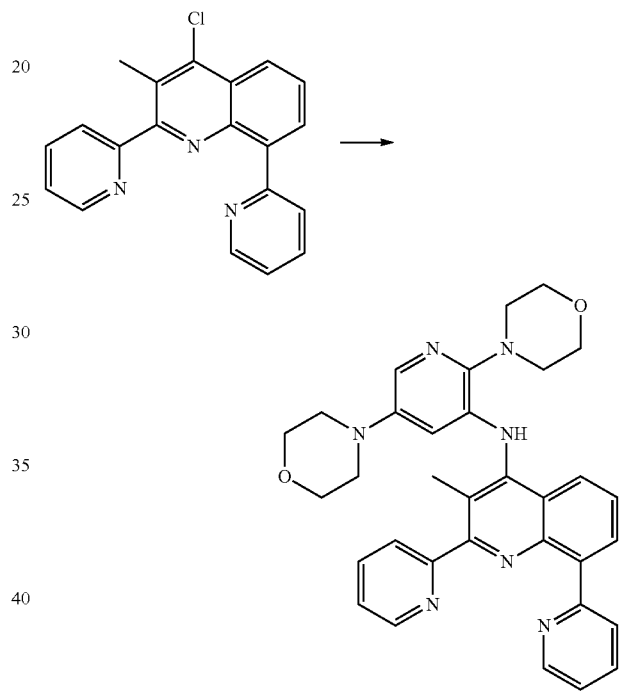

To a stirred solution of dicyclohexyl(2',4',6'-triisopropylbiphenyl-2-yl)phosphine (0.019 g, 0.040 mmol), 2,5-dimorpholinopyridin-3-amine (0.078 g, 0.30 mmol), 4-chloro-3-methyl-2,8-di(pyridin-2-yl)quinoline (0.082 g, 0.25 mmol) and $Pd_2dba_3$ (9.05 mg, 9.89 μmol) in toluene (2.5 mL) was added sodium t-butoxide (0.059 g, 0.62 mmol). The reaction mixture was heated to 120° C. and stirred for 45 min. The reaction was then cooled to rt and diluted with water (10 mL). The mixture was extracted with EtOAc (3×10 mL) and DCM (10 mL). The combined organic layers were dried over magnesium sulfate, filtered and concentrated in vacuo. The crude product was purified by column chromatography on basic alumina (0 to 100% EtOAc/DCM) to give the desired product N-(2,5-di-4-morpholinyl-3-pyridinyl)-3-methyl-2,8-di-2-pyridinyl-4-quinolinamine. $^1H$ NMR (400 MHz, $CDCl_3$) δ ppm 8.75-8.84 (1H, m), 8.69 (1H, br m), 8.28 (1H, d, J=7.6 Hz), 8.21 (1H, d, J=7.6 Hz), 7.97 (1H, d, J=7.6 Hz), 7.84 (2H, br. m.), 7.78 (1 h, m), 7.62 (2H, dd, J=16.0, 7.8 Hz), 7.28-7.35 (2H, br. m.), 6.82 (1H, br. s.), 6.25 (1H, br. s.), 3.95 (4H, br. s.), 3.73 (4H, br. s.), 3.27 (4H, br. s.), 2.93 (4H, br. s.), 2.52 (3H, s). Mass Spectrum (ESI) m/e=560.2 (M+1).

Example 56

Preparation of 8-chloro-N-(2,5-di-4-morpholinyl-3-pyridinyl)-3-methyl-2-(2-pyridinyl)-4-quinolinamine Ethyl 3-(2-chlorophenylamino)-2-methyl-3-oxopropanoate

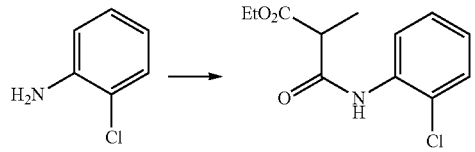 [SMILES: Nc1ccccc1Cl ; CCOC(=O)C(C)C(=O)Nc1ccccc1Cl]

The ester was prepared according to Procedure A using diethyl 2-methylmalonate (6.1 mL, 35.3 mmol), pyridine (3.80 mL, 47.0 mmol) and 2-chloroaniline (3.00 g, 23.52 mmol). The reaction mixture was heated for 6 days. The residue was purified by column chromatography on silica gel (0-30% EtOAc/hexanes) to give ethyl 3-(2-chlorophenylamino)-2-methyl-3-oxopropanoate. Mass Spectrum (ESI) m/e=256.1 (M+1).

3-(2-Chlorophenylamino)-2-methyl-3-oxopropanoic acid

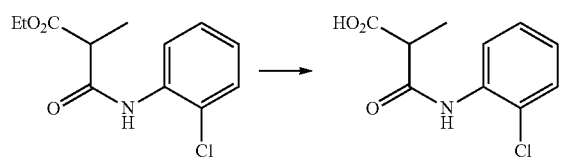 [SMILES: CCOC(=O)C(C)C(=O)Nc1ccccc1Cl ; CC(C(=O)O)C(=O)Nc1ccccc1Cl]

The acid was prepared according to Procedure B using ethyl 3-(2-chlorophenylamino)-2-methyl-3-oxopropanoate (1.8 g, 7.04 mmol) in THF (7.0 mL) to give 3-(2-chlorophenylamino)-2-methyl-3-oxopropanoic acid. Mass Spectrum (ESI) m/e=228.1 (M+1).

2,4,8-Trichloro-3-methylquinoline

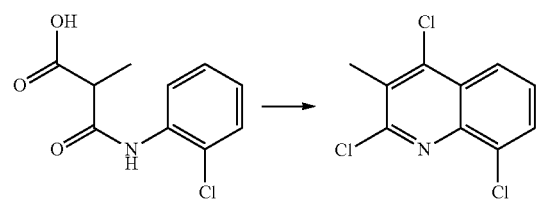

The diol was prepared according to Procedure C using 3-(2-chlorophenylamino)-2-methyl-3-oxopropanoic acid (1.6 g, 7.03 mmol) and polyphosphoric acid (10 mL, 7.03 mmol) to give 8-chloro-3-methylquinoline-2,4-diol. The diol was used crude in the next reaction. The trichloride was prepared according to Procedure D using 8-chloro-3-methylquinoline-2,4-diol (1.4 g, 6.68 mmol) and phosphorus oxychloride (6.23 mL, 66.8 mmol). The mixture was heated for 18 h to give 2,4,8-trichloro-3-methylquinoline. Mass Spectrum (ESI) m/e=245.9 (M+1).

4,8-Dichloro-3-methyl-2-(pyridin-2-yl)quinoline

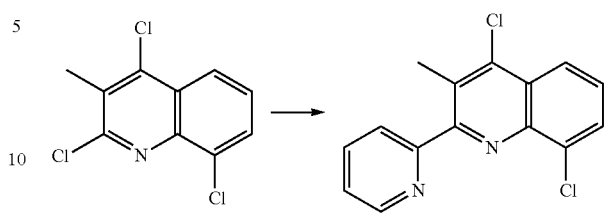

The dichloride was prepared according to Procedure E using 2,4,8-trichloro-3-methylquinoline (0.475 g, 1.927 mmol), 2-(tributylstannyl)pyridine (0.780 mL, 2.120 mmol), palladium tetrakistriphenylphosphine (0.223 g, 0.193 mmol) in toluene (3.85 mL) to give 4,8-dichloro-3-methyl-2-(pyridin-2-yl)quinoline as a white solid. Mass Spectrum (ESI) m/e=289.0 (M+1).

8-Chloro-N-(2,5-di-4-morpholinyl-3-pyridinyl)-3-methyl-2-(2-pyridinyl)-4-quinolinamine

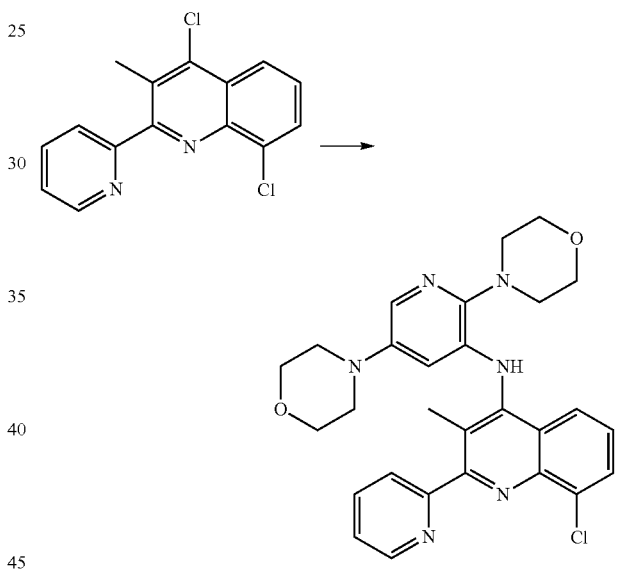

To a stirred solution of dicyclohexyl(2',4',6'-triisopropylbiphenyl-2-yl)phosphine (0.026 g, 0.055 mmol), 2,5-dimorpholinopyridin-3-amine (0.110 g, 0.415 mmol), 4,8-dichloro-3-methyl-2-(pyridin-2-yl)quinoline (0.10 g, 0.35 mmol) and Pd$_2$dba$_3$ (0.013 g, 0.014 mmol) in toluene (3.46 mL) was added sodium t-butoxide (0.083 g, 0.865 mmol). The reaction mixture was heated to 120° C. and stirred for 45 min. After which the reaction was cooled to rt and diluted with water (25 mL). The mixture was extracted with EtOAc (3×10 mL) and DCM (1×10 mL). The combined organic layers were dried over magnesium sulfate, filtered and concentrated in vacuo. The crude product was purified by column chromatography on basic alumina (0 to 50% EtOAc/hexane) to give the desired product 8-chloro-N-(2,5-di-4-morpholinyl-3-pyridinyl)-3-methyl-2-(2-pyridinyl)-4-quinolinamine. $^1$H NMR (400 MHz, CDCl$_3$) δ ppm 8.71 (1H, d, J=4.3 Hz), 8.15 (1H, d, J=7.8 Hz), 7.93 (1H, m), 7.82 (1H, d, J=7.4 Hz), 7.76 (1H, br. s.), 7.60 (1H, d, J=2.5 Hz), 7.34-7.47 (2H, m), 6.79 (1H, br. s.), 6.21 (1H, br. s.), 3.93 (4H, br. s.), 3.67-3.79 (4H, m), 3.25 (4H, br. s.), 2.93 (4H, br. s.), 2.49 (3H, s). Mass Spectrum (ESI) m/e=517.2 (M+1).

Example 57

Preparation of 5,7-difluoro-3-methyl-N-(5-(4-morpholinyl)-2-(1-piperidinyl)-3-pyridinyl)-2-(2-pyridinyl)-4-quinolinamine 5-Bromo-3-nitro-2-(piperidin-1-yl)pyridine

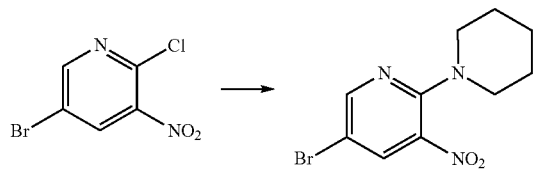 [SMILES: O=[N+]([O-])c1cc(Br)cnc1Cl ; O=[N+]([O-])c1cc(Br)cnc1N1CCCCC1]

To a 100 mL round bottom flask containing 5-bromo-2-chloro-3-nitropyridine (5.05 g, 21.3 mmol) in DMSO (20 mL) was added piperidine (4.2 mL, 42.6 mmol) dropwise. The reaction was heated to 60° C. and monitored with TLC and LC-MS. After 2.5 h, LC-MS showed that the reaction was complete. The mixture was cooled to rt then diluted with water. After extracting three times with EtOAc, the organic layers were combined then washed with brine and dried over anhydrous magnesium sulfate. After filtration, the mixture was concentrated under reduced pressure to afford an orange oil 5-bromo-3-nitro-2-(piperidin-1-yl)pyridine. $^1$H NMR (400 MHz, CDCl$_3$) δ ppm 8.30 (1H, d, J=2.3 Hz), 8.22 (1H, d, J=2.2 Hz), 3.39 (4H, d, J=5.7 Hz), 1.75 (6H, m).

5-Bromo-2-(piperidin-1-yl)pyridin-3-amine

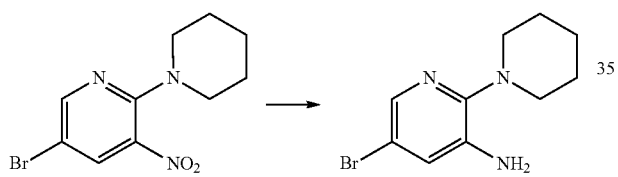

To a stirred mixture of 5-bromo-3-nitro-2-(piperidin-1-yl)pyridine (5.88 g, 20.5 mmol) in EtOAc (50 mL) was added tin(II) chloride dihydrate (23.5 g, 104 mmol) in portions. Upon complete addition of the reducing agent, the mixture was carefully heated to 90° C. After 1 h, the reaction was cooled in an ice bath, then washed with 1M NaOH, water, and brine. After drying over anhydrous sodium sulfate and filtration, the organic solvent was removed under reduced pressure. The residue was purified with silica gel chromatography (0-15% EtOAc in hexanes) to provide a white solid as 5-bromo-2-(piperidin-1-yl)pyridin-3-amine. $^1$H NMR (400 MHz, DMSO-d$_6$) δ ppm 7.57 (1H, d, J=2.2 Hz), 7.09 (1H, d, J=2.3 Hz), 5.04 (2H, s), 2.98 (4H, m), 1.73 (4H, m), 1.58 (2H, m).

N-(5-Bromo-2-(piperidin-1-yl)pyridin-3-yl)-5,7-difluoro-3-methyl-2-(pyridin-2-yl)quinolin-4-amine

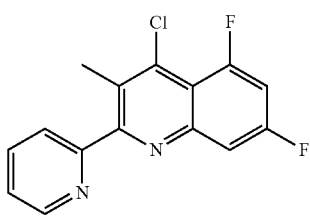

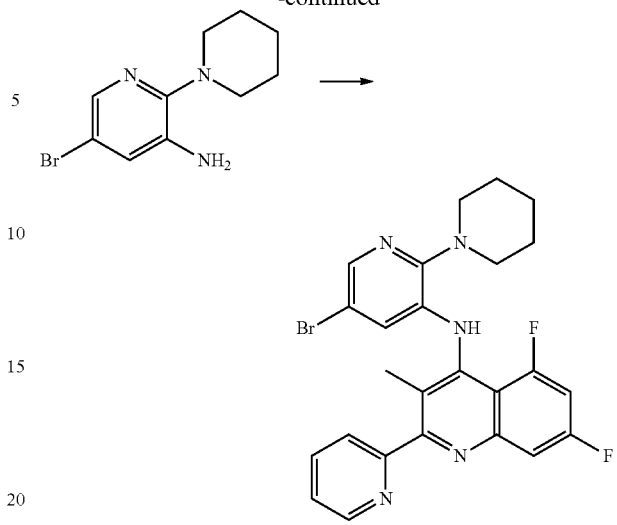

5-Bromo-2-(piperidin-1-yl)pyridin-3-amine (0.0537 g, 0.210 mmol), 4-chloro-5,7-difluoro-3-methyl-2-(pyridin-2-yl)quinoline (0.0632 g, 0.217 mmol), and hydrochloric acid, 4.0M in 1,4-dioxane (0.05 mL, 0.200 mmol) were stirred in NMP (0.50 mL) then microwaved at 150° C. After an additional 4 h, the reaction was diluted with EtOAc and washed once with satd aq. sodium bicarbonate and once with brine. After drying over anhydrous sodium sulfate, filtration, and concentration, the brown residue was purified with silica gel chromatography (0-40% EtOAc in hexanes) to yield mostly N-(5-bromo-2-(piperidin-1-yl)pyridin-3-yl)-5,7-difluoro-3-methyl-2-(pyridin-2-yl)quinolin-4-amine. Mass Spectrum (ESI) m/e=510.2 (M+1).

5,7-Difluoro-3-methyl-N-(5-(4-morpholinyl)-2-(1-piperidinyl)-3-pyridinyl)-2-(2-pyridinyl)-4-quinolinamine

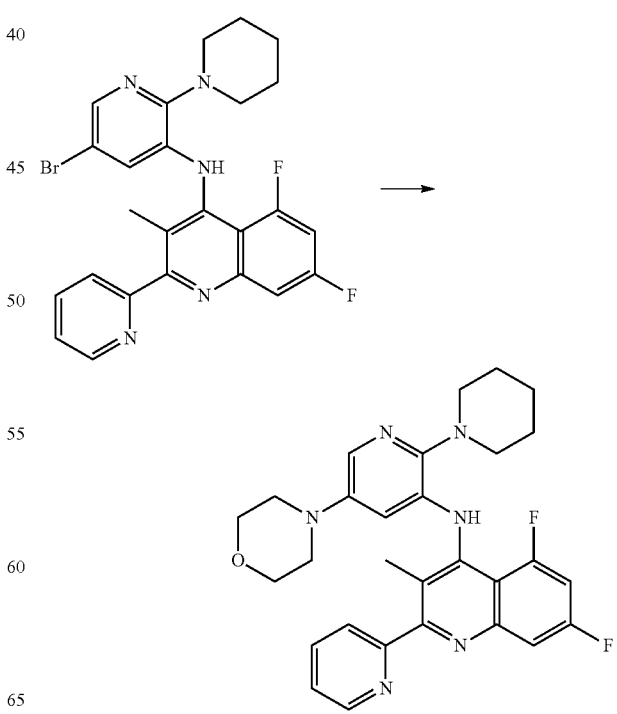

A stirred mixture of N-(5-bromo-2-(piperidin-1-yl)pyridin-3-yl)-5,7-difluoro-3-methyl-2-(pyridin-2-yl)quinolin-4-amine (0.0241 g, 0.047 mmol), tris(dibenzylideneacetone)dipalladium (0) (0.0048 g, 5.24 μmol), 2-dicyclohexylphosphino-2,4,6,-triisopropylbiphenyl (0.0049 g, 10.28 μmol), and sodium tert-butoxide (0.015 g, 0.15 mmol) in dry toluene (0.5 mL) was purged three times with argon and placed under vacuum three times. Before heating, morpholine (0.02 mL, 0.23 mmol) was added via syringe, then the mixture was heated to 100° C. After 21 h, the reaction was cooled to rt, then diluted with water and extracted three times with EtOAc. The organic extractions were combined and washed twice with brine. After drying over anhydrous sodium sulfate and filtration, the organic solvent was removed under reduced pressure. After dissolving in MeOH then syringe filtration, the mixture was purified with HPLC (10-90% of 0.1% TFA acetonitrile solution in 0.1% TFA water solution) to yield 5,7-difluoro-3-methyl-N-(5-(4-morpholinyl)-2-(1-piperidinyl)-3-pyridinyl)-2-(2-pyridinyl)-4-quinolinamine as a TFA salt. $^1$H NMR (400 MHz, MeOH) δ ppm 8.79 (1H, d, J=4.3 Hz), 8.13 (1H, td, J=7.7, 1.8 Hz), 7.92 (1H, d, J=7.8 Hz), 7.62-7.69 (2H, m), 7.52 (1H, d, J=2.7 Hz), 7.37 (1H, ddd, J=13.4, 8.9, 2.7 Hz), 6.95 (1H, d, J=2.7 Hz), 3.82 (4H, m), 3.28 (8H, m), 2.17 (3H, s), 1.64 (6H, m). Mass Spectrum (ESI) m/e=517.3 (M+1).

Example 58

N-(5-(2-Amino-4-pyrimidinyl)-2-(4-morpholinyl)-3-pyridinyl)-5,7-difluoro-3-methyl-2-(2-pyridinyl)-4-quinolinamine

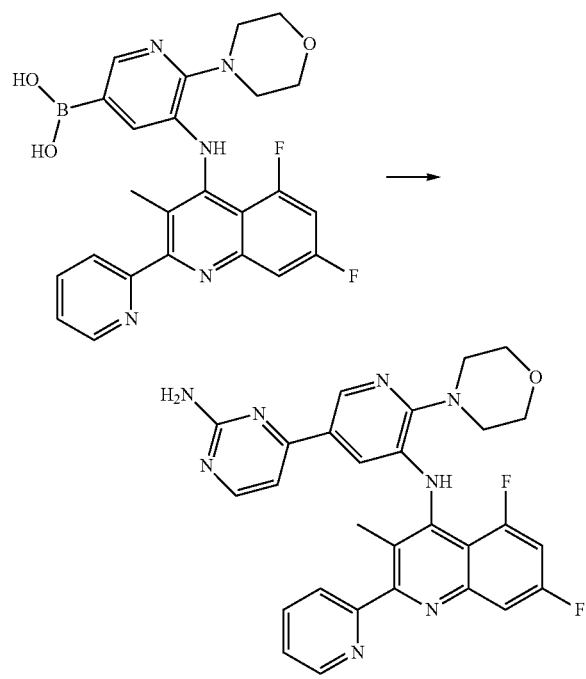

A solution of dichlorobis(triphenylphosphine)palladium (ii) (19.5 mg, 0.028 mmol), sodium carbonate (88 mg, 0.83 mmol), 2-amino-4-chloropyrimidine (35.9 mg, 0.28 mmol), 5-(5,7-difluoro-3-methyl-2-(pyridin-2-yl)quinolin-4-ylamino)-6-morpholinopyridin-3-ylboronic acid (0.28 mmol; described herein), 1,4-dioxane (6 mL), and water (1.5 mL) was heated in a microwave at 120° C. for 60 min. The reaction was then partitioned between EtOAc and water, and the organic layer dried (magnesium sulfate) and concentrated. Chromatography afforded N-(5-(2-amino-4-pyrimidinyl)-2-(4-morpholinyl)-3-pyridinyl)-5,7-difluoro-3-methyl-2-(2-pyridinyl)-4-quinolinamine as a yellow solid. $^1$H NMR (400 MHz, chloroform-d) δ ppm 8.73-8.79 (1H, m), 8.58 (1H, d, J=2.3 Hz), 8.28 (1H, d, J=5.1 Hz), 7.85-7.96 (2H, m), 7.63-7.70 (1H, m), 7.48-7.59 (2H, m), 7.41 (1H, ddd, J=6.8, 4.7, 2.2 Hz), 6.98-7.10 (2H, m), 5.35 (2H, br. s.), 3.95 (4H, d, J=2.3 Hz), 3.10-3.70 (4H, m), 2.22 (3H, s). Mass Spectrum (ESI) m/e=527.2 (M+1).

Example 59

Preparation of N-(2-(2,2-dimethyl-4-morpholinyl)-5-(4-morpholinyl)-3-pyridinyl)-5,7-difluoro-3-methyl-2-(2-pyridinyl)-4-quinolinamine 4-(5-Bromo-3-nitropyridin-2-yl)-2,2-dimethylmorpholine

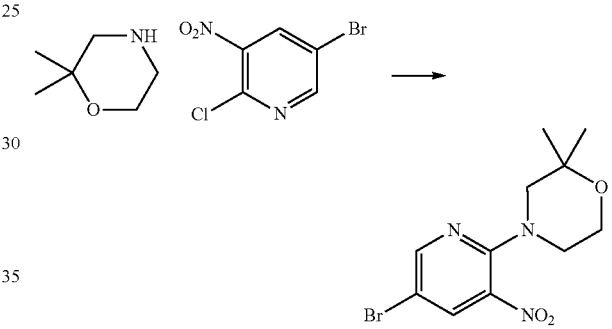

To a 100 mL round bottom flask containing 5-bromo-2-chloro-3-nitropyridine (2.00 g, 8.43 mmol) in DMSO (10 mL) was added 2,2-dimethylmorpholine (commercially available from ChemBridge Corporation) (1.9 mL, 16.9 mmol) dropwise. The reaction was heated to 60° C. and monitored with TLC and LC-MS. After 2.5 h, LC-MS showed that the reaction was complete. The mixture was cooled to rt then diluted with water. After extracting three times with EtOAc, the organic layers were combined then washed with brine and dried over anhydrous magnesium sulfate. After filtration, the mixture was concentrated under reduced pressure to afford an orange oil as 4-(5-bromo-3-nitropyridin-2-yl)-2,2-dimethylmorpholine. $^1$H NMR (400 MHz, CDCl$_3$) δ ppm 8.34 (1H, d, J=2.2 Hz), 8.25 (1H, d, J=2.2 Hz), 3.87 (2H, m), 3.36 (4H, m), 1.26 (6H, s).

5-Bromo-2-(2,2-dimethylmorpholino)pyridin-3-amine

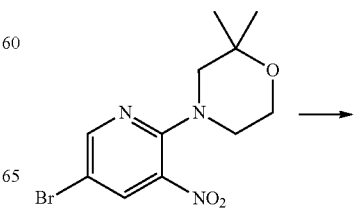

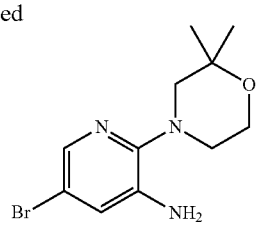

To a stirred mixture of 4-(5-bromo-3-nitropyridin-2-yl)-2,2-dimethylmorpholine (2.22 g, 7.03 mmol) in EtOAc (30 mL) was added tin(II) chloride dihydrate (8.94 g, 39.6 mmol) in portions. Upon complete addition of the reducing agent, the mixture was carefully heated to 90° C. After 1 h, the reaction was cooled to rt, then washed with 1M NaOH, water, and brine. After drying over anhydrous sodium sulfate and filtration, the organic solvent was removed under reduced pressure. The residue was purified with silica gel chromatography (0-35% EtOAc in hexanes) to provide a colorless film as 5-bromo-2-(2,2-dimethylmorpholino)-pyridin-3-amine. $^1$H NMR (400 MHz, DMSO-$d_6$) δ ppm 7.59 (1H, d, J=2.2 Hz), 7.13 (1H, d, J=2.3 Hz), 5.10 (2H, s), 3.83 (2H, m), 2.90 (2H, m), 2.77 (2H, s), 1.24 (6H, s).

N-(5-Bromo-2-(2,2-dimethylmorpholino)pyridin-3-yl)-5,7-difluoro-3-methyl-2-(pyridin-2-yl)quinolin-4-amine

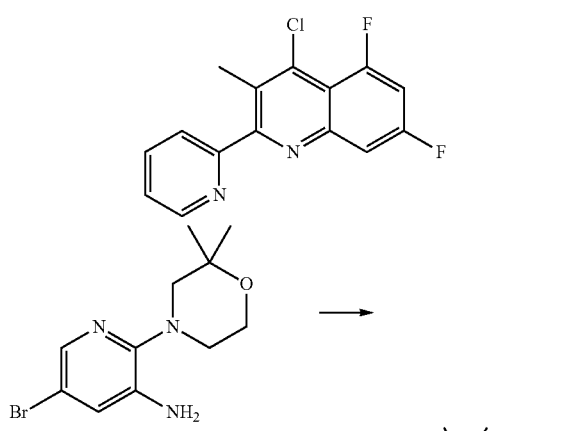

5-Bromo-2-(2,2-dimethylmorpholino)pyridin-3-amine (0.087 g, 0.31 mmol), 4-chloro-5,7-difluoro-3-methyl-2-(pyridin-2-yl)quinoline (0.071 g, 0.25 mmol), and hydrochloric acid, 4.0M in 1,4-dioxane (0.07 mL, 0.28 mmol) were stirred in NMP (0.5 mL) then microwaved at 150° C. After 2 h, the reaction was diluted with EtOAc and washed once with satd aq. sodium bicarbonate and once with brine. After drying over anhydrous sodium sulfate, filtration, and concentration, the brown residue was purified with silica gel chromatography (0-40% EtOAc in hexanes) to yield mostly N-(5-bromo-2-(2,2-dimethylmorpholino)pyridin-3-yl)-5,7-difluoro-3-methyl-2-(pyridin-2-yl)quinolin-4-amine. Mass Spectrum (ESI) m/e=540.1 (M+1).

N-(2-(2,2-Dimethyl-4-morpholinyl)-5-(4-morpholinyl)-3-pyridinyl)-5,7-difluoro-3-methyl-2-(2-pyridinyl)-4-quinolinamine

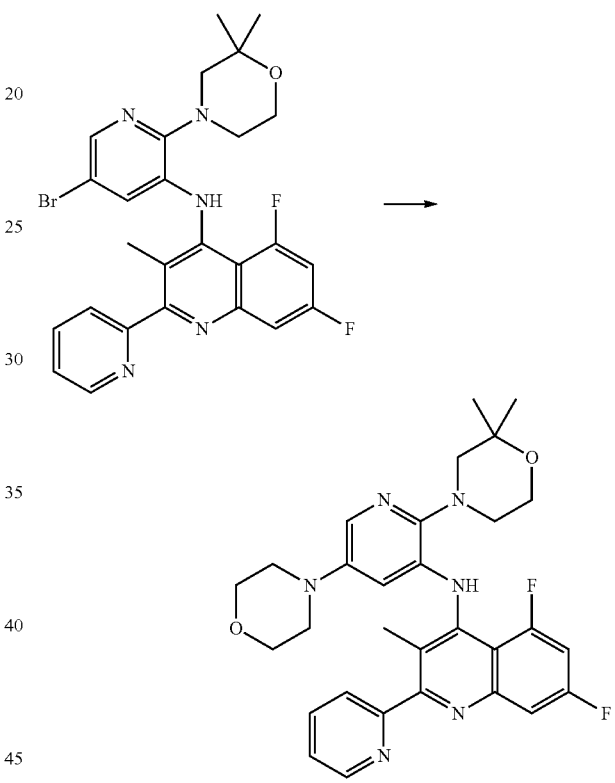

A stirred mixture of N-(5-bromo-2-(2,2-dimethylmorpholino)pyridin-3-yl)-5,7-difluoro-3-methyl-2-(pyridin-2-yl)quinolin-4-amine (0.061 g, 0.11 mmol), 2-dicyclohexylphosphino-2',4',6',-tri-i-propyl-1,1'-biphenyl (0.011 g, 0.023 mmol), tris(dibenzylideneacetone)dipalladium (0) (0.011 g, 0.012 mmol), and sodium tert-butoxide (0.034 g, 0.35 mmol) in dry toluene (1.0 mL) was purged three times with argon and placed under vacuum three times. Before heating, morpholine (0.05 mL, 0.57 mmol) was added via syringe, then the mixture was heated to 100° C. After 21 h, the reaction was cooled to rt, then diluted with water and extracted three times with EtOAc. The organic extractions were combined and washed twice with brine. After drying over anhydrous sodium sulfate and filtration, the organic solvent was removed under reduced pressure. After dissolving in MeOH then syringe filtration, the mixture was purified with HPLC (10-90% of 0.1% TFA acetonitrile solution in 0.1% TFA water solution). The desired fractions were concentrated then diluted with EtOAc. After washing twice with satd aq. sodium carbonate solution and once with brine, the solvent was removed under reduced pressure to yield N-(2-(2,2-dimethyl-4-morpholinyl)-5-(4-morpholinyl)-3-pyridinyl)-5,7-difluoro-3-methyl-2-(2-pyridinyl)-4-quinolinamine. ¹H NMR (400 MHz, MeOH) δ ppm 8.71 (1H, d, J=5.1 Hz), 8.06 (1H, td, J=7.7, 1.8 Hz), 7.84 (1H, d, J=7.8 Hz), 7.64 (3H, m), 7.29 (1H, ddd, J=13.7, 9.0, 2.3 Hz), 6.53 (1H, d, J=2.7 Hz), 4.03 (7H, m), 3.16 (7H, m), 2.10 (3H, s), 1.41 (6H, m). Mass Spectrum ESI (pos.) m/e: 547.3 (M+H)⁺.

Example 60

Preparation of 5,7-difluoro-3-methyl-N-(5-(4-morpholinyl)-3-pyridinyl)-2-(2-pyridinyl)-4-quinolinamine 5-Morpholinopyridin-3-amine

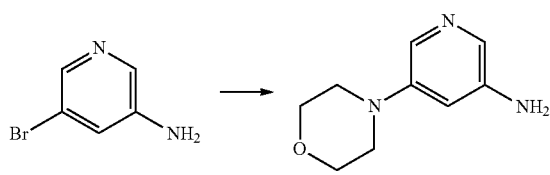 [SMILES: Nc1cncc(Br)c1 ; Nc1cncc(N2CCOCC2)c1]

To a stirred solution of 5-bromopyridin-3-amine (1.5 g, 8.67 mmol), X-Phos (0.33 g, 0.69 mmol), tris(dibenzylideneacetone)dipalladium(0) (0.32 g, 0.35 mmol) and morpholine (3.78 g, 43.3 mmol) in THF (17.3 mL) was added a 1.0M solution of lithium bis(trimethylsilyl)amide in THF (47.7 mL, 47.7 mmol). The resulting mixture was heated to 65° C. and stirring continued for 3 h. After which, the reaction was cooled to rt and then poured into water (100 mL) and extracted with EtOAc (2×150 mL) and DCM (2×150 mL). The combined organic layers were dried over magnesium sulfate, filtered and concentrated in vacuo. The crude product was purified by column chromatography on silica gel (0 to 100% DCM in EtOAc) to give 5-morpholinopyridin-3-amine. Mass Spectrum (ESI) m/e=180.1 (M+1).

5,7-Difluoro-3-methyl-N-(5-(4-morpholinyl)-3-pyridinyl)-2-(2-pyridinyl)-4-quinolinamine

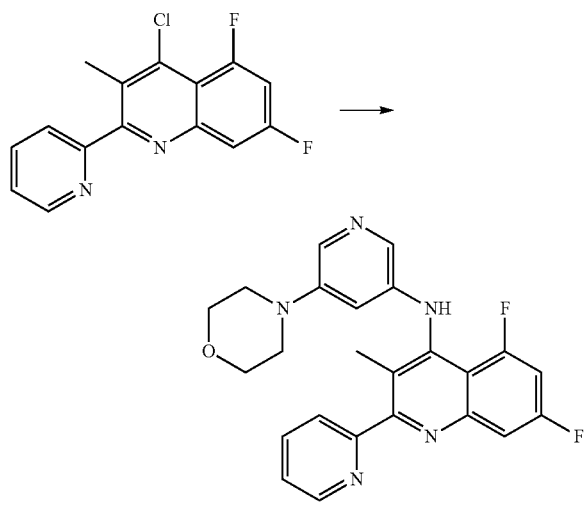

To a stirred solution of X-Phos (0.026 g, 0.055 mmol), 5-morpholinopyridin-3-amine (0.074 g, 0.413 mmol), 4-chloro-5,7-difluoro-3-methyl-2-(pyridin-2-yl)-quinoline (0.10 g, 0.344 mmol) and tris(dibenzylideneacetone)dipalladium(0) (0.013 g, 0.014 mmol) in toluene (3.44 mL) was added sodium t-butoxide (0.083 g, 0.86 mmol). The reaction mixture was heated to 120° C. and stirred for 45 min. The reaction was then cooled to rt and diluted with water (10 mL). The mixture was extracted with EtOAc (2×10 mL) and DCM (1×10 mL). The organic layers were combined and washed with brine (1×20 mL) and dried over magnesium sulfate, filtered and concentrated in vacuo. The crude product was purified by column chromatography on basic alumina (0 to 50% EtOAc in hexanes) to give the desired product 5,7-difluoro-3-methyl-N-(5-(4-morpholinyl)-3-pyridinyl)-2-(2-pyridinyl)-4-quinolinamine. ¹H NMR (400 MHz, CDCl₃) δ ppm 8.70 (1H, d, J=4.5 Hz), 7.95 (1H, s), 7.78-7.92 (3H, m), 7.62 (1H, d, J=9.8 Hz), 7.33-7.43 (1H, m), 6.97-7.14 (2H, m), 6.60 (1H, br. s.), 3.79-3.94 (4H, m), 3.12-3.30 (4H, m), 2.16 (3H, s). Mass Spectrum (ESI) m/e=434.2 (M+1).

Example 61

Preparation of N-3-(5,7-difluoro-3-methyl-2-(2-pyridinyl)-4-quinolinyl)-N-2-(3-methoxypropyl)-N-2-methyl-5-(4-morpholinyl)-2,3-pyridinediamine 5-Bromo-N-(3-methoxypropyl)-3-nitropyridin-2-amine

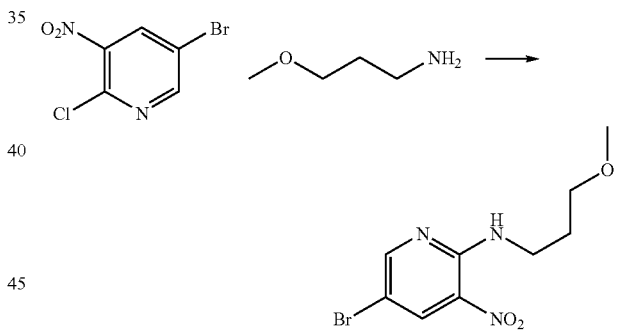

To a 100 mL round bottom flask containing 5-bromo-2-chloro-3-nitropyridine (5.12 g, 21.6 mmol) in DMSO (20.5 mL) was added 3-methoxypropylamine (4.40 mL, 43.1 mmol) dropwise. The reaction was heated to 60° C. and monitored with TLC and LC-MS. After 2.5 h, LC-MS showed that the reaction was complete. The mixture was cooled to rt then diluted with water. After extracting three times with EtOAc, the organic layers were combined then washed with brine and dried over anhydrous magnesium sulfate. After filtration, the mixture was concentrated in vacuo to give a light yellow brown solid as 5-bromo-N-(3-methoxypropyl)-3-nitropyridin-2-amine. ¹H NMR (400 MHz, CDCl₃) δ ppm 8.62 (1H, br. s.), 8.54 (1H, d, J=2.3 Hz), 8.43 (1H, d, J=2.3 Hz), 3.69-3.78 (2H, m), 3.56 (2H, t, J=5.7 Hz), 3.40 (3H, s), 1.96 (2H, dt, J=12.2, 6.2 Hz).

5-Bromo-N-(3-methoxypropyl)-N-methyl-3-nitropyridin-2-amine

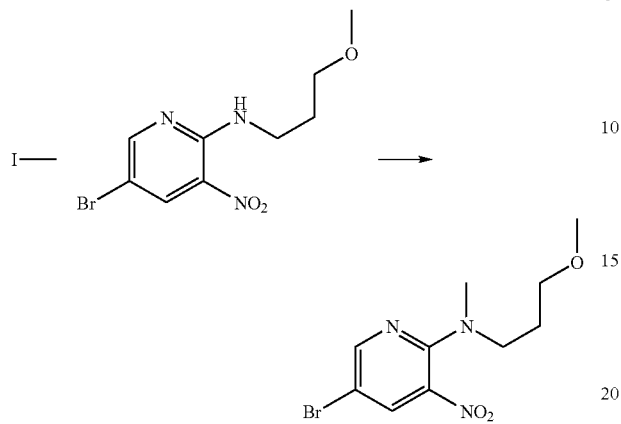

A dry round bottom flask containing 5-bromo-N-(3-methoxypropyl)-3-nitropyridin-2-amine (1.0 g, 3.45 mmol) in dry DMF (4.5 mL) was cooled to 0° C., then sodium hydride, 60% dispersion in mineral oil (0.28 g, 7.02 mmol) was added carefully in portions. The mixture was stirred at 0° C. for 15 min, then iodomethane (0.66 mL, 10.6 mmol) was added dropwise. Upon complete addition, the mixture was allowed to warm to 23° C. After 19 h, the reaction was carefully diluted with water then extracted five times with EtOAc. The organic extraction was then washed one time with brine and dried over anhydrous magnesium sulfate. After filtration and concentration, the residue was purified on silica gel (0-25% EtOAc in hexanes) to afford a light yellow oil as 5-bromo-N-(3-methoxy propyl)-N-methyl-3-nitropyridin-2-amine. $^1$H NMR (400 MHz, CDCl$_3$) δ ppm 8.31 (1H, d, J=2.3 Hz), 8.21 (1H, d, J=2.3 Hz), 3.79 (2H, m), 3.47 (2H, m), 3.33 (3H, s), 2.86 (3H, s), 2.01 (2H, m).

5-Bromo-N-2-(3-methoxypropyl)-N-2-methylpyridine-2,3-diamine

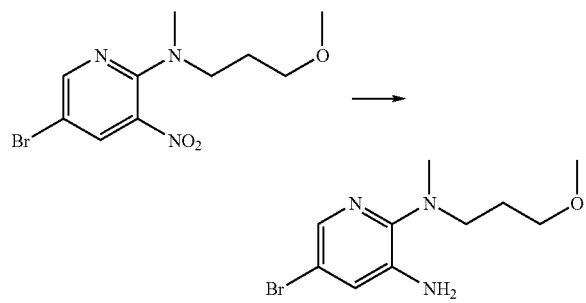

To a stirred mixture of 5-bromo-N-(3-methoxypropyl)-N-methyl-3-nitropyridin-2-amine (0.76 g, 2.51 mmol) in EtOAc (10 mL) was added tin(II) chloride dihydrate (2.84 g, 12.6 mmol). Upon complete addition of the reducing agent, the mixture was carefully heated to 90° C. After 1 h, the reaction was cooled to rt, then washed with 1M NaOH, water, and brine. After drying over anhydrous sodium sulfate and filtration, the organic solvent was removed under reduced pressure. The residue was purified with silica gel chromatography (0-50% EtOAc in hexanes) to provide a colorless liquid as 5-bromo-N-2-(3-methoxypropyl)-N-2-methylpyridine-2,3-diamine. $^1$H NMR (400 MHz, DMSO-d$_6$) δ ppm 7.56 (1H, d, J=2.3 Hz), 7.06 (1H, d, J=2.2 Hz), 5.16 (2H, s), 3.35 (2H, t, J=6.2 Hz), 3.19 (3H, s), 3.05 (2H, m), 2.61 (3H, s), 1.75 (2H, m).

5-Bromo-N-3-(5,7-difluoro-3-methyl-2-(pyridin-2-yl)quinolin-4-yl)-N-2-(3-methoxypropyl)-N-2-methylpyridine-2,3-diamine

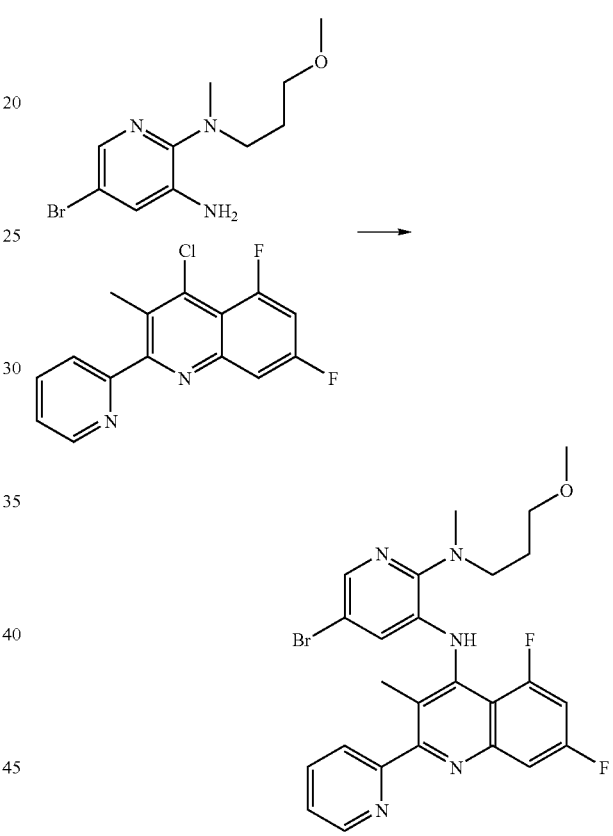

A dry flask containing 5-bromo-N-2-(3-methoxypropyl)-N-2-methylpyridine-2,3-diamine (0.16 g, 0.59 mmol) in dry DMF (4.0 mL) was cooled to 0° C., then sodium hydride, 60% dispersion in mineral oil was added carefully in portions. The mixture was stirred at 0° C. for 15 min, then 4-chloro-5,7-difluoro-3-methyl-2-(pyridin-2-yl)quinoline (0.22 g, 0.74 mmol) was added in portions. Upon complete addition, the mixture was allowed to warm to 75° C. After 22 h, the reaction was carefully diluted with water then extracted five times with 5% MeOH in DCM. The organic extraction was then washed one time with brine and dried over anhydrous magnesium sulfate. After filtration and concentration, the residue was purified on silica gel (0-10% of 89:9:1 DCM:MeOH: ammonium hydroxide solution in DCM) to afford an amorphous solid as mostly 5-bromo-N-3-(5,7-difluoro-3-methyl-2-(pyridin-2-yl)quinolin-4-yl)-N-2-(3-methoxypropyl)-N-2-methylpyridine-2,3-diamine. Mass Spectrum (ESI) m/e=528.1 (M+1).

N-3-(5,7-difluoro-3-methyl-2-(2-pyridinyl)-4-quinolinyl)-N-2-(3-methoxypropyl)-N-2-methyl-5-(4-morpholinyl)-2,3-pyridinediamine

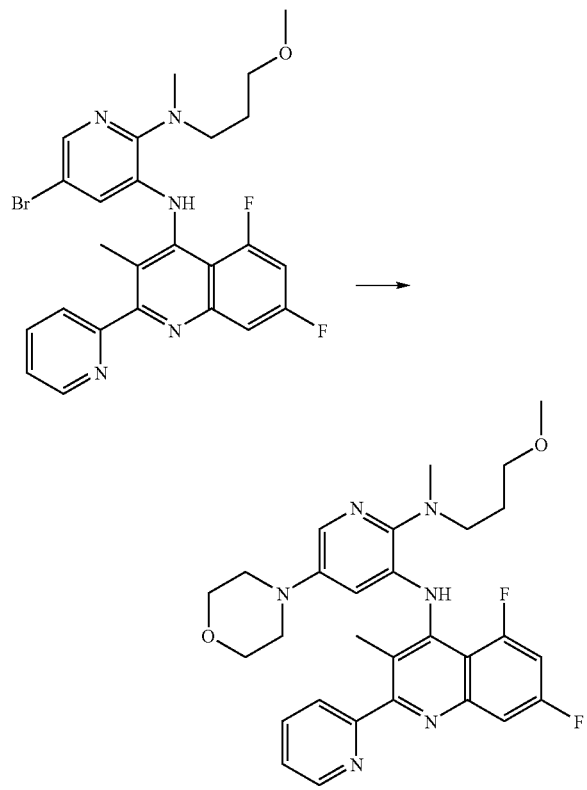

A stirred mixture of 5-bromo-N-3-(5,7-difluoro-3-methyl-2-(pyridin-2-yl)quinolin-4-yl)-N-2-(3-methoxypropyl)-N-2-methylpyridine-2,3-diamine (0.11 g, 0.21 mmol), tris(dibenzylideneacetone)dipalladium (0) (amount?), 2-(dicyclohexylphosphino)-2,4,6,-tri-i-propyl-1,1-biphenyl (amount?), and sodium tert-butoxide in dry toluene (3.0 mL) was purged three times with argon and placed under vacuum three times. Before heating, was added via syringe, then the mixture was heated to 100° C. After 19 h, the reaction was cooled to rt then treated with 1 M NaOH solution. After extracting twice with DCM:MeOH (95:5), the organics were combined and dried over anhydrous magnesium sulfate. After filtration and concentration the residue was purified on silica gel (0-65% of 89:9:1 DCM:MeOH:ammonium hydroxide solution in DCM) to afford a light orange film that was further purified with HPLC 10-90% of 0.1% TFA acetonitrile solution in 0.1% TFA water solution. The desired fractions (Prep. HPLC Retention time was –10.5 min) were concentrated then diluted with EtOAc. After washing twice with satd aq. sodium bicarbonate solution and once with brine, the solvent was removed under reduced pressure to yield a light yellow solid as N-3-(5,7-difluoro-3-methyl-2-(2-pyridinyl)-4-quinolinyl)-N-2-(3-methoxypropyl)-N-2-methyl-5-(4-morpholinyl)-2,3-pyridinediamine. $^1$H NMR (400 MHz, CDCl$_3$) δ ppm 8.76 (1H, m), 7.95 (2H, m), 7.70 (1H, d, J=8.8 Hz), 7.66 (2H, m), 7.38 (1H, ddd, J=6.8, 4.8, 2.1 Hz), 7.04 (1H, m), 6.38 (1H, d, J=2.5 Hz), 3.86 (4H, m), 3.49 (2H, t, J=6.3 Hz), 3.27 (3H, s), 3.26 (2H, m), 3.06 (4H, dd, J=5.7, 3.9 Hz), 2.81 (3H, s), 2.21 (3H, s), 1.86 (2H, quin, J=6.7 Hz). Mass Spectrum ESI (pos.) m/e: 535.3 (M+H)$^+$.

Example 62

Preparation of 6-chloro-N-(2,5-di-4-morpholinyl-3-pyridinyl)-methoxy-3-methyl-2-(2-pyridinyl)-4-quinolinamine Ethyl 3-(4-chloro-3-methoxyphenylamino)-2-methyl-3-oxopropanoate

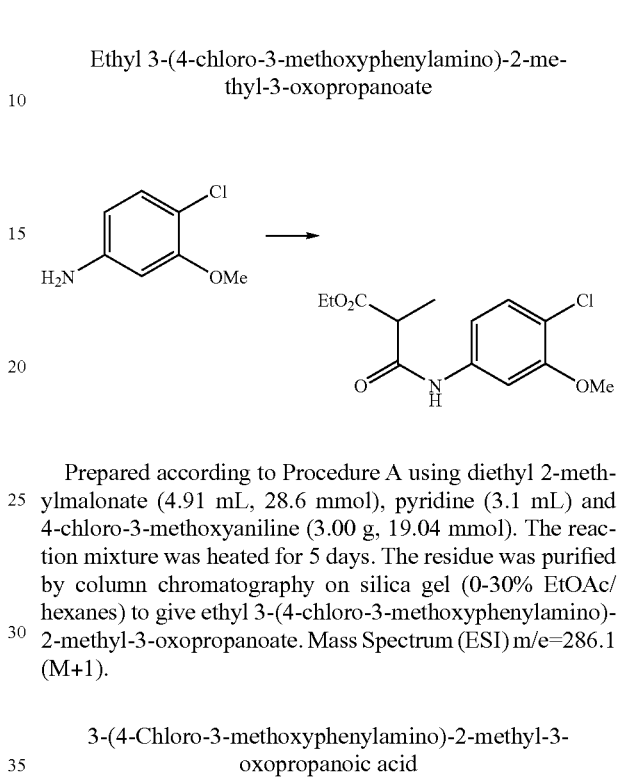

Prepared according to Procedure A using diethyl 2-methylmalonate (4.91 mL, 28.6 mmol), pyridine (3.1 mL) and 4-chloro-3-methoxyaniline (3.00 g, 19.04 mmol). The reaction mixture was heated for 5 days. The residue was purified by column chromatography on silica gel (0-30% EtOAc/hexanes) to give ethyl 3-(4-chloro-3-methoxyphenylamino)-2-methyl-3-oxopropanoate. Mass Spectrum (ESI) m/e=286.1 (M+1).

3-(4-Chloro-3-methoxyphenylamino)-2-methyl-3-oxopropanoic acid

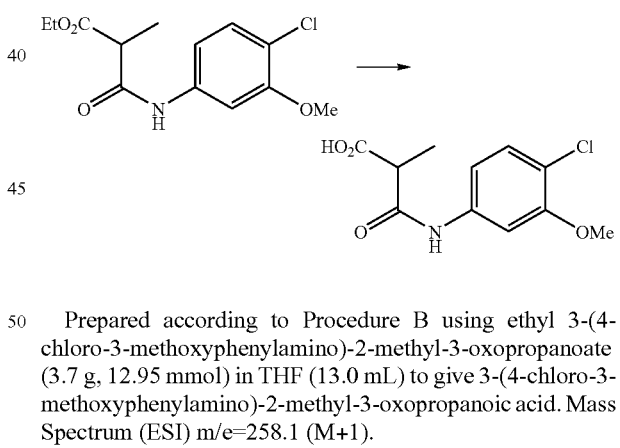

Prepared according to Procedure B using ethyl 3-(4-chloro-3-methoxyphenylamino)-2-methyl-3-oxopropanoate (3.7 g, 12.95 mmol) in THF (13.0 mL) to give 3-(4-chloro-3-methoxyphenylamino)-2-methyl-3-oxopropanoic acid. Mass Spectrum (ESI) m/e=258.1 (M+1).

2,4,6-Trichloro-7-methoxy-3-methylquinoline

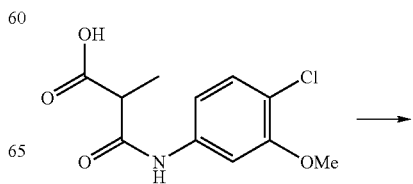

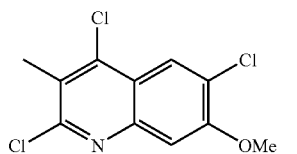

The diol was prepared according to Procedure C using 3-(4-chloro-3-methoxyphenylamino)-2-methyl-3-oxopropanoic acid (2.3 g, 8.93 mmol) and polyphosphoric acid (10 mL, 7.03 mmol) to give 6-chloro-7-methoxy-3-methylquinoline-2,4-diol. The diol was used crude in the next reaction. The trichloride was prepared according to Procedure D using 6-chloro-7-methoxy-3-methylquinoline-2,4-diol (1.4 g, 6.68 mmol) and phosphorus oxychloride (7.78 mL, 83 mmol) to give 2,4,6-trichloro-7-methoxy-3-methylquinoline. Mass Spectrum (ESI) m/e=276.0 (M+1).

4,6-Dichloro-7-methoxy-3-methyl-2-(pyridin-2-yl)quinoline

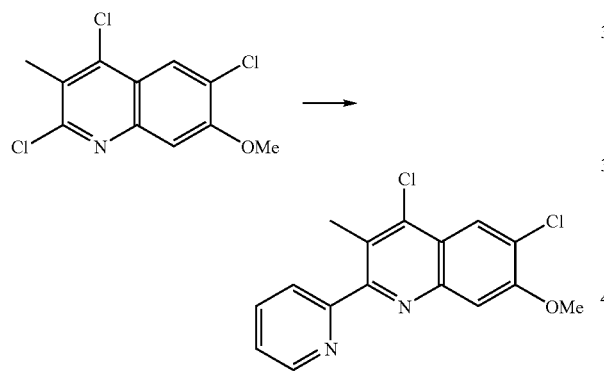

The dichloride was prepared according to Procedure E using 2,4,6-trichloro-7-methoxy-3-methylquinoline (0.69 g, 2.49 mmol), 2-(tributylstannyl)pyridine (1.01 mL, 2.74 mmol), palladium tetrakistriphenylphosphine (0.29 g, 0.25 mmol) in toluene (5.00 mL) to give 4,6-dichloro-7-methoxy-3-methyl-2-(pyridin-2-yl)quinoline as a white solid. Mass Spectrum (ESI) m/e=319.0 (M+1).

6-Chloro-N-(2,5-di-4-morpholinyl-3-pyridinyl)-7-methoxy-3-methyl-2-(2-pyridinyl)-4-quinolinamine

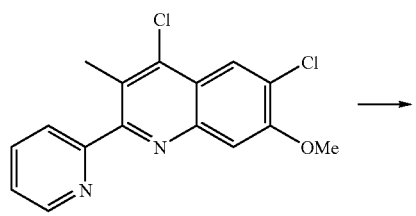

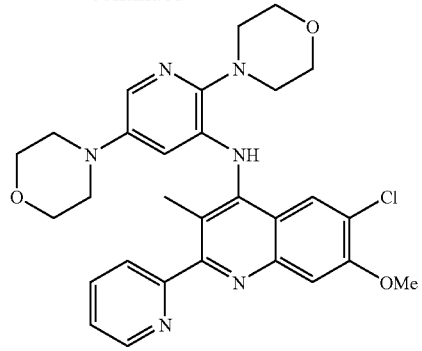

To a stirred solution of X-Phos (0.024 g, 0.050 mmol), 2,5-dimorpholinopyridin-3-amine (0.099 g, 0.38 mmol), 4,6-dichloro-7-methoxy-3-methyl-2-(pyridin-2-yl)-quinoline (0.10 g, 0.31 mmol) and tris(dibenzylideneacetone)dipalladium(0) (0.011 g, 0.013 mmol) in toluene (3.13 mL) was added sodium t-butoxide (0.075 g, 0.78 mmol). The reaction mixture was heated to 120° C. and stirred for 45 min. The reaction was then cooled to rt and diluted with water (25 mL). The mixture was extracted with EtOAc (2×10 mL) and DCM (10 mL). The organic layers were combined and washed with brine (20 mL) and dried over magnesium sulfate. The crude product was purified by column chromatography on basic alumina (0 to 50% EtOAc) to give the desired product 6-chloro-N-(2,5-di-4-morpholinyl-3-pyridinyl)-7-methoxy-3-methyl-2-(2-pyridinyl)-4-quinolinamine. $^1$H NMR (400 MHz, CDCl$_3$) δ ppm 8.72-8.79 (1H, m), 7.80-7.96 (3H, m), 7.63 (2H, br s), 7.37-7.45 (1H, m), 7.27 (1H, m), 6.79 (1H, br. s.), 6.27 (1H, m), 4.06 (3H, s), 3.93 (4H, t, J=4.6 Hz), 3.71-3.81 (4H, m), 3.24 (4H, br. s.), 2.92-3.00 (4H, m), 2.35 (3H, s). Mass Spectrum (ESI) m/e=547.2 (M+1).

Example 63

Preparation of 4-amino-6-(5-((5,7-difluoro-3-methyl-2-(2-pyridinyl)-4-quinolinyl)amino)-6-(4-morpholinyl)-3-pyridinyl)-5-pyrimidinecarbonitrile

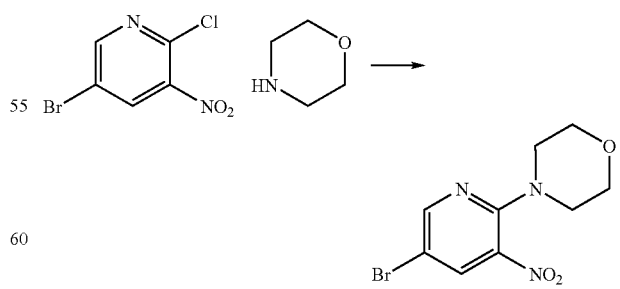

To a vial containing 5-bromo-2-chloro-3-nitropyridine (0.99 g, 4.16 mmol) in DMSO (4.0 mL) was added morpholine (0.8 mL, 9.19 mmol) dropwise. The reaction was stirred at 23° C. and monitored with TLC and LC-MS. After 20 h, LC-MS showed that the reaction was complete, then the mixture was diluted with water. After extracting three times with EtOAc, the organic layers were combined then washed with brine and dried over anhydrous magnesium sulfate. After filtration, the mixture was concentrated in vacuo to afford a yellow-orange solid as 4-(5-bromo-3-nitropyridin-2-yl)morpholine. ¹H NMR (400 MHz, DMSO-d₆) δ ppm 8.53 (1H, d, J=2.3 Hz), 8.47 (1H, d, J=2.3 Hz), 3.70 (4H, m), 3.41 (4H, m).

5-Bromo-2-morpholinopyridin-3-amine

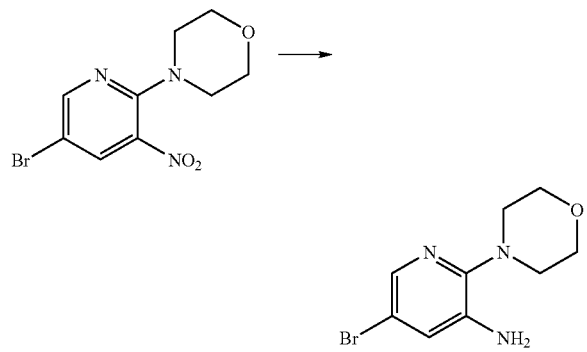

To a stirred mixture of 4-(5-bromo-3-nitropyridin-2-yl)morpholine (1.02 g, 3.54 mmol) in EtOAc (30 mL) was added tin(II) chloride dihydrate (4.01 g, 17.77 mmol) in portions. Upon complete addition of the reducing agent, the mixture was carefully heated to 90° C. After 2 h, the reaction was cooled to rt and diluted with ethyl acetate, then washed with 1M NaOH, water, and brine. After drying over anhydrous sodium sulfate and filtration, the organic solvent was removed under reduced pressure. The residue was identified as 5-bromo-2-morpholinopyridin-3-amine. ¹H NMR (400 MHz, DMSO-d₆) δ ppm 7.59 (1H, d, J=2.0 Hz), 7.12 (1H, d, J=2.0 Hz), 5.19 (2H, s), 3.80 (4H, m), 3.02 (4H, m).

N-(5-Bromo-2-morpholinopyridin-3-yl)-5,7-difluoro-3-methyl-2-(pyridin-2-yl)quinolin-4-amine

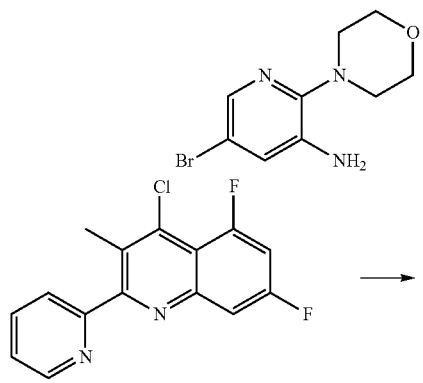

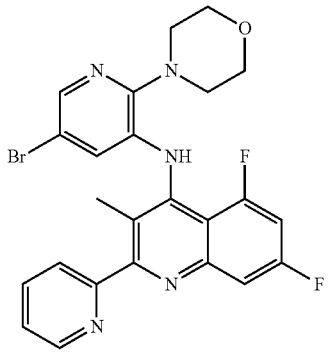

A dry flask containing 5-bromo-2-morpholinopyridin-3-amine (0.3282 g, 1.272 mmol) in dry DMF (10.0 mL) was cooled to 0° C., then sodium hydride, 60% dispersion in mineral oil (0.125 g, 3.12 mmol) was added carefully in portions. The mixture was stirred at 0° C. for 15 min, then 4-chloro-5,7-difluoro-3-methyl-2-(pyridin-2-yl)quinoline (0.46 g, 1.57 mmol) was added in portions. Upon complete addition, the mixture was warmed to 60° C. After 18 h, the reaction was cooled to rt then was carefully treated with 10% sodium carbonate solution. The black mixture was subsequently extracted five times with DCM:MeOH (90:10). The organic extraction was then washed one time with brine and dried over anhydrous magnesium sulfate. After filtration and concentration, the black residue was treated with MeOH and placed on the rotovap. (without vac.) in a 45° C. water bath. After 30 min, the solid was filtered and rinsed twice with MeOH to afford a tan solid as N-(5-bromo-2-morpholinopyridin-3-yl)-5,7-difluoro-3-methyl-2-(pyridin-2-yl)quinolin-4-amine. Mass Spectrum (ESI) m/e=512.1 (M+1).

4-Amino-6-(5-((5,7-difluoro-3-methyl-2-(2-pyridinyl)-4-quinolinyl)amino)-6-(4-morpholinyl)-3-pyridinyl)-5-pyrimidinecarbonitrile

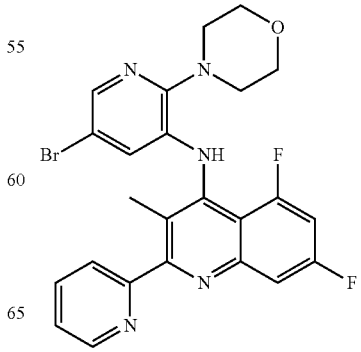

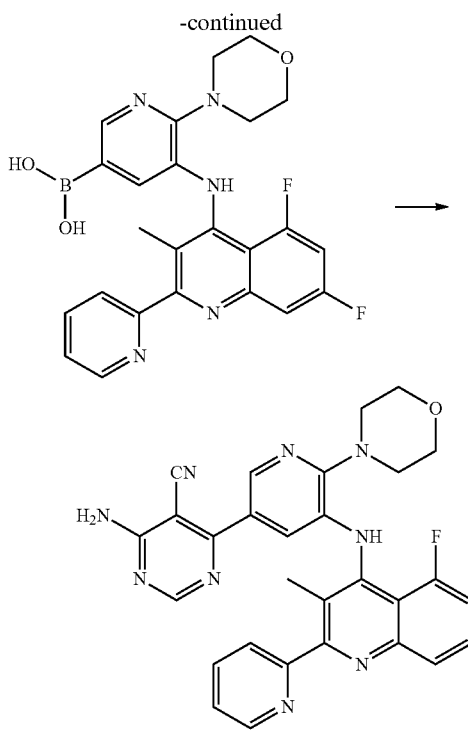

A stirred mixture of N-(5-bromo-2-morpholinopyridin-3-yl)-5,7-difluoro-3-methyl-2-(pyridin-2-yl)quinolin-4-amine (0.23 g, 0.45 mmol), 1,1'-bis(diphenylphosphino)ferrocene-palladium(II) dichloride DCM complex (0.037 g, 0.046 mmol), bis(pinacolato)diboron (0.23 g, 0.91 mmol), and potassium acetate (0.14 g, 1.4 mmol) in dry DMF (5.0 mL) was purged three times with argon and placed under vacuum three times, then the mixture was heated to 100° C. After 2.5 h, the mixture was cooled to rt and used as is without purification. Mass Spectrum (ESI) m/e=478.1 (M+1). A stirred mixture of 4-amino-6-chloropyrimidine-5-carbonitrile (0.047 g, 0.30 mmol), mostly 5-(5,7-difluoro-3-methyl-2-(pyridin-2-yl)quinolin-4-ylamino)-6-morpholinopyridin-3-ylboronic acid (0.22 g, 0.45 mmol), tetrakis(triphenylphosphine)palladium (0.035 g, 0.030 mmol), and 2.0M sodium carbonate (0.60 mL, 1.200 mmol) in DMF (5.00 mL) was purged three times with argon and placed under vacuum three times, then the mixture was heated to 100° C. After 19 h, the reaction was cooled to rt then treated with 1M NaOH solution. After extracting twice with DCM:MeOH (95:5), the organics were combined and dried over anhydrous magnesium sulfate. After filtration and concentration the residue was purified on silica gel (0-65% of 89:9:1 DCM:MeOH:ammonium hydroxide solution in DCM) to afford a light orange film that was further purified with HPLC 10-90% of 0.1% TFA acetonitrile solution in 0.1% TFA water solution. The desired fractions (Prep. HPLC Retention time was ~10.5 min) were concentrated then diluted with EtOAc. After washing twice with satd aq. sodium bicarbonate solution and once with brine, the solvent was removed under reduced pressure to yield a light yellow solid 4-amino-6-(5-((5,7-difluoro-3-methyl-2-(2-pyridinyl)-4-quinolinyl)amino)-6-(4-morpholinyl)-3-pyridinyl)-5-pyrimidinecarbonitrile. $^1$H NMR (400 MHz, CDCl$_3$) δ ppm 8.80 (1H, m), 8.66 (1H, d, J=2.3 Hz), 8.62 (1H, s), 7.94 (2H, m), 7.68 (1H, d, J=8.6 Hz), 7.40 (1H, ddd, J=6.9, 4.8, 2.0 Hz), 7.29 (1H, d, J=2.0 Hz), 7.22 (1H, d, J=11.0 Hz), 7.03 (1H, ddd, J=13.4, 8.5, 2.7 Hz), 5.68 (2H, s), 3.95 (4H, br. s.), 3.62 (4H, m), 2.30 (3H, s). Mass Spectrum ESI (pos.) m/e: 552.1 (M+H)$^+$.

Example 64

Preparation of N-(2,5-di-1-cyclohexen-1-yl-3-pyridinyl)-5,7-difluoro-3-methyl-2-(2-pyridinyl)-4-quinolinamine 2,5-Dibromopyridin-3-amine

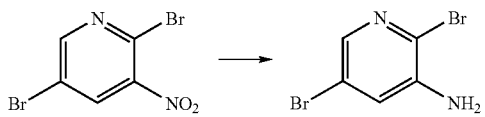 [SMILES: O=[N+]([O-])c1cc(Br)cnc1Br ; Nc1cc(Br)cnc1Br]

To a stirred mixture of 2,5-dibromo-3-nitropyridine (0.99 g, 3.50 mmol) in EtOAc (30.0 mL) was added tin(II) chloride dihydrate (4.02 g, 17.80 mmol) in portions. Upon complete addition of the reducing agent, the mixture was carefully heated to 90° C. After 2 h, the reaction was cooled to rt and diluted with ethyl acetate, then washed with 1M NaOH, water, and brine. After drying over anhydrous sodium sulfate and filtration, the organic solvent was removed under reduced pressure. The residue was identified as 2,5-dibromopyridin-3-amine. $^1$H NMR (400 MHz, DMSO-d$_6$) δ ppm 7.65 (1H, d, J=2.5 Hz), 7.27 (1H, d, J=2.5 Hz), 5.82 (2H, br, s).

5-Bromo-2-cyclohexenylpyridin-3-amine and 2,5-dicyclohexenylpyridin-3-amine

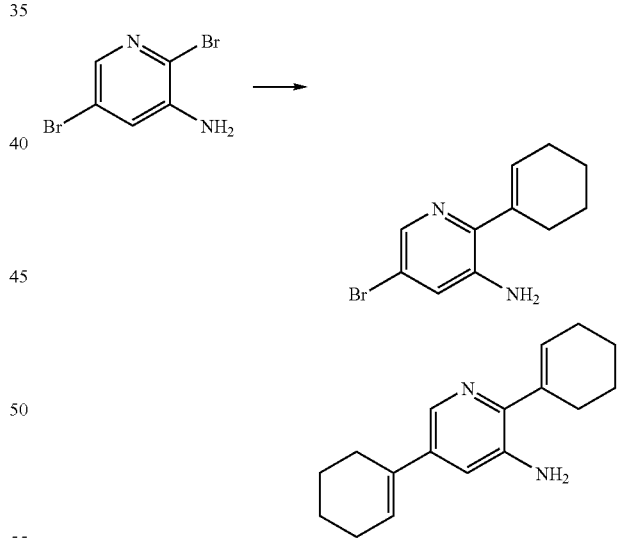

A stirred mixture of 2,5-dibromopyridin-3-amine (0.2135 g, 0.848 mmol), 1-cyclohexen-1-yl-boronic acid pinacol ester (0.30 mL, 1.40 mmol), tetrakis(triphenylphosphine)palladium (0.098 g, 0.084 mmol), and 2.0M sodium carbonate (2.0 mL, 4.00 mmol) in toluene (1.5 mL) and ethanol (0.5 mL) was heated to 90° C. After 2.5 h, the reaction was cooled to rt then diluted with water. After extraction with EtOAc, the organic extraction was dried over anhydrous sodium sulfate. After filtration and concentration, the residue was purified on silica gel (0-35% EtOAc in hexanes) to afford a white solid as 5-bromo-2-cyclohexenylpyridin-3-amine. $^1$H NMR (400

MHz, CDCl₃) δ ppm 8.01 (1H, d, J=2.0 Hz), 7.10 (1H, d, J=2.3 Hz), 6.00 (1H, tt, J=3.7, 2.0 Hz), 3.96 (2H, br. s.), 2.45 (2H, m), 2.26 (2H, m), 1.87 (4H, m). 2,5-Dicyclohexenylpyridin-3-amine was also isolated. ¹H NMR (400 MHz, CDCl₃) δ ppm 8.07 (1H, d, J=2.0 Hz), 6.95 (1H, d, J=2.0 Hz), 6.16 (1H, m), 6.05 (1H, m), 3.81 (2H, br. s.), 2.48 (4H, m), 2.27 (4H, m), 1.87 (8H, m).

N-(2,5-Di-1-cyclohexen-1-yl-3-pyridinyl)-5,7-difluoro-3-methyl-2-(2-pyridinyl)-4-quinolinamine

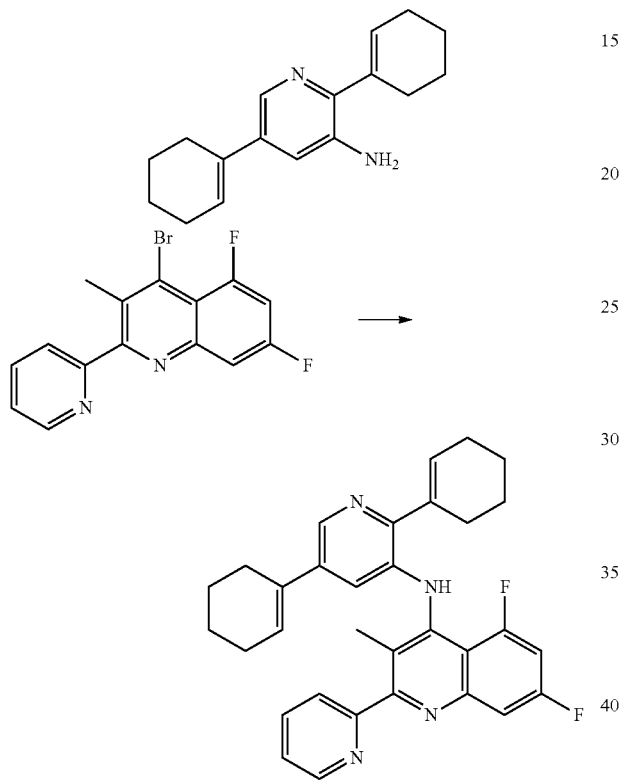

A stirred mixture of mostly 2,5-dicyclohexenylpyridin-3-amine (0.047 g, 0.19 mmol), 4-bromo-5,7-difluoro-3-methyl-2-(pyridin-2-yl)quinoline (0.085 g, 0.26 mmol), 2-dicyclohexylphosphino-2,4,6,-triisopropylbiphenyl (0.019 g, 0.039 mmol), tris(dibenzylideneacetone)dipalladium (0) (0.018 g, 0.019 mmol), and sodium tert-butoxide (0.056 g, 0.58 mmol) in dry toluene (2.0 mL) was purged three times with argon and placed under vacuum three times, then the mixture was heated to 100° C. After 2.5 h, the reaction was cooled to rt. After extracting twice with EtOAc, the organics were combined and dried over anhydrous magnesium sulfate. After filtration and concentration the residue was purified on silica gel (0-10% of 89:9:1 DCM:MeOH:ammonium hydroxide solution in DCM) to afford an impure light yellow film. The light yellow film was further purified with HPLC 10-90% of 0.1% TFA acetonitrile solution in 0.1% TFA water solution. The desired fractions (Prep. HPLC Retention time was ~14.1 min) were concentrated then diluted with EtOAc. After washing twice with satd aq. sodium bicarbonate solution and once with brine, the solvent was removed under reduced pressure to yield a light yellow solid as N-(2,5-di-1-cyclohexen-1-yl-3-pyridinyl)-5,7-difluoro-3-methyl-2-(2-pyridinyl)-4-quinolinamine. ¹H NMR (500 MHz, CDCl₃) δ ppm 8.74 (1H, ddd, J=4.9, 1.7, 1.0 Hz), 8.23 (1H, d, J=2.0 Hz), 7.91 (1H, m), 7.85 (1H, m), 7.62 (1H, ddd, J=9.7, 2.4, 1.1 Hz), 7.38 (1H, ddd, J=7.4, 4.8, 1.2 Hz), 7.33 (1H, d, J=11.5 Hz), 7.00 (1H, ddd, J=13.6, 8.6, 2.6 Hz), 6.86 (1H, d, J=2.0 Hz), 6.18 (1H, m), 6.14 (1H, m), 2.48 (2H, br. s.), 2.33 (2H, br. s.), 2.29 (2H, m), 2.22 (2H, m), 2.14 (3H, s), 1.88 (2H, m), 1.79 (4H, m), 1.67 (2H, m). Mass Spectrum ESI (pos.) m/e: 509.2 (M+H)⁺.

Example 65

Preparation of N-(2-(1-cyclohexen-1-yl)-5-(4-morpholinyl)-3-pyridinyl)-5,7-difluoro-3-methyl-2-(2-pyridinyl)-4-quinolinamine N-(5-Bromo-2-cyclohexenylpyridin-3-yl)-5,7-difluoro-3-methyl-2-(pyridin-2-yl)quinolin-4-amine

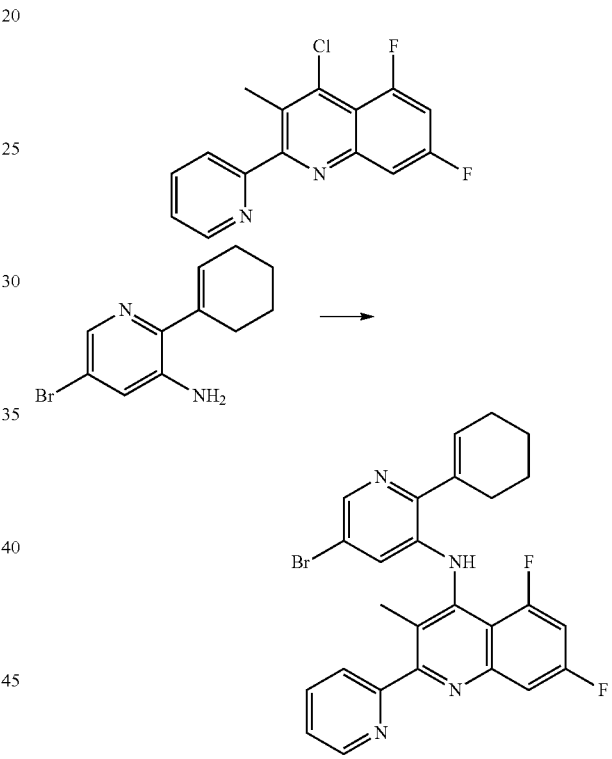

A dry flask containing 5-bromo-2-cyclohexenylpyridin-3-amine (0.19 g, 0.76 mmol) in dry DMF (5.0 mL) was cooled to 0° C., then sodium hydride, 60% dispersion in mineral oil (0.061 g, 1.53 mmol) was added carefully in portions. The mixture was stirred at 0° C. for 15 min, then 4-chloro-5,7-difluoro-3-methyl-2-(pyridin-2-yl)quinoline (0.26 g, 0.91 mmol) was added in portions. Upon complete addition, the mixture was warmed to 70° C. After 18 h, the incomplete reaction was cooled to rt then was carefully treated with 10% sodium carbonate solution. The black mixture was subsequently extracted five times with DCM:MeOH (90:10). The organic extraction was then washed one time with brine and dried over anhydrous magnesium sulfate. After filtration and concentration, the black residue was treated with MeOH and placed on the rotovap. (without vac.) in a 45° C. water bath. After 30 min, the solid was filtered and rinsed twice with MeOH to afford a tan solid as N-(2-(1-cyclohexen-1-yl)-5-(4-morpholinyl)-3-pyridinyl)-5,7-difluoro-3-methyl-2-(2- pyridinyl)-4-quinolinamine. $^1$H NMR (500 MHz, DMSO-$d_6$) δ ppm 8.72 (1H, d, J=3.9 Hz), 8.15 (3H, m), 7.89 (1H, d, J=7.8 Hz), 7.68 (1H, d, J=9.0 Hz), 7.53 (1H, ddd, J=7.6, 4.9, 1.2 Hz), 7.46 (1H, m.), 7.01 (1H, s), 5.92 (1H, m.), 2.37 (1H, dd, J=3.5, 1.8 Hz), 2.16 (3H, s), 1.99 (2H, m), 1.63 (2H, m), 1.46 (2H, m.).

alumina (10-50% EtOAc in hexanes) to afford a light yellow solid as 1-(5-((5,7-difluoro-3-methyl-2-(2-pyridinyl)-4-quinolinyl)amino)-6-(4-morpholinyl)-3-pyridinyl)-4-piperidinecarbonitrile. Mass Spectrum ESI (pos.) m/e: 542.2 $(M+H)^+$.

Example 67

Preparation of 5,7-difluoro-N-(5-(4-methoxy-1-piperidinyl)-2-(4-morpholinyl)-3-pyridinyl)-3-methyl-2-(2-pyridinyl)-4-quinolinamine Example 66

Preparation of 1-(5-((5,7-difluoro-3-methyl-2-(2-pyridinyl)-4-quinolinyl)amino)-6-(4-morpholinyl)-3-pyridinyl)-4-piperidinecarbonitrile

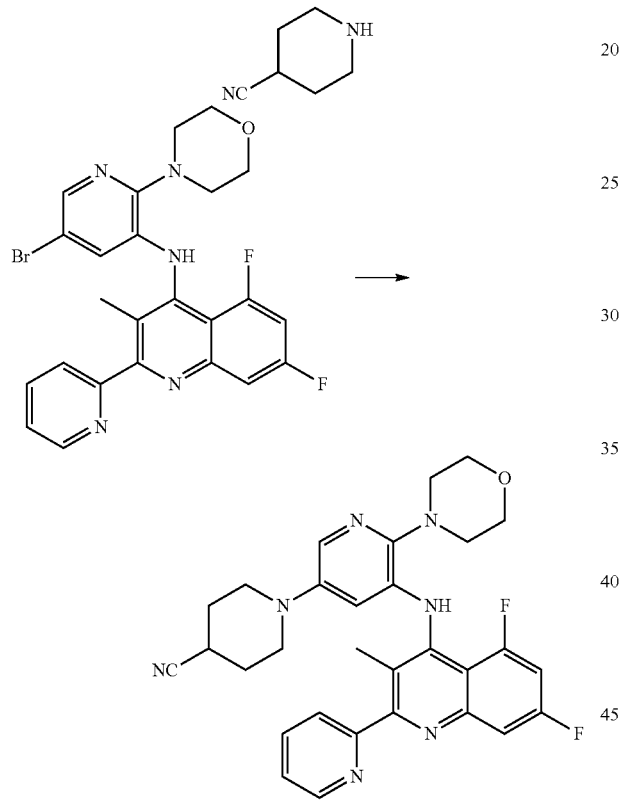

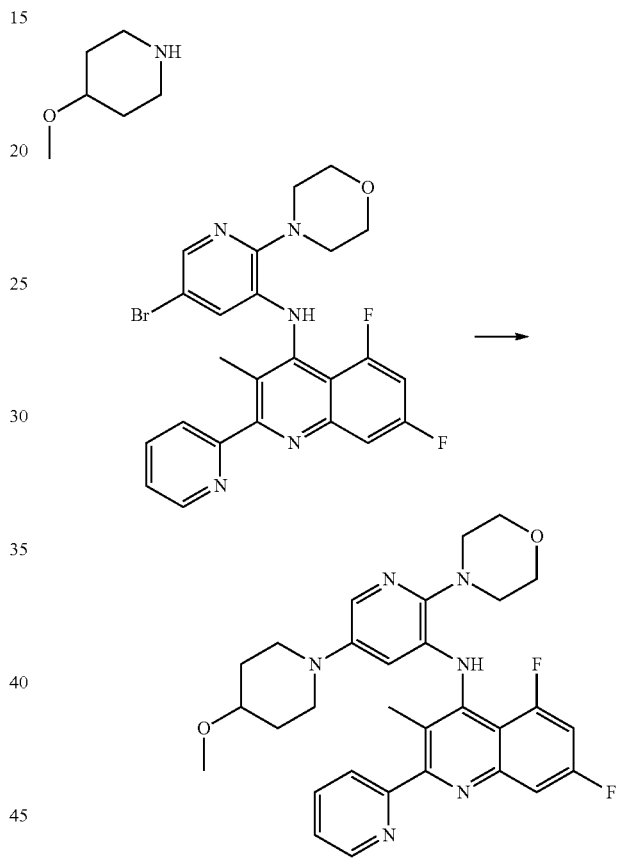

A stirred mixture of N-(5-bromo-2-morpholinopyridin-3-yl)-5,7-difluoro-3-methyl-2-(pyridin-2-yl)quinolin-4-amine (0.049 g, 0.096 mmol), piperidine-4-carbonitrile (commercially available from Oakwood Products, Inc.) (0.023 g, 0.21 mmol), 2-dicyclohexylphosphino-2,4,6,-triisopropylbiphenyl (0.0097 g, 0.020 mmol), tris(dibenzylideneacetone)dipalladium (0) (0.0095 g, 10.4 µmol), and sodium tert-butoxide (0.044 g, 0.46 mmol) in dry toluene (3.0 mL) was purged three times with argon and placed under vacuum three times, then the mixture was heated to 100° C. After 21.5 h, the reaction was cooled to rt, then treated with water. After extracting twice with DCM:MeOH (95:5), the organics were combined and dried over anhydrous magnesium sulfate. After filtration and concentration the residue was purified on basic A stirred mixture of N-(5-bromo-2-morpholinopyridin-3-yl)-5,7-difluoro-3-methyl-2-(pyridin-2-yl)quinolin-4-amine (0.057 g, 0.110 mmol), 4-methoxypiperidine (commercially available from Oakwood Products, Inc.) (0.035 g, 0.30 mmol), tris(dibenzylideneacetone)dipalladium (0) (0.013 g, 0.014 mmol), 2-dicyclohexylphosphino-2,4,6,-triisopropylbiphenyl (0.012 g, 0.026 mmol), and sodium tert-butoxide (0.056 g, 0.58 mmol) in dry toluene (3.0 mL) was purged three times with argon and placed under vacuum three times, then the mixture was heated to 100° C. After 21.5 h, the reaction was cooled to rt, then treated with water. After extracting twice with DCM:MeOH (95:5), the organics were combined and dried over anhydrous magnesium sulfate. After filtration and concentration the residue was purified on basic alumina (0-35% EtOAc in hexanes) to afford a light yellow solid as 5,7-difluoro-N-(5-(4-methoxy-1-piperidinyl)-2-(4-morpholinyl)-3-pyridinyl)-3-methyl-2-(2-pyridinyl)-4-quinolinamine. Mass Spectrum ESI (pos.) m/e: 547.2 $(M+H)^+$.

Example 68

Preparation of N-(2,5-di-4-morpholinyl-3-pyridinyl)-5,7-difluoro-2-(2-pyridinyl)-4-quinolinamine Methyl 3-(3,5-difluorophenylamino)-3-oxopropanoate

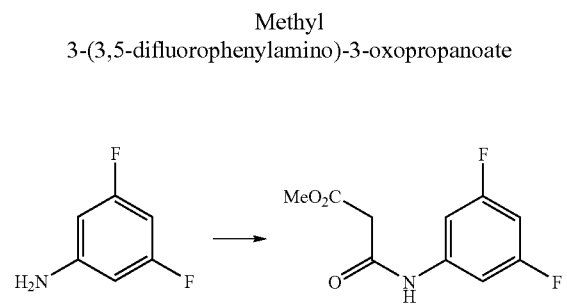

Prepared according to Procedure A using 3,5-difluoroaniline (5.00 g, 38.7 mmol) and dimethyl malonate to give methyl 3-(3,5-difluorophenylamino)-3-oxopropanoate. Mass Spectrum (ESI) m/e=230.1 (M+1).

3-(3,5-Difluorophenylamino)-3-oxopropanoic acid

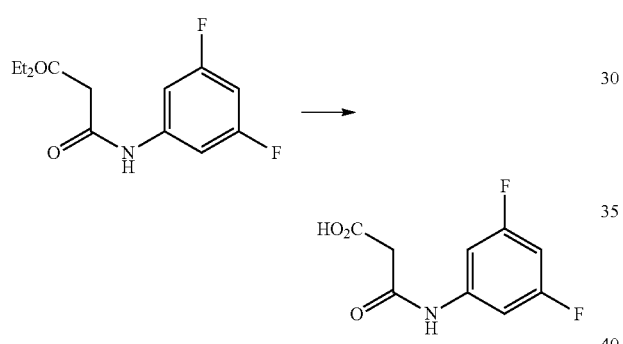

Prepared according to Procedure B using methyl 3-(3,5-difluorophenylamino)-3-oxopropanoate (1.20 g, 5.20 mmol) to give 3-(3,5-difluorophenylamino)-3-oxopropanoic acid. Mass Spectrum (ESI) m/e=216.1 (M+1).

5,7-Difluoroquinoline-2,4-diol

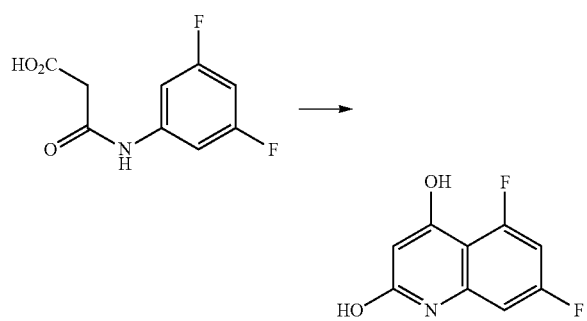

Prepared according to Procedure C using 3-(3,5-difluorophenylamino)-3-oxopropanoic acid (1.10 g, 5.20 mmol) to give 5,7-difluoroquinoline-2,4-diol. Mass Spectrum (ESI) m/e=198.1 (M+1).

2,4-Dichloro-5,7-difluoroquinoline

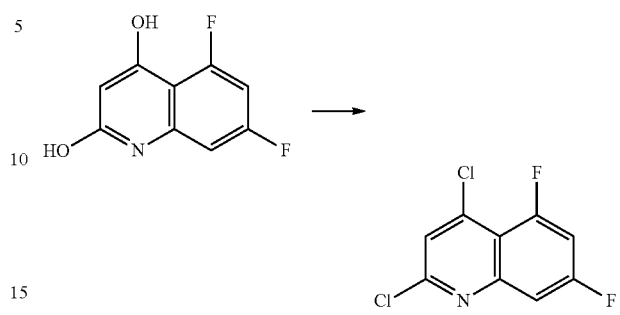

Prepared according to Procedure D using 5,7-difluoroquinoline-2,4-diol (800 mg, 4.06 mmol) to give 2,4-dichloro-5,7-difluoroquinoline. 1H NMR (400 MHz, CDCl3) δ ppm 7.54 (1H, ddd, J=9.1, 2.6, 1.6 Hz), 7.47 (1H, d, J=0.8 Hz), 7.14 (1H, ddd, J=11.5, 8.8, 2.7 Hz).

4-Chloro-5,7-difluoro-2-(pyridin-2-yl)quinoline

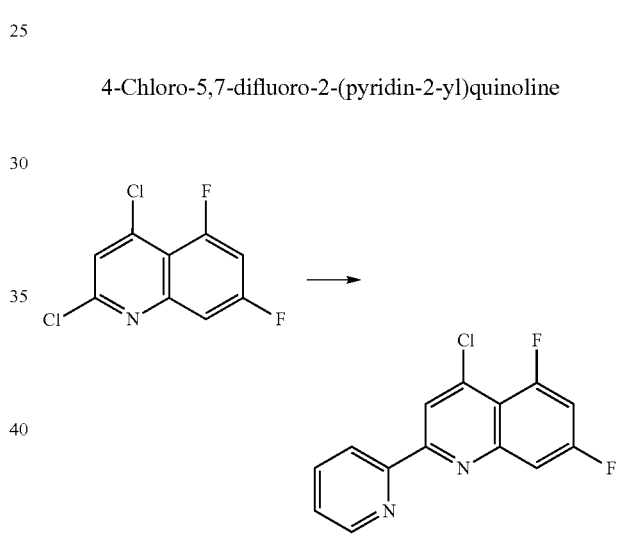

Prepared according to procedure E using 2,4-dichloro-5,7-difluoroquinoline (350 mg, 1.50 mmol) to give 4-chloro-5,7-difluoro-2-(pyridin-2-yl)quinoline. Mass Spectrum (ESI) m/e=277.0 (M+1).

N-(2,5-Di-4-morpholinyl-3-pyridinyl)-5,7-difluoro-2-(2-pyridinyl)-4-quinolinamine

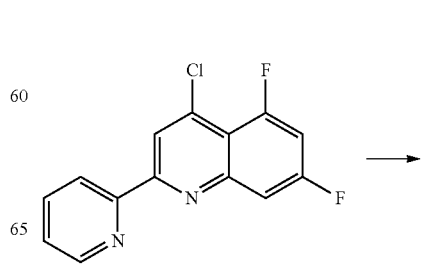

143
-continued

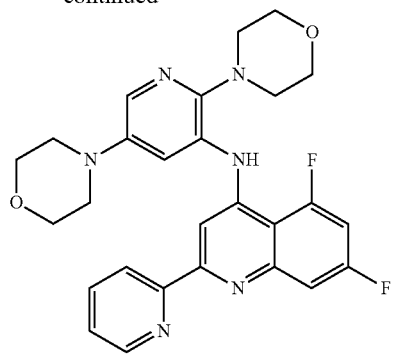

Prepared according to Procedure H using 4-chloro-5,7-difluoro-2-(pyridin-2-yl)-quinoline (40.0 mg, 0.145 mmol) and 2,5-dimorpholinopyridin-3-amine in toluene to give N-(2,5-di-4-morpholinyl-3-pyridinyl)-5,7-difluoro-2-(2-pyridinyl)-4-quinolinamine. $^1$H NMR (CDCl$_3$) δ ppm 8.65 (1H, d, J=7.2 Hz), 8.62 (1H, dt, J=4.8, 0.8 Hz), 8.54 (1H, s), 8.46 (1H, d, J=17.8 Hz), 7.87 (1H, td, J=7.7, 2.0 Hz), 7.83 (1H, d, J=2.7 Hz), 7.69 (1H, d, J=2.7 Hz), 7.66 (1H, br. s.), 7.36 (1H, ddd, J=7.5, 4.7, 1.1 Hz), 7.02 (1H, ddd, J=14.1, 8.4, 2.5 Hz), 3.89 (4H, dd, J=5.7, 3.9 Hz), 3.80-3.87 (4H, m), 3.24 (4H, dd, J=5.7, 3.9 Hz), 3.03-3.17 (4H, m). Mass Spectrum (ESI) m/e=505.1 (M+1).

Example 69

Preparation of 5,7-difluoro-N-(2-(4-methoxyphenyl)-5-(4-morpholinyl)-3-pyridinyl)-3-methyl-2-(2-pyridinyl)-4-quinolinamine 5-Bromo-2-(4-methoxyphenyl)-3-nitropyridine

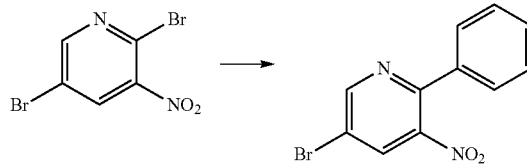

A stirred mixture of 2,5-dibromo-3-nitropyridine (0.2563 g, 0.909 mmol), 4-methoxyphenylboronic acid (0.14 g, 0.93 mmol), tetrakis(triphenylphosphine)-palladium (0.072 g, 0.062 mmol), and 2.0M sodium carbonate (2.3 mL, 4.60 mmol) in toluene (3.0 mL) and ethanol (1.0 mL) was heated to 70° C. After 2.5 h, the reaction was cooled to rt then diluted with water. After extraction with EtOAc, the organic extraction was dried over anhydrous sodium sulfate. After filtration and concentration, the residue was purified on silica gel (0-15% EtOAc in hexanes) to afford a yellow solid as 5-bromo-2-(4-methoxyphenyl)-3-nitropyridine. $^1$H NMR (400 MHz, CDCl$_3$) δ ppm 8.88 (1H, d, J=2.0 Hz), 8.23 (1H, d, J=2.2 Hz), 7.53 (2H, m), 6.99 (2H, m), 3.87 (3H, s).

144

5-Bromo-2-(4-methoxyphenyl)pyridin-3-amine

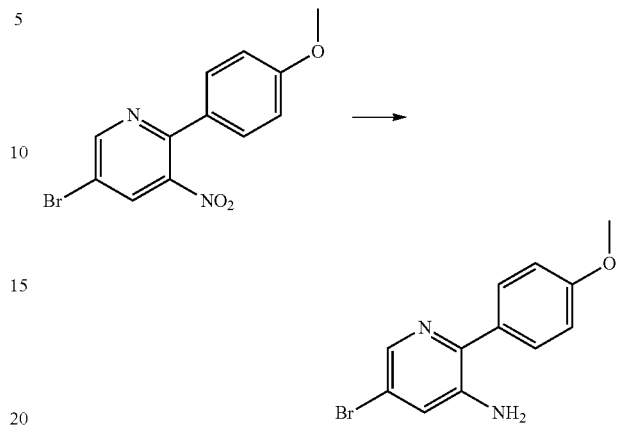

To a stirred mixture of 5-bromo-2-(4-methoxyphenyl)-3-nitropyridine (0.19 g, 0.60 mmol) in EtOAc (10 mL) was added tin(II) chloride dihydrate (0.67 g, 3.00 mmol) in portions. Upon complete addition of the reducing agent, the mixture was carefully heated to 70° C. After 20 h, the reaction was cooled to rt and diluted with ethyl acetate, then washed with 1M NaOH, water, and brine. After drying over anhydrous sodium sulfate and filtration, the organic solvent was removed under reduced pressure. The light yellow solid was identified as 5-bromo-2-(4-methoxyphenyl)pyridin-3-amine. $^1$H NMR (400 MHz, DMSO-d$_6$) δ ppm 7.90 (1H, d, J=2.0 Hz), 7.57 (2H, d, J=8.8 Hz), 7.35 (1H, d, J=2.0 Hz), 7.01 (2H, d, J=8.8 Hz), 5.36 (2H, s), 3.80 (3H, s).

N-(5-Bromo-2-(4-methoxyphenyl)pyridin-3-yl)-5,7-difluoro-3-methyl-2-(pyridin-2-yl)quinolin-4-amine

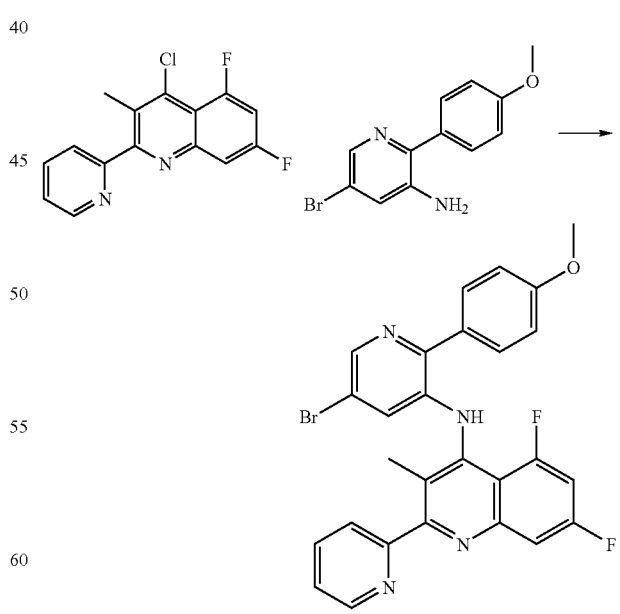

A dry flask containing 5-bromo-2-(4-methoxyphenyl)pyridin-3-amine (0.14 g, 0.52 mmol) in dry DMF (5.0 mL) was cooled to 0° C., then sodium hydride, 60% dispersion in mineral oil (0.043 g, 1.07 mmol) was added carefully in portions. The mixture was stirred at 0° C. for 15 min, then 4-chloro-5,7-difluoro-3-methyl-2-(pyridin-2-yl)quinoline (0.18 g, 0.62 mmol) was added in portions. Upon complete addition, the mixture was warmed to 60° C. After 18 h, the reaction was cooled to rt then was carefully treated with 10% sodium carbonate solution. The black mixture was subsequently extracted five times with DCM:MeOH (90:10). The organic extraction was then washed one time with brine and dried over anhydrous magnesium sulfate. After filtration and concentration, the black residue was purified on silica gel (50-100% EtOAc in hexanes) to afford a mostly N-(5-bromo-2-(4-methoxyphenyl)pyridin-3-yl)-5,7-difluoro-3-methyl-2-(pyridin-2-yl)quinolin-4-amine. Mass Spectrum (ESI) m/e=533.0 (M+1).

5,7-Difluoro-N-(2-(4-methoxyphenyl)-5-(4-morpholinyl)-3-pyridinyl)-3-methyl-2-(2-pyridinyl)-4-quinolinamine

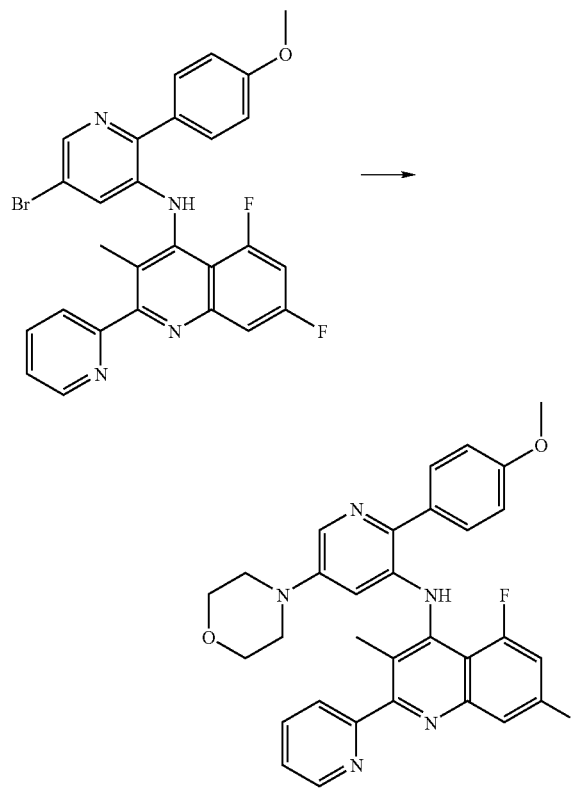

A stirred mixture of mostly N-(5-bromo-2-(4-methoxyphenyl)pyridin-3-yl)-5,7-difluoro-3-methyl-2-(pyridin-2-yl)quinolin-4-amine (0.093 g, 0.18 mmol), 2-dicyclohexylphosphino-2,4,6,-triisopropylbiphenyl (0.017 g, 0.035 mmol), tris(dibenzylideneacetone)dipalladium (0) (0.017 g, 0.018 mmol), and sodium tert-butoxide (0.058 g, 0.60 mmol) in dry toluene (3.0 mL) was purged three times with argon and placed under vacuum three times, then morpholine (0.2 mL, 2.30 mmol) was added to the mixture by syringe. Upon complete addition, the mixture was heated to 100° C. After 23.5 h, the reaction was cooled to rt, then treated with 1M Na$_2$CO$_3$ solution. After extracting twice with DCM:MeOH (95:5), the organics were combined and dried over anhydrous magnesium sulfate. After filtration and concentration the residue was purified on silica gel (0-40% of 89:9:1 DCM:MeOH: ammonium hydroxide solution in DCM) to afford an impure light yellow film. This film was submitted to analytical group for SFC purification. After concentration, the residue was identified as 5,7-difluoro-N-(2-(4-methoxyphenyl)-5-(4-morpholinyl)-3-pyridinyl)-3-methyl-2-(2-pyridinyl)-4-quinolinamine. $^1$H NMR (400 MHz, CDCl$_3$) δ ppm 8.74 (1H, m), 8.05 (1H, m), 7.94 (2H, m), 7.76 (2H, m), 7.64 (1H, m), 7.42 (1H, m), 7.07 (3H, m), 6.99 (1H, m), 6.54 (1H, m), 3.92 (7H, m), 3.22 (4H, m), 2.22 (3H, s). Mass Spectrum ESI (pos.) m/e: 540.3 (M+H)$^+$.

Example 70

Preparation of 5,7-difluoro-N-(2-(3-methoxyphenyl)-5-(4-morpholinyl)-3-pyridinyl)-3-methyl-2-(2-pyridinyl)-4-quinolinamine 5-Bromo-2-(3-methoxyphenyl)-3-nitropyridine

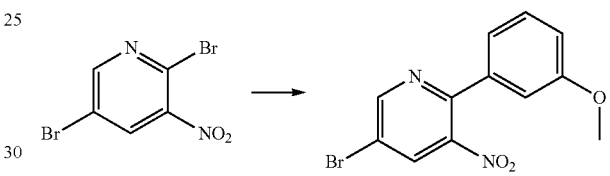

A stirred mixture of 2,5-dibromo-3-nitropyridine (0.2621 g, 0.930 mmol), 3-methoxyphenylboronic acid (0.155 g, 1.02 mmol), tetrakis(triphenylphosphine)-palladium (0.076 g, 0.065 mmol), and 2.0M sodium carbonate (2.4 mL, 4.80 mmol) in toluene (3.0 mL) and ethanol (1.0 mL) was heated to 70° C. After 2.5 h, the reaction was cooled to rt then diluted with water. After extraction with EtOAc, the organic extraction was dried over anhydrous sodium sulfate. After filtration and concentration, the residue was purified on silica gel (0-20% EtOAc in hexanes) to afford a yellow solid as 5-bromo-2-(3-methoxyphenyl)-3-nitropyridine. $^1$H NMR (400 MHz, CDCl$_3$) δ ppm 8.91 (1H, d, J=2.2 Hz), 8.27 (1H, d, J=2.2 Hz), 7.42 (1H, m), 7.14 (3H, m), 3.86 (3H, s).

5-Bromo-2-(3-methoxyphenyl)pyridin-3-amine

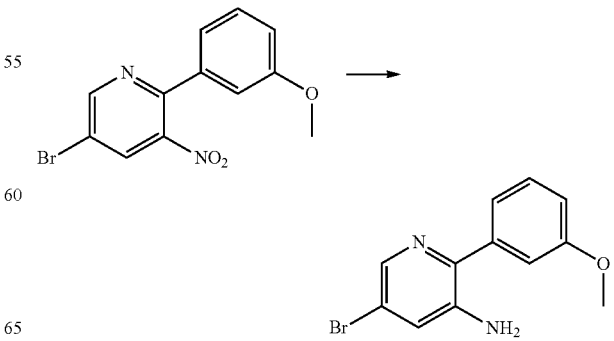

To a stirred mixture of 5-bromo-2-(3-methoxyphenyl)-3-nitropyridine (0.19 g, 0.61 mmol) in EtOAc (10 mL) was added tin(II) chloride dihydrate (0.70 g, 3.10 mmol) in portions. Upon complete addition of the reducing agent, the mixture was carefully heated to 70° C. After 23 h, the reaction was cooled to rt and diluted with ethyl acetate, then washed with 1M NaOH, water, and brine. After drying over anhydrous sodium sulfate and filtration, the organic solvent was removed under reduced pressure. The beige solid was identified as mostly 5-bromo-2-(3-methoxyphenyl)pyridin-3-amine. $^1$H NMR (400 MHz, CDCl$_3$) δ ppm 7.99 (1H, quin, J=1.6 Hz), 7.30 (1H, m), 7.12 (2H, m), 6.87 (1H, m), 3.96 (2H, br. s.), 3.72 (3H, t, J=1.4 Hz).

N-(5-Bromo-2-(3-methoxyphenyl)pyridin-3-yl)-5,7-difluoro-3-methyl-2-(pyridin-2-yl)quinolin-4-amine

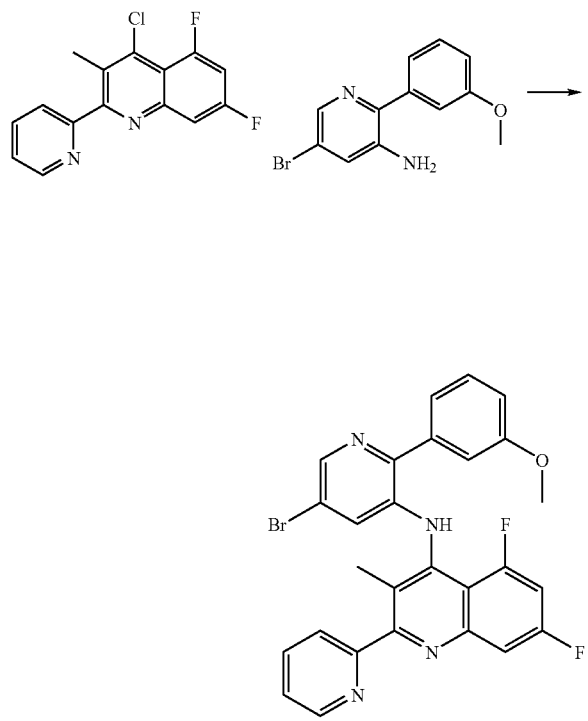

A dry flask containing 5-bromo-2-(3-methoxyphenyl)pyridin-3-amine (0.156 g, 0.56 mmol) in dry DMF (10.0 mL) was cooled to 0° C., then sodium hydride, 60% dispersion in mineral oil (0.0454 g, 1.14 mmol) was added carefully in portions. The mixture was stirred at 0° C. for 15 min, then 4-chloro-5,7-difluoro-3-methyl-2-(pyridin-2-yl)quinoline (0.25 g, 0.86 mmol) was added in portions. Upon complete addition, the mixture was warmed to 60° C. After 3 h, the reaction was cooled to rt then was carefully treated with 10% sodium carbonate solution. The black mixture was subsequently extracted five times with DCM:MeOH (90:10). The organic extraction was then washed one time with brine and dried over anhydrous magnesium sulfate. After filtration and concentration, the black residue was treated with MeOH and placed on the rotovap. (without vac.) in a 45° C. water bath. After 30 min, the solid was filtered and rinsed twice with MeOH to afford a tan solid as mostly N-(5-bromo-2-(3-methoxyphenyl)pyridin-3-yl)-5,7-difluoro-3-methyl-2-(pyridin-2-yl)quinolin-4-amine. Mass Spectrum (ESI) m/e=533.0 (M+1).

5,7-Difluoro-N-(2-(3-methoxyphenyl)-5-(4-morpholinyl)-3-pyridinyl)-3-methyl-2-(2-pyridinyl)-4-quinolinamine

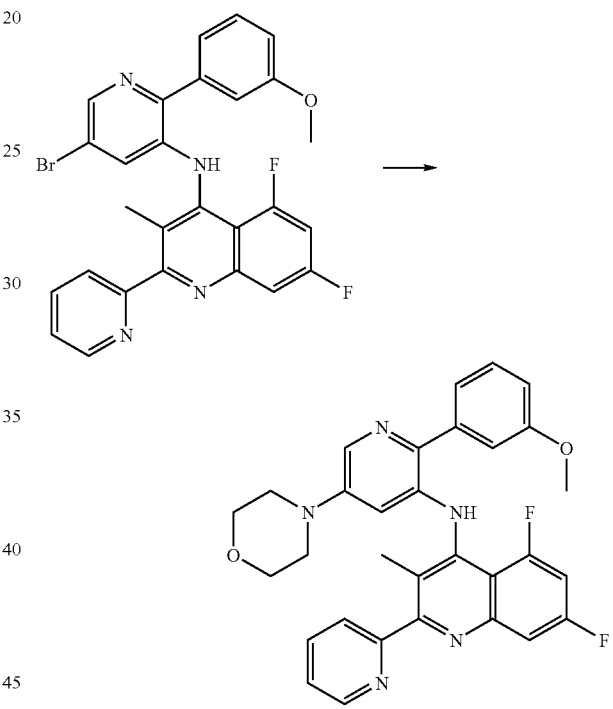

A stirred mixture of N-(5-bromo-2-(3-methoxyphenyl)pyridin-3-yl)-5,7-difluoro-3-methyl-2-(pyridin-2-yl)quinolin-4-amine (0.103 g, 0.19 mmol), morpholine (0.04 mL, 0.46 mmol), tris(dibenzylideneacetone)dipalladium (0) (0.019 g, 0.021 mmol), 2-dicyclohexylphosphino-2,4,6,-triisopropylbiphenyl (0.0188 g, 0.039 mmol), and sodium tert-butoxide (0.058 g, 0.608 mmol) in dry toluene (3.0 mL) was purged three times with argon and placed under vacuum three times, then the mixture was heated to 100° C. After 21.5 h, the reaction was cooled to rt, then treated with water. After extracting twice with DCM:MeOH (95:5), the organics were combined and dried over anhydrous magnesium sulfate. After filtration and concentration the residue was purified on basic alumina (0-30% EtOAc in hexanes) to afford a light yellow solid as 5,7-difluoro-N-(2-(3-methoxyphenyl)-5-(4-morpholinyl)-3-pyridinyl)-3-methyl-2-(2-pyridinyl)-4-quinolinamine. $^1$H NMR (500 MHz, CDCl$_3$) δ ppm 8.73 (1H, m), 8.02 (1H, d, J=2.4 Hz), 7.95 (2H, m), 7.63 (1H, m.), 7.50 (4H, m), 7.05 (2H, m), 6.56 (1H, m.), 3.94 (7H, m), 3.32 (4H, m), 2.24 (3H, s). Mass Spectrum ESI (pos.) m/e: 540.3 (M+H)$^+$.

Example 71

Preparation of 5,7-difluoro-N-(2-fluoro-5-(4-morpholinyl)-3-pyridinyl)-3-methyl-2-(2-pyridinyl)-4-quinolinamine 2-Fluoro-5-morpholinopyridin-3-amine

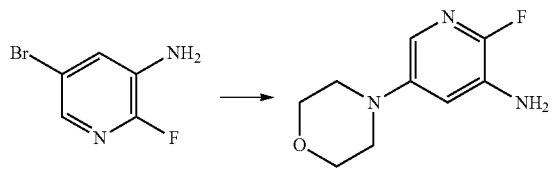 [SMILES: Nc1cc(Br)cnc1F ; Nc1cc(N2CCOCC2)cnc1F]

A stirred mixture of 3-amino-5-bromo-2-fluoropyridine (0.96 g, 5.02 mmol), L-proline (0.12 g, 1.01 mmol), potassium carbonate (1.39 g, 10.1 mmol), copper(I) iodide (0.096 g, 0.50 mmol), and morpholine (1.31 mL, 15.04 mmol) in dry DMSO (3.0 mL) was purged three times with argon and placed under vacuum three times, then the mixture was heated to 90° C. After 21.5 h, the reaction was cooled to rt, then treated with water. After extracting twice with EtOAc, the organics were combined and dried over anhydrous sodium sulfate. After filtration and concentration the residue was purified on basic alumina (10-50% EtOAc in hexanes) to afford a white solid as 2-fluoro-5-morpholinopyridin-3-amine. $^1$H NMR (400 MHz, DMSO-d$_6$) δ ppm 6.96 (1H, t, J=2.6 Hz), 6.75 (1H, dd, J=9.6, 2.7 Hz), 5.25 (2H, br. s.), 3.80 (4H, m), 3.08 (4H, m). Mass Spectrum ESI (pos.) m/e: 198.1 (M+H)$^+$.

5,7-Difluoro-N-(2-fluoro-5-(4-morpholinyl)-3-pyridinyl)-3-methyl-2-(2-pyridinyl)-4-quinolinamine

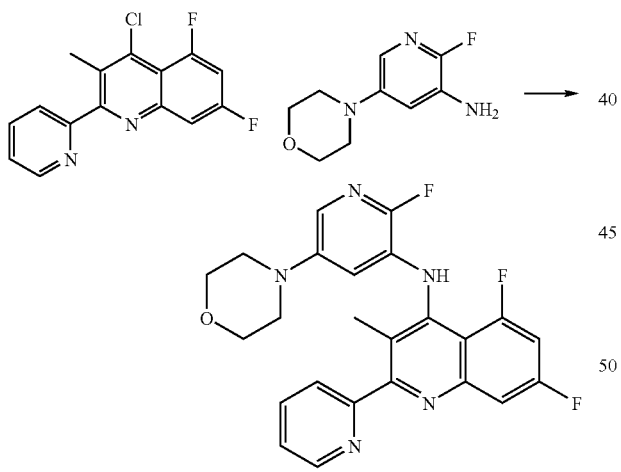

A mixture of 2-fluoro-5-morpholinopyridin-3-amine (0.12 g, 0.60 mmol), 4-chloro-5,7-difluoro-3-methyl-2-(pyridin-2-yl)quinoline (0.261 g, 0.90 mmol), tris(dibenzylideneacetone)dipalladium (0) (0.055 g, 0.060 mmol), 2-dicyclohexylphosphino-2,4,6,-triisopropylbiphenyl (0.058 g, 0.121 mmol), and sodium tert-butoxide (0.176 g, 1.83 mmol) in dry toluene (5.0 mL) was degassed by nitrogen. The mixture was heated to 90° C. After 21.5 h, the reaction was cooled to rt, then treated with water. After extracting twice with EtOAc, the organics were combined and dried over anhydrous magnesium sulfate. After filtration and concentration the residue was purified on basic alumina (0-60% EtOAc in hexanes) to afford an light yellow solid as 5,7-difluoro-N-(2-fluoro-5-(4-morpholinyl)-3-pyridinyl)-3-methyl-2-(2-pyridinyl)-4-quinolinamine. $^1$H NMR (500 MHz, CDCl$_3$) δ ppm 8.71 (1H, d, J=4.6 Hz), 7.93 (2H, m), 7.70 (1H, m), 7.42 (1H, d, J=2.7 Hz), 7.32 (1H, m), 7.15 (1H, m), 7.01 (1H, m), 6.58 (1H, d, J=7.1 Hz), 3.88 (4H, m), 3.16 (4H, m), 2.23 (3H, s). Mass Spectrum ESI (pos.) m/e: 452.2 (M+H)$^+$.

Example 72

N-(2,5-Di-4-morpholinyl-3-pyridinyl)-7-fluoro-2-(5-fluoro-3-pyridinyl)-3-methyl-4-quinolinamine 4-(5-Chloro-3-nitropyridin-2-yl)morpholine

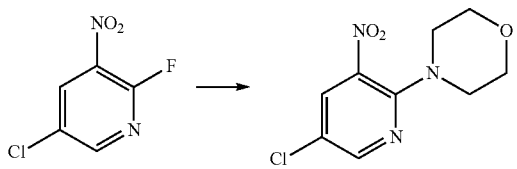 [SMILES: O=[N+]([O-])c1cc(Cl)cnc1F ; O=[N+]([O-])c1cc(Cl)cnc1N1CCOCC1]

To a stirred solution of 5-chloro-2-fluoro-3-nitropyridine (5 g, 28 mmol) in THF (40 mL) was added morpholine (4 mL, 42 mmol). The reaction was stirred at 0° C. for ten min, at rt for 1 h, and refluxed for four h. The reaction was then cooled to rt, taken up in EtOAc, and washed with satd aq. sodium bicarbonate and brine. The organic layer was dried (magnesium sulfate) and concentrated, affording 4-(5-chloro-3-nitropyridin-2-yl)morpholine as a yellow oil. Mass Spectrum (ESI) m/e=244.0 (M+1).

4-(6-Morpholino-5-nitropyridin-3-yl)morpholine

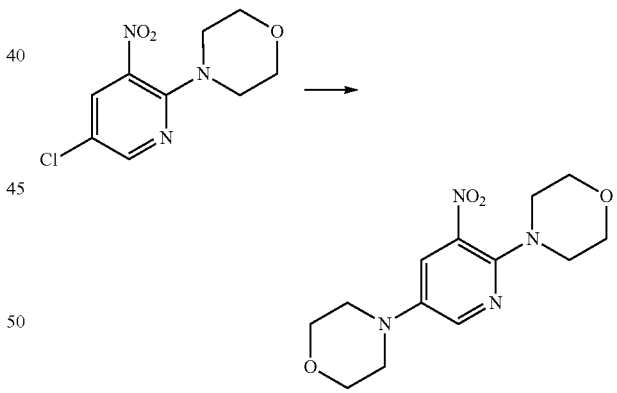

To a stirred solution of 4-(5-chloro-3-nitropyridin-2-yl)morpholine (2.48 g, 10 mmol; described herein) in toluene (190 mL) were sequentially added morpholine (1.8 mL, 20 mmol), tris(dibenzylideneacetone)dipalladium(o) (0.65 g, 0.71 mmol), 2-(dicyclohexylphosphino)-2,4,6,-tri-i-propyl-1,1-biphenyl (0.73 g, 1.5 mmol), and sodium tert-butoxide (2.0 g, 20 mmol). The reaction was heated to reflux overnight, cooled to rt, and concentrated. The resulting residue was taken up in EtOAc, washed with satd aq. sodium bicarbonate solution and brine, and the organic layer dried (magnesium sulfate) and concentrated. Column chromatography afforded 4-(6-morpholino-5-nitropyridin-3-yl)morpholine as a red oil. Mass Spectrum (ESI) m/e=295.1 (M+1).

2,5-Dimorpholinopyridin-3-amine

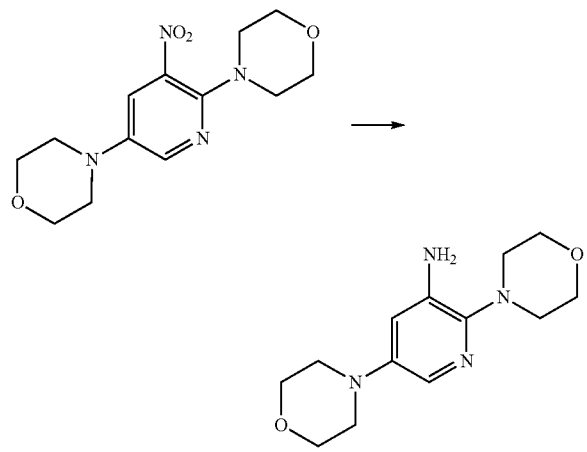

To a stirring solution of 4-(5-morpholino-3-nitropyridin-2-yl)morpholine (1.22 g, 4.15 mmol; described herein) and EtOAc (50 mL) was added tin(II) chloride dihydrate (4.52 g, 20.7 mmol). The mixture was stirred at rt for ten min, refluxed for 2 h, and then cooled to rt. A solid was removed by filtration and both this and the EtOAc solution were washed with water and brine. The combined aq. portions were basified with 1M NaOH and the product extracted with EtOAc, dried (magnesium sulfate), and concentrated, affording 2,5-dimorpholinopyridin-3-amine as a beige solid. Mass Spectrum (ESI) m/e=265.2 (M+1).

Prepared according to Procedure K, method 2 using 2,5-dimorpholinopyridin-3-amine (43 mg, 0.16 mmol; described herein), 4-chloro-7-fluoro-2-(5-fluoropyridin-3-yl)-3-methylquinoline (47 mg, 0.16 mmol; described herein), 4.0M hydrochloric acid in 1,4-dioxane (4 µL, 0.1 equiv, 16 µmol), and NMP (190 µL, 1.9 mmol). The reaction was heated in a microwave at 150° C. for 4 h. Purification afforded N-(2,5-di-4-morpholinyl-3-pyridinyl)-7-fluoro-2-(5-fluoro-3-pyridinyl)-3-methyl-4-quinolinamine as a yellow solid. ¹H NMR (400 MHz, chloroform-d) δ ppm 8.69 (1H, m), 8.60 (1H, d, J=2.7 Hz), 7.84 (1H, m), 7.76 (2H, m), 7.64 (1H, d, J=2.7 Hz), 7.33 (1H, m), 6.81 (1H, s), 6.21 (1H, d, J=2.7 Hz), 3.89-3.97 (4H, m), 3.72-3.79 (4H, m), 3.24 (4H, m), 2.89-2.98 (4H, m), 2.33 (3H, s). Mass Spectrum (ESI) m/e=519.0 (M+1).

Example 73

N-(2,5-Di-4-morpholinyl-3-pyridinyl)-7-fluoro-3-methyl-2-(2-pyridinyl)-4-quinolinamine

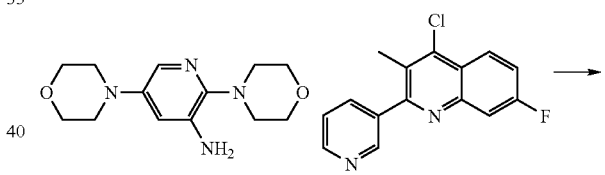

N-(2,5-Di-4-morpholinyl-3-pyridinyl)-7-fluoro-2-(5-fluoro-3-pyridinyl)-3-methyl-4-quinolinamine

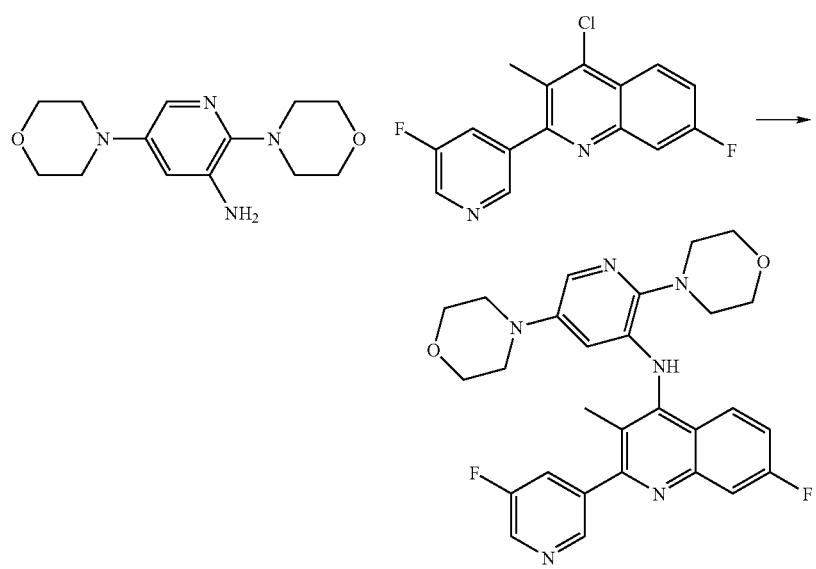

-continued

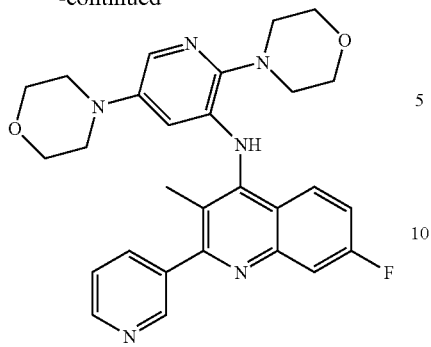

Prepared according to Procedure K, method 2 using 2,5-dimorpholinopyridin-3-amine (143 mg, 0.543 mmol; described herein), 4-chloro-7-fluoro-3-methyl-2-(pyridin-2-yl)quinoline (148 mg, 0.54 mmol; described herein), 4.0M hydrochloric acid in 1,4-dioxane (140 µL, 0.54 mmol), and NMP (780 µL, 8.1 mmol). The reaction was heated in a microwave at 160° C. for three h. Purification afforded N-(2,5-di-4-morpholinyl-3-pyridinyl)-7-fluoro-3-methyl-2-(2-pyridinyl)-4-quinolinamine as a yellow solid. $^1$H NMR (400 MHz, chloroform-d) δ ppm 8.75 (1H, dd, J=4.3, 0.8 Hz), 7.93 (3H, d, J=5.5 Hz), 7.86 (1H, br. s.), 7.60-7.69 (1H, m), 7.38-7.46 (1H, m), 7.29-7.36 (2H, m), 6.31 (1H, br. s.), 3.91 (4H, br. s.), 3.68-3.81 (4H, m), 3.25 (4H, br. s.), 2.95 (4H, br. s.), 2.38 (3H, s). Mass Spectrum (ESI) m/e=501.2 (M+1).

Example 74

N-(2,5-Di-4-morpholinyl-3-pyridinyl)-5-fluoro-3-methyl-2-(2-pyridinyl)-4-quinolinamine

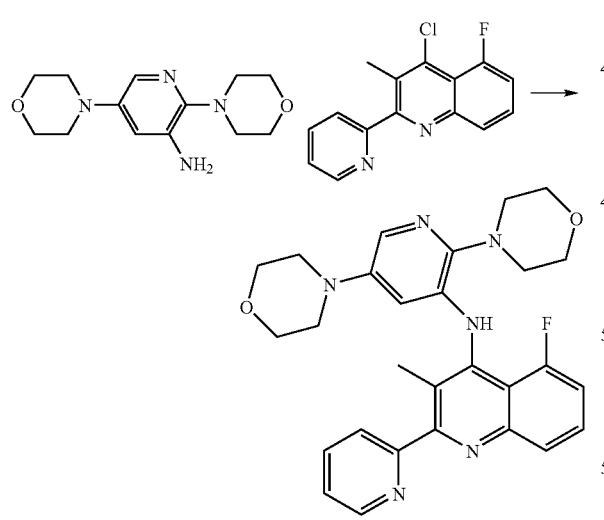

Prepared according to Procedure K, method 2 using 2,5-dimorpholinopyridin-3-amine (157 mg, 0.594 mmol; described herein), 4-chloro-5-fluoro-3-methyl-2-(pyridin-2-yl)quinoline (162 mg, 0.59 mmol; described herein), 4.0M hydrochloric acid in 1,4-dioxane (150 µL, 0.59 mmol), and NMP (590 µL, 7.1 mmol), and heating in a microwave at 160° for 3 h. Purification afforded N-(2,5-di-4-morpholinyl-3-pyridinyl)-5-fluoro-3-methyl-2-(2-pyridinyl)-4-quinolinamine as a yellow solid. $^1$H NMR (400 MHz, chloroform-d) δ ppm 8.70 (1H, d, J=4.7 Hz), 7.98 (1H, d, J=8.2 Hz), 7.87-7.93 (2H, m), 7.83 (1H, d, J=11.7 Hz), 7.55-7.65 (2H, m), 7.38 (1H, m), 7.13-7.24 (1H, m), 6.46 (1H, d, J=2.7 Hz), 3.88-4.03 (4H, m), 3.77-3.88 (4H, m), 3.01-3.28 (4H, br. s.), 3.04-3.14 (4H, m), 2.23 (3H, s). Mass Spectrum (ESI) m/e=501.2 (M+1).

Example 75

N-(5-(2,2-Dimethyl-4-morpholinyl)-2-(4-morpholinyl)-3-pyridinyl)-7-fluoro-3-methyl-2-(2-pyridinyl)-4-quinolinamine 2,2-Dimethyl-4-(6-morpholino-5-nitropyridin-3-yl)morpholine

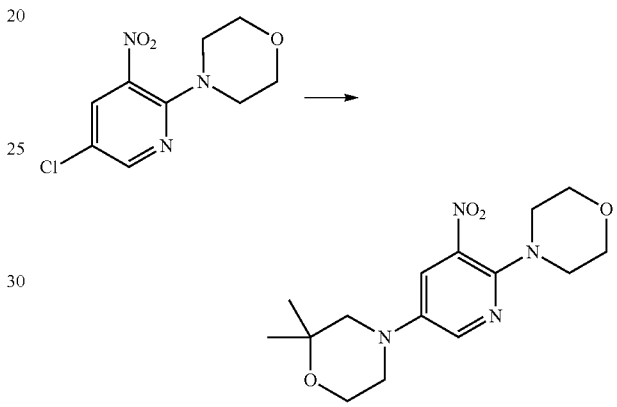

A solution of 4-(5-chloro-3-nitropyridin-2-yl)morpholine (850 mg, 3.49 mmol; described herein), 2,2-dimethylmorpholine (480 µL, 4180 µmol), tris(dibenzylideneacetone)dipalladium(o) (224 mg, 0.244 mmol), 2-(dicyclohexylphosphino)-2,4,6,-tri-i-propyl-1,1-biphenyl (249 mg, 0.523 mmol), sodium 2-methylpropan-2-olate (671 mg, 6.98 mmol), and toluene (517 mL) was refluxed overnight, then cooled to rt and concentrated. The resulting residue was taken up in EtOAc, washed with satd aq. sodium bicarbonate and brine, then the organic layer dried (magnesium sulfate) and concentrated. Column chromatography afforded 2,2-dimethyl-4-(6-morpholino-5-nitropyridin-3-yl)morpholine as a red solid. Mass Spectrum (ESI) m/e=323.2 (M+1).

5-(2,2-Dimethylmorpholino)-2-morpholinopyridin-3-amine

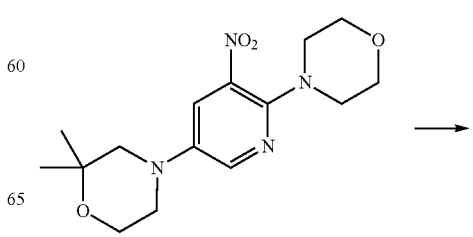

-continued

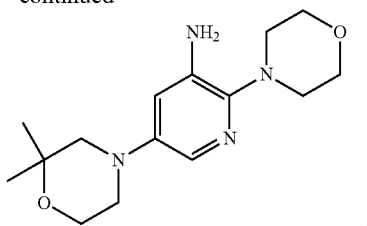

A solution of 2,2-dimethyl-4-(6-morpholino-5-nitropyridin-3-yl)morpholine (490 mg, 1.52 mmol; described herein) in 30 mL MeOH was reduced in a Thalles H-Cube® hydrogenator using a 10% Pd/C CatCart column (20 bar, 25° C., 1 mL/min flow rate.) The reaction mixture was then concentrated, diluted with EtOAc, and extracted with 1M HCl. The aq. layer was washed with DCM and basified with 1M NaOH. The product was extracted with EtOAc, dried (magnesium sulfate), and concentrated, affording 5-(2,2-dimethylmorpholino)-2-morpholinopyridin-3-amine as a beige powder. Mass Spectrum (ESI) m/e=293.2 (M+1).

N-(5-(2,2-Dimethyl-4-morpholinyl)-2-(4-morpholinyl)-3-pyridinyl)-7-fluoro-3-methyl-2-(2-pyridinyl)-4-quinolinamine

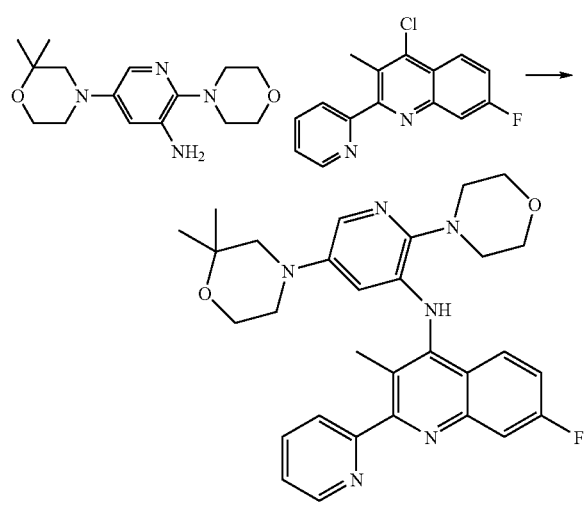

Prepared according to Procedure K, method 2 using 4-chloro-7-fluoro-3-methyl-2-(pyridin-2-yl)quinoline (66.3 mg, 0.24 mmol; described herein), 5-(2,2-dimethylmorpholino)-2-morpholinopyridin-3-amine (71.0 mL, 0.243 mmol, described herein), 4.0M hydrochloric acid in 1,4-dioxane (60 μL, 0.24 mmol), and NMP (350 μL, 3.6 mmol), and heating in a microwave at 160° C. for 3 h. Purification afforded N-(5-(2,2-dimethyl-4-morpholinyl)-2-(4-morpholinyl)-3-pyridinyl)-7-fluoro-3-methyl-2-(2-pyridinyl)-4-quinolinamine as a yellow solid. $^1$H NMR (400 MHz, chloroform-d) δ ppm 8.74 (1H, dd, J=3.5, 1.2 Hz), 7.86-7.95 (2H, m), 7.78-7.86 (2H, m), 7.58 (1H, d, J=2.7 Hz), 7.40 (1H, ddd, J=6.9, 5.0, 1.8 Hz), 7.28-7.33 (1H, m), 6.83 (1H, s), 6.22 (1H, d, J=2.7 Hz), 3.93 (4H, t, J=4.7 Hz), 3.72-3.84 (3H, m), 3.65 (1H, t, J=5.9 Hz), 3.09-3.33 (4H, m), 2.80-2.93 (2H, m), 2.74 (2H, s), 2.37 (3H, s), 1.25-1.31 (4H, m). Mass Spectrum (ESI) m/e=529.2 (M+1).

Example 76

N-(5-(2,2-Dimethyl-4-morpholinyl)-2-(4-morpholinyl)-3-pyridinyl)-5-fluoro-3-methyl-2-(2-pyridinyl)-4-quinolinamine

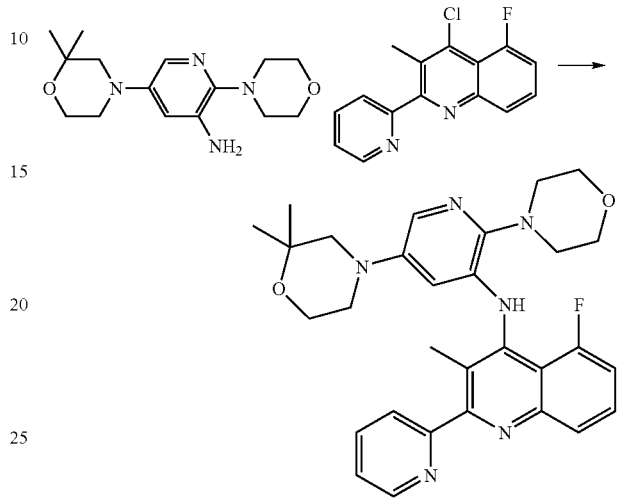

Prepared according to Procedure K, method 2 using 5-(2,2-dimethylmorpholino)-2-morpholinopyridin-3-amine (62 mg, 0.213 mmol; described herein), 4-chloro-5-fluoro-3-methyl-2-(pyridin-2-yl)quinoline (58 mg, 0.213 mmol; described herein), 4.0M hydrochloric acid in 1,4-dioxane (50 μL, 0.21 mmol), and NMP (310 μL, 3.2 mmol), and heating in a microwave for 3 h at 160° C. Purification afforded N-(5-(2,2-dimethyl-4-morpholinyl)-2-(4-morpholinyl)-3-pyridinyl)-5-fluoro-3-methyl-2-(2-pyridinyl)-4-quinolinamine as a yellow solid. $^1$H NMR (400 MHz, chloroform-d) δ ppm 8.70 (1H, d, J=4.7 Hz), 7.86-8.04 (4H, m), 7.54-7.66 (2H, m), 7.38 (1H, ddd, J=6.7, 4.7, 2.0 Hz), 7.19 (1H, dd, J=13.7, 7.8 Hz), 6.45 (1H, d, J=2.3 Hz), 3.93 (4H, t, J=4.3 Hz), 3.78-3.87 (2H, m), 3.02-3.31 (6H, m), 2.88 (2H, s), 2.21 (3H, s) 1.24-1.34 (6H, m). Mass Spectrum (ESI) m/e=529.2 (M+1).

Example 77

7-Fluoro-3-methyl-N-(5-((2S)-2-methyl-4-morpholinyl)-2-(4-morpholinyl)-3-pyridinyl)-2-(2-pyridinyl)-4-quinolinamine

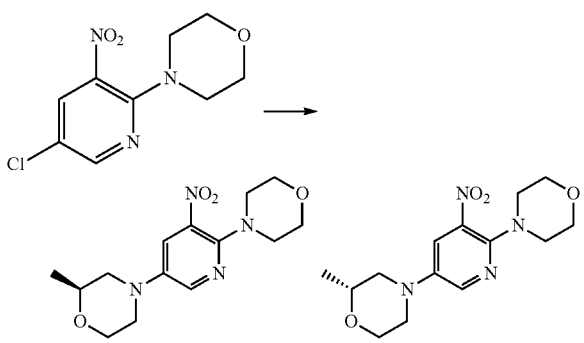

A solution of 4-(5-chloro-3-nitropyridin-2-yl)morpholine (2 g, 8.21 mmol; described herein), 2-methylmorpholine (996 mg, 9.85 mmol), tris(dibenzylideneacetone)dipalladium(0) (526 mg, 0.58 mmol), 2-(dicyclohexylphosphino)-2,4,6,-tri-i-propyl-1,1-biphenyl (587 mg, 1.23 mmol), sodium 2-methylpropan-2-olate (1.6 g, 16.4 mmol), and toluene (126 mL, 119 mmol) was refluxed overnight then cooled to rt and concentrated. The resulting residue was taken up in EtOAc, washed with satd aq. sodium bicarbonate and brine, and the organic layer dried (magnesium sulfate) and concentrated. Column chromatography and chiral separation afforded (S)-2-methyl-4-(6-morpholino-5-nitropyridin-3-yl)morpholine and (R)-2-methyl-4-(6-morpholino-5-nitropyridin-3-yl)morpholine as red solids (absolute configuration not determined and assigned randomly). Mass Spectrum (ESI) m/e=309.2 (M+1).

(S)-5-(2-Methylmorpholino)-2-morpholinopyridin-3-amine and (R)-5-(2-methylmorpholino)-2-morpholinopyridin-3-amine

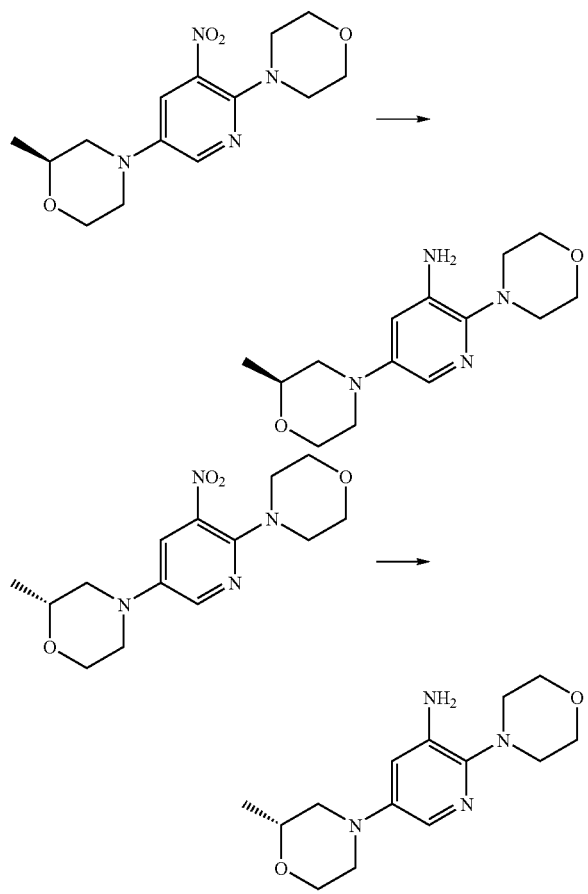

Solutions of (S)-2-methyl-4-(6-morpholino-5-nitropyridin-3-yl)morpholine (310 mg; 1.00 mmol; described herein) and (R)-2-methyl-4-(6-morpholino-5-nitropyridin-3-yl)morpholine (250 mg, 0.811 mmol; described herein) in MeOH (0.006M) were separately reduced in a Thalles HCube™ hydrogenator using a 10% Pd/C CatCart™ column (20 bar, 25° C., 1 mL/min flow rate.) The reaction mixtures were then concentrated, diluted with EtOAc, and extracted with 1M HCl. The aq. layers were washed with DCM, basified with 1M NaOH, and the products extracted with EtOAc, dried (magnesium sulfate), and concentrated, affording racemic product (absolute configurations not determined) as a beige solid. Mass Spectrum (ESI) m/e=279.2 (M+1).

7-Fluoro-3-methyl-N-(5-((2S)-2-methyl-4-morpholinyl)-2-(4-morpholinyl)-3-pyridinyl)-2-(2-pyridinyl)-4-quinolinamine

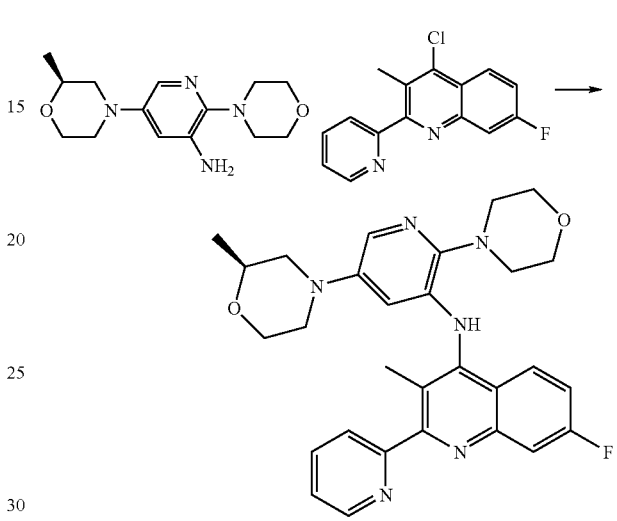

Prepared according to Procedure K, method 2 using (S)-5-(2-methylmorpholino)-2-morpholinopyridin-3-amine (85 mg, 0.305 mmol; described herein), 4-chloro-7-fluoro-3-methyl-2-(pyridin-2-yl)quinoline (83 mg, 0.305 mmol; described herein), 4.0M hydrochloric acid in 1,4-dioxane (80 µL, 0.31 mmol), and NMP (350 µL, 3.7 mmol), and heating in a microwave at 165° C. for 3 h. Purification afforded 7-fluoro-3-methyl-N-(5-((2S)-2-methyl-4-morpholinyl)-2-(4-morpholinyl)-3-pyridinyl)-2-(2-pyridinyl)-4-quinolinamine as a yellow solid (absolute configuration of stereocenter not determined) ¹H NMR (500 MHz, chloroform-d) δ ppm 8.70-8.76 (1H, m), 7.85-7.94 (2H, m), 7.75-7.85 (2H, m), 7.59 (1H, d, J=2.7 Hz), 7.39 (1H, ddd, J=7.1, 5.0, 1.6 Hz), 7.25-7.33 (1H, m), 6.77 (1H, s), 6.23 (1H, d, J=2.7 Hz), 3.84-3.99 (5H, m), 3.56-3.71 (2H, m), 3.23 (4H, br. s.), 3.15 (1H, dt, J=11.7, 2.2 Hz), 3.02-3.11 (1H, m), 2.63-2.74 (1H, m), 2.31-2.43 (4H, m), 1.16 (3H, d, J=6.4 Hz). Mass Spectrum (ESI) m/e=515.2 (M+1).

Example 78

7-Fluoro-3-methyl-N-(5-((2R)-2-methyl-4-morpholinyl)-2-(4-morpholinyl)-3-pyridinyl)-2-(2-pyridinyl)-4-quinolinamine

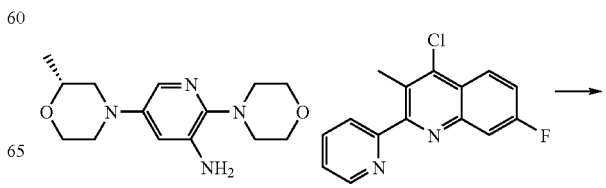

-continued

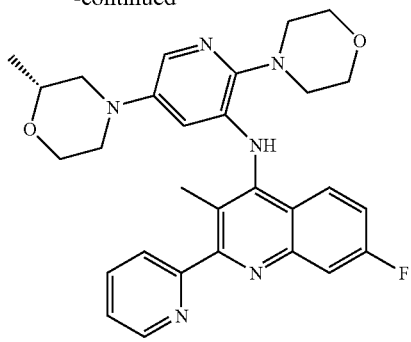

Prepared according to Procedure K, method 2 using (R)-5-(2-methylmorpholino)-2-morpholinopyridin-3-amine (68 mg, 0.25 mmol; described herein), 4-chloro-7-fluoro-3-methyl-2-(pyridin-2-yl)quinoline (67 mg, 0.25 mmol; described herein), 4.0M hydrochloric acid in 1,4-dioxane (60 μL, 0.25 mmol), and NMP (280 μL, 3.0 mmol), and heating in a microwave at 165° C. for 3 h. Purification afforded 7-fluoro-3-methyl-N-(5-((2R)-2-methyl-4-morpholinyl)-2-(4-morpholinyl)-3-pyridinyl)-2-(2-pyridinyl)-4-quinolinamine as a yellow solid (absolute configuration of stereocenter not determined) $^1$H NMR (500 MHz, chloroform-d) δ ppm 8.68-8.76 (1H, m), 7.84-7.94 (2H, m), 7.75-7.84 (2H, m), 7.58 (1H, d, J=2.7 Hz), 7.39 (1H, ddd, J=7.3, 4.8, 1.6 Hz), 7.28 (1H, ddd, J=9.2, 8.0, 2.6 Hz), 6.76 (1H, s), 6.22 (1H, d, J=2.7 Hz), 3.82-3.97 (5H, m), 3.56-3.72 (2H, m), 3.22 (4H, m), 3.14 (1H, m), 2.97-3.10 (1H, m), 2.60-2.72 (1H, m), 2.29-2.42 (4H, m), 1.15 (3H, d, J=6.4 Hz). Mass Spectrum (ESI) m/e=515.2 (M+1).

Example 79

N-(2,5-Di-4-morpholinyl-3-pyridinyl)-3-methyl-2-(2-pyridinyl)-4-quinolinamine

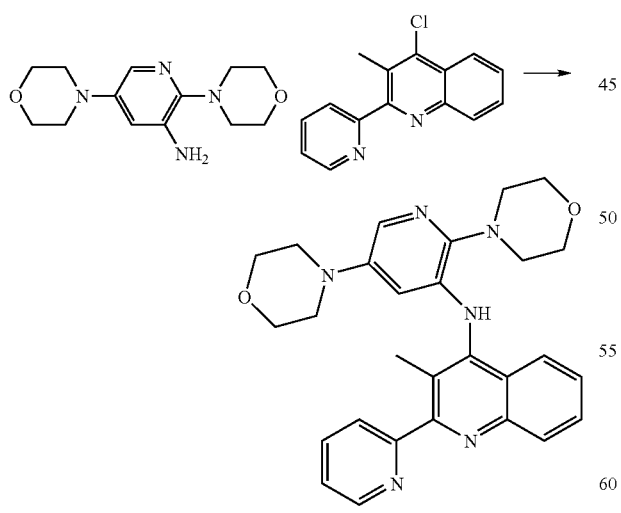

Prepared according to Procedure K, method 2 using 2,5-dimorpholinopyridin-3-amine (63.5 mg, 0.24 mmol; described herein), 4-chloro-3-methyl-2-(pyridin-2-yl)quinoline (61.2 mg, 0.24 mmol; described herein), 4.0M hydrogen chloride in 1,4-dioxane (60 μL, 0.24 mmol), and NMP (280 μL, 2.9 mmol), and heating in a microwave at 165° C. for 3 h. Purification afforded N-(2,5-di-4-morpholinyl-3-pyridinyl)-3-methyl-2-(2-pyridinyl)-4-quinolinamine as a yellow solid. $^1$H NMR (400 MHz, chloroform-d) δ ppm 8.74 (1H, d, J=4.7 Hz), 8.19 (1H, d, J=8.2 Hz), 7.85-7.95 (2H, m), 7.81 (1H, dd, J=8.2, 0.8 Hz), 7.71 (1H, td, J=7.6, 1.2 Hz), 7.59 (1H, d, J=2.7 Hz), 7.47-7.55 (1H, m), 7.34-7.45 (1H, m), 6.78 (1H, s), 6.24 (1H, d, J=2.7 Hz), 3.93 (4H, t, J=4.7 Hz), 3.73 (4H, ddd, J=4.3, 2.7, 2.3 Hz), 3.13-3.36 (4H, m), 2.87-3.01 (4H, m), 2.39 (3H, s). Mass Spectrum (ESI) m/e=483.2 (M+1).

Example 80

N-(2,5-Di-4-morpholinyl-3-pyridinyl)-5,7-difluoro-3-methyl-2-(2-pyridinyl)-4-quinolinamine Ethyl 3-(3,5-difluorophenylamino)-2-methyl-3-oxopropanoate

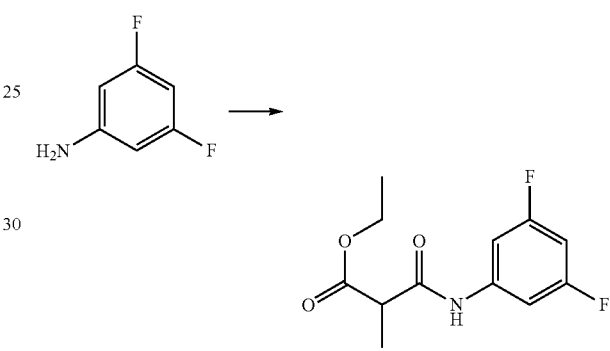

Prepared according to Procedure A using diethyl 2-methylmalonate (34.5 mL, 205 mmol), pyridine (15.6 mL, 190 mmol), and 3,5-difluorobenzenamine (12.4 g, 96 mmol). The reaction was heated to 130° C. for 2 days. Purification afforded ethyl 3-(3,5-difluorophenylamino)-2-methyl-3-oxopropanoate. Mass Spectrum (ESI) m/e=258.2 (M+1).

3-(3,5-Difluorophenylamino)-2-methyl-3-oxopropanoic acid

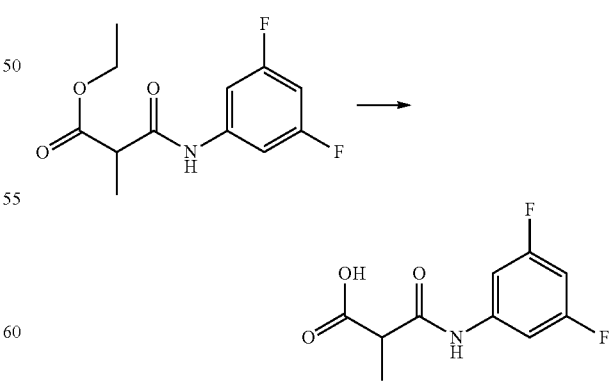

Prepared according to Procedure B using ethyl 3-(3,5-difluorophenylamino)-2-methyl-3-oxopropanoate (11.4 g, 44.3 mmol; described herein) in THF (40 mL), and sodium hydroxide (1.22 g, 53.2 mmol) in water (10 mL). The reaction was stirred at rt for 2 h, affording 3-(3,5-difluorophenylamino)-2-methyl-3-oxopropanoic acid. Mass Spectrum (ESI) m/e=230.0 (M+1).

5,7-Difluoro-3-methylquinoline-2,4(1H,3H)-dione

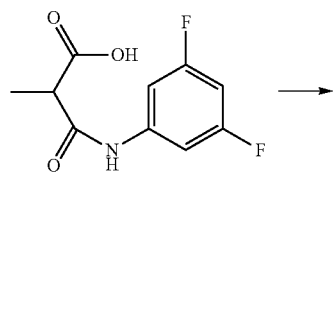

Prepared according to Procedure C using 3-(3,5-difluorophenylamino)-2-methyl-3-oxopropanoic acid (6.70 g, 29.2 mmol; described herein) in polyphosphoric acid (40 mL), affording 5,7-difluoro-3-methylquinoline-2,4(1H,3H)-dione. Mass Spectrum (ESI) m/e=212.0 (M+1).

2,4-Dichloro-5,7-difluoro-3-methylquinoline

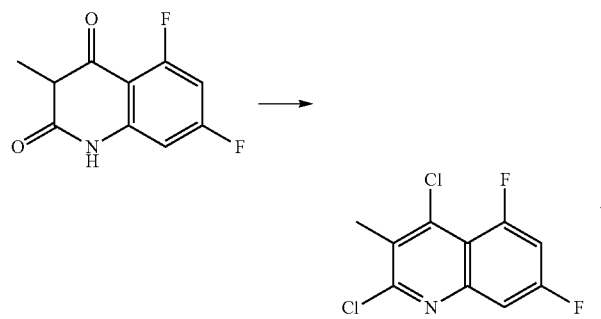

5,7-Difluoro-3-methylquinoline-2,4(1H,3H)-dione (5.20 g, 24.6 mmol; described herein) was stirred in phosphoryl chloride (23.0 mL, 246 mmol) and heated at 100° C. for 6 h. The reaction was then quenched over ice and the product extracted with EtOAc, washed with brine, dried (magnesium sulfate), filtered, and concentrated. The resulting crude residue was triturated with MeOH and dried, affording 2,4-dichloro-5,7-difluoro-3-methylquinoline. Mass Spectrum (ESI) m/e=248.0 (M+1).

4-Chloro-5,7-difluoro-3-methyl-2-(pyridin-2-yl)quinoline

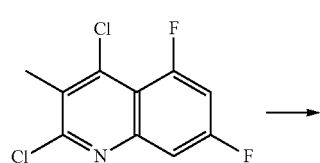

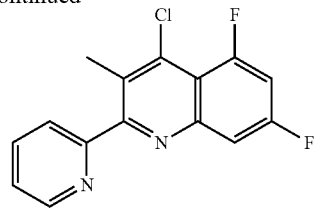

Prepared according to Procedure E using 2,4-dichloro-5,7-difluoro-3-methylquinoline (1.94 g, 7.8 mmol; described herein), 2-(tributylstannyl)pyridine (2.9 mL, 7.8 mmol), and tetrakis(triphenylphosphine)palladium(0) (0.69 g, 0.59 mmol) in toluene. The reaction was stirred at 100° C. for 18 h, then cooled to rt, concentrated, and the resulting residue triturated with hexanes. Column chromatography afforded 4-chloro-5,7-difluoro-3-methyl-2-(pyridin-2-yl)quinoline as a white solid. Mass Spectrum (ESI) m/e=291.0 (M+1).

N-(2,5-Di-4-morpholinyl-3-pyridinyl)-5,7-difluoro-3-methyl-2-(2-pyridinyl)-4-quinolinamine

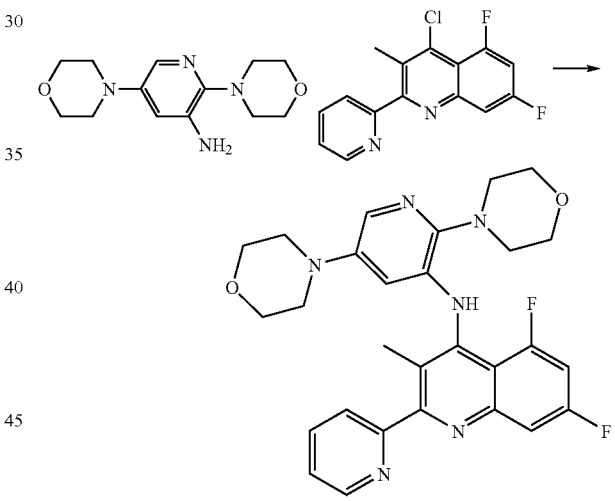

Prepared according to Procedure K, method 2 using 2,5-dimorpholinopyridin-3-amine (118 mg, 0.45 mmol; described herein), 4-chloro-5,7-difluoro-3-methyl-2-(pyridin-2-yl)quinoline (130 mg, 0.45 mmol; described herein), 4.0M hydrogen chloride in 1,4-dioxane (110 µL, 0.45 mmol), and NMP (450 µL). Purification afforded N-(2,5-di-4-morpholinyl-3-pyridinyl)-5,7-difluoro-3-methyl-2-(2-pyridinyl)-4-quinolinamine as a yellow solid. $^1$H NMR (500 MHz, chloroform-d) δ ppm 8.66-8.74 (1H, m), 7.85-7.94 (2H, m), 7.73 (1H, d, J=11.0 Hz), 7.57-7.66 (2H, m), 7.38 (1H, ddd, J=6.0, 4.9, 2.8 Hz), 7.02 (1H, ddd, J=13.4, 8.5, 2.6 Hz), 6.44 (1H, d, J=2.9 Hz), 3.86-3.98 (4H, m), 3.76-3.85 (4H, m), 2.91-3.47 (8H, m), 2.21 (3H, s). Mass Spectrum (ESI) m/e=519.0 (M+1).

Example 81

Preparation of N-(2,5-di(4-morpholinyl)phenyl)-3-methyl-2,8-di(2-pyridinyl)-4-quinolinamine 4-Chloro-3-methyl-2,8-di(pyridin-2-yl)quinoline

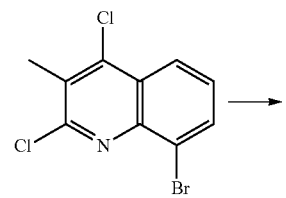

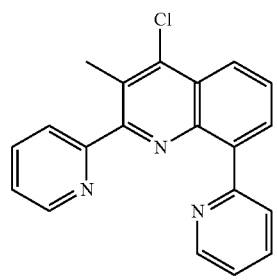

To a stirred solution of 8-bromo-2,4-dichloro-3-methylquinoline (0.35 g, 1.21 mmol) in toluene (2.4 mL) was added 2-(tributylstannyl)pyridine (0.94 mL, 2.55 mmol), and palladium tetrakistriphenylphosphine (0.140 g, 0.12 mmol). The reaction was stirred at 100° C. and stirring continued for 19 h. After which the reaction mixture was cooled to rt and concentrated in vacuo. The crude product was purified by column chromatography on silica gel (0 to 50% EtOAc in hexane) to give the desired product 4-chloro-3-methyl-2,8-di(pyridin-2-yl)quinoline as a white solid. Mass Spectrum (ESI) m/e=332.0 (M+1).

N-(2,5-Di-(4-morpholinyl)phenyl)-3-methyl-2,8-di(2-pyridinyl)-4-quinolinamine

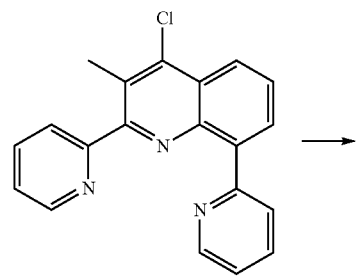

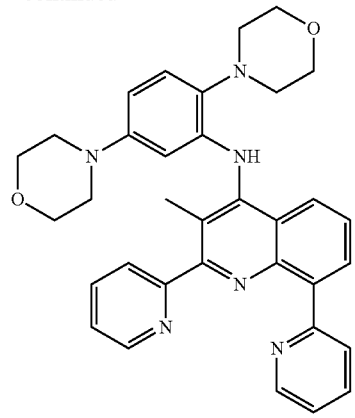

To a stirred solution of dicyclohexyl(2',4',6'-triisopropylbiphenyl-2-yl)phosphine (0.023 g, 0.048 mmol), 2,5-dimorpholinoaniline (0.095 g, 0.36 mmol), 4-chloro-3-methyl-2,8-di(pyridin-2-yl)quinoline (0.1 g, 0.30 mmol) and Pd$_2$dba$_3$ (0.011 g, 0.012 mmol) in toluene (3.00 mL) was added sodium tert-butoxide (0.072 g, 0.753 mmol). The reaction mixture was heated to 120° C. and stirred for 45 min. The reaction was then cooled to rt and diluted with water (25 mL). The mixture was extracted with EtOAc (2×10 mL) and DCM (1×10 mL). The organic layers were combined and washed with brine (1×20 mL) and dried over magnesium sulfate. The crude product was purified by column chromatography on basic alumina (0 to 50% EtOAc in hexane) to give the desired product N-(2,5-di(4-morpholinyl)phenyl)-3-methyl-2,8-di(2-pyridinyl)-4-quinolinamine. 1H NMR (400 MHz, CDCl$_3$) δ ppm 8.78 (1H, d, J=4.1 Hz), 8.69 (1H, m), 8.30 (1H, m), 8.20 (1H, m), 7.96 (2H, m), 7.80 (2H, m), 7.59 (1H, dd, J=8.3, 7.3 Hz), 7.32 (2H, m), 7.10 (1H, m), 6.43 (1H, m), 6.03 (1H, br. s), 3.92 (4H, br. s), 3.71 (4H, br. s), 3.08 (4H, br. s), 2.91 (4H, br. s), 2.53 (3H, s). Mass Spectrum (ESI) m/e=559.3 (M+1).

Example 82

Preparation of N-ethyl-5,7-difluoro-3-methyl-N-(5-(4-morpholinyl)-3-pyridinyl)-2-(2-pyridinyl)-4-quinolinamine

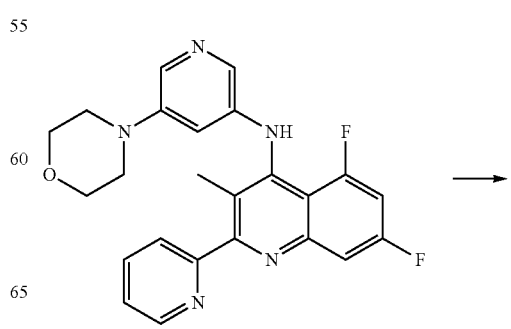

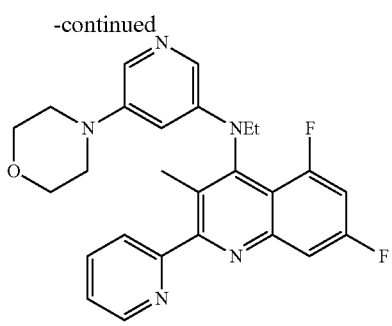

To a stirred solution of 5,7-difluoro-3-methyl-N-(5-morpholinopyridin-3-yl)-2-(pyridin-2-yl)quinolin-4-amine (0.06 g, 0.14 mmol) in N,N-dimethylformamide (1.4 mL) was added sodium hydride (0.011 g, 0.28 mmol) followed by iodoethane (0.043 g, 0.28 mmol). Stirring continued at 60° C. for 2 h. After which the reaction was quenched with water (25 mL). The mixture was extracted with EtOAc (2×10 mL) and DCM (1×10 mL). The organic layers were combined and washed with brine (1×20 mL) and dried over magnesium sulfate. The crude product was purified by column chromatography on basic alumina (0 to 50% EtOAc in hexane) to give the desired product N-ethyl-5,7-difluoro-3-methyl-N-(5-(4-morpholinyl)-3-pyridinyl)-2-(2-pyridinyl)-4-quinolinamine. 1H NMR (400 MHz, CDCl$_3$) δ ppm 8.74 (1H, d, J=4.7 Hz), 7.83-7.96 (2H, m), 7.74 (2H, m), 7.34-7.50 (2H, m), 7.26 (1H, br. s), 6.93-7.04 (1H, m), 6.31 (1H, br s), 3.77-3.94 (5H, m), 3.70 (1H, m), 3.10 (4H, br. s), 2.33-2.40 (3H, s), 1.29 (3H, t, J=7.2 Hz). Mass Spectrum (ESI) m/e=462.2 (M+1).

Example 83

Preparation of N-(3-chloro-5-(4-morpholinyl)phenyl)-5,7-difluoro-3-methyl-2-(2-pyridinyl)-4-quinolinamine 3-Chloro-5-morpholinoaniline

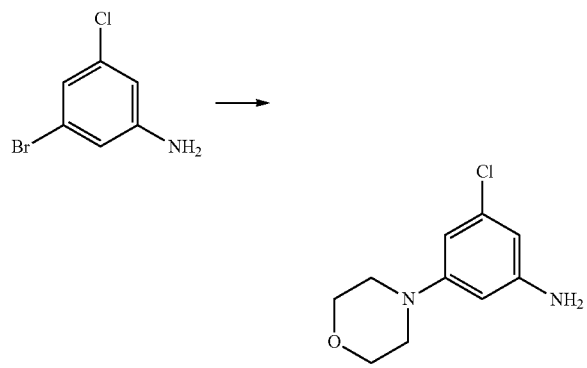

To a stirred solution of 3-bromo-5-chloroaniline (1.00 g, 4.84 mmol), dicyclohexyl(2',4',6'-triisopropylbiphenyl-2-yl)phosphine (0.19 g, 0.39 mmol), Pd$_2$dba$_3$ (0.177 g, 0.19 mmol) and morpholine (0.464 g, 5.33 mmol) in THF (9.70 mL). To this mixture was added LHMDS in THF (19.37 mL, 19.37 mmol) and the resulting reaction was heated to 65° C. Stirring continued for 2.5 h. After which the reaction was cooled to rt and then poured into water (100 mL) and extracted with EtOAc (2×150 mL) and DCM (2×150 mL). The combined organic layers were dried over magnesium sulfate and the crude product was purified on silica gel (0 to 100% DCM in EtOAc) to give 3-chloro-5-morpholinoaniline. Mass Spectrum (ESI) m/e=213.1 (M+1).

N-(3-Chloro-5-(4-morpholinyl)phenyl)-5,7-difluoro-3-methyl-2-(2-pyridinyl)-4-quinolinamine

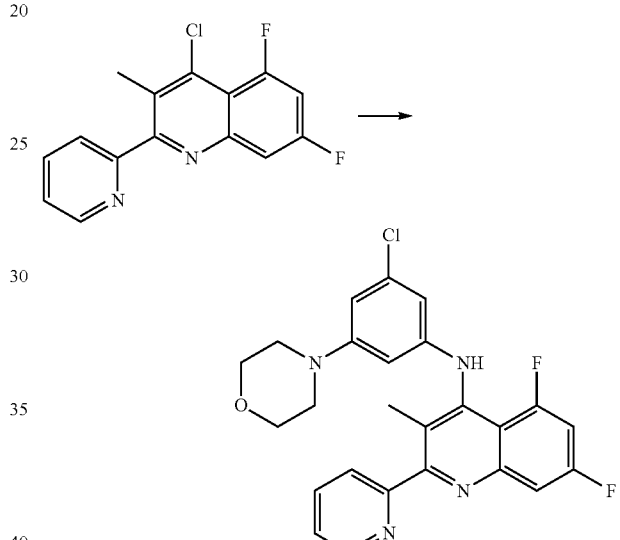

To a stirred solution of dicyclohexyl(2',4',6'-triisopropylbiphenyl-2-yl)phosphine (0.026 g, 0.055 mmol), 3-chloro-5-morpholinoaniline (0.088 g, 0.41 mmol), 4-chloro-5,7-difluoro-3-methyl-2-(pyridin-2-yl)quinoline (0.1 g, 0.34 mmol) and Pd$_2$dba$_3$ (0.013 g, 0.014 mmol) in toluene (3.40 mL) was added sodium t-butoxide (0.083 g, 0.860 mmol). The reaction mixture was heated to 120° C. and stirred for 45 min. The reaction was then cooled to rt and diluted with water (25 mL). The mixture was extracted with EtOAc (2×10 mL) and DCM (1×10 mL). The organic layers were combined and washed with brine (1×20 mL) and dried over magnesium sulfate. The crude product was purified by column chromatography on basic alumina (0 to 50% EtOAc in hexane) to give the desired product N-(3-chloro-5-(4-morpholinyl)phenyl)-5,7-difluoro-3-methyl-2-(2-pyridinyl)-4-quinolinamine. 1H NMR (400 MHz, CDCl$_3$) δ ppm 8.72 (1H, ddd, J=4.9, 1.8, 1.0 Hz), 7.85-7.92 (1H, dt, J=7.9, 1.8 Hz), 7.79-7.85 (1H, d, J=7.9 Hz), 7.67 (1H, br. s), 7.38 (1H, ddd, J=7.5, 4.8, 1.2 Hz), 7.02 (2H, ddd, J=13.7, 8.6, 2.5 Hz), 6.49-6.54 (1H, m), 6.36 (1H, m), 6.27 (1H, m), 3.79-3.90 (4H, m), 3.09-3.23 (4H, m), 2.17 (3H, s). Mass Spectrum (ESI) m/e=467.2 (M+1).

Example 84

Preparation of 3-methyl-N-(5-(4-morpholinyl)-3-pyridinyl)-2,8-di(2-pyridinyl)-4-quinolinamine

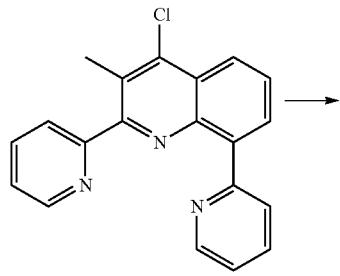

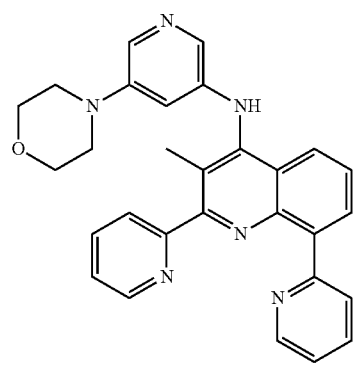

To a stirred solution of dicyclohexyl(2',4',6'-triisopropylbiphenyl-2-yl)phosphine (0.023 g, 0.048 mmol), 5-morpholinopyridin-3-amine (0.065 g, 0.36 mmol), dicyclohexyl(2',4',6'-triisopropylbiphenyl-2-yl)phosphine (0.023 g, 0.048 mmol), sodium t-butoxide (0.072 g, 0.75 mmol) and Pd$_2$dba$_3$ (0.011 g, 0.012 mmol) in toluene (3.00 mL). The reaction mixture was heated to 120° C. and stirring continued for 80 h. The reaction was then cooled to rt and diluted with water (25 mL). The mixture was extracted with EtOAc (2×10 mL) and DCM (1×10 mL). The organic layers were combined and washed with brine (1×20 mL) and dried over magnesium sulfate. The crude product was purified by column chromatography on basic alumina (0 to 50% EtOAc/hexanes) to give the desired product 3-methyl-N-(5-(4-morpholinyl)-3-pyridinyl)-2,8-di(2-pyridinyl)-4-quinolinamine. 1H NMR (400 MHz, CDCl$_3$) δ ppm 8.79 (1H, dd, J=4.0, 0.9 Hz), 8.68 (1H, dd, J=4.0, 0.9 Hz), 8.23 (1H, dd, J=7.9, 1.1 Hz), 8.11 (1H, dd, J=7.1, 1.3 Hz), 7.88-7.94 (1H, m), 7.80-7.88 (4H, m), 7.72-7.80 (1H, m), 7.44-7.53 (1H, m), 7.31 (2H, m), 6.45 (1H, s), 6.29-6.35 (1H, m), 3.73-3.82 (4H, m), 3.00-3.10 (4H, m), 2.45 (3H, s). Mass Spectrum (ESI) m/e=475.1 (M+1).

Example 85

Preparation of N-(2,5-di(4-morpholinyl)-3-pyridinyl)-5,7-difluoro-3-methyl-2-(3-methyl-2-pyridinyl)-4-quinolinamine 4-Chloro-5,7-difluoro-3-methyl-2-(3-methylpyridin-2-yl)quinoline

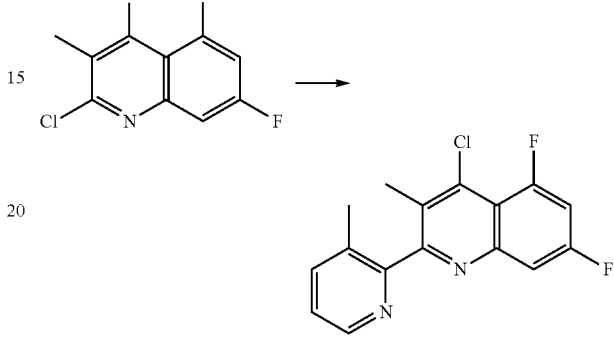

To a stirred solution of 2,4-dichloro-5,7-difluoro-3-methylquinoline (0.17 g, 0.685 mmol) in toluene (1.40 mL) was added 3-methyl-2-(tributylstannyl)pyridine (0.29 g, 0.75 mmol), and palladium tetrakistriphenylphosphine (0.079 g, 0.069 mmol). The reaction was stirred at 100° C. and stirring continued for 68 h. The reaction mixture was cooled to rt and concentrated in vacuo. The crude material was purified by column chromatography on silica gel, eluting with (0-50% EtOAc in hexanes) to provide 4-chloro-5,7-difluoro-3-methyl-2-(3-methylpyridin-2-yl)quinoline as a white solid. Mass Spectrum (ESI) m/e=305.0 (M+1).

N-(2,5-Di(4-morpholinyl)-3-pyridinyl)-5,7-difluoro-3-methyl-2-(3-methyl-2-pyridinyl)-4-quinolinamine

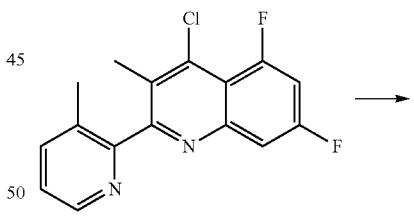

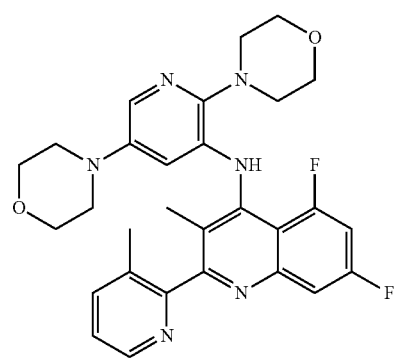

To a stirred solution of dicyclohexyl(2',4',6'-triisopropylbiphenyl-2-yl)phosphine (0.023 g, 0.047 mmol), 2,5-dimorpholinopyridin-3-amine (0.094 g, 0.354 mmol), 4-chloro-5,7-difluoro-3-methyl-2-(3-methylpyridin-2-yl)quinoline (0.090 g, 0.295 mmol) and Pd$_2$dba$_3$ (10.8 mg, 0.012 mmol) in toluene (3.00 mL) was added sodium t-butoxide (0.071 g, 0.738 mmol). The reaction mixture was heated to 120° C. for 2 h. After which the reaction was cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-3-methyl-2-(3-methyl-2-pyridinyl)-4-quinolinamine. 1H NMR (400 MHz, CDCl$_3$) δ ppm 8.56 (1H, d, J=4.5 Hz), 7.71 (2H, m), 7.62 (2H, d, J=2.5 Hz), 7.35 (1H, m), 7.02 (1H, m), 6.39 (1H, br. s.), 3.93 (4H, br. s.), 3.76-3.87 (4H, m), 3.23 (4H, br. s.), 3.05 (4H, br. s.), 2.28 (3H, s), 1.95 (3H, br. s.). Mass Spectrum (ESI) m/e=533.2 (M+1).

N-(2,5-Di(4-morpholinyl)-3-pyridinyl)-5,7-difluoro-3-methyl-2-(6-methyl-2-pyridinyl)-4-quinolinamine

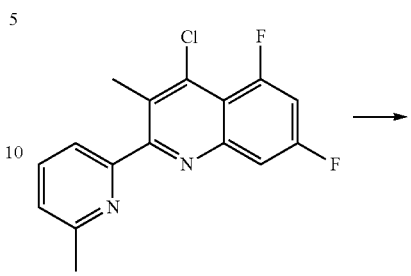

Example 86

Preparation of N-(2,5-di(4-morpholinyl)-3-pyridinyl)-5,7-difluoro-3-methyl-2-(6-methyl-2-pyridinyl)-4-quinolinamine 4-Chloro-5,7-difluoro-3-methyl-2-(6-methyl-2-pyridinyl)quinoline

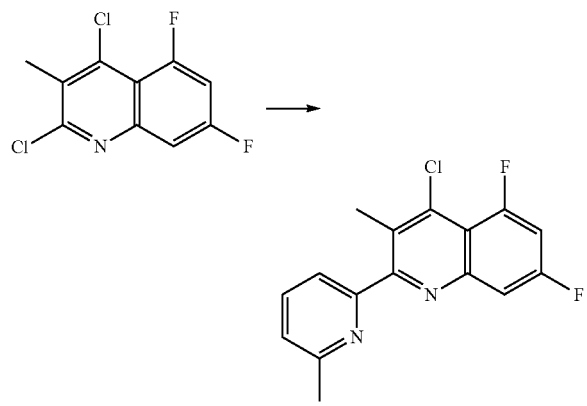

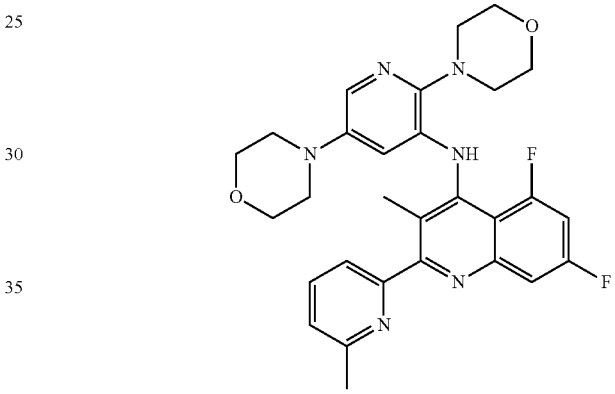

To a stirred solution of 2,4-dichloro-5,7-difluoro-3-methylquinoline (0.2 g, 0.806 mmol) in toluene (1.60 mL) was added 2-methyl-6-(tributylstannyl)pyridine (0.34 g, 0.89 mmol), and palladium tetrakistriphenylphosphine (0.093 g, 0.081 mmol). The reaction was stirred at 100° C. and stirring continued for 18 h. The reaction mixture was cooled to rt and concentrated in vacuo. The crude material was purified by column chromatography on silica gel, eluting with (0-50% EtOAc in hexanes) to provide 4-chloro-5,7-difluoro-3-methyl-2-(6-methylpyridin-2-yl)quinoline as a white solid. Mass Spectrum (ESI) m/e=305.0 (M+1).

To a stirred solution of dicyclohexyl(2',4',6'-triisopropylbiphenyl-2-yl)phosphine (0.025 g, 0.053 mmol), 2,5-dimorpholinopyridin-3-amine (0.104 g, 0.39 mmol), 4-chloro-5,7-difluoro-3-methyl-2-(6-methylpyridin-2-yl)quinoline (0.10 g, 0.33 mmol) and Pd$_2$dba$_3$ (0.012 g, 0.013 mmol) in toluene (3.28 mL) was added sodium t-butoxide (0.079 g, 0.820 mmol). The reaction mixture was heated to 120° C. for 2 h. The reaction was then cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-3-methyl-2-(6-methyl-2-pyridinyl)-4-quinolinamine. 1H NMR (400 MHz, CDCl$_3$) δ ppm 7.79 (2H, t, J=7.6 Hz), 7.58-7.72 (3H, m), 7.25 (1H, d, J=7.8 Hz), 6.97-7.07 (1H, m), 6.49 (1H, br. s.), 3.92 (4H, br. s.), 3.78-3.86 (4H, m), 3.30 (4H, br s), 3.06-3.15 (5H, m), 2.60 (3H, s), 2.18 (3H, s). Mass Spectrum (ESI) m/e=533.2 (M+1).

Example 87

Preparation of N-(2,5-di(4-morpholinyl)-3-pyridinyl)-5,7-difluoro-3-methyl-2-(4-pyridinyl)-4-quinolinamine 4-Chloro-5,7-difluoro-3-methyl-2-(4-pyridinyl)quinoline

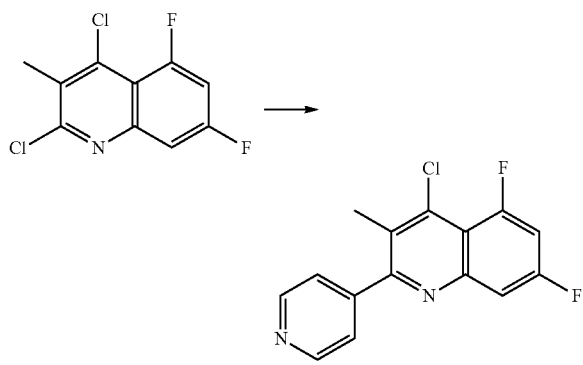

To a stirred solution of 2,4-dichloro-5,7-difluoro-3-methylquinoline (1.0 g, 4.03 mmol) in toluene (8.06 mL) was added pyridin-4-ylboronic acid (0.743 g, 6.05 mmol), potassium carbonate (1.11 g, 8.06 mmol) and palladium tetrakistriphenylphosphine (0.466 g, 0.403 mmol). The reaction was stirred at 100° C. and stirring continued for 15 h. The reaction mixture was cooled to rt and concentrated in vacuo. The crude material was purified by column chromatography on silica gel, eluting with (0-50% EtOAc in hexanes) to provide 4-chloro-5,7-difluoro-3-methyl-2-(4-pyridinyl)quinoline as a white solid. Mass Spectrum (ESI) m/e=291.1 (M+1).

N-(2,5-Di(4-morpholinyl)-3-pyridinyl)-5,7-difluoro-3-methyl-2-(4-pyridinyl)-4-quinolinamine

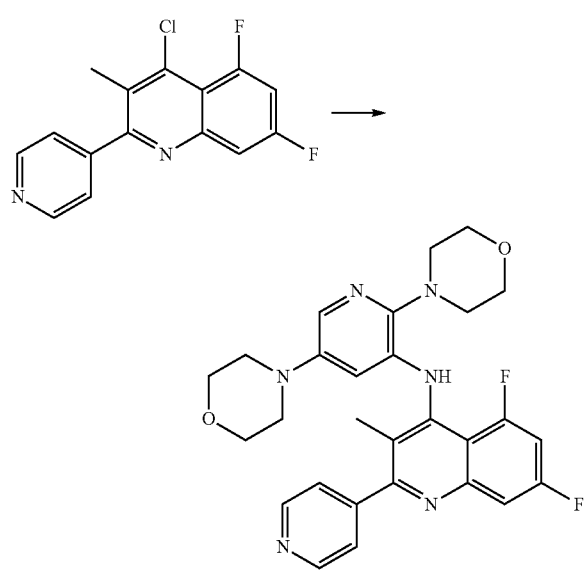

To a stirred solution of dicyclohexyl(2',4',6'-triisopropylbiphenyl-2-yl)phosphine (0.026 g, 0.055 mmol), 2,5-dimorpholinopyridin-3-amine (0.109 g, 0.413 mmol), 4-chloro-5,7-difluoro-3-methyl-2-(pyridin-4-yl)quinoline (0.1 g, 0.344 mmol) and Pd$_2$dba$_3$ (0.013 g, 0.014 mmol) in toluene (3.44 mL) was added sodium t-butoxide (0.083 g, 0.860 mmol). The reaction mixture was heated to 120° C. and stirred for 2 h. The reaction was then cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-3-methyl-2-(4-pyridinyl)-4-quinolinamine. Mass Spectrum (ESI) m/e=519.2 (M+1). 1H NMR (400 MHz, CDCl$_3$) δ ppm 8.76-8.83 (2H, dd, J=5.9, 1.6 Hz), 7.73 (1H, br s), 7.68 (1H, d, J=2.5 Hz), 7.62 (1H, ddd, J=9.3, 2.5, 1.3 Hz), 7.52 (2H, dd, J=4.6, 1.5 Hz), 6.99-7.10 (1H, m), 6.34 (1H, br. s.), 3.91 (4H, br s), 3.78-3.86 (4H, m), 3.21 (4H, br. s.), 2.99-3.09 (4H, m), 2.16 (3H, br. s.)

Example 88

Preparation of N-(2,5-di(4-morpholinyl)-3-pyridinyl)-5,7-difluoro-2-(2-methoxy-3-pyridinyl)-3-methyl-4-quinolinamine 4-Chloro-5,7-difluoro-2-(2-methoxy-3-pyridinyl)-3-methylquinoline

To a stirred solution of 2,4-dichloro-5,7-difluoro-3-methylquinoline (1.0 g, 4.03 mmol) in toluene (8.06 mL) was added 2-methoxypyridin-3-ylboronic acid (0.925 g, 6.05 mmol), potassium carbonate (1.67 g, 12.1 mmol) and palladium tetrakistriphenylphosphine (0.466 g, 0.403 mmol). The reaction was stirred at 100° C. and stirring continued for 18 h. The reaction mixture was cooled to rt and concentrated in vacuo. The crude material was purified by column chromatography on silica gel, eluting with (0-50% EtOAc in hexanes) to provide 4-chloro-5,7-difluoro-2-(2-methoxy-3-pyridinyl)-3-methylquinoline as a white solid. Mass Spectrum (ESI) m/e=321.1 (M+1).

N-(2,5-Di-(4-morpholinyl)-3-pyridinyl)-5,7-difluoro-2-(2-methoxy-3-pyridinyl)-3-methyl-4-quinolinamine

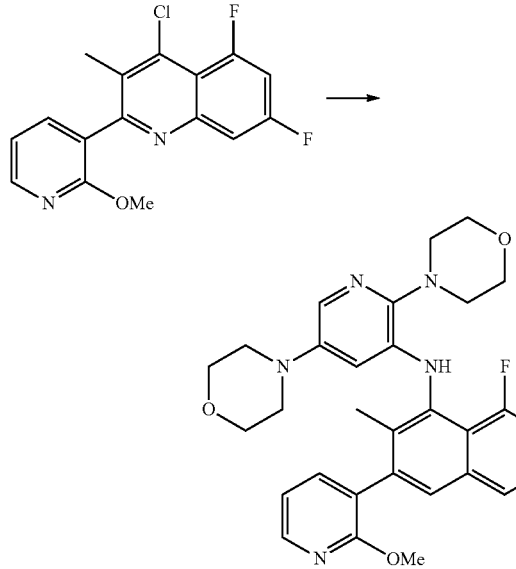

To a stirred solution of dicyclohexyl(2',4',6'-triisopropylbiphenyl-2-yl)phosphine (0.024 g, 0.050 mmol), 2,5-dimorpholinopyridin-3-amine (0.099 g, 0.37 mmol), 4-chloro-5,7-difluoro-2-(2-methoxypyridin-3-yl)-3-methylquinoline (0.10 g, 0.312 mmol) and Pd$_2$dba$_3$ (0.011 g, 0.012 mmol) in toluene (3.12 mL) was added sodium t-butoxide (0.075 g, 0.78 mmol). The reaction mixture was heated to 120 C. and stirring continued for 2 h. The reaction was cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-2-(2-methoxy-3-pyridinyl)-3-methyl-4-quinolinamine. 1H NMR (400 MHz, CDCl$_3$) δ ppm 8.33 (1H, dd, J=4.9, 1.8 Hz), 7.76 (1H, m), 7.64 (2H, br. s.), 7.11 (1H, dd, J=7.2, 5.1 Hz), 7.00 (1H, m), 6.39 (1H, br. s.), 3.96 (3H, s), 3.92 (4H, br s), 3.78-3.86 (4H, m), 3.39 (2H, br. s.), 3.06 (6H, br. s.), 2.00 (3H, s). Mass Spectrum (ESI) m/e=549.3 (M+1).

Example 89

Preparation of N-(2,5-di(4-morpholinyl)-3-pyridinyl)-5,7-difluoro-2-(5-methoxy-3-pyridinyl)-3-methyl-4-quinolinamine 4-Chloro-5,7-difluoro-2-(5-methoxy-3-pyridinyl)-3-methylquinoline

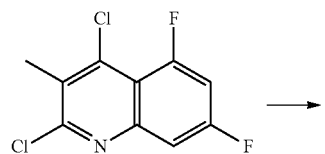

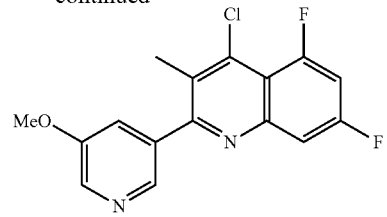

To a stirred solution of 2,4-dichloro-5,7-difluoro-3-methylquinoline (0.35 g, 1.411 mmol) in toluene (2.80 mL) was added 3-methoxy-5-(4,4,5,5-tetramethyl-1,3,2-dioxaborolan-2-yl)pyridine (0.50 g, 2.12 mmol), potassium carbonate (0.585 g, 4.23 mmol) and palladium tetrakistriphenylphosphine (0.163 g, 0.141 mmol). The reaction was stirred at 100° C. and stirring continued for 15 h. The reaction mixture was cooled to rt and concentrated in vacuo. The crude material was purified by column chromatography on silica gel, eluting with (0-50% EtOAc in hexanes) to provide 4-chloro-5,7-difluoro-2-(5-methoxy-3-pyridinyl)-3-methylquinoline as a white solid. Mass Spectrum (ESI) m/e=321.1 (M+1).

N-(2,5-Di(4-morpholinyl)-3-pyridinyl)-5,7-difluoro-2-(5-methoxy-3-pyridinyl)-3-methyl-4-quinolinamine

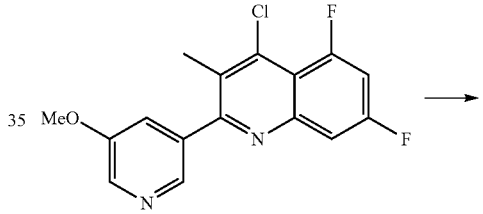

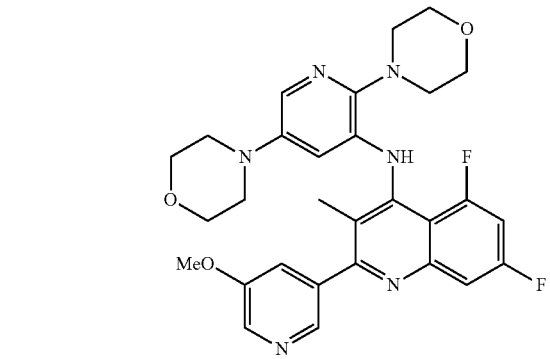

To a stirred solution of dicyclohexyl(2',4',6'-triisopropylbiphenyl-2-yl)phosphine (0.024 g, 0.050 mmol), 2,5-dimorpholinopyridin-3-amine (0.099 g, 0.37 mmol), 4-chloro-5,7-difluoro-2-(5-methoxypyridin-3-yl)-3-methylquinoline (0.10 g, 0.312 mmol) and Pd$_2$dba$_3$ (0.011 g, 0.012 mmol) in toluene (3.1 mL) was added sodium t-butoxide (0.075 g, 0.78 mmol). The reaction mixture was heated to 120° C. and stirring continued for 5 h. The reaction was cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-2-(5-methoxy-3-pyridinyl)-3-methyl-4-quinolinamine. 1H NMR (400 MHz, CDCl₃) δ ppm 8.43 (2H, t, J=2.1 Hz), 7.80 (1H, br. s.), 7.67 (1H, d, J=2.7 Hz), 7.49-7.54 (1H, m), 6.99-7.09 (1H, m), 6.38 (1H, br. s.), 3.97 (3H, s), 3.91 (4H, br. s.), 3.79-3.86 (4H, m), 3.21 (4H, br. s.), 3.00-3.09 (4H, m), 2.18 (3H, s). Mass Spectrum (ESI) m/e=549.3 (M+1).

Example 90

Preparation of N-(2,5-di(4-morpholinyl)-3-pyridinyl)-5,7-difluoro-3-methyl-2-(1-methyl-1H-indol-5-yl)-4-quinolinamine 4-Chloro-5,7-difluoro-3-methyl-2-(1-methyl-1H-indol-5-yl)quinoline

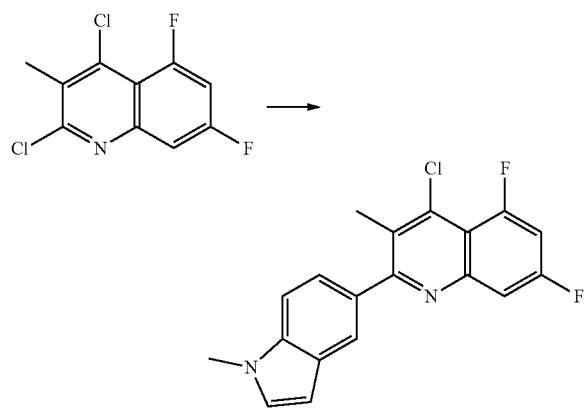

To a stirred solution of 2,4-dichloro-5,7-difluoro-3-methylquinoline (1.0 g, 4.03 mmol) in toluene (8.1 mL) was added 1-methylindole-5-boronic acid pinacol ester (1.037 g, 4.03 mmol), potassium carbonate (1.67 g, 12.09 mmol) and palladium tetrakistriphenylphosphine (0.466 g, 0.403 mmol). The reaction was stirred at 100° C. and stirring continued for 16 h. The reaction mixture was cooled to rt and concentrated in vacuo. The crude material was purified by column chromatography on silica gel, eluting with 0-50% EtOAc in hexanes to provide 4-chloro-5,7-difluoro-3-methyl-2-(1-methyl-1H-indol-5-yl)quinoline as a clear solid. Mass Spectrum (ESI) m/e=343.1 (M+1).

N-(2,5-Di-(4-morpholinyl)-3-pyridinyl)-5,7-difluoro-3-methyl-2-(1-methyl-1H-indol-5-yl)-4-quinolinamine

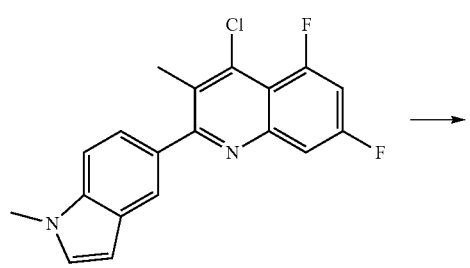

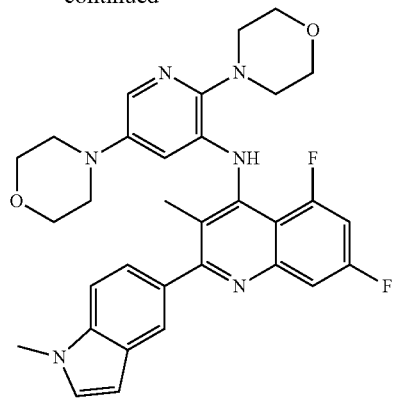

To a stirred solution of dicyclohexyl(2',4',6'-triisopropylbiphenyl-2-yl)phosphine (0.022 g, 0.047 mmol), 2,5-dimorpholinopyridin-3-amine (0.093 g, 0.350 mmol), 4-chloro-5,7-difluoro-3-methyl-2-(1-methyl-1H-indol-5-yl)quinoline (0.1 g, 0.292 mmol) and Pd₂dba₃ (10.7 mg, 0.012 mmol) in toluene (2.92 mL) was added sodium t-butoxide (0.070 g, 0.73 mmol). The reaction mixture was heated to 120° C. and stirring continued for 2 h. The reaction was cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-3-methyl-2-(1-methyl-1H-indol-5-yl)-4-quinolinamine. 1H NMR (400 MHz, CDCl₃) δ ppm 7.87 (1H, s), 7.66 (3H, m), 7.46 (2H, s), 7.15 (1H, d, J=3.1 Hz), 6.94-7.04 (1H, m), 6.57 (1H, d, J=2.9 Hz), 6.43 (1H, br. s.), 3.89-3.96 (4H, m), 3.88 (3H, s), 3.83-3.87 (4H, m), 3.30 (4H, br s), 3.03-3.14 (4H, m), 2.20 (3H, s). Mass Spectrum (ESI) m/e=571.3 (M+1).

Example 91

Preparation of N-(2,5-Di-(4-morpholinyl)-3-pyridinyl)-5,7-difluoro-3-methyl-2-(1-methyl-1H-indol-5-yl)-4-quinolinamine 4-Chloro-5,7-difluoro-2-(1H-indol-4-yl)-3-methylquinoline

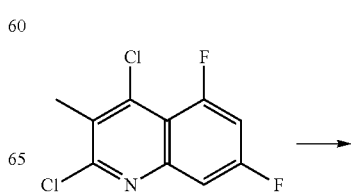

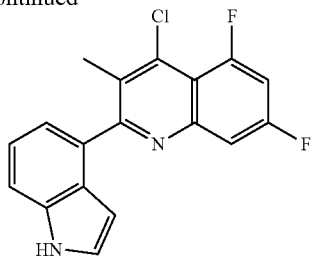

To a stirred solution of 2,4-dichloro-5,7-difluoro-3-methylquinoline (1.0 g, 4.03 mmol) in toluene (8.06 mL) was added 1H-indol-4-ylboronic acid (0.973 g, 6.05 mmol), potassium carbonate (1.671 g, 12.1 mmol) and palladium tetrakistriphenylphosphine (0.466 g, 0.403 mmol). The reaction was stirred at 100° C. and stirring continued for 19 h. The reaction mixture was cooled to rt and concentrated in vacuo. The crude product was placed in DCM and filtered to give the desired product. The filtrate was purified by column chromatography on silica gel, eluting with 0-50% EtOAc in hexanes to provide 4-chloro-5,7-difluoro-2-(1H-indol-4-yl)-3-methylquinoline as a yellow solid. Mass Spectrum (ESI) m/e=329.0 (M+1).

N-(2,5-Di-(4-morpholinyl)-3-pyridinyl)-5,7-difluoro-2-(1H-indol-4-yl)-3-methyl-4-quinolinamine

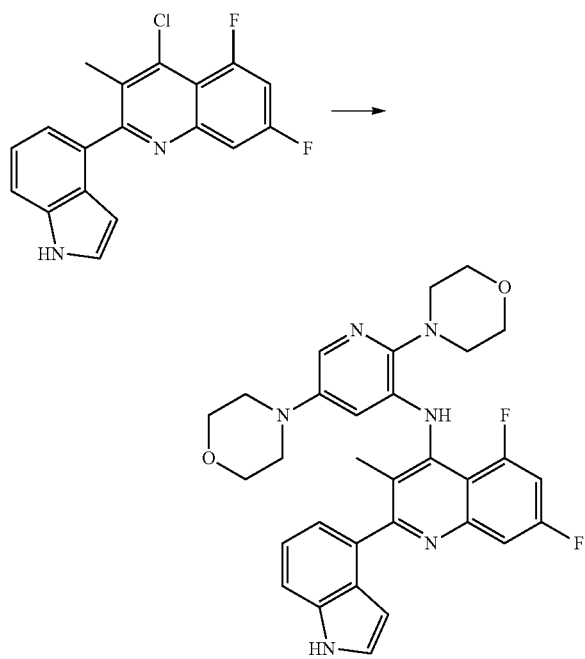

To a stirred solution of dicyclohexyl(2',4',6'-triisopropylbiphenyl-2-yl)phosphine (0.023 g, 0.049 mmol), 2,5-dimorpholinopyridin-3-amine (0.096 g, 0.37 mmol), 4-chloro-5,7-difluoro-2-(1H-indol-4-yl)-3-methylquinoline (0.1 g, 0.30 mmol) and Pd$_2$dba$_3$ (0.011 g, 0.012 mmol) in toluene (3.04 mL) was added sodium t-butoxide (0.073 g, 0.760 mmol). The reaction mixture was heated to 120° C. and stirring continued for 7 h. The reaction was cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-2-(1H-indol-4-yl)-3-methyl-4-quinolinamine. 1H NMR (400 MHz, CDCl$_3$) δ ppm 8.41 (1H, br. s.), 7.81 (1H, br. s), 7.66 (2H, br. s.), 7.51 (1H, m), 7.32 (1H, br. s), 7.19-7.26 (2H, m), 7.05 (1H, br. s.), 6.44 (1H, br. s.), 6.31 (1H, br. s.), 3.92 (4H, br. s.), 3.80-3.88 (4H, m), 3.27 (4H, br. s), 3.02-3.14 (4H, m), 2.02 (3H, s). Mass Spectrum (ESI) m/e=557.2 (M+1).

Example 92

Preparation of N-(2,5-di(4-morpholinyl)-3-pyridinyl)-5,7-difluoro-3-methyl-2-(4-(2-methyl-2-propanyl)phenyl)-4-quinolinamine 4-Chloro-5,7-difluoro-3-methyl-2-(4-(2-methyl-2-propanyl)phenyl)quinoline

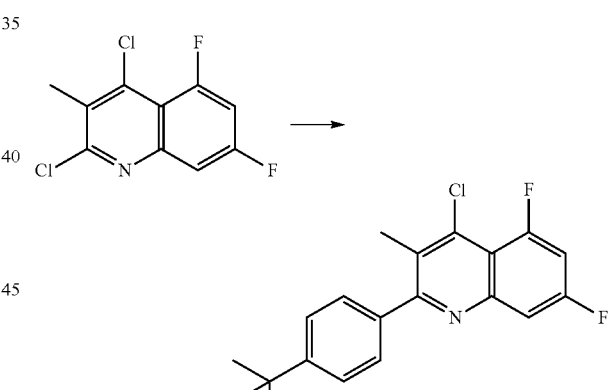

To a stirred solution of 2,4-dichloro-5,7-difluoro-3-methylquinoline (1.0 g, 4.03 mmol) in toluene (8.06 mL) was added 4-tert-butylphenylboronic acid (1.08 g, 6.05 mmol), potassium carbonate (1.67 g, 12.10 mmol) and palladium tetrakistriphenylphosphine (0.47 g, 0.40 mmol). The reaction was stirred at 100° C. and stirring continued for 19 h. The reaction mixture was cooled to rt and concentrated in vacuo. The crude material was purified by column chromatography on silica gel, eluting with 0-50% EtOAc in hexanes to provide 4-chloro-5,7-difluoro-3-methyl-2-(4-(2-methyl-2-propanyl)phenyl)quinoline as a yellow oil. Mass Spectrum (ESI) m/e=346.1 (M+1).

179

N-(2,5-Di-(4-morpholinyl)-3-pyridinyl)-5,7-difluoro-3-methyl-2-(4-(2-methyl-2-propanyl)phenyl)-4-quinolinamine

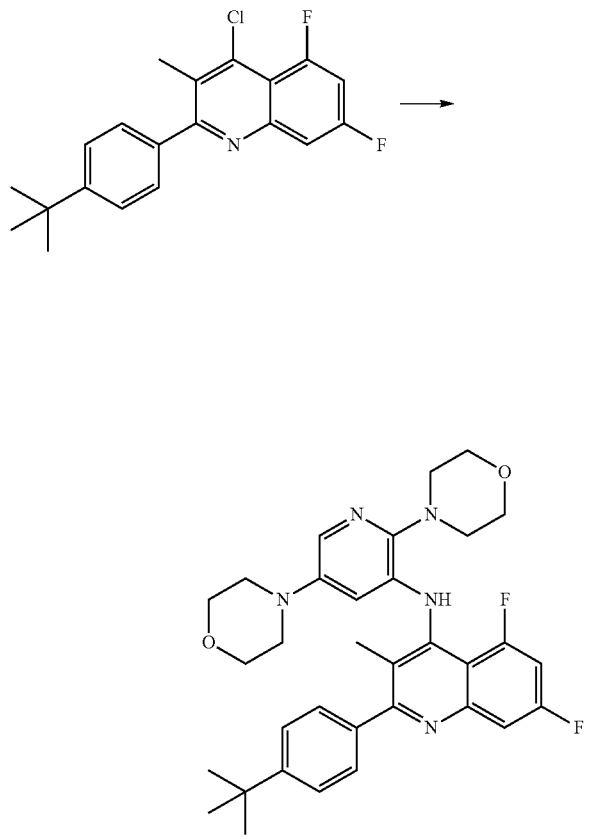

To a stirred solution of dicyclohexyl(2',4',6'-triisopropylbiphenyl-2-yl)phosphine (0.022 g, 0.046 mmol), 2,5-dimorpholinopyridin-3-amine (0.092 g, 0.35 mmol), 2-(4-tert-butylphenyl)-4-chloro-5,7-difluoro-3-methylquinoline (0.1 g, 0.29 mmol) and Pd₂dba₃ (10.6 mg, 0.012 mmol) in toluene (2.89 mL) was added sodium t-butoxide (0.069 g, 0.72 mmol). The reaction mixture was heated to 120° C. and stirring continued for 1.5 h. The reaction was cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-3-methyl-2-(4-(2-methyl-2-propanyl)phenyl)-4-quinolinamine. 1H NMR (400 MHz, CDCl₃) δ ppm 7.59-7.73 (3H, m), 7.50-7.57 (4H, m), 6.98 (1H, m), 6.37 (1H, br. s.), 3.92 (4H, br. s.), 3.79-3.87 (4H, m), 3.25 (4H, br. s.), 2.99-3.09 (4H, m), 2.18 (3H, s), 1.36-1.45 (9H, s). Mass Spectrum (ESI) m/e=574.3 (M+1).

180

Example 93

Preparation of N-(2,5-di(4-morpholinyl)-3-pyridinyl)-5,7-difluoro-3-methyl-2-(4-(2-methyl-2-propanyl)phenyl)-4-quinolinamine 4-Chloro-5,7-difluoro-3-methyl-2-(5-methyl-2-pyridinyl)quinoline

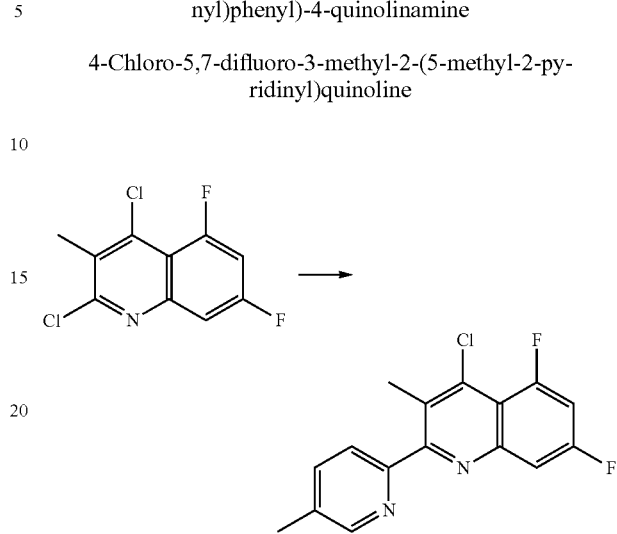

To a stirred solution of 2,4-dichloro-5,7-difluoro-3-methylquinoline (0.6 g, 2.419 mmol) in toluene (4.84 mL) was added 5-methyl-2-(tributylstannyl)pyridine (1.02 g, 2.66 mmol), and palladium tetrakistriphenylphosphine (0.280 g, 0.24 mmol). The reaction was stirred at 100° C. and stirring continued for 42 h. The reaction mixture was cooled to rt and concentrated in vacuo. The crude material was purified by column chromatography on silica gel, eluting with 0-50% EtOAc in hexanes to provide 4-chloro-5,7-difluoro-3-methyl-2-(5-methyl-2-pyridinyl)-quinoline as a white solid. Mass Spectrum (ESI) m/e=305.0 (M+1).

N-(2,5-Di(4-morpholinyl)-3-pyridinyl)-5,7-difluoro-3-methyl-2-(5-methyl-2-pyridinyl)-4-quinolinamine

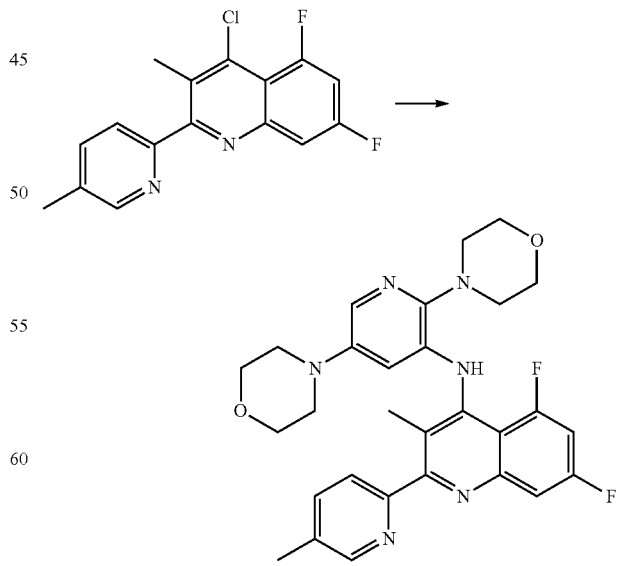

To a stirred solution of dicyclohexyl(2',4',6'-triisopropylbiphenyl-2-yl)phosphine (0.025 g, 0.053 mmol), 2,5-dimorpholinopyridin-3-amine (0.104 g, 0.39 mmol), 4-chloro-5,7-difluoro-3-methyl-2-(5-methylpyridin-2-yl)quinoline (0.10 g, 0.33 mmol) and Pd₂dba₃ (0.012 g, 0.013 mmol) in toluene (3.28 mL) was added sodium t-butoxide (0.079 g, 0.820 mmol). The reaction mixture was heated to 120° C. and stirring continued for 7 h. The reaction was then cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-3-methyl-2-(5-methyl-2-pyridinyl)-4-quinolinamine. 1H NMR (400 MHz, CDCl₃) δ ppm 8.55 (1H, d, J=4.9 Hz), 7.70 (2H, m), 7.63 (2H, m), 7.22 (1H, br. s.), 7.02 (1H, m), 6.46 (1H, br. s.), 3.92 (4H, br. s.), 3.78-3.87 (4H, m), 3.22 (4H, m), 3.09 (4H, m), 2.50 (3H, s), 2.20 (3H, s). Mass Spectrum (ESI) m/e=533.2 (M+1).

Example 94

Preparation of N-(2,5-di(4-morpholinyl)-3-pyridinyl)-5,7-difluoro-3-methyl-2-(4-methyl-2-pyridinyl)-4-quinolinamine 4-Chloro-5,7-difluoro-3-methyl-2-(4-methylpyridin-2-yl)quinoline

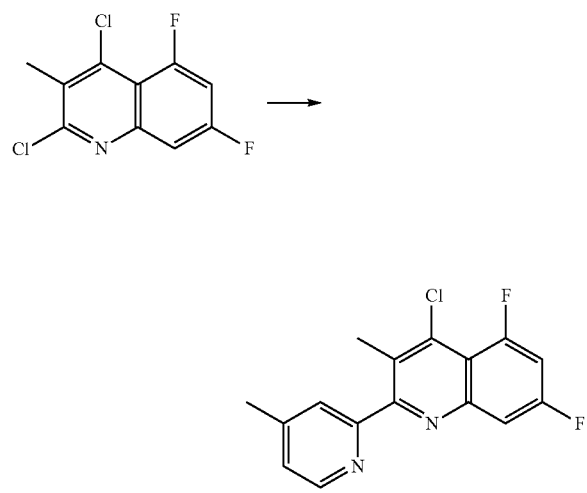 [SMILES: Cc1c(Cl)nc2cc(F)cc(F)c2c1Cl ; Cc1c(-c2ccccn2)nc2cc(F)cc(F)c2c1Cl]

To a stirred solution of 2,4-dichloro-5,7-difluoro-3-methylquinoline (0.60 g, 2.42 mmol) in toluene (4.84 mL) was added 4-methyl-2-(tributylstanyl)pyridine (1.02 g, 2.66 mmol), and palladium tetrakistriphenylphosphine (0.280 g, 0.24 mmol). The reaction was stirred at 100° C. and stirring continued for 5 days. The reaction mixture was cooled to rt and concentrated in vacuo. The crude material was purified by column chromatography on silica gel, eluting with 0-50% EtOAc in hexanes to provide 4-chloro-5,7-difluoro-3-methyl-2-(4-methylpyridin-2-yl)-quinoline as a white solid. Mass Spectrum (ESI) m/e=305.0 (M+1).

N-(2,5-Di(4-morpholinyl)-3-pyridinyl)-5,7-difluoro-3-methyl-2-(4-methyl-2-pyridinyl)-4-quinolinamine

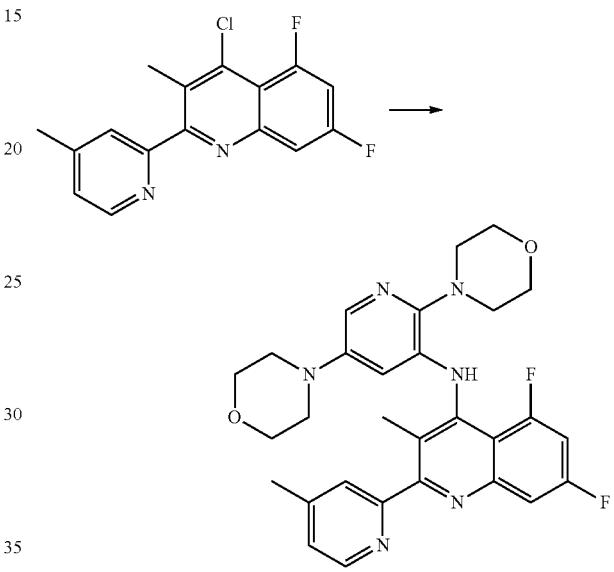

To a stirred solution of dicyclohexyl(2',4',6'-triisopropylbiphenyl-2-yl)phosphine (0.025 g, 0.053 mmol), 2,5-dimorpholinopyridin-3-amine (0.104 g, 0.39 mmol), 4-chloro-5,7-difluoro-3-methyl-2-(4-methylpyridin-2-yl)quinoline (0.1 g, 0.33 mmol) and Pd₂dba₃ (0.012 g, 0.013 mmol) in toluene (3.28 mL) was added sodium t-butoxide (0.079 g, 0.820 mmol). The reaction mixture was heated to 120° C. and stirring continued for 2.5 h. The reaction was then cooled to rt and diluted with water (15 mL). The mixture was extracted with EtOAc (2×15 mL) and DCM (1×15 mL). The organic layers were combined and washed with brine (1×20 mL) and dried over magnesium sulfate. The crude product was purified by column chromatography on basic alumina (0 to 50% hexanes/EtOAc) to give the desired product N-(2,5-di(4-morpholinyl)-3-pyridinyl)-5,7-difluoro-3-methyl-2-(4-methyl-2-pyridinyl)-4-quinolinamine. 1H NMR (400 MHz, CDCl₃) δ ppm 8.53 (1H, d, J=2.2 Hz), 7.81 (1H, d, J=7.8 Hz), 7.71 (2H, dd, J=7.6, 2.0 Hz), 7.63 (2H, d, J=2.5 Hz), 6.96-7.06 (1H, m), 6.45 (1H, br. s.), 3.92 (4H, br. s.), 3.78-3.87 (4H, m), 3.23 (4H, br. s.), 3.03-3.12 (4H, m), 2.45 (3H, s), 2.22 (3H, s). Mass Spectrum (ESI) m/e=533.2 (M+1).

Example 95

Preparation of N-(2,5-di-4-morpholinylphenyl)-5,7-difluoro-3-methyl-2-(2-(methylsulfonyl)phenyl)-4-quinolinamine

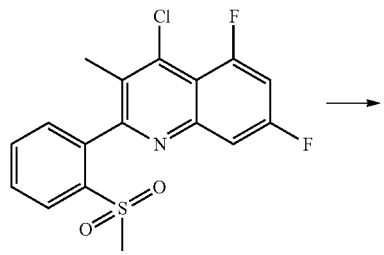

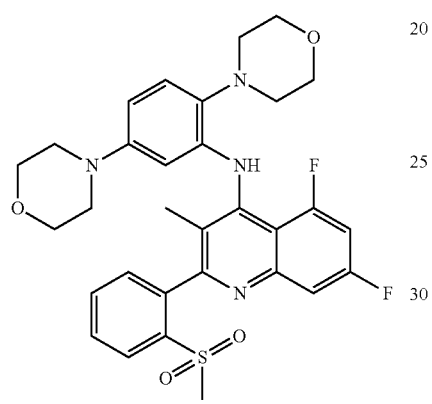

Prepared according to Procedure H using 4-chloro-5,7-difluoro-3-methyl-2-(2-(methylsulfonyl)phenyl)quinoline (39.0 mg, 0.110 mmol) and 2,5-dimorpholinoaniline in toluene to give N-(2,5-di-4-morpholinylphenyl)-5,7-difluoro-3-methyl-2-(2-(methylsulfonyl)phenyl)-4-quinolinamine. $^1$H NMR (CDCl$_3$) δ ppm 8.21 (2H, d, J=7.6 Hz), 7.78 (1H, t, J=7.6 Hz), 7.69 (1H, t, J=7.2 Hz), 7.47 (1H, d, J=9.2 Hz), 7.40 (1H, d, J=7.4 Hz), 6.98-7.09 (2H, m), 6.40 (1H, br. s.), 6.24 (1H, br. s.), 3.90 (4H, m), 3.78 (4H, m), 2.74-3.33 (8H, m), 1.95 (3H, m). Mass Spectrum (ESI) m/e=595.3 (M+1).

Example 96

Preparation of N-(2,5-di-4-morpholinylphenyl)-5,7-difluoro-3-methyl-2-(1-piperidinyl)-4-quinolinamine

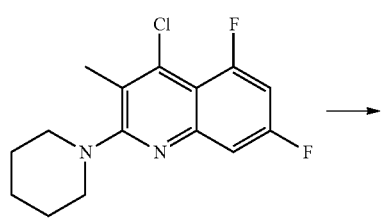

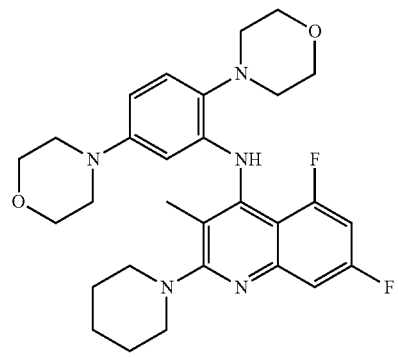

Essentially prepared according to Procedure H using 4-chloro-5,7-difluoro-3-methyl-2-(piperidin-1-yl)quinoline (34.0 mg, 0.120 mmol) and 2,5-dimorpholinoaniline in toluene to give N-(2,5-di-4-morpholinylphenyl)-5,7-difluoro-3-methyl-2-(1-piperidinyl)-4-quinolinamine. $^1$H NMR (CDCl$_3$) δ ppm 7.97 (1H, d, J=7.6 Hz), 7.08 (1H, d, J=8.6 Hz), 6.67-6.82 (1H, m), 6.45 (1H, d, J=9.6 Hz), 6.06 (1H, d, J=2.2 Hz), 3.88 (4H, t, J=4.3 Hz), 3.70-3.82 (4H, m), 3.36 (4H, br. s.), 2.96-3.24 (4H, m), 2.70-2.97 (4H, m), 2.11 (3H, s), 1.58-1.92 (7H, m). Mass Spectrum (ESI) m/e=524.3 (M+1).

Example 97

Preparation of 1-(4-((2,5-Di-4-morpholinyl-3-pyridinyl)amino)-5,7-difluoro-3-methyl-2-quinolinyl)-2(1H)-pyridinone 2,4-Dibromo-5,7-difluoro-3-methylquinoline

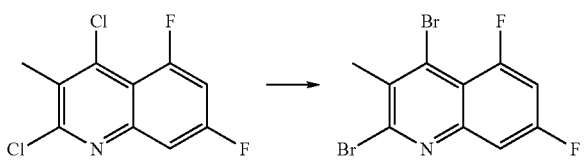

The phosphorus oxybromide (40.5 g, 141 mmol) was added to 2,4-dichloro-5,7-difluoro-3-methylquinoline (5.00 g, 20.2 mmol). The resulting mixed solid was then heated to 100° C. The resulting melt was stirred for 3.5 h. The reaction was cooled and then diluted with DCM (150 mL). This mixture was poured into a chilled sodium hydroxide solution (40 g of NaOH in 800 mL of ice water). The layers were separated and the aq. layer was extracted with DCM (2×500 mL). The combined organic layers were dried over magnesium sulfate. The crude product was then purified by medium pressure chromatography (silica, 0 to 30% EtOAc:hexanes) to give 2,4-dibromo-5,7-difluoro-3-methylquinoline. Mass Spectrum (ESI) m/e=337.9 (M+1).

1-(4-Bromo-5,7-difluoro-3-methylquinolin-2-yl)pyridin-2(1H)-one

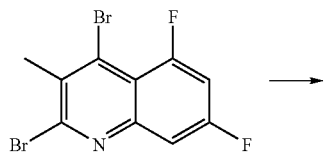

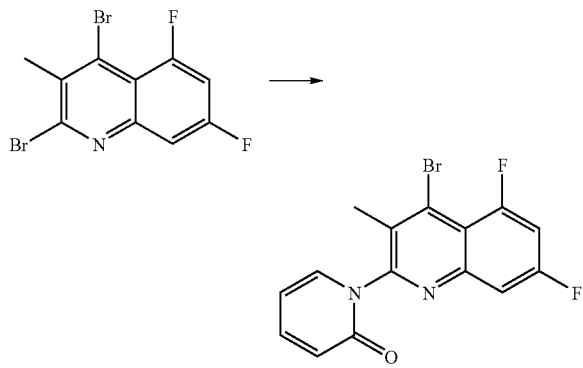

The procedure was followed as described in Leung, et. al.; Tetrahedron, 2005, pp. 2931. The reaction mixture was refluxed for 16 h and was purified by medium pressure chromatography (silica, 0 to 20% EtOAc:hexanes) to give 1-(4-bromo-5,7-difluoro-3-methylquinolin-2-yl)pyridin-2(1H)-one. Mass Spectrum (ESI) m/e=351.0 (M+1).

1-(4-((2,5-Di-4-morpholinyl-3-pyridinyl)amino)-5,7-difluoro-3-methyl-2-quinolinyl)-2(1H)-pyridinone

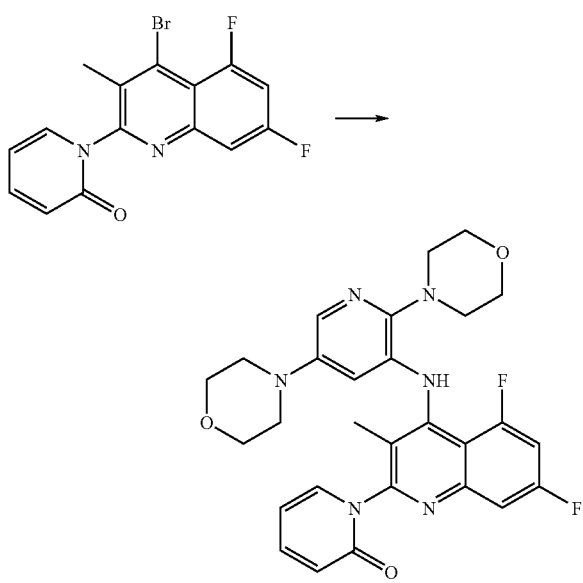

Essentially prepared according to Procedure H using 1-(4-bromo-5,7-difluoro-3-methylquinolin-2-yl)pyridin-2(1H)-one (50.0 mg, 0.140 mmol) and 2,5-dimorpholinopyridin-3-amine in toluene to give 1-(4-((2,5-di-4-morpholinyl-3-pyridinyl)amino)-5,7-difluoro-3-methyl-2-quinolinyl)-2(1H)-pyridinone. $^1$H NMR (CDCl$_3$) δ ppm 8.29 (1H, dd, J=4.8, 1.1 Hz), 7.80-7.88 (1H, m), 7.72 (1H, d, J=10.2 Hz), 7.62 (1H, d, J=2.5 Hz), 7.27-7.33 (1H, m), 7.14-7.23 (2H, m), 6.91 (1H, ddd, J=13.3, 8.9, 2.4), 6.35 (1H, d, J=2.2 Hz), 3.92 (4H, br. s.), 3.76-3.83 (4H, m), 3.12-3.46 (4H, m), 2.98-3.07 (4H, m), 2.15 (3H, s). Mass Spectrum (ESI) m/e=535.2 (M+1).

Example 98

Preparation of 4-(4-((2,5-di-4-morpholinyl-3-pyridinyl)amino)-5,7-difluoro-3-methyl-2-quinolinyl)-1-methyl-2-piperazinone

4-(4-Chloro-5,7-difluoro-3-methylquinolin-2-yl)piperazin-2-one

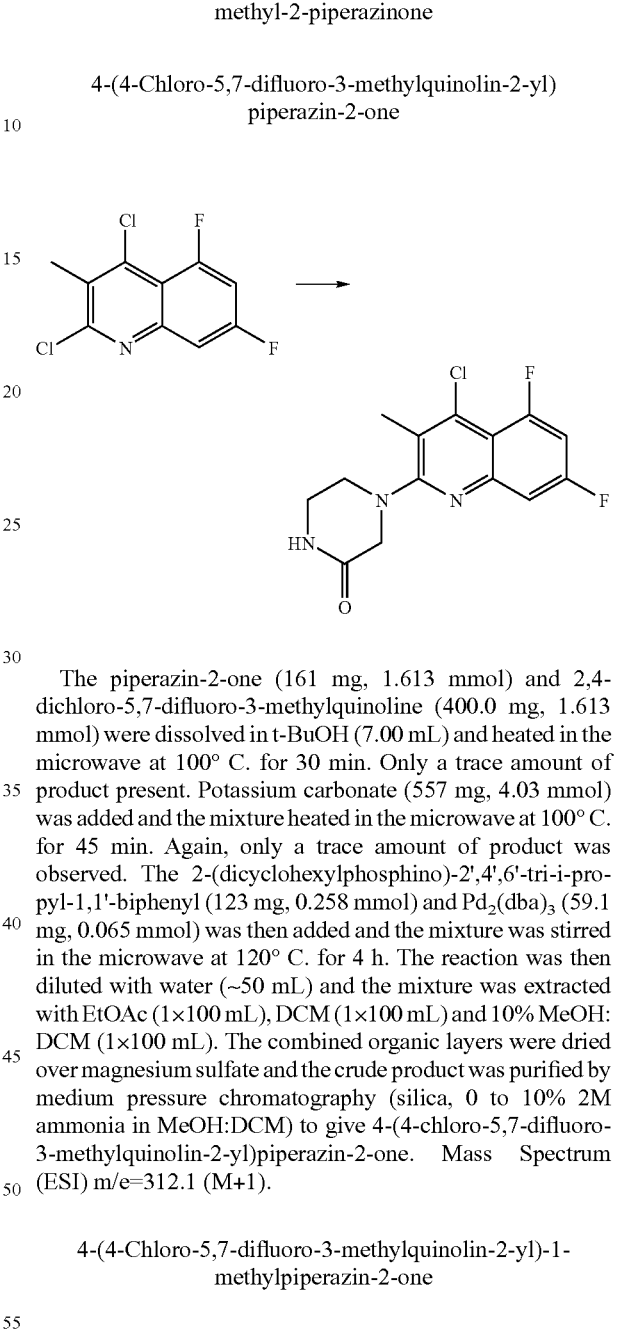

The piperazin-2-one (161 mg, 1.613 mmol) and 2,4-dichloro-5,7-difluoro-3-methylquinoline (400.0 mg, 1.613 mmol) were dissolved in t-BuOH (7.00 mL) and heated in the microwave at 100° C. for 30 min. Only a trace amount of product present. Potassium carbonate (557 mg, 4.03 mmol) was added and the mixture heated in the microwave at 100° C. for 45 min. Again, only a trace amount of product was observed. The 2-(dicyclohexylphosphino)-2',4',6'-tri-i-propyl-1,1'-biphenyl (123 mg, 0.258 mmol) and Pd$_2$(dba)$_3$ (59.1 mg, 0.065 mmol) was then added and the mixture was stirred in the microwave at 120° C. for 4 h. The reaction was then diluted with water (~50 mL) and the mixture was extracted with EtOAc (1×100 mL), DCM (1×100 mL) and 10% MeOH:DCM (1×100 mL). The combined organic layers were dried over magnesium sulfate and the crude product was purified by medium pressure chromatography (silica, 0 to 10% 2M ammonia in MeOH:DCM) to give 4-(4-chloro-5,7-difluoro-3-methylquinolin-2-yl)piperazin-2-one. Mass Spectrum (ESI) m/e=312.1 (M+1).

4-(4-Chloro-5,7-difluoro-3-methylquinolin-2-yl)-1-methylpiperazin-2-one

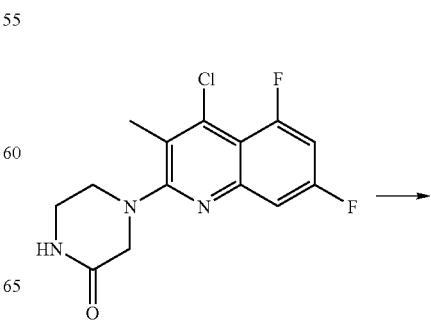

-continued

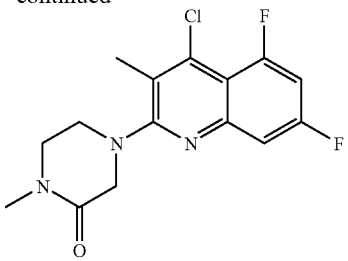

The 4-(4-chloro-5,7-difluoro-3-methylquinolin-2-yl)piperazin-2-one (30 mg, 0.096 mmol) was dissolved in THF (1.0 mL) and sodium hydride (10.0 mg, 0.42 mmol) (60% suspension) was added followed by addition of iodomethane (17.0 µL, 0.27 mmol). The mixture was stirred for 1.5 h, then diluted with water. The mixture was extracted with EtOAc (2×15 mL). The combined organic layers were dried over magnesium sulfate. The filtrate was concentrated to give the desired product. Mass Spectrum (ESI) m/e=326.0 (M+1).

4-(4-((2,5-di-4-morpholinyl-3-pyridinyl)amino)-5,7-difluoro-3-methyl-2-quinolinyl)-1-methyl-2-piperazinone

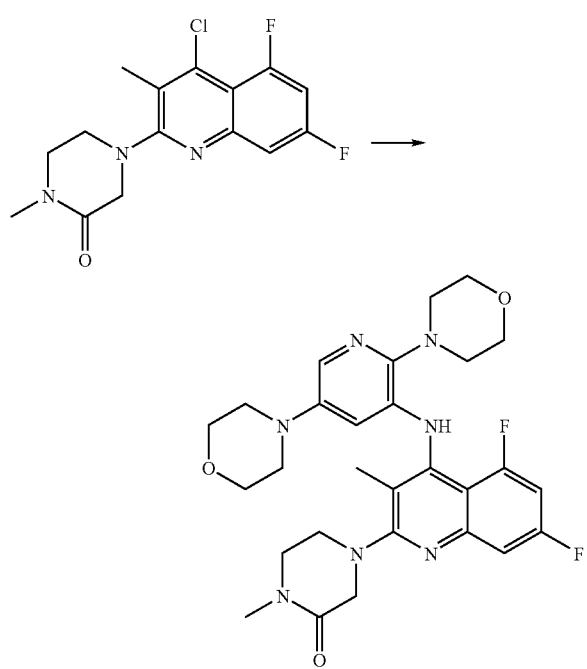

Prepared according to Procedure H using 1-(4-chloro-5,7-difluoro-3-methylquinolin-2-yl)-4-methylpiperazin-2-one (31.0 mg, 0.095 mmol) and 2,5-dimorpholinopyridin-3-amine in toluene to give 4-(4-((2,5-di-4-morpholinyl-3-pyridinyl)amino)-5,7-difluoro-3-methyl-2-quinolinyl)-1-methyl-2-piperazinone. $^1$H NMR (CDCl$_3$) δ ppm 7.67 (1H, d, J=11.0 Hz), 7.62 (1H, d, J=2.7 Hz), 7.30 (1H, ddd, J=9.8, 2.4, 1.2 Hz), 6.82 (1H, ddd, J=13.4, 8.7, 2.6 Hz), 6.28 (1H, d, J=2.7 Hz), 3.94-4.09 (2H, m), 3.87-3.94 (4H, m), 3.83-3.87 (2H, m), 3.77-3.83 (4H, m), 3.69 (2H, br. s.), 3.13-3.39 (2H, m), 3.07-3.11 (1H, m), 3.04-3.06 (1H, m), 3.03 (3H, s), 2.96-3.02 (4H, m), 2.11 (3H, s). Mass Spectrum (ESI) m/e=554.2 (M+1).

Example 99

Preparation of 1-(4-((2,5-di-4-morpholinyl-3-pyridinyl)amino)-3-ethyl-5,7-difluoro-2-quinolinyl)-2-piperidinone 1-(4-Chloro-3-ethyl-5,7-difluoroquinolin-2-yl)piperidin-2-one

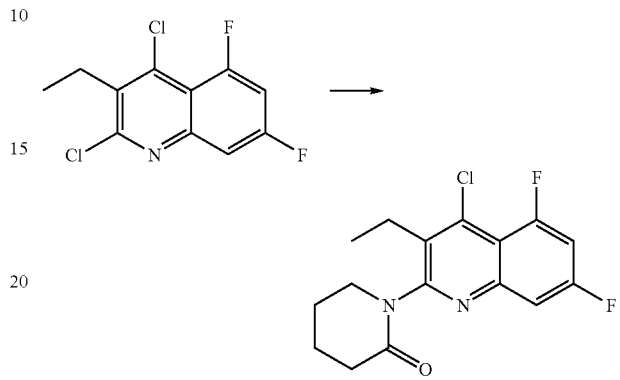

Prepared according to Procedure I using 2,4-dichloro-5,7-difluoro-3-ethylquinoline (400 mg, 1.50 mmol) and piperidin-2-one to give 1-(4-chloro-3-ethyl-5,7-difluoroquinolin-2-yl)piperidin-2-one. Mass Spectrum (ESI) m/e=325.1 (M+1).

1-(4-((2,5-Di-4-morpholinyl-3-pyridinyl)amino)-3-ethyl-5,7-difluoro-2-quinolinyl)-2-piperidinone

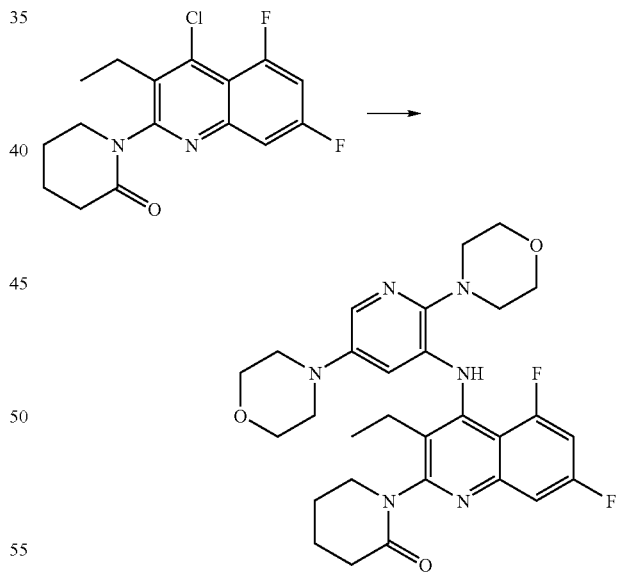

Prepared according to Procedure H using 1-(4-chloro-3-ethyl-5,7-difluoroquinolin-2-yl)piperidin-2-one (40.0 mg, 0.120 mmol) and 2,5-dimorpholinopyridin-3-amine in toluene to give 1-(4-((2,5-di-4-morpholinyl-3-pyridinyl)amino)-3-ethyl-5,7-difluoro-2-quinolinyl)-2-piperidinone.
1H NMR (400 MHz, chloroform-d) δ ppm 7.96 (1H, d, J=11.9 Hz), 7.60 (1H, d, J=2.7 Hz), 7.46 (1H, d, J=9.0 Hz), 6.90-7.07 (1H, m), 6.71 (1H, br. s.), 4.38 (1H, br. s.), 3.85-4.03 (4H, m), 3.71-3.84 (4H, m), 3.58 (1H, d, J=11.0 Hz), 3.34 (2H, ddd, J=11.9, 6.1, 2.9 Hz), 3.08-3.19 (3H, m), 2.92-

3.07 (2H, m), 2.43-2.62 (3H, m), 1.92-2.26 (6H, m), 0.97-1.11 (3H, m). Mass Spectrum (ESI) m/e=554.2 (M+1).

Example 100

Preparation of 1-(3-ethyl-5,7-difluoro-4-((5-(4-morpholinyl)-3-pyridinyl)amino)-2-quinolinyl)-2-piperidinone

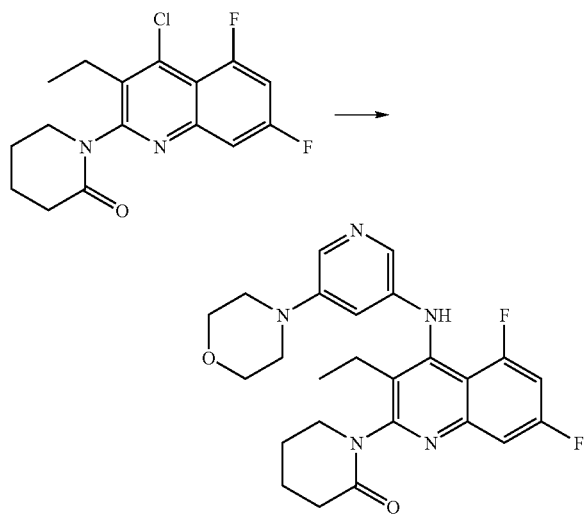

Prepared according to Procedure H using 1-(4-chloro-3-ethyl-5,7-difluoroquinolin-2-yl)piperidin-2-one (40.0 mg, 0.120 mmol) and 5-morpholinopyridin-3-amine in toluene to give 1-(3-ethyl-5,7-difluoro-4-((5-(4-morpholinyl)-3-pyridinyl)amino)-2-quinolinyl)-2-piperidinone. 1H NMR (400 MHz, chloroform-d) δ ppm 7.84 (2H, dd, J=7.2, 2.3 Hz), 7.46 (1H, ddd, J=9.6, 2.5, 1.4 Hz), 7.08 (1H, d, J=11.7 Hz), 6.97 (1H, ddd, J=13.5, 8.6, 2.5 Hz), 6.65 (1H, t, J=2.3 Hz), 4.24-4.39 (1H, m), 3.80 (4H, t, J=4.8 Hz), 3.50-3.60 (1H, m), 3.10-3.30 (4H, m), 2.38-2.64 (4H, m), 1.88-2.17 (4H, m), 1.01 (3H, t, J=7.4 Hz). Mass Spectrum (ESI) m/e=468.2 (M+1).

Example 101

Preparation of N-(2,5-di-4-morpholinyl-3-pyridinyl)-7-fluoro-3-(1-methylethyl)-2-(2-pyridinyl)-4-quinolinamine Ethyl 2-(3-fluorophenylcarbamoyl)-3-methylbutanoate

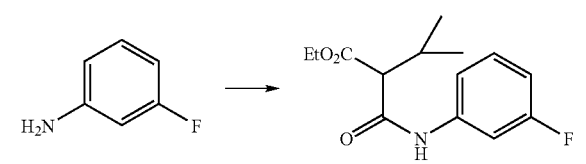 [SMILES: Nc1cccc(F)c1 ; CCOC(=O)C(C(=O)Nc1cccc(F)c1)C(C)C]

Prepared according to procedure A using 3-fluoroaniline (8.70 mL, 90 mmol), pyridine (10.92 mL, 135 mmol) and diethyl isopropylmalonate (20.02 mL, 99 mmol). The crude was purified by column chromatography (Hexanes:EtOAc, 1:0 to 4:1) to give ethyl 2-(3-fluorophenylcarbamoyl)-3-methylbutanoate.

2-(3-Fluorophenylcarbamoyl)-3-methylbutanoic acid

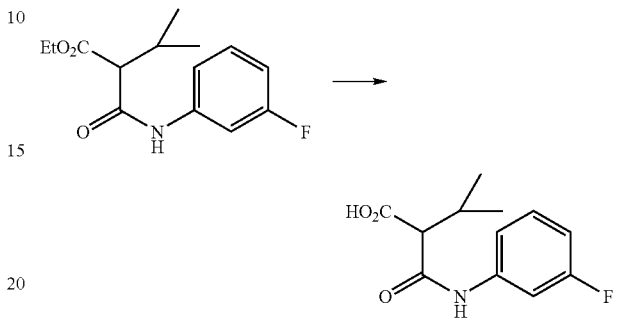

Prepared according to procedure B using ethyl 2-(3-fluorophenylcarbamoyl)-3-methylbutanoate (5.2 g, 19.45 mmol) in THF (20 mL) to give 2-(3-fluorophenylcarbamoyl)-3-methylbutanoic acid as a white solid.

7-Fluoro-3-isopropylquinoline-2,4-diol and 5-fluoro-3-isopropylquinoline-2,4-diol

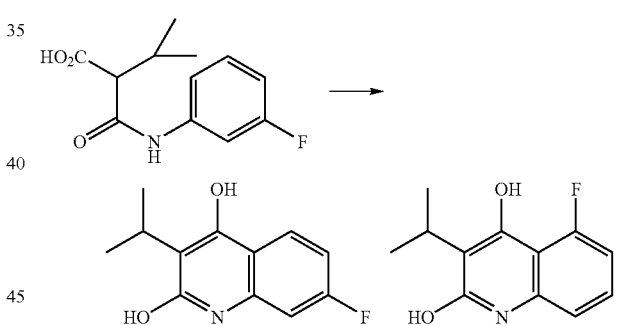

Prepared according to procedure C using 2-(3-fluorophenylcarbamoyl)-3-methylbutanoic acid (2.4 g, 10.03 mmol) and polyphosphoric acid (15 mL) to give a mixture of 7-fluoro-3-isopropylquinoline-2,4-diol and 5-fluoro-3-isopropylquinoline-2,4-diol as a white solid.

2,4-Dichloro-7-fluoro-3-isopropylquinoline and 2,4-dichloro-5-fluoro-3-isopropylquinoline

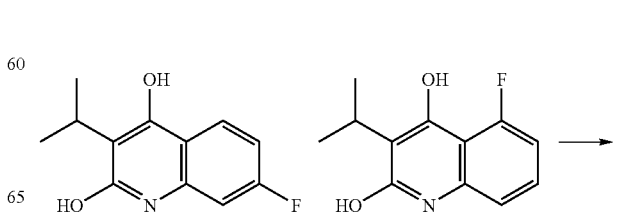

-continued

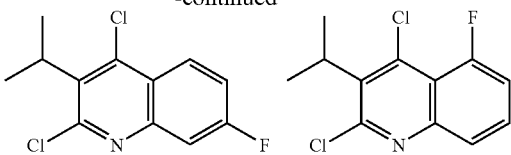

Prepared according to procedure D using 7-fluoro-3-isopropylquinoline-2,4-diol and 5-fluoro-3-isopropylquinoline-2,4-diol (1.0 g, 4.5 mmol) to give a mixture of 2,4-dichloro-7-fluoro-3-isopropylquinoline and 2,4-dichloro-5-fluoro-3-isopropylquinoline as a white solid. Mass Spectrum (ESI) m/e=258 (M+1).

4-Chloro-7-fluoro-3-isopropyl-2-(pyridin-2-yl)quinoline and 4-chloro-5-fluoro-3-isopropyl-2-(pyridin-2-yl)quinoline

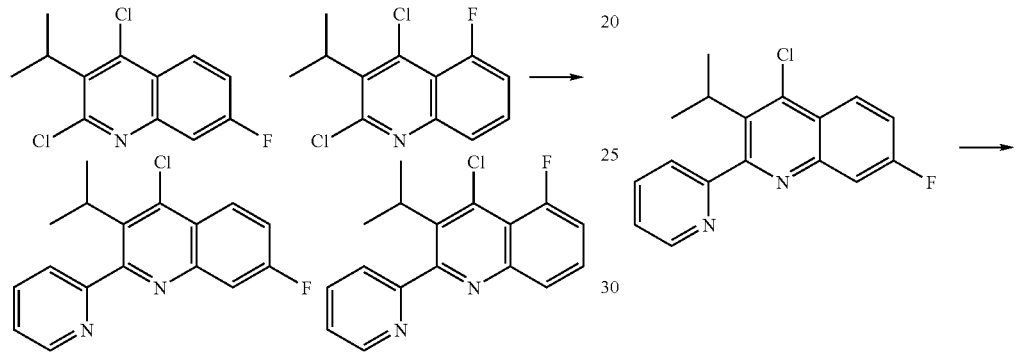

Prepared according to procedure E using 2,4-dichloro-7-fluoro-3-isopropylquinoline and 2,4-dichloro-5-fluoro-3-isopropylquinoline (700 mg, 2.71 mmol), palladium tetrakistriphenylphosphine (157 mg, 0.14 mmol) in toluene (10 mL) to give a separable mixture of 4-chloro-7-fluoro-3-isopropyl-2-(pyridin-2-yl)-quinoline and 4-chloro-5-fluoro-3-isopropyl-2-(pyridin-2-yl)quinoline.

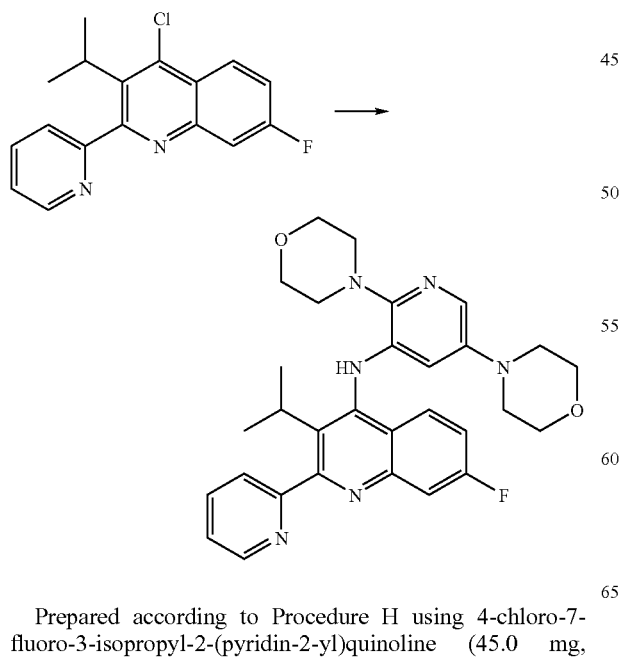

Prepared according to Procedure H using 4-chloro-7-fluoro-3-isopropyl-2-(pyridin-2-yl)quinoline (45.0 mg, 0.150 mmol) and 2,5-dimorpholinopyridin-3-amine in toluene to give N-(2,5-di-4-morpholinyl-3-pyridinyl)-7-fluoro-3-(1-methylethyl)-2-(2-pyridinyl)-4-quinolinamine. 1H NMR (400 MHz, chloroform-d) δ ppm 8.73 (1H, ddd, J=4.8, 1.7, 0.9 Hz), 7.88 (1H, td, J=7.7, 1.9 Hz), 7.72-7.79 (2H, m), 7.67 (1H, dt, J=7.8, 1.0 Hz), 7.58 (1H, d, J=2.7 Hz), 7.39 (1H, ddd, J=7.4, 4.9, 1.2 Hz), 7.23 (1H, ddd, J=9.4, 8.0, 2.5 Hz), 7.13 (1H, s), 6.11 (1H, d, J=2.5 Hz), 3.83-4.04 (4H, m), 3.67-3.79 (4H, m), 3.49 (2H, ddd, J=12.0, 6.3, 2.6 Hz), 3.25-3.42 (1H, m), 2.97 (2H, ddd, J=11.9, 6.2, 2.6 Hz), 2.85 (4H, t, J=4.8 Hz), 1.52 (3H, d, J=7.2 Hz), 1.12 (3H, d, J=7.0 Hz). Mass Spectrum (ESI) m/e=529.3 (M+1).

Example 102

Preparation of 7-fluoro-3-(1-methylethyl)-N-(5-(4-morpholinyl)-3-pyridinyl)-2-(2-pyridinyl)-4-quinolinamine

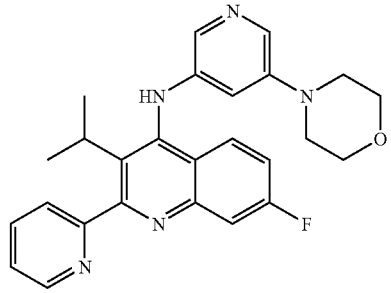

Prepared according to Procedure H using 4-chloro-7-fluoro-3-isopropyl-2-(pyridin-2-yl)quinoline (45.0 mg, 0.150 mmol) and 5-morpholinopyridin-3-amine in toluene to give 7-fluoro-3-(1-methylethyl)-N-(5-(4-morpholinyl)-3-pyridinyl)-2-(2-pyridinyl)-4-quinolinamine. 1H NMR (400 MHz, chloroform-d) δ ppm 8.69-8.76 (1H, m), 7.84-7.92 (2H, m), 7.71-7.83 (3H, m), 7.68 (1H, d, J=7.8 Hz), 7.39 (1H, ddd, J=7.6, 4.9, 1.2 Hz), 7.18 (1H, ddd, J=9.2, 8.1, 2.6 Hz), 6.25 (1H, t, J=2.3 Hz), 6.03 (1H, s), 3.71-3.83 (4H, m), 3.33-3.43 (1H, m), 2.95-3.08 (4H, m), 1.32 (6H, d, J=7.2 Hz). Mass Spectrum (ESI) m/e=444.2 (M+1).

Example 103

Preparation of 1-(4-((2,5-di-4-morpholinyl-3-pyridinyl)-amino)-5,7-difluoro-3-methyl-2-quinolinyl)-2-pyrrolidinone

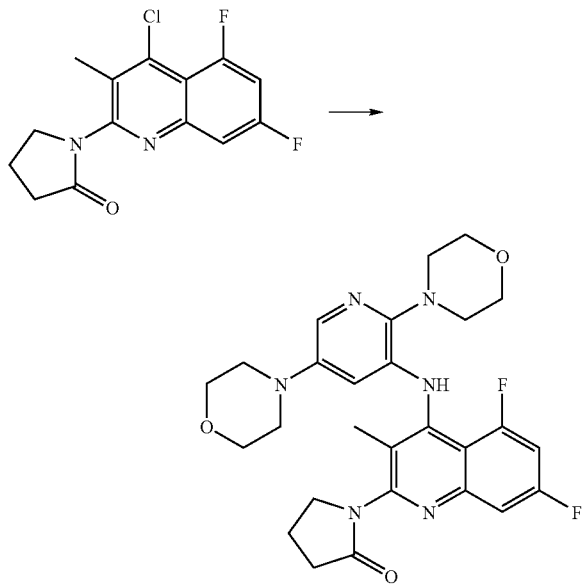

Prepared according to Procedure H using 1-(4-chloro-5,7-difluoro-3-methylquinolin-2-yl)pyrrolidin-2-one (35.0 mg, 0.120 mmol) and 2,5-dimorpholinopyridin-3-amine in toluene to give 1-(4-((2,5-di-4-morpholinyl-3-pyridinyl)-amino)-5,7-difluoro-3-methyl-2-quinolinyl)-2-pyrrolidinone. 1H NMR (400 MHz, chloroform-d) δ ppm 8.09 (1H, d, J=13.5 Hz), 7.65 (1H, d, J=2.7 Hz), 7.42 (1H, ddd, J=9.6, 2.5, 1.4 Hz), 6.97 (1H, ddd, J=13.7, 8.6, 2.5 Hz), 6.62 (1H, d, J=2.5 Hz), 4.51 (1H, br. s.), 3.92 (4H, br. s.), 3.68-3.86 (4H, m), 3.22-3.52 (3H, m), 3.15-3.22 (4H, m), 3.02 (2H, br. s.), 2.62 (2H, t, J=7.8 Hz), 2.19-2.37 (2H, m), 2.03 (3H, s). Mass Spectrum (ESI) m/e=525.3 (M+1).

Example 104

Preparation of 1-(5,7-difluoro-3-methyl-4-((5-(4-morpholinyl)-3-pyridinyl)amino)-2-quinolinyl)-4-methyl-2-piperazinone 1-(4-Chloro-5,7-difluoro-3-methylquinolin-2-yl)piperazin-2-one

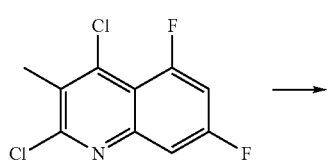

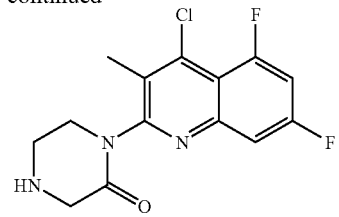

The 2,4-dichloro-5,7-difluoro-3-methylquinoline (400.0 mg, 1.613 mmol) and the other reagents along with-need to list reagents? 3 A molecular sieves were combined in t-BuOH (7.00 mL) and the mixture was stirred in the microwave at 120° C. for 4 h. The reaction was filtered and then washed with EtOAc. The filtrate was concentrated to dryness and the residue was taken up in water and then extracted with EtOAc (2×75 mL). The combined organic layers were dried over magnesium sulfate and the crude product was purified by medium pressure chromatography (silica, 0 to 100% EtOAc:DCM to 0 to 10% 2M ammonia in MeOH:DCM) to give 1-(4-chloro-5,7-difluoro-3-methylquinolin-2-yl)piperazin-2-one. Mass Spectrum (ESI) m/e=312.1 (M+1).

1-(4-Chloro-5,7-difluoro-3-methylquinolin-2-yl)-4-methylpiperazin-2-one

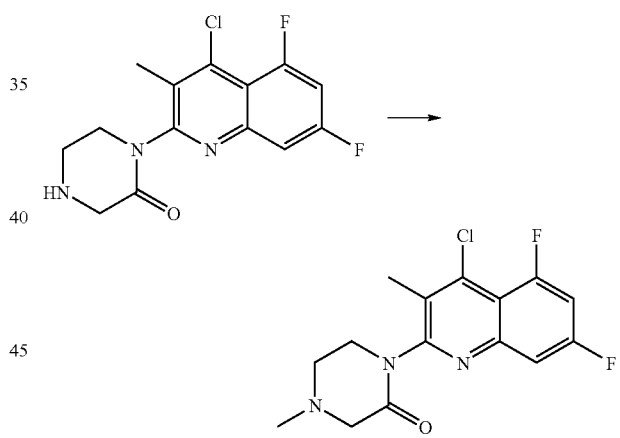

The 1-(4-chloro-5,7-difluoro-3-methylquinolin-2-yl)piperazin-2-one (52.0 mg, 0.167 mmol) and paraformaldehyde (5.01 mg, 0.167 mmol) were dissolved in 1.5 mL of a 2:1 dichloroethane:MeOH solution. The sodium triacetoxyborohydride (106 mg, 0.500 mmol) was added and the reaction mixture was stirred for 6.5 h. The reaction by LCMS had only progressed ~30%. Some sodium cyanoborohydride (50 mg, 0.796 mmol) was added turning the mixture into a solution again and stirred overnight. The reaction was then diluted with DCM and water. The layers were separated and the organic layer was washed with brine (1×10 mL) and dried over magnesium sulfate to give crude 1-(4-chloro-5,7-difluoro-3-methylquinolin-2-yl)-4-methylpiperazin-2-one. Mass Spectrum (ESI) m/e=312.1 (M+1).

1-(5,7-Difluoro-3-methyl-4-((5-(4-morpholinyl)-3-pyridinyl)amino)-2-quinolinyl)-4-methyl-2-piperazinone

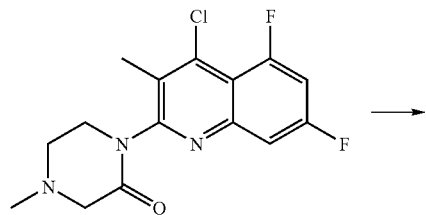

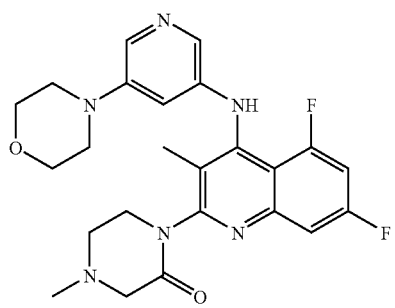

Prepared according to Procedure H using 1-(4-chloro-5,7-difluoro-3-methylquinolin-2-yl)-4-methylpiperazin-2-one (25.0 mg, 0.077 mmol) and 5-morpholinopyridin-3-amine in toluene to give 1-(5,7-difluoro-3-methyl-4-((5-(4-morpholinyl)-3-pyridinyl)amino)-2-quinolinyl)-4-methyl-2-piperazinone. 1H NMR (400 MHz, chloroform-d) δ ppm 7.92 (1H, br. s.), 7.88 (1H, br. s.), 7.47 (1H, ddd, J=9.6, 2.5, 1.4 Hz), 7.23 (1H, d, J=14.9 Hz), 7.01 (1H, ddd, J=13.9, 8.6, 2.5 Hz), 6.53 (1H, t, J=2.1 Hz), 4.41 (1H, ddd, J=11.8, 5.2, 5.1 Hz), 3.75-3.89 (4H, m), 3.53-3.67 (1H, m), 3.29-3.43 (1H, m), 3.11-3.27 (5H, m), 2.82-2.96 (2H, m), 2.44 (3H, s), 1.95 (3H, s). Mass Spectrum (ESI) m/e=326.0 (M+1).

Example 105

Preparation of 1-(4-((2,5-di-4-morpholinyl-3-pyridinyl)-amino)-5,7-difluoro-3-methyl-2-quinolinyl)-4-methyl-2-piperazinone

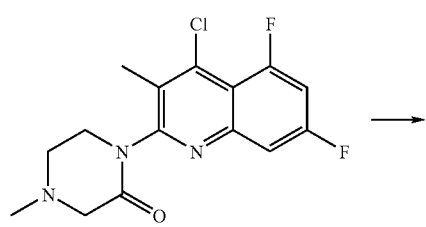

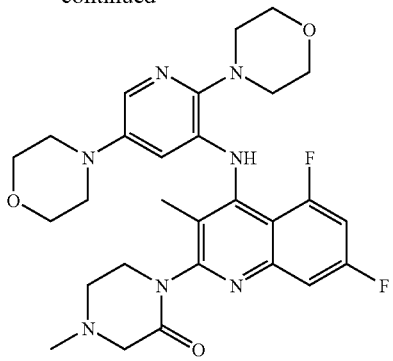

Prepared according to Procedure H using 1-(4-chloro-5,7-difluoro-3-methylquinolin-2-yl)-4-methylpiperazin-2-one (25.0 mg, 0.077 mmol) and 2,5-dimorpholinopyridin-3-amine in toluene to give 1-(4-((2,5-di-4-morpholinyl-3-pyridinyl)amino)-5,7-difluoro-3-methyl-2-quinolinyl)-4-methyl-2-piperazinone. 1H NMR (400 MHz, chloroform-d) δ ppm 8.12 (1H, br. s.), 7.68 (1H, d), 7.45 (1H, d, J=9.4 Hz), 7.04 (1H, ddd, J=13.6, 8.6, 2.4 Hz), 6.51 (1H, br. s.), 4.64 (1H, d, J=12.9 Hz), 3.84-4.00 (6H, m), 3.73-3.84 (4H, m), 3.36-3.54 (3H, m), 3.20-3.36 (2H, m), 3.15 (4H, br. s.), 2.93-3.09 (2H, m), 2.78 (3H, br. s.), 1.98 (3H, s). Mass Spectrum (ESI) m/e=554.3 (M+1).

Example 106

Preparation of 4-(5,7-difluoro-3-methyl-4-((5-(4-morpholinyl)-3-pyridinyl)amino)-2-quinolinyl)-1-methyl-2-piperazinone

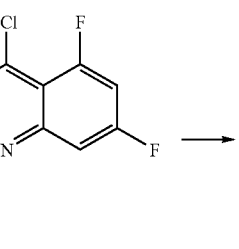

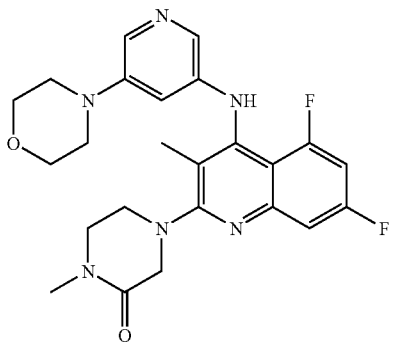

Prepared according to Procedure H using 4-(4-chloro-5,7-difluoro-3-methylquinolin-2-yl)-1-methylpiperazin-2-one (31.0 mg, 0.095 mmol) and 5-morpholinopyridin-3-amine in toluene to give 4-(5,7-difluoro-3-methyl-4-((5-(4-morpholinyl)-3-pyridinyl)amino)-2-quinolinyl)-1-methyl-2-piperazinone. 1H NMR (400 MHz, chloroform-d) δ ppm 7.95 (1H, br.

s.), 7.71 (1H, br. s.), 7.31 (1H, ddd, J=9.8, 2.6, 1.3 Hz), 6.94 (1H, d, J=13.1 Hz), 6.83 (1H, ddd, J=13.9, 8.6, 2.5 Hz), 6.60 (1H, s), 4.07 (2H, s), 3.84-3.91 (4H, m), 3.67 (2H, t, J=5.4 Hz), 3.53 (2H, t, J=5.4 Hz), 3.13-3.21 (4H, m), 3.03 (3H, s), 2.08 (3H, s). Mass Spectrum (ESI) m/e=469.3 (M+1).

Example 107

Preparation of 1-(5,7-difluoro-3-methyl-4-((5-(4-morpholinyl)-3-pyridinyl)amino)-2-quinolinyl)-2-pyrrolidinone 1-(4-Bromo-5,7-difluoro-3-methylquinolin-2-yl)pyrrolidin-2-one

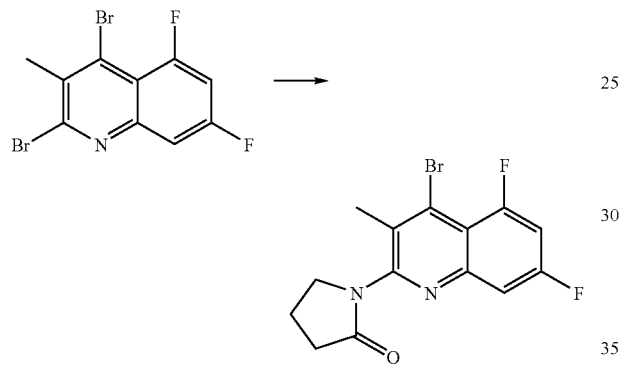

The 2,4-dibromo-5,7-difluoro-3-methylquinoline (500 mg, 1.50 mmol), pyrrolidin-2-one (0.110 mL, 1.50 mmol), copper (I) iodide (14 mg, 0.074 mmol), (1S,2S)—N1,N2-dimethylcyclohexane-1,2-diamine (0.023 mL, 0.150 mmol) and potassium phosphate tribasic (630 mg, 3.00 mmol) were slurried in dioxane (5 mL) and stirred in a microwave reactor at 110° C. for 2 h. The resulting slurry was dissolved and partitioned between water and EtOAc (2×75 mL). The combined organic layers were washed with brine (1×50 mL) and dried over magnesium sulfate. The crude product was purified by medium pressure chromatography (silica, 0 to 100% EtOAc:DCM) to give 1-(4-bromo-5,7-difluoro-3-methylquinolin-2-yl)pyrrolidin-2-one. Mass Spectrum (ESI) m/e=341.0 (M+1).

1-(5,7-Difluoro-3-methyl-4-(5-(4-morpholinyl)-3-pyridinyl)amino)-2-quinolinyl)-2-pyrrolidinone

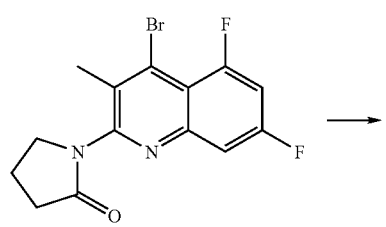

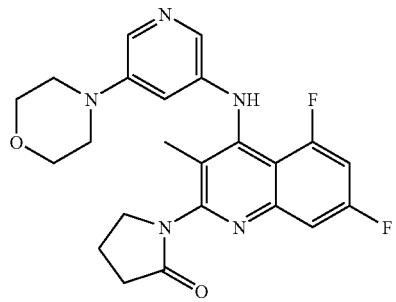

Prepared according to Procedure H using 1-(4-bromo-5,7-difluoro-3-methylquinolin-2-yl)pyrrolidin-2-one (44.0 mg, 0.130 mmol) and 5-morpholinopyridin-3-amine in toluene to give 1-(5,7-difluoro-3-methyl-4-((5-(4-morpholinyl)-3-pyridinyl)amino)-2-quinolinyl)-2-pyrrolidinone. 1H NMR (400 MHz, chloroform-d) δ ppm 7.93 (2H, dd, J=4.3, 2.3 Hz), 7.43 (1H, ddd, J=9.5, 2.5, 1.3 Hz), 7.36 (1H, d, J=14.5 Hz), 6.99 (1H, ddd, J=13.9, 8.6, 2.5 Hz), 6.64 (1H, t, J=2.2 Hz), 4.16 (2H, br. s.), 3.77-3.89 (4H, m), 3.20-3.30 (4H, m), 2.60 (2H, t, J=7.9 Hz), 2.27 (2H, qd, J=7.5, 7.3 Hz), 2.01 (3H, s). Mass Spectrum (ESI) m/e=440.2 (M+1).

Example 108

Preparation of 4-((5,7-difluoro-3-methyl-4-((5-(4-morpholinyl)-3-pyridinyl)amino)-2-quinolinyl)amino)butanoic acid

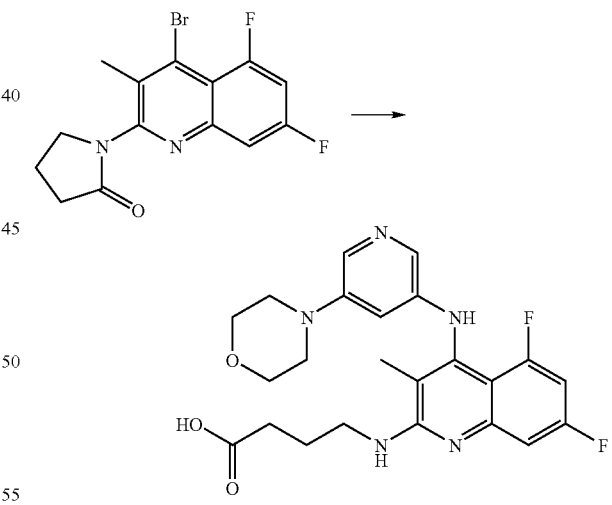

Prepared according to Procedure H using 1-(4-bromo-5,7-difluoro-3-methylquinolin-2-yl)pyrrolidin-2-one (44.0 mg, 0.130 mmol) and 5-morpholinopyridin-3-amine in toluene to give 1-(5,7-difluoro-3-methyl-4-((5-(4-morpholinyl)-3-pyridinyl)amino)-2-quinolinyl)-2-pyrrolidinone. 1H NMR (400 MHz, MeOH) δ ppm 7.90 (1H, br. s.), 7.52-7.62 (1H, m), 7.49 (1H, ddd, J=9.6, 1.8, 1.7 Hz), 6.98-7.11 (2H, m), 3.81-3.87 (4H, m), 3.70 (2H, t, J=7.2 Hz), 3.26-3.30 (4H, m), 2.57 (2H, t, J=6.6 Hz), 2.13 (3H, s), 2.08 (2H, quin, J=6.9 Hz). Mass Spectrum (ESI) m/e=458.2 (M+1).

Example 109

Preparation of 1-(5,7-difluoro-3-methyl-4-((5-(4-morpholinyl)-3-pyridinyl)amino)-2-quinolinyl)-2-piperidinone

1-(4-Bromo-5,7-difluoro-3-methylquinolin-2-yl) piperidin-2-one

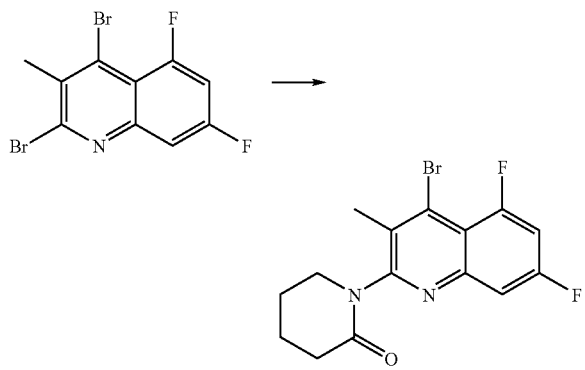

The 2,4-dibromo-5,7-difluoro-3-methylquinoline (2.000 g, 5.90 mmol), piperidin-2-one (590 mg, 5.90 mmol), copper (I) iodide (57.0 mg, 0.300 mmol), (1S,2S)—N1,N2-dimethylcyclohexane-1,2-diamine (0.094 mL, 0.59 mmol) and potassium phosphate tribasic (2.50 g, 11.9 mmol) were combined in 1,4-dioxane (10 mL) and stirred in the microwave reactor for 3.5 h. The reaction was diluted with water and extracted with EtOAc (2×100 mL). The combined organic layers were washed with brine and dried over magnesium sulfate. The crude product was then purified by medium pressure chromatography (silica, 0 to 100% EtOAc:hexanes) to give 1-(4-bromo-5,7-difluoro-3-methylquinolin-2-yl)piperidin-2-one. Mass Spectrum (ESI) m/e=355.1 (M+1).

1-(5,7-Difluoro-3-methyl-4-((5-(4-morpholinyl)-3-pyridinyl)amino)-2-quinolinyl)-2-piperidinone

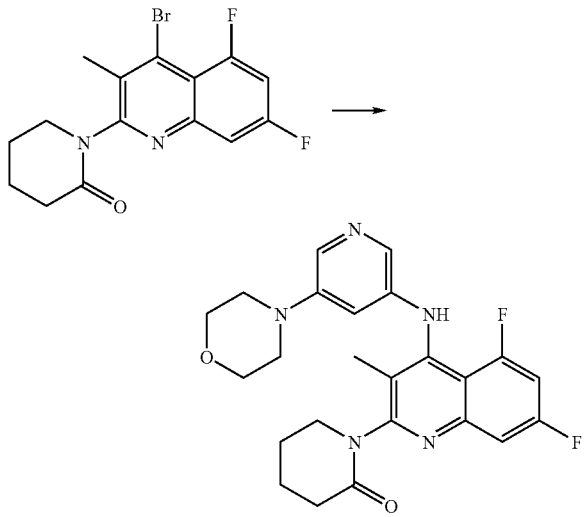

Prepared according to Procedure H using 1-(4-bromo-5,7-difluoro-3-methylquinolin-2-yl)piperidin-2-one (75.0 mg, 0.210 mmol) and 5-morpholinopyridin-3-amine in toluene to give 1-(5,7-difluoro-3-methyl-4-(5-(4-morpholinyl)-3-pyridinyl)amino)-2-quinolinyl)-2-pyrrolidinone. 1H NMR (400 MHz, chloroform-d) δ ppm 7.90 (1H, d, J=2.5 Hz), 7.86 (1H, d, J=2.3 Hz), 7.46 (1H, ddd, J=9.6, 2.5, 1.4 Hz), 7.24 (1H, d, J=14.1 Hz), 6.99 (1H, ddd, J=13.9, 8.6, 2.5 Hz), 6.54 (1H, t, J=2.4 Hz), 4.22-4.33 (1H, m), 3.82 (4H, t, J=4.8 Hz), 3.48-3.58 (1H, m), 3.13-3.28 (4H, m), 2.50-2.58 (2H, m), 2.07-2.14 (1H, m), 1.95-2.04 (3H, m), 1.94 (3H, s). Mass Spectrum (ESI) m/e=454.1 (M+1).

Example 110

Preparation of 5,7-difluoro-N-(2-(2-methoxyphenyl)-3-pyridinyl)-3-methyl-2-(2-pyridinyl)-4-quinolinamine

2-(2-Methoxyphenyl)-3-nitropyridine

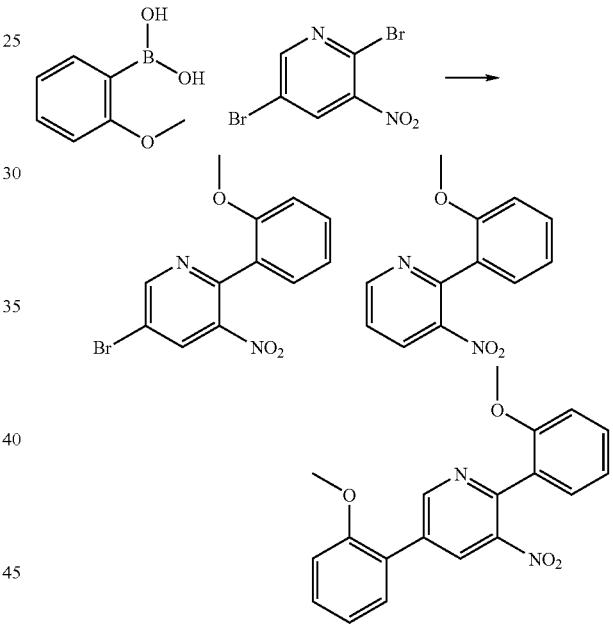

A stirred mixture of 2,5-dibromo-3-nitropyridine (0.32 g, 1.13 mmol), 2-methoxybenzeneboronic acid (0.19 g, 1.25 mmol), tetrakis(triphenylphosphine)palladium (65.5 mg, 0.057 mmol), and 2.0M sodium carbonate (3.0 mL, 6.00 mmol) in toluene (3.0 mL) and EtOH (1.0 mL) was heated to 70° C. After 19 h, the reaction was cooled to rt then diluted with water. After extraction with EtOAc, the organic layer was dried over anhydrous sodium sulfate. After filtration and concentration, the residue was purified on silica gel (0-25% EtOAc in hexanes) to afford a light yellow solid as 5-bromo-2-(2-methoxyphenyl)-3-nitropyridine. ¹H NMR (400 MHz, CDCl₃) δ ppm 8.93 (1H, d, J=2.0 Hz), 8.37 (1H, d, J=2.0 Hz), 7.66 (1H, dd, J=7.5, 1.7 Hz), 7.52 (1H, m), 7.16 (1H, td, J=7.5, 1.0 Hz), 6.92 (1H, dd, J=8.3, 0.7 Hz), 3.72 (3H, s).

2-(2-Methoxyphenyl)-3-nitropyridine

¹H NMR (400 MHz, CDCl₃) δ ppm 8.88 (1H, dd, J=4.9, 1.6 Hz), 8.22 (1H, dd, J=8.2, 1.6 Hz), 7.68 (1H, dd, J=7.4, 1.8

Hz), 7.50 (2H, m), 7.16 (1H, td, J=7.5, 1.0 Hz), 6.92 (1H, d, J=8.2 Hz), 3.72 (3H, s). Mass Spectrum (pos.) m/e: 230.9 (M+1).

2,5-bis(2-Methoxyphenyl)-3-nitropyridine $^1$H NMR (500 MHz, CDCl$_3$) δ ppm 9.05 (1H, d, J=2.0 Hz), 8.44 (1H, d, J=2.0 Hz), 7.74 (1H, dd, J=7.6, 1.7 Hz), 7.50 (3H, m), 7.22 (2H, m), 7.07 (1H, d, J=8.3 Hz), 6.95 (1H, d, J=8.3 Hz), 3.90 (3H, s), 3.80 (3H, s). Mass Spectrum (pos.) m/e: 337.0 (M+1).

2-(2-Methoxyphenyl)-3-pyridinamine

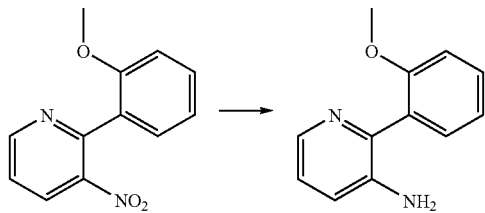 [SMILES: COc1ccccc1-c1ncccc1[N+](=O)[O-] ; COc1ccccc1-c1ncccc1N]

To a stirred mixture of 2-(2-methoxyphenyl)-3-nitropyridine (34.3 mg, 0.15 mmol) in EtOAc (5.0 mL) was added tin(II) chloride dihydrate (0.17 g, 0.76 mmol) in portions. Upon complete addition of the reducing agent, the mixture was carefully heated to 65° C. After 19 h, the reaction was cooled to rt and diluted with EtOAc, then washed with 1M NaOH (10 mL), water (10 mL), and brine (10 mL). After drying over anhydrous sodium sulfate and filtration, the organic solvent was removed under reduced pressure. The residue was identified as mostly 2-(2-Methoxyphenyl)-3-pyridinamine. Mass Spectrum (pos.) m/e: 201.1 (M+1).

5,7-Difluoro-N-(2-(2-methoxyphenyl)-3-pyridinyl)-3-methyl-2-(2-pyridinyl)-4-quinolinamine

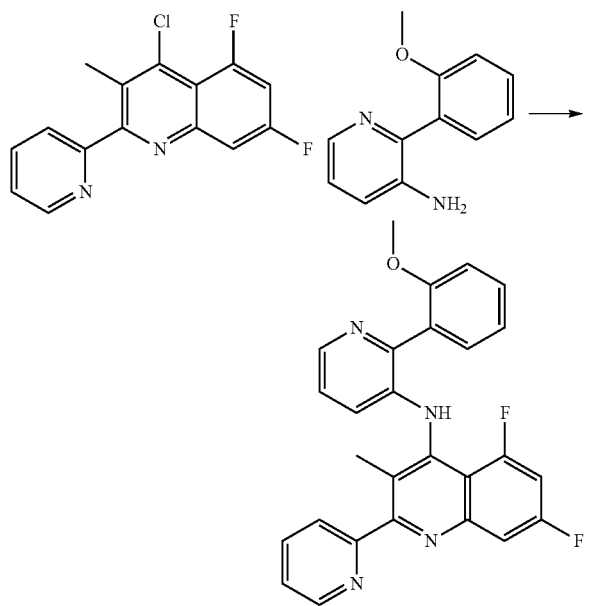

A mixture of 2-(2-methoxyphenyl)-3-pyridinamine (30.8 mg, 0.15 mmol), 4-chloro-5,7-difluoro-3-methyl-2-(2-pyridinyl)quinoline (67.8 mg, 0.23 mmol), 2-dicyclohexylphosphino-2,4,6,-triisopropylbiphenyl (15.5 mg, 0.03 mmol), tris (dibenzylideneacetone)dipalladium (0) (14.5 mg, 0.016 mmol), and sodium tert-butoxide (45.1 mg, 0.47 mmol) in dry toluene (2.0 mL) was degassed by nitrogen. The mixture was heated to 90° C. After 21.5 h, the reaction was cooled to rt, then treated with water. After extracting twice with EtOAc, the organic layers were combined and dried over anhydrous magnesium sulfate. After filtration and concentration the residue was purified on basic alumina (0-30% EtOAc in hexanes) to afford an light yellow solid as 5,7-difluoro-N-(2-(2-methoxyphenyl)-3-pyridinyl)-3-methyl-2-(2-pyridinyl)-4-quinolinamine. $^1$H NMR (400 MHz, CDCl$_3$) δ ppm 8.67 (1H, m), 8.31 (1H, d, J=4.5 Hz), 7.82 (1H, m), 7.70 (1H, m), 7.54 (3H, m), 7.30 (1H, m), 7.18 (1H, m), 7.06 (2H, t, J=7.5 Hz), 7.01 (1H, m), 6.87 (1H, ddd, J=13.2, 8.7, 2.0 Hz), 3.86 (3H, s), 1.82 (3H, br. s.). Mass Spectrum (pos.) m/e: 455.2 (M+1).

Example 111

Preparation of N-(2,5-Bis(2-methoxyphenyl)-3-pyridinyl)-5,7-difluoro-3-methyl-2-(2-pyridinyl)-4-quinolinamine 2,5-Bis(2-methoxyphenyl)-3-pyridinamine

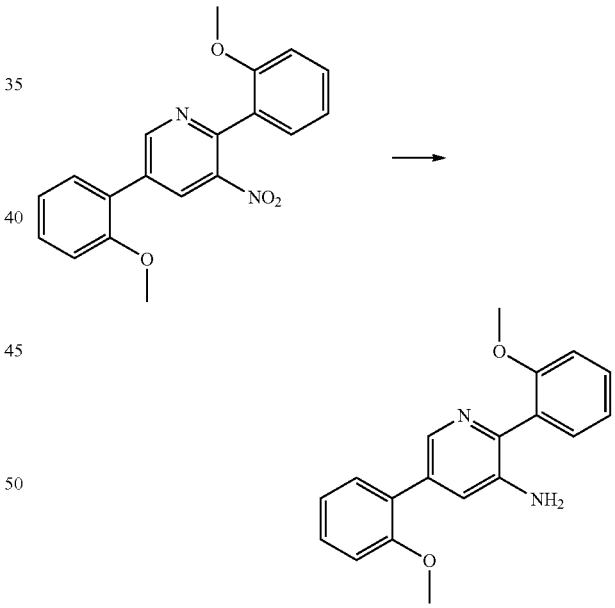

To a stirred mixture of 2,5-bis(2-methoxyphenyl)-3-nitropyridine (97.3 mg, 0.29 mmol) in EtOAc (5.0 mL) was added tin(II) chloride dihydrate (0.33 g, 1.45 mmol) in portions. Upon complete addition of the reducing agent, the mixture was carefully heated to 65° C. After 2 h, the reaction was cooled to rt and diluted with EtOAc, then washed with 1M NaOH (15 mL), water (15 mL), and brine (15 mL). After drying over anhydrous sodium sulfate and filtration, the organic solvent was removed under reduced pressure. The residue was identified as mostly 2,5-bis(2-methoxyphenyl)-3-pyridinamine. Mass Spectrum (pos.) m/e: 307.1 (M+1).

N-(2,5-Bis(2-methoxyphenyl)-3-pyridinyl)-5,7-difluoro-3-methyl-2-(2-pyridinyl)-4-quinolinamine

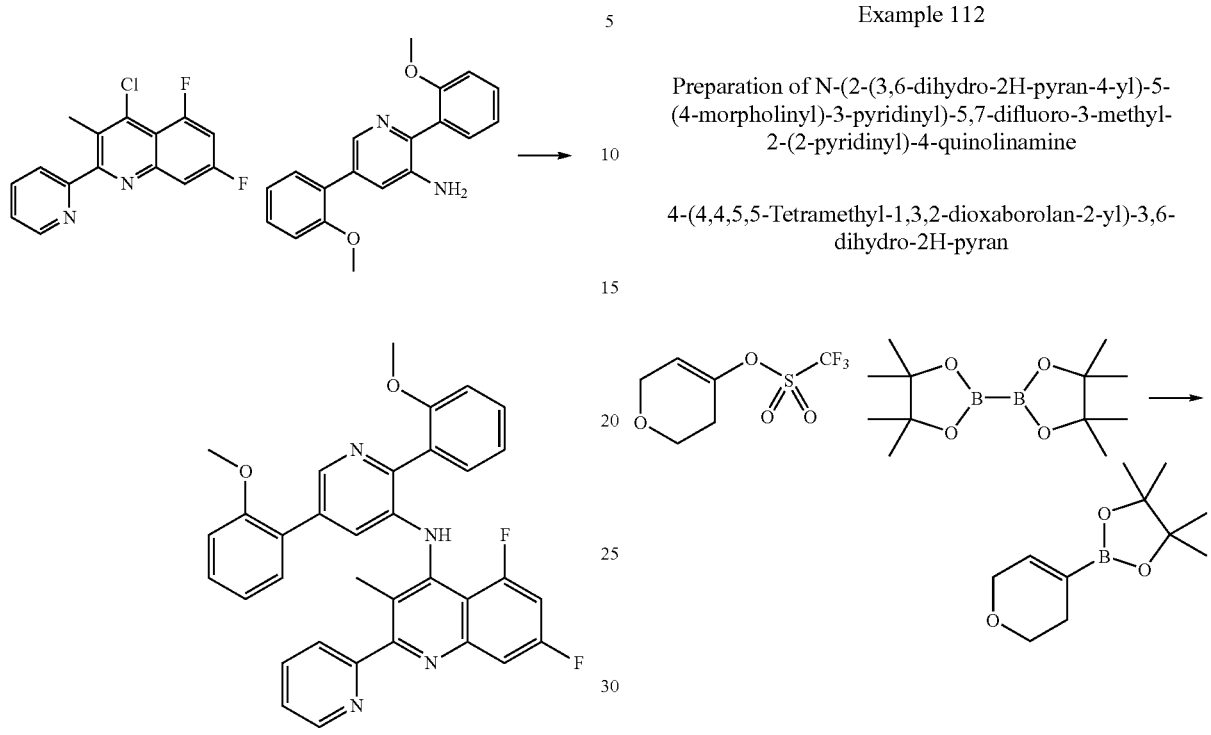

A mixture of 2,5-bis(2-methoxyphenyl)-3-pyridinamine (37.5 mg, 0.12 mmol), 4-chloro-5,7-difluoro-3-methyl-2-(2-pyridinyl)quinoline (54.7 mg, 0.19 mmol), 2-dicyclohexylphosphino-2,4,6,-triisopropylbiphenyl (12.1 mg, 0.025 mmol), tris(dibenzylideneacetone)dipalladium (0) (11.9 mg, 0.013 mmol), and sodium tert-butoxide (36.7 mg, 0.38 mmol) in dry toluene (2.0 mL) was degassed by nitrogen. The mixture was heated to 90° C. After 21.5 h, the reaction was cooled to rt, then treated with water. After extracting twice with EtOAc, the organic layers were combined and dried over anhydrous magnesium sulfate. After filtration and concentration the residue was purified on basic alumina (0-30% EtOAc in hexanes) to afford an impure light yellow film. The film was further purified by HPLC (10-90% of 0.1% TFA acetonitrile solution in 0.1% TFA water solution.) The desired fractions were concentrated then diluted with EtOAc. After washing twice with satd aq. sodium bicarbonate solution and once with brine, the solvent was removed under reduced pressure to yield a white solid as N-(2,5-bis(2-methoxyphenyl)-3-pyridinyl)-5,7-difluoro-3-methyl-2-(2-pyridinyl)-4-quinolinamine. $^1$H NMR (500 MHz, CDCl$_3$) δ ppm 8.69 (1H, d, J=4.6 Hz), 8.52 (1H, d, J=1.7 Hz), 7.84 (1H, td, J=7.7, 1.7 Hz), 7.76 (1H, d, J=7.6 Hz), 7.62 (2H, m), 7.50 (1H, m), 7.41 (4H, m), 7.16 (1H, t, J=7.5 Hz), 7.08 (1H, d, J=8.1 Hz), 7.04 (3H, m), 3.98 (3H, s), 3.83 (3H, s), 2.06 (3H, br. s.). Mass Spectrum ESI (pos.) m/e: 561.3 (M+1).

Example 112

Preparation of N-(2-(3,6-dihydro-2H-pyran-4-yl)-5-(4-morpholinyl)-3-pyridinyl)-5,7-difluoro-3-methyl-2-(2-pyridinyl)-4-quinolinamine 4-(4,4,5,5-Tetramethyl-1,3,2-dioxaborolan-2-yl)-3,6-dihydro-2H-pyran A mixture of 3,6-dihydro-2H-pyran-4-yl trifluoromethanesulfonate (commercially available from J&W Pharmlab) (0.54 g, 2.338 mmol), bis(pinacolato)diboron (0.74 g, 2.92 mmol), 1,1'-bis(diphenylphosphino)ferrocenepalladium (II) dichloride adduct (0.19 g, 0.23 mmol), and potassium acetate (0.92 g, 9.38 mmol) in dry 1,4-dioxane (10.0 mL) was degassed by nitrogen. The mixture was heated to 90° C. After 19 h, the reaction was cooled to rt then filtered. After concentration, the residue was purified on silica gel using 0-5% EtOAc in hexanes to yield a white solid as 4-(4,4,5,5-tetramethyl-1,3,2-dioxaborolan-2-yl)-3,6-dihydro-2H-pyran. $^1$H NMR (400 MHz, CDCl$_3$) δ ppm 6.49 (1H, t, J=2.0 Hz), 4.15 (2H, q, J=2.7 Hz), 3.72 (2H, t, J=5.4 Hz), 2.19 (2H, tq, J=5.1, 2.7 Hz), 1.23 (12H, s).

5-Bromo-2-(3,6-dihydro-2H-pyran-4-yl)-3-nitropyridine

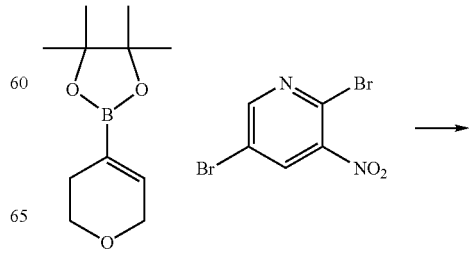

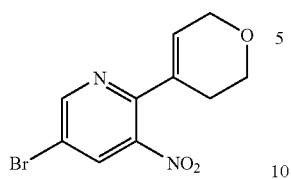

A stirred mixture of 2,5-dibromo-3-nitropyridine (0.31 g, 1.11 mmol), 4-(4,4,5,5-tetramethyl-1,3,2-dioxaborolan-2-yl)-3,6-dihydro-2H-pyran (0.26 g, 1.23 mmol), tetrakis(triphenylphosphine)palladium (64.7 mg, 0.056 mmol), and 2.0M sodium carbonate (3.0 mL, 6.00 mmol) in toluene (3.0 mL) and EtOH (1.0 mL) was heated to 70° C. After 19 h, the reaction was cooled to rt then diluted with water. After extraction with EtOAc, the organic layer was dried over anhydrous sodium sulfate. After filtration and concentration, the residue was purified on silica gel (0-20% EtOAc in hexanes) to afford a light yellow solid as 5-bromo-2-(3,6-dihydro-2H-pyran-4-yl)-3-nitropyridine. $^1$H NMR (400 MHz, CDCl$_3$) δ ppm 8.81 (1H, d, J=2.0 Hz), 8.20 (1H, d, J=2.0 Hz), 6.09 (1H, m), 4.30 (2H, q, J=2.8 Hz), 3.94 (2H, t, J=5.4 Hz), 2.61 (2H, m).

5-Bromo-2-(3,6-dihydro-2H-pyran-4-yl)-3-pyridinamine

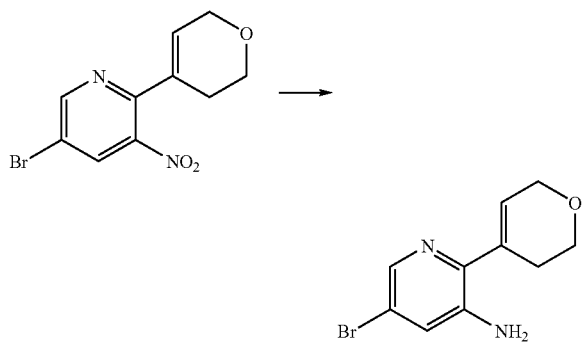

To a stirred mixture of as 5-bromo-2-(3,6-dihydro-2H-pyran-4-yl)-3-nitropyridine (0.19 g, 0.69 mmol) in EtOAc (10 mL) was added tin(II) chloride dihydrate (0.78 g, 3.48 mmol) in portions. Upon complete addition of the reducing agent, the mixture was carefully heated to 65° C. After 19 h, the reaction was cooled to rt and diluted with EtOAc, then washed with 1M NaOH (20 mL), water (20 mL), and brine (20 mL). After drying over anhydrous sodium sulfate and filtration, the organic solvent was removed under reduced pressure. The residue was identified as mostly 5-bromo-2-(3,6-dihydro-2H-pyran-4-yl)-3-pyridinamine.

N-(5-Bromo-2-(3,6-dihydro-2H-pyran-4-yl)-3-pyridinyl)-5,7-difluoro-3-methyl-2-(2-pyridinyl)-4-quinolinamine

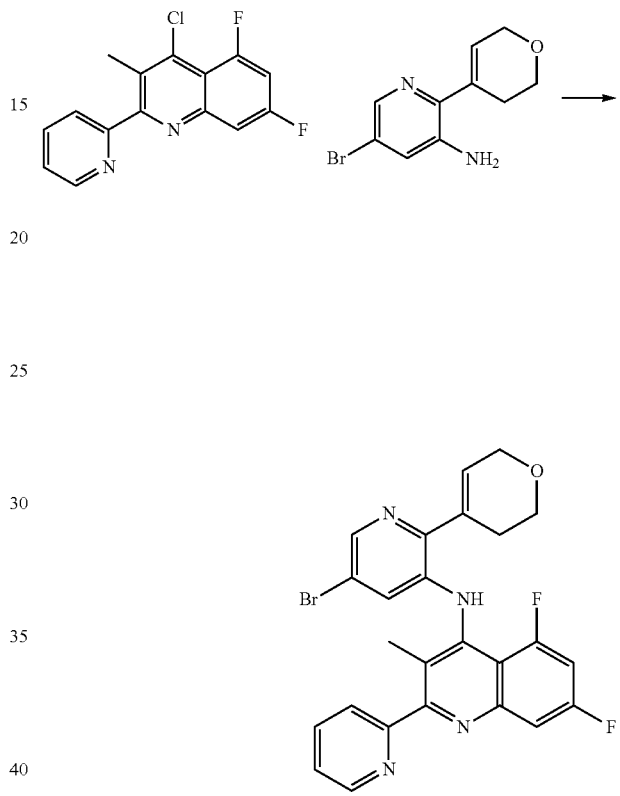

A dry flask containing 5-bromo-2-(3,6-dihydro-2H-pyran-4-yl)-3-pyridinamine (0.17 g, 0.67 mmol) in dry DMF (5.0 mL) was cooled to 0° C., then sodium hydride, 60% dispersion in mineral oil (54.9 mg, 1.37 mmol) was added carefully in portions. The mixture was stirred at 0° C. for 15 min, then 4-chloro-5,7-difluoro-3-methyl-2-(2-pyridinyl)quinoline (0.22 g, 0.74 mmol) was added in portions. Upon complete addition, the mixture was warmed to 60° C. After 18 h, the reaction was cooled to rt then was carefully treated with 10% sodium carbonate solution. The black mixture was subsequently extracted five times with DCM:MeOH (90:10). The organic extraction was then washed one time with brine and dried over anhydrous magnesium sulfate. After filtration and concentration, the brownish residue was treated with isopropanol and warmed to 45° C. After 30 min, the solid was filtered and rinsed twice with MeOH to afford a tan solid as mostly N-(5-bromo-2-(3,6-dihydro-2H-pyran-4-yl)-3-pyridinyl)-5,7-difluoro-3-methyl-2-(2-pyridinyl)-4-quinolinamine.

N-(2-(3,6-Dihydro-2H-pyran-4-yl)-5-(4-morpholinyl)-3-pyridinyl)-5,7-difluoro-3-methyl-2-(2-pyridinyl)-4-quinolinamine

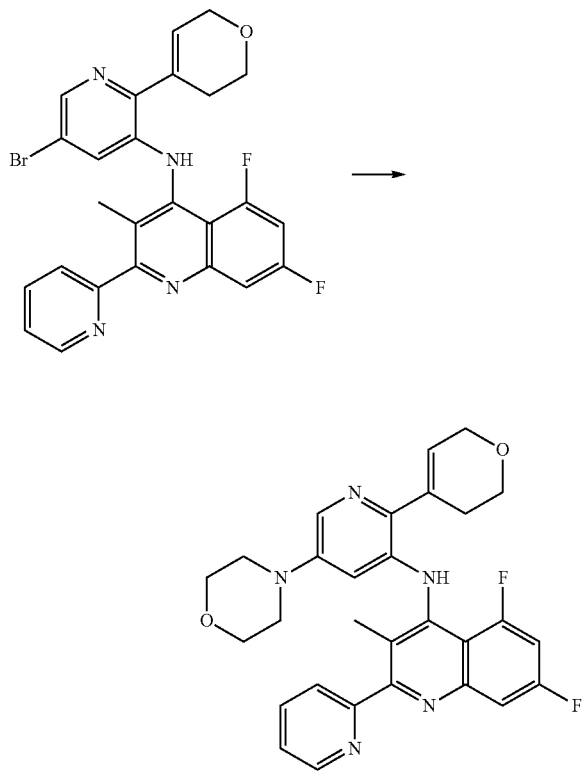 [SMILES: Cc1c(-c2ccccn2)nc2cc(F)cc(F)c2c1Nc1cc(Br)cnc1C1=CCOCC1 ; Cc1c(-c2ccccn2)nc2cc(F)cc(F)c2c1Nc1cc(N2CCOCC2)cnc1C1=CCOCC1]

A mixture of N-(5-bromo-2-(3,6-dihydro-2H-pyran-4-yl)-3-pyridinyl)-5,7-difluoro-3-methyl-2-(2-pyridinyl)-4-quinolinamine (35.5 mg, 0.07 mmol), 2-dicyclohexylphosphino-2,4,6,-triisopropylbiphenyl (7.1 mg, 0.015 mmol), tris(dibenzylideneacetone)dipalladium (0) (6.9 mg, 7.54 µmol), morpholine (0.05 mL, 0.57 mmol), and sodium tert-butoxide (20.7 mg, 0.215 mmol) in dry toluene (2.0 mL) was degassed by nitrogen. The mixture was heated to 100° C. After 21.5 h, the reaction was cooled to rt, then treated with water. After extracting twice with EtOAc, the organic layers were combined and dried over anhydrous magnesium sulfate. After filtration and concentration, the light orange film was purified by HPLC 10-60% of 0.1% TFA acetonitrile solution in 0.1% TFA water solution. The desired fractions were concentrated then diluted with EtOAc. After washing twice with satd aq. sodium bicarbonate solution and once with brine, the solvent was removed under reduced pressure to yield a white solid as N-(2-(3,6-dihydro-2H-pyran-4-yl)-5-(4-morpholinyl)-3-pyridinyl)-5,7-difluoro-3-methyl-2-(2-pyridinyl)-4-quinolinamine. Mass Spectrum (pos.) m/e: 516.3 (M+1)$^+$.

Example 113

Preparation of 2-(3,5-difluorophenyl)-N-(2,5-di-4-morpholinylphenyl)-3-methyl-1,8-naphthyridin-4-amine 4-Chloro-2-(3,5-difluorophenyl)-3-methyl-1,8-naphthyridine

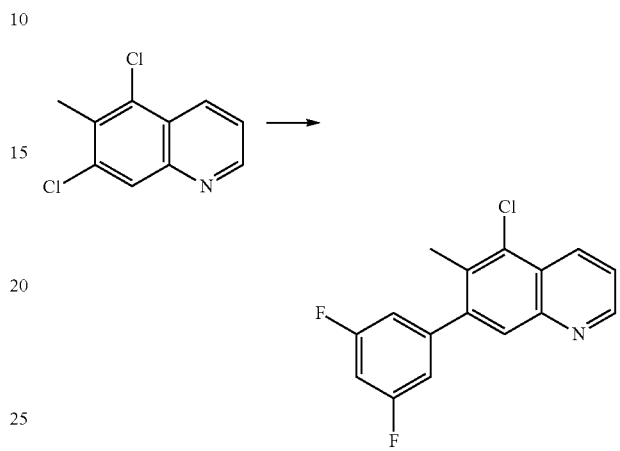

The Suzuki coupled product was prepared according to Procedure F using 2,4-dichloro-3-methyl-1,8-naphthyridine (0.4 g, 1.877 mmol), 3,5-difluorophenylboronic acid (0.445 g, 2.82 mmol), Pd(PPh$_3$)$_4$ (0.217 g, 0.188 mmol), potassium carbonate (0.519 g, 3.75 mmol) in toluene (6 mL) and heating at 95° C. for 18 h. Purification by column chromatography (silica gel; 0-25% EtOAc in hexanes) gave 4-chloro-2-(3,5-difluorophenyl)-3-methyl-1,8-naphthyridine as a yellow amorphous solid. Mass Spectrum (ESI) m/e=291.0 (M+1).

2-(3,5-Difluorophenyl)-N-(2,5-di-4-morpholinylphenyl)-3-methyl-1,8-naphthyridin-4-amine

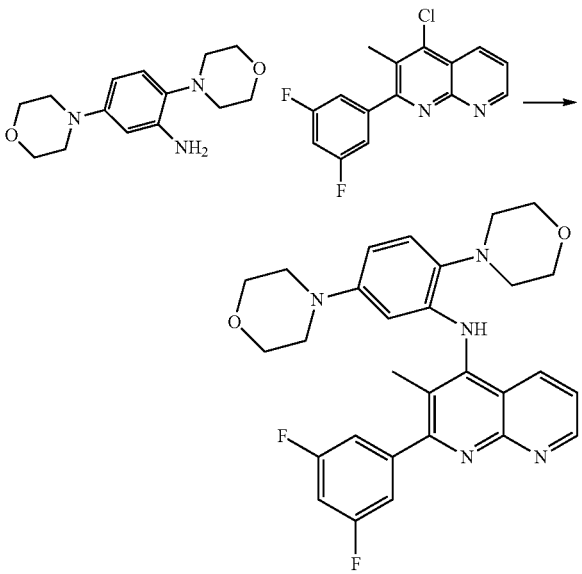

To a stirred solution of 4-chloro-2-(3,5-difluorophenyl)-3-methyl-1,8-naphthyridine (40 mg, 0.14 mmol), 4-(3,3-dimethyl-2,3-dihydro-1H-pyrrolo[3,2-b]-pyridin-6-yl)morpholine (32 mg, 0.14 mmol) and XPhos precatalyst (10 mg, 0.014 mmol) in toluene (4 mL) was added sodium tert-butoxide (26 mg, 0.27 mmol) and the reaction was heated at reflux for 2 h. Purification by reverse phase HPLC (10 to 60% acetonitrile in water) gave 2-(3,5-difluorophenyl)-N-(2,5-di-4-morpholinylphenyl)-3-methyl-1,8-naphthyridin-4-amine. H NMR (400 MHz, chloroform-d) δ ppm 9.10 (1H, dd, J=4.1, 2.0 Hz), 8.26 (1H, dd, J=8.4, 2.0 Hz), 7.40 (1H, dd, J=8.4, 4.1 Hz), 7.21-7.31 (2H, m), 7.13 (1H, d, J=8.6 Hz), 6.91-6.93 (1H, m), 6.48 (1H, dd, J=8.7, 2.6 Hz), 5.96 (1H, d, J=2.7 Hz), 3.91 (4H, t, J=4.6 Hz), 3.71-3.73 (4H, m), 3.05 (4H, br s), 2.87-2.90 (4H, m), 2.38 (3H, s). Mass Spectrum (ESI) m/e=518.2 (M+1).

Example 114

Preparation of N-(5-(3,6-dihydro-2H-pyran-4-yl)-3-pyridinyl)-5,7-difluoro-3-methyl-2-(2-pyridinyl)-4-quinolinamine N-(5-Bromo-3-pyridinyl)-5,7-difluoro-3-methyl-2-(2-pyridinyl)-4-quinolinamine

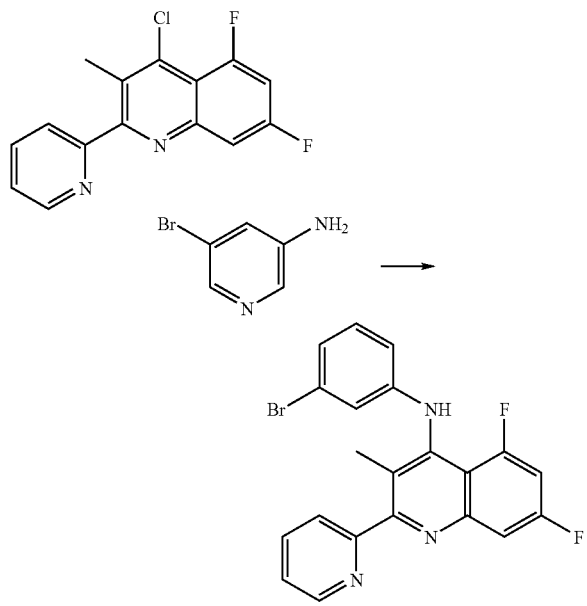

A dry flask containing 3-amino-5-bromopyridine (0.13 g, 0.78 mmol) in dry DMF (5.0 mL) was cooled to 0° C., then sodium hydride, 60% dispersion in mineral oil (63.6 mg, 1.59 mmol) was added carefully in portions. The mixture was stirred at 0° C. for 15 min, then 4-chloro-5,7-difluoro-3-methyl-2-(2-pyridinyl)quinoline (0.25 g, 0.86 mmol) was added in portions. Upon complete addition, the mixture was warmed to 60° C. After 18 h, the reaction was cooled to rt then was carefully treated with 10% sodium carbonate solution. The black mixture was subsequently extracted five times with DCM:MeOH (90:10). The organic extraction was then washed one time with brine and dried over anhydrous magnesium sulfate. After filtration and concentration, the black residue was treated with MeOH and warmed to 45° C. After 30 min, the solid was filtered and rinsed twice with MeOH to afford a tan solid as mostly N-(5-bromo-3-pyridinyl)-5,7-difluoro-3-methyl-2-(2-pyridinyl)-4-quinolinamine.

N-(5-(3,6-Dihydro-2H-pyran-4-yl)-3-pyridinyl)-5,7-difluoro-3-methyl-2-(2-pyridinyl)-4-quinolinamine

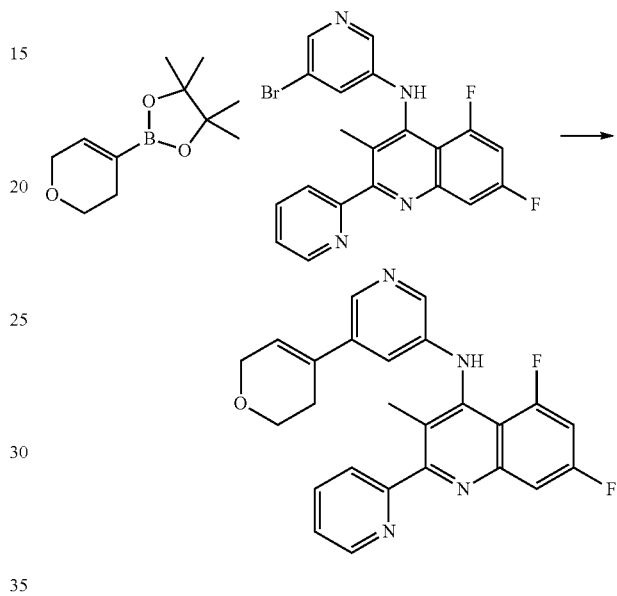

A mixture of N-(5-bromo-3-pyridinyl)-5,7-difluoro-3-methyl-2-(2-pyridinyl)-4-quinolinamine (38.0 mg, 0.089 mmol), 4-(4,4,5,5-tetramethyl-1,3,2-dioxaborolan-2-yl)-3,6-dihydro-2H-pyran (29.1 mg, 0.139 mmol), 2-dicyclohexylphosphino-2,6-dimethoxybiphenyl (S-Phos) (7.7 mg, 0.019 mmol), palladium(II) acetate (6.9 mg, 10.24 µmol), and potassium phosphate tribasic (60.4 mg, 0.29 mmol) in DMF (1 mL) and water (0.05 mL) was degassed by nitrogen. The mixture was heated to 90° C. After 21.5 h, the reaction was cooled to rt, then treated with water. After extracting twice with EtOAc, the organic layers were combined and dried over anhydrous magnesium sulfate. After filtration and concentration the residue was purified on basic alumina (0-35% EtOAc in hexanes) to afford an impure yellow residue. The light yellow film was further purified by HPLC (10-60% of 0.1% TFA acetonitrile solution in 0.1% TFA water solution.) The desired fractions were concentrated then diluted with EtOAc. After washing twice with satd aq. sodium bicarbonate solution and once with brine, the solvent was removed under reduced pressure to yield a white solid as N-(5-(3,6-dihydro-2H-pyran-4-yl)-3-pyridinyl)-5,7-difluoro-3-methyl-2-(2-pyridinyl)-4-quinolinamine. $^1$H NMR (400 MHz, CDCl$_3$) δ ppm 8.76 (1H, m), 8.31 (1H, d, J=1.8 Hz), 8.18 (1H, d, J=2.5 Hz), 7.94 (2H, m), 7.69 (1H, m), 7.38 (1H, dddd, J=7.4, 4.9, 1.3, 0.7 Hz), 7.12 (3H, m), 6.25 (1H, m), 4.33 (2H, q, J=2.7 Hz), 3.94 (2H, t, J=5.5 Hz), 2.51 (2H, td, J=5.0, 2.2 Hz), 2.17 (3H, s). Mass Spectrum (pos.) m/e: 431.1 (M+1).

Example 115

Preparation of N-(5,7-Difluoro-3-methyl-2-(2-pyridinyl)-4-quinolinyl)-5'-fluoro-2'-methoxy-3,4'-bipyridin-5-amine N-(5,7-Difluoro-3-methyl-2-(2-pyridinyl)-4-quinolinyl)-5'-fluoro-2'-methoxy-3,4'-bipyridin-5-amine

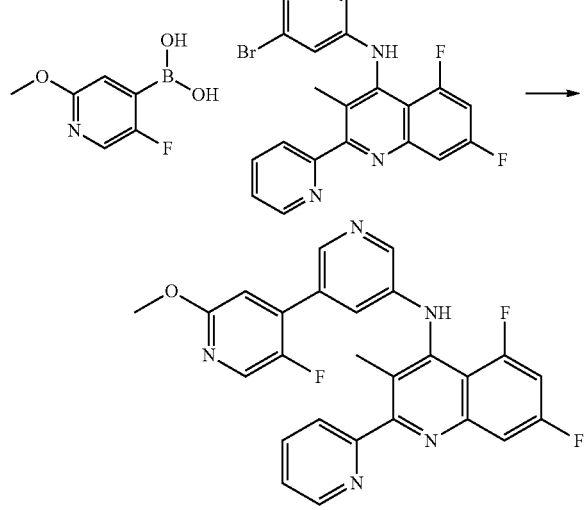

A mixture of N-(5-bromo-3-pyridinyl)-5,7-difluoro-3-methyl-2-(2-pyridinyl)-4-quinolinamine (28.1 mg, 0.066 mmol), 5-fluoro-2-methoxypyridin-4-ylboronic acid (commercially available from Asymchem) (17.7 mg, 0.104 mmol), 2-dicyclohexylphosphino-2,6-dimethoxybiphenyl, (S-Phos) (5.9 mg, 0.014 mmol), palladium(II) acetate (5.1 mg, 7.57 µmol), and potassium phosphate tribasic (45.1 mg, 0.21 mmol) in DMF (1.0 mL) and water (0.05 mL) was degassed by nitrogen. The mixture was heated to 90° C. After 21.5 h, the reaction was cooled to rt, then treated with water. After extracting twice with EtOAc, the organic layers were combined and dried over anhydrous magnesium sulfate. After filtration and concentration, the residue was purified on basic alumina (0-35% EtOAc in hexanes) to afford an impure yellow residue. The light yellow film was further purified by HPLC (10-60% of 0.1% TFA acetonitrile solution in 0.1% TFA water solution.) The desired fractions were concentrated then diluted with EtOAc. After washing twice with satd aq. sodium bicarbonate solution and once with brine, the solvent was removed under reduced pressure to yield a white solid as N-(5,7-difluoro-3-methyl-2-(2-pyridinyl)-4-quinolinyl)-5'-fluoro-2'-methoxy-3,4'-bipyridin-5-amine. $^1$H NMR (400 MHz, CDCl$_3$) δ ppm 8.77 (1H, ddd, J=4.8, 1.8, 0.9 Hz), 8.43 (1H, t, J=1.7 Hz), 8.36 (1H, d, J=2.7 Hz), 8.09 (1H, d, J=2.2 Hz), 7.94 (2H, m), 7.66 (1H, ddd, J=9.6, 2.5, 1.4 Hz), 7.40 (1H, ddd, J=7.4, 4.8, 1.5 Hz), 7.11 (2H, m), 6.86 (1H, d, J=5.3 Hz), 3.95 (3H, s), 2.24 (3H, s). Mass Spectrum (pos.) m/e: 474.1 (M+1).

Example 116

Preparation of: N-(2,5-di-4-morpholinylphenyl)-3-methyl-2-(2-pyridinyl)-1,7-naphthyridin-4-amine-3-methyl-1,7-naphthyridine-2,4-diol

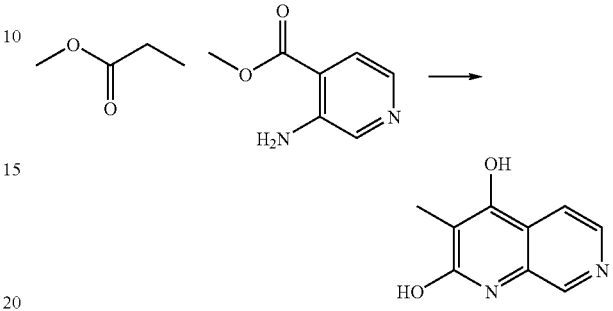

To a stirred solution of methyl 3-aminonicotinate (2.0 g, 13.14 mmol) and methyl propionate (30.9 mL, 329 mmol) in THF (30 mL) was added sodium tert-butoxide (3.16 g, 32.9 mmol) portionwise over 1 min. The reaction was stirred at rt for 40 min and at 100° C. for 4 h. After this time the reaction was cooled to rt and evaporated in vacuo. The resulting solid was dissolved in water (20 mL) and neutralized to pH 7 with 1.0M aqueous HCl. The resulting precipitate was filtered and dried under vacuum overnight to give 3-methyl-1,7-naphthyridine-2,4-diol. Mass Spectrum (ESI) m/e=177.2 (M+1).

2,4-Dichloro-3-methyl-1,7-naphthyridine

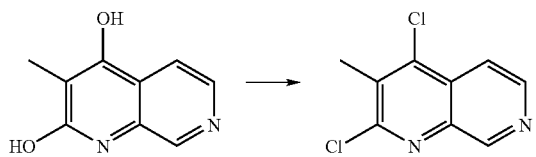

A stirred suspension of 3-methyl-1,7-naphthyridine-2,4-diol (0.5 g, 2.84 mmol) in phosphorus oxychloride (2.64 mL, 28.4 mmol) was heated at 120° C. for 3 h. After this time the reaction was allowed to cool to rt and evaporated in vacuo. The resulting residue was carefully basified to pH>10 with an aqueous solution of Na$_2$CO$_3$ and the resulting precipitate was filtered, washed with water and dried under vacuum to give 2,4-dichloro-3-methyl-1,7-naphthyridine. H NMR (400 MHz, chloroform-d) δ ppm 9.41 (1H, d, J=1.0 Hz), 8.72 (1H, d, J=5.9 Hz), 7.95 (1H, dd, J=5.9, 1.0 Hz), 2.73 (3H, s)

4-Chloro-3-methyl-2-(pyridin-2-yl)-1,7-naphthyridine

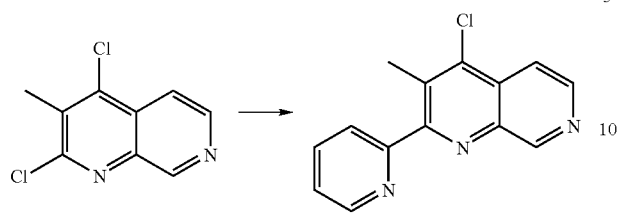

The Stille product was prepared according to Procedure E using 2,4-dichloro-3-methyl-1,8-naphthyridine (200 mg, 0.94 mmol), 2-(1,1,1-tributylstannyl)pyridine (346 μL, 0.93 mmol), Pd(PPh$_3$)$_4$ (108 mg, 0.09 mmol) in toluene (10 mL) and heating at reflux for 14 h. The reaction was allowed to cool to rt and evaporated in vacuo. The resulting residue was triturated with hexanes and the solid was dried under vacuum to give 4-chloro-3-methyl-2-(pyridin-2-yl)-1,7-naphthyridine. H NMR (400 MHz, chloroform-d) δ ppm 9.53 (1H, d, J=1.0 Hz), 8.68-8.80 (2H, m), 8.03 (1H, dd, J=5.8, 0.9 Hz), 7.85-7.96 (2H, m), 7.38-7.49 (1H, m), 2.70 (3H, s)

N-(2,5-Di-4-morpholinylphenyl)-3-methyl-2-(2-pyridinyl)-1,7-naphthyridin-4-amine

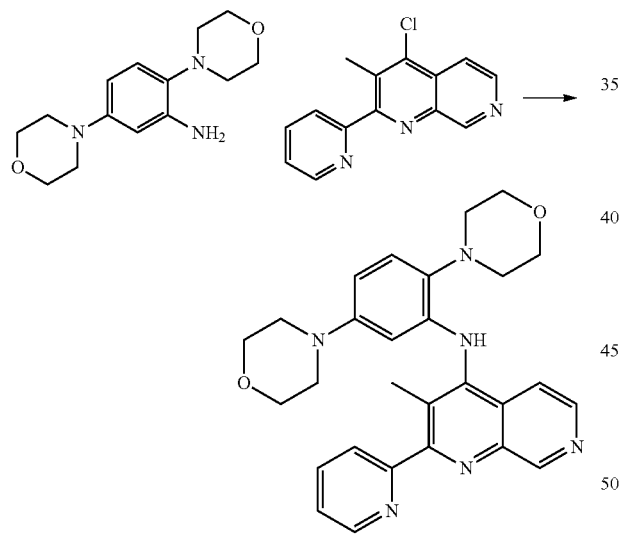

To a stirred solution of 4-chloro-3-methyl-2-(pyridin-2-yl)-1,7-naphthyridine (70 mg, 0.27 mmol), 6'-morpholino-1',2,2',3,5,6-hexahydrospiro[pyran-4,3'-pyrrolo[3,2-b]pyridine] (75 mg, 0.27 mmol) and XPhos™ precatalyst (20 mg, 0.03 mmol) in toluene (3 mL) was added sodium tert-butoxide (53 mg, 0.55 mmol) and the reaction was heated at reflux for 2 h. After this time the reaction was allowed to cool to rt and partitioned between EtOAc (60 mL) and water (20 mL). The separated organic layer was dried over MgSO$_4$, filtered and evaporated in vacuo. Purification by reverse phase HPLC (10 to 60% acetonitrile in water) gave N-(2,5-di-4-morpholinylphenyl)-3-methyl-2-(2-pyridinyl)-1,7-naphthyridin-4-amine. H NMR (400 MHz, chloroform-d) δ ppm 9.54 (1H, d, J=1.0 Hz), 8.73-8.78 (1H, m), 8.51 (1H, d, J=5.7 Hz), 7.91-7.99 (2H, m), 7.64 (1H, dd, J=5.8, 1.1 Hz), 7.41 (1H, td, J=4.9, 3.6 Hz), 7.22 (1H, s), 7.12 (1H, d, J=8.6 Hz), 6.48 (1H, dd, J=8.6, 2.7 Hz), 6.03 (1H, d, J=2.7 Hz), 3.89 (4H, t, J=4.6 Hz), 3.69-3.77 (4H, m), 3.01-3.12 (4H, m), 2.88-2.95 (4H, m), 2.45 (3H, s). Mass Spectrum (ESI) m/e=483.2 (M+1).

Example 117

2-Benzyl-N-(2,5-di-4-morpholinyl-3-pyridinyl)-5,7-difluoro-3-methyl-4-quinolinamine

2-Benzyl-4-chloro-5,7-difluoro-3-methylquinoline

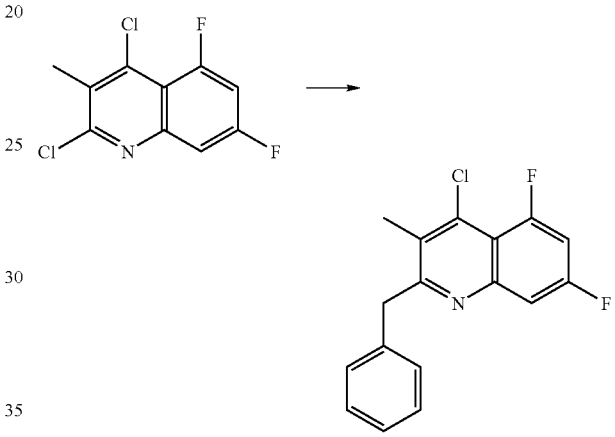

A screw cap vial was sequentially charged with 2,4-dichloro-5,7-difluoro-3-methylquinoline (250 mg, 1.00 mmol), tetrakis(triphenylphosphine)palladium(0) (116 mg, 0.10 mmol), and dry THF (2.52 mL). The mixture was then sparged with N$_2$ prior to the addition of benzylzinc(II) bromide (0.5M in THF, 2.12 mL, 1.06 mmol). The reaction was stirred under N$_2$ at 60° C. for 2 h. The reaction was then cooled to rt, slowly poured over satd aq. ammonium chloride and ice, and extracted with EtOAc. The organic layer was washed with water and brine, dried (MgSO$_4$), and concentrated. The crude product then was triturated with toluene, affording 2-benzyl-4-chloro-5,7-difluoro-3-methylquinoline (155 mg, 0.510 mmol). Mass Spectrum (ESI) m/e=304.0 (M+1).

2-Benzyl-N-(2,5-di-4-morpholinyl-3-pyridinyl)-5,7-difluoro-3-methyl-4-quinolinamine

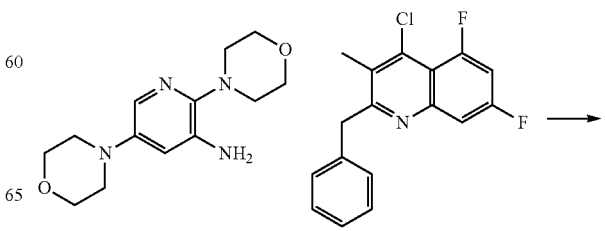

-continued

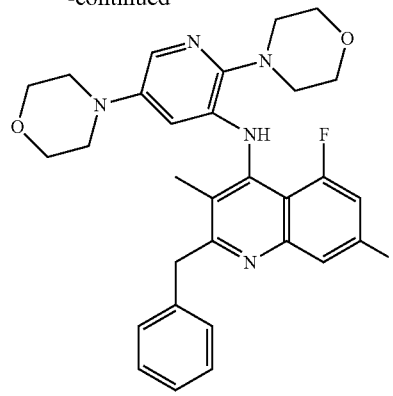

A screw cap vial was charged with 2-benzyl-4-chloro-5,7-difluoro-3-methylquinoline (43.3 mg, 0.143 mmol), 2,5-dimorpholinopyridin-3-amine (56.5 mg, 0.171 mmol), sodium tert-butoxide (41.1 mg, 0.428 mmol), tris(dibenzylideneacetone)dipalladium(0) (19.6 mg, 0.021 mmol), 2-(dicyclohexylphosphino)-2',4',6',-tri-i-propyl-1,1'-biphenyl (20.4 mg, 0.043 mmol), and toluene (1.43 mL). The mixture was stirred at 105° C. under $N_2$ for 2 h, then concentrated, diluted with EtOAc, and washed with satd aq. sodium bicarbonate, water, brine, and 1M NaOH. The organic layer was dried ($MgSO_4$) and concentrated, and the resulting crude product was purified by flash chromatography, eluting with a gradient of 0-66% EtOAc in hexanes. This afforded 2-benzyl-N-(2,5-di-4-morpholinyl-3-pyridinyl)-5,7-difluoro-3-methyl-4-quinolinamine (70 mg, 0.13 mmol) as a yellow solid. 1H NMR (400 MHz, chloroform-d) δ ppm 7.56-7.73 (1H, m), 7.49-7.55 (1H, m), 7.19-7.27 (5H, m), 6.98 (1H, m), 5.83 (1H, dd, J=2.3, 0.4 Hz), 4.40 (2H, br. s.), 3.90 (4H, br. s.), 3.66-3.72 (4H, m), 3.13-3.42 (2H, m), (2.83-3.13 (2H, m), 2.73 (4H, dd, J=5.1, 4.5 Hz), 2.05 (3H, s). Mass Spectrum (ESI) m/e=532.2 (M+1).

Example 118

Preparation of N-(2,5-di(4-morpholinyl)-3-pyridinyl)-6,8-difluoro-3-methyl-2-(2-pyridinyl)-4-quinolinamine Ethyl 3-(2,4-difluorophenylamino)-2-methyl-3-oxopropanoate

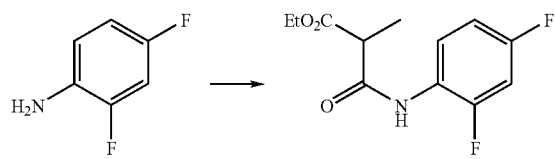 [SMILES: Nc1ccc(F)cc1F ; CCOC(=O)C(C)C(=O)Nc1ccc(F)cc1F]

The ester was prepared according to Procedure A using diethyl 2-methylmalonate (5.99 mL, 34.9 mmol), pyridine (3.76 mL, 46.5 mmol) and 2,4-difluoroaniline (2.34 mL, 23.2 mmol). The residue was purified by column chromatography on silica gel (0-30% EtOAc/hexanes) to give ethyl 3-(2,4-difluorophenylamino)-2-methyl-3-oxopropanoate as a red oil. Mass Spectrum (ESI) m/e=258.1 (M+1).

3-(2,4-Difluorophenylamino)-2-methyl-3-oxopropanoic acid

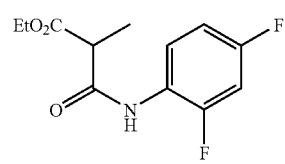

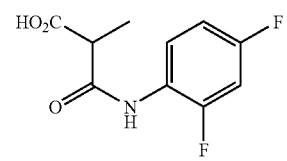

The acid was prepared according to Procedure B using ethyl 3-(2,4-difluorophenylamino)-2-methyl-3-oxopropanoate (5.1 g, 19.83 mmol) in THF (19.8 mL) to give 3-(2,4-difluorophenylamino)-2-methyl-3-oxopropanoic acid. Mass Spectrum (ESI) m/e=230.1 (M+1).

6,8-Difluoro-3-methylquinoline-2,4-diol

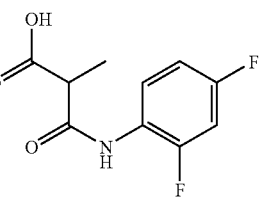

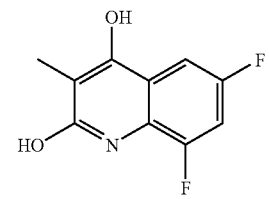

The diols were prepared according to Procedure C using 3-(2,4-difluorophenylamino)-2-methyl-3-oxopropanoic acid (4.4 g, 19.20 mmol) and polyphosphoric acid (25 mL, 19.20 mmol) to give 6,8-difluoro-3-methylquinoline-2,4-diol. Mass Spectrum (ESI) m/e=212.1 (M+1).

2,4-Dichloro-6,8-difluoro-3-methylquinoline

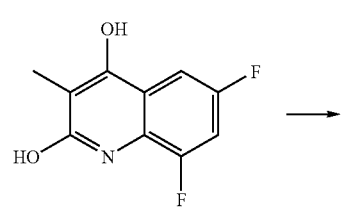

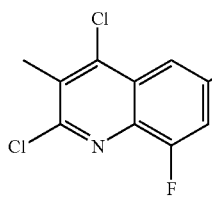

The dichloride was prepared according to Procedure D using a mixture of 6,8-difluoro-3-methylquinoline-2,4-diol (4.05 g, 19.18 mmol) to give 2,4-dichloro-6,8-difluoro-3-methylquinoline. Mass Spectrum (ESI) m/e=247.9 (M+1).

4-Dichloro-6,8-difluoro-3-methyl-2-(pyridin-2-yl)quinoline

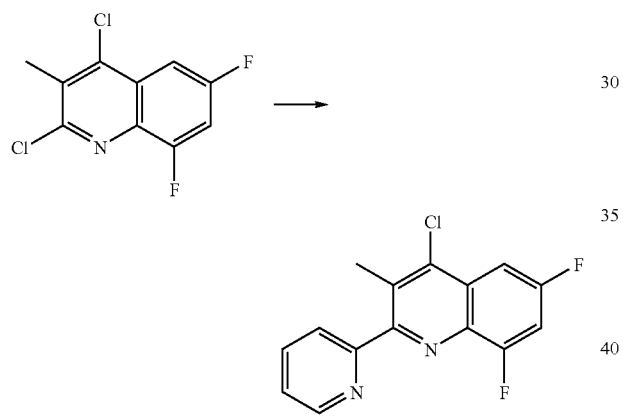

The Stille coupled product was prepared according to Procedure E using, 4-dichloro-6,8-difluoro-3-methylquinoline (0.518 g, 2.09 mmol), 2-(tributylstannyl)-pyridine (0.81 g, 2.19 mmol), palladium tetrakistriphenylphosphine (0.24 g, 0.21 mmol) in toluene (2 mL) to give 4-chloro-6,8-difluoro-3-methyl-2-(pyridin-2-yl)-quinoline as a white solid. Mass Spectrum (ESI) m/e=291.1 (M+1).

N-(2,5-Dimorpholinopyridin-3-yl)-6,8-difluoro-3-methyl-2-(pyridin-2-yl)-quinolin-4-amine

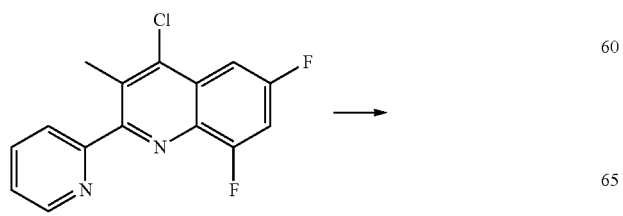

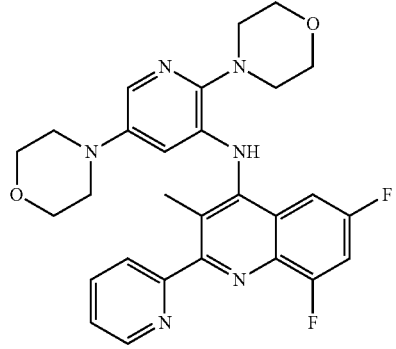

The Buchwald coupled product was prepared according to Procedure H using dicyclohexyl(2',4',6'-triisopropylbiphenyl-2-yl)phosphine (0.026 g, 0.055 mmol), 2,5-dimorpholinopyridin-3-amine (0.109 g, 0.41 mmol), 4-chloro-6,8-difluoro-3-methyl-2-(pyridin-2-yl)quinoline (0.1 g, 0.34 mmol), Pd$_2$dba$_3$ (0.013 g, 0.014 mmol) and sodium tert-butoxide (0.083 g, 0.86 mmol) in toluene (3.4 mL) at 120° C. for 3 h. The crude product was purified by column chromatography on basic alumina (0 to 50% hexanes/EtOAc) to give the desired product N-(2,5-dimorpholinopyridin-3-yl)-6,8-difluoro-3-methyl-2-(pyridin-2-yl)quinolin-4-amine. $^1$H NMR (400 MHz, CDCl$_3$-d) δ ppm 8.73 (1H, dd, J=1.6, 1.2 Hz), 7.89-8.00 (2H, m), 7.62 (1H, d, J=2.5 Hz), 7.40 (1H, ddd, J=7.4, 4.9, 1.4 Hz), 7.21-7.26 (2H, m), 6.70 (1H, br. s.), 6.19 (1H, m), 3.95-3.93 (4H, br. s.), 3.77-3.75 (4H, br. s.), 3.25 (4H, br s), 2.9-2.95 (4H, m), 2.44 (3H, s). Mass Spectrum (ESI) m/e=519.2 (M+1).

Example 119

Preparation of N-(2,5-dimorpholinopyridin-3-yl)-5,7-difluoro-2-(2-fluorophenyl)-3-methylquinolin-4-amine 4-Chloro-5,7-difluoro-2-(2-fluorophenyl)-3-methylquinoline

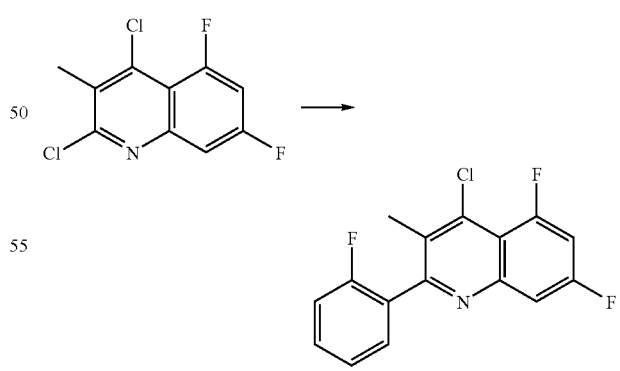

The Suzuki coupled product was prepared according to Procedure F using, 2,4-dichloro-5,7-difluoro-3-methylquinoline (2.00 g, 8.06 mmol), 2-fluorobenzeneboronic acid (1.24 g, 8.9 mmol), palladium tetrakistriphenylphosphine (0.24 g, 0.21 mmol), potassium carbonate (2.23 g, 16.13 mmol) in toluene (16 mL) at 100° C. for 48 h to give 4-chloro-5,7-difluoro-2-(2-fluorophenyl)-3-methylquinoline as a white solid. Mass Spectrum (ESI) m/e=308.0 (M+1).

N-(2,5-Dimorpholinopyridin-3-yl)-5,7-difluoro-2-(2-fluorophenyl)-3-methylquinolin-4-amine

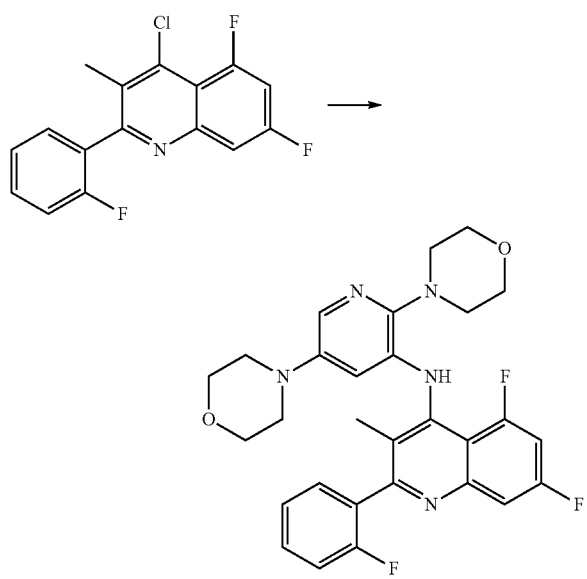

The Buchwald coupled product was prepared according to Procedure H using dicyclohexyl(2',4',6'-triisopropylbiphenyl-2-yl)phosphine (0.025 g, 0.052 mmol), 2,5-dimorpholinopyridin-3-amine (0.103 g, 0.39 mmol), 4-chloro-5,7-difluoro-2-(2-fluorophenyl)-3-methylquinoline (0.1 g, 0.33 mmol), Pd$_2$dba$_3$ (0.012 g, 0.013 mmol) and sodium tert-butoxide (0.078 g, 0.81 mmol) in toluene (3.3 mL) at 120° C. for 3 h. The crude product was purified by column chromatography on basic alumina (0 to 50% hexanes/EtOAc) to give the desired product N-(2,5-dimorpholinopyridin-3-yl)-5,7-difluoro-2-(2-fluorophenyl)-3-methylquinolin-4-amine. $^1$H NMR (400 MHz, CDCl$_3$-d) δ ppm 7.59-7.68 (3H, m), 7.47-7.54 (1H, m), 7.36 (1H, td, J=7.5, 1.2 Hz), 7.20 (1H, m,), 7.05 (1H, ddd, J=13.6, 8.6, 2.6 Hz), 6.42 (1H, br. s.), 3.93 (4H, br. s.), 3.83 (4H, m), 3.40 (2H, br. s.), 3.08 (4H, br. s.), 3.01 (2H, br s), 2.07 (3H, d, J=2.0 Hz). Mass Spectrum (ESI) m/e=536.2 (M+1).

Example 120

Preparation of 8-chloro-N-(2,5-dimorpholinopyridin-3-yl)-7-fluoro-3-methyl-2-(pyridin-2-yl)quinolin-4-amine Ethyl 3-(2-chloro-3-fluorophenylamino)-2-methyl-3-oxopropanoate

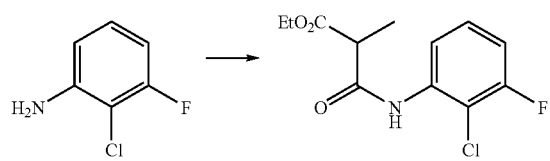 [SMILES: Nc1cccc(F)c1Cl ; CCOC(=O)C(C)C(=O)Nc1cccc(F)c1Cl]

The ester was prepared according to Procedure A using diethyl 2-methylmalonate (5.32 mL, 30.9 mmol), pyridine (3.33 mL, 41.2 mmol) and 2-chloro-3-fluoroaniline (3.00 g, 20.61 mmol) over 7 days. The residue was purified by column chromatography on silica gel (0-30% EtOAc/hexanes) to give ethyl 3-(2-chloro-3-fluorophenylamino)-2-methyl-3-oxopropanoate as a red oil. Mass Spectrum (ESI) m/e=274.0 (M+1).

3-(2-Chloro-3-fluorophenylamino)-2-methyl-3-oxopropanoic acid

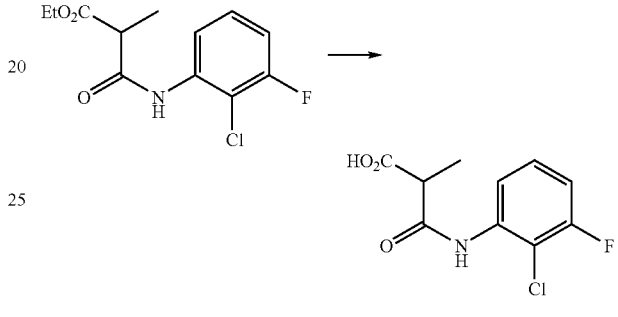

The acid was prepared according to Procedure B using ethyl 3-(2-chloro-3-fluorophenylamino)-2-methyl-3-oxopropanoate (5.0 g, 18.27 mmol) in THF (18.3 mL) to give 3-(2-chloro-3-fluorophenylamino)-2-methyl-3-oxopropanoic acid. Mass Spectrum (ESI) m/e=245.9 (M+1).

8-Chloro-7-fluoro-3-methylquinoline-2,4-diol

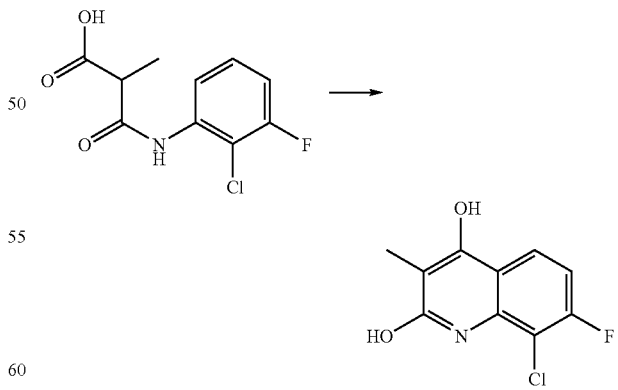

The diols were prepared according to Procedure C using 3-(2-chloro-3-fluorophenylamino)-2-methyl-3-oxopropanoic acid (4.4 g, 17.91 mmol) and polyphosphoric acid (25 mL, 19.20 mmol) to give 8-chloro-7-fluoro-3-methylquinoline-2,4-diol. Mass Spectrum (ESI) m/e=228.0 (M+1).

2,4,8-Trichloro-7-fluoro-3-methylquinoline

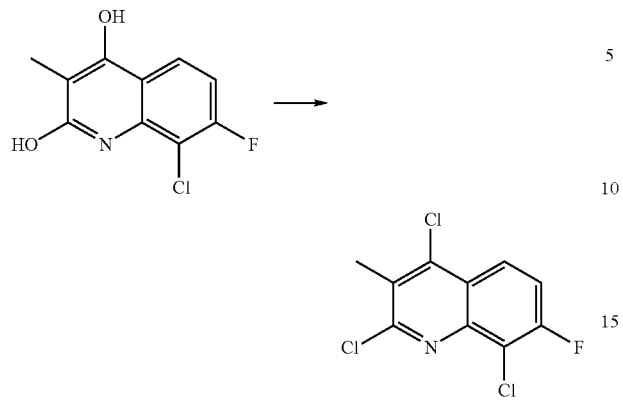

The trichloride was prepared according to Procedure D using a mixture of 8-chloro-7-fluoro-3-methylquinoline-2,4-diol (3.1 g, 13.62 mmol) to give 2,4,8-trichloro-7-fluoro-3-methylquinoline. Mass Spectrum (ESI) m/e=264.0 (M+1).

4,8-Dichloro-7-fluoro-3-methyl-2-(pyridin-2-yl)quinoline

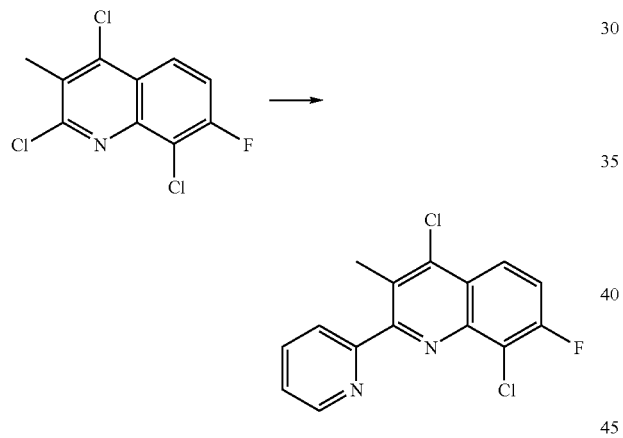

The Stille coupled product was prepared according to Procedure E using 2,4,8-trichloro-7-fluoro-3-methylquinoline (0.6 g, 2.27 mmol), 2-(tributylstannyl)pyridine (0.877 g, 2.38 mmol), palladium tetrakistriphenylphosphine (0.26 g, 0.23 mmol) in toluene (2 mL) to give 4,8-dichloro-7-fluoro-3-methyl-2-(pyridin-2-yl)quinoline as a white solid. Mass Spectrum (ESI) m/e=307.0 (M+1).

8-Chloro-N-(2,5-dimorpholinopyridin-3-yl)-7-fluoro-3-methyl-2-(pyridin-2-yl)quinolin-4-amine

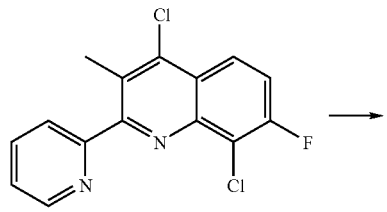

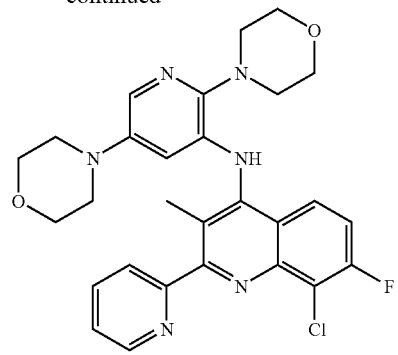

The Buchwald coupled product was prepared according to Procedure H using dicyclohexyl(2',4',6'-triisopropylbiphenyl-2-yl)phosphine (0.025 g, 0.052 mmol), 2,5-dimorpholinopyridin-3-amine (0.103 g, 0.39 mmol), 4,8-dichloro-7-fluoro-3-methyl-2-(pyridin-2-yl)quinoline (0.1 g, 0.33 mmol), $Pd_2dba_3$ (0.012 g, 0.013 mmol) and sodium tert-butoxide (0.078 g, 0.812 mmol) in toluene (3.3 mL) at 120° C. for 3 h. The crude product was purified by column chromatography on basic alumina (0 to 50% hexanes/EtOAc) to give the desired product 8-chloro-N-(2,5-dimorpholinopyridin-3-yl)-7-fluoro-3-methyl-2-(pyridin-2-yl)quinolin-4-amine. $^1$H NMR (400 MHz, $CDCl_3$) δ ppm 8.72 (1H, d, J=1.6 Hz), 8.14 (1H, d, J=7.8 Hz), 7.94 (1H, td, J=7.7, 1.8 Hz), 7.75 (1H, br s.), 7.61 (1H, d, J=0.4 Hz), 7.42-7.39 (1H, m), 7.36 (1H, t, J=8.6 Hz), 6.80 (1H, br s.), 6.19 (1H, br. s.), 3.93 (4H, br s.), 3.74 (4H, m), 3.25 (4H, br. s.), 2.92 (4H, br. m.), 2.47 (3H, s). Mass Spectrum (ESI) m/e=535.2 (M+1).

Example 121

Preparation of 8-chloro-N-(2,5-dimorpholinopyridin-3-yl)-5-fluoro-3-methyl-2-(pyridin-2-yl)quinolin-4-amine Ethyl 3-(2-chloro-5-fluorophenylamino)-2-methyl-3-oxopropanoate

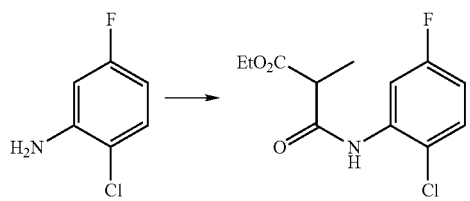 [SMILES: Nc1cc(F)ccc1Cl ; CCOC(=O)C(C)C(=O)Nc1cc(F)ccc1Cl]

The ester was prepared according to Procedure A using diethyl 2-methylmalonate (7.09 mL, 41.2 mmol), pyridine (4.45 mL, 55.0 mmol) and 2-chloro-5-fluoroaniline (4.0 g, 27.5 mmol) over 6 days. The residue was purified by column chromatography on silica gel (0-30% EtOAc/hexanes) to give ethyl 3-(2-chloro-5-fluorophenylamino)-2-methyl-3-oxopropanoate as a red oil. Mass Spectrum (ESI) m/e=274.0 (M+1).

3-(2-Chloro-5-fluorophenylamino)-2-methyl-3-oxo-propanoic acid

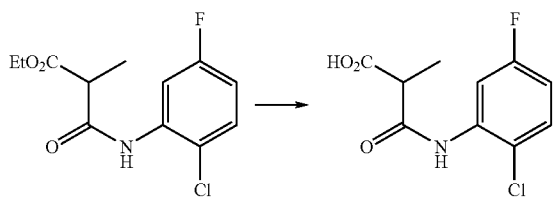 [SMILES: CCOC(=O)C(C)C(=O)Nc1cc(F)ccc1Cl ; CC(C(=O)O)C(=O)Nc1cc(F)ccc1Cl]

The acid was prepared according to Procedure B using ethyl 3-(2-chloro-5-fluorophenylamino)-2-methyl-3-oxopropanoate (5.0 g, 18.27 mmol) in THF (18.3 mL) to give 3-(2-chloro-5-fluorophenylamino)-2-methyl-3-oxopropanoic acid. Mass Spectrum (ESI) m/e=245.9 (M+1).

8-Chloro-5-fluoro-3-methylquinoline-2,4-diol

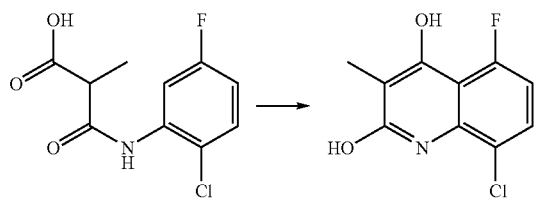 [SMILES: CC(C(=O)O)C(=O)Nc1cc(F)ccc1Cl ; Cc1c(O)nc2c(Cl)ccc(F)c2c1O]

The diols were prepared according to Procedure C using 3-(2-chloro-5-fluorophenylamino)-2-methyl-3-oxopropanoic acid (4.4 g, 17.91 mmol) and polyphosphoric acid (25 mL, 19.20 mmol) to give 8-chloro-5-fluoro-3-methylquinoline-2,4-diol.

2,4,8-Trichloro-5-fluoro-3-methylquinoline

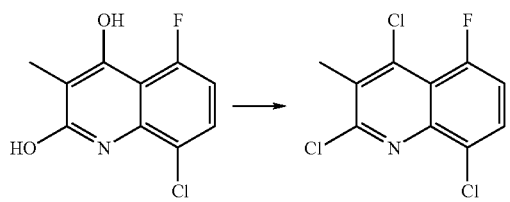

The trichloride was prepared according to Procedure D using a mixture of 8-chloro-5-fluoro-3-methylquinoline-2,4-diol (1.93 g, 8.48 mmol) to give 2,4,8-trichloro-5-fluoro-3-methylquinoline. Mass Spectrum (ESI) m/e=264.0 (M+1).

4,8-Dichloro-5-fluoro-3-methyl-2-(pyridin-2-yl)quinoline

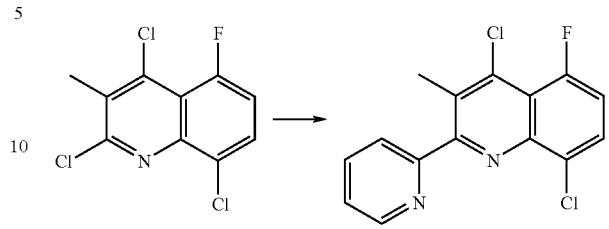

The Stille coupled product was prepared according to Procedure E using 2,4,8-trichloro-5-fluoro-3-methylquinoline (0.61 g, 2.306 mmol), 2-(tributylstannyl)-pyridine (0.89 g, 2.42 mmol), palladium tetrakistriphenylphosphine (0.27 g, 0.23 mmol) in toluene (2 mL) to give 4,8-dichloro-5-fluoro-3-methyl-2-(pyridin-2-yl)-quinoline as a white solid. Mass Spectrum (ESI) m/e=307.0 (M+1).

8-Chloro-N-(2,5-dimorpholinopyridin-3-yl)-5-fluoro-3-methyl-2-(pyridin-2-yl)quinolin-4-amine

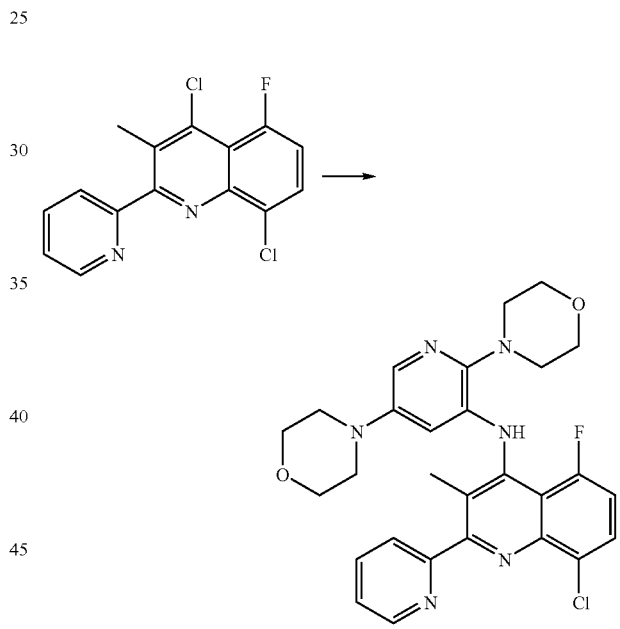

The Buchwald coupled product was prepared according to Procedure H using dicyclohexyl(2',4',6'-triisopropylbiphenyl-2-yl)phosphine (0.025 g, 0.052 mmol), 2,5-dimorpholinopyridin-3-amine (0.103 g, 0.39 mmol), 4,8-dichloro-5-fluoro-3-methyl-2-(pyridin-2-yl)quinoline (0.1 g, 0.33 mmol), $Pd_2dba_3$ (0.012 g, 0.013 mmol) and sodium tert-butoxide (0.078 g, 0.812 mmol) in toluene (3.3 mL) at 120° C. for 3 h. The crude product was purified by column chromatography on basic alumina (0 to 50% hexanes/EtOAc) to give the desired product 8-chloro-N-(2,5-dimorpholinopyridin-3-yl)-5-fluoro-3-methyl-2-(pyridin-2-yl)quinolin-4-amine. $^1$H NMR (400 MHz, $CDCl_3$) δ ppm 8.67 (1H, m), 8.19 (1H, dt, J=7.8, 1.1 Hz), 7.90-7.92 (1H, td, J=7.7, 1.8 Hz), 7.86 (1H, d, J=12.0 Hz), 7.73 (1H, dd, J=8.4, 5.1 Hz), 7.63 (1H, d, J=2.7 Hz), 7.38 (1H, ddd, J=7.6, 4.8, 1.3 Hz), 7.12 (1H, dd, J=12.9, 8.4 Hz), 6.45 (1H, d, J=2.2 Hz), 3.94 (4H, br. s.), 3.81 (4H, m), 3.18 (4H, br. s.), 3.09 (4H, m), 2.34 (3H, s). Mass Spectrum (ESI) m/e=535.2 (M+1).

Example 122

Preparation of 8-chloro-N-(2,5-dimorpholinopyridin-3-yl)-5,7-difluoro-3-methyl-2-(pyridin-2-yl)quinolin-4-amine Ethyl 3-(2-chloro-3,5-difluorophenylamino)-2-methyl-3-oxopropanoate

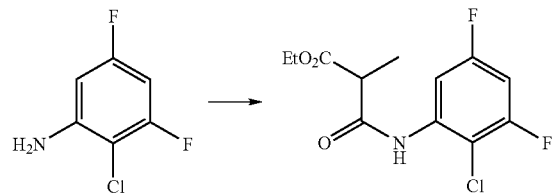 [SMILES: Nc1cc(F)cc(F)c1Cl ; CCOC(=O)C(C)C(=O)Nc1cc(F)cc(F)c1Cl]

The ester was prepared according to Procedure A using diethyl 2-methylmalonate (6.31 mL, 36.7 mmol), pyridine (3.96 mL, 48.9 mmol) and 2-chloro-3,5-difluoroaniline (4.00 g, 24.46 mmol) over 3 days. The residue was purified by column chromatography on silica gel (0-30% EtOAc/hexanes) to give ethyl 3-(2-chloro-3,5-difluorophenylamino)-2-methyl-3-oxopropanoate as a red oil. Mass Spectrum (ESI) m/e=292.0 (M+1).

3-(2-Chloro-3,5-difluorophenylamino)-2-methyl-3-oxopropanoic acid

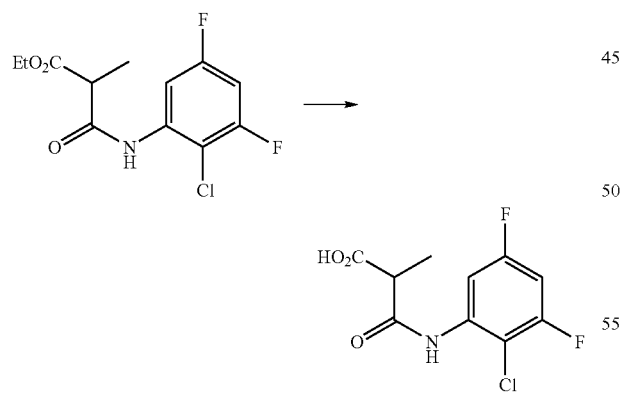

The acid was prepared according to Procedure B using ethyl 3-(2-chloro-3,5-difluorophenylamino)-2-methyl-3-oxopropanoate (5.0 g, 17.14 mmol) in THF (17.1 mL) to give 3-(2-chloro-3,5-difluorophenylamino)-2-methyl-3-oxopropanoic acid. Mass Spectrum (ESI) m/e=264.0 (M+1).

8-Chloro-5,7-difluoro-3-methylquinoline-2,4-diol

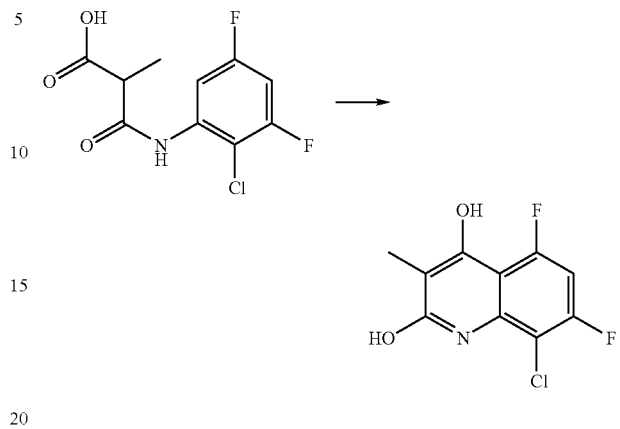

The diols were prepared according to Procedure C using 3-(2-chloro-3,5-difluorophenylamino)-2-methyl-3-oxopropanoic acid (4.4 g, 16.69 mmol) and polyphosphoric acid (25 mL, 19.20 mmol) to give 8-chloro-5,7-difluoro-3-methylquinoline-2,4-diol.

2,4,8-Trichloro-5,7-difluoro-3-methylquinoline

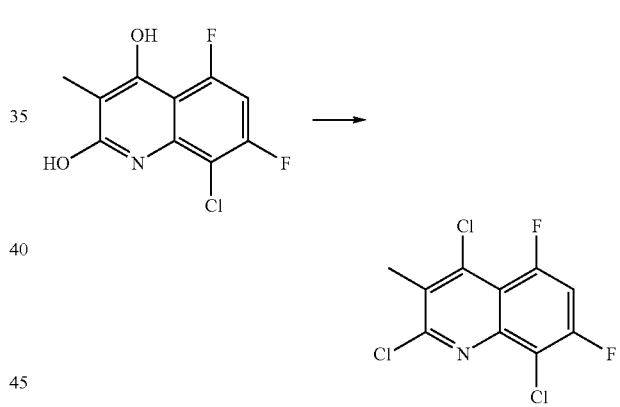

The trichloride was prepared according to Procedure D using a mixture of 8-chloro-5,7-difluoro-3-methylquinoline-2,4-diol (1.38 g, 5.63 mmol) to give 2,4,8-trichloro-5,7-difluoro-3-methylquinoline. Mass Spectrum (ESI) m/e=282.0 (M+1).

4,8-Dichloro-5,7-difluoro-3-methyl-2-(pyridin-2-yl)quinoline

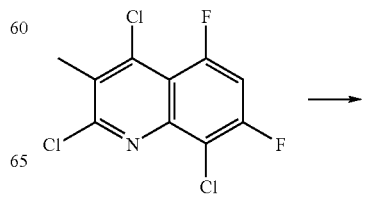

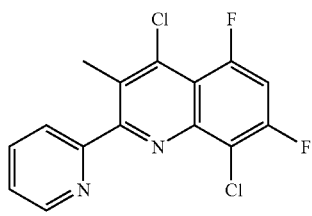

The Stille coupled product was prepared according to Procedure E using 2,4,8-trichloro-5,7-difluoro-3-methylquinoline (0.3 g, 1.06 mmol), 2-(tributylstannyl)-pyridine (0.410 g, 1.12 mmol), palladium tetrakistriphenylphosphine (0.123 g, 0.106 mmol) in toluene (2 mL) to give 4,8-dichloro-5,7-difluoro-3-methyl-2-(pyridin-2-yl)quinoline as a tan solid. Mass Spectrum (ESI) m/e=325.0 (M+1).

8-Chloro-N-(2,5-dimorpholinopyridin-3-yl)-5,7-difluoro-3-methyl-2-(pyridinyl)quinolin-4-amine

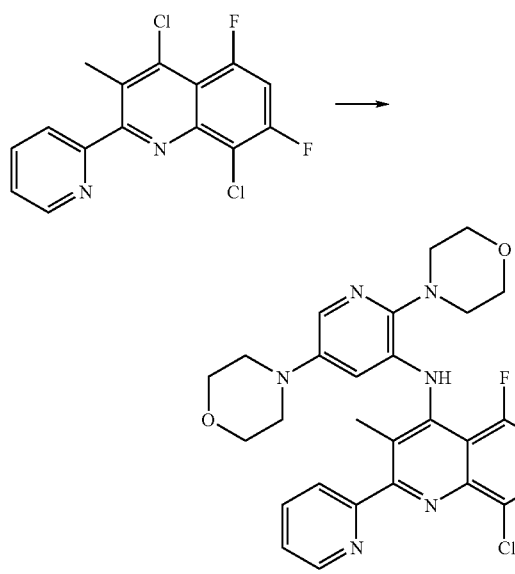

The Buchwald coupled product was prepared according to Procedure H using dicyclohexyl(2',4',6'-triisopropylbiphenyl-2-yl)phosphine (0.023 g, 0.049 mmol), 2,5-dimorpholinopyridin-3-amine (0.098 g, 0.37 mmol), 4,8-dichloro-5,7-difluoro-3-methyl-2-(pyridin-2-yl)quinoline (0.1 g, 0.31 mmol), Pd$_2$dba$_3$ (0.011 g, 0.012 mmol) and sodium tert-butoxide (0.074 g, 0.77 mmol) in toluene (3.1 mL) at 120° C. for 3 h. The crude product was purified by column chromatography on basic alumina (0 to 50% hexanes/EtOAc) to give the desired product 8-chloro-N-(2,5-dimorpholinopyridin-3-yl)-5,7-difluoro-3-methyl-2-(pyridin-2-yl)quinolin-4-amine. $^1$H NMR (400 MHz, CDCl$_3$) δ ppm 8.68 (1H, d, J=4.6 Hz), 8.18 (1H, d, J=8.0 Hz), 7.93 (1H, td, J=7.7, 1.8 Hz), 7.79 (1H, br. d., J=10.4 Hz), 7.64 (1H, d, J=2.5 Hz), 7.40 (1H, dd, J=7.4, 4.6 Hz), 7.11 (1H, dd, J=13.0, 8.7 Hz), 6.45 (1H, br. s.), 3.93 (4H, s), 3.81 (4H, app. dd, J=4.1, 2.5 Hz), 3.25 (4H, br. s), 3.09 (4H, app. dd, J=5.9, 3.9 Hz), 2.32 (3H, s). Mass Spectrum (ESI) m/e=553.2 (M+1).

Example 123

Preparation of 2-(2,3-dimethylphenyl)-N-(2,5-dimorpholinopyridin-3-yl)-5,7-difluoro-3-methylquinolin-4-amine 4-Chloro-2-(2,3-dimethylphenyl)-5,7-difluoro-3-methylquinoline

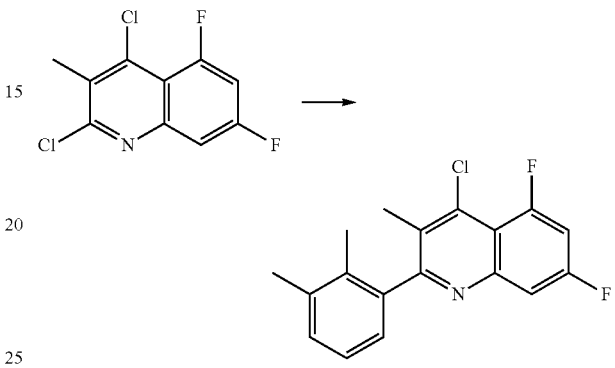

The Suzuki coupled product was prepared according to Procedure F using 2,4-dichloro-5,7-difluoro-3-methylquinoline (0.5 g, 2.02 mmol), 2,3-dimethylphenylboronic acid (0.333 g, 2.22 mmol), palladium tetrakistriphenylphosphine (0.23 g, 0.20 mmol), potassium carbonate (0.557 g, 4.03 mmol) in toluene (4 mL) at 100° C. for 16 h to give 4-chloro-2-(2,3-dimethylphenyl)-5,7-difluoro-3-methylquinoline as a white solid. Mass Spectrum (ESI) m/e=318.1 (M+1).

2-(2,3-Dimethylphenyl)-N-(2,5-dimorpholinopyridin-3-yl)-5,7-difluoro-3-methylquinolin-4-amine

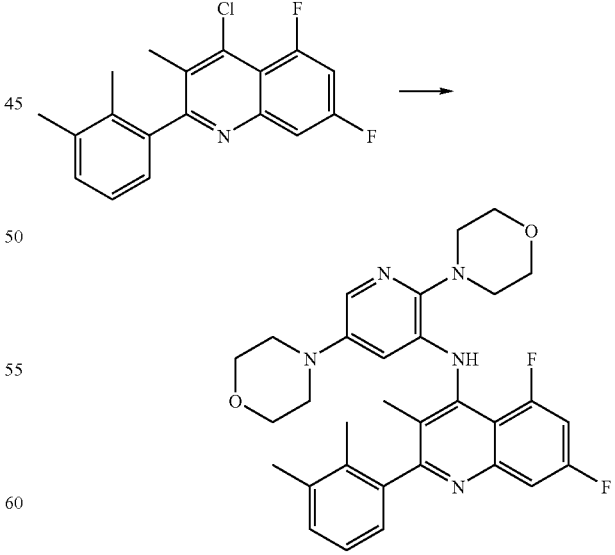

The Buchwald coupled product was prepared according to Procedure H using dicyclohexyl(2',4',6'-triisopropylbiphenyl-2-yl)phosphine (0.022 g, 0.045 mmol), 2,5-dimorpholinopyridin-3-amine (0.090 g, 0.34 mmol), 4-chloro-2-(2,3- dimethylphenyl)-5,7-difluoro-3-methylquinoline (0.090 g, 0.28 mmol), Pd$_2$dba$_3$ (0.010 g, 0.011 mmol) and sodium tert-butoxide (0.068 g, 0.71 mmol) in toluene (2.8 mL) at 120° C. for 1 h. The crude product was purified by column chromatography on basic alumina (0 to 50% hexanes/EtOAc) to give the desired product 2-(2,3-dimethylphenyl)-N-(2,5-dimorpholinopyridin-3-yl)-5,7-difluoro-3-methylquinolin-4-amine. $^1$H NMR (400 MHz, CDCl$_3$) δ ppm 7.71-7.68 (1H, br d, J=10.0 Hz), 7.63 (2H, m), 7.22-7.28 (2H, m), 6.98-7.11 (2H, m), 6.26 (1H, d, J=2.3 Hz), 3.93 (4H, m), 3.80 (4H, app t, J=4.2 Hz), 3.35 (4H, br. s), 3.01 (4H, app t, J=4.2 Hz), 2.37 (3H, s), 2.07 (3H, s), 1.94 (3H, s). Mass Spectrum (ESI) m/e=546.3 (M+1).

Example 124

Preparation of 2-(3,4-dimethylphenyl)-N-(2,5-dimorpholinopyridin-3-yl)-5,7-difluoro-3-methylquinolin-4-amine 4-Chloro-2-(3,4-dimethylphenyl)-5,7-difluoro-3-methylquinoline

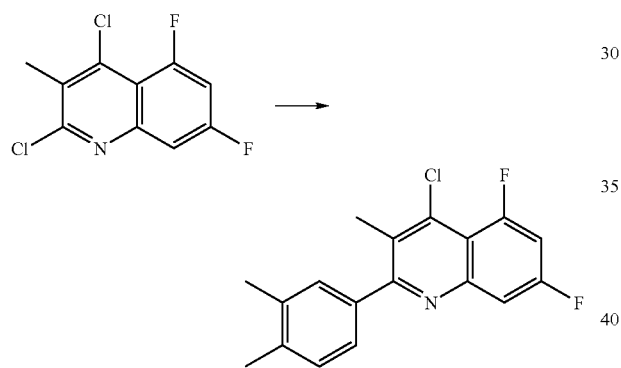

The Suzuki coupled product was prepared according to Procedure F using 2,4-dichloro-5,7-difluoro-3-methylquinoline (0.5 g, 2.02 mmol), 3,4-dimethylphenylboronic acid (0.333 g, 2.22 mmol), palladium tetrakistriphenylphosphine (0.23 g, 0.20 mmol), potassium carbonate (0.557 g, 4.03 mmol) in toluene (4 mL) at 100° C. for 48 h to give 4-chloro-2-(3,4-dimethylphenyl)-5,7-difluoro-3-methylquinoline as a white solid. Mass Spectrum (ESI) m/e=318.1 (M+1).

2-(3,4-Dimethylphenyl)-N-(2,5-dimorpholinopyridin-3-yl)-5,7-difluoro-3-methylquinolin-4-amine

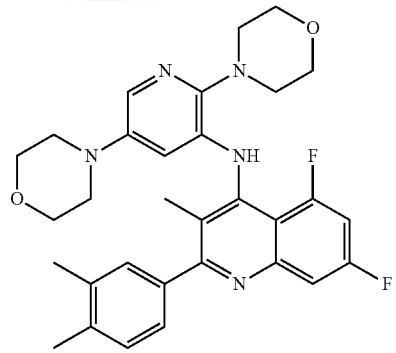

The Buchwald coupled product was prepared according to Procedure H using dicyclohexyl(2',4',6'-triisopropylbiphenyl-2-yl)phosphine (0.022 g, 0.045 mmol), 2,5-dimorpholinopyridin-3-amine (0.090 g, 0.34 mmol), 4-chloro-2-(3,4-dimethylphenyl)-5,7-difluoro-3-methylquinoline (0.090 g, 0.283 mmol), Pd$_2$dba$_3$ (0.010 g, 0.011 mmol) and sodium tert-butoxide (0.068 g, 0.71 mmol) in toluene (2.8 mL) at 120° C. for 1 h. The crude product was purified by column chromatography on basic alumina (0 to 50% hexanes/EtOAc) to give the desired product 2-(3,4-dimethylphenyl)-N-(2,5-dimorpholinopyridin-3-yl)-5,7-difluoro-3-methylquinolin-4-amine. $^1$H NMR (400 MHz, CDCl$_3$) δ ppm 7.71-7.68 (1H, br d, J=10.0 Hz), 7.63 (2H, m), 7.37 (1H, br s), 7.28 (2H, m), 6.98 (1H, ddd, J=13.3, 8.6, 2.5 Hz), 6.36 (1H, d, J=2.2 Hz), 3.92 (4H, m), 3.83 (4H, app t, J=4.3 Hz), 3.25 (4H, br. s), 3.06 (4H, app t, J=4.3 Hz), 2.36 (6H, s), 2.15 (3H, s). Mass Spectrum (ESI) m/e=546.3 (M+1)

Example 125

Preparation of N-(2,5-dimorpholinopyridin-3-yl)-5,7-difluoro-3-methyl-2-(1-methyl-1H-indol-4-yl)quinolin-4-amine 5,7-Difluoro-3-methyl-2-(1-methyl-1H-indol-4-yl)quinoline

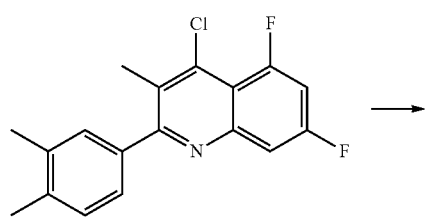

The Suzuki coupled product was prepared according to Procedure F using 2,4-dichloro-5,7-difluoro-3-methylquinoline (0.5 g, 2.016 mmol), 1-methyl-4-(4,4,5,5-tetramethyl-1,3,2-dioxaborolan-2-yl)-1H-indole (0.57 g, 2.22 mmol), palladium tetrakistriphenylphosphine (0.23 g, 0.20 mmol), potassium carbonate (0.557 g, 4.03 mmol) in toluene (4 mL) at 100° C. for 44 h to give 4-chloro-5,7-difluoro-3-methyl-2-(1-methyl-1H-indol-4-yl)quinoline as a light yellow solid. Mass Spectrum (ESI) m/e=343.0 (M+1).

N-(2,5-Dimorpholinopyridin-3-yl)-5,7-difluoro-3-methyl-2-(1-methyl-1H-indol-4-yl)quinolin-4-amine

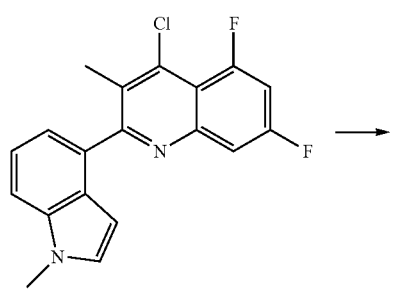

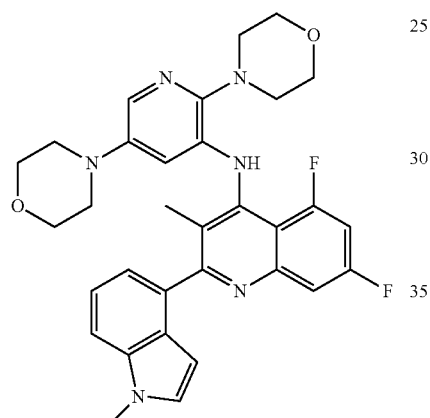

The Buchwald prepared according to Procedure H using dicyclohexyl(2',4',6'-triisopropylbiphenyl-2-yl)phosphine (0.020 g, 0.042 mmol), 2,5-dimorpholinopyridin-3-amine (0.083 g, 0.32 mmol), 4-chloro-5,7-difluoro-3-methyl-2-(1-methyl-1H-indol-4-yl)quinoline (0.090 g, 0.26 mmol), Pd₂dba₃ (9.62 mg, 10.50 mmol) and sodium tert-butoxide (0.068 g, 0.71 mmol) in toluene (2.6 mL) at 120° C. for 3.5 h. The crude product was purified by column chromatography on basic alumina (0 to 50% hexanes/EtOAc) to give the desired product N-(2,5-dimorpholinopyridin-3-yl)-5,7-difluoro-3-methyl-2-(1-methyl-1H-indol-4-yl)quinolin-4-amine. ¹H NMR (400 MHz, CDCl₃) δ ppm 7.79 (3H, d, J=11.5 Hz), 7.65 (1H, m), 7.63 (1H, d, J=2.7 Hz), 7.45 (1H, d, J=8.2 Hz), 7.38 (1H, app t, J=8.2 Hz), 7.22 (1H, d, J=0.6 Hz), 7.09 (1H, d, J=3.1 Hz), 7.02 (3H, ddd, J=13.5, 8.6, 2.5 Hz), 6.41 (1H, d, J=2.3 Hz), 6.25 (1H, d, J=3.1 Hz), 3.93 (4H, br. s), 3.87 (3H, s), 3.84 (4H, m), 3.25 (4H, br. s), –3.07 (4H, br. s.), 2.03 (3H, s). Mass Spectrum (ESI) m/e=571.3 (M+1).

Example 126

Preparation of N-(2,5-dimorpholinopyridin-3-yl)-5,7-difluoro-3-methyl-2-(1-methyl-1H-indazol-4-yl)quinolin-4-amine 4-Chloro-5,7-difluoro-3-methyl-2-(1-methyl-1H-indazol-4-yl)quinoline

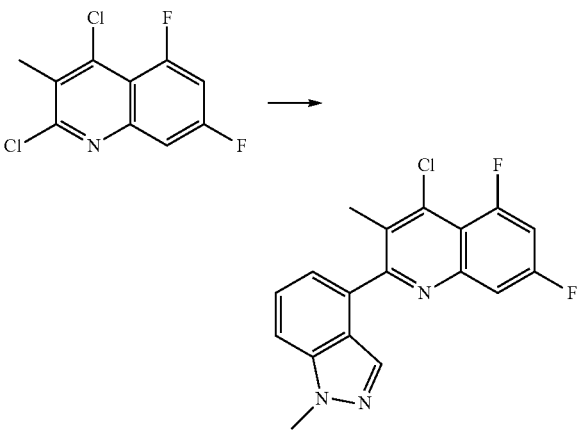

The Suzuki coupled product was prepared according to Procedure F using 2,4-dichloro-5,7-difluoro-3-methylquinoline (0.50 g, 2.02 mmol), 1-methyl-1H-indazol-4-ylboronic acid (0.53 g, 3.02 mmol), palladium tetrakistriphenylphosphine (0.23 g, 0.20 mmol), potassium carbonate (0.56 g, 4.03 mmol) in toluene (4 mL) at 100° C. for 17 h to give 4-chloro-5,7-difluoro-3-methyl-2-(1-methyl-1H-indazol-4-yl)quinoline as a yellow solid. Mass Spectrum (ESI) m/e=344.0 (M+1).

N-(2,5-Dimorpholinopyridin-3-yl)-5,7-difluoro-3-methyl-2-(1-methyl-1H-indazol-4-yl)quinolin-4-amine

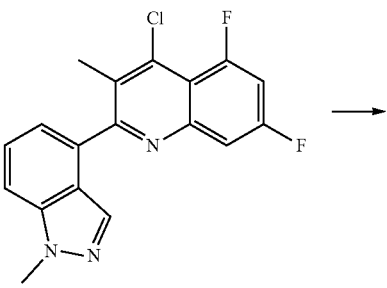

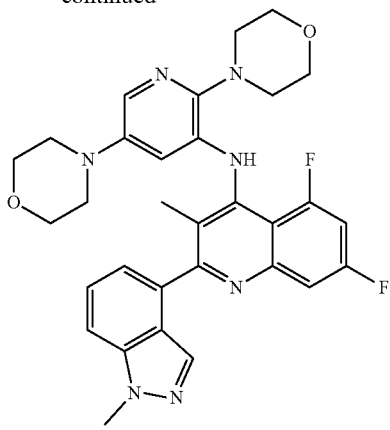

The Buchwald coupled product was prepared according to Procedure H using dicyclohexyl(2',4',6'-triisopropylbiphenyl-2-yl)phosphine (0.020 g, 0.042 mmol), 2,5-dimorpholinopyridin-3-amine (0.083 g, 0.32 mmol), 4-chloro-5,7-difluoro-3-methyl-2-(1-methyl-1H-indazol-4-yl)quinoline (0.090 g, 0.26 mmol), Pd$_2$dba$_3$ (9.6 mg, 10.50 μmol) and sodium tert-butoxide (0.063 g, 0.66 mmol) in toluene (2.6 mL) at 120° C. for 3.3 h. The crude product was purified by column chromatography on basic alumina (0 to 50% hexanes/EtOAc) to give the desired product N-(2,5-dimorpholinopyridin-3-yl)-5,7-difluoro-3-methyl-2-(1-methyl-1H-indazol-4-yl)quinolin-4-amine. $^1$H NMR (400 MHz, CDCl$_3$) δ ppm 7.84 (1H, s), 7.80 (1H, br m), 7.65 (1H, d, J=2.5 Hz), 7.63 (1H, br. s.), 7.53 (4H, s), 7.54 (2H, m), 7.25 (1H, m), 7.05 (1H, ddd, J=13.4, 8.5, 2.7 Hz), 6.41 (1H, br. s.), 4.16 (3H, s), 3.92 (4H, app t, J=4.8 Hz), 3.85 (4H, app dd, J=5.7, 3.9 Hz), 3.25 (4H, br s.), 3.08 (11H, app dd, J=4.3, 2.3 Hz), 2.06 (3H, s). Mass Spectrum (ESI) m/e=572.2 (M+1).

Example 127

Preparation of N-(2,5-dimorpholinopyridin-3-yl)-7-fluoro-3-isopropyl-2-(4-methylpyridin-2-yl)quinolin-4-amine 4-Chloro-5,7-difluoro-3-methyl-2-(1-methyl-1H-indazol-4-yl)quinoline

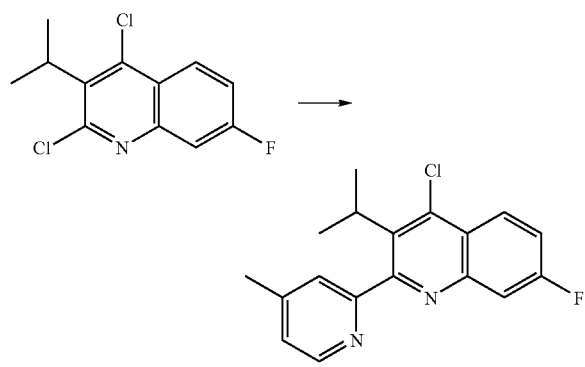

The Stille coupled product was prepared according to Procedure E using 2,4-dichloro-7-fluoro-3-isopropylquinoline (0.3 g, 1.162 mmol), 4-methyl-2-(tributylstannyl)pyridine (0.489 g, 1.28 mmol) and palladium tetrakistriphenylphosphine (0.134 g, 0.12 mmol) in toluene (2.3 mL) at 100° C. for 6.5 days to give 4-chloro-7-fluoro-3-isopropyl-2-(4-methylpyridin-2-yl)quinoline as a white solid. Mass Spectrum (ESI) m/e=315.1 (M+1).

N-(2,5-Dimorpholinopyridin-3-yl)-7-fluoro-3-isopropyl-2-(4-methylpyridin-2-yl)quinolin-4-amine

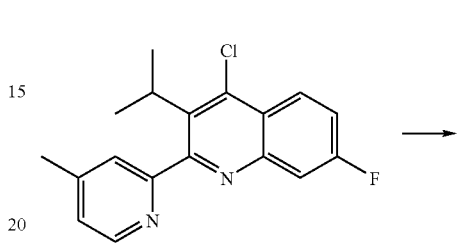

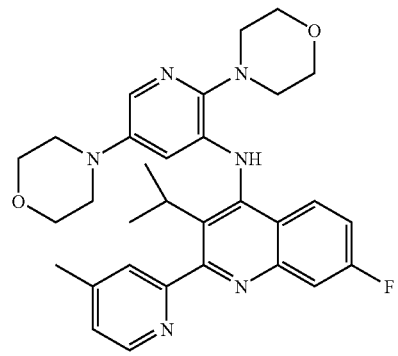

The Buchwald coupled product was prepared according to Procedure H using dicyclohexyl(2',4',6'-triisopropylbiphenyl-2-yl)phosphine (0.025 g, 0.053 mmol), 2,5-dimorpholinopyridin-3-amine (0.106 g, 0.40 mmol), 4-chloro-7-fluoro-3-isopropyl-2-(4-methylpyridin-2-yl)quinoline (0.105 g, 0.33 mmol), Pd$_2$dba$_3$ (0.012 g, 0.013 mmol) and sodium tert-butoxide (0.080 g, 0.83 mmol) in toluene (3.3 mL) at 120° C. for 4.6 h. The crude product was purified by column chromatography on basic alumina (0 to 50% hexanes/EtOAc) to give the desired product N-(2,5-dimorpholinopyridin-3-yl)-7-fluoro-3-isopropyl-2-(4-methylpyridin-2-yl)-quinolin-4-amine. $^1$H NMR (400 MHz, CDCl$_3$) δ ppm 8.58 (1H, dd, J=5.1, 0.6 Hz), 7.96 (1H, br s), 7.55-7.62 (2H, m), 7.52 (1H, m), 7.22 (1H, m), 7.13 (1H, br s), 7.07 (2H, dd, J=4.6, 1.1 Hz), 6.19 (1H, s), 3.96-3.91 (4H, m), 3.71 (4H, m), 3.50 (2H, br. s.), 3.40 (1H, m), 3.00 (1H, br s), 2.86 (4H, t, J=4.8 Hz), 2.48 (3H, s), 1.52 (3H, d, J=7.4 Hz), 1.13 (3H, d, J=7.4 Hz). Mass Spectrum (ESI) m/e=543.2 (M+1).

Example 128

Preparation of N-(2,5-dimorpholinopyridin-3-yl)-7-fluoro-3-methyl-2-(4-methylpyridin-2-yl)quinolin-4-amine 4-Chloro-7-fluoro-3-methyl-2-(4-methylpyridin-2-yl)quinoline

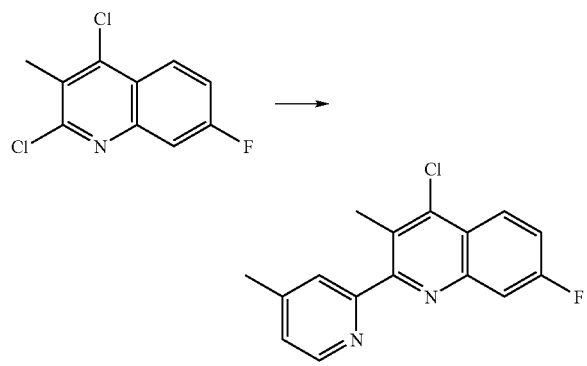

The Stille coupled product was prepared according to Procedure E using 2,4-dichloro-7-fluoro-3-methylquinoline (0.109 g, 0.47 mmol), 4-methyl-2-(tributylstannyl)pyridine (0.199 g, 0.52 mmol), palladium tetrakistriphenylphosphine (0.055 g, 0.047 mmol) in toluene (2 mL) to give 4-chloro-7-fluoro-3-methyl-2-(4-methylpyridin-2-yl)quinoline as a white solid. Mass Spectrum (ESI) m/e=287.0 (M+1).

N-(2,5-Dimorpholinopyridin-3-yl)-7-fluoro-3-methyl-2-(4-methylpyridin-2-yl)quinolin-4-amine

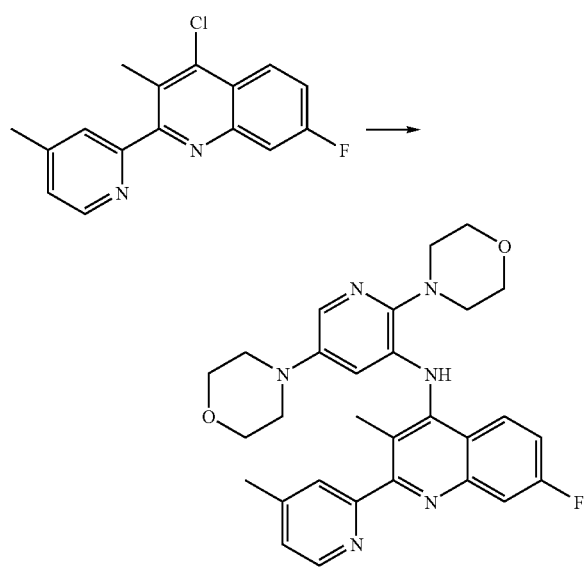

The Buchwald coupled product was prepared according to Procedure H using dicyclohexyl(2',4',6'-triisopropylbiphenyl-2-yl)phosphine (0.020 g, 0.042 mmol), 2,5-dimorpholinopyridin-3-amine (0.083 g, 0.31 mmol), 4-chloro-7-fluoro-3-methyl-2-(4-methylpyridin-2-yl)quinoline (0.075 g, 0.26 mmol), Pd$_2$dba$_3$ (9.58 mg, 10.46 µmol) and sodium tert-butoxide (0.063 g, 0.65 mmol) in toluene (2.6 mL) at 120° C. for 4.6 h. The crude product was purified by column chromatography on basic alumina (0 to 50% hexanes/EtOAc) to give the desired product N-(2,5-dimorpholinopyridin-3-yl)-7-fluoro-3-methyl-2-(4-methylpyridin-2-yl)-quinolin-4-amine. 1H NMR (400 MHz, CDCl$_3$) δ ppm 8.58 (2H, d, J=5.1 Hz), 7.81 (2H, m), 7.69 (1H, s), 7.59 (1H, m), 7.32-7.25 (1H, m), 7.22 (1H, d, J=4.9 Hz), 6.74 (1H, s), 6.21 (1H, m), 3.92 (4H, t, J=4.7 Hz), 3.74 (4H, app t, J=5.0, 4.7 Hz), 3.23 (4H, br. s.), 2.92 (6H, app t, J=4.7 Hz), 2.49 (3H, s), 2.36 (3H, s). Mass Spectrum (ESI) m/e=515.2 (M+1).

Example 129

Preparation of N-(2,5-dimorpholinopyridin-3-yl)-5,7-difluoro-3-methyl-2-(pyrazin-2-yl)quinolin-4-amine 4-Chloro-5,7-difluoro-3-methyl-2-(pyrazin-2-yl)quinoline

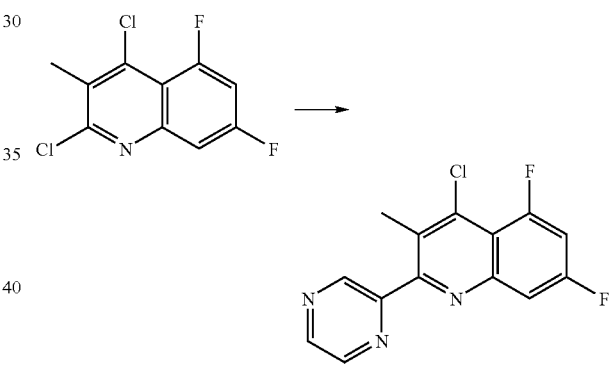

The Stille coupled product was prepared according to Procedure E using 2,4-dichloro-5,7-difluoro-3-methylquinoline (0.5 g, 2.02 mmol), 2-(tributylstannyl)-pyrazine (0.818 g, 2.22 mmol), palladium tetrakistriphenylphosphine (0.233 g, 0.20 mmol) in toluene (4 mL) to give 4-chloro-5,7-difluoro-3-methyl-2-(pyrazin-2-yl)quinoline as a white solid. Mass Spectrum (ESI) m/e=292.0 (M+1).

N-(2,5-dimorpholinopyridin-3-yl)-5,7-difluoro-3-methyl-2-(pyrazin-2-yl)-quinolin-4-amine

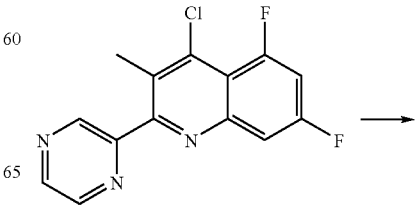

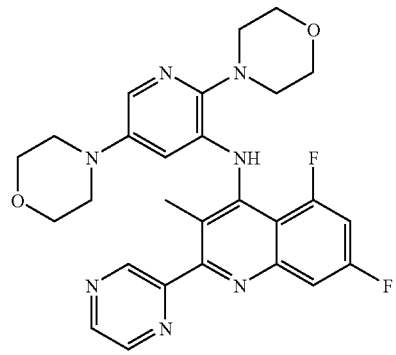

The Buchwald coupled product was prepared according to Procedure H using dicyclohexyl(2',4',6'-triisopropylbiphenyl-2-yl)phosphine (0.024 g, 0.049 mmol), 2,5-dimorpholinopyridin-3-amine (0.098 g, 0.37 mmol), 4-chloro-5,7-difluoro-3-methyl-2-(pyrazin-2-yl)quinoline (0.090 g, 0.31 mmol), Pd$_2$dba$_3$ (0.011 g, 0.012 mmol) and sodium tert-butoxide (0.074 g, 0.77 mmol) in toluene (3.1 mL) at 120° C. for 5 h. The crude product was purified by column chromatography on basic alumina (0 to 50% hexanes/EtOAc) to give the desired product N-(2,5-dimorpholinopyridin-3-yl)-5,7-difluoro-3-methyl-2-(pyrazin-2-yl)quinolin-4-amine. $^1$H NMR (400 MHz, CDCl$_3$) δ ppm 9.25 (1H, d, J=1.6 Hz), 8.67 (2H, m), 7.81 (1H, d, J=11.7 Hz), 7.65 (1H, d, J=2.7 Hz), 7.63 (1H, m), 7.02-7.10 (1H, ddd, J=13.5, 8.6, 2.5 Hz), 6.42 (1H, d, J=2.3 Hz), 3.92 (4H, br. s.), 3.81 (4H, app t, J=4.3 Hz), 3.25 (4H, br. s), 3.07 (4H, app t, J=4.3 Hz), 2.25 (3H, s). Mass Spectrum (ESI) m/e=520.2 (M+1).

Example 130

Preparation of N-(2,5-dimorpholinopyridin-3-yl)-5,7-difluoro-3-methyl-2-(pyridin-3-yl)quinolin-4-amine

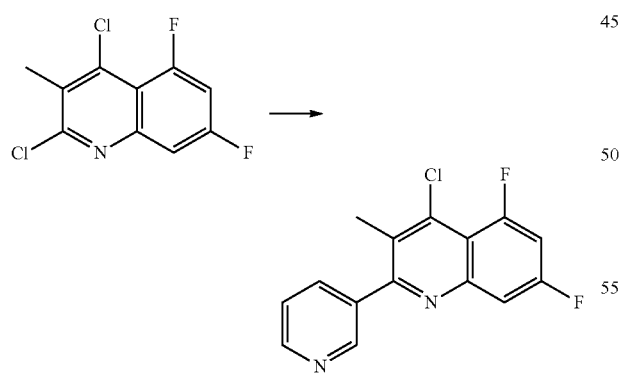

The Stille coupled product was prepared according to Procedure E using 2,4-dichloro-5,7-difluoro-3-methylquinoline (0.5 g, 2.02 mmol), 3-(tributylstannyl)-pyridine (0.82 g, 2.22 mmol), palladium tetrakistriphenylphosphine (0.23 g, 0.20 mmol) in toluene (4 mL) to give 4-chloro-5,7-difluoro-3-methyl-2-(pyrazin-2-yl)-quinoline as a white solid. Mass Spectrum (ESI) m/e=291.1 (M+1).

N-(2,5-Dimorpholinopyridin-3-yl)-5,7-difluoro-3-methyl-2-(pyridin-3-yl)-quinolin-4-amine

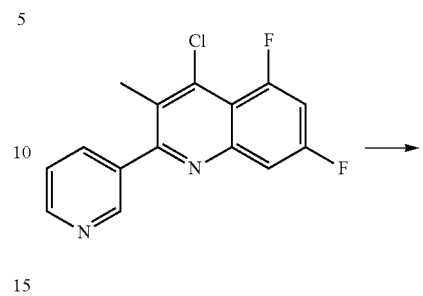

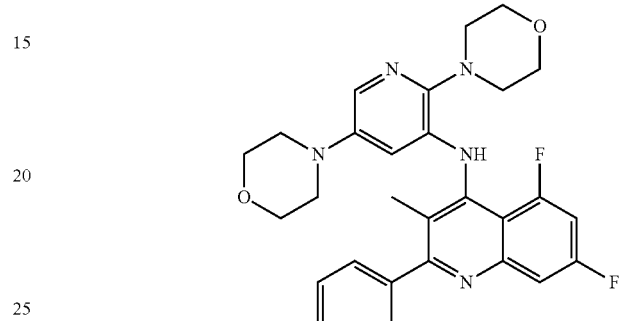

The Buchwald coupled product was prepared according to Procedure H using dicyclohexyl(2',4',6'-triisopropylbiphenyl-2-yl)phosphine (0.024 g, 0.05 mmol), 2,5-dimorpholinopyridin-3-amine (0.098 g, 0.37 mmol), 4-chloro-5,7-difluoro-3-methyl-2-(pyridin-3-yl)quinoline (0.090 g, 0.31 mmol), Pd$_2$dba$_3$ (0.011 g, 0.012 mmol) and sodium tert-butoxide (0.074 g, 0.77 mmol) in toluene (3.1 mL) at 120° C. for 5 h. The crude product was purified by column chromatography on basic alumina (0 to 50% hexanes/EtOAc) to give the desired product N-(2,5-dimorpholinopyridin-3-yl)-5,7-difluoro-3-methyl-2-(pyridin-3-yl)quinolin-4-amine. $^1$H NMR (400 MHz, CDCl$_3$) δ ppm 8.86 (1H, d, J=2.3 Hz), 8.73 (1H, dd, J=4.9, 1.8 Hz), 7.99 (1H, dt, J=7.8, 2.0 Hz), 7.76 (1H, d, J=11.2 Hz), 7.67 (1H, d, J=2.7 Hz), 7.62 (1H, br d, J=9.0 Hz), 7.50 (1H, dd, J=7.8, 4.9 Hz), 7.04 (1H, ddd, J=13.3, 8.4, 2.4 Hz), 6.37 (1H, d, J=2.2 Hz), 3.91 (4H, m), 3.82 (4H, app t, J=4.1 Hz), 3.23 (4H, br. s.), 3.05 (4H, app t, J=4.3 Hz), 2.18 (3H, s). Mass Spectrum (ESI) m/e=519.2 (M+1).

Example 131

Preparation of 2-(2,4-bis(trifluoromethyl)phenyl)-N-(2,5-dimorpholinopyridin-3-yl)-5,7-difluoro-3-methylquinolin-4-amine

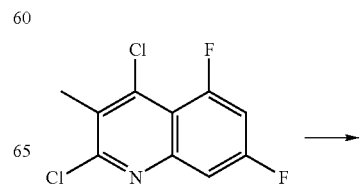

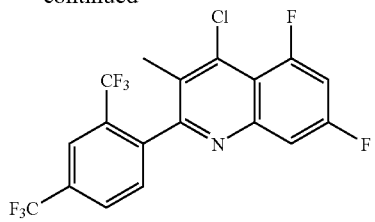

The Suzuki coupled product was prepared according to Procedure F using 2,4-dichloro-5,7-difluoro-3-methylquinoline (0.50 g, 2.02 mmol), 2,4-bis(trifluoromethyl)phenylboronic acid (0.572 g, 2.22 mmol), palladium tetrakistriphenylphosphine (0.23 g, 0.20 mmol), potassium carbonate (0.56 g, 4.03 mmol) in toluene (4 mL) at 100° C. for 22 h to give 2-(2,4-bis(trifluoromethyl)phenyl)-4-chloro-5,7-difluoro-3-methylquinoline as a crystalline solid. Mass Spectrum (ESI) m/e=426.0 (M+1).

2-(2,4-bis(Trifluoromethyl)phenyl)-N-(2,5-dimorpholinopyridin-3-yl)-5,7-difluoro-3-methylquinolin-4-amine

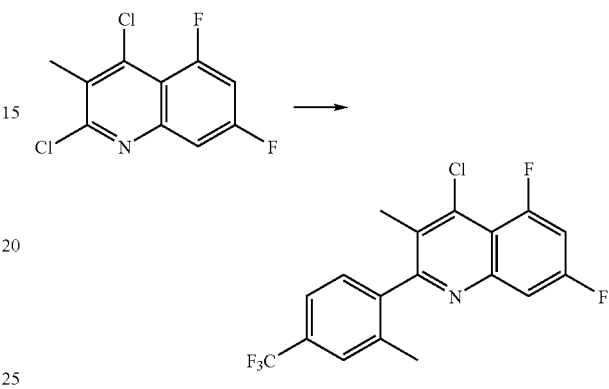

The Buchwald coupled product was prepared according to Procedure H using dicyclohexyl(2',4',6'-triisopropylbiphenyl-2-yl)phosphine (0.016 g, 0.034 mmol), 2,5-dimorpholinopyridin-3-amine (0.067 g, 0.25 mmol), 2-(2,4-bis(trifluoromethyl)phenyl)-4-chloro-5,7-difluoro-3-methylquinoline (0.090 g, 0.21 mmol), Pd$_2$dba$_3$ (7.74 mg, 8.46 μmol) and sodium tert-butoxide (0.051 g, 0.53 mmol) in toluene (2.1 mL) at 120° C. for 75 h. The crude product was purified by column chromatography on basic alumina (0 to 50% hexanes/EtOAc) to give the desired product 2-(2,4-bis(trifluoromethyl)phenyl)-N-(2,5-dimorpholinopyridin-3-yl)-5,7-difluoro-3-methylquinolin-4-amine. $^1$H NMR (400 MHz, CDCl$_3$) δ ppm 8.10 (1H, s), 7.98 (1H, d, J=8.0 Hz), 7.81 (1H, br. s), 7.62 (1H, J=2.4 Hz), 7.59-7.54 (2H, m), 7.10 (1H, ddd, J=13.3, 8.4, 2.5 Hz), 6.24 (1H, br. s.), 3.93 (4H, m), 3.79 (4H, app t, J=4.7 Hz), 3.40 (4H, br. s.), 3.01 (4H, app t, J=4.9 Hz), 1.92 (3H, s). Mass Spectrum (ESI) m/e=654.3 (M+1).

Example 132

Preparation of N-(2,5-dimorpholinopyridin-3-yl)-5,7-difluoro-3-methyl-2-(2-methyl-4-(trifluoromethyl)phenyl)quinolin-4-amine 4-Chloro-5,7-difluoro-3-methyl-2-(2-methyl-4-(trifluoromethyl)phenyl)-quinoline

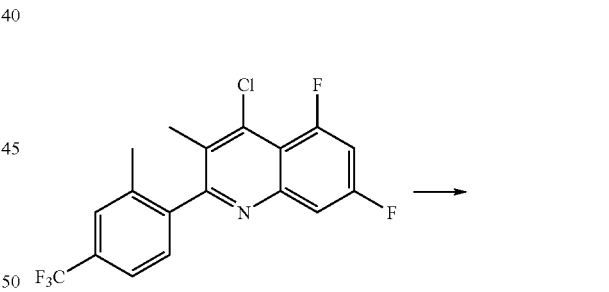

The Suzuki coupled product was prepared according to Procedure F using 2,4-dichloro-5,7-difluoro-3-methylquinoline (0.50 g, 2.02 mmol), 2-methyl-4-(trifluoromethyl)phenylboronic acid (0.411 g, 2.02 mmol), palladium tetrakistriphenylphosphine (0.23 g, 0.20 mmol), potassium carbonate (0.56 g, 4.03 mmol) in toluene (4 mL) at 100° C. for 3 h to give 4-chloro-5,7-difluoro-3-methyl-2-(2-methyl-4-(trifluoromethyl)phenyl)quinoline as a yellow oil. Mass Spectrum (ESI) m/e=372.1 (M+1).

N-(2,5-Dimorpholinopyridin-3-yl)-5,7-difluoro-3-methyl-2-(2-methyl-4-(trifluoromethyl)phenyl)quinolin-4-amine

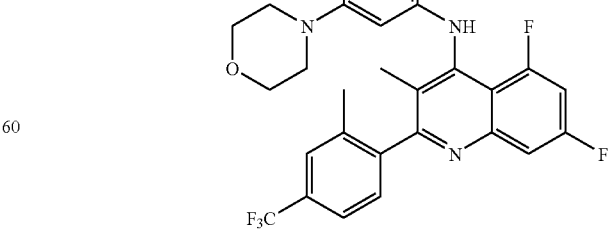

The Buchwald coupled product was prepared according to Procedure H using dicyclohexyl(2',4',6'-triisopropylbiphenyl-2-yl)phosphine (0.018 g, 0.039 mmol), 2,5-dimorpholinopyridin-3-amine (0.077 g, 0.29 mmol), 4-chloro-5,7-difluoro-3-methyl-2-(2-methyl-4-(trifluoromethyl)phenyl)quinoline (0.090 g, 0.24 mmol), Pd$_2$dba$_3$ (7.74 mg, 8.46 μmol) and sodium tert-butoxide (0.058 g, 0.61 mmol) in toluene (2.4 mL) at 120° C. for 4 h. The crude product was purified by column chromatography on basic alumina (0 to 50% hexanes/EtOAc) to give the desired product N-(2,5-dimorpholinopyridin-3-yl)-5,7-difluoro-3-methyl-2-(2-methyl-4-(trifluoromethyl)phenyl)quinolin-4-amine. $^1$H NMR (400 MHz, CDCl$_3$) δ ppm 7.75 (1H, br. s), 7.58-7.66 (4H, m), 7.38 (1H, m), 7.06 (1H, m), 6.26 (1H, br. s.), 3.93 (4H, br. s), 3.80 (4H, app t, J=4.1 Hz), 3.20 (4H, br. s.), 3.01 (4H, app t, J=4.4 Hz), 2.25 (3H, s), 1.94 (3H, s). Mass Spectrum (ESI) m/e=600.2 (M+1).

Example 133

Preparation of 2-(4-chloropyridin-2-yl)-N-(2,5-dimorpholinopyridin-3-yl)-5,7-difluoro-3-methylquinolin-4-amine 4-Chloro-2-(4-chloropyridin-2-yl)-5,7-difluoro-3-methylquinoline

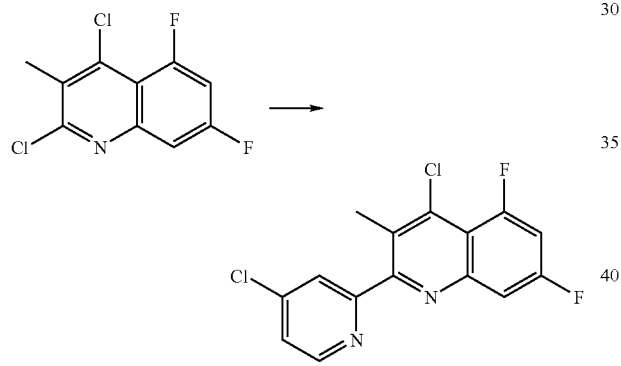

The Stille coupled product was prepared according to Procedure E using 2,4-dichloro-5,7-difluoro-3-methylquinoline (0.5 g, 2.02 mmol), 4-chloro-2-(tributylstannyl)pyridine (0.893 g, 2.22 mmol), palladium tetrakistriphenylphosphine (0.23 g, 0.20 mmol) in toluene (4 mL) to give 4-chloro-2-(4-chloropyridin-2-yl)-5,7-difluoro-3-methylquinoline as a white solid. Mass Spectrum (ESI) m/e=325.0 (M+1).

2-(4-Chloropyridin-2-yl)-N-(2,5-dimorpholinopyridin-3-yl)-5,7-difluoro-3-methylquinolin-4-amine

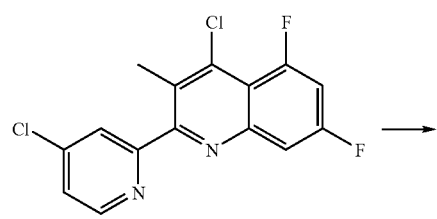

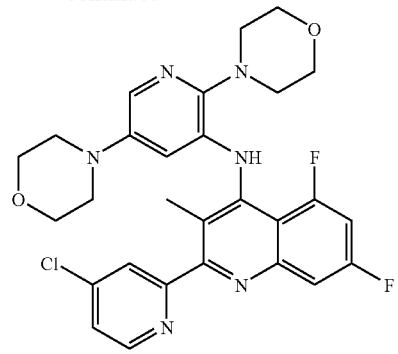

The Buchwald coupled product was prepared according to Procedure H using dicyclohexyl(2',4',6'-triisopropylbiphenyl-2-yl)phosphine (0.021 g, 0.044 mmol), 2,5-dimorpholinopyridin-3-amine (0.088 g, 0.33 mmol), 4-chloro-2-(4-chloropyridin-2-yl)-5,7-difluoro-3-methylquinoline (0.090 g, 0.28 mmol), Pd$_2$dba$_3$ (10.14 mg, 0.011 mmol) and sodium tert-butoxide (0.067 g, 0.69 mmol) in toluene (2.8 mL) at 120° C. for 28 h. The crude product was purified by column chromatography on basic alumina (0 to 50% hexanes/EtOAc) to give the desired product 2-(4-chloropyridin-2-yl)-N-(2,5-dimorpholinopyridin-3-yl)-5,7-difluoro-3-methylquinolin-4-amine. $^1$H NMR (400 MHz, CDCl$_3$) δ ppm 8.59 (1H, d, J=5.3 Hz), 7.98 (1H, d, J=0.6 Hz), 7.78 (1H, br. d, J=11.9 Hz), 7.64 (1H, d, J=2.5 Hz), 7.62 (1H, m), 7.40 (1H, dd, J=5.4, 2.1 Hz), 7.03 (2H, ddd, J=13.3, 8.61, 2.4 Hz), 6.44 (1H, br s), 3.93 (4H, br. s.), 3.82 (4H, app t, J=4.8 Hz), 3.25 (4H, br. s), 3.08 (4H, app t., J=4.8 Hz), 2.22 (3H, s). Mass Spectrum (ESI) m/e=553.2 (M+1).

Example 134

Preparation of 2-(2,4-dimethylphenyl)-N-(2,5-dimorpholinopyridin-3-yl)-5,7-difluoro-3-methylquinolin-4-amine

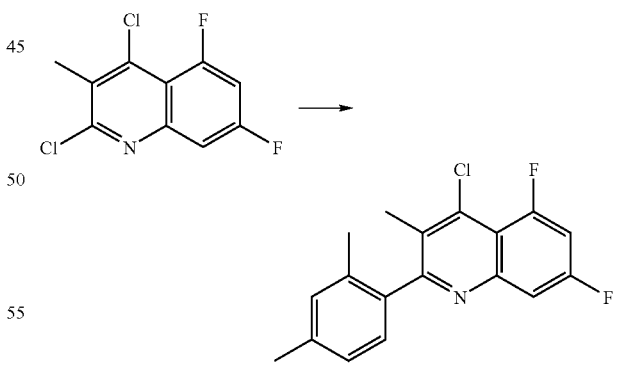

The Suzuki coupled product was prepared according to Procedure F using 2,4-dichloro-5,7-difluoro-3-methylquinoline (0.50 g, 2.02 mmol), 2,4-dimethylphenylboronic acid (0.333 g, 2.22 mmol), palladium tetrakistriphenylphosphine (0.23 g, 0.20 mmol), potassium carbonate (0.56 g, 4.03 mmol) in toluene (4 mL) at 100° C. for 4 days to give 4-chloro-2-(2,4-dimethylphenyl)-5,7-difluoro-3-methylquinoline as a yellow oil. Mass Spectrum (ESI) m/e=325.0 (M+1).

2-(2,4-Dimethylphenyl)-N-(2,5-dimorpholinopyridin-3-yl)-5,7-difluoro-3-methylquinolin-4-amine

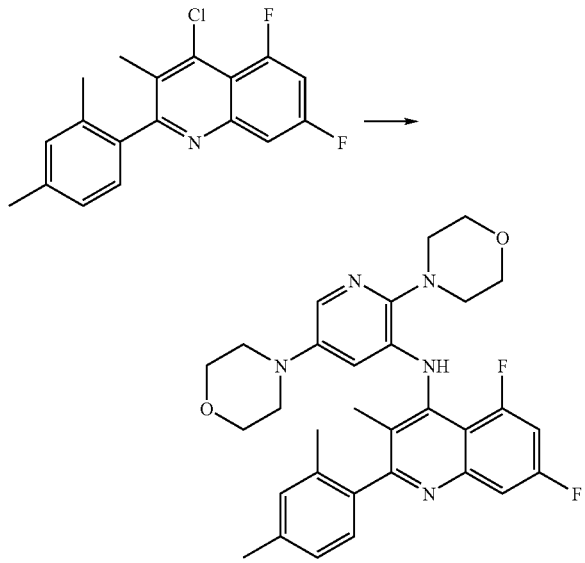

The Buchwald coupled product was prepared according to Procedure H using dicyclohexyl(2',4',6'-triisopropylbiphenyl-2-yl)phosphine (0.022 g, 0.045 mmol), 2,5-dimorpholinopyridin-3-amine (0.090 g, 0.34 mmol), 4-chloro-2-(2,4-dimethylphenyl)-5,7-difluoro-3-methylquinoline (0.090 g, 0.28 mmol), Pd$_2$dba$_3$ (10.4 mg, 0.011 mmol) and sodium tert-butoxide (0.068 g, 0.71 mmol) in toluene (2.8 mL) at 120° C. for 3.3 h. The crude product was purified by column chromatography on basic alumina (0 to 50% hexanes/EtOAc) to give the desired product 2-(2,4-dimethylphenyl)-N-(2,5-dimorpholinopyridin-3-yl)-5,7-difluoro-3-methylquinolin-4-amine. $^1$H NMR (400 MHz, DMSO-d$_6$) δ ppm 9.46 (1H, s), 8.70 (1H, d, J=4.8 Hz), 8.02 (1H, td, J=7.8, 1.8 Hz), 7.98 (1H, d, J=5.7 Hz), 7.89 (1H, dt, J=7.8, 1.2 Hz), 7.67 (1H, br. dd, J=2.2, 1.8 Hz), 7.65 (2H, dt, J=8.4, 1.6 Hz), 7.52 (1H, ddd, J=7.6, 4.9, 1.4 Hz), 7.47 (1H, ddd, J=12.1, 9.2, 2.5 Hz), 6.10 (1H, br. s), 3.48 (4H, br s), 3.40-3.30 (8H, m), 2.27 (3H, s). Mass Spectrum (ESI) m/e=546.3 (M+1).

Example 135

Preparation of 2-(5-chloropyridin-3-yl)-N-(2,5-dimorpholinopyridin-3-yl)-5,7-difluoro-3-methylquinolin-4-amine 4-Chloro-2-(5-chloropyridin-3-yl)-5,7-difluoro-3-methylquinoline

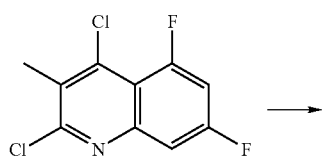

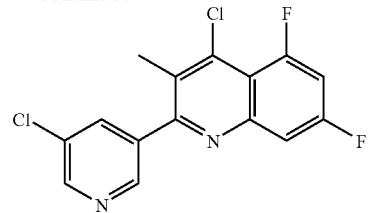

The Suzuki coupled product was prepared according to Procedure F using 2,4-dichloro-5,7-difluoro-3-methylquinoline (0.50 g, 2.02 mmol), 3-chloropyridine-5-boronic acid (0.381 g, 2.42 mmol), palladium tetrakistriphenylphosphine (0.23 g, 0.20 mmol), potassium carbonate (0.56 g, 4.03 mmol) in toluene (4 mL) at 100° C. for 19.5 h to give 4-chloro-2-(5-chloropyridin-3-yl)-5,7-difluoro-3-methylquinoline as an off white solid. Mass Spectrum (ESI) m/e=325.0 (M+1).

2-(5-Chloropyridin-3-yl)-N-(2,5-dimorpholinopyridin-3-yl)-5,7-difluoro-3-methylquinolin-4-amine

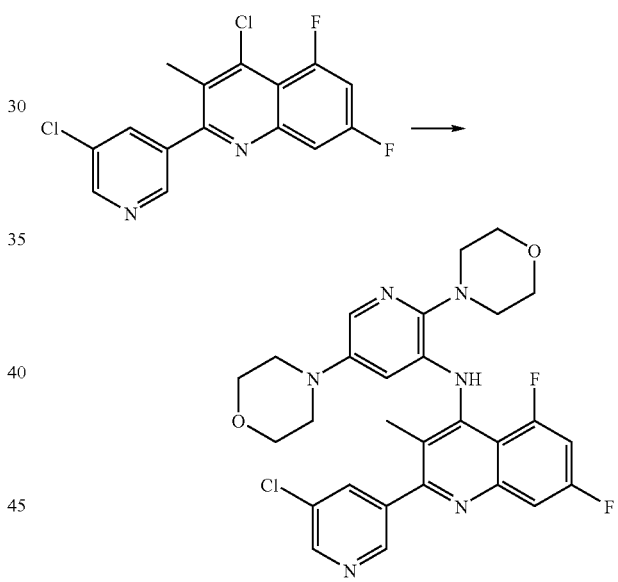

The Buchwald coupled product was prepared according to Procedure H using dicyclohexyl(2',4',6'-triisopropylbiphenyl-2-yl)phosphine (0.023 g, 0.049 mmol), 2,5-dimorpholinopyridin-3-amine (0.098 g, 0.37 mmol), 4-chloro-2-(5-chloropyridin-3-yl)-5,7-difluoro-3-methylquinoline (0.1 g, 0.31 mmol), Pd$_2$dba$_3$ (0.011 g, 0.012 mmol) and sodium tert-butoxide (0.074 g, 0.77 mmol) in toluene (3.1 mL) at 120° C. for 3.2 h. The crude product was purified by column chromatography on basic alumina (0 to 50% hexanes/EtOAc) to give the desired product 2-(5-chloropyridin-3-yl)-N-(2,5-dimorpholinopyridin-3-yl)-5,7-difluoro-3-methylquinolin-4-amine. $^1$H NMR (400 MHz, CDCl$_3$) δ ppm 8.71 (2H, dd, J=11.5, 2.2 Hz), 8.00 (1H, t, J=2.2 Hz), 7.79 (1H, d, J=11.0 Hz), 7.68 (1H, d, J=2.7 Hz), 7.61 (1H, d, J=9.4 Hz), 7.05 (1H, ddd, J=13.1, 8.4, 2.4 Hz.), 6.36 (1H, br. s.), 3.91 (4H, br. s.), 3.83 (4H, app t, J=4.7 Hz), 3.22 (4H, br. s.), 3.05 (4H, app t, J=4.9 Hz), 2.18 (3H, s). Mass Spectrum (ESI) m/e=553.2 (M+1).

Example 136

Preparation of N-(2,5-dimorpholinopyridin-3-yl)-5,7-difluoro-2-(6-methoxypyridin-3-yl)-3-methylquinolin-4-amine 4-Chloro-5,7-difluoro-2-(6-methoxypyridin-3-yl)-3-methylquinoline

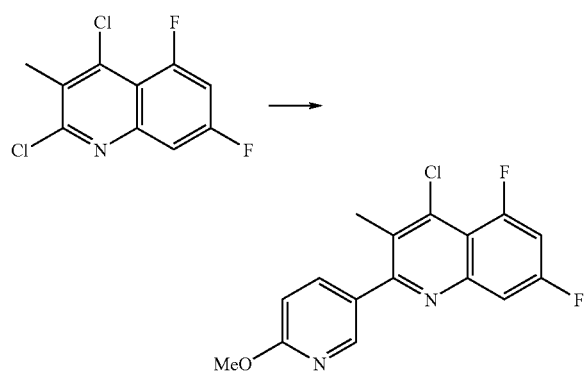

The Suzuki coupled product was prepared according to Procedure F using 2,4-dichloro-5,7-difluoro-3-methylquinoline (0.50 g, 2.02 mmol), 6-methoxypyridin-3-ylboronic acid (0.308 g, 2.0 mmol), palladium tetrakistriphenylphosphine (0.23 g, 0.20 mmol), potassium carbonate (0.56 g, 4.03 mmol) in toluene (4 mL) at 100° C. for 19.5 h to give 4-chloro-5,7-difluoro-2-(6-methoxypyridin-3-yl)-3-methylquinoline as a white solid. Mass Spectrum (ESI) m/e=321.0 (M+1).

N-(2,5-Dimorpholinopyridin-3-yl)-5,7-difluoro-2-(6-methoxypyridin-3-yl)-3-methylquinolin-4-amine

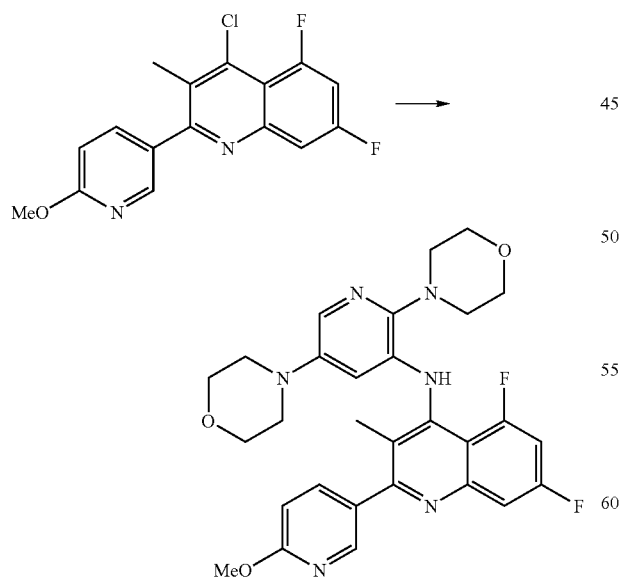

The Buchwald coupled product was prepared according to Procedure H using dicyclohexyl(2',4',6'-triisopropylbiphenyl-2-yl)phosphine (0.024 g, 0.050 mmol), 2,5-dimorpholinopyridin-3-amine (0.099 g, 0.37 mmol), 4-chloro-5,7-difluoro-2-(6-methoxypyridin-3-yl)-3-methylquinoline (0.1 g, 0.31 mmol), Pd₂dba₃ (0.011 g, 0.012 mmol) and sodium tert-butoxide (0.075 g, 0.78 mmol) in toluene (3.1 mL) at 120° C. for 3.2 h. The crude product was purified by column chromatography on basic alumina (0 to 50% hexanes/EtOAc) to give the desired product N-(2,5-dimorpholinopyridin-3-yl)-5,7-difluoro-2-(6-methoxypyridin-3-yl)-3-methylquinolin-4-amine. $^{1}$H NMR (400 MHz, CDCl$_3$) δ ppm 8.45 (1H, d, J=2.4 Hz), 7.92 (1H, dd, J=8.5, 2.4 Hz), 7.72 (1H, br d, J=11.2 Hz), 7.66 (1H, d, J=2.5 Hz), 7.60 (1H, br d, J=8.0 Hz), 7.00 (1H, ddd, J=8.5, 0.7 Hz), 6.92 (1H, d, J=13.5, 8.6, 2.7 Hz), 6.35 (3H, d, J=2.3 Hz), 4.03 (3H, s), 3.91 (4H, t, J=4.7 Hz), 3.82 (4H, app t, J=4.7 Hz), 3.25 (4H, br. s.), 3.04 (4H, app t, J=4.9 Hz), 2.21 (3H, s). Mass Spectrum (ESI) m/e=549.3 (M+1).

Example 137

Preparation of N-(2,5-dimorpholinopyridin-3-yl)-5,7-difluoro-2-(2-methoxypyridin-4-yl)-3-methylquinolin-4-amine 4-Chloro-5,7-difluoro-2-(2-methoxypyridin-4-yl)-3-methylquinoline

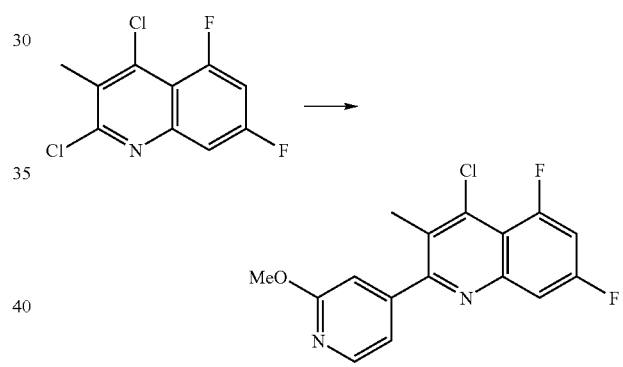

The Suzuki coupled product was prepared according to Procedure F using 2,4-dichloro-5,7-difluoro-3-methylquinoline (0.50 g, 2.02 mmol), 2-methoxypyridin-4-ylboronic acid (0.308 g, 2.0 mmol), palladium tetrakistriphenylphosphine (0.23 g, 0.20 mmol), potassium carbonate (0.56 g, 4.03 mmol) in toluene (4 mL) at 100° C. for 19.7 h to give 4-chloro-5,7-difluoro-2-(2-methoxypyridin-4-yl)-3-methylquinoline as an off white solid. Mass Spectrum (ESI) m/e=321.0 (M+1).

N-(2,5-Dimorpholinopyridin-3-yl)-5,7-difluoro-2-(2-methoxypyridin-4-yl)-3-methylquinolin-4-amine

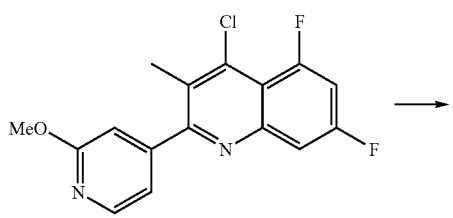

-continued

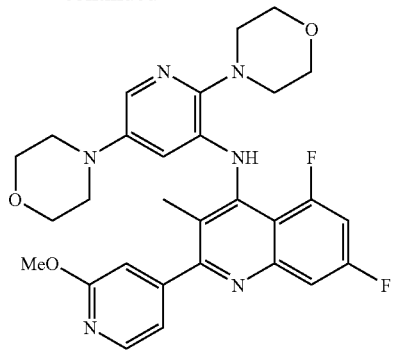

The Buchwald coupled product was prepared according to Procedure H using dicyclohexyl(2',4',6'-triisopropylbiphenyl-2-yl)phosphine (0.024 g, 0.050 mmol), 2,5-dimorpholinopyridin-3-amine (0.099 g, 0.37 mmol), 4-chloro-5,7-difluoro-2-(2-methoxypyridin-4-yl)-3-methylquinoline (0.1 g, 0.31 mmol), $Pd_2dba_3$ (0.011 g, 0.012 mmol) and sodium tert-butoxide (0.075 g, 0.78 mmol) in toluene (3.1 mL) at 120° C. for 3.2 h. The crude product was purified by column chromatography on basic alumina (0 to 50% hexanes/EtOAc) to give the desired product N-(2,5-dimorpholinopyridin-3-yl)-5,7-difluoro-2-(2-methoxypyridin-4-yl)-3-methylquinolin-4-amine. $^1$H NMR (400 MHz, $CDCl_3$) δ ppm 8.33 (1H, dd, J=5.2, 0.7 Hz), 7.72 (1H, d, J=11.0 Hz), 7.66 (1H, d, J=2.7 Hz), 7.60 (1H, m), 7.07-7.01 (2H, m), 6.91 (1H, s), 6.32 (1H, d, J=2.3 Hz), 4.02 (3H, s), 3.91 (4H, t, J=4.7 Hz), 3.83 (4H, app t, J=4.7 Hz), 3.25 (4H, br. s), 3.03 (4H, app t, J=4.9 Hz), 2.13 (3H, s). Mass Spectrum (ESI) m/e=549.3 (M+1).

Example 138

Preparation of N-(2,5-dimorpholinopyridin-3-yl)-5,7-difluoro-3-methyl-2-(4-phenylpyridin-2-yl)quinolin-4-amine 4-Chloro-5,7-difluoro-3-methyl-2-(4-phenylpyridin-2-yl)quinoline The Stille coupled product was prepared according to Procedure E using 2,4-dichloro-5,7-difluoro-3-methylquinoline (0.3 g, 1.21 mmol), 4-phenyl-2-(tributylstannyl)pyridine (0.591 g, 1.33 mmol), palladium tetrakistriphenylphosphine (0.140 g, 0.12 mmol) in toluene (2 mL) to give 4-chloro-5,7-difluoro-3-methyl-2-(4-phenylpyridin-2-yl)quinoline as a yellow solid. Mass Spectrum (ESI) m/e=367.0 (M+1).

N-(2,5-Dimorpholinopyridin-3-yl)-5,7-difluoro-3-methyl-2-(4-phenylpyridin-2-yl)quinolin-4-amine

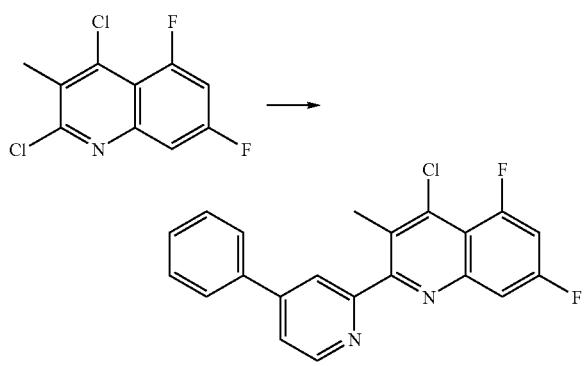

The Buchwald coupled product was prepared according to Procedure H using dicyclohexyl(2',4',6'-triisopropylbiphenyl-2-yl)phosphine (0.021 g, 0.044 mmol), 2,5-dimorpholinopyridin-3-amine (0.086 g, 0.33 mmol), 4-chloro-5,7-difluoro-3-methyl-2-(4-phenylpyridin-2-yl)quinoline (0.1 g, 0.27 mmol), $Pd_2dba_3$ (0.010 g, 0.011 mmol) and sodium tert-butoxide (0.066 g, 0.68 mmol) in toluene (2.7 mL) at 120° C. for 3.25 h. The crude product was purified by column chromatography on basic alumina (0 to 50% hexanes/EtOAc) to give the desired product N-(2,5-dimorpholinopyridin-3-yl)-5,7-difluoro-3-methyl-2-(4-phenylpyridin-2-yl)-quinolin-4-amine. $^1$H NMR (400 MHz, $CDCl_3$) δ ppm 8.75 (1H, d, J=5.1 Hz), 8.10 (1H, s), 7.76 (3H, m), 7.64-7.61 (3H, m), 7.57-7.49 (3H, m), 7.03 (1H, ddd, J=13.5, 8.4, 2.5 Hz), 6.48 (1H, br. s.), 3.93 (4H, app t, J=4.8 Hz), 3.81 (4H, app t, J=4.5 Hz), 3.25 (4H, br. s), 3.09 (11H, app t, J=4.9 Hz), 2.25 (3H, s). Mass Spectrum (ESI) m/e=595.3 (M+1).

Example 139

Preparation of N-(2,5-dimorpholinopyridin-3-yl)-5,7-difluoromethyl-2-(2-methylpyridin-4-yl)quinolin-4-amine 4-Chloro-5,7-difluoro-3-methyl-2-(2-methylpyridin-4-yl)quinoline

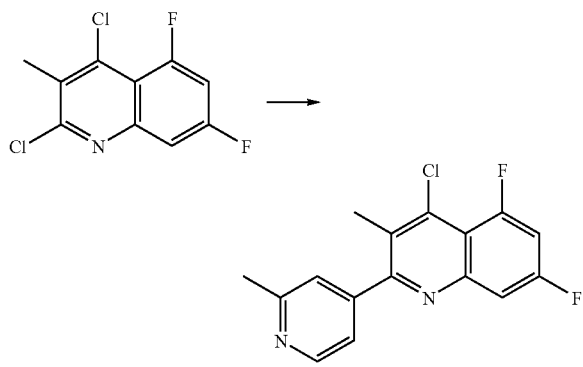

The Suzuki coupled product was prepared according to Procedure F using 2,4-dichloro-5,7-difluoro-3-methylquinoline (0.50 g, 2.02 mmol), 2-methylpyridin-4-ylboronic acid (0.28 g, 2.02 mmol), palladium tetrakistriphenylphosphine (0.23 g, 0.20 mmol), potassium carbonate (0.56 g, 4.03 mmol) in toluene (4 mL) at 100° C. for 44 h to give 4-chloro-5,7-difluoro-3-methyl-2-(2-methylpyridin-4-yl)quinoline as a white solid. Mass Spectrum (ESI) m/e=305.0 (M+1).

N-(2,5-Dimorpholinopyridin-3-yl)-5,7-difluoro-3-methyl-2-(2-methylpyridin-4-yl)quinolin-4-amine

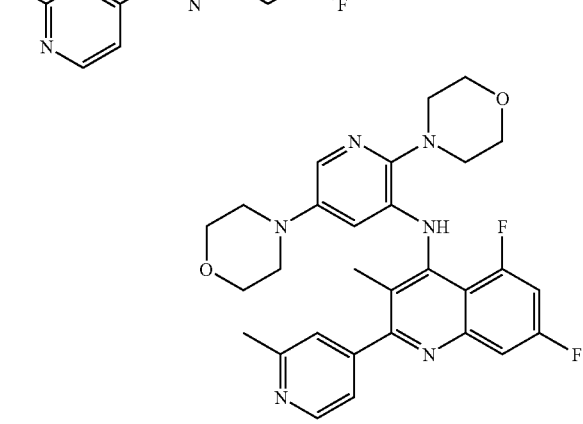

The Buchwald coupled product was prepared according to Procedure H using dicyclohexyl(2',4',6'-triisopropylbiphenyl-2-yl)phosphine (0.023 g, 0.047 mmol), 2,5-dimorpholinopyridin-3-amine (0.094 g, 0.35 mmol), 4-chloro-5,7-difluoro-3-methyl-2-(2-methylpyridin-4-yl)quinoline (0.090 g, 0.30 mmol), Pd$_2$dba$_3$ (0.011 g, 0.012 mmol) and sodium tert-butoxide (0.071 g, 0.74 mmol) in toluene (2.7 mL) at 120° C. for 2 h. The crude product was purified by column chromatography on basic alumina (0 to 50% hexanes/EtOAc) to give the desired product N-(2,5-dimorpholinopyridin-3-yl)-5,7-difluoro-3-methyl-2-(2-methylpyridin-4-yl)quinolin-4-amine. $^1$H NMR (400 MHz, CDCl$_3$) δ ppm 8.67 (1H, dd, J=4.9, 0.6 Hz), 7.71 (1H, d, J=11.0 Hz), 7.67 (1H, d, J=2.5 Hz), 7.62 (1H, ddd, J=9.4, 2.5, 1.4 Hz), 7.39 (1H, br s), 7.28 (1H, br s), 7.04 (1H, ddd, J=13.4, 8.6, 2.5 Hz), 6.33 (1H, dd, J=2.3, 0.4 Hz), 3.91 (4H, t, J=4.7 Hz), 3.83 (4H, app t, J=4.7 Hz), 3.20 (4H, br. s), 3.03 (4H, app t, J=4.9 Hz), 2.69 (3H, s), 2.13 (3H, s). Mass Spectrum (ESI) m/e=533.2 (M+1).

Example 140

Preparation of 5,7-difluoro-3-methyl-2-(4-methylpyridin-2-yl)-N-(5-morpholinopyridin-3-yl)quinolin-4-amine 5,7-Difluoro-3-methyl-2-(4-methylpyridin-2-yl)-N-(5-morpholinopyridin-3-yl)quinolin-4-amine

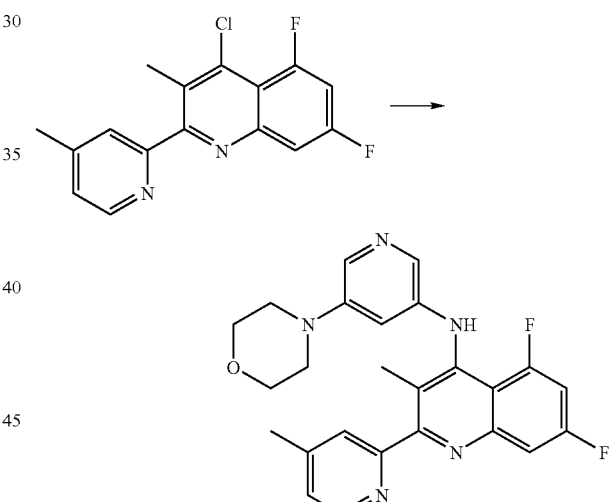

The Buchwald coupled product was prepared according to Procedure H using dicyclohexyl(2',4',6'-triisopropylbiphenyl-2-yl)phosphine (0.023 g, 0.047 mmol), 5-morpholinopyridin-3-amine (0.064 g, 0.35 mmol), 4-chloro-5,7-difluoro-3-methyl-2-(4-methylpyridin-2-yl)quinoline (0.09 g, 0.30 mmol) Pd$_2$dba$_3$ (0.011 g, 0.012 mmol) and sodium tert-butoxide (0.071 g, 0.74 mmol) in toluene (2.7 mL) at 120° C. for 10 days. The crude product was purified by column chromatography on basic alumina (0 to 50% hexanes/EtOAc) to give the desired product 5,7-difluoro-3-methyl-2-(4-methylpyridin-2-yl)-N-(5-morpholinopyridin-3-yl)-quinolin-4-amine. $^1$H NMR (400 MHz, CDCl$_3$) δ ppm 8.55 (1H, d, J=4.9 Hz), 7.95 (1H, d, J=2.2 Hz), 7.81 (1H, d, J=2.2 Hz), 7.65-7.62 (2H, m), 7.20 (1H, m), 6.98-7.07 (2H, m), 6.62 (2H, app t, J=4.5 Hz), 3.86 (4H, t, J=1.9 Hz), 3.20 (4H, t, J=1.9 Hz), 2.48 (3H, s), 2.15 (3H, s). Mass Spectrum (ESI) m/e=448.1 (M+1).

Example 141

Preparation of 5,7-difluoro-3-methyl-2-(5-methylpyridin-2-yl)-N-(5-morpholinopyridin-3-yl)quinolin-4-amine 5,7-Difluoro-3-methyl-2-(5-methylpyridin-2-yl)-N-(5-morpholinopyridin-3-yl)quinolin-4-amine

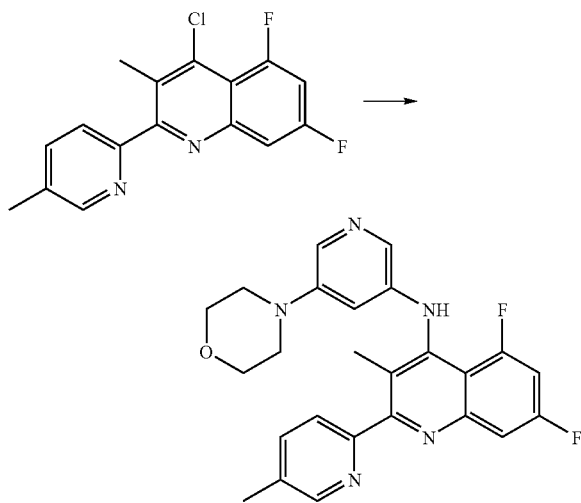

The Buchwald coupled product was prepared according to Procedure H using dicyclohexyl(2',4',6'-triisopropylbiphenyl-2-yl)phosphine (0.023 g, 0.047 mmol), 5-morpholinopyridin-3-amine (0.064 g, 0.35 mmol), 4-chloro-5,7-difluoro-3-methyl-2-(5-methylpyridin-2-yl)quinoline (0.09 g, 0.30 mmol) Pd$_2$dba$_3$ (0.011 g, 0.012 mmol) and sodium tert-butoxide (0.071 g, 0.74 mmol) in toluene (2.7 mL) at 120° C. for 10 days. The crude product was purified by column chromatography on basic alumina (0 to 50% hexanes/EtOAc) to give the desired product 5,7-difluoro-3-methyl-2-(5-methylpyridin-2-yl)-N-(5-morpholinopyridin-3-yl)quinolin-4-amine.
$^1$H NMR (400 MHz, CDCl$_3$) δ ppm 8.55 (1H, d, J=4.9 Hz), 7.95 (1H, d, J=2.5 Hz), 7.81 (1H, d, J=2.3 Hz), 7.63 (2H, m), 7.19 (1H, m), 6.98-7.07 (2H, m), 6.62 (1H, app t, J=2.4 Hz), 3.86 (4H, app t, J=4.9 Hz), 3.19 (9H, app t, J=4.9 Hz), 2.48 (3H, s), 2.15 (3H, s). Mass Spectrum (ESI) m/e=448.1 (M+1).

Example 142

Preparation of N-(2,5-dimorpholinopyridin-3-yl)-5,7-difluoro-3-methyl-2-(6-methylpyridin-3-yl)quinolin-4-amine 4-Chloro-5,7-difluoro-3-methyl-2-(6-methylpyridin-3-yl)quinoline

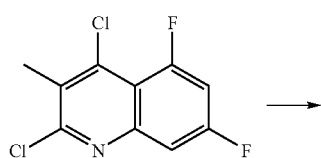

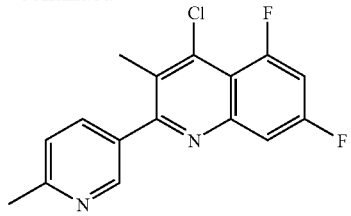

The Suzuki coupled product was prepared according to Procedure F using 2,4-dichloro-5,7-difluoro-3-methylquinoline (0.50 g, 2.02 mmol), 6-methylpyridin-3-ylboronic acid (0.276 g, 2.02 mmol), palladium tetrakistriphenylphosphine (0.23 g, 0.20 mmol), potassium carbonate (0.56 g, 4.03 mmol) in toluene (4 mL) at 100° C. for 24 h to give 4-chloro-5,7-difluoro-3-methyl-2-(6-methylpyridin-3-yl)quinoline as a white solid. Mass Spectrum (ESI) m/e=305.0 (M+1).

N-(2,5-Dimorpholinopyridin-3-yl)-5,7-difluoro-3-methyl-2-(6-methylpyridin-3-yl)quinolin-4-amine

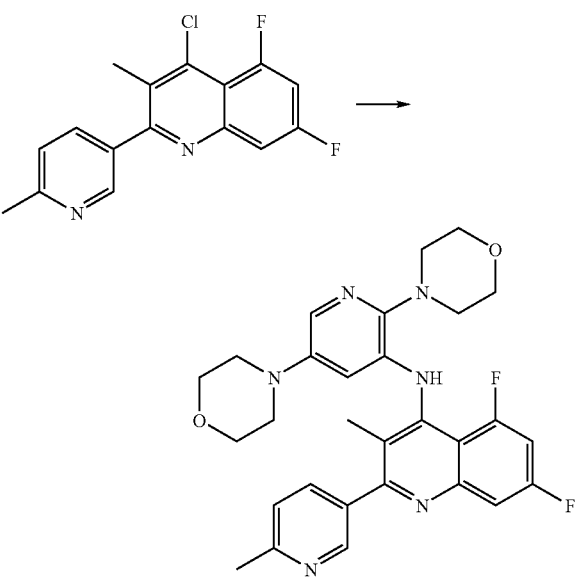

The Buchwald coupled product was prepared according to Procedure H using dicyclohexyl(2',4',6'-triisopropylbiphenyl-2-yl)phosphine (0.025 g, 0.053 mmol), 2,5-dimorpholinopyridin-3-amine (0.104 g, 0.39 mmol), 4-chloro-5,7-difluoro-3-methyl-2-(6-methylpyridin-3-yl)quinoline (0.1 g, 0.33 mmol), Pd$_2$dba$_3$ (0.012 g, 0.013 mmol) and sodium tert-butoxide (0.079 g, 0.82 mmol) in toluene (2.7 mL) at 120° C. for 7 days. The crude product was purified by column chromatography on basic alumina (0 to 50% hexanes/EtOAc) to give the desired product N-(2,5-dimorpholinopyridin-3-yl)-5,7-difluoro-3-methyl-2-(6-methylpyridin-3-yl)-quinolin-4-amine. $^1$H NMR (400 MHz, CDCl$_3$) δ ppm 8.74 (1H, d, J=2.0 Hz), 7.90 (1H, dd, J=8.0, 2.3 Hz), 7.75 (1H, d, J=11.2 Hz), 7.66 (1H, J=2.7 Hz), 7.61 (1H, br d, J=9.2 Hz), 7.36 (4H, d, J=8.0 Hz), 6.98-7.06 (1H, ddd, J=13.3, 8.4, 2.4 Hz), 6.36 (1H, d, J=2.5 Hz), 3.91 (4H, t, J=4.8 Hz), 3.81 (4H, app t, J=4.37 Hz), 3.22 (4H, br. s.), 3.03 (3H, app t, J=4.9 Hz), 2.68 (3H, s), 2.18 (3H, s). Mass Spectrum (ESI) m/e=533.2 (M+1).

Example 143

Preparation of N-(2,5-dimorpholinopyridin-3-yl)-5,7-difluoromethyl-2-(6-(trifluoromethyl)pyridin-3-yl)quinolin-4-amine

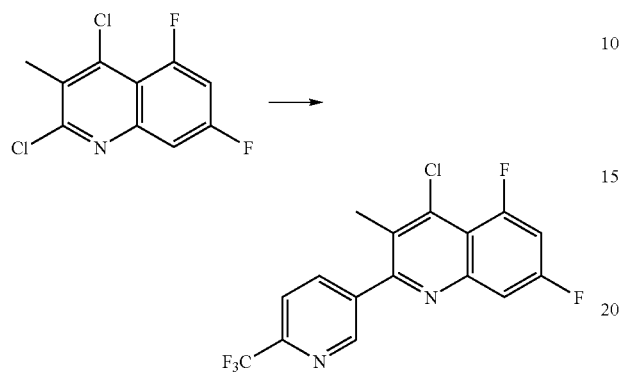

The Suzuki coupled product was prepared according to Procedure F using 2,4-dichloro-5,7-difluoro-3-methylquinoline (0.50 g, 2.02 mmol), 2-(trifluoromethyl)-pyridine-5-boronic acid (0.385 g, 2.02 mmol), palladium tetrakistriphenylphosphine (0.23 g, 0.20 mmol), potassium carbonate (0.56 g, 4.03 mmol) in toluene (4 mL) at 100° C. for 18 h to give 4-chloro-5,7-difluoro-3-methyl-2-(6-(trifluoromethyl)pyridin-3-yl)quinoline as a white solid. Mass Spectrum (ESI) m/e=359.0 (M+1).

N-(2,5-Dimorpholinopyridin-3-yl)-5,7-difluoro-3-methyl-2-(6-(trifluoromethyl)pyridin-3-yl)quinolin-4-amine

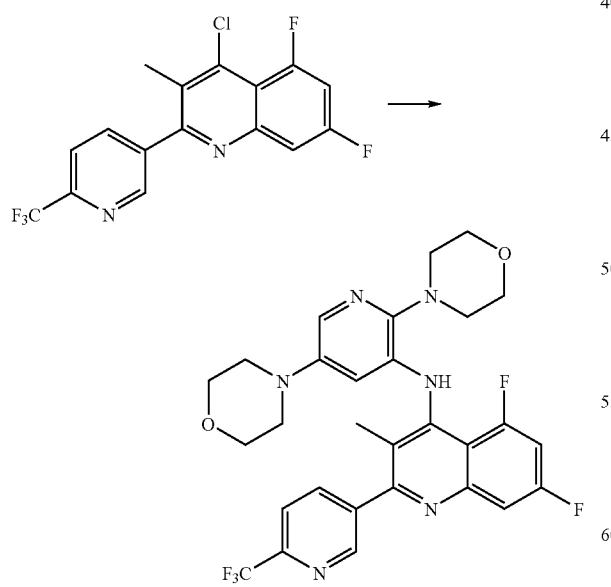

The Buchwald coupled product was prepared according to Procedure H using dicyclohexyl(2',4',6'-triisopropylbiphenyl-2-yl)phosphine (0.021 g, 0.045 mmol), 2,5-dimorpholinopyridin-3-amine (0.088 g, 0.34 mmol), 4-chloro-5,7-difluoro-3-methyl-2-(6-(trifluoromethyl)pyridin-3-yl)quinoline (0.1 g, 0.28 mmol), Pd$_2$dba$_3$ (0.010 g, 0.011 mmol) and sodium tert-butoxide (0.079 g, 0.82 mmol) in toluene (2.8 mL) at 120° C. for 43 h. The crude product was purified by column chromatography on basic alumina (0 to 50% hexanes/EtOAc) to give the desired product N-(2,5-dimorpholinopyridin-3-yl)-5,7-difluoro-3-methyl-2-(6-(trifluoromethyl)-pyridin-3-yl)quinolin-4-amine. $^1$H NMR (400 MHz, DMSO-d$_6$) δ ppm 9.04 (1H, d, J=1.8 Hz), 8.35 (1H, dd, J=7.8, 1.6 Hz), 8.11 (1H, d, J=8.0 Hz), 7.86 (1H, d, J=6.1 Hz), 7.69 (1H, m), 7.56 (1H, d, J=2.5 Hz), 7.53, (1H, ddd, J=12.9, 9.0, 2.5 Hz), 6.51 (1H, d, J=2.5 Hz), 3.67 (8H, m), 3.17 (2H, br. s), 3.02 (4H, m), 2.85 (2H, br. s), 2.06 (3H, s). Mass Spectrum (ESI) m/e=587.2 (M+1).

Example 144

Preparation of N-(2,5-dimorpholinopyridin-3-yl)-5,7-difluoro-3-methyl-2-(4-methylpyridin-3-yl)quinolin-4-amine

4-Chloro-5,7-difluoro-3-methyl-2-(4-methylpyridin-3-yl)quinoline

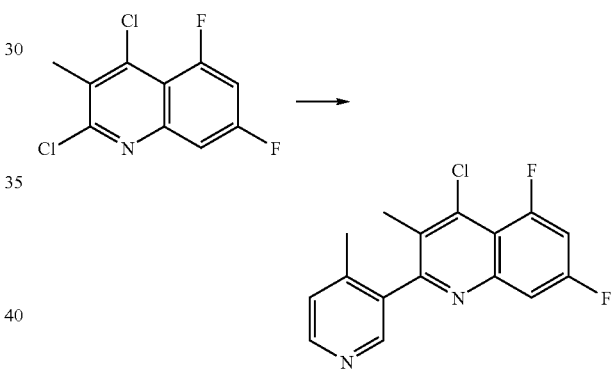

The Suzuki coupled product was prepared according to Procedure F using 2,4-dichloro-5,7-difluoro-3-methylquinoline (0.50 g, 2.02 mmol), 4-methylpyridine-3-boronic acid (0.28 g, 2.02 mmol), palladium tetrakistriphenylphosphine (0.23 g, 0.20 mmol), potassium carbonate (0.56 g, 4.03 mmol) in toluene (4 mL) at 100° C. for 45 h to give 4-chloro-5,7-difluoro-3-methyl-2-(4-methylpyridin-3-yl)quinoline as a brown solid. Mass Spectrum (ESI) m/e=305.0 (M+1).

N-(2,5-Dimorpholinopyridin-3-yl)-5,7-difluoro-3-methyl-2-(4-methylpyridin-3-yl)quinolin-4-amine

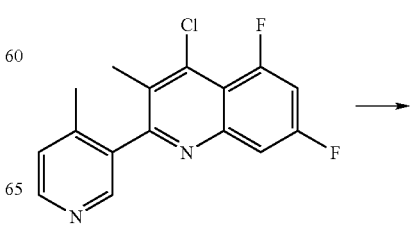

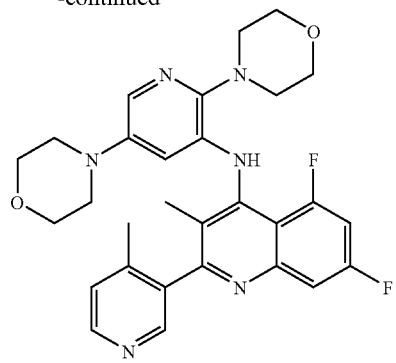

The Buchwald coupled product was prepared according to Procedure H using dicyclohexyl(2',4',6'-triisopropylbiphenyl-2-yl)phosphine (0.025 g, 0.053 mmol), 2,5-dimorpholinopyridin-3-amine (0.104 g, 0.39 mmol), 4-chloro-5,7-difluoro-3-methyl-2-(4-methylpyridin-3-yl)quinoline (0.1 g, 0.33 mmol), Pd$_2$dba$_3$ (0.012 g, 0.013 mmol) and sodium tert-butoxide (0.079 g, 0.82 mmol) in toluene (3.3 mL) at 120° C. for 19 h. The crude product was purified by column chromatography on basic alumina (0 to 50% hexanes/EtOAc) to give the desired product N-(2,5-dimorpholinopyridin-3-yl)-5,7-difluoro-3-methyl-2-(4-methylpyridin-3-yl)quinolin-4-amine. $^1$H NMR (400 MHz, DMSO-d$_6$) δ ppm 8.54 (1H, d, J=5.1 Hz), 8.48 (1H, br. s), 7.78 (1H, d, J=5.7 Hz), 7.65 (1H, m), 7.55 (1H, d, J=2.5 Hz), 7.51 (1H, ddd, J=13.3, 9.2, 2.5 Hz), 7.41 (1H, d, J=5.1 Hz), 6.34 (1H, s), 3.74 (1H, br. s), 3.65 (4H, app t, J=4.3 Hz), br. s.), 3.19 (2H, br. s), 2.96 (4H, app t, J=5.0 Hz), 2.2 (2H, br. s), 2.15 (3H, s), 1.87 (3H, s). Mass Spectrum (ESI) m/e=533.2 (M+1).

Example 145

Preparation of N-(2,5-dimorpholinopyridin-3-yl)-5,7-difluoro-3-methyl-2-(2-methylpyridin-3-yl)quinolin-4-amine 4-Chloro-5,7-difluoro-3-methyl-2-(2-methylpyridin-3-yl)quinoline

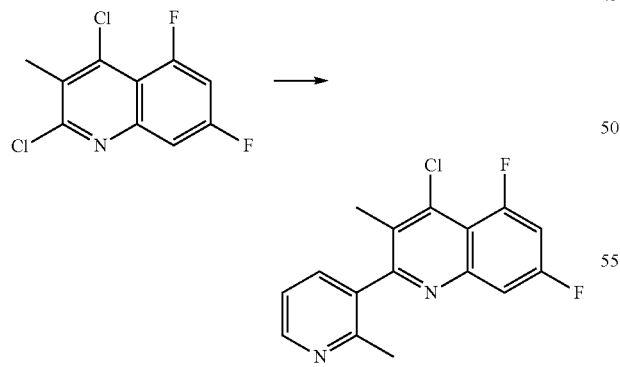

The Suzuki coupled product was prepared according to Procedure F using 2,4-dichloro-5,7-difluoro-3-methylquinoline (0.50 g, 2.02 mmol), 2-methyl-3-(4,4,5,5-tetramethyl-1,3,2-dioxaborolan-2-yl)pyridine (0.442 g, 2.02 mmol), palladium tetrakistriphenylphosphine (0.23 g, 0.20 mmol), potassium carbonate (0.56 g, 4.03 mmol) in toluene (4 mL) at 100° C. for 18 h to give 4-chloro-5,7-difluoro-3-methyl-2-(6-(piperidin-1-yl)pyridin-3-yl)quinoline as a white solid. Mass Spectrum (ESI) m/e=305.0 (M+1).

N-(2,5-Dimorpholinopyridin-3-yl)-5,7-difluoro-3-methyl-2-(2-methylpyridin-3-yl)quinolin-4-amine

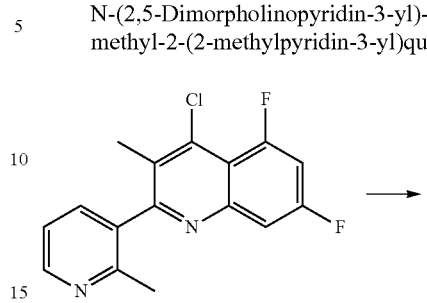

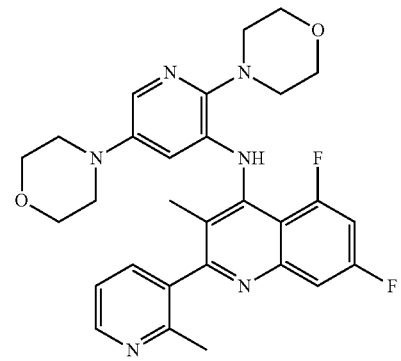

The Buchwald coupled product was prepared according to Procedure H using dicyclohexyl(2',4',6'-triisopropylbiphenyl-2-yl)phosphine (0.025 g, 0.053 mmol), 2,5-dimorpholinopyridin-3-amine (0.104 g, 0.39 mmol), 4-chloro-5,7-difluoro-3-methyl-2-(2-methylpyridin-3-yl)quinoline (0.1 g, 0.33 mmol), Pd$_2$dba$_3$ (0.012 g, 0.013 mmol) and sodium tert-butoxide (0.064 g, 0.67 mmol) in toluene (3.3 mL) at 100° C. for 43 h. The crude product was purified by column chromatography on basic alumina (0 to 50% hexanes/EtOAc) to give the desired product N-(2,5-dimorpholinopyridin-3-yl)-5,7-difluoro-3-methyl-2-(2-methylpyridin-3-yl)-quinolin-4-amine. $^1$H NMR (400 MHz, DMSO-d$_6$) δ ppm 8.57 (1H, dd, J=4.9, 2.0 Hz)), 7.76 (1H, m), 7.72 (1H, m), 7.63 (1H, m), 7.55 (1H, d, J=2.5 Hz), 7.50 (1H, m), 7.38 (1H, dd, J=7.4, 4.7 Hz), 6.31 (1H, br. s.), 3.73 (4H, br. s), 3.65 (4H, app t, J=4.5 Hz), 3.17 (2H, br. s), 2.94 (4H, app t, J=4.5 Hz), 2.82 (2H, br. s), 2.29 (3H, s), 1.87 (3H, s). Mass Spectrum (ESI) m/e=533.2 (M+1).

Example 146

Preparation of N-(2,5-dimorpholinopyridin-3-yl)-2-(6-ethoxypyridin-3-yl)-5,7-difluoro-3-methylquinolin-4-amine 4-Chloro-2-(6-ethoxypyridin-3-yl)-5,7-difluoro-3-methylquinoline

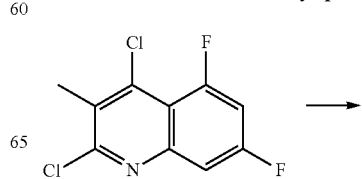

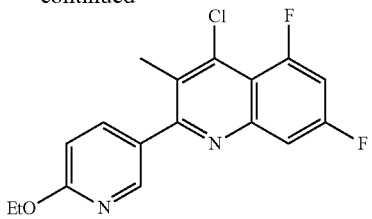

The Suzuki coupled product was prepared according to Procedure F using 2,4-dichloro-5,7-difluoro-3-methylquinoline (0.50 g, 2.02 mmol), 6-ethoxypyridin-3-ylboronic acid (0.337 g, 2.02 mmol), palladium tetrakistriphenylphosphine (0.23 g, 0.20 mmol), potassium carbonate (0.56 g, 4.03 mmol) in toluene (4 mL) at 100° C. for 18 h to give 4-chloro-2-(6-ethoxypyridin-3-yl)-5,7-difluoro-3-methylquinoline as a white solid. Mass Spectrum (ESI) m/e=335.0 (M+1).

N-(2,5-Dimorpholinopyridin-3-yl)-2-(6-ethoxypyridin-3-yl)-5,7-difluoro-3-methylquinolin-4-amine

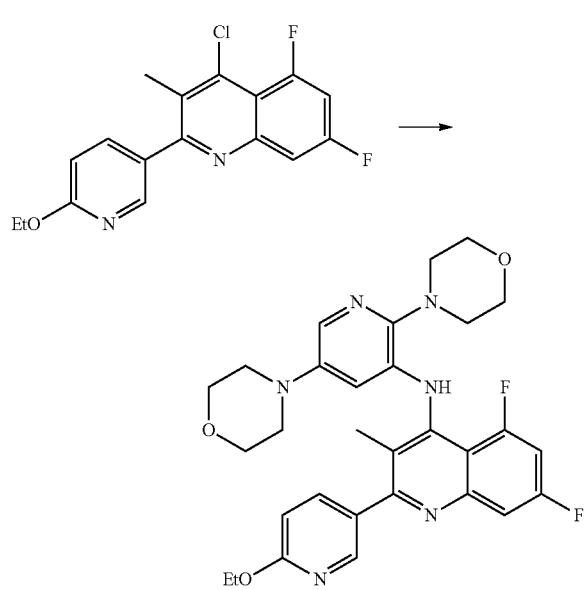

The Buchwald coupled product was prepared according to Procedure H using dicyclohexyl(2',4',6'-triisopropylbiphenyl-2-yl)phosphine (0.023 g, 0.048 mmol), 2,5-dimorpholinopyridin-3-amine (0.095 g, 0.36 mmol), 4-chloro-2-(6-ethoxypyridin-3-yl)-5,7-difluoro-3-methylquinoline (0.1 g, 0.30 mmol), Pd₂dba₃ (0.011 g, 0.012 mmol) and sodium tert-butoxide (0.045 g, 0.47 mmol) in toluene (3.0 mL) at 100° C. for 2 h. The crude product was purified by column chromatography on basic alumina (0 to 50% hexanes/EtOAc) to give the desired product N-(2,5-dimorpholinopyridin-3-yl)-2-(6-ethoxypyridin-3-yl)-5,7-difluoro-3-methylquinolin-4-amine. ¹H NMR (500 MHz, DMSO-d₆) δ ppm 8.46 (1H, d, J=2.0 Hz), 8.01 (1H, dd, J=8.6, 2.4 Hz), 7.79 (1H, d, J=5.6 Hz), 7.65 (1H, dd, J=9.8, 1.7 Hz), 7.56 (1H, d, J=2.4 Hz), 7.47 (1H, ddd, J=13.1, 9.4, 2.4 Hz), 6.96 (1H, d, J=8.6 Hz), 6.44 (1H, d, J=2.7 Hz), 4.40 (2H, q, J=6.9 Hz), 3.58-3.83 (9H, m), 3.16 (2H, br. s.), 2.94-3.06 (5H, m), 2.84 (2H, br. s.), 2.11 (3H, s), 1.37 (3H, t, J=7.1 Hz). Mass Spectrum (ESI) m/e=563.3 (M+1).

Example 147

Preparation of N-(2,5-dimorpholinopyridin-3-yl)-5,7-difluoro-2-(6-fluoropyridin-3-yl)-3-methylquinolin-4-amine 4-Chloro-5,7-difluoro-2-(6-fluoropyridin-3-yl)-3-methylquinoline

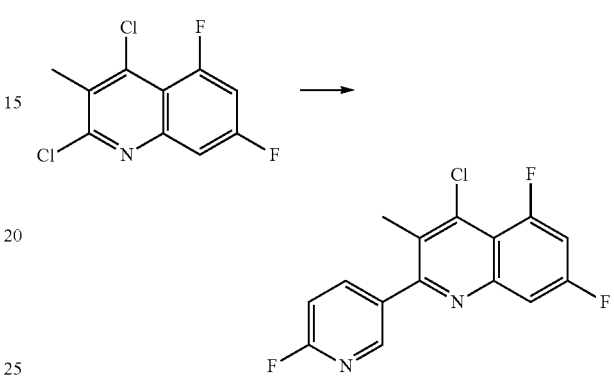

The Suzuki coupled product was prepared according to Procedure F using 2,4-dichloro-5,7-difluoro-3-methylquinoline (0.50 g, 2.02 mmol), 6-fluoropyridin-3-ylboronic acid (0.284 g, 2.016 mmol), palladium tetrakistriphenylphosphine (0.23 g, 0.20 mmol), potassium carbonate (0.56 g, 4.03 mmol) in toluene (4 mL) at 100° C. for 47 h to give 4-chloro-5,7-difluoro-2-(6-fluoropyridin-3-yl)-3-methylquinoline as a white solid. Mass Spectrum (ESI) m/e=309.0 (M+1).

N-(2,5-Dimorpholinopyridin-3-yl)-5,7-difluoro-2-(6-fluoropyridin-3-yl)-3-methylquinolin-4-amine

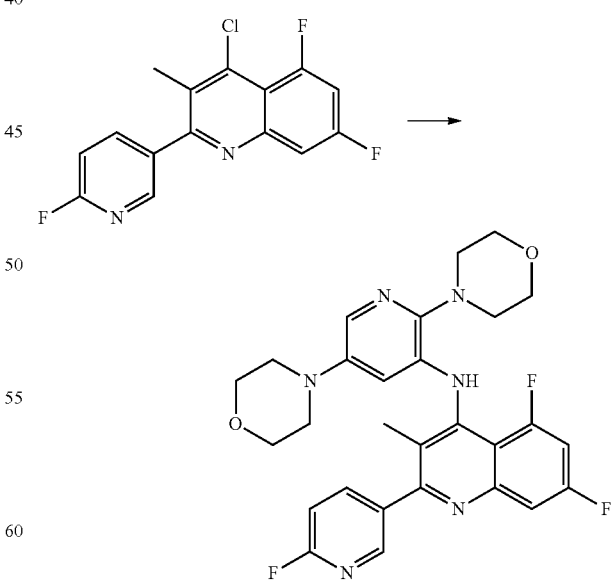

The Buchwald coupled product was prepared according to Procedure H using dicyclohexyl(2',4',6'-triisopropylbiphenyl-2-yl)phosphine (0.025 g, 0.052 mmol), 2,5-dimorpholinopyridin-3-amine (0.103 g, 0.39 mmol), 4-chloro-5,7-difluoro-2-(6-fluoropyridin-3-yl)-3-methylquinoline (0.1 g, 0.32 mmol), Pd$_2$dba$_3$ (0.012 g, 0.013 mmol) and sodium tert-butoxide (0.078 g, 0.81 mmol) in toluene (3.2 mL) at 100° C. for 2.1 h. The crude product was purified by column chromatography on basic alumina (0 to 50% hexanes/EtOAc) to give the desired product N-(2,5-dimorpholinopyridin-3-yl)-5,7-difluoro-2-(6-fluoropyridin-3-yl)-3-methylquinolin-4-amine. $^1$H NMR (500 MHz, DMSO-d$_6$) δ ppm 8.52 (1H, d, J=2.4 Hz), 8.27 (1H, td, J=8.2, 2.4 Hz), 7.82 (1H, d, J=5.9 Hz), 7.67 (1H, d, J=10.0 Hz), 7.56 (1H, d, J=2.7 Hz), 7.47-7.53 (1H, m), 7.38 (1H, dd, J=8.4, 2.6 Hz), 6.47 (1H, d, J=2.7 Hz), 3.61-3.77 (8H, m), 3.15 (2H, br. s.), 2.96-3.05 (4H, m), 2.83 (2H, br. s.), 2.06 (3H, s). Mass Spectrum (ESI) m/e=563.3 (M+1).

Example 148

Preparation of N-(2,5-dimorpholinopyridin-3-yl)-5,7-difluoro-3-methyl-2-(2-methylpyridin-3-yl)quinolin-4-amine N-(2,5-Dimorpholinopyridin-3-yl)-5,7-difluoro-3-methyl-2-(2-methylpyridin-3-yl)quinolin-4-amine

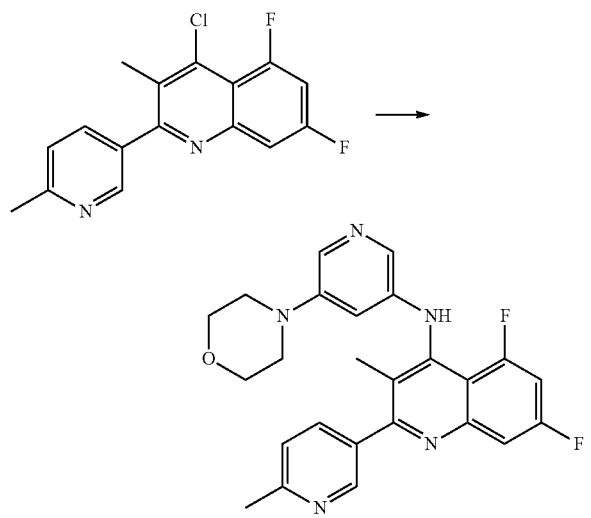

The Buchwald coupled product was prepared according to Procedure H using dicyclohexyl(2',4',6'-triisopropylbiphenyl-2-yl)phosphine (0.025 g, 0.052 mmol), 5-morpholinopyridin-3-amine (0.071 g, 0.39 mmol), 4-chloro-5,7-difluoro-3-methyl-2-(6-methylpyridin-3-yl)quinoline (0.1 g, 0.33 mmol), Pd$_2$dba$_3$ (0.012 g, 0.013 mmol) and sodium tert-butoxide (0.079 g, 0.82 mmol) in toluene (3.3 mL) at 100° C. for 2.1 h. The crude product was purified with HPLC (10-90% of 0.1% TFA acetonitrile solution in 0.1% TFA water solution.) The desired fractions were cond then diluted with EtOAc. After washing twice with satd aq. sodium bicarbonate solution, the solvent was removed under reduced pressure to yield desired product N-(2,5-dimorpholinopyridin-3-yl)-5,7-difluoro-3-methyl-2-(2-methylpyridin-3-yl)quinolin-4-amine.
$^1$H NMR (500 MHz, DMSO-d$_6$) δ ppm 8.72 (1H, d, J=2.2 Hz), 8.50 (1H, d, J=1.2 Hz), 7.97 (1H, dd, J=7.9, 2.3 Hz), 7.80 (1H, d, J=2.4 Hz), 7.64 (1H, dd, J=10.0, 1.7 Hz), 7.59 (1H, d, J=2.2 Hz), 7.45 (1H, m), 7.41 (1H, d, J=8.1 Hz), 6.59 (1H, t, J=2.3 Hz), 3.67-3.76 (4H, m), 3.05-3.14 (4H, m), 2.56 (3H, s), 2.13 (3H, s). Mass Spectrum (ESI) m/e=448.1 (M+1).

Example 149

Preparation of 2-(6-(dimethylamino)pyridin-3-yl)-N-(2,5-dimorpholinopyridin-3-yl)-5,7-difluoro-3-methylquinolin-4-amine 5-(4-Chloro-5,7-difluoro-3-methylquinolin-2-yl)-N,N-dimethylpyridin-2-amine

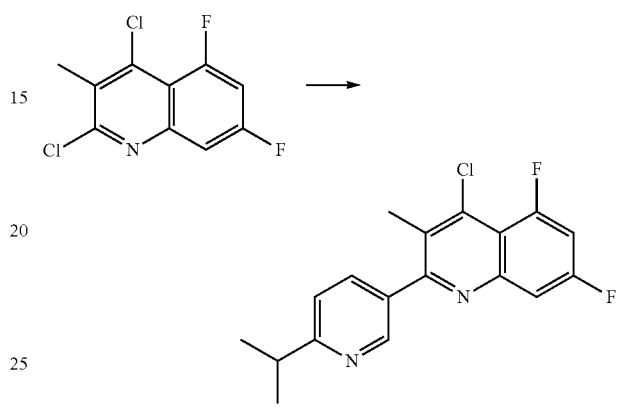

The Suzuki coupled product was prepared according to Procedure F using 2,4-dichloro-5,7-difluoro-3-methylquinoline (0.50 g, 2.02 mmol), 2-(N,N-dimethylamino)pyridine-5-boronic acid hydrate (0.335 g, 2.02 mmol), palladium tetrakistriphenylphosphine (0.23 g, 0.20 mmol), potassium carbonate (0.56 g, 4.03 mmol) in toluene (4 mL) at 100° C. for 1.3 h to give 5-(4-chloro-5,7-difluoro-3-methylquinolin-2-yl)-N,N-dimethylpyridin-2-amine as a yellow solid. Mass Spectrum (ESI) m/e=344.1 (M+1).

2-(6-(Dimethylamino)pyridin-3-yl)-N-(2,5-dimorpholinopyridin-3-yl)-5,7-difluoro-3-methylquinolin-4-amine

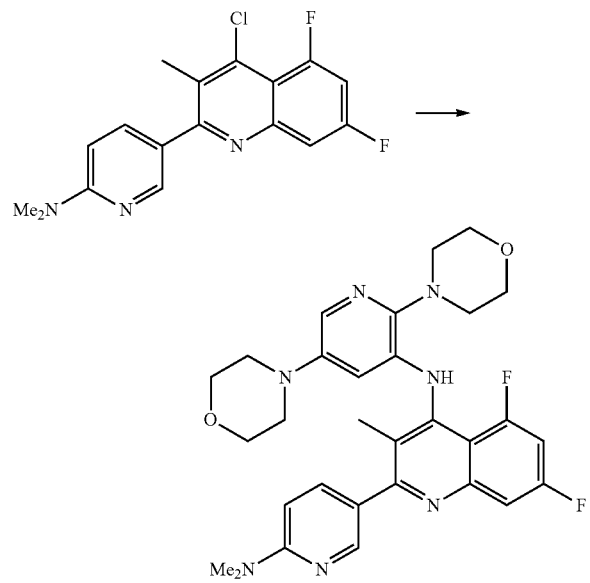

The Buchwald coupled product was prepared according to Procedure H using dicyclohexyl(2',4',6'-triisopropylbiphenyl-2-yl)phosphine (0.023 g, 0.048 mmol), 2,5-dimorpholinopyridin-3-amine (0.095 g, 0.36 mmol), 5-(4-chloro-5,7-difluoro-3-methylquinolin-2-yl)-N,N-dimethylpyridin-2-amine (0.1 g, 0.30 mmol), Pd$_2$dba$_3$ (0.011 g, 0.012 mmol) and sodium tert-butoxide (0.072 g, 0.75 mmol) in toluene (3.0 mL) at 100° C. for 2 h. The crude product was purified by column chromatography on silica gel (0 to 100% DCM/MeOH/ammonium hydroxide (90/9/1)) to give the desired product 2-(6-(dimethylamino)pyridin-3-yl)-N-(2,5-dimorpholinopyridin-3-yl)-5,7-difluoro-3-methylquinolin-4-amine. $^1$H NMR (400 MHz, DMSO-d$_6$) δ ppm 8.44 (1H, dd, J=2.4, 0.6 Hz), 7.85 (1H, dd, J=8.9, 2.4 Hz), 7.74 (1H, d, J=5.9 Hz), 7.57-7.63 (1H, m), 7.55 (1H, d, J=2.7 Hz), 7.34-7.45 (1H, m), 6.78 (1H, d, J=8.4 Hz), 6.40 (1H, d, J=2.5 Hz), 3.61-3.80 (8H, m), 3.16 (2H, br. s.), 3.11 (6H, s), 2.95-3.02 (4H, m), 2.13 (3H, s). Mass Spectrum (ESI) m/e=562.3 (M+1).

Example 150

Preparation of 2-(6-ethoxypyridin-3-yl)-5,7-difluoro-3-methyl-N-(5-morpholinopyridin-3-yl)quinolin-4-amine 2-(6-Ethoxypyridin-3-yl)-5,7-difluoro-3-methyl-N-(5-morpholinopyridin-3-yl)quinolin-4-amine

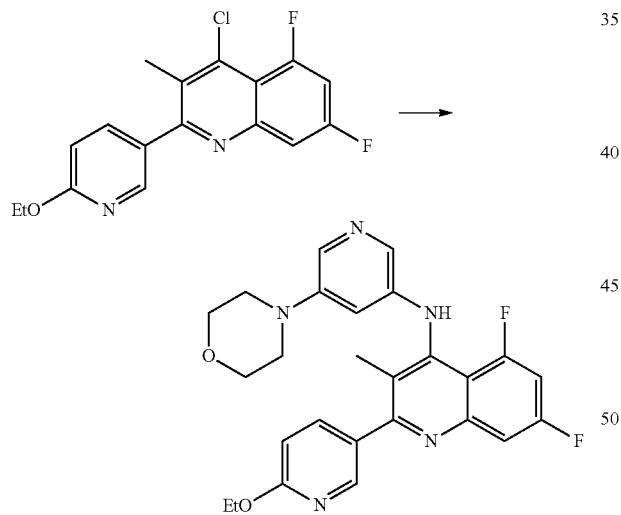

The Buchwald coupled product was prepared according to Procedure H using dicyclohexyl(2',4',6'-triisopropylbiphenyl-2-yl)phosphine (0.023 g, 0.048 mmol), 5-morpholinopyridin-3-amine (0.064 g, 0.36 mmol), 4-chloro-2-(6-ethoxypyridin-3-yl)-5,7-difluoro-3-methylquinoline (0.1 g, 0.30 mmol), Pd$_2$dba$_3$ (0.011 g, 0.012 mmol) and sodium tert-butoxide (0.072 g, 0.75 mmol) in toluene (3.0 mL) at 100° C. for 43 h. The crude product was purified by column chromatography on silica gel (0 to 100% DCM/MeOH/ammonium hydroxide (90/9/1)) to give the desired product 2-(6-ethoxypyridin-3-yl)-5,7-difluoro-3-methyl-N-(5-morpholinopyridin-3-yl)quinolin-4-amine. $^1$H NMR (400 MHz, DMSO-d$_6$) δ ppm 8.47 (1H, d, J=1.4 Hz), 8.45-8.47 (1H, dd, J=2.4, 0.6 Hz), 8.02 (1H, dd, J=8.5, 2.4 Hz), 7.80 (1H, d, J=2.5 Hz), 7.62 (1H, m), 7.59 (1H, d, J=2.2 Hz), 7.39-7.46 (1H, m), 6.92-6.96 (1H, d, J=8.4, 0.6 Hz), 6.57 (1H, t, J=2.4 Hz), 4.39 (2H, q, J=7.0 Hz), 3.67-3.76 (4H, m), 3.05-3.13 (4H, m), 2.16 (3H, s), 1.36 (3H, t, J=7.0 Hz). Mass Spectrum (ESI) m/e=478.3 (M+1).

Example 151

Preparation of (R)-5,7-difluoro-3-methyl-N-(5-(3-methylmorpholino)-2-morpholinopyridin-3-yl)-2-(pyridin-3-yl)quinolin-4-amine and (S)-5,7-difluoro-3-methyl-N-(5-(3-methylmorpholino)-2-morpholinopyridin-3-yl)-2-(pyridin-3-yl)quinolin-4-amine 5-(3-Methylmorpholino)-2-morpholinopyridin-3-amine

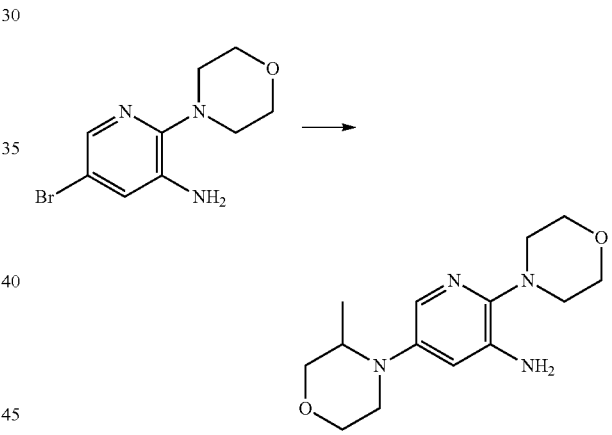

To a stirred solution of 5-bromo-2-morpholinopyridin-3-amine (0.5 g, 1.94 mmol), dicyclohexyl(2',4',6'-triisopropylbiphenyl-2-yl)phosphine (0.074 g, 0.16 mmol), Pd$_2$dba$_3$ (0.071 g, 0.08 mmol) and 3-methylmorpholine (0.98 g, 9.7 mmol) in THF (3.9 mL). To this mixture was added LHMDS in THF (1.0 M, 10.65 mL, 10.65 mmol) and the resulting reaction was heated to 65° C. The reaction was stirred for 2.25 h. After which, the reaction was cooled to rt and then poured into water (50 mL) and extracted with EtOAc (2×50 mL) and DCM (2×50 mL). The combined organic layers were dried over magnesium sulfate and the crude product was purified on basic alumina (0-100% EtOAc/hexane) to give 5-(3-methylmorpholino)-2-morpholinopyridin-3-amine. Mass Spectrum (ESI) m/e=279.2 (M+1).

(R)-5,7-Difluoro-3-methyl-N-(5-(3-methylmorpholino)-2-morpholinopyridin-3-yl)-2-(pyridin-3-yl)quinolin-4-amine and (S)-5,7-difluoro-3-methyl-N-(5-(3-methylmorpholino)-2-morpholinopyridin-3-yl)-2-(pyridin-3-yl)quinolin-4-amine

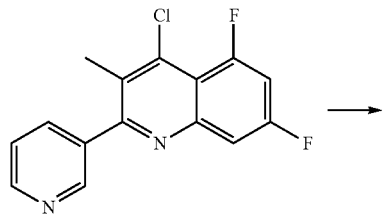

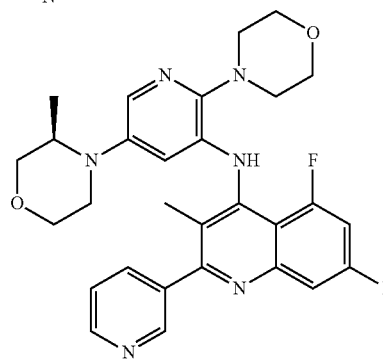

The Buchwald coupled products were prepared according to Procedure H using a solution of dicyclohexyl(2',4',6'-triisopropylbiphenyl-2-yl)phosphine (0.021 g, 0.044 mmol), 5-(3-methylmorpholino)-2-morpholinopyridin-3-amine (0.092 g, 0.33 mmol), 4-chloro-5,7-difluoro-3-methyl-2-(pyridin-3-yl)quinoline (0.08 g, 0.28 mmol), Pd$_2$dba$_3$ (0.010 g, 0.011 mmol) and sodium tert-butoxide (0.066 g, 0.69 mmol) in toluene (2.8 mL) at 100° C. for 27 h. The crude product was purified by column chromatography on silica gel (0 to 100% DCM/MeOH/ammonium hydroxide (90/9/1)) to give the desired product 5,7-difluoro-3-methyl-N-(5-(3-methylmorpholino)-2-morpholinopyridin-3-yl)-2-(pyridin-3-yl)quinolin-4-amine. The mixture of enantiomers was separated on chiral IC (3×8×15 cm) using 30% isopropanol (0.1% DEA)/CO$_2$, at a flow rate of 100 bar 70 mL/min, (230 nM, injection vol.: 1.5 mL, 4 mg/mL) to give both enantiomers with an ee of 99%; The initial peak (R)-5,7-difluoro-3-methyl-N-(5-(3-methylmorpholino)-2-morpholinopyridin-3-yl)-2-(pyridin-3-yl)quinolin-4-amine or (S)-5,7-difluoro-3-methyl-N-(5-(3-methylmorpholino)-2-morpholinopyridin-3-yl)-2-(pyridin-3-yl)-quinolin-4-amine. $^1$H NMR (400 MHz, DMSO-d$_6$) δ ppm 6.89 (1H, m), 8.01 (1H, td, J=7.8, 1.8 Hz), 7.90 (1H, m), 7.77 (1H, br. s), 7.66 (1H, m), 7.53-7.46 (3H, m), 6.33 (1H, m), 3.82-3.47 (10H, m), 3.02-2.88 (5H, m), 2.12 (3H, s), 0.92 (3H, br. s.). Mass Spectrum (ESI) m/e=533.2 (M+1). Further elution gave (S)-5,7-difluoro-3-methyl-N-(5-(3-methylmorpholino)-2-morpholinopyridin-3-yl)-2-(pyridin-3-yl)quinolin-4-amine or (R)-5,7-difluoro-3-methyl-N-(5-(3-methylmorpholino)-2-morpholinopyridin-3-yl)-2-(pyridin-3-yl)quinolin-4-amine. $^1$H NMR (400 MHz, DMSO-d$_6$) δ ppm 6.89 (1H, m), 8.01 (1H, td, J=7.8, 1.8 Hz), 7.90 (1H, m), 7.77 (1H, br. s), 7.66 (1H, m), 7.53-7.46 (3H, m), 6.33 (1H, m), 3.82-3.47 (10H, m), 3.02-2.88 (5H, m), 2.12 (3H, s), 0.92 (3H, br. s.). Mass Spectrum (ESI) m/e=533.2 (M+1). These compounds were arbitrarily assigned as R and S.

Example 152

Preparation of 5,7-difluoro-2-(5-methoxypyridin-3-yl)-3-methyl-N-(5-morpholinopyridin-3-yl)quinolin-4-amine 4-Chloro-5,7-difluoro-2-(5-methoxypyridin-3-yl)-3-methylquinoline

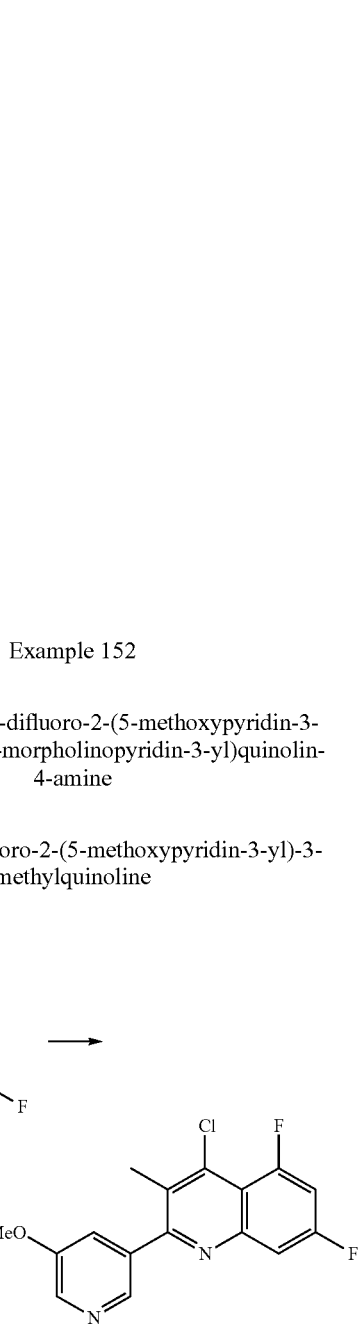

The Suzuki coupled product was prepared according to Procedure F using 2,4-dichloro-5,7-difluoro-3-methylquinoline (0.35 g, 1.4 mmol), 3-methoxy-5-(4,4,5,5-tetramethyl-1,3,2-dioxaborolan-2-yl)pyridine (0.50 g, 2.12 mmol), palladium tetrakistriphenylphosphine (0.16 g, 0.14 mmol), potassium carbonate (0.49 g, 4.23 mmol) in toluene (2.8 mL) at 100° C. for 17.6 h to give 4-chloro-5,7-difluoro-2-(5-methoxypyridin-3-yl)-3-methylquinoline as a white solid. Mass Spectrum (ESI) m/e=321.0 (M+1).

5,7-Difluoro-2-(5-methoxypyridin-3-yl)-3-methyl-N-(5-morpholinopyridin-3-yl)quinolin-4-amine

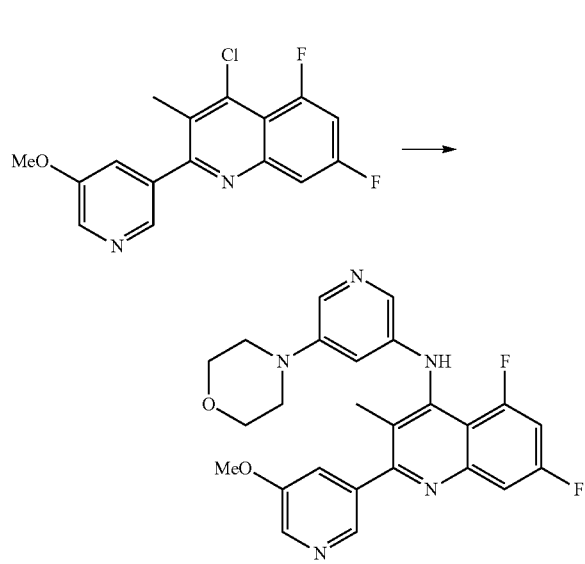 [SMILES: COc1cncc(-c2nc3cc(F)cc(F)c3c(Cl)c2C)c1 ; COc1cncc(-c2nc3cc(F)cc(F)c3c(Nc3cncc(N4CCOCC4)c3)c2C)c1]

The Buchwald coupled product was prepared according to Procedure H using dicyclohexyl(2',4',6'-triisopropylbiphenyl-2-yl)phosphine (0.024 g, 0.050 mmol), 5-morpholinopyridin-3-amine (0.067 g, 0.37 mmol), 4-chloro-5,7-difluoro-2-(5-methoxypyridin-3-yl)-3-methylquinoline (0.1 g, 0.31 mmol), Pd$_2$dba$_3$ (0.011 g, 0.012 mmol) and sodium tert-butoxide (0.075 g, 0.78 mmol) in toluene (3.1 mL) at 100° C. for 1.6 h. The crude product was purified by column chromatography on silica gel (0 to 100% DCM/MeOH/ammonium hydroxide (90/9/1)) to give the desired product 5,7-difluoro-2-(5-methoxypyridin-3-yl)-3-methyl-N-(5-morpholinopyridin-3-yl)quinolin-4-amine. $^1$H NMR (400 MHz, DMSO-d$_6$) δ ppm 8.51 (1H, d, J=1.8 Hz), 8.39-8.45 (2H, m), 7.80 (1H, d, J=2.3 Hz), 7.59-7.69 (3H, m), 7.43-7.51 (1H, m), 6.60 (1H, t, J=2.3 Hz), 3.90 (3H, s), 3.67-3.77 (4H, m), 3.05-3.17 (4H, m), 2.11 (3H, s). Mass Spectrum (ESI) m/e=464.1 (M+1).

Example 153

Preparation of 5,7-difluoro-2-(2-methoxypyridin-4-yl)-3-methyl-N-(5-morpholinopyridin-3-yl)quinolin-4-amine 5,7-Difluoro-2-(2-methoxypyridin-4-yl)-3-methyl-N-(5-morpholinopyridin-3-yl)quinolin-4-amine

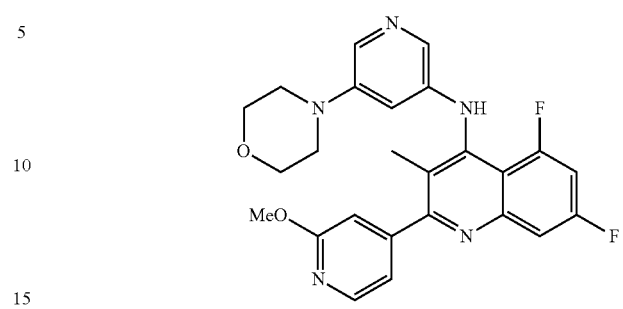

The Buchwald coupled product was prepared according to Procedure H using dicyclohexyl(2',4',6'-triisopropylbiphenyl-2-yl)phosphine (0.024 g, 0.050 mmol), 5-morpholinopyridin-3-amine (0.067 g, 0.37 mmol), 4-chloro-5,7-difluoro-2-(2-methoxypyridin-4-yl)-3-methylquinoline (0.1 g, 0.31 mmol), Pd$_2$dba$_3$ (0.011 g, 0.012 mmol) and sodium tert-butoxide (0.075 g, 0.78 mmol) in toluene (3.1 mL) at 100° C. for 46.5 h. The crude product was purified by column chromatography on silica gel (0 to 100% DCM/MeOH/ammonium hydroxide (90/9/1)) to give the desired product 5,7-difluoro-2-(2-methoxypyridin-4-yl)-3-methyl-N-(5-morpholinopyridin-3-yl)quinolin-4-amine. $^1$H NMR (400 MHz, DMSO-d$_6$) δ ppm 8.50 (1H, d, J=1.6 Hz), 8.30-8.34 (1H, dd, J=5.1, 0.6 Hz), 7.80 (1H, d, J=2.3 Hz), 7.64 (1H, m), 7.58 (1H, d, J=2.3 Hz), 7.43-7.51 (1H, m), 7.21 (1H, dd, J=5.2, 1.5 Hz), 7.03 (1H, s), 6.59 (1H, t, J=2.3 Hz), 3.92 (3H, s), 3.70 (4H, m), 3.08 (4H, m), 2.08 (3H, s). Mass Spectrum (ESI) m/e=464.1 (M+1).

Example 154

Preparation of N-(2,5-dimorpholinopyridin-3-yl)-5,7-difluoro-3-methyl-2-(4-vinylpyridin-2-yl)quinolin-4-amine 4-Chloro-5,7-difluoro-3-methyl-2-(4-vinylpyridin-2-yl)quinoline

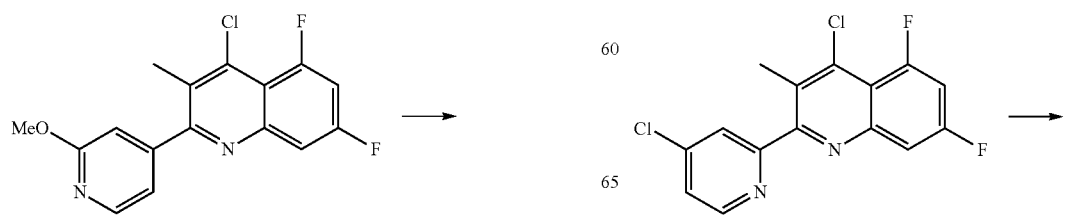

-continued

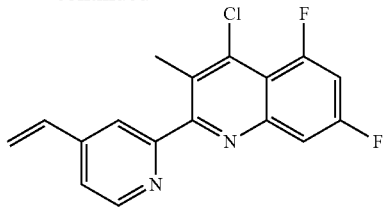

To a stirred solution of dicyclohexyl(2',4',6'-triisopropylbiphenyl-2-yl)phosphine (0.023 g, 0.049 mmol), 4-chloro-2-(4-chloropyridin-2-yl)-5,7-difluoro-3-methylquinoline (0.10 g, 0.31 mmol), vinyl boronic acid MIDA ester (0.056 g, 0.31 mmol) and Pd$_2$dba$_3$ (0.011 g, 0.012 mmol) in toluene (3.1 mL) was added sodium tert-butoxide (0.074 g, 0.77 mmol). The reaction mixture was heated to 100° C. and stirring continued for 76 h. The crude product was purified by column chromatography on silica gel (0 to 50% hexanes/EtOAc) to give the desired product 4-chloro-5,7-difluoro-3-methyl-2-(4-vinylpyridin-2-yl)quinoline. Mass Spectrum (ESI) m/e=317.0 (M+1).

N-(2,5-Dimorpholinopyridin-3-yl)-5,7-difluoro-3-methyl-2-(4-vinylpyridin-2-yl)quinolin-4-amine

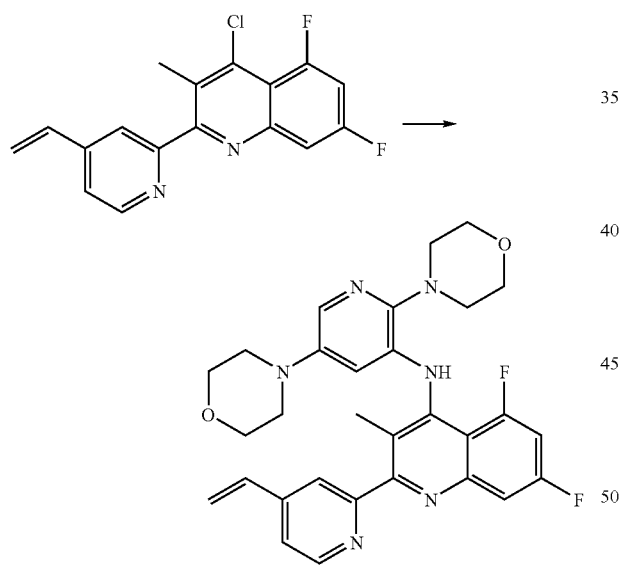

The Buchwald coupled product was prepared according to Procedure H using dicyclohexyl(2',4',6'-triisopropylbiphenyl-2-yl)phosphine (0.019 g, 0.040 mmol), 2,5-dimorpholinopyridin-3-amine (0.080 g, 0.30 mmol), 4-chloro-5,7-difluoro-3-methyl-2-(4-vinylpyridin-2-yl)quinoline (0.08 g, 0.25 mmol), Pd$_2$dba$_3$ (0.009 g, 0.010 mmol) and sodium tert-butoxide (0.061 g, 0.63 mmol) in toluene (2.5 mL) at 100° C. for 4.5 h. The crude product was purified by column chromatography on silica gel (0 to 100% DCM/MeOH/ammonium hydroxide (90/9/1)) to give the desired product N-(2,5-dimorpholinopyridin-3-yl)-5,7-difluoro-3-methyl-2-(4-vinylpyridin-2-yl)quinolin-4-amine. $^1$H NMR (400 MHz, DMSO-d$_6$) δ ppm 8.54 (1H, br. s), 8.28 (1H, d, J=5.9 Hz), 7.83 (1H, d, J=2.7 Hz), 7.50-7.58 (2H, m), 7.28 (1H, d, J=2.7 Hz), 7.24 (1H, m), 7.08 (1H, d, J=2.2 Hz), 6.87 (1H, dd, J=5.7, 2.3 Hz), 5.76 (1H, m), 5.41 (1H, dd, 17.8, 1.6 Hz), 3.71-3.76 (4H, m), 3.55-3.60 (4H, m), 3.08 (4H, m), 3.02 (4H, m), 2.40 (3H, s). Mass Spectrum (ESI) m/e=545.2 (M+1).

Example 155

Preparation of 2-(6-(dimethylamino)pyridin-3-yl)-5,7-difluoro-3-methyl-N-(5-morpholinopyridin-3-yl)quinolin-4-amine 2-(6-(Dimethylamino)pyridin-3-yl)-5,7-difluoro-3-methyl-N-(5-morpholinopyridin-3-yl)quinolin-4-amine The Buchwald coupled product was prepared according to Procedure H using dicyclohexyl(2',4',6'-triisopropylbiphenyl-2-yl)phosphine (0.023 g, 0.048 mmol), 5-morpholinopyridin-3-amine (0.064 g, 0.36 mmol), 5-(4-chloro-5,7-difluoro-3-methylquinolin-2-yl)-N,N-dimethylpyridin-2-amine (0.1 g, 0.30 mmol) and Pd$_2$dba$_3$ (0.011 g, 0.012 mmol) and sodium tert-butoxide (0.072 g, 0.75 mmol) in toluene (3.0 mL) at 100° C. for 2 h. The crude product was purified by column chromatography on silica gel (0 to 100% DCM/MeOH/ammonium hydroxide (90/9/1)) to give the desired product 2-(6-(dimethylamino)pyridin-3-yl)-5,7-difluoro-3-methyl-N-(5-morpholinopyridin-3-yl)quinolin-4-amine. $^1$H NMR (400 MHz, DMSO-d$_6$) δ ppm 8.44 (2H, m), 7.87 (1H, dd, J=8.8, 2.5 Hz), 7.79 (1H, d, J=2.3 Hz), 7.56-7.59 (2H, m), 7.36 (1H, ddd, J=12.6, 9.5, 2.5 Hz), 6.76 (1H, d, J=8.8 Hz), 6.55 (1H, t, J=2.2 Hz), 3.70 (4H, m), 3.11-3.06 (10H, m), 2.19 (3H, s). Mass Spectrum (ESI) m/e=477.2 (M+1).

Example 156

Preparation of N-(5,7-difluoro-3-methyl-2-(pyridin-3-yl)-quinolin-4-yl)-2,2,2-trifluoro-N-(5-morpholinopyridin-3-yl)acetamide N-(5,7-Difluoro-3-methyl-2-(pyridin-3-yl)quinolin-4-yl)-2,2,2-trifluoro-N-(5-morpholinopyridin-3-yl)acetamide

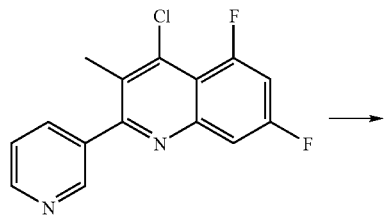

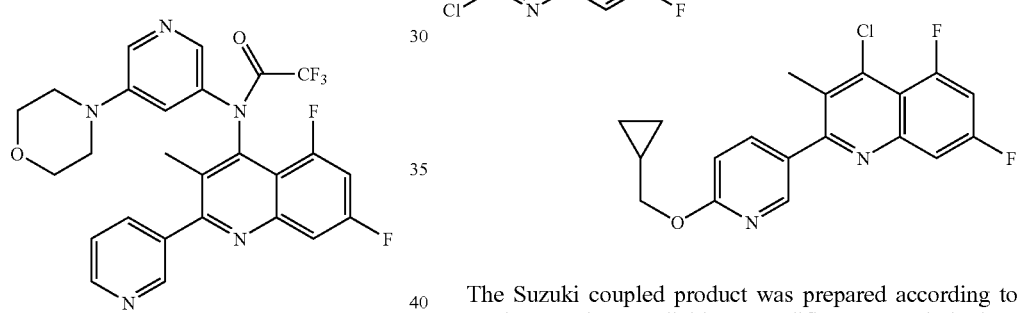

The Buchwald coupled product was prepared according to Procedure H using dicyclohexyl(2',4',6'-triisopropylbiphenyl-2-yl)phosphine (0.026 g, 0.055 mmol), 5-morpholinopyridin-3-amine (0.074 g, 0.41 mmol), 4-chloro-5,7-difluoro-3-methyl-2-(pyridin-3-yl)quinoline (0.1 g, 0.34 mmol) and Pd$_2$dba$_3$ (0.013 g, 0.014 mmol) and sodium tert-butoxide (0.083 g, 0.86 mmol) in toluene (3.4 mL) at 100° C. for 2.8 h. The crude reaction mixture was filtered through a plug of alumina eluting with (DCM/MeOH; 3/1), the filtrate was cond in vacuo. The filtrate was dissolved in pyridine (1 mL) and trifluoroacetic anhydride (1 mL, 7.1 mmol) was added. The reaction mixture was stirred at rt for 1 h, after which water was added to quench the reaction and the mixture was extracted with EtOAc. The combined organic phases were cond in vacuo. The crude product was purified by column chromatography on silica gel (0 to 100% DCM/MeOH/ammonium hydroxide (90/9/1) to give the desired product N-(5,7-difluoro-3-methyl-2-(pyridin-3-yl)-quinolin-4-yl)-2,2,2-trifluoro-N-(5-morpholinopyridin-3-yl)acetamide. $^1$H NMR (400 MHz, DMSO-d$_6$) δ ppm 8.69 (0.6H, m), 8.64 (0.6H, m), 8.36 (0.4H, d, J=2.5 Hz), 8.26 (0.6H, d, J=2.5 Hz), 8.10 (0.4H, br. s), 8.04 (1H, m), 7.97-7.80 (3H, m), 7.78 (0.6H, br. s), 7.50-7.56 (2H, m), 3.72 (4H, m), 3.25-3.15 (4H, m), 2.41 (1.8H, s), 2.35 (1.2H, s). Mass Spectrum (ESI) m/e=530.2 (M+1).

Example 157

Preparation of 2-(6-(cyclopropylmethoxy)pyridin-3-yl)-N-(2,5-dimorpholinopyridin-3-yl)-5,7-difluoro-3-methylquinolin-4-amine 4-Chloro-2-(6-(cyclopropylmethoxy)pyridin-3-yl)-5,7-difluoro-3-methylquinoline The Suzuki coupled product was prepared according to Procedure F using 2,4-dichloro-5,7-difluoro-3-methylquinoline (0.5 g, 2.0 mmol), 2-(cyclopropylmethoxy)-5-(4,4,5,5-tetramethyl-1,3,2-dioxaborolan-2-yl)pyridine (0.666 g, 2.42 mmol), palladium tetrakistriphenylphosphine (0.23 g, 0.20 mmol), potassium carbonate (0.84 g, 6.1 mmol) in toluene (4.0 mL) at 100° C. for 18.3 h to give 4-chloro-2-(6-(cyclopropylmethoxy)pyridin-3-yl)-5,7-difluoro-3-methylquinoline as a light yellow solid. Mass Spectrum (ESI) m/e=361.1 (M+1).

2-(6-(Cyclopropylmethoxy)pyridin-3-yl)-N-(2,5-dimorpholinopyridin-3-yl)-5,7-difluoro-3-methylquinolin-4-amine

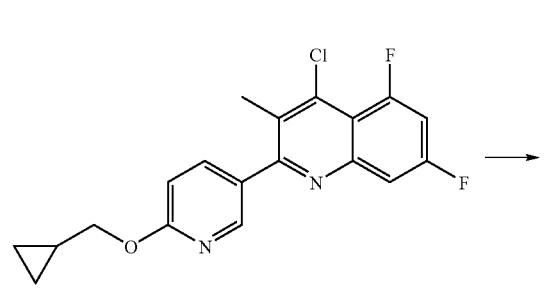

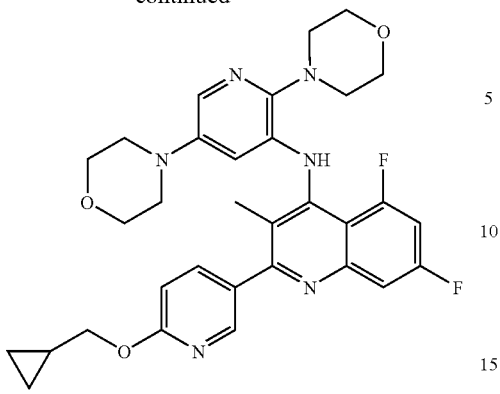

The Buchwald coupled product was prepared according to Procedure H using dicyclohexyl(2',4',6'-triisopropylbiphenyl-2-yl)phosphine (0.021 g, 0.044 mmol), 2,5-dimorpholinopyridin-3-amine (0.088 g, 0.33 mmol), 4-chloro-2-(6-(cyclopropylmethoxy)pyridin-3-yl)-5,7-difluoro-3-methylquinoline (0.1 g, 0.28 mmol) and Pd₂dba₃ (0.010 g, 0.011 mmol) and sodium tert-butoxide (0.067 g, 0.70 mmol) in toluene (2.8 mL) at 100° C. for 1.6 h. The crude product was purified by column chromatography on silica gel (0 to 100% DCM/MeOH/ammonium hydroxide (90/9/1)) to give the desired product 2-(6-(cyclopropylmethoxy)-pyridin-3-yl)-N-(2,5-dimorpholinopyridin-3-yl)-5,7-difluoro-3-methylquinolin-4-amine. $^1$H NMR (400 MHz, DMSO-d₆) δ ppm 8.43 (1H, d, J=1.8 Hz), 8.00 (1H, dd, J=8.5, 2.4 Hz), 7.77 (1H, d, J=4.9 Hz), 7.63 (1H, dd, J=10.0, 1.6 Hz), 7.55 (1H, d, J=2.7 Hz), 7.41-7.49 (1H, m), 6.98 (1H, d, J=8.6 Hz), 6.43 (1H, d, J=2.7 Hz), 5.75 (1H, s), 4.18 (2H, d, J=7.2 Hz), 3.57-3.84 (8H, m), 3.15 (2H, br. s.), 2.99 (4H, m), 2.83 (2H, br. s.), 2.09 (3H, s), 1.23-1.34 (1H, m), 0.54-0.62 (2H, m), 0.33-0.41 (2H, m). Mass Spectrum (ESI) m/e=589.3 (M+1).

Example 158

Preparation of 8-chloro-3-methyl-N-(5-morpholinopyridin-3-yl)-2-(pyridin-2-yl)quinolin-4-amine 8-Chloro-3-methyl-N-(5-morpholinopyridin-3-yl)-2-(pyridin-2-yl)quinolin-4-amine

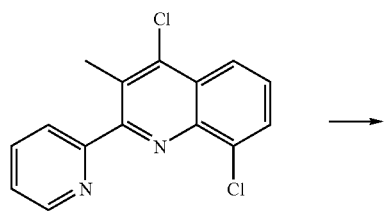

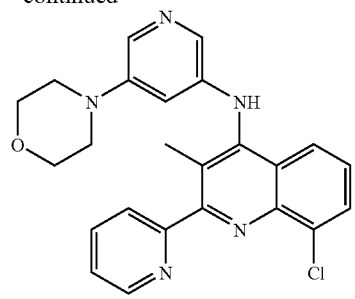

The Buchwald coupled product was prepared according to Procedure H using dicyclohexyl(2',4',6'-triisopropylbiphenyl-2-yl)phosphine (0.026 g, 0.055 mmol), 5-morpholinopyridin-3-amine (0.074 g, 0.42 mmol), 4,8-dichloro-3-methyl-2-(pyridin-2-yl)quinoline (0.1 g, 0.35 mmol) and Pd₂dba₃ (0.013 g, 0.014 mmol) and sodium tert-butoxide (0.083 g, 0.87 mmol) in toluene (3.5 mL) at 100° C. for 1.1 h. The crude product was purified by column chromatography on silica gel (0 to 100% DCM/MeOH/ammonium hydroxide (90/9/1)) to give the desired product 8-chloro-3-methyl-N-(5-morpholinopyridin-3-yl)-2-(pyridin-2-yl)quinolin-4-amine. $^1$H NMR (400 MHz, DMSO-d₆) δ ppm 8.69-8.73 (2H, m), 7.95-8.06 (3H, m), 7.92 (1H, dd, J=7.4, 1.2 Hz), 7.81 (1H, d, J=2.3 Hz), 7.50-7.56 (3H, m), 6.56 (1H, t, J=2.4 Hz), 3.70 (4H, m), 3.06 (4H, m), 2.25 (3H, s). Mass Spectrum (ESI) m/e=432.1 (M+1).

Example 159

Preparation of 8-chloro-N-(2,5-dimorpholinopyridin-3-yl)-3-methyl-2-(4-methylpyridin-2-yl)quinolin-4-amine 4,8-Dichloro-3-methyl-2-(4-methylpyridin-2-yl)quinoline

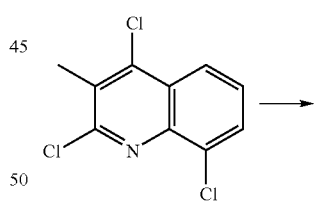

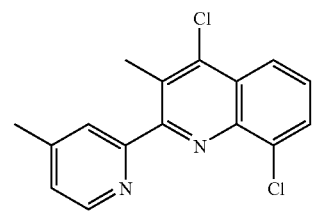

The Stille coupled product was prepared according to Procedure E using 2,4,8-trichloro-3-methylquinoline (0.15 g, 0.61 mmol), 4-methyl-2-(tributylstannyl)-pyridine (0.26 g, 0.67 mmol), palladium tetrakistriphenylphosphine (0.070 g, 0.06 mmol) in toluene (1.2 mL) to give 4,8-dichloro-3-methyl-2-(4-methylpyridin-2-yl)quinoline as a light yellow solid. Mass Spectrum (ESI) m/e=303.0 (M+1).

8-Chloro-N-(2,5-dimorpholinopyridin-3-yl)-3-methyl-2-(4-methylpyridin-2-yl)quinolin-4-amine

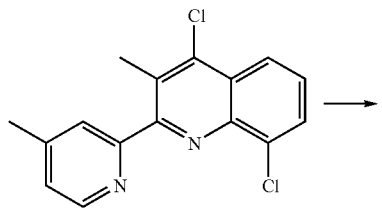

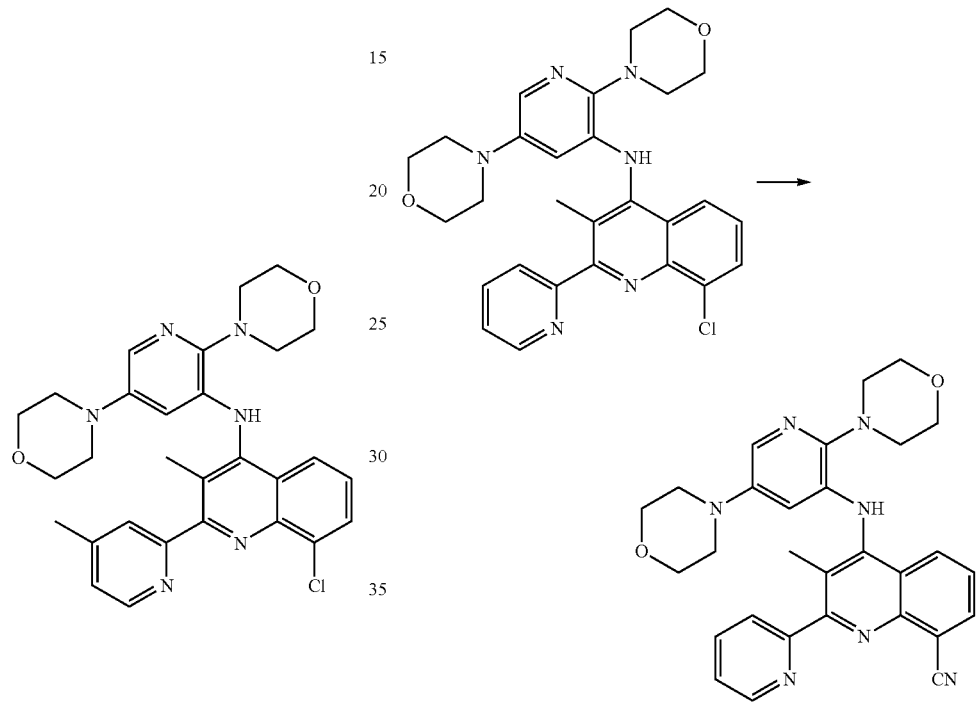

Example 160

Preparation of 4-(2,5-dimorpholinopyridin-3-ylamino)-3-methyl-2-(pyridin-2-yl)quinoline-8-carbonitrile 4-(2,5-Dimorpholinopyridin-3-ylamino)-3-methyl-2-(pyridin-2-yl)quinoline-8-carbonitrile The Buchwald coupled product was prepared according to Procedure H using dicyclohexyl(2',4',6'-triisopropylbiphenyl-2-yl)phosphine (0.025 g, 0.053 mmol), 2,5-dimorpholinopyridin-3-amine (0.105 g, 0.40 mmol), 4,8-dichloro-3-methyl-2-(4-methylpyridin-2-yl)quinoline (0.1 g, 0.33 mmol) and Pd$_2$dba$_3$ (0.012 g, 0.013 mmol) and sodium tert-butoxide (0.079 g, 0.83 mmol) in toluene (3.3 mL) at 100° C. for 1.6 h. The crude product was purified by column chromatography on silica gel (0 to 100% DCM/MeOH/ammonium hydroxide (90/9/1)). The desired product was further purified with HPLC (10-90% of 0.1% TFA acetonitrile solution in 0.1% TFA water solution.) The desired fractions were concd then diluted with EtOAc. After washing twice with satd aq. sodium bicarbonate solution, the solvent was removed under reduced pressure to yield pure product 8-chloro-N-(2,5-dimorpholinopyridin-3-yl)-3-methyl-2-(4-methylpyridin-2-yl)-quinolin-4-amine. $^1$H NMR (400 MHz, CD$_2$Cl$_2$) δ ppm 8.57 (1H, d, J=4.9 Hz), 7.82 (3H, m), 7.57 (1H, d, J=2.5 Hz), 7.43 (1H, dd, J=8.4, 7.4 Hz), 7.27 (1H, d, J=4.3 Hz.), 6.89 (1H, br. s.), 6.22 (1H, br. s.), 3.88 (4H, br. s.), 3.68 (4H, m), 3.20 (4H, br. s.), 2.90 (4H, m), 2.51 (3H, m), 2.39 (3H, s). Mass Spectrum (ESI) m/e=531.2 (M+1).

To a stirred solution of 8-chloro-N-(2,5-dimorpholinopyridin-3-yl)-3-methyl-2-(pyridin-2-yl)quinolin-4-amine (0.180 g, 0.35 mmol) in 1-methylpyrrolidin-2-one (3.46 mL) was added palladium bis(trifluoroacetate) (0.017 g, 0.052 mmol), 2-(dicyclohexylphosphino)-2',4',6'-triisopropyl-biphenyl (0.050 g, 0.11 mmol) followed by tri-n-butyltin cyanide (0.109 g, 0.35 mmol). The reaction was heated to 160° C. for 36 h. A further 0.3 eq of palladium bis(trifluoroacetate) and 0.6 eq of dicyclohexyl(2',4',6'-triisopropylbiphenyl-2-yl)phosphine was added. The reaction was further heated at 160° C. for 3 h. After which, the reaction was cooled to 23° C. The crude product was filtered through a plug of alumina eluting with EtOAc. The organic layer was washed with water, dried over MgSO$_4$ and filtered and evaporated in vacuo. The crude product was purified by column chromatography on alumina (0 to 50% EtOAc/hexane)) to give the desired product 4-((2,5-dimorpholinopyridin-3-ylamino)-3-methyl-2-(pyridin-2-yl)quinoline-8-carbonitrile. $^1$H NMR (400 MHz, DMSO-d$_6$) δ ppm 8.72 (1H, ddd, J=4.8, 1.8, 1.0 Hz), 8.29 (1H, dd, J=7.1, 1.3 Hz), 8.19 (1H, dd, J=8.5, 1.3 Hz), 8.03-8.08 (2H, m), 7.96 (1H, dt, J=7.9, 1.1 Hz), 7.61-7.65 (2H, m), 7.53 (1H, ddd, J=7.6, 4.8, 1.3 Hz), 6.55 (1H, d, J=2.7 Hz), 3.65 (4H, m), 3.39 (4H, m), 2.95 (4H, m), 2.88 (4H, m), 2.19 (3H, s). Mass Spectrum (ESI) m/e=508.3 (M+1).

Example 161

Preparation of 8-chloro-3-methyl-2-(4-methylpyridin-2-yl)-N-(5-morpholinopyridin-3-yl)quinolin-4-amine 8-Chloro-3-methyl-2-(4-methylpyridin-2-yl)-N-(5-morpholinopyridin-3-yl)-quinolin-4-amine

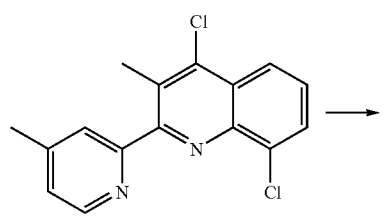

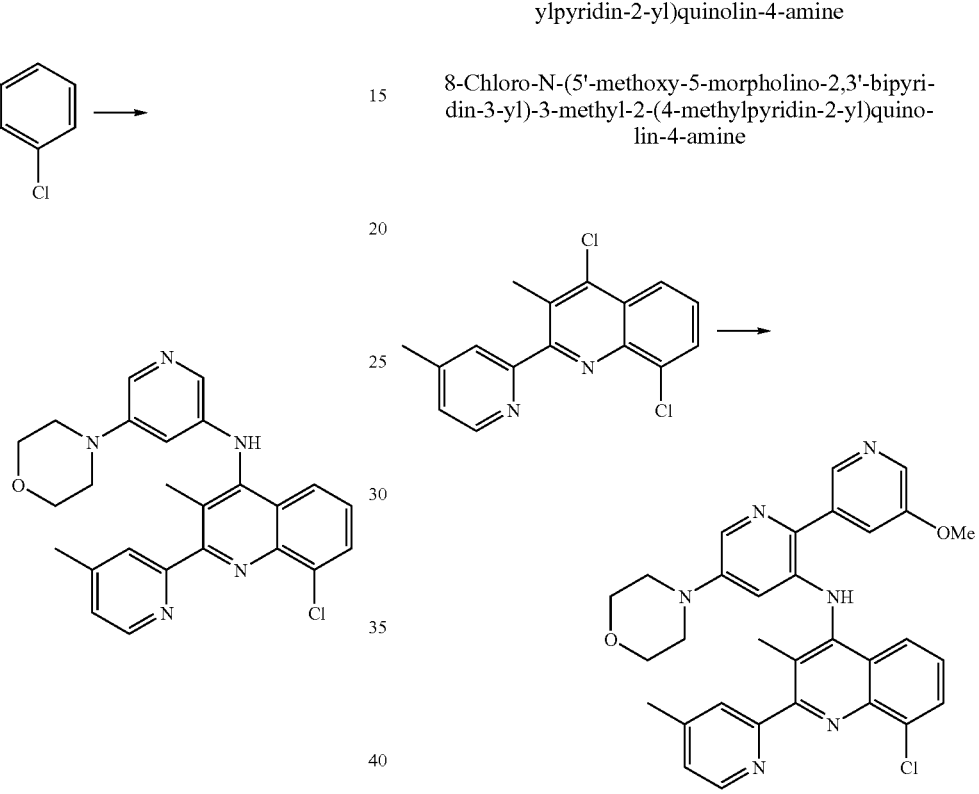

Example 162

Preparation of 8-chloro-N-(5'-methoxy-5-morpholino-2,3'-bipyridin-3-yl)-3-methyl-2-(4-methylpyridin-2-yl)quinolin-4-amine 8-Chloro-N-(5'-methoxy-5-morpholino-2,3'-bipyridin-3-yl)-3-methyl-2-(4-methylpyridin-2-yl)quinolin-4-amine The Buchwald coupled product was prepared according to Procedure H using dicyclohexyl(2',4',6'-triisopropylbiphenyl-2-yl)phosphine (0.021 g, 0.044 mmol), 5-morpholinopyridin-3-amine (0.060 g, 0.33 mmol), 4,8-dichloro-3-methyl-2-(4-methylpyridin-2-yl)quinoline (0.084 g, 0.28 mmol) and $Pd_2dba_3$ (0.010 g, 0.011 mmol) and sodium tert-butoxide (0.067 g, 0.70 mmol) in toluene (2.8 mL) at 100° C. for 1.6 h. The crude product was purified by column chromatography on alumina (0 to 50% EtOAc in hexanes). The desired product was further purified with HPLC (10-90% of 0.1% TFA acetonitrile solution in 0.1% TFA water solution.) The desired fractions were cond then diluted with EtOAc. After washing twice with satd aq. sodium bicarbonate solution, the solvent was removed under reduced pressure to yield pure product 8-chloro-3-methyl-2-(4-methylpyridin-2-yl)-N-(5-morpholinopyridin-3-yl)quinolin-4-amine. $^1$H NMR (400 MHz, DMSO-$d_6$) δ ppm 8.70 (1H, s), 8.57 (1H, d, J=4.9 Hz), 8.02 (1H, dd, J=8.6, 1.2 Hz), 7.92 (1H, dd, J=7.5, 1.1 Hz), 7.82 (1H, d, J=2.5 Hz), 7.77 (1H, s), 7.53-7.57 (1H, m), 7.52 (1H, m), 7.34-7.36 (1H, m), 6.57 (1H, t, J=2.3 Hz), 3.68-3.72 (4H, m), 3.05-3.09 (4H, m), 2.47 (3H, s), 2.22 (3H, s). Mass Spectrum (ESI) m/e=446.1 (M+1).

The Buchwald coupled product was prepared according to Procedure H using dicyclohexyl(2',4',6'-triisopropylbiphenyl-2-yl)phosphine (0.020 g, 0.042 mmol), 5'-methoxy-5-morpholino-2,3'-bipyridin-3-amine (0.091 g, 0.32 mmol), 4,8-dichloro-3-methyl-2-(4-methylpyridin-2-yl)quinoline (0.08 g, 0.26 mmol) and $Pd_2dba_3$ (0.010 g, 0.011 mmol) and sodium tert-butoxide (0.063 g, 0.66 mmol) in toluene (2.6 mL) at 100° C. for 48.3 h. The crude product was purified by column chromatography on alumina (0 to 50% EtOAc in hexanes) to give the desired product 8-chloro-N-(5'-methoxy-5-morpholino-2,3'-bipyridin-3-yl)-3-methyl-2-(4-methylpyridin-2-yl)quinolin-4-amine. $^1$H NMR (400 MHz, DMSO-$d_6$) δ ppm 8.55 (1H, d, J=4.9 Hz), 8.35 (1H, s), 8.12 (2H, dd, J=4.6, 2.2 Hz), 7.89 (2H, dd, J=8.0, 2.3 Hz), 7.85 (1H, s), 7.66 (1H, s), 7.53 (1H, t, J=7.6 Hz), 7.34 (1H, m), 7.29 (1H, dd, J=2.7, 1.8 Hz), 5.70-5.72 (1H, m), 3.76 (3H, s), 3.60 (4H, t, J=4.8 Hz), 3.23 (4H, m), 2.46 (3H, s), 2.27 (3H, s). Mass Spectrum (ESI) m/e=553.3 (M+1).

Example 163

Preparation of 3-methyl-2-(4-methylpyridin-2-yl)-4-(5-morpholinopyridin-3-ylamino)quinoline-8-carbonitrile 3-Methyl-2-(4-methylpyridin-2-yl)-4-(5-morpholinopyridin-3-ylamino)-quinoline-8-carbonitrile

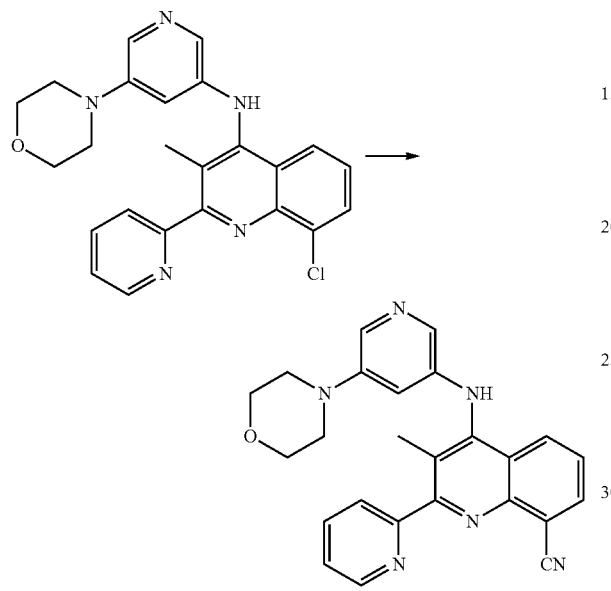

To a stirred solution of dicyclohexyl(2',4',6'-triisopropylbiphenyl-2-yl)phosphine (0.025 g, 0.053 mmol), tri-n-butyltin cyanide (0.104 g, 0.33 mmol), 8-chloro-3-methyl-2-(4-methylpyridin-2-yl)-N-(5-morpholinopyridin-3-yl)quinolin-4-amine (0.15 g, 0.33 mmol) and $Pd_2dba_3$ (0.012 g, 0.013 mmol) in toluene (3.30 mL) was added sodium tert-butoxide (0.079 g, 0.82 mmol). The reaction mixture was heated to 100° C. for 66 h. After which, the reaction mixture was filtered through a plug of alumina eluting with (EtOAc), the filtrate was cond in vacuo. The crude product was purified by column chromatography on alumina (0 to 50% EtOAc in hexanes) to give the desired product. The desired product was further purified with HPLC (10-90% of 0.1% TFA acetonitrile solution in 0.1% TFA water solution). The desired fractions were cond then diluted with EtOAc. After washing twice with satd aq. sodium bicarbonate solution, the solvent was removed under reduced pressure to yield pure product 3-methyl-2-(4-methylpyridin-2-yl)-4-(5-morpholinopyridin-3-ylamino)quinoline-8-carbonitrile. $^1$H NMR (400 MHz, $CD_2Cl_2$) δ ppm 8.59 (1H, d, J=5.5 Hz), 8.06 (2H, ddd, J=14.8, 7.9, 1.4 Hz), 7.86 (1H, d, J=2.5 Hz), 7.78-7.83 (1H, m), 7.67 (1H, d, J=2.3 Hz), 7.48 (1H, dd, J=8.5, 7.1 Hz), 7.27 (1H, m), 6.60 (1H, s), 6.43 (1H, t, J=2.3 Hz), 3.75 (4H, m), 3.05 (4H, m), 2.51 (3H, s), 2.36 (3H, s). Mass Spectrum (ESI) m/e=437.1 (M+1).

Example 164

Preparation of 4-(5'-methoxy-5-morpholino-2,3'-bipyridin-3-ylamino)-3-methyl-2-(4-methylpyridin-2-yl)quinoline-8-carbonitrile 4-(5'-Methoxy-5-morpholino-2,3'-bipyridin-3-ylamino)-3-methyl-2-(4-methylpyridin-2-yl)quinoline-8-carbonitrile

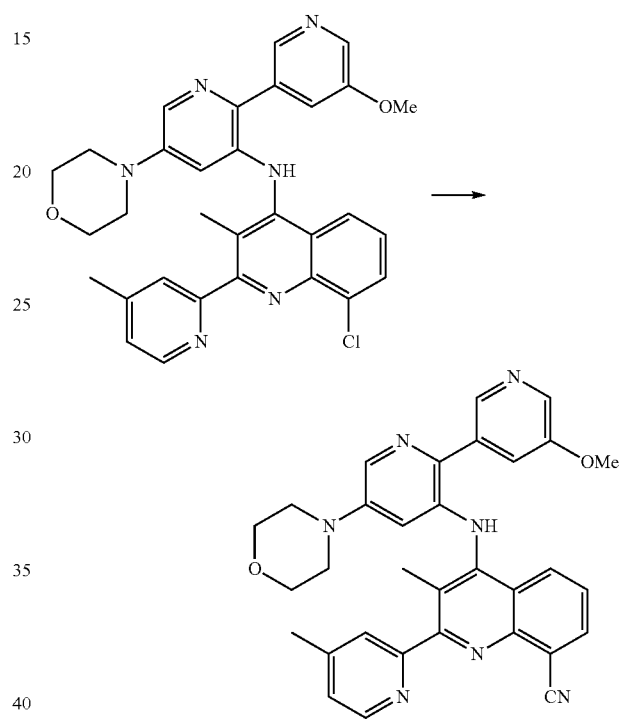

To a stirred solution of dicyclohexyl(2',4',6'-triisopropylbiphenyl-2-yl)phosphine (1.9 mg, 4.05 μmol), tri-n-butyltin cyanide (8.00 mg, 0.025 mmol), 8-chloro-N-(5'-methoxy-5-morpholino-2,3'-bipyridin-3-yl)-3-methyl-2-(4-methylpyridin-2-yl)quinolin-4-amine (0.014 g, 0.025 mmol) in 1-methylpyrrolidin-2-one (2.0 mL) was added $Pd_2dba_3$ (0.927 mg, 1.01 μmol). The reaction mixture was heated to 100° C. and stirred for 21.5 h. The crude product was filtered through a plug of alumina eluting with EtOAc. The filtrate was cond in vacuo. The crude product was purified by column chromatography on alumina (0 to 50% EtOAc in hexanes) to give the desired product. The desired product was further purified with HPLC (10-90% of 0.1% TFA acetonitrile solution in 0.1% TFA water solution). The desired fractions were cond then diluted with EtOAc. After washing twice with satd aq. sodium bicarbonate solution, the solvent was removed under reduced pressure to yield pure product 4-(5'-methoxy-5-morpholino-2,3'-bipyridin-3-ylamino)-3-methyl-2-(4-methylpyridin-2-yl)quinoline-8-carbonitrile. $^1$H NMR (400 MHz, $CD_2Cl_2$) δ ppm 8.53 (1H, d, J=5.1 Hz), 8.42 (1H, d, J=1.8 Hz), 8.30 (1H, d, J=2.7 Hz), 8.06-8.15 (2H, m), 7.97 (1H, s), 7.84 (1H, m), 7.56 (1H, dd, J=8.4, 7.2 Hz), 7.39 (1H, dd, J=2.8, 1.9 Hz), 7.24 (1H, m), 6.30 (1H, br. s.), 5.47 (1H, s), 3.90 (3H, s), 3.64 (4H, t, J=4.9 Hz), 3.25 (4H, br. s.), 2.50 (3H, s), 2.43 (3H, s). Mass Spectrum (ESI) m/e=544.2 (M+1).

Example 165

Preparation of 5,7-difluoro-N-(5'-fluoro-2'-methoxy-5-morpholino-2,4'-bipyridin-3-yl)-3-methyl-2-(pyridin-2-yl)quinolin-4-amine 5-Bromo-5'-fluoro-2'-methoxy-3-nitro-2,4'-bipyridine

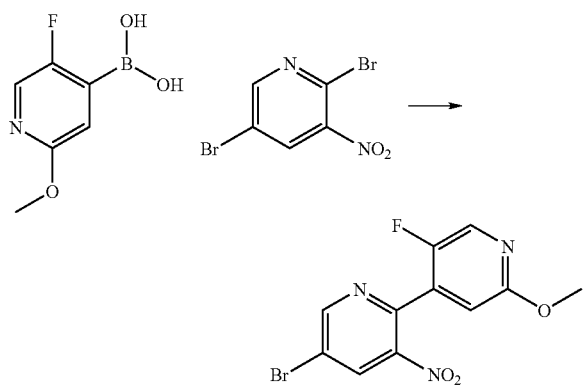

A mixture of 2,5-dibromo-3-nitropyridine, commercially available from Matrix Scientific (0.72 g, 2.55 mmol), 5-fluoro-2-methoxypyridin-4-ylboronic acid, commercially available from Asymchem (0.39 g, 2.34 mmol), dichlorobis(triphenyl-phosphine)palladium (II) (90 mg, 0.13 mmol), and 1.0M sodium carbonate (3.5 mL, 7.0 mmol) in 1,4-dioxane (10 mL) was degassed by nitrogen. The mixture was heated to 90° C. After 21.5 h, the reaction was cooled to rt then treated with water. After extracting twice with EtOAc, the organic layer was combined and dried over anhydrous magnesium sulfate. After filtration and concentration, the yellowish brown residue was treated with MeOH and placed on the rotoevaporator (without vac.) in a 45° C. water bath. After 30 min, the solid was filtered and rinsed twice with MeOH to afford a tan solid as 5-bromo-5'-fluoro-2'-methoxy-3-nitro-2,4'-bipyridine. $^1$H NMR (500 MHz, CDCl$_3$) δ ppm 9.01 (1H, d, J=2.0 Hz), 8.56 (1H, d, J=2.0 Hz), 8.06 (1H, d, J=1.2 Hz), 7.02 (1H, d, J=4.6 Hz), 4.04 (3H, m).

5-Bromo-5'-fluoro-2'-methoxy-2,4'-bipyridin-3-amine

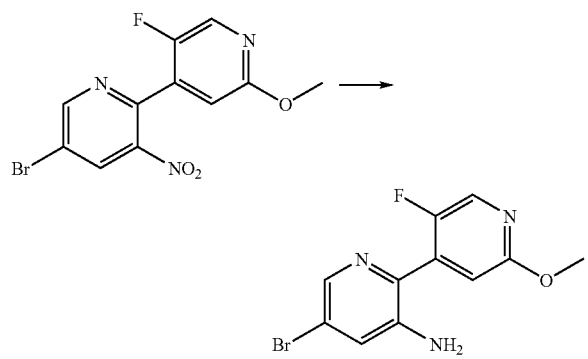

To a stirred mixture of 5-bromo-5'-fluoro-2'-methoxy-3-nitro-2,4'-bipyridine (0.22 g, 0.67 mmol) in EtOAc (15 mL) was added tin(II) chloride dihydrate (0.76 g, 3.37 mmol) in portions. Upon complete addition of the reducing agent, the mixture was carefully heated to 70° C. After 19 h, the reaction was cooled to rt and diluted with EtOAc, then washed with 1M NaOH, water, and brine. After drying over anhydrous sodium sulfate, filtration, and concentration, the residue was purified on basic alumina (0-15% EtOAc in hexanes) to afford a residue as 5-bromo-5'-fluoro-2'-methoxy-2,4'-bipyridin-3-amine. $^1$H NMR (500 MHz, CDCl$_3$) δ ppm 8.19 (1H, d, J=2.0 Hz), 8.13 (1H, d, J=1.5 Hz), 7.29 (1H, d, J=2.0 Hz), 6.89 (1H, d, J=4.9 Hz), 3.95 (3H, s).

N-(5-Bromo-5'-fluoro-2'-methoxy-2,4'-bipyridin-3-yl)-5,7-difluoro-3-methyl-2-(pyridin-2-yl)quinolin-4-amine

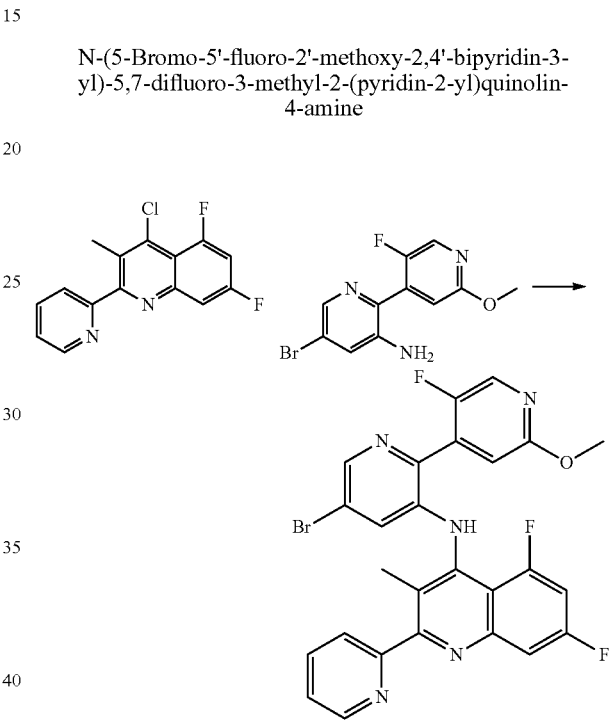

A dry flask containing 5-bromo-5'-fluoro-2'-methoxy-2,4'-bipyridin-3-amine (54.1 mg, 0.18 mmol) in dry DMF (3 mL) was cooled to 0° C., then sodium hydride, 60% dispersion in mineral oil (22.1 mg, 0.55 mmol) was added carefully in portions. The mixture was stirred at 0° C. for 15 min, then 4-chloro-5,7-difluoro-3-methyl-2-(pyridin-2-yl)quinoline (55.7 mg, 0.19 mmol) was added in portions. Upon complete addition, the mixture was warmed to 70° C. After 18 h, the reaction was cooled to rt then was carefully treated with 10% sodium carbonate solution. The black mixture was subsequently extracted 5 times with DCM:MeOH (90:10). The organic extraction was then washed one time with brine and dried over anhydrous magnesium sulfate. After filtration and concentration, the residue was purified on basic alumina (0-35% EtOAc in hexanes) to afford a yellow residue as N-(5-bromo-5'-fluoro-2'-methoxy-2,4'-bipyridin-3-yl)-5,7-difluoro-3-methyl-2-(pyridin-2-yl)quinolin-4-amine that was used without further purification.

5,7-Difluoro-N-(5'-fluoro-2'-methoxy-5-morpholino-2,4'-bipyridin-3-yl)-3-methyl-2-(pyridin-2-yl)quinolin-4-amine

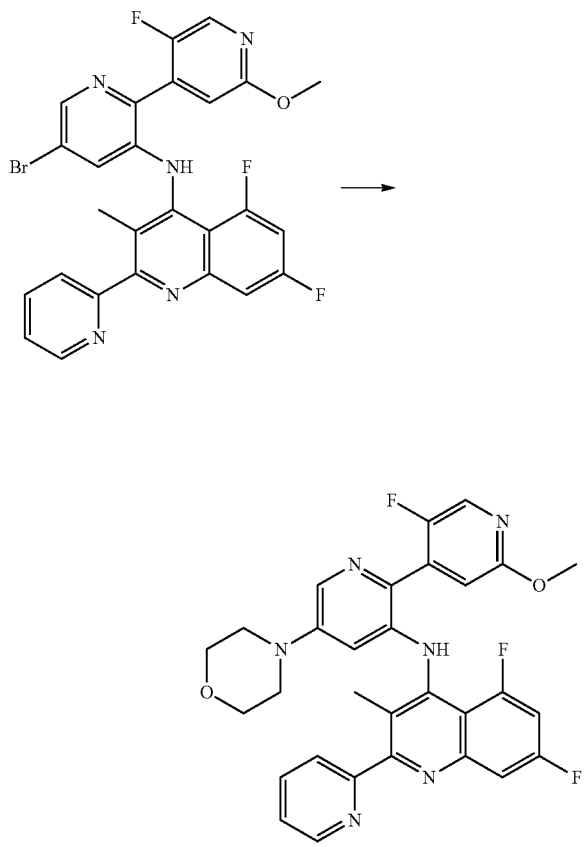

A mixture of N-(5-bromo-5'-fluoro-2'-methoxy-2,4'-bipyridin-3-yl)-5,7-difluoro-3-methyl-2-(pyridin-2-yl)quinolin-4-amine (50.2 mg, 0.091 mmol), morpholine (0.03 mL, 0.34 mmol), 2-dicyclohexylphosphino-2,4,6,-triisopropylbiphenyl (9.1 mg, 0.019 mmol), tris(dibenzylideneacetone)dipalladium (0) (8.5 mg, 9.28 µmol), and sodium tert-butoxide (26.7 mg, 0.28 mmol) in dry Toluene (3 mL) was degassed by nitrogen. The mixture was heated to 90° C. After 21.5 h, the reaction was cooled to rt, then treated with water. After extracting twice with EtOAc, the organic layer was combined and dried over anhydrous magnesium sulfate. After filtration and concentration, the light orange film was purified with HPLC 10-60% of 0.1% TFA acetonitrile solution in 0.1% TFA water solution. The impure fractions were further purified with SFC chromatography to afford a white solid as 5,7-difluoro-N-(5'-fluoro-2'-methoxy-5-morpholino-2,4'-bipyridin-3-yl)-3-methyl-2-(pyridin-2-yl)quinolin-4-amine.
$^1$H NMR (400 MHz, CDCl$_3$) δ ppm 8.68 (1H, br. s.), 8.10 (2H, t, J=2.0 Hz), 7.96 (2H, m), 7.66 (1H, m.), 7.38 (1H, m), 7.07 (2H, m), 6.61 (1H, m), 3.96 (3H, s), 3.91 (4H, m), 3.30 (4H, m), 2.17 (3H, s). Mass Spectrum (pos.) m/e: 559.2 (M+1).

Example 166

Preparation of 5,7-difluoro-N-(6'-methoxy-5-morpholino-2,3'-bipyridin-3-yl)-3-methyl-2-(pyridin-2-yl)quinolin-4-amine 5-Bromo-6'-methoxy-3-nitro-2,3'-bipyridine

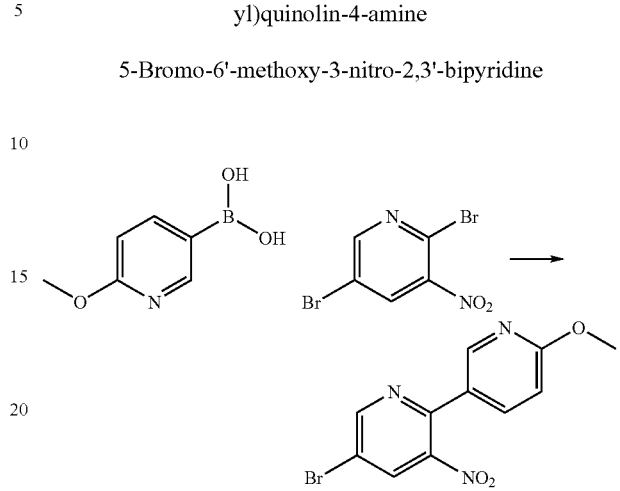

A mixture of 2,5-dibromo-3-nitropyridine (0.53 g, 1.88 mmol), 6-methoxypyr-3-ylboronic acid (0.29 g, 1.9 mmol), trans-dichlorobis(triphenylphosphine)palladium (II) (67.4 mg, 0.096 mmol) and 2.0M sodium carbonate (2.9 mL, 5.8 mmol) in 1,4-dioxane (6 mL) and was degassed by nitrogen. The mixture was heated to 90° C. After 7 h, the reaction was cooled to rt, then treated with water. After extracting twice with EtOAc, the organic layer was combined and dried over anhydrous magnesium sulfate. After filtration and concentration the residue was purified on silica gel (0-15% EtOAc in hexanes) to afford a yellow solid as 5-bromo-6'-methoxy-3-nitro-2,3'-bipyridine. $^1$H NMR (400 MHz, CDCl$_3$) δ ppm 8.92 (1H, d, J=2.0 Hz), 8.39 (1H, dd, J=2.5, 0.8 Hz), 8.32 (1H, d, J=2.0 Hz), 7.77 (1H, dd, J=8.8, 2.5 Hz), 6.87 (1H, m), 4.01 (3H, s).

5-Bromo-6'-methoxy-2,3'-bipyridin-3-amine

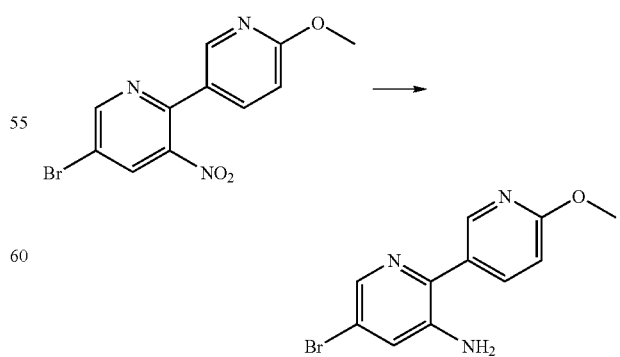

To a stirred mixture of 5-bromo-6'-methoxy-3-nitro-2,3'-bipyridine (0.34 g, 1.10 mmol) in EtOAc (10 mL) was added tin(II) chloride dihydrate (1.26 g, 5.57 mmol) in portions. Upon complete addition of the reducing agent, the mixture was carefully heated to 70° C. After 19 h, the reaction was cooled to rt and diluted with EtOAc, then washed with 1M NaOH, water, and brine. After drying over anhydrous sodium sulfate, filtration, and concentration, the residue was identified as mostly 5-bromo-6'-methoxy-2,3'-bipyridin-3-amine. $^1$H NMR (500 MHz, CDCl$_3$) δ ppm 8.50 (1H, d, J=2.4 Hz), 8.18 (1H, d, J=2.0 Hz), 7.90 (1H, dd, J=8.6, 2.4 Hz), 7.26 (1H, m), 6.88 (1H, d, J=8.6 Hz), 4.07 (5H, m).

N-(5-Bromo-6'-methoxy-2,3'-bipyridin-3-yl)-5,7-difluoro-3-methyl-2-(pyridin-2-yl)quinolin-4-amine (353.1 mg, 1.21 mmol) was added in portions. Upon complete addition, the mixture was warmed to 70° C. After 3 h, the reaction was cooled to rt then was carefully treated with 10% sodium carbonate solution. The black mixture was subsequently extracted 5 times with DCM:MeOH (90:10). The organic extraction was then washed one time with brine and dried over anhydrous magnesium sulfate. After filtration and concentration, the residue was purified on basic alumina (0-35% EtOAc in hexanes) to afford a yellow residue as mostly N-(5-bromo-6'-methoxy-2,3'-bipyridin-3-yl)-5,7-difluoro-3-methyl-2-(pyridin-2-yl)-quinolin-4-amine that was used without further purification.

5,7-Difluoro-N-(6'-methoxy-5-morpholino-2,3'-bipyridin-3-yl)-3-methyl-2-(pyridin-2-yl)quinolin-4-amine

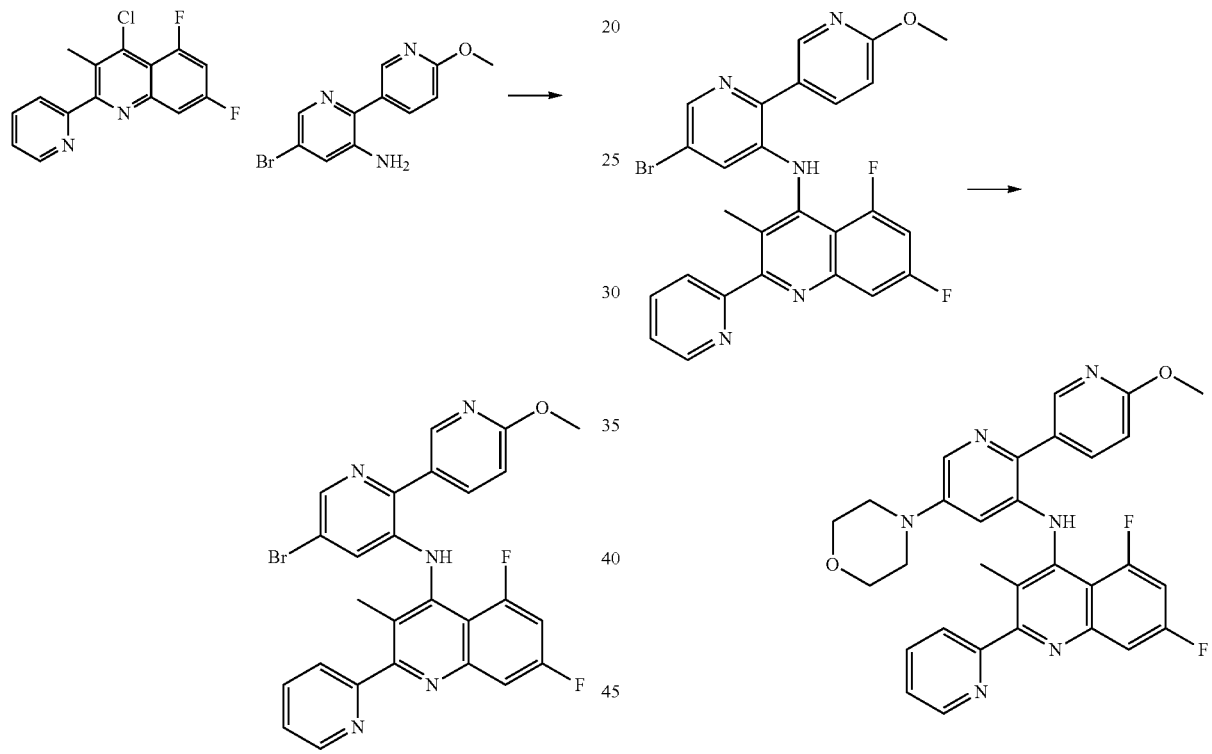

A dry flask containing 5-bromo-6'-methoxy-2,3'-bipyridin-3-amine (226.0 mg, 0.81 mmol) in dry DMF (5 mL) was cooled to 0° C., then sodium hydride, 60% dispersion in mineral oil (100.7 mg, 2.52 mmol) was added carefully in portions. The mixture was stirred at 0° C. for 15 min, then 4-chloro-5,7-difluoro-3-methyl-2-(pyridin-2-yl)quinoline A mixture of N-(5-bromo-6'-methoxy-2,3'-bipyridin-3-yl)-5,7-difluoro-3-methyl-2-(pyridin-2-yl)quinolin-4-amine (142.1 mg, 0.27 mmol), 2-dicyclohexylphosphino-2,4,6,-triisopropylbiphenyl, (X-Phos) (25.8 mg, 0.054 mmol), tris(dibenzylideneacetone)dipalladium (0) (25.1 mg, 0.027 mmol), morpholine (0.05 mL, 0.57 mmol), and sodium tert-butoxide (74.9 mg, 0.78 mmol) in dry toluene (5 mL) was degassed by nitrogen. The mixture was heated to 100° C. After 23 h, the reaction was cooled to rt then treated with water. After extracting twice with EtOAc, the organic layer was combined and dried over anhydrous magnesium sulfate. After filtration and concentration, the residue was purified on basic alumina (5-20% EtOAc in hexanes) to afford an impure orange residue that was further purified with SFC chromatography to afford a yellow solid as 5,7-difluoro-N-(6'-methoxymorpholino-2,3'-bipyridin-3-yl)-3-methyl-2-(pyridin-2-yl)quinolin-4-amine. $^1$H NMR (400 MHz, CDCl$_3$) δ ppm 8.74 (2H, m), 8.10 (2H, m), 7.95 (2H, m), 7.61 (1H, d, J=9.6 Hz), 7.39 (1H, ddd, J=6.7, 4.8, 2.0 Hz), 7.01 (3H, m), 6.53 (1H, d, J=2.3 Hz), 4.07 (3H, m), 3.91 (4H, m), 3.24 (4H, m), 2.23 (3H, s). Mass Spectrum (pos.) m/e: 541.2 (M+1).

Example 167

Preparation of 5,7-Difluoro-N-(2-(2-methoxyphenyl)-5-morpholinopyridin-3-yl)-3-methyl-2-(pyridin-2-yl)quinolin-4-amine 5-Bromo-2-(2-methoxyphenyl)-3-nitropyridine

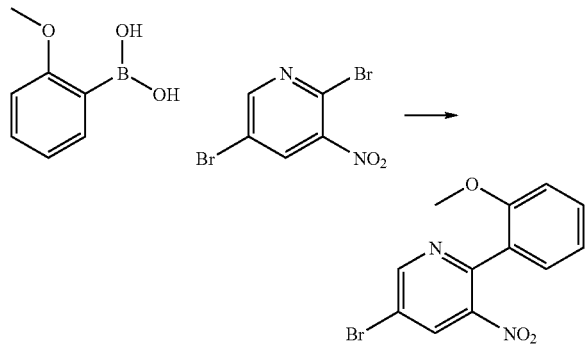

A mixture of 2,5-dibromo-3-nitropyridine (0.533 g, 1.89 mmol), 2-methoxyphenylboronic acid (0.29 g, 1.91 mmol), trans-dichlorobis(triphenylphosphine)-palladium (II) (68.9 mg, 0.098 mmol), and 2.0M sodium carbonate (2.9 mL, 5.8 mmol) in 1,4-dioxane (6 mL) was degassed by nitrogen. The mixture was heated to 90° C. After 7 h, the reaction was cooled to rt, then treated with water. After extracting twice with EtOAc, the organic layer was combined and dried over anhydrous magnesium sulfate. After filtration and concentration the residue was purified on silica gel (0-15% EtOAc in hexanes) to afford a yellow solid as 5-bromo-2-(2-methoxyphenyl)-3-nitropyridine. $^1$H NMR (400 MHz, CDCl$_3$) δ ppm 8.93 (1H, d, J=2.2 Hz), 8.37 (1H, d, J=2.0 Hz), 7.66 (1H, dd, J=7.6, 1.8 Hz), 7.51 (1H, m), 7.16 (1H, td, J=7.5, 1.0 Hz), 6.92 (1H, dd, J=8.3, 0.9 Hz), 3.72 (3H, s).

5-Bromo-2-(2-methoxyphenyl)pyridin-3-amine

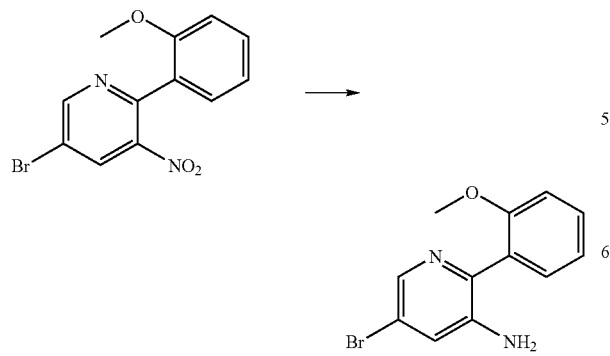

To a stirred mixture of 5-bromo-2-(2-methoxyphenyl)-3-nitropyridine (0.2618 g, 0.85 mmol) in EtOAc (10.0 mL) was added tin(II) chloride dihydrate (0.9667 g, 4.28 mmol) in portions. Upon complete addition of the reducing agent, the mixture was carefully heated to 70° C. After 19 h, the reaction was cooled to rt and diluted with EtOAc, then washed with 1M NaOH, water, and brine. After drying over anhydrous sodium sulfate, filtration, and concentration, the residue was identified as 5-bromo-2-(2-methoxyphenyl)pyridin-3-amine. $^1$H NMR (500 MHz, CDCl$_3$) δ ppm 8.19 (1H, d, J=2.0 Hz), 7.46 (2H, m), 7.24 (1H, d, J=1.2 Hz), 7.14 (1H, m), 7.03 (1H, d, J=8.3 Hz), 3.84 (3H, s).

N-(5-bromo-2-(2-methoxyphenyl)pyridin-3-yl)-5,7-difluoro-3-methyl-2-(pyridin-2-yl)quinolin-4-amine

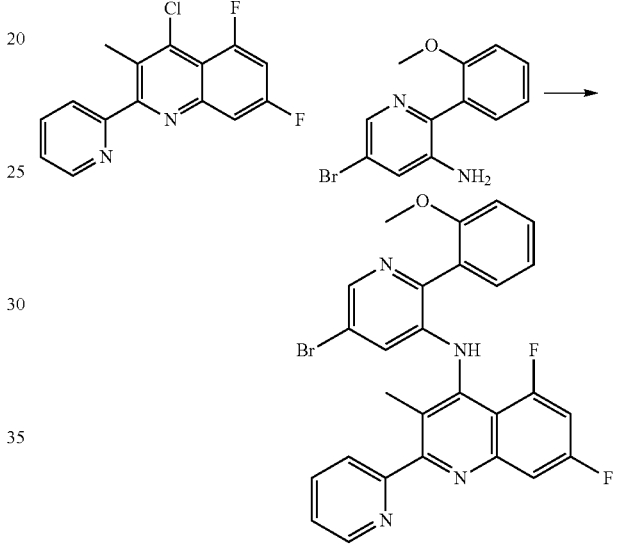

A dry flask containing 5-bromo-2-(2-methoxyphenyl)pyridin-3-amine (194.5 mg, 0.7 mmol) in dry DMF (5 mL) was cooled to 0° C., then sodium hydride, 60% dispersion in mineral oil (90.8 mg, 2.27 mmol) was added carefully in portions. The mixture was stirred at 0° C. for 15 min, then 4-chloro-5,7-difluoro-3-methyl-2-(pyridin-2-yl)quinoline (308.7 mg, 1.06 mmol) was added in portions. Upon complete addition, the mixture was warmed to 70° C. After 3 h, the reaction was cooled to rt then was carefully treated with 10% sodium carbonate solution. The black mixture was subsequently extracted 5 times with DCM:MeOH (90:10). The organic extraction was then washed one time with brine and dried over anhydrous magnesium sulfate. After filtration and concentration, the residue was purified on basic alumina (0-35% EtOAc in hexanes) to afford a yellow residue as mostly N-(5-bromo-2-(2-methoxyphenyl)pyridin-3-yl)-5,7-difluoro-3-methyl-2-(pyridin-2-yl)quinolin-4-amine that was used without further purification.

287

5,7-Difluoro-N-(2-(2-methoxyphenyl)-5-morpholinopyridin-3-yl)-3-methyl-2-(pyridin-2-yl)quinolin-4-amine

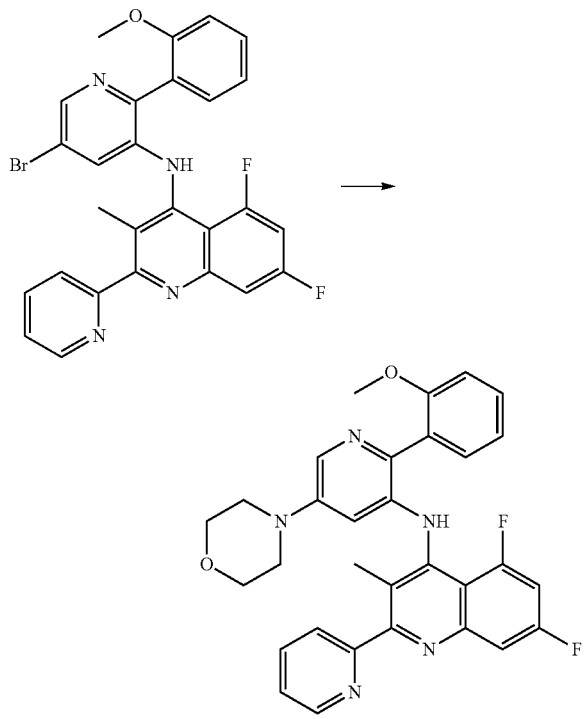

A mixture of N-(5-bromo-2-(2-methoxyphenyl)pyridin-3-yl)-5,7-difluoro-3-methyl-2-(pyridin-2-yl)quinolin-4-amine (84.1 mg, 0.158 mmol), 2-dicyclohexylphosphino-2,4,6,-triisopropylbiphenyl, (X-Phos) (16.6 mg, 0.035 mmol), tris(dibenzylideneacetone)dipalladium (0) (15.4 mg, 0.017 mmol), morpholine (0.03 mL, 0.345 mmol), and sodium tert-butoxide (47.8 mg, 0.5 mmol) in dry toluene (5 mL) was degassed by nitrogen. The mixture was heated to 100° C. After 23 h, the reaction was cooled to rt, then treated with water. After extracting twice with EtOAc, the organic layer was combined and dried over anhydrous magnesium sulfate. After filtration and concentration, the residue was purified on basic alumina (5-20% EtOAc in hexanes) to afford an impure orange residue. The light orange film was further purified with SFC chromatography to afford 5,7-difluoro-N-(2-(2-methoxyphenyl)-5-morpholinopyridin-3-yl)-3-methyl-2-(pyridin-2-yl)quinolin-4-amine. $^1$H NMR (400 MHz, CDCl$_3$) δ ppm 8.67 (1H, ddd, J=4.9, 1.8, 1.0 Hz), 8.10 (1H, d, J=2.5 Hz), 7.92 (1H, m), 7.75 (1H, d, J=7.8 Hz), 7.57 (1H, ddd, J=9.7, 2.5, 1.3 Hz), 7.49 (1H, dd, J=7.4, 1.8 Hz), 7.46 (1H, m), 7.34 (1H, ddd, J=7.6, 4.8, 1.3 Hz), 7.13 (1H, td, J=7.4, 1.0 Hz), 7.08 (1H, m), 6.96 (1H, ddd, J=13.4, 8.7, 2.3 Hz), 6.65 (1H, m), 3.95 (3H, s), 3.90 (4H, m), 3.29 (4H, m), 1.94 (3H, br. s.) Mass Spectrum (pos.) m/e: 540.3 (M+1).

288

Example 168

Preparation of N-(5-(3,6-dihydro-2H-pyran-4-yl)pyridin-3-yl)-5,7-difluoro-3-methyl-2-(4-methylpyridin-2-yl)quinolin-4-amine 5-(3,6-Dihydro-2H-pyran-4-yl)pyridin-3-amine

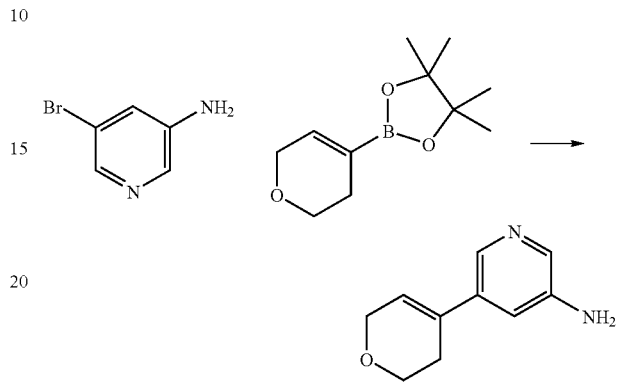

A stirred mixture of 3-amino-5-bromopyridine (0.25 g, 1.4 mmol), 2-(3,6-dihydro-2H-pyran-4-yl)-4,4,5,5-tetramethyl-1,3,2-dioxaborolane (0.33 g, 1.6 mmol), tetrakis(triphenylphosphine)palladium (83.3 mg, 0.072 mmol), and 2.0M sodium carbonate (3.6 mL, 7.2 mmol) in toluene (3.0 mL) and EtOH (1.0 mL) was heated to 70° C. After 19 h, the reaction was cooled to rt then diluted with water. After extraction with EtOAc, the organic extraction was dried over anhydrous sodium sulfate. After filtration and concentration, the residue was purified on basic alumina (0-35% EtOAc in hexanes) to afford a white solid as 5-(3,6-dihydro-2H-pyran-4-yl)pyridin-3-amine. $^1$H NMR (500 MHz, CDCl$_3$) δ ppm 8.05 (1H, d, J=2.0 Hz), 7.96 (1H, d, J=2.7 Hz), 6.95 (1H, m), 6.10 (1H, tt, J=2.9, 1.5 Hz), 4.28 (2H, q, J=2.9 Hz), 3.90 (2H, t, J=5.5 Hz), 3.81 (1H, br. s.), 2.48 (2H, m). Mass Spectrum (pos.) m/e: 177.1 (M+1).

N-(5-(3,6-Dihydro-2H-pyran-4-yl)pyridin-3-yl)-5,7-difluoro-3-methyl-2-(4-methylpyridin-2-yl)quinolin-4-amine

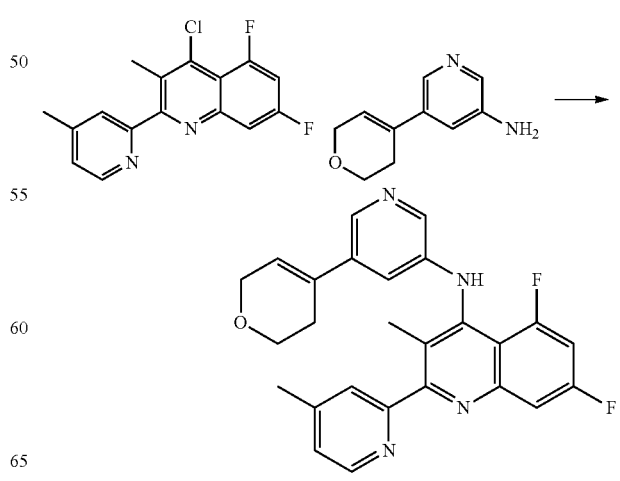

A mixture of 5-(3,6-dihydro-2H-pyran-4-yl)pyridin-3-amine (38.8 mg, 0.22 mmol), 4-chloro-5,7-difluoro-3-methyl-2-(4-methylpyridin-2-yl)quinoline (52.8 mg, 0.17 mmol), 2-dicyclohexylphosphino-2,4,6,-triisopropylbiphenyl, (X-Phos) (14.4 mg, 0.03 mmol), tris(dibenzylideneacetone)dipalladium (0) (7.2 mg, 7.9 µmol), and sodium tert-butoxide (45.1 mg, 0.47 mmol) in dry toluene (1.5 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on basic alumina (0-30% EtOAc in hexanes) to afford an orange film as N-(5-(3,6-dihydro-2H-pyran-4-yl)pyridin-3-yl)-5,7-difluoro-3-methyl-2-(4-methylpyridin-2-yl)quinolin-4-amine. $^1$H NMR (400 MHz, CDCl$_3$) δ ppm 8.63 (1H, m), 8.28 (1H, d, J=2.0 Hz), 8.17 (1H, d, J=2.5 Hz), 7.66 (2H, m), 7.20 (1H, ddd, J=5.0, 1.7, 0.8 Hz), 7.14 (1H, d, J=11.9 Hz), 7.10 (2H, m), 6.20 (1H, tt, J=3.0, 1.5 Hz), 4.32 (2H, q, J=2.7 Hz), 3.93 (2H, t, J=5.4 Hz), 2.55 (5H, m), 2.14 (3H, s). Mass Spectrum (pos.) m/e: 445.1 (M+1).

Example 169

Preparation of 5,7-difluoro-N-(2-(4-methoxyphenyl)-5-morpholinopyridin-3-yl)-3-methyl-2-(4-methylpyridin-2-yl)quinolin-4-amine 2,5-Dibromopyridin-3-amine

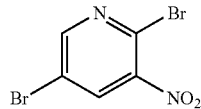  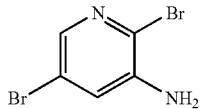

To a stirred mixture of 2,5-dibromo-3-nitropyridine (0.99 g, 3.5 mmol) in EtOAc (30 mL) was added tin(II) chloride dihydrate (4.0 g, 17.8 mmol) in portions. Upon complete addition of the reducing agent, the mixture was carefully heated to 90° C. After 2 h, the reaction was cooled to rt and diluted with EtOAc, then washed with 1M NaOH, water, and brine. After drying over anhydrous sodium sulfate and filtration, the organic solvent was removed under reduced pressure. The residue was identified as 2,5-dibromopyridin-3-amine. $^1$H NMR (400 MHz, DMSO-d$_6$) δ ppm 7.65 (1H, d, J=2.0 Hz), 7.27 (1H, d, J=2.3 Hz), 5.82 (1H, s).

5-Bromo-2-(4-methoxyphenyl)pyridin-3-amine

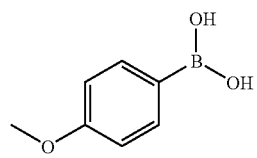  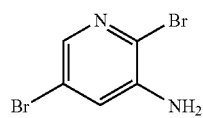

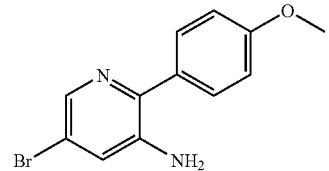

A stirred mixture of 2,5-dibromopyridin-3-amine (860 mg, 3.41 mmol), 4-methoxyphenylboronic acid (519 mg, 3.41 mmol), trans-dichlorobis(triphenylphosphine)palladium (II) (120.5 mg, 0.17 mmol), and 2.0M sodium carbonate (5.1 mL, 10.2 mmol) in 1,4-dioxane (15 mL) was heated to 90° C. After 19 h, the reaction was cooled to rt then diluted with water. After extraction with EtOAc, the organic extraction was dried over anhydrous sodium sulfate. After filtration and concentration, the residue was purified on silica gel (0-20% EtOAc in hexanes) to afford a white solid as 5-bromo-2-(4-methoxyphenyl)pyridin-3-amine. $^1$H NMR (400 MHz, CDCl$_3$) δ ppm 8.15 (1H, d, J=2.0 Hz), 7.65 (2H, m), 7.20 (1H, d, J=2.0 Hz), 7.06 (2H, m), 4.11 (5H, m).

2-(4-Methoxyphenyl)-5-morpholinopyridin-3-amine

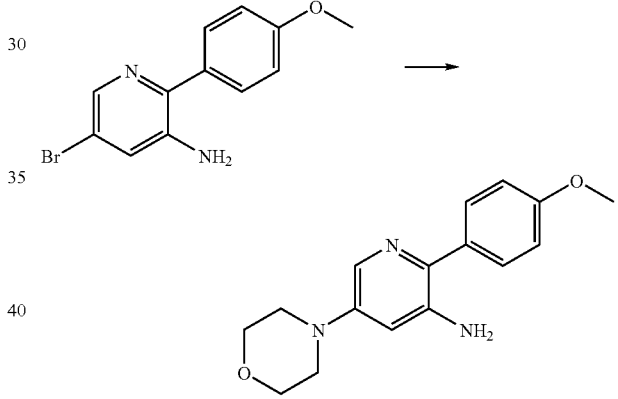

A mixture of 5-bromo-2-(4-methoxyphenyl)pyridin-3-amine (424.5 mg, 1.52 mmol), 2-dicyclohexylphosphino-2,4,6,-triisopropylbiphenyl, (X-Phos) (58.8 mg, 0.12 mmol), tris(dibenzylideneacetone)dipalladium (0) (56.1 mg, 0.061 mmol), and morpholine (0.66 mL, 7.58 mmol) in dry THF (3.2 mL) was degassed by nitrogen. To this mixture was added lithium bis(trimethylsilyl)amide, 1.0M in THF (8.4 mL, 8.40 mmol) dropwise, and the resulting reaction was heated to 60° C. After 2.5 h, the reaction was cooled to rt then poured into water. After extracting twice with EtOAc and twice with DCM, the combined organic layers were dried over anhydrous magnesium sulfate. After filtration and concentration, the residue was purified on silica gel (0-100% DCM in EtOAc) to yield 2-(4-methoxyphenyl)-5-morpholinopyridin-3-amine. $^1$H NMR (400 MHz, CDCl$_3$) δ ppm 7.84 (1H, d, J=2.5 Hz), 7.57 (2H, m), 6.98 (2H, m), 6.53 (1H, d, J=2.5 Hz), 3.92 (9H, m), 3.22 (4H, m). Mass Spectrum (pos.) m/e: 286.1 (M+1).

5,7-Difluoro-N-(2-(4-methoxyphenyl)-5-morpholinopyridin-3-yl)-3-methyl-2-(4-methylpyridin-2-yl)quinolin-4-amine

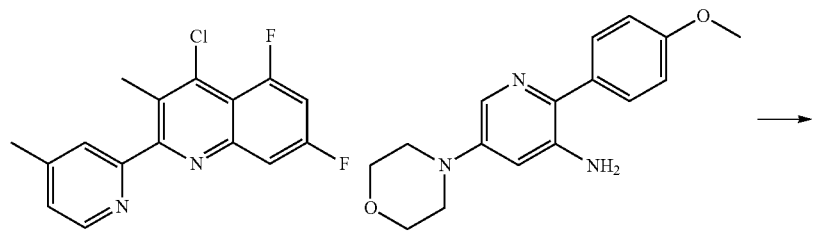

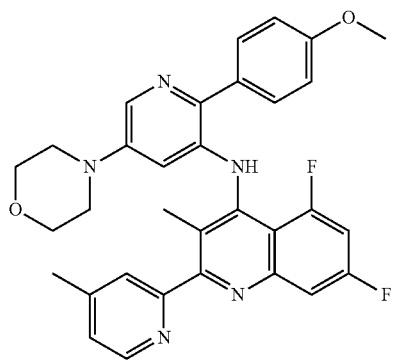

A mixture of 2-(4-methoxyphenyl)-5-morpholinopyridin-3-amine (60.3 mg, 0.21 mmol), 4-chloro-5,7-difluoro-3-methyl-2-(4-methylpyridin-2-yl)quinoline (52.0 mg, 0.17 mmol), 2-dicyclohexylphosphino-2,4,6,-triisopropylbiphenyl, (X-Phos) (14.7 mg, 0.031 mmol), tris(dibenzylideneacetone)dipalladium (0) (6.8 mg, 7.43 μmol), and sodium tert-butoxide (42.9 mg, 0.45 mmol) in dry toluene (1.5 mL) was degassed by nitrogen. The resulting reaction was heated to 100° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on basic alumina (10-40% EtOAc in hexanes) to afford a >80% pure light yellow film that was triturated with isopropanol to afford a light yellow solid as 5,7-difluoro-N-(2-(4-methoxyphenyl)-5-morpholinopyridin-3-yl)-3-methyl-2-(4-methylpyridin-2-yl)-quinolin-4-amine. $^1$H NMR (400 MHz, CDCl$_3$) δ ppm 8.54 (1H, d, J=5.1 Hz), 8.00 (1H, d, J=2.3 Hz), 7.81 (4H, m), 7.61 (1H, d, J=9.6 Hz), 7.20 (1H, d, J=4.7 Hz), 7.10 (4H, m), 6.53 (1H, d, J=2.3 Hz), 3.99 (7H, m), 3.26 (4H, m), 2.48 (3H, s), 2.21 (3H, s). Mass Spectrum (pos.) m/e: 554.2 (M+1).

Example 170

Preparation 5,7-difluoro-N-(2-(6-methoxypyridin-3-yl)-5-morpholinophenyl)-3-methyl-2-(4-methylpyridin-2-yl)quinolin-4-amine 2-Chloro-5-morpholinoaniline

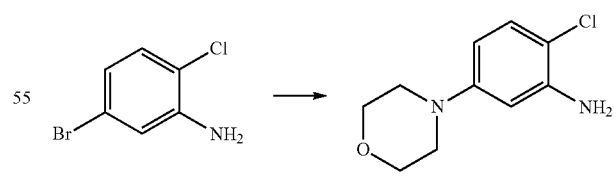

A mixture of 5-bromo-2-chloroaniline (1.09 g, 5.29 mmol), 2-dicyclohexylphosphino-2,4,6,-triisopropylbiphenyl, (X-Phos) (202 mg, 0.42 mmol), tris(dibenzylideneacetone)dipalladium (0) (198 mg, 0.22 mmol), and morpholine (2.3 mL, 26.4 mmol) in dry THF (12 mL) was degassed by nitrogen. To this mixture was added lithium bis(trimethylsilyl)amide, 1.0M in THF (25.0 mL, 25.0 mmol) dropwise, and the resulting reaction was heated to 60° C. After 2.5 h, the reaction was cooled to rt then poured into water. After extracting twice with EtOAc and twice with DCM, the combined organic layers were dried over anhydrous magnesium sulfate. After filtration and concentration, the residue was purified on silica gel (0-45% EtOAc in hexanes) to yield 2-chloro-5-morpholinoaniline. $^1$H NMR (400 MHz, CDCl$_3$) δ ppm 7.12 (1H, d, J=8.6 Hz), 6.42 (2H, m), 4.00 (2H, br. s.), 3.93 (4H, m), 3.22 (4H, m).

2-(6-Methoxypyridin-3-yl)-5-morpholinoaniline

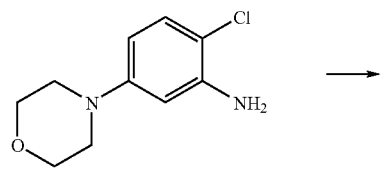

organic extractions were combined and washed twice with brine. After drying over anhydrous sodium sulfate and filtration, the organic solvent was removed under reduced pressure. The residue was purified over basic alumina (0-20% EtOAc in hexanes) to afford a tan solid as 2-(6-methoxypyridin-3-yl)-5-morpholinoaniline. $^1$H NMR (400 MHz, DMSO-d$_6$) δ ppm 8.12 (1H, d, J=1.8 Hz), 7.69 (1H, dd, J=8.6, 2.5 Hz), 6.92 (2H, m), 6.34 (1H, d, J=2.3 Hz), 6.28 (1H, dd, J=8.4, 2.5 Hz), 4.68 (2H, s), 3.87 (3H, s), 3.78 (4H, m), 3.12 (4H, m). Mass Spectrum (pos.) m/e: 286.1 (M+1).

5,7-Difluoro-N-(2-(6-methoxypyridin-3-yl)-5-morpholinophenyl)-3-methyl-2-(4-methylpyridin-2-yl)quinolin-4-amine

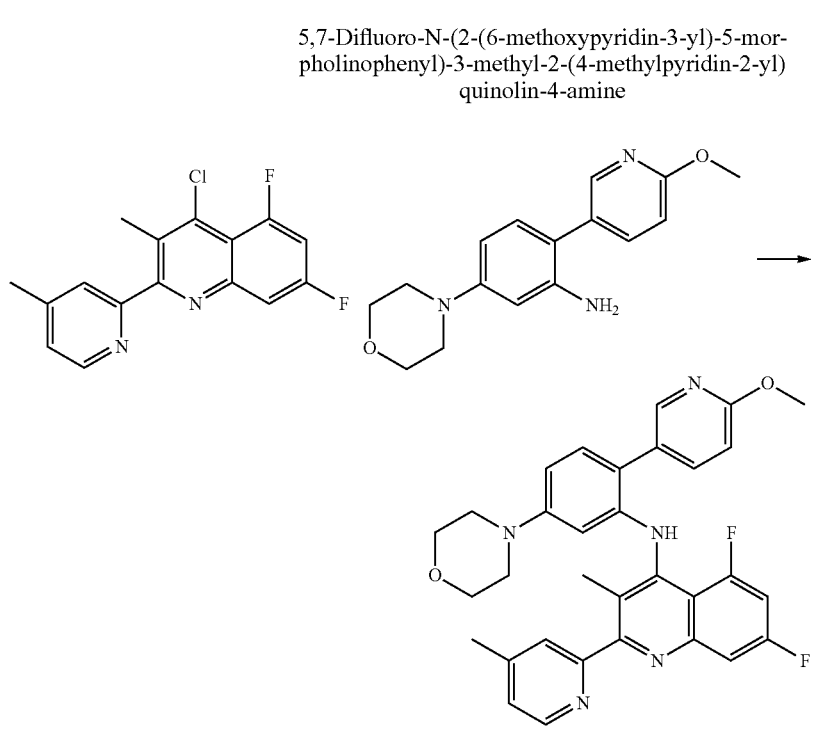

-continued

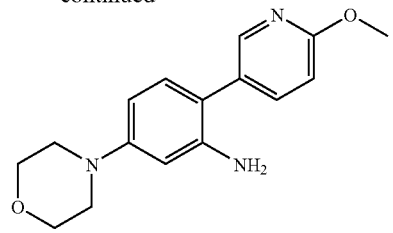

A stirred mixture of 2-chloro-5-morpholinoaniline (608 mg, 2.86 mmol), grounded 2-dicyclohexylphosphino-2,6-dimethoxybiphenyl, (S-Phos) (236 mg, 0.57 mmol), palladium (II) acetate (64.7 mg, 0.29 mmol), 6-methoxypyridin-3-ylboronic acid (876 mg, 5.72 mmol), and potassium phosphate tribasic (1.82 g, 8.59 mmol) in DMF (7.0 mL) and water (0.3 mL) was purged 3 times with argon and placed under vacuum 3 times. The reaction mixture was carefully heated to 90° C. After 21 h, the reaction was cooled to rt, then diluted with water and extracted 3 times with EtOAc. The A mixture of 2-(6-methoxypyridin-3-yl)-5-morpholinoaniline (61.1 mg, 0.21 mmol), 4-chloro-5,7-difluoro-3-methyl-2-(4-methylpyridin-2-yl)quinoline (53.9 mg, 0.18 mmol), 2-dicyclohexylphosphino-2,4,6,-triisopropylbiphenyl, (X-Phos) (17.2 mg, 0.036 mmol), tris(dibenzylideneacetone)dipalladium (0) (7.1 mg, 7.75 mmol), and sodium tert-butoxide (44.4 mg, 0.46 mmol) in dry toluene (1.5 mL) was degassed by nitrogen. The resulting reaction was heated to 100° C. and monitored with TLC and LC-MS. After 20 h, the reaction was cooled to rt then poured into water. After extracting twice with EtOAc and twice with DCM, the combined organic extractions were dried over anhydrous magnesium sulfate. After filtration and concentration, the residue was purified on basic alumina (10-30% EtOAc in hexanes) to afford an impure orange residue. The light orange film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield an orange solid as 5,7-difluoro-N-(2-(6-methoxypyridin-3-yl)-5-morpholinophenyl)-3-methyl-2-(4-methylpyridin-2-yl)quinolin-4-amine. $^1$H NMR (400 MHz, DMSO-d$_6$) δ ppm 8.64 (1H, d, J=5.1 Hz), 7.99 (1H, d, J=2.2 Hz), 7.65 (1H, m), 7.58 (4H, m), 7.14 (1H, d, J=8.4 Hz), 6.80 (1H, d, J=7.8 Hz), 6.62 (2H, d, J=8.6 Hz), 3.84 (7H, m), 3.18 (4H, m), 2.48 (3H, s), 2.06 (3H, s). Mass Spectrum (pos.) m/e: 554.2 (M+1).

Example 171

Preparation 5,7-difluoro-N-(2-(6-methoxypyridin-3-yl)-5-morpholinophenyl)-3-methyl-2-(pyridin-2-yl)quinolin-4-amine 5,7-Difluoro-N-(2-(6-methoxypyridin-3-yl)-5-morpholinophenyl)-3-methyl-2-(pyridin-2-yl)quinolin-4-amine orange residue. The light orange film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a light yellow solid as 5,7-difluoro-N-(2-(6-methoxypyridin-3-yl)-5-morpholinophenyl)-3-methyl-2-(pyridin-2-yl)quinolin-4-amine. $^1$H NMR (400 MHz, DMSO-d$_6$) δ ppm 8.68 (1H, ddd, J=4.8, 1.7, 1.0 Hz), 8.13 (1H, m), 7.99 (1H, td, J=7.7, 1.7 Hz), 7.78 (1H, dt, J=7.8, 1.0 Hz), 7.69 (2H, m), 7.55 (2H, m), 7.43 (1H, m), 7.06 (1H, d, J=8.4 Hz), 6.69 (1H, dd, J=8.4, 0.6 Hz), 6.66 (1H, m), 6.26 (1H, d, J=2.3 Hz), 3.80 (3H, s), 3.72 (4H, m), 3.05 (4H, m), 2.09 (3H, s). Mass Spectrum (pos.) m/e: 540.3 (M+1).

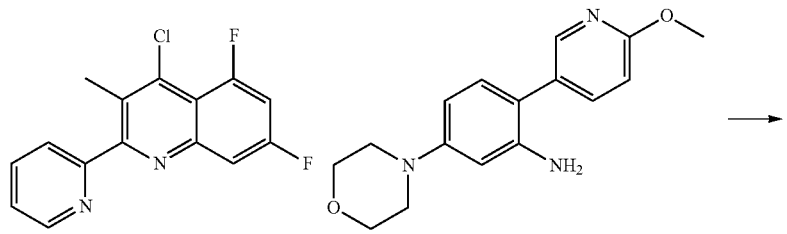

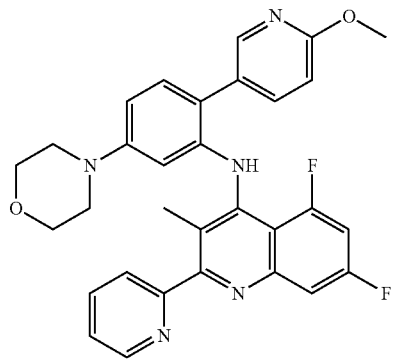

A mixture of 2-(6-methoxypyridin-3-yl)-5-morpholinoaniline (60.7 mg, 0.21 mmol), 4-chloro-5,7-difluoro-3-methyl-2-(pyridin-2-yl)quinoline (50.9 mg, 0.17 mmol), 2-dicyclohexylphosphino-2,4,6,-triisopropylbiphenyl, (X-Phos) (13.9 mg, 0.029 mmol), tris(dibenzylideneacetone)dipalladium (0) (6.5 mg, 7.10 μmol), and sodium tert-butoxide (43.3 mg, 0.45 mmol) in dry toluene (1.5 mL) was degassed by nitrogen. The resulting reaction was heated to 100° C. and monitored with TLC and LC-MS. After 21 h, the reaction was cooled to rt then poured into water. After extracting twice with EtOAc and twice with DCM, the combined organic extractions were dried over anhydrous magnesium sulfate. After filtration and concentration, the residue was purified on basic alumina (10-30% EtOAc in hexanes) to afford an impure

Example 172

Preparation of 5,7-difluoro-N-(6'-methoxy-5-morpholino-2,3'-bipyridin-3-yl)-3-methyl-2-(4-methylpyridin-2-yl)quinolin-4-amine 5-Bromo-6'-methoxy-3-nitro-2,3'-bipyridine

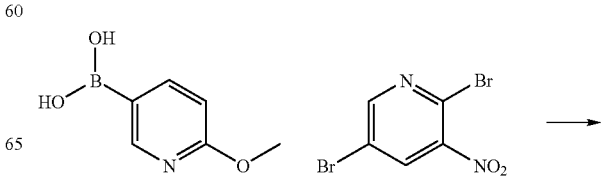

J=2.4, 0.7 Hz), 7.98 (2H, m), 7.34 (1H, d, J=2.0 Hz), 6.90 (1H, dd, J=8.6, 0.7 Hz), 5.49 (2H, s), 3.90 (3H, s).

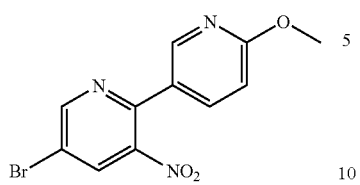

A stirred mixture of 2,5-dibromo-3-nitropyridine (1.57 g, 5.57 mmol), 6-methoxypyridin-3-ylboronic acid (1.03 g, 6.73 mmol), trans-dichlorobis(triphenylphosphine)palladium (II) (0.2 g, 0.28 mmol), and 2.0M sodium carbonate (8.4 mL, 16.8 mmol) in 1,4-dioxane (27 mL) was heated to 90° C. After 19 h, the reaction was cooled to rt then diluted with water. After extraction with EtOAc, the organic extraction was dried over anhydrous sodium sulfate. After filtration and concentration, the residue was purified on silica gel (0-20% EtOAc in hexanes) to afford a light yellow solid as 5-bromo-6'-methoxy-3-nitro-2,3'-bipyridine. $^1$H NMR (400 MHz, CDCl$_3$) δ ppm 8.92 (1H, d, J=2.2 Hz), 8.40 (1H, dd, J=2.5, 0.6 Hz), 8.32 (1H, d, J=2.2 Hz), 7.78 (1H, dd, J=8.6, 2.5 Hz), 6.85 (1H, dd, J=8.7, 0.7 Hz), 4.02 (3H, s).

5-Bromo-6'-methoxy-2,3'-bipyridin-3-amine

To a stirred mixture of 5-bromo-6'-methoxy-3-nitro-2,3'-bipyridine (776.9 mg, 2.50 mmol) in EtOAc (25 mL) was added tin(II) chloride dihydrate (2.83 g, 12.56 mmol) in portions. Upon complete addition of the reducing agent, the mixture was carefully heated to 90° C. After 2 h, the reaction was cooled to rt and diluted with EtOAc, then washed with 1M NaOH, water, and brine. After drying over anhydrous sodium sulfate, filtration, and concentration, the light tan solid was identified as 5-bromo-6'-methoxy-2,3'-bipyridin-3-amine. $^1$H NMR (500 MHz, DMSO-d$_6$) δ ppm 8.42 (1H, dd, 6'-Methoxy-5-morpholino-2,3'-bipyridin-3-amine

A mixture of 5-bromo-6'-methoxy-2,3'-bipyridin-3-amine (711 mg, 2.54 mmol), morpholine (1.1 mL, 12.63 mmol), 2-dicyclohexylphosphino-2,4,6,-triisopropyl-biphenyl, (X-Phos) (97.7 mg, 0.21 mmol), and tris(dibenzylideneacetone)-dipalladium (0) (93.8 mg, 0.102 mmol) in dry THF (6.0 mL) was degassed by nitrogen. To this mixture was added lithium bis(trimethylsilyl)amide, 1.0M in THF (14.0 mL, 14.0 mmol) dropwise, and the resulting reaction was heated to 60° C. After 2.5 h, the reaction was cooled to rt then poured into water. After extracting twice with EtOAc and twice with DCM, the combined organic layers were dried over anhydrous magnesium sulfate. After filtration and concentration, the residue was purified on silica gel (0-60% of 89:9:1 DCM:MeOH:ammonium hydroxide in DCM) to afford an orange tan solid as 6'-methoxy-5-morpholino-2,3'-bipyridin-3-amine. $^1$H NMR (400 MHz, CDCl$_3$) δ ppm 8.46 (1H, dd, J=2.4, 0.7 Hz), 7.90 (2H, m), 6.83 (1H, dd, J=8.6, 0.8 Hz), 6.53 (1H, d, J=2.5 Hz), 3.97 (3H, s), 3.89 (4H, m), 3.78 (2H, s), 3.21 (4H, m). Mass Spectrum (pos.) m/e: 287.0 (M+1).

5,7-Difluoro-N-(6'-methoxy-5-morpholino-2,3'-bipyridin-3-yl)-3-methyl-2-(4-methylpyridin-2-yl)quinolin-4-amine

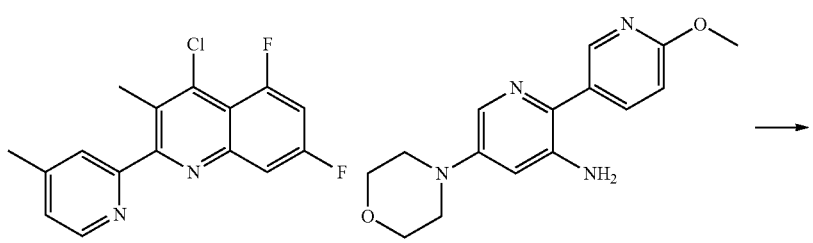

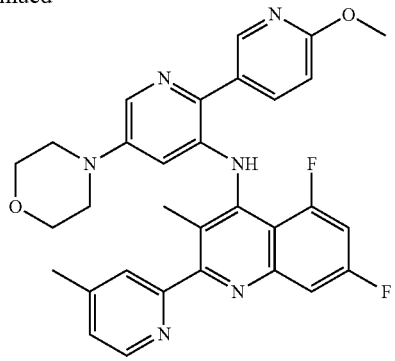

A mixture of 6'-methoxy-5-morpholino-2,3'-bipyridin-3-amine (51.7 mg, 0.18 mmol), 4-chloro-5,7-difluoro-3-methyl-2-(4-methylpyridin-2-yl)quinoline (45.2 mg, 0.15 mmol), 2-dicyclohexylphosphino-2,4,6,-triisopropylbiphenyl, (X-Phos) (12.6 mg, 0.026 mmol), tris(dibenzylideneacetone)dipalladium (0) (6.4 mg, 6.99 μmol), and sodium tert-butoxide (36.6 mg, 0.38 mmol) in dry toluene (1.5 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on basic alumina (5-50% EtOAc in hexanes) to afford an impure orange residue. The light orange film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a light yellow solid as 5,7-difluoro-N-(6'-methoxy-5-morpholino-2,3'-bipyridin-3-yl)-3-methyl-2-(4-methylpyridin-2-yl)quinolin-4-amine. $^1$H NMR (400 MHz, CDCl$_3$) δ ppm 8.65 (1H, dd, J=2.4, 0.7 Hz), 8.54 (1H, dd, J=4.9, 0.6 Hz), 8.08 (2H, m), 7.71 (1H, m), 7.61 (1H, ddd, J=9.7, 2.4, 1.4 Hz), 7.20 (1H, ddd, J=5.0, 1.6, 0.8 Hz), 7.00 (3H, m), 6.53 (1H, d, J=2.5 Hz), 4.00 (3H, s), 3.92 (4H, m), 3.25 (4H, m), 2.49 (3H, s), 2.21 (3H, s). Mass Spectrum (pos.) m/e: 555.2 (M+1).

Example 173

Preparation of 5,7-difluoro-3-methyl-2-(pyridin-2-yl)-N-(5-(tetrahydro-2H-pyran-4-yl)pyridin-3-yl)quinolin-4-amine 5-(Tetrahydro-2H-pyran-4-yl)pyridin-3-amine

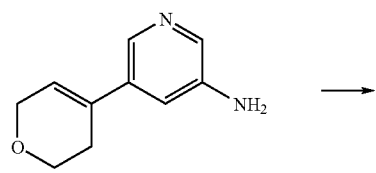

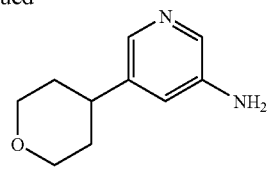

To a flask containing 5-(3,6-dihydro-2H-pyran-4-yl)pyridin-3-amine (61.6 mg, 0.35 mmol) in EtOAc (3.0 mL) and EtOH (1.0 mL) was added 10% palladium on activated carbon (75.7 mg, 0.071 mmol). After purging, the mixture was stirred under an atmosphere of hydrogen at 23° C. The reaction was monitored with TLC and LC-MS. After 19 h, the reaction was filtered through Celite™. After concentration, the residue was identified as 5-(tetrahydro-2H-pyran-4-yl)pyridin-3-amine that was used without purification. Mass Spectrum (pos.) m/e: 179.1 (M+1).

5,7-Difluoro-3-methyl-2-(pyridin-2-yl)-N-(5-(tetrahydro-2H-pyran-4-yl)-pyridin-3-yl)quinolin-4-amine

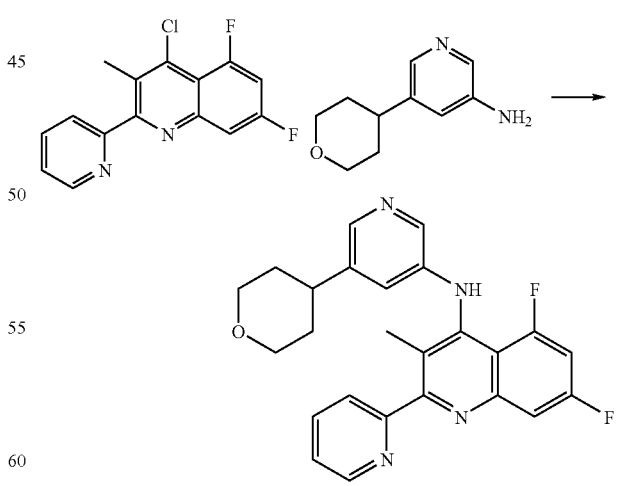

A mixture of 5-(tetrahydro-2H-pyran-4-yl)pyridin-3-amine (71.7 mg, 0.40 mmol), 4-chloro-5,7-difluoro-3-methyl-2-(pyridin-2-yl)quinoline (96.7 mg, 0.33 mmol), 2-dicyclohexylphosphino-2,4,6,-triisopropylbiphenyl, (X-Phos) (25.9 mg, 0.054 mmol), tris(dibenzylideneacetone)dipalladium (0) (12.8 mg, 0.014 mmol), and sodium tert-butoxide (88.8 mg, 0.92 mmol) in dry Toluene (2.0 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on basic alumina (0-70% EtOAc in hexanes) to afford an impure orange residue. The light orange film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a light yellow film as 5,7-difluoro-3-methyl-2-(pyridin-2-yl)-N-(5-(tetrahydro-2H-pyran-4-yl)pyridin-3-yl)-quinolin-4-amine. $^1$H NMR (500 MHz, CDCl$_3$) δ ppm 8.79 (1H, m), 8.23 (1H, d, J=2.4 Hz), 8.12 (1H, d, J=1.7 Hz), 7.94 (2H, m), 7.65 (1H, ddd, J=9.5, 2.4, 1.2 Hz), 7.39 (1H, ddd, J=7.5, 4.9, 1.3 Hz), 7.25 (2H, br. s.), 7.08 (2H, m), 4.12 (2H, m), 3.59 (2H, m), 2.85 (1H, m), 2.18 (3H, s), 1.86 (4H, m). Mass Spectrum (pos.) m/e: 433.1 (M+1).

Example 174

Preparation of 5,7-difluoro-N-(2'-methoxy-5-morpholino-2,3'-bipyridin-3-yl)-3-methyl-2-(pyridin-2-yl)quinolin-4-amine 2-Chloro-5-morpholinopyridin-3-amine

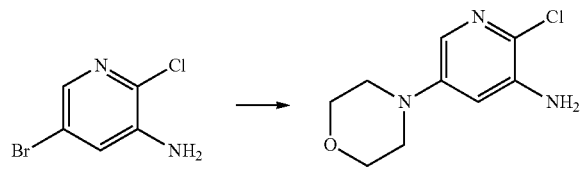 [SMILES: Nc1cc(Br)cnc1Cl ; Nc1cc(N2CCOCC2)cnc1Cl]

A mixture of 5-bromo-2-chloropyridin-3-amine (1.01 g, 4.89 mmol), morpholine (0.85 mL, 9.76 mmol), 2-dicyclohexylphosphino-2,4,6,-triisopropylbiphenyl, (X-Phos) (187.2 mg, 0.39 mmol), and tris(dibenzylideneacetone)dipalladium (0) (180.6 mg, 0.20 mmol) in dry THF (10 mL) was degassed by nitrogen. To this mixture was added lithium bis(trimethylsilyl)amide, 1.0M in THF (15.0 mL, 15.0 mmol) dropwise, and the resulting reaction was heated to 60° C. After 2.5 h, the reaction was cooled to rt then poured into water. After extracting twice with EtOAc and twice with DCM, the combined organic layers were dried over anhydrous magnesium sulfate. After filtration and concentration, the residue was purified on basic alumina (0-20% EtOAc in hexanes) to afford an off-white solid as 2-chloro-5-morpholinopyridin-3-amine. $^1$H NMR (400 MHz, CDCl$_3$) δ ppm 7.49 (1H, d, J=2.7 Hz), 6.57 (1H, d, J=2.7 Hz), 3.93 (4H, m), 3.49 (2H, s), 3.22 (4H, m).

N-(2-Chloro-5-morpholinopyridin-3-yl)-5,7-difluoro-3-methyl-2-(pyridin-2-yl)quinolin-4-amine

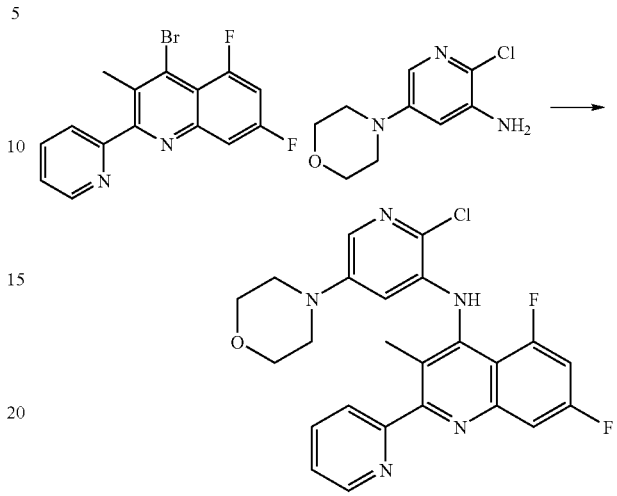

A mixture of 2-chloro-5-morpholinopyridin-3-amine (183.1 mg, 0.86 mmol), 4-bromo-5,7-difluoro-3-methyl-2-(pyridin-2-yl)quinoline (160.1 mg, 0.48 mmol), 2-dicyclohexylphosphino-2,4,6,-triisopropylbiphenyl, (X-Phos) (37.7 mg, 0.079 mmol), tris(dibenzylideneacetone)dipalladium (0) (17.5 mg, 0.019 mmol), and sodium tert-butoxide (120.7 mg, 1.26 mmol) in dry toluene (3.0 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on basic alumina (5-20% EtOAc in hexanes) to afford a light yellow solid as N-(2-chloro-5-morpholinopyridin-3-yl)-5,7-difluoro-3-methyl-2-(pyridin-2-yl)quinolin-4-amine. $^1$H NMR (500 MHz, CDCl$_3$) δ ppm 8.69 (1H, dt, J=4.8, 1.3 Hz), 7.98 (2H, m), 7.73 (2H, m), 7.41 (1H, q, J=4.8 Hz), 7.21 (1H, d, J=9.8 Hz), 7.07 (1H, ddd, J=13.2, 8.6, 2.4 Hz), 6.42 (1H, d, J=2.7 Hz), 3.86 (4H, m), 3.71 (1H, s), 3.17 (4H, m), 2.21 (3H, s). Mass Spectrum (pos.) m/e: 468.1 (M+1).

5,7-Difluoro-N-(2'-methoxy-5-morpholino-2,3'-bipyridin-3-yl)-3-methyl-2-(pyridin-2-yl)quinolin-4-amine

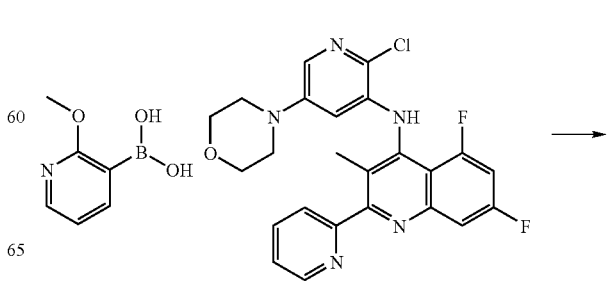

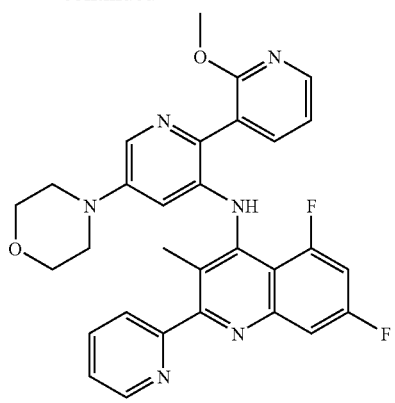

A stirred mixture of N-(2-chloro-5-morpholinopyridin-3-yl)-5,7-difluoro-3-methyl-2-(pyridin-2-yl)quinolin-4-amine (50.1 mg, 0.11 mmol), 2-methoxypyridin-3-ylboronic acid (32.9 g, 0.22 mmol), ground 2-dicyclohexylphosphino-2,6-dimethoxybiphenyl, (S-Phos) (9.1 mg, 0.022 mmol), palladium (II) acetate (2.7 mg, 0.012 mmol), and potassium phosphate tribasic (70.5 g, 0.33 mmol) in DMF (1.0 mL) and Water (0.04 mL) was purged 3 times with argon and placed under vacuum 3 times. The reaction mixture was carefully heated to 90° C. After 21 h, the reaction was cooled to rt, then diluted with water and extracted 3 times with EtOAc. The organic extractions were combined and washed twice with brine. After drying over anhydrous sodium sulfate and filtration, the organic solvent was removed under reduced pressure. The residue was purified over basic alumina (0-50% EtOAc in hexanes) to afford an impure yellow film. This film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a solid as 5,7-difluoro-N-(2'-methoxy-5-morpholino-2,3'-bipyridin-3-yl)-3-methyl-2-(pyridin-2-yl)quinolin-4-amine. Mass Spectrum (pos.) m/e: 541.2 (M+1).

Example 175

Preparation of N-(2,5-bis(3,6-dihydro-2H-pyran-4-yl)pyridin-3-yl)-5,7-difluoro-3-methyl-2-(pyridin-2-yl)quinolin-4-amine 2-Chloro-5-(3,6-dihydro-2H-pyran-4-yl)pyridin-3-amine and 2,5-bis(3,6-dihydro-2H-pyran-4-yl)pyridin-3-amine

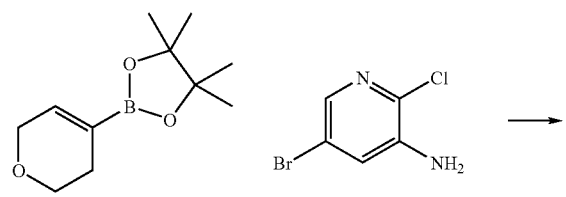

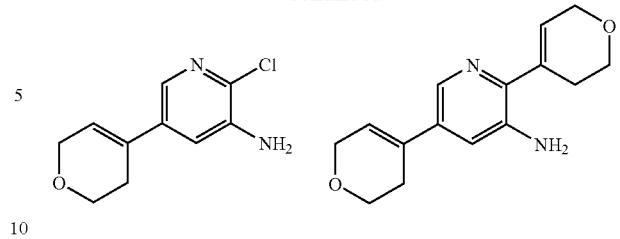

A stirred mixture of 5-bromo-2-chloropyridin-3-amine (0.39 g, 1.9 mmol), 2-(3,6-dihydro-2H-pyran-4-yl)-4,4,5,5-tetramethyl-1,3,2-dioxaborolane (0.48 g, 2.3 mmol), ground 2-dicyclohexylphosphino-2,6-dimethoxybiphenyl, (S-Phos) (0.15 g, 0.37 mmol), palladium (II) acetate (42.9 mg, 0.19 mmol), and potassium phosphate tribasic (1.20 g, 5.7 mmol) in DMF (9 mL) and water (0.4 mL) was purged 3 times with argon and placed under vacuum 3 times. The reaction mixture was carefully heated to 90° C. After 4.5 h, the reaction was cooled to rt, then diluted with water and extracted 3 times with EtOAc. The organic extractions were combined and washed twice with brine. After drying over anhydrous sodium sulfate and filtration, the organic solvent was removed under reduced pressure. The residue was purified using silica gel chromatography (0-100% EtOAc in hexanes) to afford a light yellow solid as 2-chloro-5-(3,6-dihydro-2H-pyran-4-yl)pyridin-3-amine. $^1$H NMR (400 MHz, CDCl$_3$) δ ppm 7.87 (1H, d, J=1.8 Hz), 7.05 (1H, m), 6.16 (1H, m), 4.32 (2H, q, J=2.9 Hz), 3.93 (2H, t, J=5.5 Hz), 2.51 (2H, m). 2,5-bis(3,6-dihydro-2H-pyran-4-yl)pyridin-3-amine was also isolated. $^1$H NMR (400 MHz, CDCl$_3$) δ ppm 8.13 (1H, d, J=2.0 Hz), 7.11 (1H, br. s.), 6.34 (2H, m), 4.46 (4H, m), 4.20 (6H, m), 2.67 (2H, m), 2.55 (2H, m). Mass Spectrum (pos.) m/e: 259.1 (M+1).

N-(2,5-bis(3,6-Dihydro-2H-pyran-4-yl)pyridin-3-yl)-5,7-difluoro-3-methyl-2-(pyridin-2-yl)quinolin-4-amine

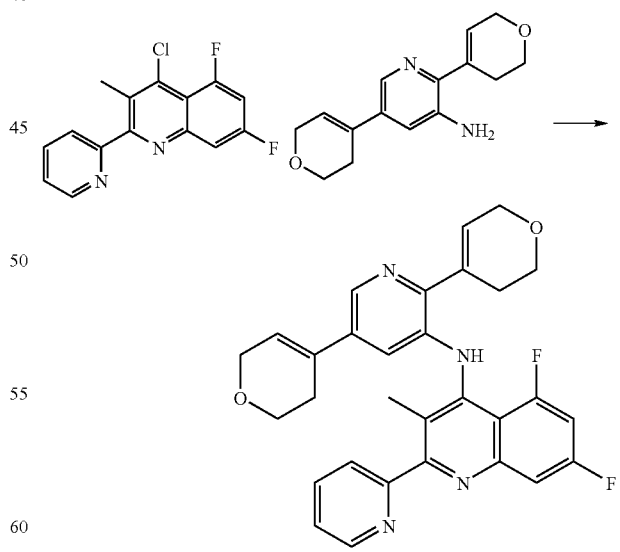

A mixture of 2,5-bis(3,6-dihydro-2H-pyran-4-yl)pyridin-3-amine (47.3 mg, 0.18 mmol), 4-chloro-5,7-difluoro-3-methyl-2-(pyridin-2-yl)quinoline (47.8 mg, 0.16 mmol), 2-dicyclohexylphosphino-2,4,6,-triisopropylbiphenyl, (X-Phos) (12.6 mg, 0.026 mmol), tris(dibenzylideneacetone)dipalladium (0) (7 mg, 7.6 μmol), and sodium tert-butoxide (56.6 mg, 0.59 mmol) in dry toluene (1.5 mL) was degassed by nitrogen. The resulting reaction was heated to 90° C. and monitored with TLC and LC-MS. After 21 h, the reaction was cooled to rt then poured into water. After extracting twice with EtOAc and twice with DCM, the combined organic extractions were dried over anhydrous magnesium sulfate. After filtration and concentration, the residue was purified on basic alumina (10-30% EtOAc in hexanes) to afford a yellow solid as N-(2,5-bis(3,6-dihydro-2H-pyran-4-yl)-pyridin-3-yl)-5,7-difluoro-3-methyl-2-(pyridin-2-yl)quinolin-4-amine. $^1$H NMR (500 MHz, CDCl$_3$) δ ppm 8.71 (1H, dt, J=4.9, 1.2 Hz), 8.27 (1H, d, J=1.7 Hz), 7.96 (2H, m), 7.66 (1H, m), 7.44 (1H, m), 7.32 (1H, d, J=10.3 Hz), 7.03 (2H, ddd, J=13.4, 8.6, 2.4 Hz), 6.37 (1H, m), 6.19 (1H, m), 4.40 (2H, m), 4.30 (2H, q, J=2.7 Hz), 4.04 (2H, t, J=5.4 Hz), 3.90 (2H, t, J=5.5 Hz), 2.72 (2H, m), 2.45 (2H, m), 2.18 (3H, s). Mass Spectrum (pos.) m/e: 513.1 (M+1).

Example 176

Preparation of N-(6'-ethoxy-5-morpholino-2,3'-bipyridin-3-yl)-5,7-difluoro-3-methyl-2-(pyridin-2-yl)quinolin-4-amine N-(6'-ethoxy-5-morpholino-2,3'-bipyridin-3-yl)-5,7-difluoro-3-methyl-2-(pyridin-2-yl)quinolin-4-amine

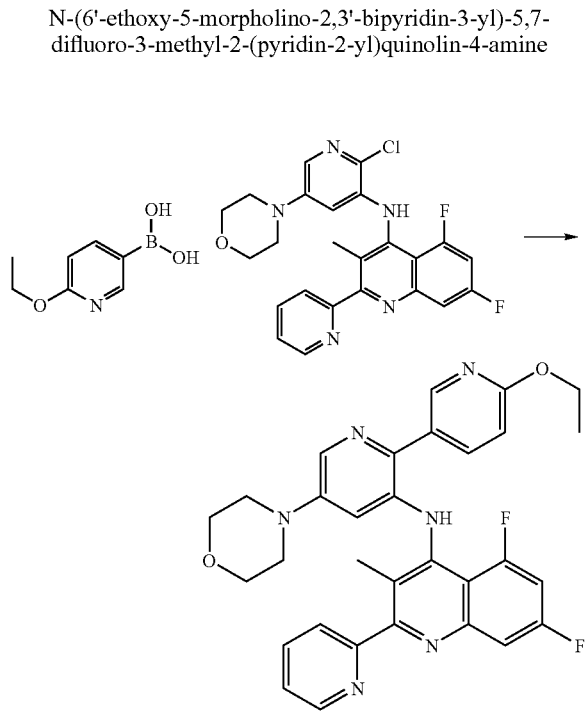

N-(2-Chloro-5-morpholinopyridin-3-yl)-5,7-difluoro-3-methyl-2-(pyridin-2-yl)-quinolin-4-amine (32.7 mg, 0.07 mmol), 6-ethoxypyridin-3-ylboronic acid (14.1 mg, 0.084 mmol), tris(dibenzylideneacetone)dipalladium (0) (3.3 mg, 3.6 μmol), and tricyclohexylphosphine (2.1 mg, 7.5 μmol) were added to a flask then degassed and backfilled with argon. To the flask, 1,4-dioxane (0.5 mL) and aq. 1.3M potassium phosphate tribasic (0.1 mL, 0.13 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on basic alumina (0-45% EtOAc in hexanes) to afford a light yellow solid as N-(6'-ethoxy-5-morpholino-2,3'-bipyridin-3-yl)-5,7-difluoro-3-methyl-2-(pyridin-2-yl)quinolin-4-amine. $^1$H NMR (500 MHz, CDCl$_3$) δ ppm 8.71 (1H, d, J=4.9 Hz), 8.66 (1H, d, J=2.4 Hz), 8.10 (2H, m), 7.94 (2H, d, J=3.9 Hz), 7.68 (1H, m), 7.46 (1H, m), 7.01 (2H, ddd, J=13.4, 8.6, 2.4 Hz), 6.93 (1H, d, J=8.8 Hz), 6.62 (1H, m), 4.45 (2H, q, J=7.1 Hz), 3.90 (4H, m), 3.28 (4H, m), 2.28 (3H, s), 1.45 (3H, t, J=7.1 Hz). Mass Spectrum (pos.) m/e: 555.2 (M+1).

Example 177

Preparation of 5,7-difluoro-N-(4'-methoxy-4-morpholinobiphenyl-2-yl)-3-methyl-2-(pyridin-2-yl)quinolin-4-amine 2-Chloro-5-morpholinoaniline

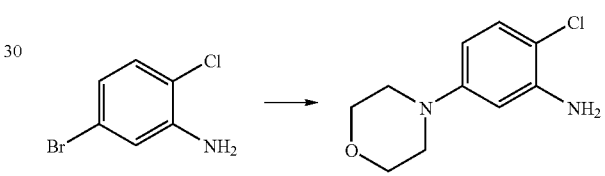

A mixture of 5-bromo-2-chloroaniline (2.0 g, 9.74 mmol), morpholine (4.3 mL, 49 mmol), 2-dicyclohexylphosphino-2,4,6,-triisopropylbiphenyl, (X-Phos) (0.37 g, 0.79 mmol), and tris(dibenzylideneacetone)dipalladium (0) (0.37 g, 0.4 mmol) in dry THF (20 mL) was degassed by nitrogen. To this mixture was added 1.0M lithium bis(trimethylsilyl)amide in THF (54 mL) dropwise, and the resulting reaction was heated to 60° C. After 2 h, the reaction was cooled to rt then cond under reduced pressure to ~5 mL. After pouring into water, the mixture was extracted twice with EtOAc and twice with DCM. After the combined organic layers were dried over anhydrous magnesium sulfate, filtration, and concentration, the residue was purified on silica gel (0-30% EtOAc in hexanes) to yield 2-chloro-5-morpholinoaniline. $^1$H NMR (400 MHz, CDCl$_3$) δ ppm 7.19 (1H, m), 6.41 (2H, m), 4.00 (2H, br. s.), 3.93 (4H, m), 3.22 (4H, m).

N-(2-Chloro-5-morpholinophenyl)-5,7-difluoro-3-methyl-2-(pyridin-2-yl)-quinolin-4-amine

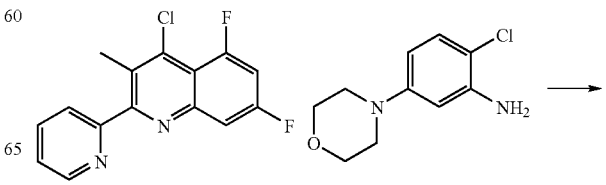

-continued

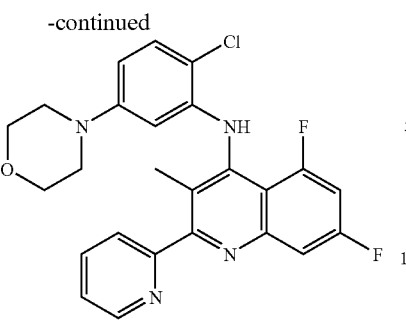

A mixture of 2-chloro-5-morpholinoaniline (0.14 g, 0.65 mmol), 4-chloro-5,7-difluoro-3-methyl-2-(pyridin-2-yl)quinoline (0.15 g, 0.54 mmol), 2-dicyclohexylphosphino-2,4,6,-tri-i-propyl-1,1-biphenyl, (X-Phos) (41.9 mg, 0.088 mmol), tris(dibenzylideneacetone)dipalladium (0) (20.7 mg, 0.023 mmol), and sodium tert-butoxide (0.16 g, 1.7 mmol) in dry toluene (3.0 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on silica gel (0-40% EtOAc in hexanes) to afford an off white solid as N-(2-chloro-5-morpholinophenyl)-5,7-difluoro-3-methyl-2-(pyridin-2-yl)quinolin-4-amine. $^1$H NMR (500 MHz, CDCl$_3$) δ ppm 8.73 (1H, m), 7.94 (2H, m), 7.64 (1H, d, J=9.3 Hz), 7.37 (1H, ddd, J=7.0, 5.0, 1.7 Hz), 7.33 (2H, m), 7.03 (1H, ddd, J=13.4, 8.6, 2.4 Hz), 6.46 (1H, dd, J=8.8, 2.7 Hz), 6.22 (1H, d, J=2.7 Hz), 3.87 (4H, m), 3.14 (4H, m), 2.18 (3H, s). Mass Spectrum (pos.) m/e: 467.0 (M+1).

5,7-Difluoro-N-(4'-methoxy-4-morpholinobiphenyl-2-yl)-3-methyl-2-(pyridin-2-yl)quinolin-4-amine mmol), tricyclohexylphosphine (3.2 mg, 0.011 mmol), and tris(dibenzylideneacetone)dipalladium (0) (3.7 mg, 4 μmol) were added to a flask then degassed and backfilled with argon. To the flask, 1,4-dioxane (1.0 mL) and aq. 1.3M potassium phosphate tribasic (0.1 mL, 0.13 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-50% EtOAc in hexanes) to afford an impure orange residue. The light orange film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a solid as 5,7-difluoro-N-(4'-methoxy-4-morpholinobiphenyl-2-yl)-3-methyl-2-(pyridin-2-yl)quinolin-4-amine. $^1$H NMR (400 MHz, CDCl$_3$) δ ppm 8.74 (1H, d, J=4.9 Hz), 8.05 (4H, m), 7.46 (1H, ddd, J=7.4, 4.9, 1.2 Hz), 7.34 (2H, m), 7.30 (1H, m), 7.07 (1H, m), 6.93 (2H, m), 6.83 (1H, dd, J=8.5, 2.4 Hz), 6.57 (1H, d, J=2.3 Hz), 3.91 (4H, m), 3.82 (3H, s), 3.24 (4H, m), 2.03 (3H, s). Mass Spectrum (pos.) m/e: 539.2 (M+1).

Example 178

Preparation of N-(2-(3,6-dihydro-2H-pyran-4-yl)-5-morpholinophenyl)-5,7-difluoro-3-methyl-2-(pyridin-2-yl)quinolin-4-amine N-(2-(3,6-Dihydro-2H-pyran-4-yl)-5-morpholinophenyl)-5,7-difluoro-3-methyl-2-(pyridin-2-yl)quinolin-4-amine

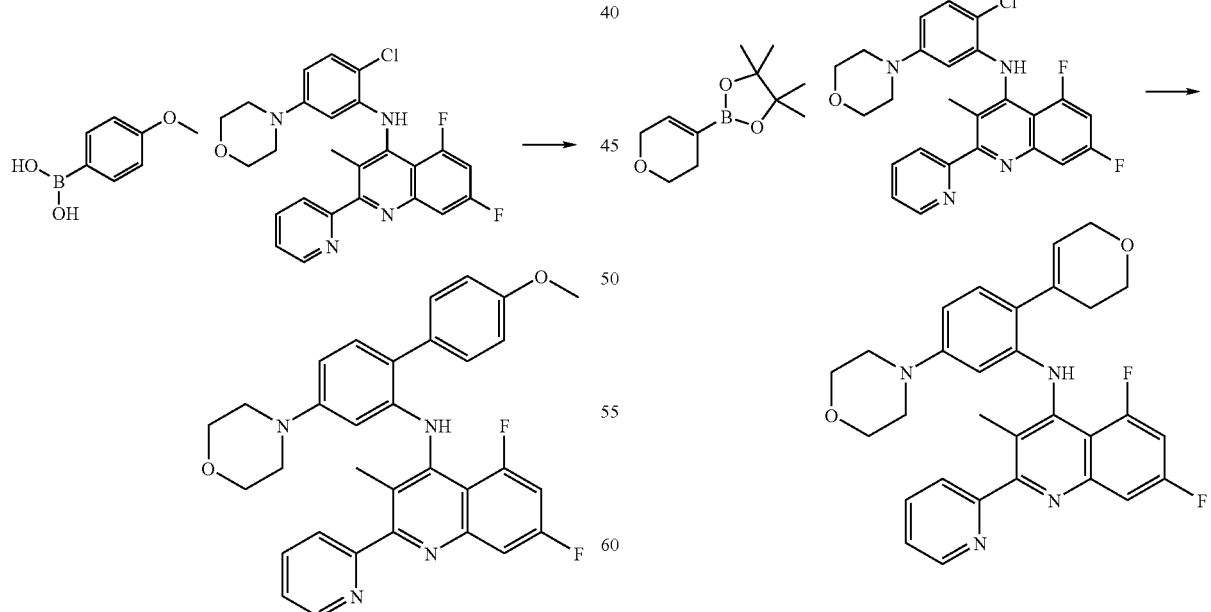

N-(2-chloro-5-morpholinophenyl)-5,7-difluoro-3-methyl-2-(pyridin-2-yl)quinolin-4-amine (30.3 mg, 0.065 mmol), 4-methoxyphenylboronic acid (15.1 mg, 0.099

N-(2-Chloro-5-morpholinophenyl)-5,7-difluoro-3-methyl-2-(pyridin-2-yl)quinolin-4-amine (33.9 mg, 0.073 mmol), 2-(3,6-dihydro-2H-pyran-4-yl)-4,4,5,5-tetramethyl-1,3,2-dioxaborolane (22.8 mg, 0.11 mmol), tricyclohexylphosphine (3.9 mg, 0.014 mmol), and tris(dibenzylideneacetone)dipalladium (0) (4.1 mg, 4.5 µmol) were added to a flask then degassed and backfilled with argon. To the flask, 1,4-dioxane (1.0 mL) and aq. 1.3M potassium phosphate tribasic (0.12 mL, 0.16 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-100% EtOAc in hexanes) to afford an impure orange residue. The light orange film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a brown solid as N-(2-(3,6-dihydro-2H-pyran-4-yl)-5-morpholinophenyl)-5,7-difluoro-3-methyl-2-(pyridin-2-yl)quinolin-4-amine. $^1$H NMR (400 MHz, CDCl$_3$) δ ppm 8.70 (1H, dt, J=4.8, 1.3 Hz), 8.00 (3H, m), 7.75 (1H, m), 7.48 (1H, m), 7.13 (1H, d, J=8.4 Hz), 7.05 (1H, ddd, J=13.9, 8.3, 2.4 Hz), 6.66 (1H, dd, J=8.4, 2.3 Hz), 6.39 (1H, d, J=2.3 Hz), 5.92 (1H, m), 4.29 (2H, d, J=2.5 Hz), 3.94 (6H, m), 3.23 (4H, m), 2.44 (2H, m), 2.06 (3H, s). Mass Spectrum (pos.) m/e: 515.2 (M+1).

Example 179

Preparation of 5,7-difluoro-N-(3'-methoxy-5-morpholino-2,4'-bipyridin-3-yl)-3-methyl-2-(pyridin-2-yl)quinolin-4-amine 3-Methoxypyridin-4-ylboronic acid

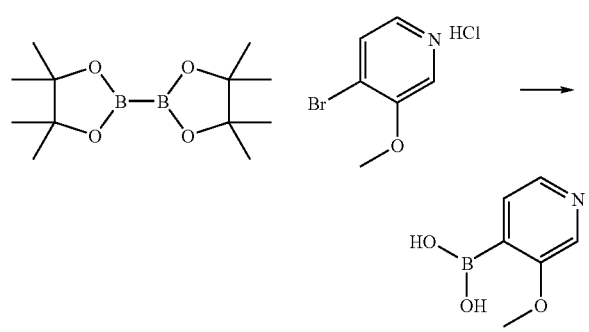

A mixture of 4-bromo-3-methoxypyridine hydrochloride (0.34 g, 1.5 mmol), 1,1'-bis(diphenylphosphino)ferrocene-palladium dichloride (0.13 g, 0.16 mmol), bis(pinacolato) diboron (0.47 g, 1.85 mmol), and potassium acetate (0.75 g, 7.7 mmol) in dry 1,4-dioxane (6.0 mL) was degassed by nitrogen. The mixture was heated to 90° C. After 19 h, the reaction was cooled to rt then filtered. After concentration, the residue was identified as 3-methoxypyridin-4-ylboronic acid that was used without purification.

5,7-Difluoro-N-(3'-methoxy-5-morpholino-2,4'-bipyridin-3-yl)-3-methyl-2-(pyridin-2-yl)quinolin-4-amine

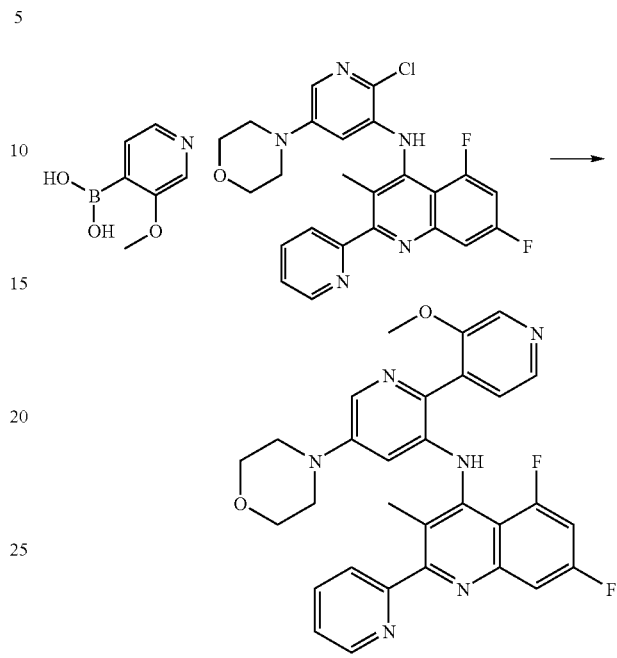

N-(2-chloro-5-morpholinopyridin-3-yl)-5,7-difluoro-3-methyl-2-(pyridin-2-yl)-quinolin-4-amine (60.5 mg, 0.13 mmol), 3-methoxypyridin-4-ylboronic acid (97.1 mg, 0.63 mmol), tris(dibenzylideneacetone)dipalladium (0) (7.5 mg, 8.2 µmol), and tricyclohexylphosphine (4.8 mg, 0.017 mmol) were added to a flask then degassed and backfilled with argon. To the flask, 1,4-dioxane (1.0 mL) and aq. 1.3M potassium phosphate tribasic (0.3 mL, 0.39 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on basic alumina (0-100% EtOAc in hexanes) to afford an impure orange residue. The light orange film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a yellow film as 5,7-difluoro-N-(3'-methoxy-5-morpholino-2,4'-bipyridin-3-yl)-3-methyl-2-(pyridin-2-yl)quinolin-4-amine. $^1$H NMR (400 MHz, CDCl$_3$) δ ppm 8.73 (2H, m), 8.47 (1H, d, J=5.3 Hz), 8.22 (1H, d, J=2.5 Hz), 7.95 (3H, m), 7.76 (1H, d, J=5.1 Hz), 7.69 (1H, dt, J=9.2, 1.2 Hz), 7.41 (1H, ddd, J=7.4, 4.9, 1.4 Hz), 7.06 (1H, ddd, J=13.8, 8.4, 2.4 Hz), 6.69 (1H, d, J=2.5 Hz), 4.15 (3H, s), 3.90 (4H, m), 3.31 (4H, m), 1.94 (3H, s). Mass Spectrum (pos.) m/e: 541.2 (M+1).

Example 180

Preparation of 5,7-difluoro-N-(2'-methoxy-5-morpholino-2,4'-bipyridin-3-yl)-3-methyl-2-(pyridin-2-yl)quinolin-4-amine 5,7-Difluoro-N-(2'-methoxy-5-morpholino-2,4'-bipyridin-3-yl)-3-methyl-2-(pyridin-2-yl)quinolin-4-amine

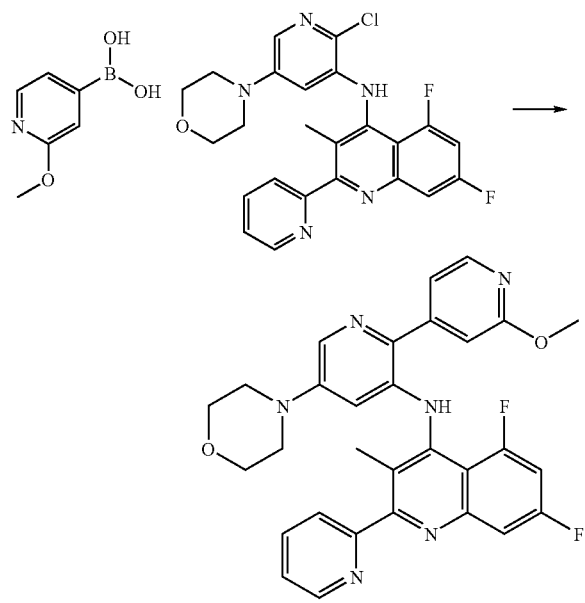

N-(2-chloro-5-morpholinopyridin-3-yl)-5,7-difluoro-3-methyl-2-(pyridin-2-yl)-quinolin-4-amine (42.8 mg, 0.091 mmol), 2-methoxypyridin-4-ylboronic acid (28.7 mg, 0.19 mmol), tricyclohexylphosphine (5.1 mg, 0.018 mmol), and tris(dibenzylideneacetone)dipalladium (0) (5.7 mg, 6.2 µmol) were added to a flask then degassed and backfilled with argon. To the flask, 1,4-dioxane (1.0 mL) and aq. 1.3M potassium phosphate tribasic (0.22 mL, 0.29 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on basic alumina (0-100% EtOAc in hexanes) to afford an impure yellow residue. The light yellow film was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a light yellow solid as 5,7-difluoro-N-(2'-methoxy-5-morpholino-2,4'-bipyridin-3-yl)-3-methyl-2-(pyridin-2-yl)quinolin-4-amine.
$^1$H NMR (400 MHz, CDCl$_3$) δ ppm 8.69 (1H, dt, J=4.8, 1.4 Hz), 8.35 (1H, m), 8.10 (1H, m), 7.98 (2H, m), 7.70 (1H, m), 7.47 (1H, m), 7.37 (1H, m), 7.21 (1H, s), 7.00 (2H, ddd, J=13.5, 8.6, 2.5 Hz), 6.55 (1H, d, J=2.3 Hz), 4.05 (3H, m), 3.89 (4H, m), 3.28 (4H, m), 2.31 (3H, m). Mass Spectrum (pos.) m/e: 541.2 (M+1).

Example 181

Preparation of 5,7-difluoro-N-(5'-methoxy-5-morpholino-2,3'-bipyridin-3-yl)-3-methyl-2-(pyridin-2-yl)quinolin-4-amine 2-Chloro-5-morpholinopyridin-3-amine

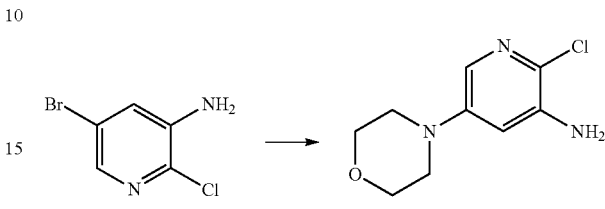

A mixture of 3-amino-5-bromo-2-chloropyridine (2.0 g, 9.7 mmol), morpholine (1.3 mL, 14.9 mmol), 2-(dicyclohexylphosphino)-2',4',6',-triisopropyl-biphenyl, (X-Phos) (0.37 g, 0.8 mmol), and tris(dibenzylideneacetone)dipalladium (0) (0.36 g, 0.39 mmol) in dry THF (15.0 mL) was degassed by nitrogen. To this mixture was added 1.0M lithium bis(trimethylsilyl)amide in THF (25 mL) dropwise, and the resulting reaction was heated to 60° C. After 2.5 h, the reaction was cooled to rt then poured into water. After extracting twice with EtOAc and twice with DCM, the combined organic layers were dried over anhydrous magnesium sulfate. After filtration and concentration, the residue was purified on basic alumina (0-20% EtOAc in hexanes) to afford an off-white solid as 2-chloro-5-morpholinopyridin-3-amine. $^1$H NMR (500 MHz, DMSO-d$_6$) δ ppm 7.35 (1H, d, J=2.7 Hz), 6.67 (1H, d, J=2.7 Hz), 5.33 (2H, s), 3.79 (4H, m), 3.11 (4H, m).

5'-Methoxy-5-morpholino-2,3'-bipyridin-3-amine

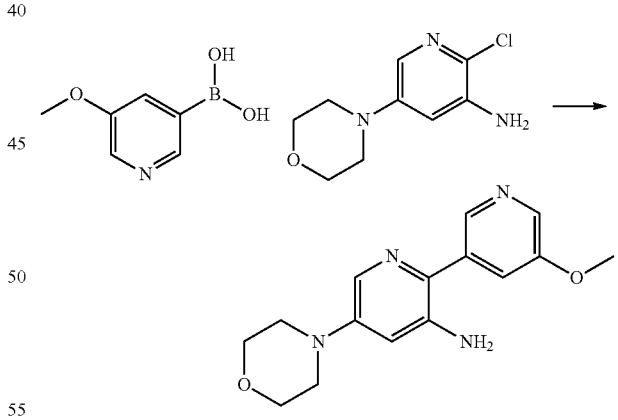

2-Chloro-5-morpholinopyridin-3-amine (0.26 g, 1.2 mmol), 5-methoxypyridin-3-ylboronic acid (0.24 g, 1.6 mmol), tricyclohexylphosphine (42.7 mg, 0.15 mmol), and tris(dibenzylideneacetone)dipalladium (0) (68.4 mg, 0.075 mmol) were added to a flask then degassed and backfilled with argon. To the flask, 1,4-dioxane (5.0 mL) and aq. 1.3M potassium phosphate tribasic (2.3 mL, 3 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extrac-

5,7-Difluoro-N-(5'-methoxy-5-morpholino-2,3'-bipyridin-3-yl)-3-methyl-2-(pyridin-2-yl)quinolin-4-amine

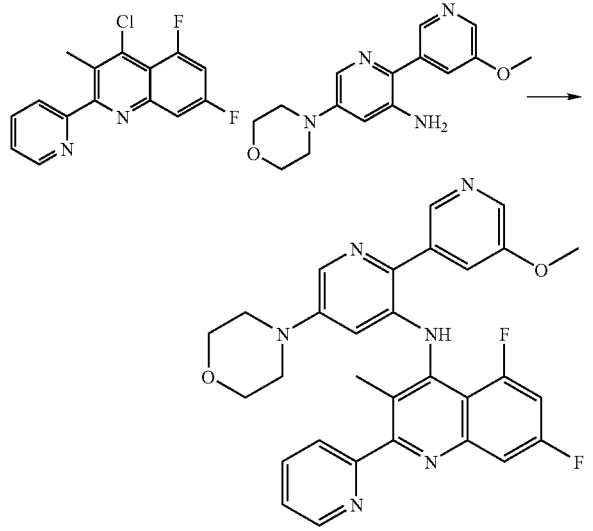

A mixture of 5'-methoxy-5-morpholino-2,3'-bipyridin-3-amine (75.1 mg, 0.26 mmol), 4-chloro-5,7-difluoro-3-methyl-2-(pyridin-2-yl)quinoline (0.11 g, 0.4 mmol), 2-(dicyclohexylphosphino)-2',4',6',-triisopropyl-biphenyl, (X-Phos) (20.7 mg, 0.043 mmol), tris(dibenzylideneacetone)dipalladium (0) (11 mg, 0.012 mmol), and sodium tert-butoxide (76.4 mg, 0.8 mmol) in dry toluene (3.0 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on silica gel (30-50% of a premixed solution of 89:9:1 DCM:MeOH:ammonium hydroxide in DCM) to afford an impure yellow solid. The light yellow solid was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a light yellow solid as 5,7-difluoro-N-(5'-methoxy-5-morpholino-2,3'-bipyridin-3-yl)-3-methyl-2-(pyridin-2-yl)quinolin-4-amine. $^1$H NMR (500 MHz, CDCl$_3$) δ ppm 8.76 (1H, d, J=1.5 Hz), 8.69 (1H, dt, J=4.6, 1.3 Hz), 8.39 (1H, d, J=2.9 Hz), 8.11 (1H, d, J=2.4 Hz), 7.96 (2H, m), 7.82 (1H, br. s.), 7.64 (1H, dt, J=9.4, 1.2 Hz), 7.44 (1H, m), 7.06 (2H, m), 6.57 (1H, d, J=2.4 Hz), 3.97 (3H, s), 3.89 (4H, m), 3.29 (4H, m), 2.24 (3H, s). Mass Spectrum (pos.) m/e: 541.2 (M+1).

Example 182

Preparation 4-(3-(5,7-Difluoro-3-methyl-2-(pyridin-2-yl)-quinolin-4-ylamino)-5-morpholinopyridin-2-yl)benzonitrile 4-(3-Amino-5-morpholinopyridin-2-yl)benzonitrile

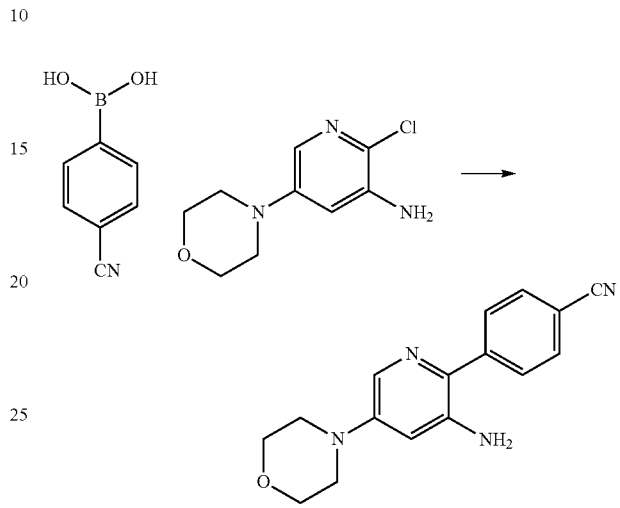

2-Chloro-5-morpholinopyridin-3-amine (0.25 g, 1.2 mmol), 4-cyanophenylboronic acid (0.21 g, 1.4 mmol), tricyclohexylphosphine (39.4 mg, 0.14 mmol), and tris(dibenzylideneacetone)dipalladium (0) (64.8 g, 0.07 mmol) were added to a flask then degassed and backfilled with argon. To the flask, 1,4-dioxane (3.0 mL) and aq. 1.3M potassium phosphate tribasic (2.7 mL, 3.5 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-30% of a premixed solution of 89:9:1 DCM:MeOH:ammonium hydroxide in DCM) to afford a light yellow solid as 4-(3-amino-5-morpholinopyridin-2-yl)benzonitrile. $^1$H NMR (500 MHz, DMSO-d$_6$) δ ppm 7.91 (5H, m), 6.67 (1H, d, J=2.4 Hz), 5.19 (2H, s), 3.82 (4H, m), 3.21 (4H, m). Mass Spectrum (pos.) m/e: 281.0 (M+1).

4-(3-(5,7-Difluoro-3-methyl-2-(pyridin-2-yl)quinolin-4-ylamino)-5-morpholinopyridin-2-yl)benzonitrile

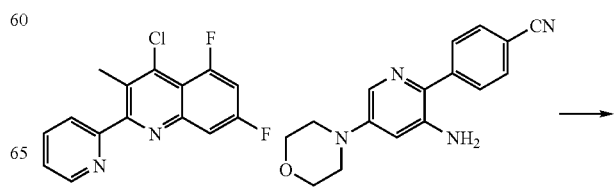

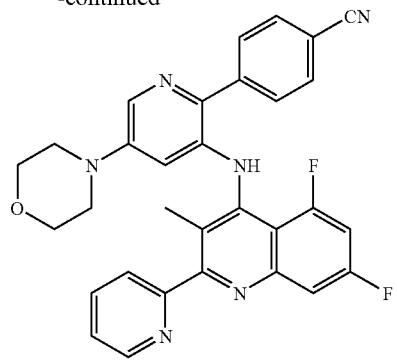

A mixture of 4-(3-amino-5-morpholinopyridin-2-yl)benzonitrile (54.9 mg, 0.2 mmol), 4-chloro-5,7-difluoro-3-methyl-2-(pyridin-2-yl)quinoline (85.7 mg, 0.3 mmol), 2-(dicyclohexylphosphino)-2',4',6',-triisopropyl-biphenyl, (X-Phos) (15.2 mg, 0.03 mmol), tris(dibenzylideneacetone)dipalladium (0) (8.2 mg, 9 µmol), and sodium tert-butoxide (58.8 mg, 0.6 mmol) in dry toluene (2.0 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on silica gel (0-45% of a premixed solution of 89:9:1 DCM:MeOH:ammonium hydroxide in DCM) to afford a film that was triturated with MeOH to afford a white solid as 4-(3-(5,7-difluoro-3-methyl-2-(pyridin-2-yl)quinolin-4-ylamino)-5-morpholinopyridin-2-yl)benzonitrile. $^1$H NMR (500 MHz, CDCl$_3$) δ ppm 8.74 (1H, m), 8.06 (1H, d, J=2.4 Hz), 7.98 (2H, m), 7.95 (2H, m), 7.78 (2H, m), 7.65 (1H, d, J=7.8 Hz), 7.40 (1H, td, J=5.3, 2.8 Hz), 6.98 (1H, dd, J=13.6, 8.4 Hz), 6.98 (1H, dd, J=13.6, 8.4 Hz), 6.55 (1H, d, J=2.0 Hz), 3.90 (4H, m), 3.30 (4H, m), 2.25 (3H, s). Mass Spectrum (pos.) m/e: 535.2 (M+1).

Example 183

Preparation of 5,7-difluoro-N-(2-(4-methoxy-2,6-dimethylphenyl)-5-morpholinopyridin-3-yl)-3-methyl-2-(pyridin-2-yl)quinolin-4-amine 2-(4-Methoxy-2,6-dimethylphenyl)-5-morpholinopyridin-3-amine

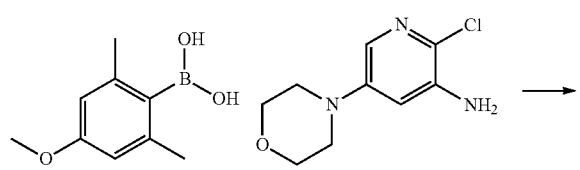

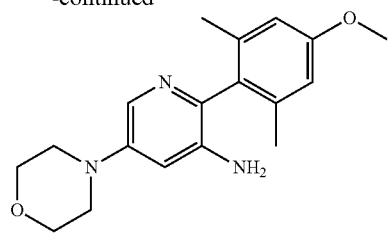

2-Chloro-5-morpholinopyridin-3-amine (62 mg, 0.29 mmol), 4-methoxy-2,6-dimethylphenylboronic acid (0.07 g, 0.39 mmol), tricyclohexylphosphine (12 mg, 0.042 mmol), and tris(dibenzylideneacetone)dipalladium (0) (19 mg, 0.02 mmol) were added to a flask then degassed and backfilled with argon. To the flask, 1,4-dioxane (3 mL) and aq. 1.3M potassium phosphate tribasic (0.67 mL, 0.87 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-30% of a premixed solution of 89:9:1 DCM:MeOH:ammonium hydroxide in DCM) to afford a light yellow solid as 2-(4-methoxy-2,6-dimethylphenyl)-5-morpholinopyridin-3-amine. $^1$H NMR (500 MHz, CDCl$_3$) δ ppm 7.75 (1H, br. s.), 6.75 (3H, m), 3.95 (4H, m), 3.85 (3H, m), 3.54 (2H, br. s.), 3.28 (4H, m), 2.04 (6H, s). Mass Spectrum (pos.) m/e: 314.2 (M+1).

5,7-Difluoro-N-(2-(4-methoxy-2,6-dimethylphenyl)-5-morpholinopyridin-3-yl)-3-methyl-2-(pyridin-2-yl)quinolin-4-amine

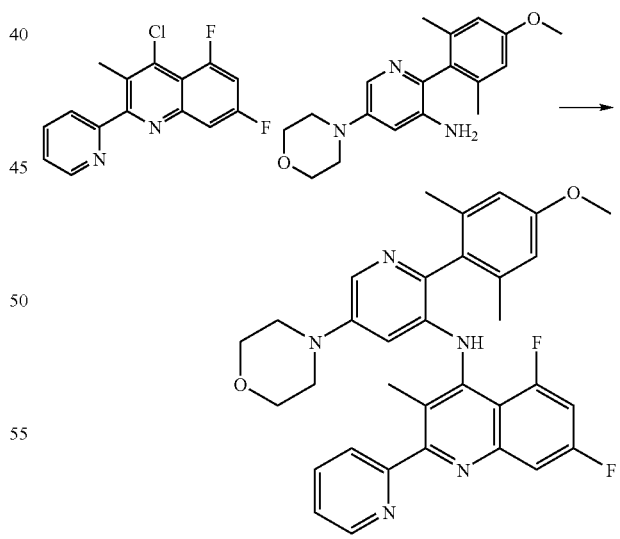

A mixture of 2-(4-methoxy-2,6-dimethylphenyl)-5-morpholinopyridin-3-amine (41 mg, 0.13 mmol), 4-chloro-5,7-difluoro-3-methyl-2-(pyridin-2-yl)quinoline (57 mg, 0.2 mmol), 2-(dicyclohexylphosphino)-2',4',6',-triisopropyl-biphenyl, (X-Phos) (7.9 mg, 0.017 mmol), tris(dibenzylideneacetone)dipalladium (0) (7.8 mg, 8.5 µmol), and sodium tert-butoxide (36.9 mg, 0.38 mmol) in dry toluene (2 mL) was degassed by nitrogen. The resulting reaction was heated to 100° C. and monitored with TLC and LC-MS. After 18 h, the reaction was cooled to rt then poured into water. After extracting twice with EtOAc and twice with DCM, the combined organic extractions were dried over anhydrous magnesium sulfate. After filtration and concentration, the residue was purified on silica gel (0-60% of a premixed solution of 89:9:1 DCM:MeOH:ammonium hydroxide in DCM) to afford a yellow film that was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a light yellow solid as 5,7-difluoro-N-(2-(4-methoxy-2,6-dimethylphenyl)-5-morpholinopyridin-3-yl)-3-methyl-2-(pyridin-2-yl)quinolin-4-amine. $^1$H NMR (400 MHz, CDCl$_3$) δ ppm 8.69 (1H, dt, J=4.7, 1.3 Hz), 8.00 (1H, d, J=2.5 Hz), 7.93 (2H, m), 7.63 (1H, m), 7.38 (1H, ddd, J=6.1, 4.8, 2.7 Hz), 6.95 (1H, ddd, J=13.3, 8.6, 2.5 Hz), 6.75 (2H, s), 6.60 (2H, m), 3.95 (7H, m), 3.28 (4H, m), 2.21 (3H, s), 2.15 (6H, s). Mass Spectrum (pos.) m/e: 568.2 (M+1).

Example 184

Preparation of 5,7-difluoro-3-methyl-N-(2-(4-(methylsulfonyl)-phenyl)-5-morpholinopyridin-3-yl)-2-(pyridin-2-yl)quinolin-4-amine 5,7-Difluoro-3-methyl-N-(2-(4-(methylsulfonyl)phenyl)-5-morpholinopyridin-3-yl)-2-(pyridin-2-yl)quinolin-4-amine

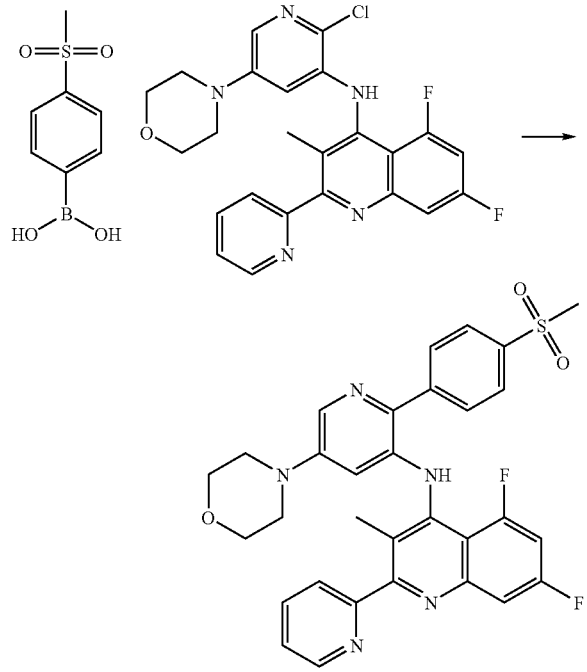

N-(2-chloro-5-morpholinopyridin-3-yl)-5,7-difluoro-3-methyl-2-(pyridin-2-yl)-quinolin-4-amine (60.7 mg, 0.13 mmol), 4-(methylsulfonyl)phenylboronic acid (40.1 mg, 0.2 mmol), tricyclohexylphosphine (6.2 mg, 0.022 mmol), and tris(dibenzylideneacetone)dipalladium (0) (10.4 mg, 0.011 mmol) were added to a flask then degassed and backfilled with argon. To the flask, 1,4-dioxane (2.0 mL) and aq. 1.3M potassium phosphate tribasic (0.3 mL, 0.39 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-60% of a premixed solution of 89:9:1 DCM:MeOH:ammonium hydroxide in DCM) to afford a film that was triturated with MeOH to afford a light yellow solid as 5,7-difluoro-3-methyl-N-(2-(4-(methylsulfonyl)phenyl)-5-morpholinopyridin-3-yl)-2-(pyridin-2-yl)quinolin-4-amine. $^1$H NMR (500 MHz, CDCl$_3$) δ ppm 8.69 (1H, dt, J=4.8, 1.2 Hz), 8.12 (5H, m), 7.96 (2H, m), 7.62 (1H, d, J=8.8 Hz), 7.39 (1H, ddd, J=6.8, 4.8, 2.1 Hz), 7.02 (2H, m), 6.55 (1H, d, J=2.4 Hz), 3.91 (4H, m), 3.28 (4H, m), 3.09 (3H, s), 2.25 (3H, s). Mass Spectrum (pos.) m/e: 602.0 (M+1).

Example 185

Preparation of N-(5,7-difluoro-3-methyl-2-(pyridin-2-yl)quinolin-4-yl)-2,2,2-trifluoro-N-(5'-methoxy-5-morpholino-2,3'-bipyridin-3-yl)-acetamide N-(5,7-Difluoro-3-methyl-2-(pyridin-2-yl)quinolin-4-yl)-2,2,2-trifluoro-N-(5'-methoxy-5-morpholino-2,3'-bipyridin-3-yl)acetamide

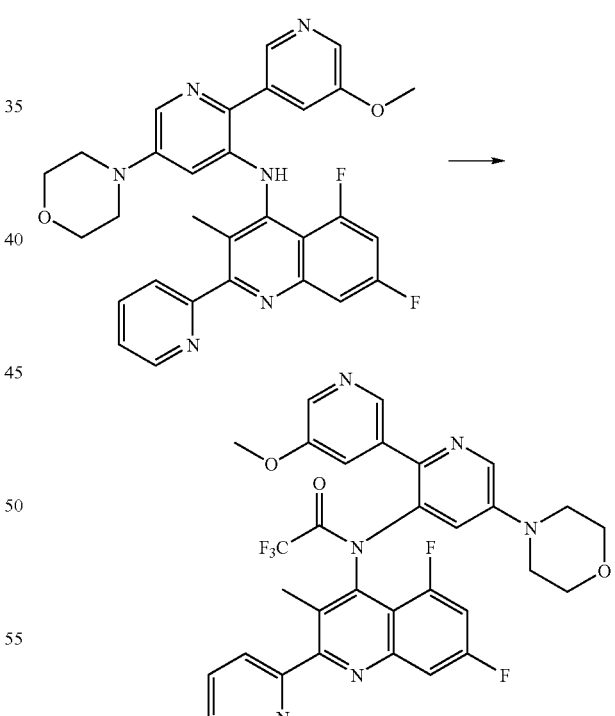

A screw-cap vial was charged with 5,7-difluoro-N-(5'-methoxy-5-morpholino-2,3'-bipyridin-3-yl)-3-methyl-2-(pyridin-2-yl)quinolin-4-amine (67.1 mg, 0.12 mmol), triethylamine (0.03 mL, 0.22 mmol) and dry DCM (1.0 mL). To this yellow solution was added trifluoroacetic acid anhydride (0.03 mL, 0.21 mmol) dropwise. The reaction was stirred at 23° C. and monitored with TLC and LC-MS. After 2 h, the reaction was diluted with DCM then washed once with water and once with satd aq. sodium bicarbonate solution. The organic layer was dried over anhydrous magnesium sulfate. After filtration and concentration, the residue was purified on silica gel (0-60% of a premixed solution of 89:9:1 DCM:MeOH:ammonium hydroxide in DCM) to afford a yellow film that was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a light yellow solid as N-(5,7-difluoro-3-methyl-2-(pyridin-2-yl)quinolin-4-yl)-2,2,2-trifluoro-N-(5'-methoxy-5-morpholino-2,3'-bipyridin-3-yl)acetamide. $^1$H NMR (500 MHz, DMSO-d$_6$) δ ppm 9.00 (1H, s), 8.74 (1H, d, J=4.4 Hz), 8.52 (1H, m), 8.36 (1H, d, J=2.7 Hz), 8.06 (1H, td, J=7.7, 1.5 Hz), 7.94 (1H, d, J=7.8 Hz), 7.74 (1H, dd, J=9.4, 1.6 Hz), 7.66 (3H, m), 6.28 (1H, s), 3.88 (3H, s), 3.71 (4H, t, J=4.3 Hz), 3.05 (4H, m), 2.35 (3H, s). Mass Spectrum (pos.) m/e: 637.1 (M+1).

Example 186

Preparation of 5,7-difluoro-N-(2-(5-methoxypyridin-3-yl)-5-morpholinophenyl)-3-methyl-2-(pyridin-2-yl)quinolin-4-amine 5,7-Difluoro-N-(2-(5-methoxypyridin-3-yl)-5-morpholinophenyl)-3-methyl-2-(pyridin-2-yl)quinolin-4-amine was cooled to rt then poured into water. After extracting twice with EtOAc and twice with DCM, the combined organic extractions were dried over anhydrous magnesium sulfate. After filtration and concentration, the residue was purified on silica gel (0-45% of a premixed solution of 89:9:1 DCM:MeOH:ammonium hydroxide in DCM) to afford a yellow film that was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a yellow solid as 5,7-difluoro-N-(2-(5-methoxypyridin-3-yl)-5-morpholinophenyl)-3-methyl-2-(pyridin-2-yl)quinolin-4-amine. $^1$H NMR (500 MHz, CDCl$_3$) δ ppm 8.69 (1H, d, J=4.4 Hz), 8.42 (1H, d, J=1.7 Hz), 8.28 (1H, d, J=2.7 Hz), 7.88 (1H, td, J=7.6, 1.7 Hz), 7.82 (1H, d, J=7.8 Hz), 7.71 (1H, m), 7.43 (2H, m), 7.22 (1H, d, J=8.6 Hz), 6.93 (1H, dd, J=8.4, 2.6 Hz), 6.95 (1H, dd, J=8.6, 2.4 Hz), 6.65 (1H, dd, J=8.4, 2.3 Hz), 6.36 (1H, d, J=2.2 Hz), 3.89 (3H, s), 3.86 (4H, m), 3.21 (4H, m), 2.18 (3H, s). Mass Spectrum (pos.) m/e: 540.1 (M+1).

Example 187

Preparation of 4-(3-(5,7-difluoro-3-methyl-2-(pyridin-2-yl)-quinolin-4-ylamino)-5-morpholinopyridin-2-yl)phenol 4-(3-(5,7-Difluoro-3-methyl-2-(pyridin-2-yl)quinolin-4-ylamino)-5-morpholinopyridin-2-yl)phenol

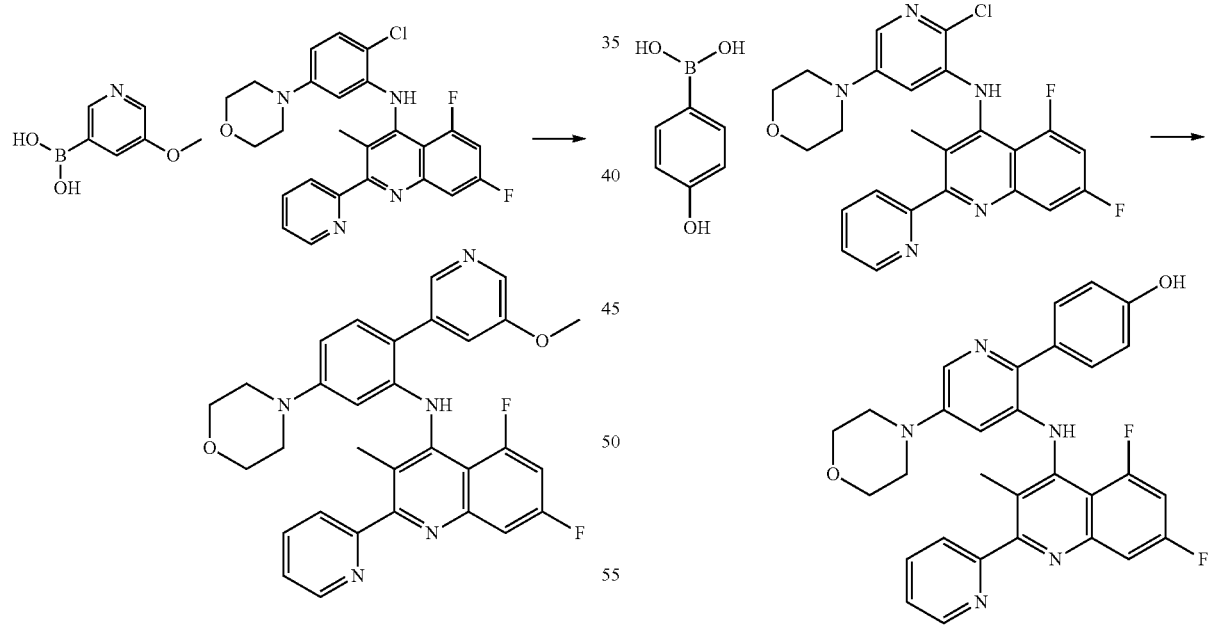

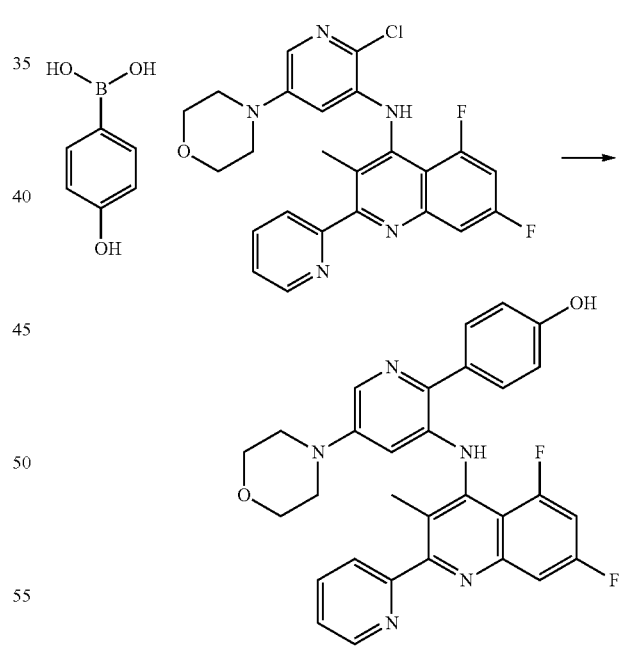

N-(2-chloro-5-morpholinophenyl)-5,7-difluoro-3-methyl-2-(pyridin-2-yl)quinolin-4-amine (62.7 mg, 0.13 mmol), 5-methoxypyridin-3-ylboronic acid (31.9 mg, 0.21 mmol), tricyclohexylphosphine (6.3 mg, 0.022 mmol), and tris(dibenzylideneacetone)dipalladium (0) (10.6 mg, 0.012 mmol) were added to a flask then degassed and backfilled with argon. To the flask, 1,4-dioxane (2.0 mL) and aq. 1.3M potassium phosphate tribasic (0.31 mL, 0.4 mmol) were added by syringe. The resulting reaction was heated to 90° C. and monitored with TLC and LC-MS. After 22 h, the reaction N-(2-chloro-5-morpholinopyridin-3-yl)-5,7-difluoro-3-methyl-2-(pyridin-2-yl)-quinolin-4-amine (60.6 mg, 0.13 mmol), 4-hydroxyphenylboronic acid (36.7 mg, 0.27 mmol), tricyclohexylphosphine (7.7 mg, 0.027 mmol), and tris(dibenzylideneacetone)dipalladium (0) (12.1 mg, 0.013 mmol) were added to a flask then degassed and backfilled with argon. To the flask, 1,4-dioxane (2.0 mL) and aq. 1.3M potassium phosphate tribasic (0.3 mL, 0.39 mmol) were added by syringe. The resulting reaction was heated to 90° C.

and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-55% of a premixed solution of 89:9:1 DCM:MeOH:ammonium hydroxide in DCM) to afford a film that was further purified with HPLC (10-90% of 0.1% TFA acetonitrile solution in 0.1% TFA water solution). The desired fractions were cond then diluted with EtOAc. After washing twice with satd aq. sodium bicarbonate solution and once with brine, the solvent was removed under reduced pressure to yield a yellow solid as 4-(3-(5,7-difluoro-3-methyl-2-(pyridin-2-yl)quinolin-4-ylamino)-5-morpholinopyridin-2-yl)phenol. $^1$H NMR (500 MHz, DMSO-d$_6$) δ ppm 9.49 (1H, s), 8.70 (1H, dq, J=4.8, 0.9 Hz), 8.01 (1H, td, J=7.7, 1.7 Hz), 7.94 (1H, d, J=2.4 Hz), 7.83 (1H, d, J=7.6 Hz), 7.65 (2H, m), 7.54 (4H, m), 6.79 (2H, m), 6.45 (1H, d, J=2.4 Hz), 3.76 (4H, m), 3.14 (4H, m), 2.13 (3H, s). Mass Spectrum (pos.) m/e: 526.2 (M+1).

Example 188

Preparation of N-(2-(3-(difluoromethoxy)phenyl)-5-morpholinopyridin-3-yl)-5,7-difluoro-3-methyl-2-(pyridin-2-yl)quinolin-4-amine N-(2-(3-(Difluoromethoxy)phenyl)-5-morpholinopyridin-3-yl)-5,7-difluoro-3-methyl-2-(pyridin-2-yl)quinolin-4-amine

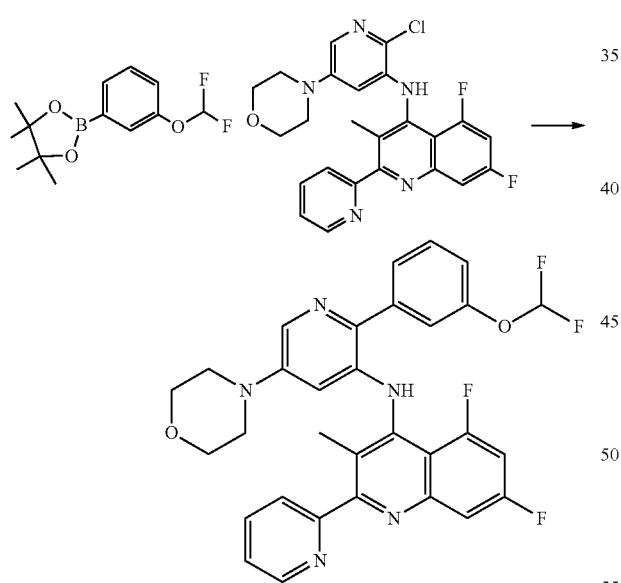

N-(2-chloro-5-morpholinopyridin-3-yl)-5,7-difluoro-3-methyl-2-(pyridin-2-yl)-quinolin-4-amine (49.1 mg, 0.10 mmol), 2-(3-(difluoromethoxy)phenyl)-4,4,5,5-tetramethyl-1,3,2-dioxaborolane (56.9 mg, 0.21 mmol), tricyclohexylphosphine (5.1 mg, 0.018 mmol), and tris(dibenzylideneacetone)dipalladium (0) (8.9 mg, 9.7 µmol) were added to a flask then degassed and backfilled with argon. To the flask, 1,4-dioxane (2.0 mL) and aq. 1.3M potassium phosphate tribasic (0.21 mL, 0.27 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-45% of a premixed solution of 89:9:1 DCM:MeOH:ammonium hydroxide in DCM) to afford a film that was triturated with MeOH to afford a yellow solid as N-(2-(3-(difluoromethoxy)phenyl)-5-morpholinopyridin-3-yl)-5,7-difluoro-3-methyl-2-(pyridin-2-yl)quinolin-4-amine. $^1$H NMR (500 MHz, DMSO-d$_6$) δ ppm 8.69 (1H, d, J=4.9 Hz), 8.06 (2H, m), 7.91 (1H, d, J=3.7 Hz), 7.80 (1H, d, J=7.8 Hz), 7.59 (2H, m), 7.47 (2H, m), 7.36 (4H, m), 6.54 (1H, d, J=2.4 Hz), 3.76 (4H, m), 3.15 (4H, m), 2.14 (3H, s). Mass Spectrum (pos.) m/e: 576.1 (M+1).

Example 189

Preparation of N-(2-(4-(difluoromethoxy)phenyl)-5-morpholinopyridin-3-yl)-5,7-difluoro-3-methyl-2-(pyridin-2-yl)quinolin-4-amine N-(2-(4-(Difluoromethoxy)phenyl)-5-morpholinopyridin-3-yl)-5,7-difluoro-3-methyl-2-(pyridin-2-yl)quinolin-4-amine

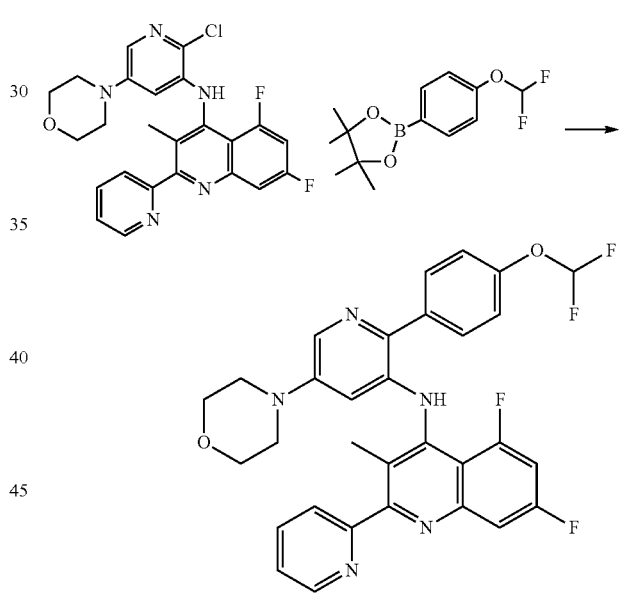

N-(2-chloro-5-morpholinopyridin-3-yl)-5,7-difluoro-3-methyl-2-(pyridin-2-yl)-quinolin-4-amine (49.7 mg, 0.11 mmol), 2-(4-(difluoromethoxy)phenyl)-4,4,5,5-tetramethyl-1,3,2-dioxaborolane (58.6 mg, 0.22 mmol), tricyclohexylphosphine (5.1 mg, 0.018 mmol), and tris(dibenzylideneacetone)dipalladium (0) (8.6 mg, 9.4 µmol) were added to a flask then degassed and backfilled with argon. To the flask, 1,4-dioxane (2.0 mL) and aq. 1.3M potassium phosphate tribasic (0.21 mL, 0.27 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-40% of a premixed solution of 89:9:1 DCM:MeOH:ammonium hydroxide in DCM) to afford a film that was triturated with MeOH to afford a light yellow solid as N-(2-(4-(difluoromethoxy)phenyl)-5-morpholinopyridin-3-yl)-5,7-difluoro-3-methyl-2-(pyridin-2-yl)quinolin-4-amine. $^1$H NMR (500 MHz, DMSO-d$_6$) δ ppm 8.69 (1H, d, J=4.6 Hz), 8.05 (2H, m), 7.86 (2H, m), 7.63 (2H, m, J=8.6 Hz), 7.59 (2H, m), 7.43 (1H, m), 7.09 (3H, m), 6.48 (1H, d, J=2.0 Hz), 3.78 (4H, m), 3.14 (4H, m), 2.16 (3H, s). Mass Spectrum (pos.) m/e: 576.1 (M+1).

Example 190

Preparation of N-(2,5-dimorpholinopyridin-3-yl)-5,7-difluoro-3-methyl-2-(5-methylpyridin-3-yl)quinolin-4-amine 4-Chloro-5,7-difluoro-3-methyl-2-(5-methylpyridin-3-yl)quinoline

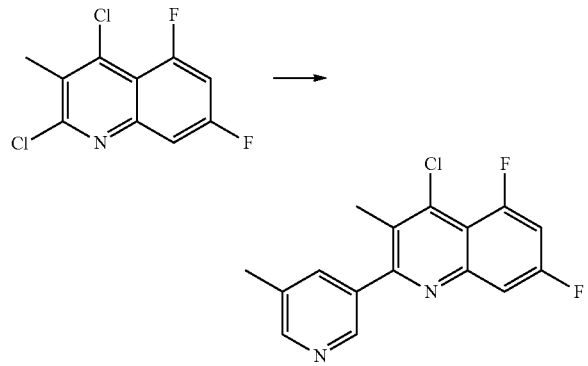

A screw-cap vial was charged with 2,4-dichloro-5,7-difluoro-3-methylquinoline (600 mg, 2.42 mmol), 5-methylpyridine-3-boronic acid (348 mg, 2.54 mmol), dichlorobis(triphenylphosphine)palladium (II) (170 mg, 0.24 mmol), sodium carbonate (769 mg, 7.26 mmol), 1,4-dioxane (6.5 mL), and water (1.6 mL). The mixture was stirred at 95° C. for 22 h, then 0.2 additional equivalents of the aforementioned boronic acid were added and the reaction was continued for 18 h. Upon completion, the reaction was cooled to rt and partitioned between EtOAc and water. The organic layer was washed with brine, dried over magnesium sulfate, and cond. The resulting crude product was purified by flash chromatography (silica gel, 0-30% EtOAc in hexanes), affording 4-chloro-5,7-difluoro-3-methyl-2-(5-methylpyridin-3-yl)quinoline. Mass Spectrum (ESI) m/e=305.0 (M+1).

N-(2,5-Dimorpholinopyridin-3-yl)-5,7-difluoro-3-methyl-2-(5-methylpyridin-3-yl)quinolin-4-amine

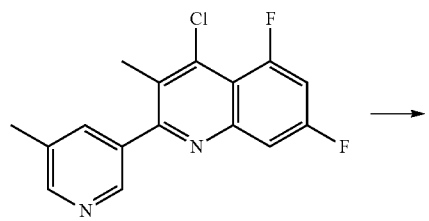

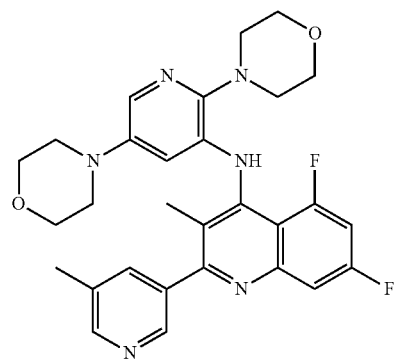

A screw-cap vial was charged with 4-chloro-5,7-difluoro-3-methyl-2-(5-methylpyridin-3-yl)quinoline (50 mg, 0.16 mmol), 2,5-dimorpholinopyridin-3-amine (43.4 mg, 0.16 mmol), tris(dibenzylideneacetone)dipalladium (0) (15.0 mg, 0.016 mmol), XPhos (15.6 mg, 0.033 mmol), sodium tert-butoxide (47.3 mg, 0.49 mmol), and toluene (1.5 mL). The mixture was stirred at 105° C. for 2 h, then cond. The resulting residue was partitioned between DCM and water, and the organic layer was dried over magnesium sulfate and cond. The crude material was purified by recrystallization in MeOH, affording N-(2,5-dimorpholinopyridin-3-yl)-5,7-difluoro-3-methyl-2-(5-methylpyridin-3-yl)quinolin-4-amine. Mass Spectrum (ESI) m/e=533.0 (M+1). $^1$H NMR (400 MHz, chloroform-d) δ ppm 8.64 (1H, d, J=1.8 Hz), 8.57 (1H, d, J=1.6 Hz), 7.83 (1H, s), 7.78 (1H, br. s.), 7.67 (1H, d, J=2.5 Hz), 7.63 (1H, d, J=9.4 Hz), 6.98-7.09 (1H, m), 6.32-6.42 (1H, m), 3.91 (4H, br. s.), 3.77-3.86 (4H, m), 3.09-3.41 (4H, br. s.), 2.99-3.09 (4H, m), 2.48 (3H, s), 2.17 (3H, s).

Example 191

Preparation of N-(2,5-dimorpholinopyridin-3-yl)-5,7-difluoro-3-methyl-2-(5-(methylthio)pyridin-3-yl)quinolin-4-amine 4-Chloro-5,7-difluoro-3-methyl-2-(5-(methylthio)pyridin-3-yl)quinoline

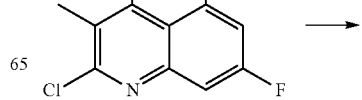

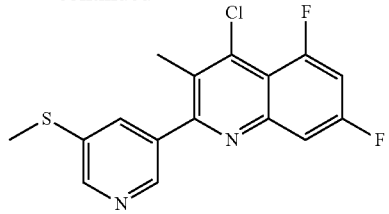

A screw-cap vial was charged with 2,4-dichloro-5,7-difluoro-3-methylquinoline (600 mg, 2.42 mmol), 5-(methylthio)pyridin-3-ylboronic acid (429 mg, 2.54 mmol), dichlorobis(triphenylphosphine)palladium (II) (170 mg, 0.24 mmol), sodium carbonate (769 mg, 7.26 mmol), 1,4-dioxane (6.5 mL), and water (1.6 mL). The mixture was stirred at 95° C. for 2 h, then cooled to rt and partitioned between EtOAc and water. The organic layer was washed with brine, dried over magnesium sulfate, and cond. The crude product was purified by flash chromatography (silica gel, 0-30% EtOAc in hexanes), affording 4-chloro-5,7-difluoro-3-methyl-2-(5-(methylthio)pyridin-3-yl)quinoline. Mass Spectrum (ESI) m/e=337.0 (M+1).

N-(2,5-Dimorpholinopyridin-3-yl)-5,7-difluoro-3-methyl-2-(5-(methylthio)-pyridin-3-yl)quinolin-4-amine

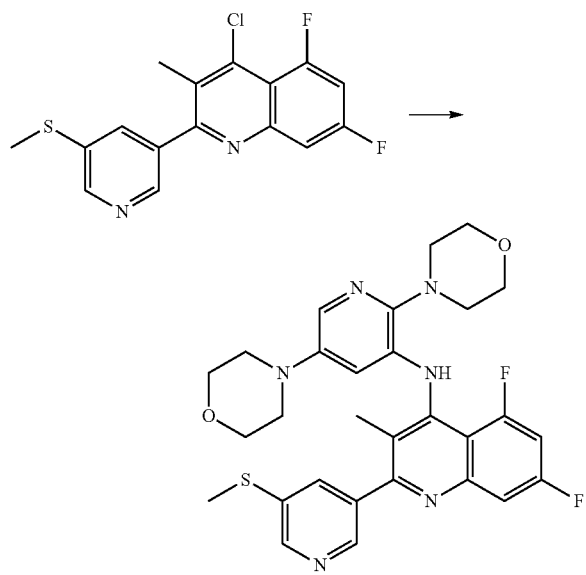

A screw-cap vial was charged with 4-chloro-5,7-difluoro-3-methyl-2-(5-(methylthio)pyridin-3-yl)quinoline (50 mg, 0.15 mmol), 2,5-dimorpholinopyridin-3-amine (39.2 mg, 0.15 mmol), tris(dibenzylideneacetone)dipalladium (0) (13.6 mg, 0.015 mmol), XPhos (14.2 mg, 0.030 mmol), sodium tert-butoxide (42.8 mg, 0.445 mmol), and toluene (1.5 mL). The mixture was stirred at 105° C. for 2 h, then cond. The resulting residue was partitioned between DCM and water, and the organic layer was dried over magnesium sulfate and cond. The crude material was purified by recrystallization in MeOH, affording N-(2,5-dimorpholinopyridin-3-yl)-5,7-difluoro-3-methyl-2-(5-(methylthio)pyridin-3-yl)quinolin-4-amine. Mass Spectrum (ESI) m/e=565.0 (M+1). $^1$H NMR (400 MHz, CDCl$_3$) δ ppm 8.61 (1H, d, J=2.3 Hz), 8.59 (1H, s), 7.86 (2H, m), 7.68 (2H, m), 7.09 (1H, m), 6.39 (1H, br. s.), 3.92 (4H, br. s.), 3.83 (4H, br. s.), 3.05-3.50 (4H, br. s.), 3.05 (4H, br. s.), 2.60 (3H, s), 2.18 (3H, br. s.).

Example 192

Preparation of N-(2,5-dimorpholinopyridin-3-yl)-5,7-difluoro-3-methyl-2-(5-(methylsulfonyl)pyridin-3-yl)quinolin-4-amine 4-Chloro-5,7-difluoro-3-methyl-2-(5-(methylsulfonyl)pyridin-3-yl)quinoline

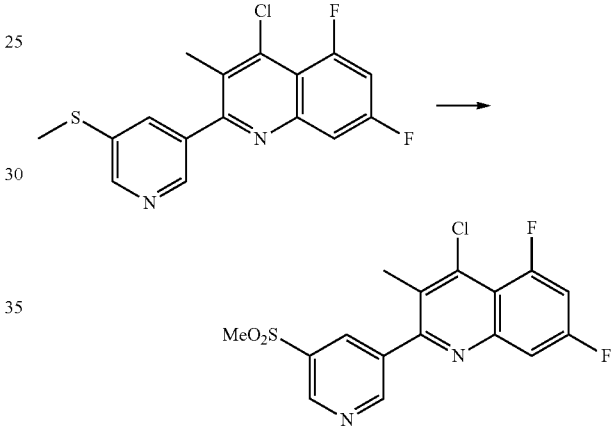

To a stirring suspension of 4-chloro-5,7-difluoro-3-methyl-2-(5-(methylthio)pyridin-3-yl)quinoline (200 mg, 0.594 mmol) in THF (4.4 mL) and water (1.4 mL) was added oxone (913 mg, 1.49 mmol). The reaction was stirred at rt for 18 h, then poured into 15 mL water and stirred for ten min. The resulting precipitate was isolated by filtration, then dissolved in EtOAc, dried over magnesium sulfate, and cond, affording 4-chloro-5,7-difluoro-3-methyl-2-(5-(methylsulfonyl)pyridin-3-yl)quinoline. Mass Spectrum (ESI) m/e=369.0 (M+1).

N-(2,5-Dimorpholinopyridin-3-yl)-5,7-difluoro-3-methyl-2-(5-(methylsulfonyl)pyridin-3-yl)quinolin-4-amine

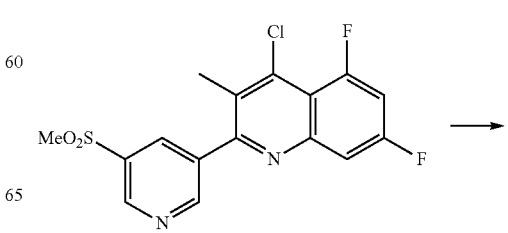

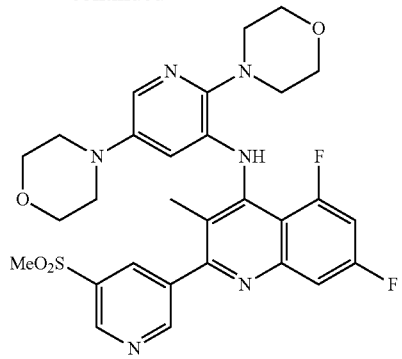

A screw-cap vial was charged with 4-chloro-5,7-difluoro-3-methyl-2-(5-(methylsulfonyl)pyridin-3-yl)quinoline (40 mg, 0.11 mmol), 2,5-dimorpholinopyridin-3-amine (28.7 mg, 0.11 mmol), tris(dibenzylideneacetone)dipalladium (0) (10.0 mg, 11.0 μmol), X-Phos (10.3 mg, 0.022 mmol), sodium tert-butoxide (31.3 mg, 0.33 mmol), and toluene (1.1 mL). The reaction was stirred at 105° C. for 30 min, then cond. The resulting residue was partitioned between DCM and water, and extracted twice with DCM. The combined organic layer was dried over magnesium sulfate and cond, and the crude product was purified by flash chromatography (basic alumina, 0-60% EtOAc in hexanes). This afforded N-(2,5-dimorpholinopyridin-3-yl)-5,7-difluoro-3-methyl-2-(5-(methylsulfonyl)pyridin-3-yl)quinolin-4-amine. Mass Spectrum (ESI) m/e=597.0 (M+1). ¹H NMR (500 MHz, CDCl3) δ ppm 9.26 (1H, d, J=2.2 Hz), 9.16 (1H, s), 8.56 (1H, s), 7.89 (1H, s), 7.72 (1H, s), 7.63 (1H, s), 7.09 (1H, s), 6.43 (1H, s), 3.88-4.08 (4H, m), 3.85 (4H, br. s.), 3.23 (4H, br. s.), 3.08 (4H, br. s.), 2.18 (3H, s), 1.57 (3H, s).

Example 193

Preparation of N-(5-(2-aminopyrimidin-4-yl)pyridin-3-yl)-5,7-difluoro-3-methyl-2-(4-methylpyridin-2-yl)quinolin-4-amine N-(5-Bromopyridin-3-yl)-5,7-difluoro-3-methyl-2-(4-methylpyridin-2-yl)-quinolin-4-amine

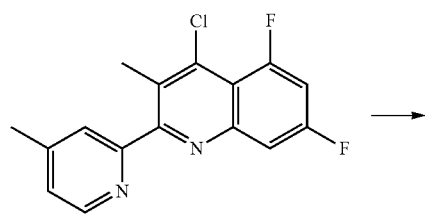

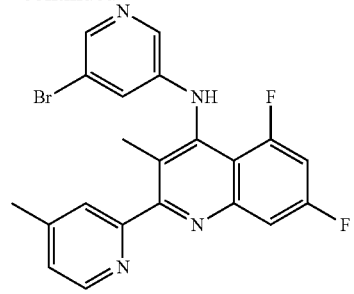

A screwcap vial was charged with a solution of 5-bromopyridin-3-amine (273 mg, 1.58 mmol) in dry DMF (8 mL) under nitrogen. To this stirring solution was slowly added sodium hydride (63.0 mg, 1.58 mmol), followed 5 min later by 4-chloro-5,7-difluoro-3-methyl-2-(4-methylpyridin-2-yl)quinoline (400 mg, 1.31 mmol). The reaction mixture was then stirred at rt for 6 h. Additional portions of sodium hydride (1.2 equivalents) were added after 2 and 4 h of stirring. Upon completion, the reaction was quenched with 10% aq. sodium carbonate and the product was extracted with EtOAc. The organic layer was washed with brine, dried over magnesium sulfate, and cond. The resulting crude residue was purified by flash-chromatography (silica gel, 0-60% EtOAc in hexanes) and subsequently by recrystallization in MeOH. This afforded N-(5-bromopyridin-3-yl)-5,7-difluoro-3-methyl-2-(4-methylpyridin-2-yl)quinolin-4-amine. Mass Spectrum (ESI) m/e=441.0 (M+1).

5-(5,7-Difluoro-3-methyl-2-(4-methylpyridin-2-yl)quinolin-4-ylamino)-pyridin-3-ylboronic acid

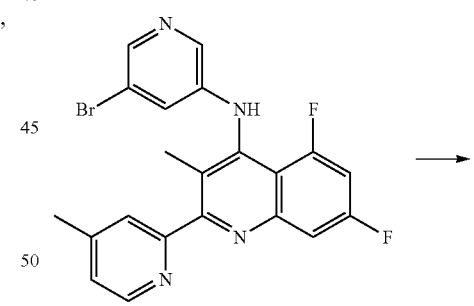

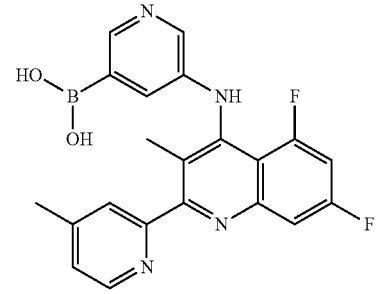

A screwcap vial was charged with N-(5-bromopyridin-3-yl)-5,7-difluoro-3-methyl-2-(4-methylpyridin-2-yl)quinolin-4-amine (225 mg, 0.510 mmol), bis(pinacolato)diboron (194 mg, 0.77 mmol), bis(triphenylphosphine)palladium (II) chloride (35.8 mg, 0.051 mmol), potassium acetate (100 mg, 1.02 mmol), and 1,4-dioxane (5 mL). The mixture was stirred at 95° C. under nitrogen for 18 h, and cooled to rt. The desired product was extracted with DCM and EtOAc, and the combined organic layer was dried over magnesium sulfate and cond. This afforded crude 5-(5,7-difluoro-3-methyl-2-(4-methylpyridin-2-yl)quinolin-4-ylamino)pyridin-3-ylboronic acid. Mass Spectrum (ESI) m/e=407.1 (M+1).

N-(5-(2-Aminopyrimidin-4-yl)pyridin-3-yl)-5,7-difluoro-3-methyl-2-(4-methylpyridin-2-yl)quinolin-4-amine

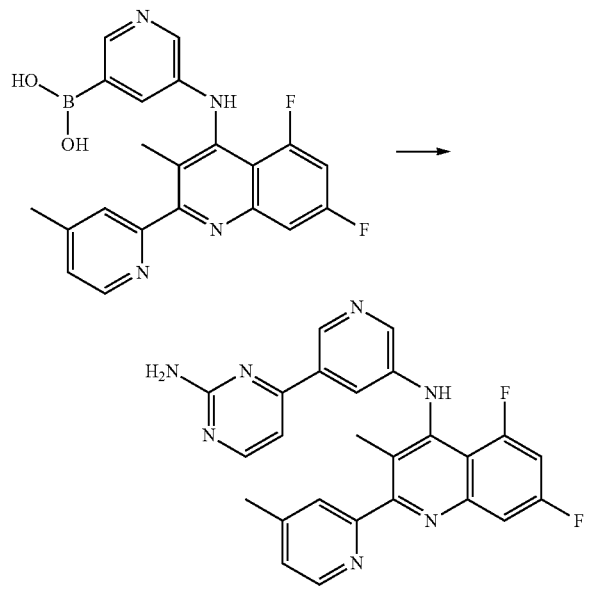

A screw-cap vial was charged with 5-(5,7-difluoro-3-methyl-2-(4-methylpyridin-2-yl)quinolin-4-ylamino)pyridin-3-ylboronic acid (200 mg, 0.49 mmol), 2-amino-4-chloropyrimidine (63.8 mg, 0.49 mmol), bis(triphenylphosphine) palladium (II) chloride (34.6 mg, 0.049 mmol), sodium carbonate (157 mg, 1.48 mmol), 1,4-dioxane (4 mL), and water (1 mL). The solution was stirred at 95° C. for 30 min, and then cooled to rt. The product was extracted with EtOAc and DCM, and the combined organic layer was dried over magnesium sulfate and cond. The crude material was purified by flash-chromatography (basic alumina, 0-10% MeOH in DCM, then recrystallized in MeOH to afford N-(5-(2-aminopyrimidin-4-yl)-pyridin-3-yl)-5,7-difluoro-3-methyl-2-(4-methylpyridin-2-yl)quinolin-4-amine. Mass Spectrum (ESI) m/e=456.0 (M+1). $^1$H NMR (400 MHz, DMSO-d$_6$) δ ppm 8.78 (1H, s), 8.63 (1H, d, J=1.8 Hz), 8.56 (1H, d), 8.31 (1H, d, J=5.3 Hz), 8.13 (1H, d), 7.75 (1H, s), 7.70 (1H, m), 7.60 (1H, m), 7.49 (1H, m), 7.35 (1H, m), 7.09 (1H, s), 6.68 (2H, s), 2.45 (3H, s), 2.20 (3H, s).

Example 194

Preparation of 5,7-difluoro-3-methyl-2-(4-methylpyridin-2-yl)-N-(2-(methylsulfonyl)-5-morpholinophenyl)quinolin-4-amine

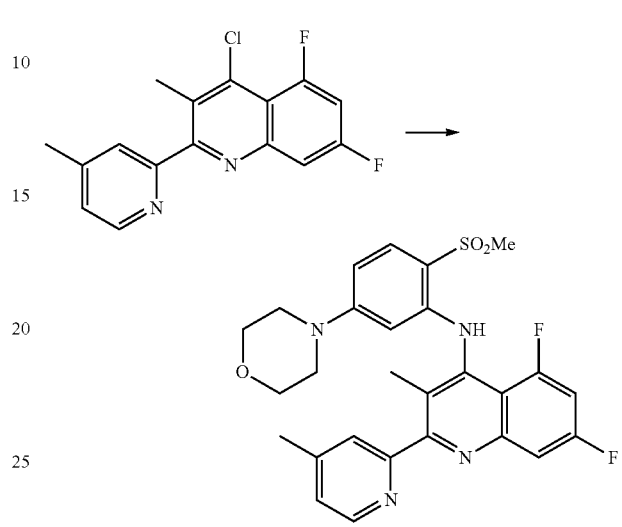

A screw-cap vial was charged with 4-chloro-5,7-difluoro-3-methyl-2-(4-methylpyridin-2-yl)quinoline (50 mg, 0.16 mmol), 2-(methylsulfonyl)-5-morpholinoaniline (Matrix Scientific; 50.5 mg, 0.20 mmol), XPhos precatalyst (CAS 1028206-56-5; 24.24 mg, 0.033 mmol), sodium tert-butoxide (39.4 mg, 0.41 mmol), and toluene (1.5 mL). The mixture was stirred at 95° C. under nitrogen gas for 3 h. The reaction was then cond and the resulting residue was dissolved in DCM. This solution was washed with water, dried over magnesium sulfate, and cond. The resulting crude product was purified by flash-chromatography (silica gel, 0-85% EtOAc in hexanes), affording 5,7-difluoro-3-methyl-2-(4-methylpyridin-2-yl)-N-(2-(methylsulfonyl)-5-morpholinophenyl)quinolin-4-amine as a white solid. Mass Spectrum (ESI) m/e=525.3 (M+1). $^1$H NMR (400 MHz, CDCl3) δ ppm 8.62 (1H, d, J=6.5 Hz), 8.55 (1H, d, J=5.1 Hz), 7.79 (1H, d, J=9.0 Hz), 7.67-7.70 (1H, m), 7.62-7.67 (1H, m), 7.18-7.25 (1H, m), 6.96-7.04 (1H, m), 6.47-6.52 (1H, m), 5.98-6.01 (1H, m), 3.70-3.80 (4H, m), 3.17 (3H, s), 3.06-3.16 (4H, m), 2.49 (3H, s), 2.28 (3H, s).

Example 195

Preparation of 5,7-difluoro-3-methyl-N-(2-(methylsulfonyl)-5-morpholinophenyl)-2-(2-(methylsulfonyl)phenyl)quinolin-4-amine

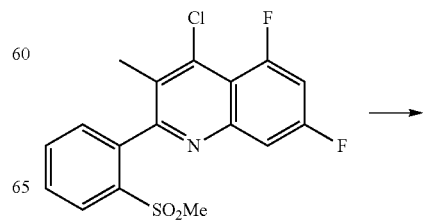

-continued

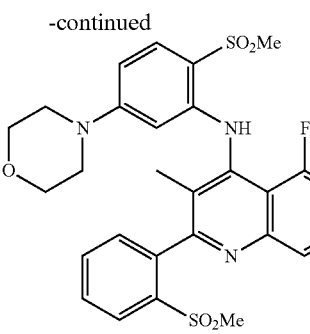

A screw-cap vial was charged with 4-chloro-5,7-difluoro-3-methyl-2-(2-(methylsulfonyl)phenyl)quinoline (50 mg, 0.136 mmol), 2-(methylsulfonyl)-5-morpholinoaniline (Matrix Scientific; 34.8 mg, 0.14 mmol), XPhos precatalyst (CAS 1028206-56-5; 10.0 mg, 0.014 mmol), sodium tert-butoxide (32.7 mg, 0.34 mmol), and toluene (1.5 mL). The mixture was stirred at 95° C. under nitrogen gas for 18 h. The reaction was then cond, and the resulting residue was dissolved in EtOAc. This solution was washed with water, and the product extracted twice with EtOAc and once with DCM. The combined organic layer was then dried over magnesium sulfate and cond, affording a crude residue that was purified by flash-chromatography (silica gel, 0-50% EtOAc in hexanes). This afforded 5,7-difluoro-3-methyl-N-(2-(methylsulfonyl)-5-morpholinophenyl)-2-(2-(methylsulfonyl)phenyl)quinolin-4-amine. Mass Spectrum (ESI) m/e=588.0 (M+1). $^1$H NMR (400 MHz, CDCl3) δ ppm 8.78 (1H, br. s.), 8.20 (1H, d, J=8.0 Hz), 7.66-7.86 (3H, m), 7.50 (1H, br. s.), 7.45 (1H, d, J=7.4 Hz), 7.08 (1H, br. s.), 6.43 (1H, d, J=8.8 Hz), 6.04 (1H, br. s.), 3.72 (4H, t, J=4.6 Hz), 3.17-3.23 (4H, m), 3.16 (3H, s), 3.13 (3H, s), 1.94 (3H, s).

Example 196

Preparation of 5-fluoro-3-methyl-N-(2-(methylsulfonyl)-5-morpholinophenyl)-2-(pyridin-2-yl)quinolin-4-amine

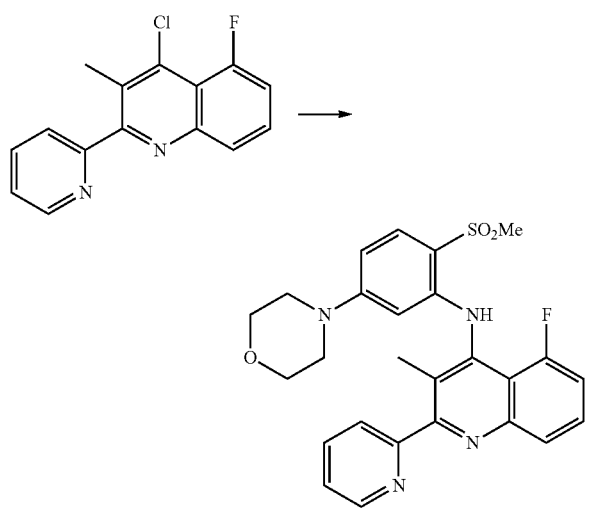

A screw-cap vial was charged with 4-chloro-5-fluoro-3-methyl-2-(pyridin-2-yl)-quinoline (50 mg, 0.18 mmol), 2-(methylsulfonyl)-5-morpholinoaniline (47.0 mg, 0.18 mmol), XPhos precatalyst (CAS 1028206-56-5; 27.1 mg, 0.037 mmol), sodium tert-butoxide (44.1 mg, 0.46 mmol), and toluene (1.8 mL). The mixture was stirred at 90° C. for 2 h, then cond. The crude residue was dissolved in EtOAc, washed with water, and the organic layer was dried over magnesium sulfate and cond. The crude product was purified by reverse-phase HPLC (0-70% acetonitrile in water), affording 5-fluoro-3-methyl-N-(2-(methylsulfonyl)-5-morpholinophenyl)-2-(pyridin-2-yl)quinolin-4-amine as an amorphous beige solid. Mass Spectrum (ESI) m/e=493.0 (M+1). $^1$H NMR (400 MHz, CDCl3) δ ppm 8.80 (1H, br. s), 8.72 (1H, d, J=4.7 Hz), 8.14 (1H, br. s), 7.95 (2H, br. s.), 7.80 (1H, d, J=9.0 Hz), 7.64 (1H, m), 7.42 (1H, d, J=3.3 Hz), 7.20 (1H, m), 6.52 (1H, d, J=9.2 Hz), 6.04 (1H, s), 3.70-3.81 (4H, m), 3.18 (3H, s), 3.05-3.17 (4H, m), 2.30 (3H, s).

Procedure L

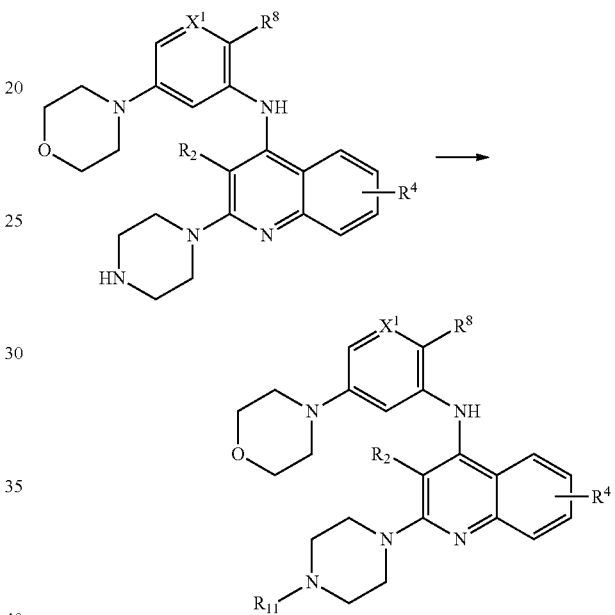

To a solution of the piperazine (0.056 mmol) and the appropriate aldehyde or ketone ($R^{11}$—CHO) (0.056 mmol) in MeOH (1.2 mL) was added sodium cyanoborohydride (0.085 mmol) at rt. The reaction mixture was stirred at rt for 4 h. The reaction mixture was cond to remove MeOH. Water was added to the residue and extracted with EtOAc (2×5 mL). The organic layer was dried over Na$_2$SO$_4$ and cond under reduced pressure. Purification was done by column chromatography using silica gel (100-200 mesh) provide the crude material which was purified using Prep HPLC to provide the desired tertiary amine.

Procedure M

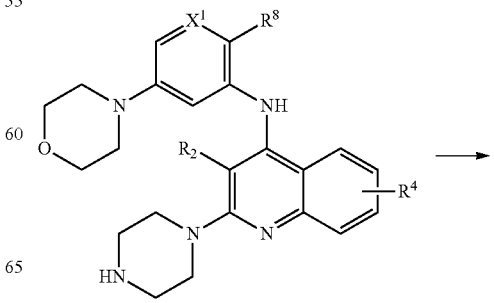

-continued

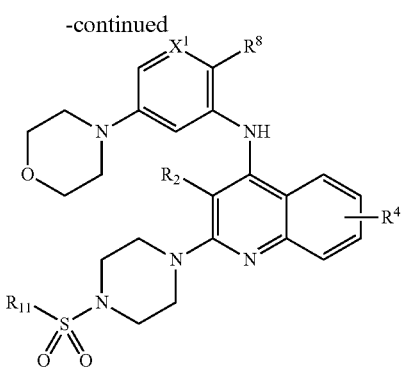

To a solution of the piperazine (0.11 mmol) and appropriate sulfonyl chloride ($R^{11}$—$SO_2Cl$) (0.11 mmol) in DCM (1 ml) was added triethylamine (0.020 mL, 0.17 mmol) at rt. The reaction mixture was stirred at rt for 3 h. Water was added to reaction mixture and extracted with EtOAc (2×5 mL). The organic layer was dried over $Na_2SO_4$ and cond under reduced pressure. Purification was done by column chromatography using silica gel (100-200 mesh) to provide crude material which was purified using Prep HPLC to provide the desired sulfonamides.

Procedure N

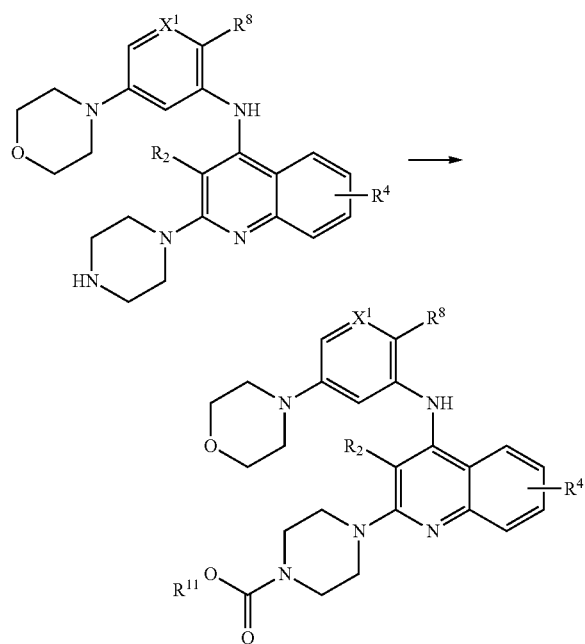

To a solution of the piperazine (0.14 mmol) in acetone (3.0 mL) was added potassium carbonate (110 mg, 0.82 mmol) and the chloroformate ($R^{11}$—COCl) (0.14 mmol) at rt. The reaction mixture was stirred at rt for 2 h. Water was added to the reaction mixture and extracted with EtOAc (2×5 mL). The organic layer was dried over $Na_2SO_4$ and cond under reduced pressure. Purification was done by column chromatography using silica gel to provide crude product which was purified using Prep HPLC to provide the final carbamates.

Procedure O Boc-Deprotection (or Tert-Butyl Ester Hydrolysis)

The tert-butyl carbamate or tert-butyl ester was dissolved in DCM (0.2 M) and cooled to 0° C. The trifluoroacetic acid (1:1 vol/vol to DCM above) was then added and the reaction mixture was allowed to slowly warm to rt. The reaction was then cond to dryness. The crude TFA salt was free based with satd sodium bicarbonate solution. The organic layer was dried over sodium sulfate and the filtrate was cond to give the desired product.

Procedure P

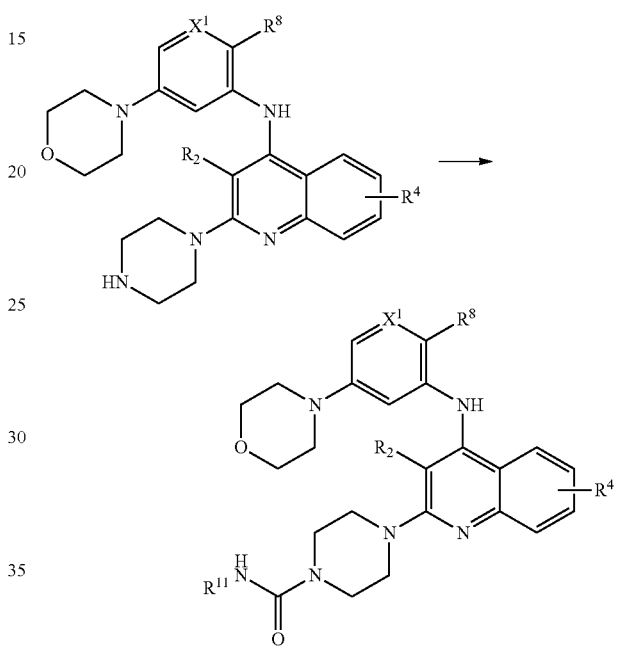

To a solution of the piperazine (40 mg, 0.090 mmol) in THF (1.6 mL) was added the isocyanate ($R_4$—NCO) (0.09 mmol). The reaction mixture was stirred at rt for 3 h. Water was added to the reaction mixture and extracted with EtOAc (2×5 mL). The organic layer was dried over $Na_2SO_4$ and cond under reduced pressure. Purification was done by column chromatography using silica gel (100-200 mesh) to provide crude material which was purified using Prep. HPLC to provide the final ureas.

Procedure Q

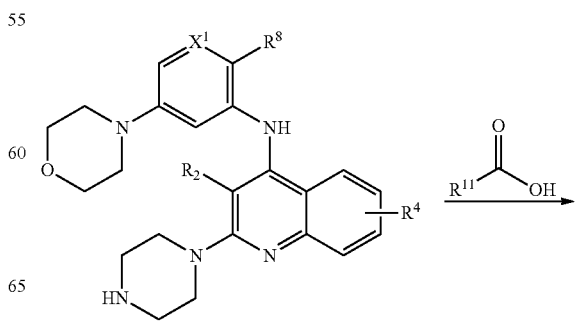

335
-continued

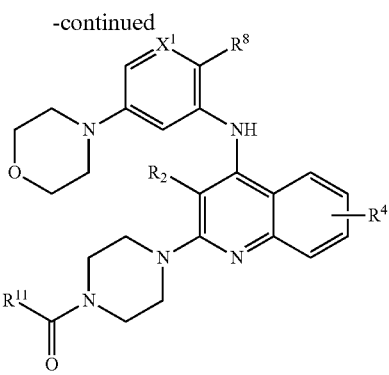

To a solution of the piperazine (0.090 mmol) and the appropriate carboxylic acid (R₄—CO₂H) (0.14 mmol) in THF (1 ml) were added EDCI-HCl (0.14 mmol), HOBT (0.14 mmol) and triethylamine (0.14 mmol) at rt. The reaction mixture was stirred at rt for 3 h. Water was added to reaction mixture and extracted with EtOAc (2×5 mL). The organic layer was dried over Na₂SO₄ and cond under reduced pressure. Purification was done by column chromatography using silica gel (100-200 mesh) to provide crude material that was purified using Prep HPLC to provide the final amides.

Procedure R

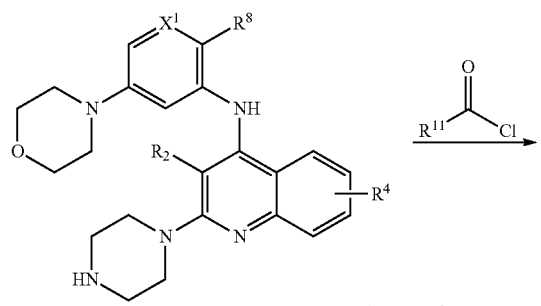

To a solution of the piperazine (0.11 mmol) in THF (1.0 mL) was added the appropriate acid chloride (R₄—COCl) (0.11 mmol) and triethylamine (0.17 mmol) at rt. The reaction mixture was stirred at rt for 3 h. Water was added to reaction mixture and extracted with EtOAc (2×5 mL). The organic layer was dried over Na₂SO₄ and cond under reduced pressure. Purification was done by column chromatography using silica gel (100-200 mesh) to provide crude product which was purified using Prep HPLC to provide the appropriate amides.

336

Preparation of 1-(5,7-Difluoro-3-methyl-4-((5-(4-morpholinyl)-3-pyridinyl)-amino)-2-quinolinyl)-2-piperidinone 1-(4-Bromo-5,7-difluoro-3-methylquinolin-2-yl)piperidin-2-one

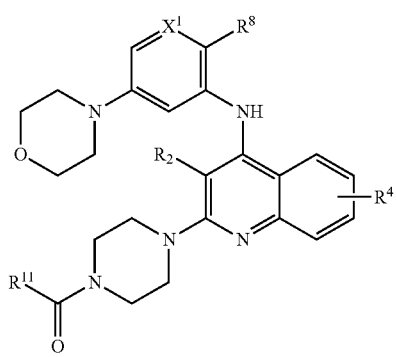

The 2,4-dibromo-5,7-difluoro-3-methylquinoline (2.00 g, 5.90 mmol), piperidin-2-one (590 mg, 5.90 mmol), copper (I) iodide (57.0 mg, 0.300 mmol), (1S,2S)—N1,N2-dimethylcyclohexane-1,2-diamine (0.094 mL, 0.59 mmol) and potassium phosphate tribasic (2.50 g, 12.0 mmol) were combined in 1,4-dioxane (10 mL) and stirred in the microwave reactor for 3.5 h. The reaction was diluted with water and extracted with EtOAc (2×100 mL). The combined organic layers were washed with brine and dried over magnesium sulfate. The crude product was then purified by medium pressure chromatography (silica gel, 0 to 100% EtOAc: hexanes) to give 1-(4-bromo-5,7-difluoro-3-methylquinolin-2-yl)piperidin-2-one. Mass Spectrum (ESI) m/e=355.1 (M+1).

1-(5,7-Difluoro-3-methyl-4-((5-(4-morpholinyl)-3-pyridinyl)amino)-2-quinolinyl)-2-piperidinone Essentially prepared according to Procedure H using 1-(4-bromo-5,7-difluoro-3-methylquinolin-2-yl)piperidin-2-one (75.0 mg, 0.21 mmol) and 5-morpholinopyridin-3-amine in toluene to give 1-(5,7-difluoro-3-methyl-4-((5-(4-morpholinyl)-3-pyridinyl)amino)-2-quinolinyl)-2-pyrrolidinone. 1H NMR (400 MHz, CDCl3) δ ppm 7.90 (1H, d, J=2.5 Hz), 7.86 (1H, d, J=2.3 Hz), 7.46 (1H, ddd, J=9.6, 2.5, 1.4 Hz), 7.24 (1H, d, J=14.1 Hz), 6.99 (1H, ddd, J=13.9, 8.6, 2.5 Hz), 6.54 (1H, t, J=2.4 Hz), 4.22-4.33 (1H, m), 3.82 (4H, t, J=4.8 Hz), 3.48-3.58 (1H, m), 3.13-3.28 (4H, m), 2.50-2.58 (2H, m), 2.07-2.14 (1H, m), 1.95-2.04 (3H, m), 1.94 (3H, s).

Example 197

Preparation of 4-(5,7-Difluoro-3-methyl-4-(5-morpholinopyridin-3-ylamino)quinolin-2-yl)-1-ethylpiperazin-2-one 4-(4-Bromo-5,7-difluoro-3-methylquinolin-2-yl)piperazin-2-one

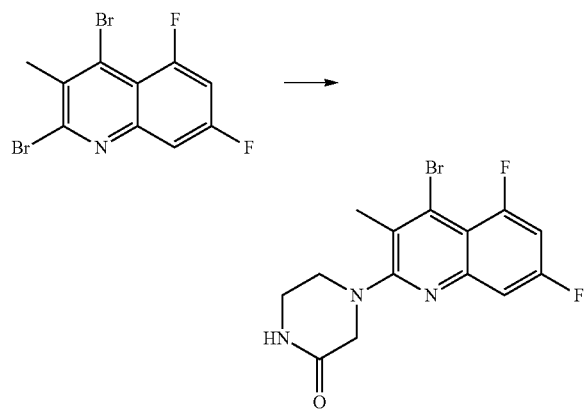

Essentially using procedure I the 2,4-dibromo-5,7-difluoro-3-methylquinoline (500 mg, 1.50 mmol) and other reagents were slurried in dioxane (5 mL) and stirred in a microwave reactor at 110° C. for 2 h. The resulting solid plug was dissolved and partitioned between water and EtOAc (2×75 mL). The combined organic layers were washed with brine (1×50 mL) and dried over magnesium sulfate. The crude product was purified by medium pressure chromatography (silica gel, 0 to 100% EtOAc:DCM to 0 to 10% 2M ammonia in MeOH:DCM) to give 4-(4-bromo-5,7-difluoro-3-methylquinolin-2-yl)piperazin-2-one (240 mg, 0.67 mmol). Mass Spectrum (ESI) m/e=358.0 (M+1).

4-(4-Bromo-5,7-difluoro-3-methylquinolin-2-yl)-1-ethylpiperazin-2-one

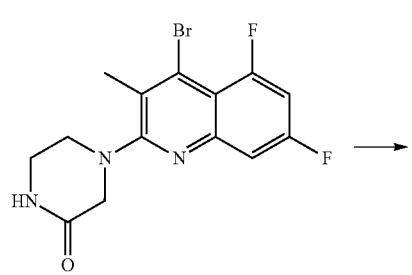

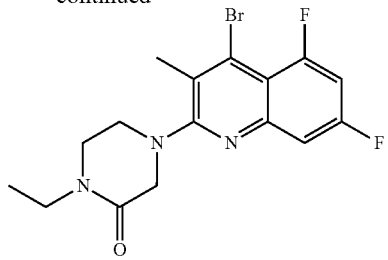

The 4-(4-bromo-5,7-difluoro-3-methylquinolin-2-yl)piperazin-2-one (70 mg, 0.20 mmol) was dissolved in THF (2.0 mL). To the solution was added sodium hydride (24.0 mg, 1.00 mmol) (60% dispersion) followed by addition of ethyl iodide (0.16 mL, 2.00 mmol). The reaction was stirred overnight. The reaction was quenched with water and the mixture was extracted with EtOAc (2×50 mL). The combined organic layers were washed with brine (1×25 mL) and dried over magnesium sulfate. The crude product was purified by medium pressure chromatography (silica gel, 0 to 100% EtOAc:hexanes) to give 4-(4-bromo-5,7-difluoro-3-methylquinolin-2-yl)-1-ethylpiperazin-2-one. Mass Spectrum (ESI) m/e=384.1 (M+1).

4-(5,7-Difluoro-3-methyl-4-(5-morpholinopyridin-3-ylamino)quinolin-2-yl)-1-ethylpiperazin-2-one

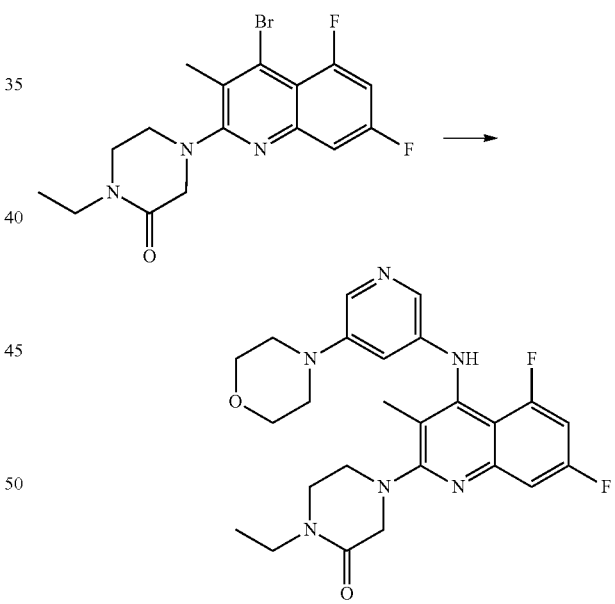

Essentially prepared according to Procedure H using 4-(4-bromo-5,7-difluoro-3-methylquinolin-2-yl)-1-ethylpiperazin-2-one (31.0 mg, 0.081 mmol) and 5-morpholinopyridin-3-amine in toluene to give 4-(5,7-difluoro-3-methyl-4-((5-(4-morpholinyl)-3-pyridinyl)amino)-2-quinolinyl)-1-ethyl-2-piperazinone. 1H NMR (400 MHz, CDCl3) δ ppm 7.85 (1H, d, J=2.2 Hz), 7.75 (1H, d, J=2.0 Hz), 7.57 (1H, d, J=6.7 Hz), 7.28-7.36 (1H, m), 6.93 (1H, s), 6.83 (1H, ddd, J=13.3, 8.7, 2.5 Hz), 4.11 (2H, s), 3.81-3.92 (4H, m), 3.72 (2H, t, J=5.3 Hz), 3.43-3.56 (4H, m), 3.19-3.30 (4H, m), 2.20 (3H, s), 1.18 (3H, t, J=7.2 Hz). Mass Spectrum (ESI) m/e=483.3 (M+1).

Example 198

Preparation of 4-(4-(2,5-Dimorpholinopyridin-3-ylamino)-5,7-difluoro-3-methylquinolin-2-yl)-1-ethylpiperazin-2-one

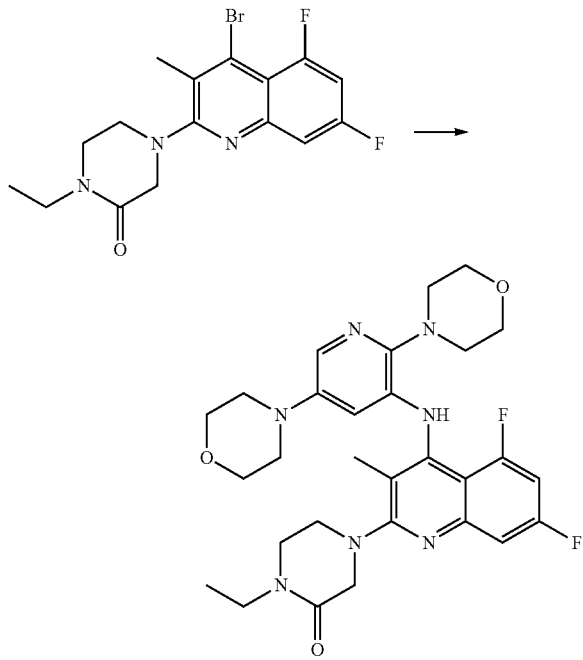

Essentially prepared according to Procedure H using 4-(4-bromo-5,7-difluoro-3-methylquinolin-2-yl)-1-ethylpiperazin-2-one (31.0 mg, 0.081 mmol) and 2,5-dimorpholinopyridin-3-amine in toluene to give 4-(4-(2,5-dimorpholinopyridin-3-ylamino)-5,7-difluoro-3-methylquinolin-2-yl)-1-ethylpiperazin-2-one. TFA Salt: $^1$H NMR (400 MHz, CDCl3) δ ppm 7.79 (1H, d, J=2.7 Hz), 7.72 (1H, d, J=11.0 Hz), 7.37-7.46 (1H, m), 6.89 (1H, ddd, J=13.5, 8.5, 2.4 Hz), 6.50 (1H, d, J=2.5 Hz), 6.24 (3H, br. s.), 4.01-4.33 (2H, m), 3.87-4.00 (5H, m), 3.76-3.85 (4H, m), 3.72 (2H, br. s.), 3.15-3.58 (7H, m), 3.01-3.14 (4H, m), 2.14 (3H, s), 1.20 (3H, t, J=7.2 Hz). Mass Spectrum (ESI) m/e=568.3 (M+1).

Example 199

Preparation of 4-(5,7-Difluoro-3-methyl-4-(5-morpholinopyridin-3-ylamino)quinolin-2-yl)-1-propylpiperazin-2-one 4-(4-Bromo-5,7-difluoro-3-methylquinolin-2-yl)-1-ethylpiperazin-2-one

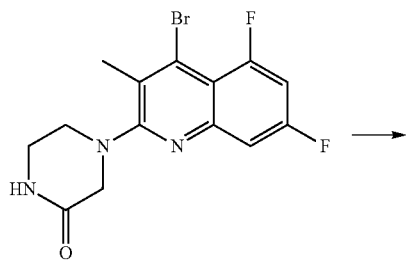

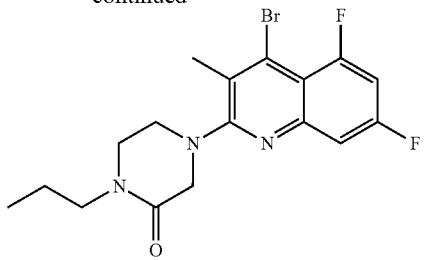

The 4-(4-bromo-5,7-difluoro-3-methylquinolin-2-yl)piperazin-2-one (70 mg, 0.200 mmol) was dissolved in THF (2.0 mL). To the solution was added sodium hydride (24.0 mg, 0.98 mmol) (60% dispersion) followed by addition of 1-iodopropane (230 μL, 2.40 mmol). The reaction was stirred overnight. The reaction was quenched with water and the mixture was extracted with EtOAc (2×50 mL). The combined organic layers were washed with brine (1×25 mL) and dried over magnesium sulfate. The crude product was purified by medium pressure chromatography (silica gel, 0 to 80% EtOAc:hexanes) to give 4-(4-bromo-5,7-difluoro-3-methylquinolin-2-yl)-1-propylpiperazin-2-one. Mass Spectrum (ESI) m/e=400.1 (M+1).

4-(5,7-Difluoro-3-methyl-4-(5-morpholinopyridin-3-ylamino)quinolin-2-yl)-1-propylpiperazin-2-one

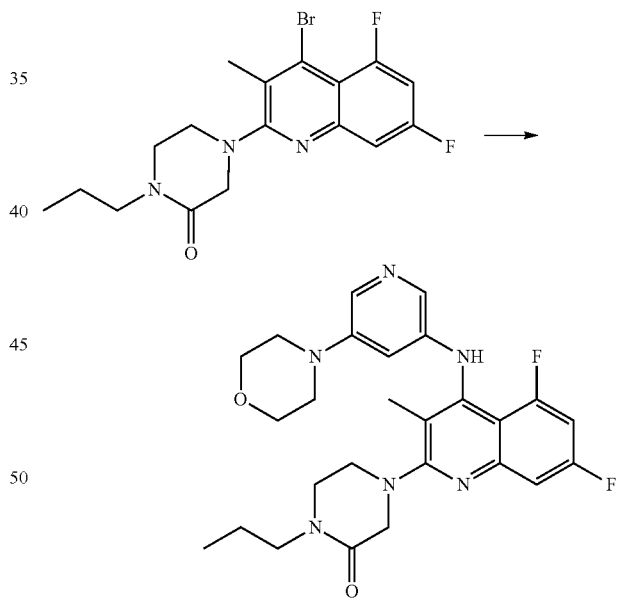

Essentially prepared according to Procedure H using 4-(4-bromo-5,7-difluoro-3-methylquinolin-2-yl)-1-propylpiperazin-2-one (70.0 mg, 0.20 mmol) and 5-morpholinopyridin-3-amine in toluene to give 4-(5,7-difluoro-3-methyl-4-(5-morpholinopyridin-3-ylamino)quinolin-2-yl)-1-propylpiperazin-2-one. TFA salt: $^1$H NMR (400 MHz, CDCl3) δ ppm 7.89 (1H, d, J=2.3 Hz), 7.78 (1H, d, J=1.8 Hz), 7.35 (1H, d, J=9.8 Hz), 7.31 (1H, d, J=7.2 Hz), 6.90 (1H, t, J=2.1 Hz), 6.86 (1H, ddd, J=13.3, 8.5, 2.6 Hz), 4.15 (2H, s), 3.82-3.93 (4H, m), 3.74 (2H, t, J=5.2 Hz), 3.49 (2H, t, J=5.2 Hz), 3.38-3.46 (2H, m), 3.19-3.31 (4H, m), 2.21 (3H, s), 1.52-1.70 (2H, m, J=14.9, 7.4, 7.4, 7.2 Hz), 0.92 (3H, t, J=7.4 Hz). Mass Spectrum (ESI) m/e=497.2 (M+1).

Example 200

Preparation of 4-(4-(2,5-Dimorpholinopyridin-3-ylamino)-5,7-difluoro-3-methylquinolin-2-yl)-1-propylpiperazin-2-one

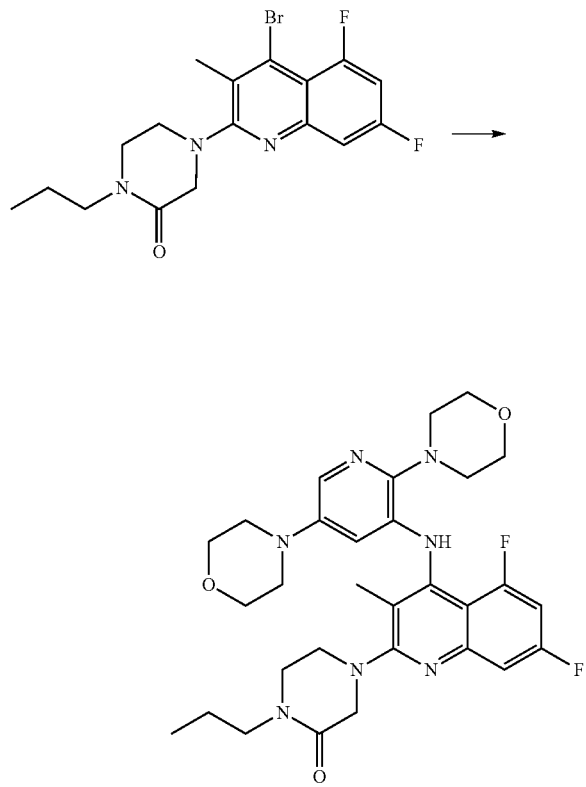

Essentially prepared according to Procedure H using 4-(4-bromo-5,7-difluoro-3-methylquinolin-2-yl)-1-ethylpiperazin-2-one (35.0 mg, 0.088 mmol) and 2,5-dimorpholinopyridin-3-amine in toluene to give 4-(4-(2,5-dimorpholinopyridin-3-ylamino)-5,7-difluoro-3-methylquinolin-2-yl)-1-propylpiperazin-2-one. $^1$H NMR (TFA salt) (400 MHz, CDCl3) δ ppm 7.79 (1H, d, J=2.5 Hz), 7.72 (1H, d, J=10.8 Hz), 7.40 (1H, ddd, J=9.7, 2.4, 1.2 Hz), 6.88 (1H, ddd, J=13.5, 8.6, 2.5 Hz), 6.47 (1H, d, J=2.7 Hz), 5.94 (3H, br. s.), 3.96-4.35 (3H, m), 3.87-3.95 (4H, m), 3.77-3.86 (4H, m), 3.54-3.76 (2H, m), 3.12-3.54 (7H, m), 2.99-3.13 (4H, m), 2.14 (3H, s), 1.63 (2H, sxt, J=7.5 Hz), 0.93 (3H, t, J=7.4 Hz). Mass Spectrum (ESI) m/e=582.2 (M+1).

Example 201

Preparation of 4-(5,7-Difluoro-3-methyl-4-(5-morpholinopyridin-3-ylamino)quinolin-2-yl)-1-isopropylpiperazin-2-one 4-(4-Bromo-5,7-difluoro-3-methylquinolin-2-yl)-1-isopropylpiperazin-2-one

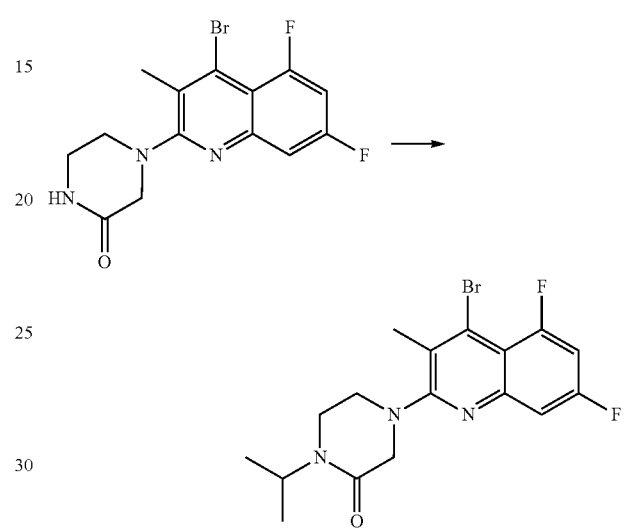

The 4-(4-bromo-5,7-difluoro-3-methylquinolin-2-yl)piperazin-2-one (89 mg, 0.25 mmol) was dissolved in THF (2.0 mL). To the solution was added sodium hydride (30.0 mg, 1.25 mmol) (60% dispersion) followed by addition of 2-iodopropane (750 µL, 7.50 mmol). The reaction was heated to reflux and stirred overnight. The reaction was quenched with water and the mixture was extracted with EtOAc (2×50 mL). The combined organic layers were washed with brine (1×25 mL) and dried over magnesium sulfate. The crude product was purified by medium pressure chromatography (silica gel, 0 to 80% EtOAc:hexanes) to give 4-(4-bromo-5,7-difluoro-3-methylquinolin-2-yl)-1-isopropylpiperazin-2-one. Mass Spectrum (ESI) m/e=400.1 (M+1).

4-(5,7-Difluoro-3-methyl-4-(5-morpholinopyridin-3-ylamino)quinolin-2-yl)-1-isopropylpiperazin-2-one

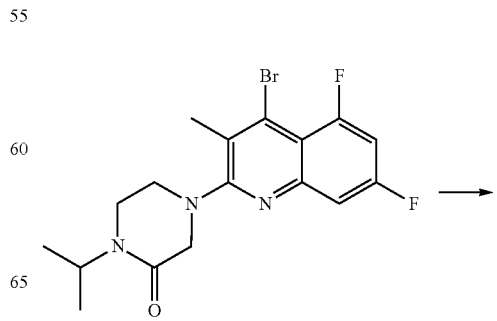

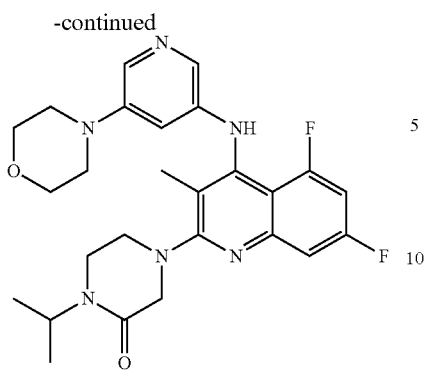

Essentially prepared according to Procedure H using 4-(4-bromo-5,7-difluoro-3-methylquinolin-2-yl)-1-isopropylpiperazin-2-one (30.0 mg, 0.075 mmol) and 5-morpholinopyridin-3-amine in toluene to give 4-(5,7-difluoro-3-methyl-4-(5-morpholinopyridin-3-ylamino)quinolin-2-yl)-1-isopropylpiperazin-2-one. TFA salt: 1H NMR (400 MHz, CDCl3) δ ppm 7.88 (1H, d, J=2.3 Hz), 7.78 (1H, d, J=1.8 Hz), 7.52 (1H, d, J=7.2 Hz), 7.35 (1H, dt, J=9.6, 1.2 Hz), 6.96 (1H, t, J=1.8 Hz), 6.84 (1H, ddd, J=13.2, 8.6, 2.4 Hz), 4.82-4.96 (1H, m), 4.19 (2H, s), 3.82-3.92 (4H, m), 3.74 (2H, t, J=5.3 Hz), 3.41 (2H, t, J=5.4 Hz), 3.19-3.34 (4H, m), 2.20 (3H, s), 1.17 (6H, d, J=6.8 Hz). Mass Spectrum (ESI) m/e=497.2 (M+1).

Example 202

Preparation of 4-(4-(2,5-Dimorpholinopyridin-3-ylamino)-5,7-difluoro-3-methylquinolin-2-yl)-1-isopropylpiperazin-2-one

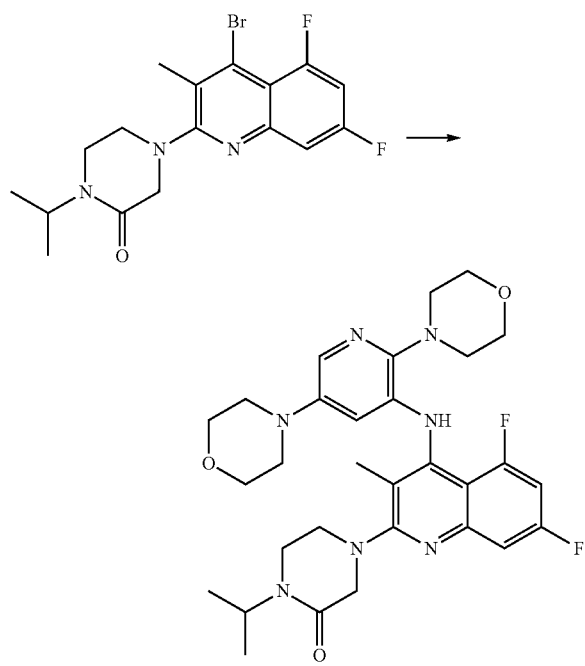

Essentially prepared according to Procedure H using 4-(4-bromo-5,7-difluoro-3-methylquinolin-2-yl)-1-ethylpiperazin-2-one (30.0 mg, 0.075 mmol) and 2,5-dimorpholinopyridin-3-amine in toluene to give 4-(4-(2,5-dimorpholinopyridin-3-ylamino)-5,7-difluoro-3-methylquinolin-2-yl)-1-isopropylpiperazin-2-one. TFA Salt: 1H NMR (400 MHz, CDCl3) δ ppm 7.75-7.83 (2H, m), 7.46 (1H, ddd, J=9.3, 2.2, 1.0 Hz), 6.92 (1H, ddd, J=13.6, 8.5, 2.5 Hz), 6.72 (4H, br. s.), 6.57 (1H, d, J=2.5 Hz), 4.81-4.96 (1H, m), 4.27 (3H, br. s.), 3.87-3.96 (4H, m), 3.76-3.86 (4H, m), 3.20-3.76 (7H, m), 3.03-3.16 (4H, m), 2.13 (3H, s), 1.20 (6H, d, J=6.8 Hz). Mass Spectrum (ESI) m/e=582.2 (M+1)

Example 203

Preparation of 5,7-Difluoro-3-methyl-2-(4-methylpiperazin-1-yl)-N-(5-morpholinopyridin-3-yl)quinolin-4-amine 4-Chloro-5,7-difluoro-3-methyl-2-(4-methylpiperazin-1-yl)quinoline

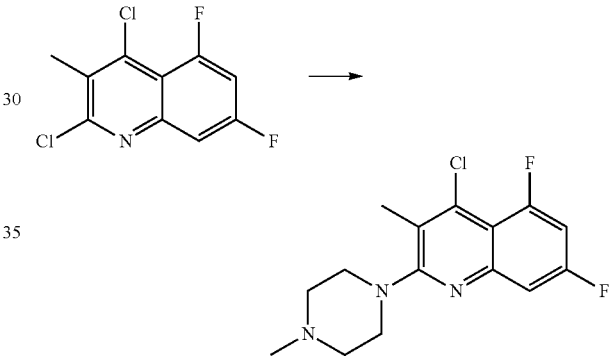

The 2,4-dichloro-5,7-difluoro-3-methylquinoline (300 mg, 1.20 mmol) and 1-methylpiperazine (140 μL, 1.20 mmol) were slurried in isopropanol (2.4 mL) and heated in a microwave reactor at 100° C. for 6 h. The reaction was cooled to rt and the resulting plug was slurried in EtOAc and filtered to give 4-chloro-5,7-difluoro-3-methyl-2-(4-methylpiperazin-1-yl)quinoline. Mass Spectrum (ESI) m/e=312.1 (M+1).

5,7-Difluoro-3-methyl-2-(4-methylpiperazin-1-yl)-N-(5-morpholinopyridin-3-yl)quinolin-4-amine

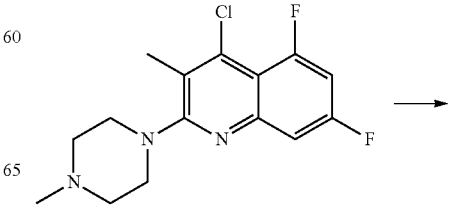

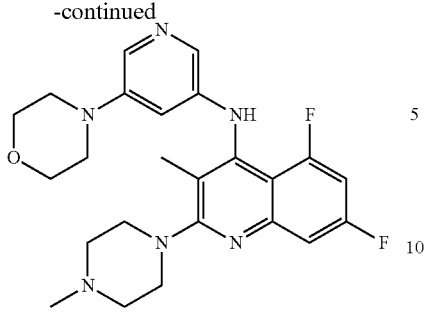

Essentially prepared according to Procedure H using 4-chloro-5,7-difluoro-3-methyl-2-(4-methylpiperazin-1-yl)quinoline (60.0 mg, 0.19 mmol) and 5-morpholinopyridin-3-amine in toluene to give 5,7-difluoro-3-methyl-2-(4-methylpiperazin-1-yl)-N-(5-morpholinopyridin-3-yl)quinolin-4-amine. TFA salt: 1H NMR (400 MHz, CDCl3) δ ppm 7.89 (2H, d, J=2.2 Hz), 7.35-7.43 (2H, m), 7.13 (1H, t, J=2.1 Hz), 6.90 (1H, ddd, J=13.5, 8.6, 2.5 Hz), 4.21 (2H, d, J=13.1 Hz), 3.87-3.98 (4H, m), 3.75 (2H, t), 3.61 (2H, d, J=9.6 Hz), 3.29-3.37 (4H, m), 3.20 (2H, t, J=11.0 Hz), 2.88 (3H, s), 2.15 (3H, s). Mass Spectrum (ESI) m/e=455.2 (M+1).

Example 204

Preparation of 5,7-difluoro-3-methyl-2-(2-(methylsulfonyl)-phenyl)-N-(5-morpholinopyridin-3-yl)quinolin-4-amine

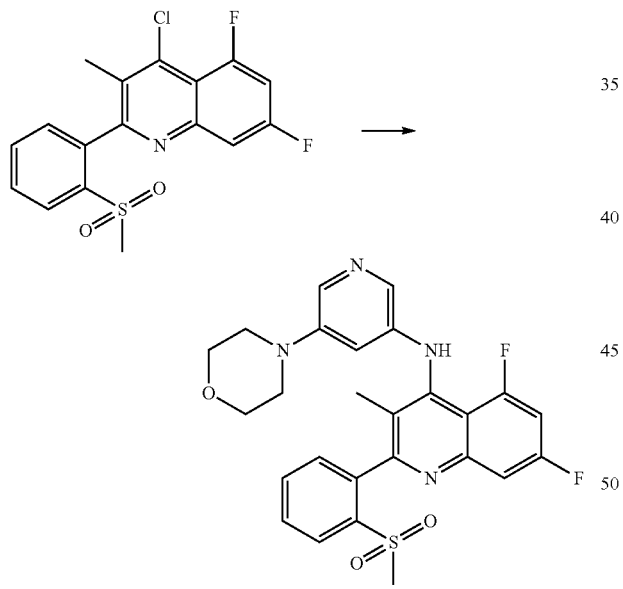

Essentially prepared according to Procedure H using 4-chloro-5,7-difluoro-3-methyl-2-(2-(methylsulfonyl)phenyl)quinoline (75.0 mg, 0.20 mmol) and 5-morpholinopyridin-3-amine in toluene to give 5,7-difluoro-3-methyl-2-(2-(methylsulfonyl)phenyl)-N-(5-morpholinopyridin-3-yl)quinolin-4-amine. ¹H NMR (CDCl₃) δ ppm 8.19 (1H, dd, J=7.9, 1.3 Hz), 7.89 (1H, d, J=2.3 Hz), 7.86 (1H, d, J=2.3 Hz), 7.78 (1H, td), 7.68 (1H, td, J=7.7, 1.2 Hz), 7.49 (1H, ddd, J=9.4, 2.4, 1.3 Hz), 7.42 (1H, dd, J=7.5, 1.3 Hz), 7.02-7.15 (2H, m), 6.55 (1H, t, J=2.3 Hz), 3.79 (4H, t, J=4.8 Hz), 3.09-3.22 (7H, m), 1.88 (3H, s). Mass Spectrum (ESI) m/e=511.1 (M+1).

Example 205

Preparation of N-(5-(3,6-dihydro-2H-pyran-4-yl)pyridin-3-yl)-5,7-difluoro-3-methyl-2-(2-(methylsulfonyl)phenyl)quinolin-4-amine

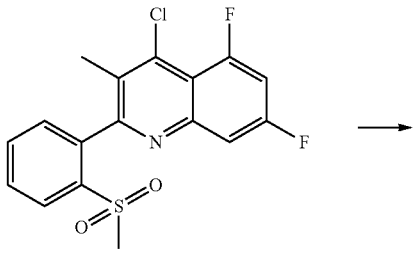

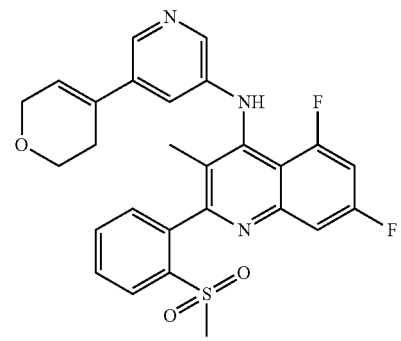

Essentially prepared according to Procedure H using 4-chloro-5,7-difluoro-3-methyl-2-(2-(methylsulfonyl)phenyl)quinoline (50.0 mg, 0.140 mmol) and 5-(3,6-dihydro-2H-pyran-4-yl)pyridin-3-amine in toluene to give N-(5-(3,6-dihydro-2H-pyran-4-yl)pyridin-3-yl)-5,7-difluoro-3-methyl-2-(2-(methylsulfonyl)phenyl)-quinolin-4-amine. ¹H NMR (CDCl₃) δ ppm 8.23 (2H, d, J=2.2 Hz), 8.20 (1H, dd, J=8.0, 1.2 Hz), 7.75-7.82 (1H, m), 7.68 (1H, td, J=7.7, 1.4 Hz), 7.50 (1H, ddd, J=9.3, 2.5, 1.3 Hz), 7.42 (1H, dd, J=7.6, 1.2 Hz), 7.15 (1H, d, J=13.7 Hz), 7.01-7.11 (2H, m), 6.22 (1H, dt, J=2.9, 1.4 Hz), 4.28 (2H, q, J=2.6 Hz), 3.89 (2H, td, J=5.4, 2.1 Hz), 3.14 (3H, s), 2.33-2.58 (2H, m), 1.86 (3H, s). Mass Spectrum (ESI) m/e=508.1 (M+1).

Example 206

Preparation of 5,7-Difluoro-3-methyl-2-morpholino-N-(5-morpholinopyridin-3-yl)quinolin-4-amine 4-(4-Chloro-5,7-difluoro-3-methylquinolin-2-yl)morpholine

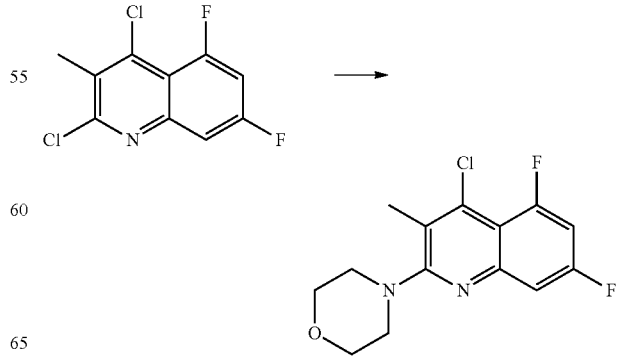

Essentially prepared according to Procedure G using 4-chloro-5,7-difluoro-3-methyl-2-(2-(methylsulfonyl)phenyl)quinoline (380.0 mg, 1.50 mmol) and morpholine to give 4-(4-chloro-5,7-difluoro-3-methylquinolin-2-yl)morpholine. Mass Spectrum (ESI) m/e=299.0 (M+1).

5,7-Difluoro-3-methyl-2-morpholino-N-(5-morpholinopyridin-3-yl)quinolin-4-amine

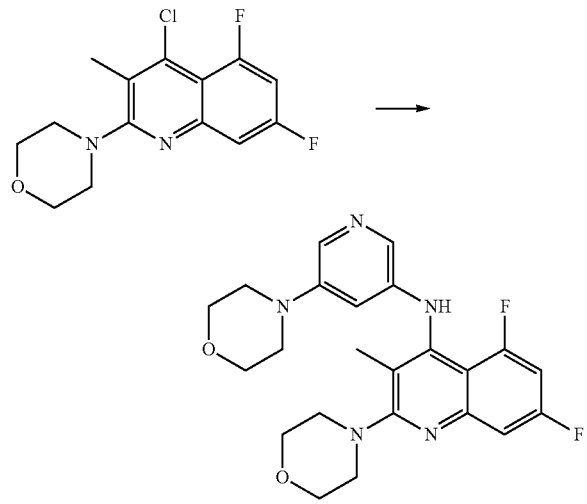

Essentially prepared according to Procedure H using 4-(4-chloro-5,7-difluoro-3-methylquinolin-2-yl)morpholine (40.0 mg, 0.130 mmol) and 5-morpholinopyridin-3-amine in toluene to give 5,7-difluoro-3-methyl-2-morpholino-N-(5-morpholinopyridin-3-yl)quinolin-4-amine. $^1$H NMR (CDCl$_3$) δ ppm 7.93 (1H, d, J=2.3 Hz), 7.69 (1H, d, J=2.2 Hz), 7.31 (1H, ddd, J=10.1, 2.5, 1.3 Hz), 6.89 (1H, d, J=12.7 Hz), 6.80 (1H, ddd, J=13.9, 8.7, 2.6 Hz), 6.58 (1H, t, J=2.4 Hz), 3.79-3.94 (8H, m), 3.33-3.41 (4H, m), 3.16 (4H, dd, J=5.7, 3.9 Hz), 2.08 (3H, s). Mass Spectrum (ESI) m/e=442.1 (M+1).

Example 207

Preparation of N-(5-(3,6-dihydro-2H-pyran-4-yl)pyridin-3-yl)-5,7-difluoro-3-methyl-2-morpholinoquinolin-4-amine

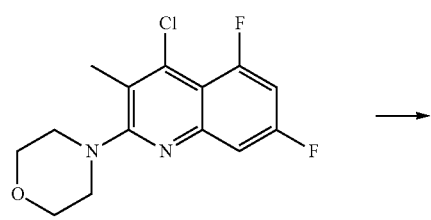

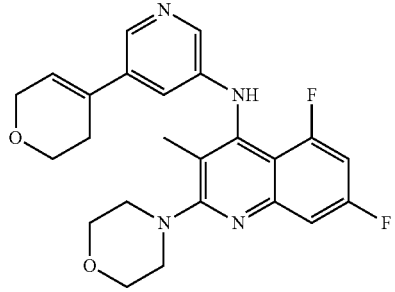

Essentially prepared according to Procedure H using 4-(4-chloro-5,7-difluoro-3-methylquinolin-2-yl)morpholine (40.0 mg, 0.130 mmol) and 5-(3,6-dihydro-2H-pyran-4-yl)pyridin-3-amine in toluene to give N-(5-(3,6-dihydro-2H-pyran-4-yl)-pyridin-3-yl)-5,7-difluoro-3-methyl-2-morpholinoquinolin-4-amine. $^1$H NMR (CDCl$_3$) δ ppm 8.28 (1H, d, J=2.0 Hz), 8.07 (1H, d, J=2.5 Hz), 7.32 (1H, ddd, J=10.0, 2.5, 1.4 Hz), 7.03 (1H, t, J=2.2 Hz), 6.94 (1H, d, J=12.7 Hz), 6.81 (1H, ddd, J=13.9, 8.6, 2.5 Hz), 6.11-6.19 (1H, m), 4.32 (2H, q, J=2.7 Hz), 3.93 (2H, t, J=5.5 Hz), 3.83-3.90 (4H, m), 3.34-3.43 (4H, m), 2.42-2.51 (2H, m), 2.06 (3H, s). Mass Spectrum (ESI) m/e=439.1 (M+1).

Example 208

Preparation of 5,7-difluoro-N-(6'-methoxy-5-morpholino-2,3'-bipyridin-3-yl)-3-methyl-2-(2-(methylsulfonyl)phenyl)quinolin-4-amine

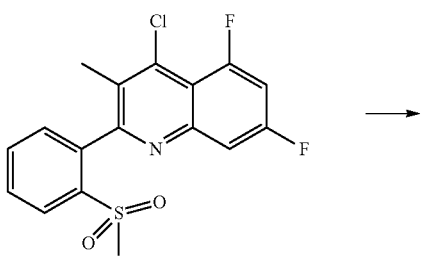

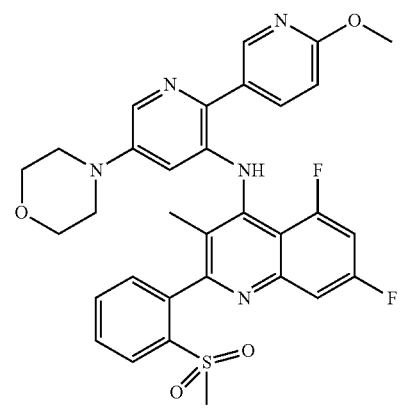

Essentially prepared according to Procedure H using 4-chloro-5,7-difluoro-3-methyl-2-(2-(methylsulfonyl)phenyl)quinoline (50.0 mg, 0.140 mmol) and 6'-methoxy-5-morpholino-2,3'-bipyridin-3-amine in toluene to give 5,7-difluoro-N-(6'-methoxy-5-morpholino-2,3'-bipyridin-3-yl)-3-methyl-2-(2-(methylsulfonyl)-phenyl)quinolin-4-amine. ¹H NMR (CDCl₃) δ ppm 8.64 (1H, d, J=1.8 Hz), 8.20 (1H, d, J=7.2 Hz), 8.00 (1H, dd, J=8.5, 2.4 Hz), 7.94 (1H, br. s.), 7.80 (1H, td, J=7.5, 1.4 Hz), 7.70 (1H, td, J=7.7, 1.4 Hz), 7.47 (1H, ddd, J=9.4, 2.4, 1.3 Hz), 7.42 (1H, d, J=7.2 Hz), 6.92-7.04 (2H, m), 6.88 (1H, dd, J=8.6, 0.8 Hz), 6.53 (1H, br. s.), 4.00 (3H, s), 3.78 (4H, t, J=4.7 Hz), 3.02-3.27 (7H, m), 1.97 (3H, s). Mass Spectrum (ESI) m/e=618.2 (M+1).

Example 209

Preparation of 5,7-difluoro-N-(2-(6-methoxypyridin-3-yl)-5-morpholinophenyl)-3-methyl-2-(2-(methylsulfonyl)phenyl)quinolin-4-amine

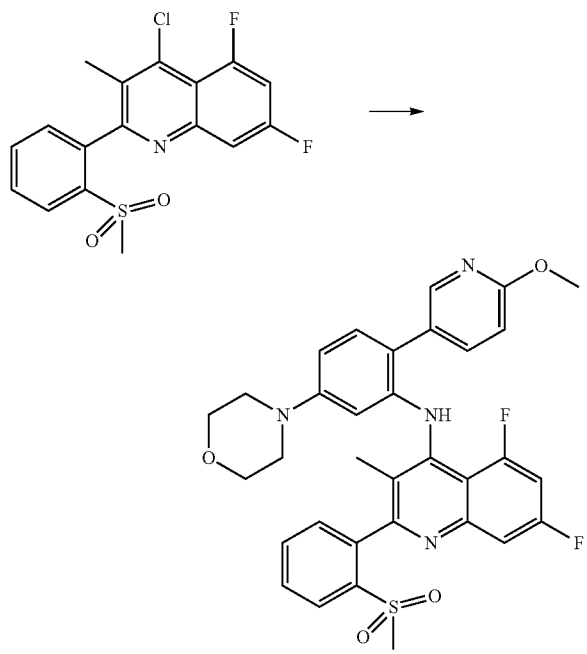

Essentially prepared according to Procedure H using 4-chloro-5,7-difluoro-3-methyl-2-(2-(methylsulfonyl)phenyl)quinoline (50.0 mg, 0.140 mmol) and 2-(6-methoxypyridin-3-yl)-5-morpholinoaniline in toluene to give 5,7-difluoro-N-(2-(6-methoxypyridin-3-yl)-5-morpholinophenyl)-3-methyl-2-(2-(methylsulfonyl)-phenyl)quinolin-4-amine. ¹H NMR (CDCl₃) δ ppm 8.34 (1H, d, J=2.0 Hz), 8.20 (1H, d, J=7.8 Hz), 7.73-7.83 (2H, m), 7.63-7.73 (1H, m), 7.40-7.47 (1H, m), 7.38 (1H, d, J=7.2 Hz), 7.14 (1H, d, J=8.4 Hz), 6.94 (1H, ddd, J=13.7, 8.6, 2.5 Hz), 6.86 (1H, d, J=13.7 Hz), 6.82 (1H, dd, J=8.5, 0.7 Hz), 6.55 (1H, d, J=7.4 Hz), 6.32 (1H, br. s.), 3.99 (3H, s), 3.78 (4H, t, J=4.2 Hz), 3.00-3.32 (7H, m), 1.96 (3H, s). Mass Spectrum (ESI) m/e=617.2 (M+1).

Example 210

Preparation of 5,7-difluoro-2-(5-fluoro-2-(methylsulfonyl)-phenyl)-3-methyl-N-(5-morpholinopyridin-3-yl)quinolin-4-amine 5-Fluoro-2-(methylthio)phenylboronic acid

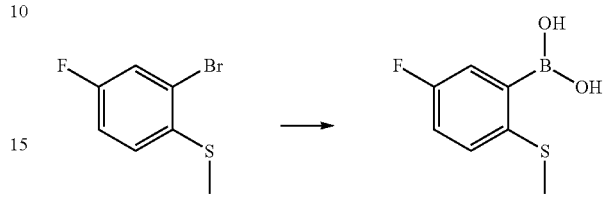

The (2-bromo-4-fluorophenyl)(methyl)sulfane (700 mg, 3.17 mmol) was dissolved in THF (5 mL) and cooled to −78° C. To the cooled solution was added n-BuLi (2.18 mL, 3.48 mmol) dropwise. The reaction was stirred for 2 min at −78° C. then the triisopropyl borate (0.804 mL, 3.48 mmol) was added dropwise and the reaction mixture was allowed to warm to 0° C. over a period of approximately 90 min. The reaction was quenched by addition of 1N HCl solution and was stirred for 5 min. The mixture was then extracted with EtOAc (2×50 mL). The combined organic layers were washed with water (1×30 mL), brine (1×30 mL) and dried over magnesium sulfate. The crude product was then triturated with hexanes. The resulting solid was purified by medium pressure chromatography (silica gel, 0 to 50% EtOAc:hexanes) to give 5-fluoro-2-(methylthio)phenylboronic acid. Mass Spectrum (ESI) m/e=187.0 (M+1).

4-Chloro-5,7-difluoro-2-(5-fluoro-2-(methylthio)phenyl)-3-methylquinoline

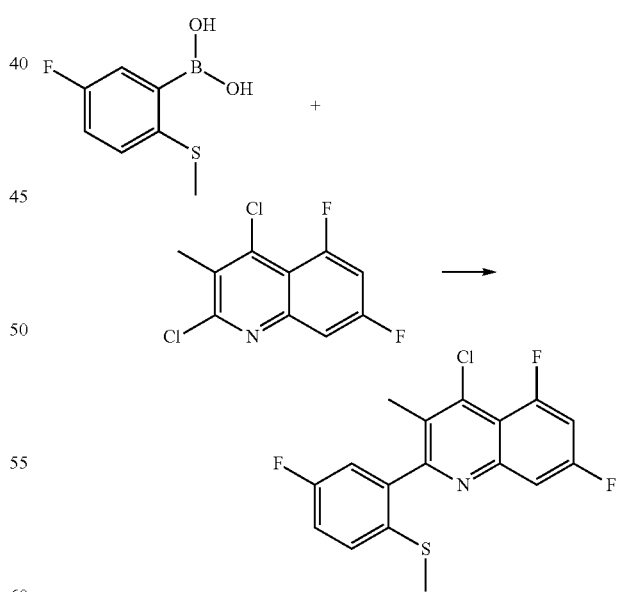

Essentially prepared according to Procedure F using 2,4-dichloro-5,7-difluoro-3-methylquinoline (270 mg, 1.10 mmol) and 5-fluoro-2-(methylthio)phenylboronic acid to give 4-chloro-5,7-difluoro-2-(5-fluoro-2-(methylthio)phenyl)-3-methylquinoline. Mass Spectrum (ESI) m/e=354.1 (M+1).

4-Chloro-5,7-difluoro-2-(5-fluoro-2-(methylsulfonyl)phenyl)-3-methylquinoline

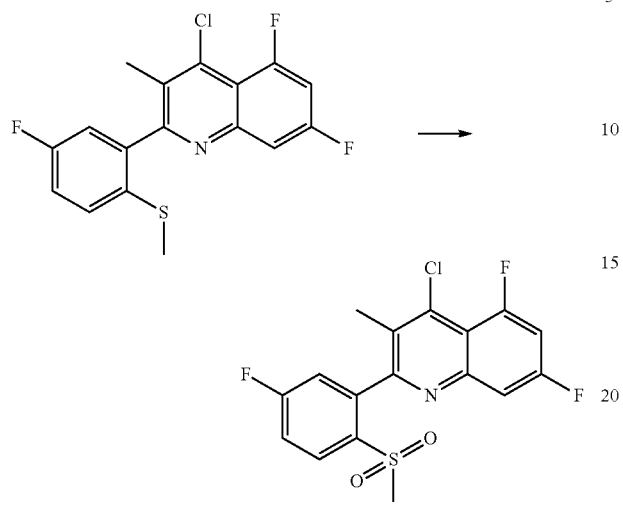

The 4-chloro-5,7-difluoro-2-(5-fluoro-2-(methylthio)phenyl)-3-methylquinoline (320 mg, 0.90 mmol) was dissolved in a mixture of THF (6.7 mL) and water (2.2 mL). To the solution was added Oxone™ (1.40 g, 2.2 mmol) and the resulting slurry was stirred vigorously for 16 h. The reaction mixture was added to 25 mL of water and stirred vigorously for 10 min and then filtered. The precipitate was dissolved in EtOAc and then dried over magnesium sulfate. The filtrate was cond to give 4-chloro-5,7-difluoro-2-(5-fluoro-2-(methylsulfonyl)phenyl)-3-methylquinoline. Mass Spectrum (ESI) m/e=386.0 (M+1).

5,7-Difluoro-2-(5-fluoro-2-(methylsulfonyl)phenyl)-3-methyl-N-(5-morpholinopyridin-3-yl)quinolin-4-amine

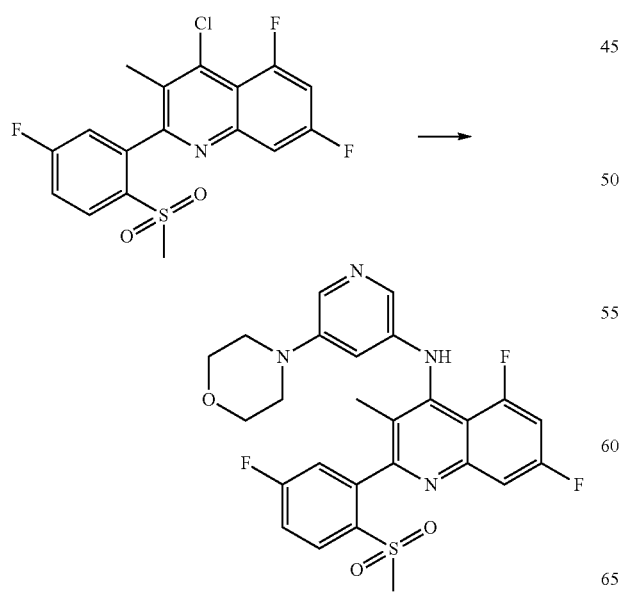

Essentially prepared according to Procedure H using 4-chloro-5,7-difluoro-2-(5-fluoro-2-(methylsulfonyl)phenyl)-3-methylquinoline (120.0 mg, 0.32 mmol) and 5-morpholinopyridin-3-amine in toluene to give 5,7-difluoro-2-(5-fluoro-2-(methylsulfonyl)phenyl)-3-methyl-N-(5-morpholinopyridin-3-yl)quinolin-4-amine. $^1$H NMR (CDCl$_3$) δ ppm 8.21 (1H, dd, J=8.8, 5.3 Hz), 7.93 (1H, d, J=2.3 Hz), 7.84 (1H, d, J=2.3 Hz), 7.49 (1H, ddd, J=9.2, 2.5, 1.4 Hz), 7.28-7.41 (2H, m), 7.14 (1H, dd, J=8.2, 2.5 Hz), 7.04-7.12 (1H, m), 6.55 (1H, t, J=2.4 Hz), 3.78 (4H, t, J=4.9 Hz), 3.11-3.24 (4H, m), 3.10 (3H, s), 1.91 (3H, s). Mass Spectrum (ESI) m/e=529.2 (M+1).

Example 211

Preparation of tert-butyl 4-(5,7-difluoro-3-methyl-4-(5-morpholinopyridin-3-ylamino)quinolin-2-yl)piperazine-1-carboxylate tert-Butyl 4-(4-chloro-5,7-difluoro-3-methylquinolin-2-yl)piperazine-1-carboxylate

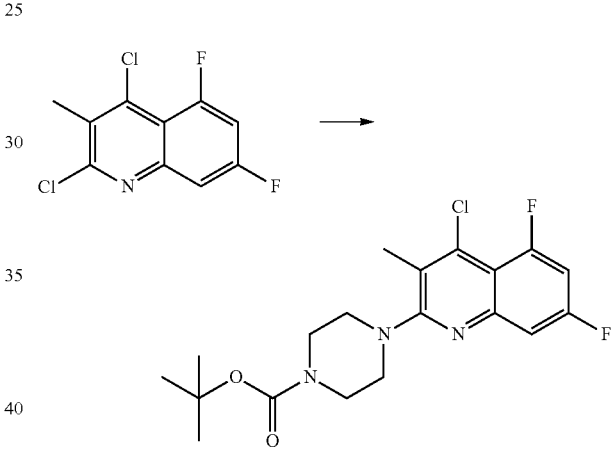

Essentially prepared according to Procedure G using 2,4-dichloro-5,7-difluoro-3-methylquinoline (610.0 mg, 2.50 mmol) and tert-butyl piperazine-1-carboxylate in isopropanol to give tert-butyl 4-(4-chloro-5,7-difluoro-3-methylquinolin-2-yl)-piperazine-1-carboxylate. Mass Spectrum (ESI) m/e=398.2 (M+1).

tert-Butyl 4-(5,7-difluoro-3-methyl-4-(5-morpholinopyridin-3-ylamino)-quinolin-2-yl)piperazine-1-carboxylate

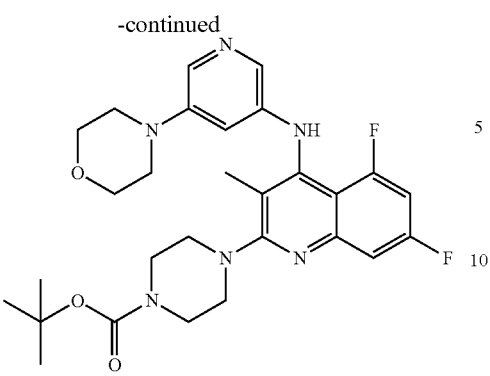

Essentially prepared according to Procedure H using tert-butyl 4-(4-chloro-5,7-difluoro-3-methylquinolin-2-yl)piperazine-1-carboxylate (85.0 mg, 0.210 mmol) and 5-morpholinopyridin-3-amine in toluene to give tert-butyl 4-(5,7-difluoro-3-methyl-4-(5-morpholinopyridin-3-ylamino)quinolin-2-yl)piperazine-1-carboxylate. $^1$H NMR (CDCl$_3$) δ ppm 7.93 (1H, d, J=2.3 Hz), 7.70 (1H, d, J=2.2 Hz), 7.29 (1H, ddd, J=10.0, 2.5, 1.2 Hz), 6.90 (1H, d, J=12.9 Hz), 6.80 (1H, ddd, J=13.8, 8.8, 2.6 Hz), 6.57 (1H, t, J=2.3 Hz), 3.85 (4H, dd, J=5.6, 4.0 Hz), 3.52-3.63 (4H, m), 3.27-3.35 (4H, m), 3.10-3.17 (4H, m), 2.07 (3H, s), 1.50 (9H, s). Mass Spectrum (ESI) m/e=541.3 (M+1).

Example 212

Preparation of 5,7-Difluoro-3-methyl-N-(5-morpholinopyridin-3-yl)-2-(piperazin-1-yl)quinolin-4-amine

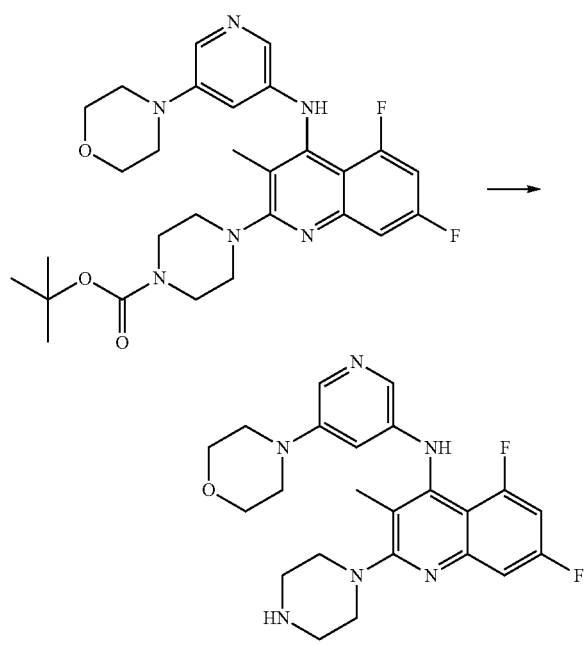

The tert-butyl 4-(5,7-difluoro-3-methyl-4-(5-morpholinopyridin-3-ylamino)-quinolin-2-yl)piperazine-1-carboxylate (32 mg, 0.059 mmol) was dissolved in DCM (1.0 mL) and cooled to 0° C. The trifluoroacetic acid (1.00 mL, 13.0 mmol) was then added and the reaction mixture was allowed to slowly warm to rt over a period of 1 h. The reaction was then cond to dryness. The crude TFA salt was treated with satd sodium bicarbonate solution. The organic layer was dried over sodium sulfate and the filtrate was cond to give 5,7-difluoro-3-methyl-N-(5-morpholinopyridin-3-yl)-2-(piperazin-1-yl)quinolin-4-amine. $^1$H NMR (CDCl$_3$) δ ppm 7.85 (1H, d, J=2.5 Hz), 7.63 (1H, d, J=2.2 Hz), 7.23 (1H, ddd, J=10.2, 2.5, 1.4 Hz), 6.79 (1H, d, J=12.9 Hz), 6.71 (1H, ddd, J=13.9, 8.8, 2.5 Hz), 6.49 (1H, t, J=2.3 Hz), 3.70-3.83 (4H, m), 3.19-3.32 (4H, m), 3.03-3.12 (4H, m), 2.92-3.03 (4H, m), 2.00 (3H, s). Mass Spectrum (ESI) m/e=441.2 (M+1).

Example 213

Preparation of 5,7-Difluoro-3-methyl-2-(2-(methylsulfonyl)-5-(trifluoromethoxy)phenyl)-N-(5-morpholinopyridin-3-yl)quinolin-4-amine 4-Chloro-5,7-difluoro-3-methyl-2-(2-(methylthio)-5-(trifluoromethoxy)-phenyl)quinoline

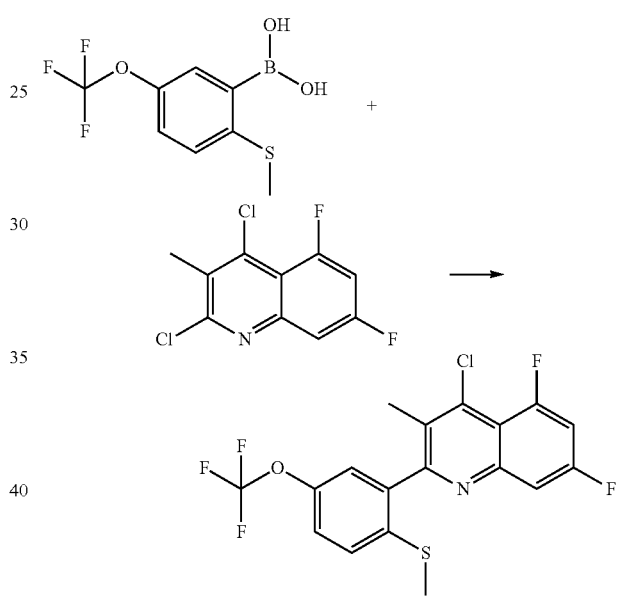

Essentially prepared according to Procedure F using 2,4-dichloro-5,7-difluoro-3-methylquinoline (400 mg, 1.60 mmol) and 2-(methylthio)-5-(trifluoromethoxy)-phenylboronic acid to give 4-chloro-5,7-difluoro-3-methyl-2-(2-(methylthio)-5-(trifluoromethoxy)phenyl)quinoline. Mass Spectrum (ESI) m/e=420.0 (M+1).

4-Chloro-5,7-difluoro-3-methyl-2-(2-(methylsulfonyl)-5-(trifluoromethoxy)-phenyl)quinoline

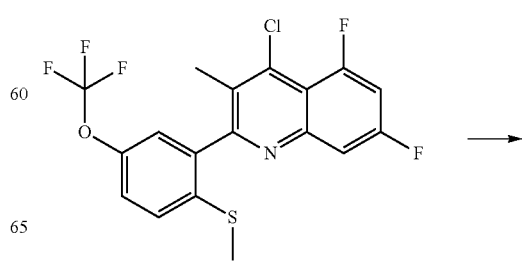

-continued

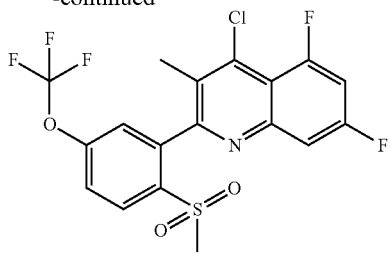

The 4-chloro-5,7-difluoro-3-methyl-2-(2-(methylthio)-5-(trifluoromethoxy)-phenyl)quinoline (560 mg, 1.30 mmol) was dissolved in a mixture of THF (10.0 mL) and water (3.3 mL). To the solution was added Oxone™ (2.1 g, 3.3 mmol) and the resulting slurry was stirred vigorously 16 h. The reaction mixture was added to 25 mL of water and stirred vigorously for 10 min and then filtered. The precipitate was dissolved in EtOAc and then dried over magnesium sulfate. The filtrate was cond to give 4-chloro-5,7-difluoro-3-methyl-2-(2-(methylsulfonyl)-5-(trifluoromethoxy)phenyl)quinoline. Mass Spectrum (ESI) m/e=452.0 (M+1).

5,7-Difluoro-3-methyl-2-(2-(methylsulfonyl)-5-(trifluoromethoxy)phenyl)-N-(5-morpholinopyridin-3-yl)quinolin-4-amine

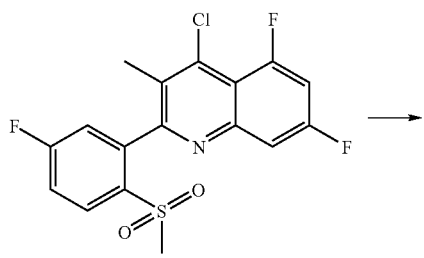

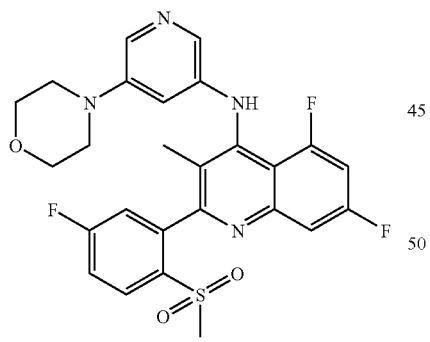

Essentially prepared according to Procedure H using 4-chloro-5,7-difluoro-3-methyl-2-(2-(methylsulfonyl)-5-(trifluoromethoxy)phenyl)quinoline (50.0 mg, 0.11 mmol) and 5-morpholinopyridin-3-amine in toluene to give 5,7-difluoro-3-methyl-2-(2-(methylsulfonyl)-5-(trifluoromethoxy) phenyl)-N-(5-morpholinopyridin-3-yl)quinolin-4-amine. $^1$H NMR (CDCl$_3$) δ ppm 8.25 (1H, d, J=8.8 Hz), 7.91 (1H, d, J=2.3 Hz), 7.87 (1H, d, J=2.3 Hz), 7.44-7.54 (2H, m), 7.25 (1H, d, J=1.6 Hz), 7.20 (1H, d, J=14.5 Hz), 7.10 (1H, ddd, J=13.9, 8.6, 2.5 Hz), 6.54 (1H, t, J=2.3 Hz), 3.79 (4H, t, J=4.8 Hz), 3.07-3.22 (7H, m), 1.89 (3H, s). Mass Spectrum (ESI) m/e=595.2 (M+1).

Example 214

Preparation of 7-Fluoro-2-(2-fluoro-5-nitrophenyl)-3-methyl-N-(5-morpholinopyridin-3-yl)quinolin-4-amine 2-(2-Fluoro-5-nitrophenyl)-4,4,5,5-tetramethyl-1,3,2-dioxaborolane

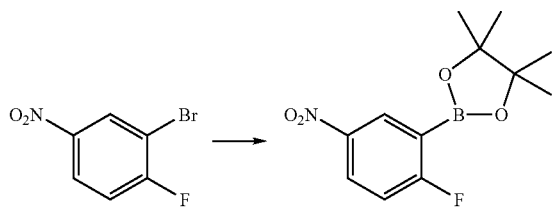 [SMILES: O=[N+]([O-])c1ccc(F)c(Br)c1 ; CC1(C)OB(c2cc([N+](=O)[O-])ccc2F)OC1(C)C]

The Pd(dppf)Cl$_2$ (0.759 g, 0.929 mmol), 4,4,4',4',5,5,5',5'-octamethyl-2,2'-bi-(1,3,2-dioxaborolane) (2.60 g, 10.22 mmol), 2-bromo-1-fluoro-4-nitrobenzene (2.04 g, 9.29 mmol), and potassium acetate (2.74 g, 27.9 mmol) were slurried in 1,4-dioxane (23.23 mL) and heated at 100° C. and stirred for 1 h. Another 0.05 eq of Pd(dppf)Cl$_2$ was added and the reaction was stirred at 100° C. for an additional 1.5 h. The reaction was cooled and then diluted with water and extracted with EtOAc (2×100 mL). The combined organic layers were washed with water (1×50 mL), brine (1×50 mL) and dried over magnesium sulfate. The crude product was purified by medium pressure chromatography (silica gel, 10 to 40% EtOAc:hexanes) to give 2-(2-fluoro-5-nitrophenyl)-4,4,5,5-tetramethyl-1,3,2-dioxaborolane. $^1$H NMR (CDCl$_3$) δ ppm 8.65 (1H, dd, J=4.8, 3.0 Hz), 8.33 (1H, ddd, J=9.0, 4.5, 3.1 Hz), 7.18 (1H, dd, J=9.0, 8.0 Hz), 1.39 (12H, s).

4-Chloro-7-fluoro-2-(2-fluoro-5-nitrophenyl)-3-methylquinoline

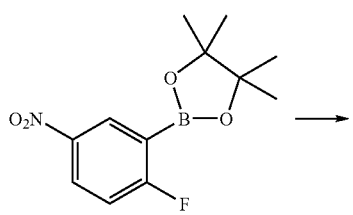

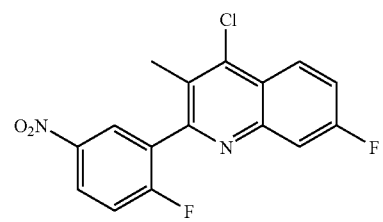

Essentially prepared according to Procedure F using a mixture of 2,4-dichloro-5-fluoro-3-methylquinoline and 2,4-dichloro-7-fluoro-3-methylquinoline (~1:4 mixture) (690 mg, 3.00 mmol) and 2-(2-fluoro-5-nitrophenyl)-4,4,5,5-tetramethyl-1,3,2-dioxaborolane to give 4-chloro-7-fluoro-2-(2-fluoro-5-nitrophenyl)-3-methylquinoline. Mass Spectrum (ESI) m/e=335.0 (M+1).

7-Fluoro-2-(2-fluoro-5-nitrophenyl)-3-methyl-N-(5-morpholinopyridin-3-yl)-quinolin-4-amine

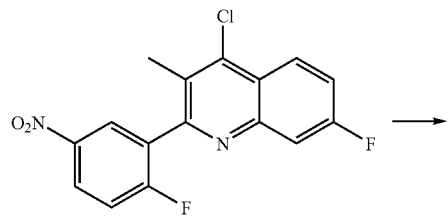

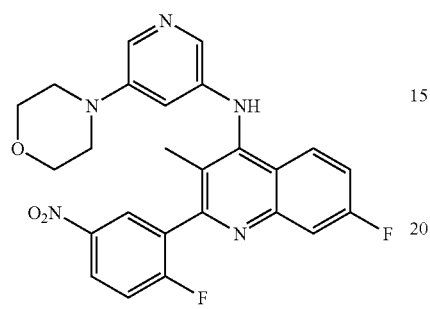

Essentially prepared according to Procedure H using 4-chloro-7-fluoro-2-(2-fluoro-5-nitrophenyl)-3-methylquinoline (26.0 mg, 0.078 mmol) and 5-morpholinopyridin-3-amine in toluene to give 7-fluoro-2-(2-fluoro-5-nitrophenyl)-3-methyl-N-(5-morpholinopyridin-3-yl)quinolin-4-amine. $^1$H NMR (CDCl$_3$) δ ppm 8.58 (1H, dd, J=6.2, 2.8 Hz), 8.39 (1H, ddd, J=9.1, 4.4, 2.9 Hz), 8.11 (1H, br. s.), 8.03 (1H, dd, J=9.4, 5.9 Hz), 7.78 (2H, dd, J=9.8, 2.5 Hz), 7.64 (1H, br. s.), 7.29-7.42 (2H, m), 6.44 (1H, t, J=2.2 Hz), 3.77-3.87 (4H, m), 3.04-3.19 (4H, m), 2.19 (3H, d, J=2.3 Hz). Mass Spectrum (ESI) m/e=478.1 (M+1).

Example 215

Preparation of N-(2,5-dimorpholinopyridin-3-yl)-7-fluoro-2-(2-fluoro-5-nitrophenyl)-3-methylquinolin-4-amine

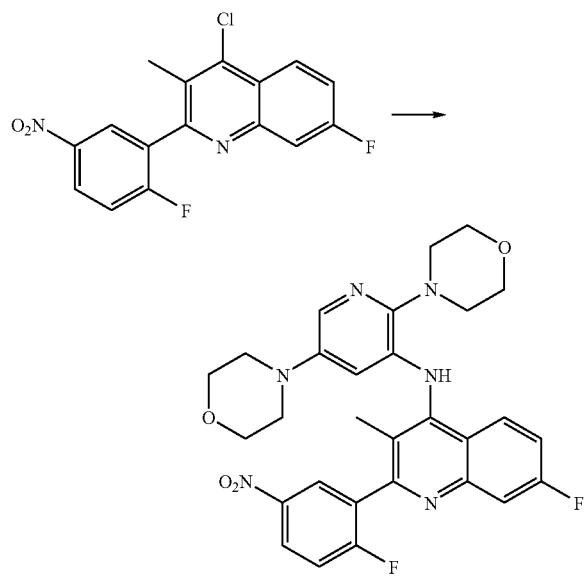

Essentially prepared according to Procedure H using 4-chloro-7-fluoro-2-(2-fluoro-5-nitrophenyl)-3-methylquinoline (150.0 mg, 0.45 mmol) and 2,5-dimorpholinopyridin-3-amine in toluene to give N-(2,5-dimorpholinopyridin-3-yl)-7-fluoro-2-(2-fluoro-5-nitrophenyl)-3-methylquinolin-4-amine. $^1$H NMR (CDCl$_3$) δ ppm 8.58 (1H, dd, J=6.2, 2.8 Hz), 8.39 (1H, ddd, J=9.0, 4.3, 2.9 Hz), 7.89 (1H, dd, J=9.0, 5.9 Hz), 7.79 (1H, dd, J=9.8, 2.5 Hz), 7.64 (1H, d, J=2.7 Hz), 7.32-7.44 (2H, m), 6.90 (1H, br. s.), 6.26 (1H, d, J=1.2 Hz), 3.94 (4H, t, J=4.6 Hz), 3.69-3.85 (4H, m), 3.13-3.32 (4H, m), 2.90-3.03 (4H, m), 2.19 (3H, d, J=2.0 Hz). Mass Spectrum (ESI) m/e=563.3 (M+1).

Example 216

Preparation of N-(2,5-dimorpholinopyridin-3-yl)-7-fluoro-3-methyl-2-(2-(methylsulfonyl)-5-nitrophenyl)quinolin-4-amine

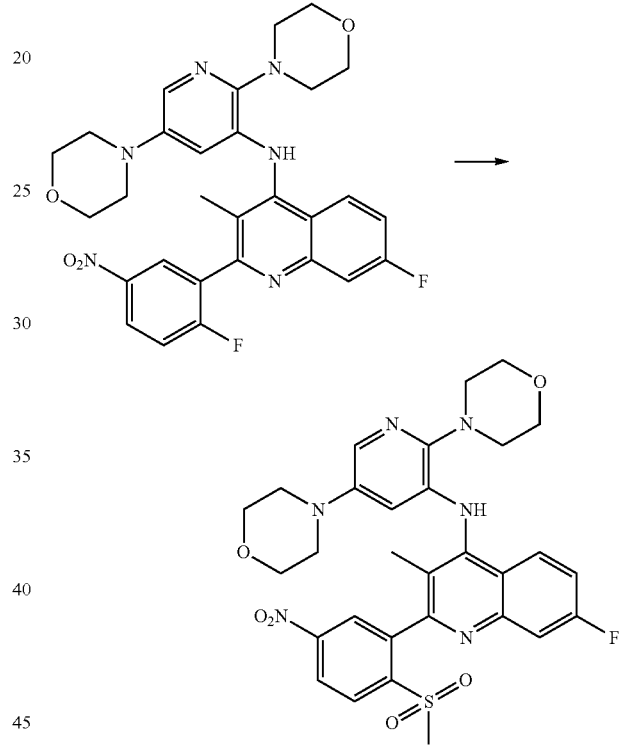

The N-(2,5-dimorpholinopyridin-3-yl)-7-fluoro-2-(2-fluoro-5-nitrophenyl)-3-methylquinolin-4-amine (66 mg, 0.112 mmol) and methanesulfinic acid, sodium salt (12.0 mg, 0.112 mmol) was added to dimethylacetamide (0.24 mL) and placed in a microwave reactor for 2 h at 150° C. An LCMS was taken and ~35% of starting material had converted to desired product. The mixture was reheated and stirred at 150° C. for 4 h. The reaction was then diluted with water (20 mL) and extracted with EtOAc (2×30 mL). The combined organic layers were washed with water (1×30 mL) and brine (1×30 mL) and dried over magnesium sulfate. The mixture was purified by reverse-phase preparative HPLC using a Phenomenex Gemini™ column, 10 micron, C18, 100 Å, 150×30 mm, 0.1% TFA in CH$_3$CN/H$_2$O, gradient 10% to 90% over 20 minutes to provide N-(2,5-dimorpholinopyridin-3-yl)-7-fluoro-3-methyl-2-(2-(methylsulfonyl)-5-nitrophenyl)-quinolin-4-amine after extraction with satd sodium bicarbonate. $^1$H NMR (CDCl$_3$) δ ppm 8.48-8.56 (1H, m), 8.40-8.47 (1H, m), 8.31 (1H, s), 7.88-8.04 (1H, m), 7.67 (1H, dd, J=9.5, 2.6 Hz), 7.62 (1H, d, J=2.0 Hz), 7.38-7.47 (1H, m), 7.01 (1H, br. s.), 6.38 (1H, br. s.), 3.89-4.06 (4H, m), 3.76 (4H, t, J=4.6 Hz), 3.37-3.56 (2H, m), 2.93-3.28 (9H, m), 2.03 (3H, s). Mass Spectrum (ESI) m/e=623.3.3 (M+1).

Example 217

Preparation of 3-(4-(2,5-Dimorpholinopyridin-3-ylamino)-7-fluoro-3-methylquinolin-2-yl)-4-(methylsulfonyl)phenol

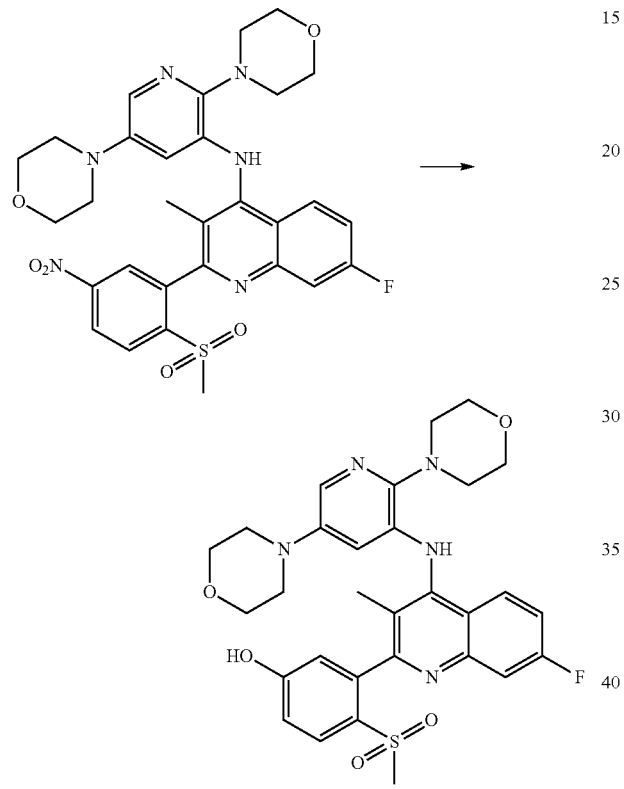

The N-(2,5-dimorpholinopyridin-3-yl)-7-fluoro-3-methyl-2-(2-(methylsulfonyl)-5-nitrophenyl)quinolin-4-amine (3.0 mg, 4.8 μmol), (Z)-benzaldehyde oxime (1.0 μL, 9.6 μmol), 325 mesh potassium carbonate (2.7 mg, 0.019 mmol) and DMSO (9.6 μL) was heated in a microwave reactor for 45 min at 100° C. The reaction was cooled and diluted with water. The mixture was extracted with EtOAc (2×35 mL). The combined organic layers were washed with brine (1×20 mL) and dried over magnesium sulfate. The crude material was purified by reverse-phase preparative HPLC using a Phenomenex Gemini column, 10 micron, C18, 100 Å, 150×30 mm, 0.1% TFA in CH₃CN/H₂O, gradient 10% to 90% over 20 min to provide 3-(4-(2,5-dimorpholinopyridin-3-ylamino)-7-fluoro-3-methylquinolin-2-yl)-4-(methylsulfonyl)phenol after extracting with satd sodium bicarbonate solution. ¹H NMR (CDCl₃) δ ppm 8.00 (1H, br. s.), 7.94 (1H, d, J=8.8 Hz), 7.84 (1H, d, J=7.8 Hz), 7.65 (1H, br. s.), 7.43 (1H, t, J=8.2 Hz), 6.91 (1H, d, J=8.4 Hz), 6.85 (1H, br. s.), 6.52 (1H, br. s.), 3.83-4.05 (4H, m), 3.76 (4H, t, J=4.7 Hz), 3.42 (2H, br. s.), 2.93-3.20 (9H, m), 1.99 (3H, br. s.). Mass Spectrum (ESI) m/e=594.2 (M+1).

Example 218

Preparation of (+/−)-5,7-Difluoro-3-methyl-2-(2-(methylsulfinyl)phenyl)-N-(5-morpholinopyridin-3-yl)quinolin-4-amine (+/−)-4-Chloro-5,7-difluoro-3-methyl-2-(2-(methylsulfinyl)phenyl)quinoline

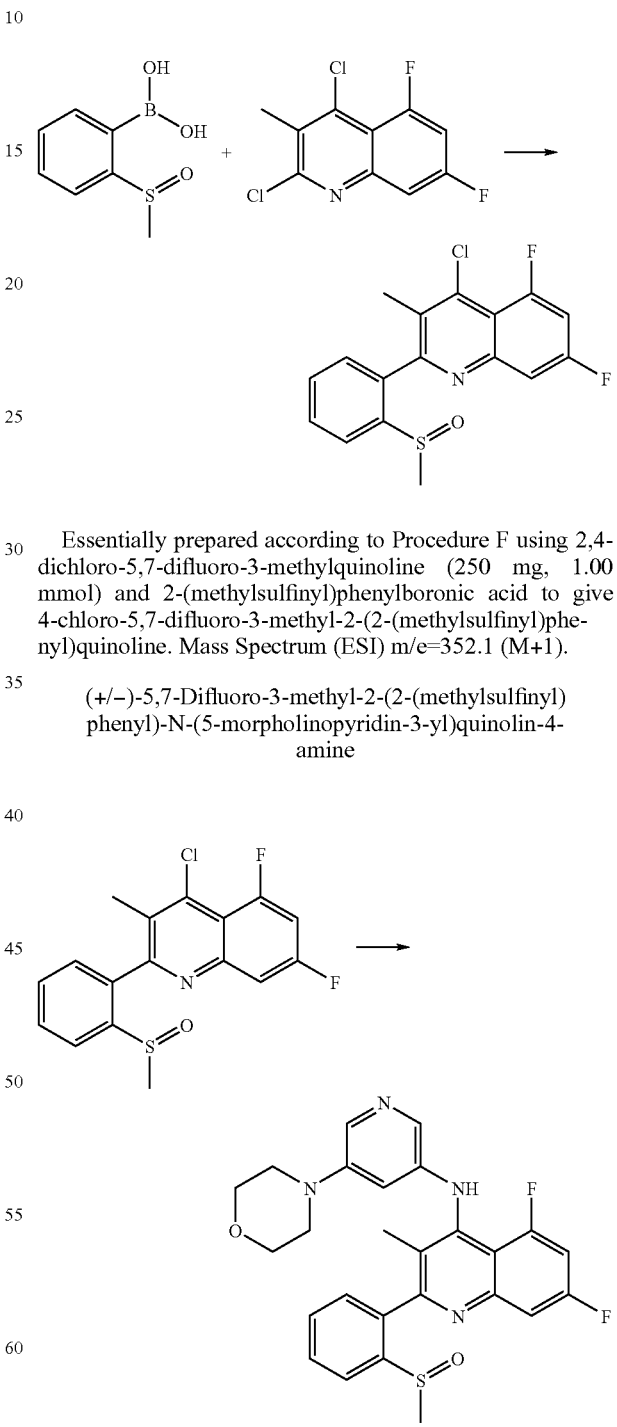

Essentially prepared according to Procedure F using 2,4-dichloro-5,7-difluoro-3-methylquinoline (250 mg, 1.00 mmol) and 2-(methylsulfinyl)phenylboronic acid to give 4-chloro-5,7-difluoro-3-methyl-2-(2-(methylsulfinyl)phenyl)quinoline. Mass Spectrum (ESI) m/e=352.1 (M+1).

(+/−)-5,7-Difluoro-3-methyl-2-(2-(methylsulfinyl)phenyl)-N-(5-morpholinopyridin-3-yl)quinolin-4-amine Essentially prepared according to Procedure H using (+/−)-4-chloro-5,7-difluoro-3-methyl-2-(2-(methylsulfinyl)phenyl)quinoline (30.0 mg, 0.085 mmol) and 5-morpholinopyridin-3-amine in toluene to give 5,7-difluoro-3-methyl-2-(2-(methylsulfinyl)phenyl)-N-(5-morpholinopyridin-3-yl)quinolin-4-amine. $^1$H NMR (CDCl$_3$) δ ppm 8.22 (1H, dd, J=7.9, 1.1 Hz), 7.96 (1H, d, J=2.3 Hz), 7.81 (1H, d, J=2.2 Hz), 7.73 (1H, td, J=7.7, 1.3 Hz), 7.63 (1H, td, J=7.5, 1.3 Hz), 7.50 (1H, ddd, J=9.2, 2.5, 1.4 Hz), 7.39 (1H, dd, J=7.6, 1.2 Hz), 7.20 (1H, d, J=14.1 Hz), 7.08 (1H, ddd, J=13.9, 8.4, 2.5 Hz), 6.60 (1H, t, J=2.2 Hz), 3.80-3.93 (4H, m), 3.12-3.28 (4H, m), 2.87 (3H, s), 1.98 (3H, s). Mass Spectrum (ESI) m/e=495.2 (M+1).

Example 219

Preparation of (+/−)-N-(2,5-Dimorpholinopyridin-3-yl)-5,7-difluoro-3-methyl-2-(2-(methylsulfinyl)phenyl)quinolin-4-amine

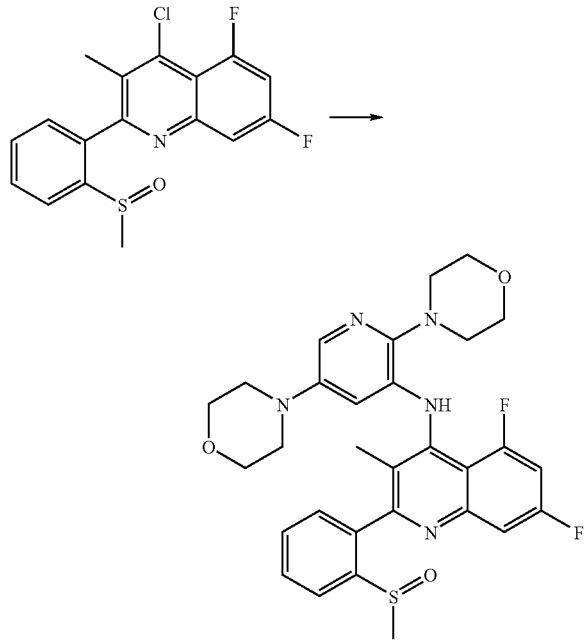

Essentially prepared according to Procedure H using (+/−)-4-chloro-5,7-difluoro-3-methyl-2-(2-(methylsulfinyl)phenyl)quinoline (22.0 mg, 0.063 mmol) and 2,5-dimorpholinopyridin-3-amine in toluene to give (+/−)-N-(2,5-dimorpholinopyridin-3-yl)-5,7-difluoro-3-methyl-2-(2-(methylsulfinyl)phenyl)quinolin-4-amine. $^1$H NMR (CDCl$_3$) δ ppm 8.21 (1H, d, J=8.0 Hz), 7.91 (1H, br. s.), 7.76 (1H, td, J=7.6, 1.4 Hz), 7.66-7.71 (1H, m), 7.65 (1H, d, J=2.5 Hz), 7.54 (1H, d, J=8.6 Hz), 7.39 (1H, d, J=7.6 Hz), 7.08 (1H, ddd, J=13.5, 8.5, 2.4 Hz), 6.38 (1H, br. s.), 3.92 (4H, br. s.), 3.84 (4H, t, J=4.8 Hz), 3.19-3.54 (3H, m), 3.00-3.18 (5H, m), 2.55-2.97 (3H, m), 2.01 (3H, br. s.). Mass Spectrum (ESI) m/e=580.3 (M+1).

Example 220

Preparation of 5,7-Difluoro-3-methyl-2-(5-methyl-2-(methylsulfonyl)phenyl)-N-(5-morpholinopyridin-3-yl)quinolin-4-amine (2-Bromo-4-methylphenyl)(methyl)sulfane

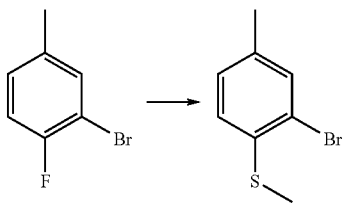

The 2-bromo-1-fluoro-4-methylbenzene (2.00 g, 10.6 mmol) was dissolved in dimethylacetamide (5.3 mL) and sodium thiomethoxide (0.82 g, 11.6 mmol) was added. The reaction was heated at 125° C. for 5.5 h. The reaction was then cooled to rt and stirred overnight. The reaction was then diluted with water (200 mL) and the mixture was extracted with ethyl acetate (3×125 mL). The combined organic layers were washed with water (1×150 mL) brine (1×100 mL) and dried over magnesium sulfate. The crude product was purified by medium pressure chromatography (silica gel, 0 to 40% EtOAc:hexanes) to give (2-bromo-4-methylphenyl)-(methyl) sulfane. $^1$H NMR (CDCl$_3$) δ ppm 7.38 (1H, d, J=0.8 Hz), 7.09-7.13 (1H, m), 7.06 (1H, d), 2.47 (3H, s), 2.31 (3H, s).

5-Methyl-2-(methylthio)phenylboronic acid

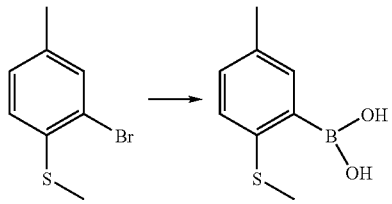

The (2-bromo-4-methylphenyl)(methyl)sulfane (700 mg, 3.20 mmol) was dissolved in THF (5.0 mL) and cooled to −78° C. To the cooled solution was added n-butyl lithium (2.2 mL, 3.60 mmol) dropwise. The reaction was stirred for 2 min at −78° C. then the triisopropyl borate (0.82 mL, 3.56 mmol) was added dropwise and the reaction mixture was allowed to warm to 0° C. over a period of approximately 90 min. The reaction was quenched by addition of 1N HCl solution and was stirred for 5 min. The mixture was then extracted with EtOAc (2×50 mL). The combined organic layers were washed with water (1×30 mL), brine (1×30 mL) and dried over magnesium sulfate. The crude product was then triturated with EtOAc and hexanes to give 5-methyl-2-(methylthio)phenylboronic acid. The mother liquor was purified by medium pressure chromatography (silica gel, 0 to 30% EtOAc:hexanes) to give more desired product. Mass Spectrum (ESI) m/e=183.1 (M+1).

363

4-Chloro-5,7-difluoro-3-methyl-2-(5-methyl-2-(methylthio)phenyl)quinoline

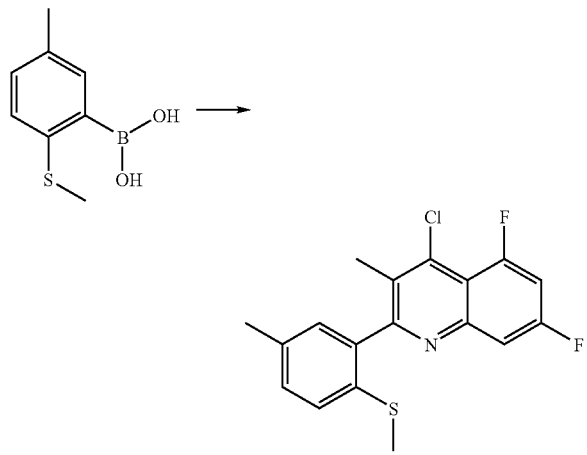

Essentially prepared according to Procedure F using 2,4-dichloro-5,7-difluoro-3-methylquinoline (130 mg, 0.51 mmol) and 5-methyl-2-(methylthio)phenylboronic acid to give 4-chloro-5,7-difluoro-3-methyl-2-(5-methyl-2-(methylthio)phenyl)-quinoline. Mass Spectrum (ESI) m/e=350.0 (M+1).

4-Chloro-5,7-difluoro-3-methyl-2-(5-methyl-2-(methylsulfonyl)phenyl)-quinoline

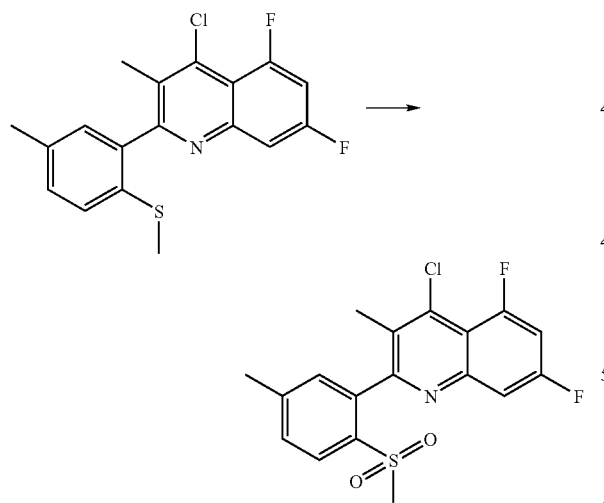

The 4-chloro-5,7-difluoro-3-methyl-2-(5-methyl-2-(methylthio)phenyl)quinoline (160 mg, 0.46 mmol) was slurried in a mixture of THF (3.4 mL) and water (1.1 mL). Oxone™ (700 mg, 1.1 mmol) was added and the mixture was stirred vigorously overnight. The reaction mixture was then poured into water (25 mL) and stirred for 10 min. The mixture was then filtered and washed with water. The ppt. was dissolved in EtOAc (50 mL) and dried over magnesium sulfate. The filtrate was cond to give crude 4-chloro-5,7-difluoro-3-methyl-2-(5-methyl-2-(methylsulfonyl)phenyl)-quinoline. Mass Spectrum (ESI) m/e=382.0 (M+1).

364

5,7-Difluoro-3-methyl-2-(5-methyl-2-(methylsulfonyl)phenyl)-N-(5-morpholinopyridin-3-yl)quinolin-4-amine

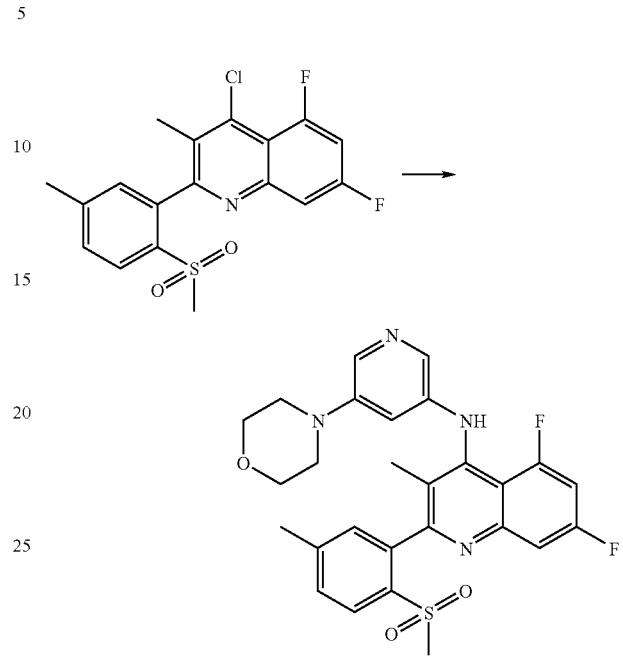

Essentially prepared according to Procedure H using 4-chloro-5,7-difluoro-3-methyl-2-(5-methyl-2-(methylsulfonyl)phenyl)quinoline (60.0 mg, 0.16 mmol) and 5-morpholinopyridin-3-amine in toluene to give 5,7-difluoro-3-methyl-2-(5-methyl-2-(methylsulfonyl)phenyl)-N-(5-morpholinopyridin-3-yl)quinolin-4-amine. $^1$H NMR (CDCl$_3$) δ ppm 8.05 (1H, d, J=8.0 Hz), 7.83-7.92 (2H, m), 7.44-7.52 (2H, m), 7.00-7.24 (3H, m), 6.54-6.59 (1H, m), 3.79 (3H, t, J=4.9 Hz), 3.09-3.25 (4H, m), 3.07 (2H, s), 2.50 (2H, s), 2.04 (1H, s), 1.89 (3H, s), 1.26 (2H, t, J=7.1 Hz). Mass Spectrum (ESI) m/e=525.3 (M+1).

Example 221

Preparation of N-(2,5-dimorpholinopyridin-3-yl)-5,7-difluoro-3-methyl-2-(5-methyl-2-(methylsulfonyl)phenyl)quinolin-4-amine

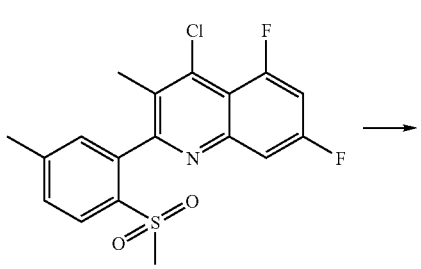

-continued

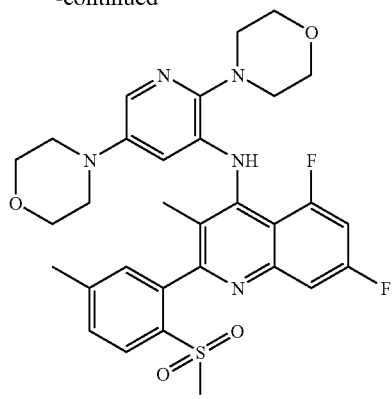

Essentially prepared according to Procedure H using 4-chloro-5,7-difluoro-3-methyl-2-(5-methyl-2-(methylsulfonyl)phenyl)quinoline (50.0 mg, 0.13 mmol) and 2,5-dimorpholinopyridin-3-amine in toluene to give N-(2,5-dimorpholinopyridin-3-yl)-5,7-difluoro-3-methyl-2-(5-methyl-2-(methylsulfonyl)phenyl)-quinolin-4-amine. $^1$H NMR (CDCl$_3$) δ ppm 8.07 (1H, d, J=8.0 Hz), 7.83 (1H, d, J=12.5 Hz), 7.42-7.58 (3H, m), 7.21 (1H, br. s.), 7.05 (1H, ddd, J=13.6, 8.6, 2.6 Hz), 6.53 (1H, br. s.), 3.84-4.04 (4H, m), 3.78 (4H, d, J=4.3 Hz), 3.41 (2H, br. s.), 2.85-3.21 (9H, m), 2.50 (3H, s), 1.93 (3H, s). Mass Spectrum (ESI) m/e=610.3 (M+1).

Example 222

Preparation of 2-(4-cyclohexylpiperazin-1-yl)-5,7-difluoro-3-methyl-N-(5-morpholinopyridin-3-yl)quinolin-4-amine 4-Chloro-5,7-difluoro-3-methyl-2-(piperazin-1-yl)quinoline 2,2,2-trifluoroacetate

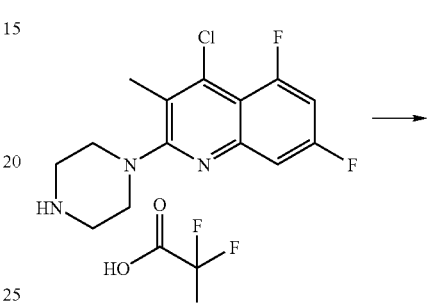

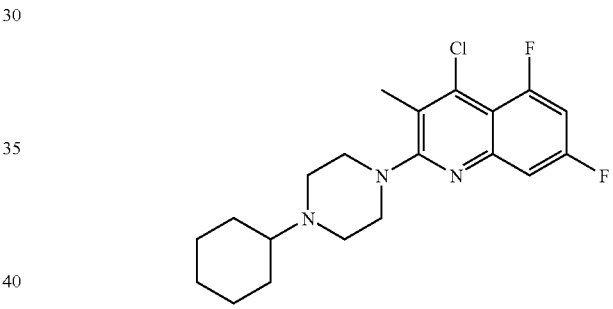

The tert-butyl 4-(4-chloro-5,7-difluoro-3-methylquinolin-2-yl)piperazine-1-carboxylate (370 mg, 0.93 mmol) was dissolved in dichloromethane (3.0 mL) and cooled to 0° C. The trifluoroacetic acid (0.50 mL, 6.5 mmol) was added and the mixture was stirred for 2 h while warming to rt. The mixture was then cond and triturated with EtOAc. The slurry was filtered to give 4-chloro-5,7-difluoro-3-methyl-2-(piperazin-1-yl)quinoline 2,2,2-trifluoroacetate. Mass Spectrum (ESI) m/e=298.1 (M+1).

4-Chloro-2-(4-cyclohexylpiperazin-1-yl)-5,7-difluoro-3-methylquinoline

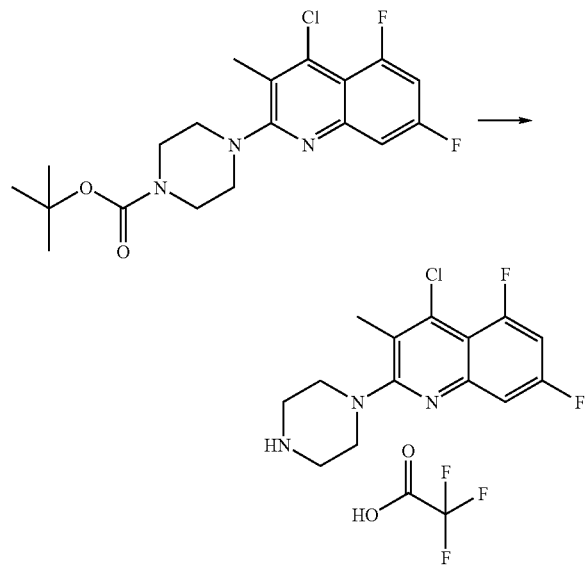

The 4-chloro-5,7-difluoro-3-methyl-2-(piperazin-1-yl)quinoline 2,2,2-trifluoroacetate (75 mg, 0.18 mmol), triethylamine (0.025 mL, 0.18 mmol) and cyclohexanone (0.019 mL, 0.18 mmol) were added to 3 mL of a 2:1 dichlorethane/MeOH mixture. The sodium triacetoxyborohydride (120 mg, 0.55 mmol) was added and the slurry was stirred at rt for 4.5 h. Sodium cyanoborohydride (55 mg, 0.87 mmol) was then added and the slurry was stirred at rt for 4.5 h. Another aliquot of sodium cyanoborohydride (55 mg, 0.87 mmol) was added and the reaction was heated to 80° C. and stirred overnight. The reaction was cooled and then diluted with DCM and water. The layers were separated and the aq. layer was extracted (2×75 mL) with EtOAc. The layers were combined and washed with brine (1×50 mL) and dried over magnesium sulfate. The crude product was purified by medium pressure chromatography (silica gel, 0 to 100% EtOAc:hexanes) to give 4-chloro-2-(4-cyclohexylpiperazin-1-yl)-5,7-difluoro-3-methylquinoline. Mass Spectrum (ESI) m/e=298.1 (M+1).

367

2-(4-Cyclohexylpiperazin-1-yl)-5,7-difluoro-3-methyl-N-(5-morpholinopyridin-3-yl)quinolin-4-amine

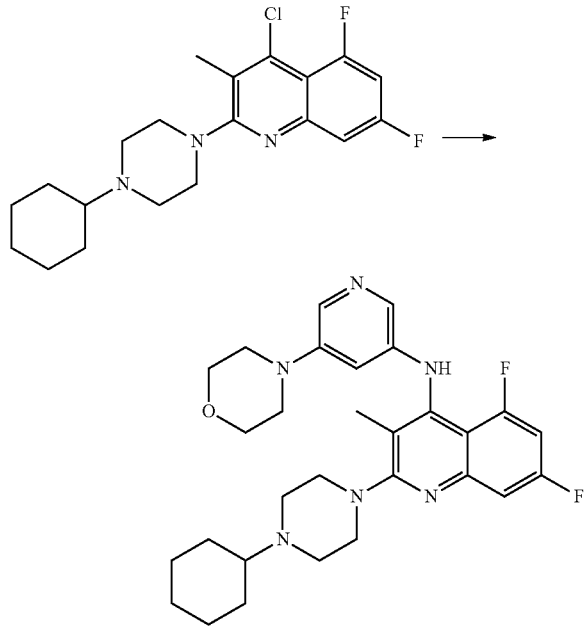

Essentially prepared according to Procedure H using 4-chloro-2-(4-cyclohexylpiperazin-1-yl)-5,7-difluoro-3-methylquinoline (22.0 mg, 0.058 mmol) and 5-morpholinopyridin-3-amine in toluene to give 2-(4-cyclohexylpiperazin-1-yl)-5,7-difluoro-3-methyl-N-(5-morpholinopyridin-3-yl)quinolin-4-amine. $^1$H NMR (CDCl$_3$) δ ppm 7.93 (1H, d, J=2.3 Hz), 7.70 (1H, d, J=1.8 Hz), 7.27-7.33 (1H, m), 6.86 (1H, d, J=12.9 Hz), 6.78 (1H, ddd, J=13.9, 8.6, 2.5 Hz), 6.57 (1H, t, J=2.3 Hz), 3.79-3.91 (4H, m), 3.35-3.61 (4H, m), 3.07-3.23 (4H, m), 2.70-2.98 (4H, m), 2.06 (3H, s), 1.91-2.03 (2H, m), 1.77-1.91 (2H, m), 1.67 (1H, d, J=12.9 Hz), 1.05-1.41 (6H, m). Mass Spectrum (ESI) m/e=524.3 (M+1).

Example 223

Preparation of 5,7-Difluoro-3-methyl-N-(5-morpholinopyridin-3-yl)-2-(4-phenylpiperazin-1-yl)quinolin-4-amine 4-Chloro-5,7-difluoro-3-methyl-2-(4-phenylpiperazin-1-yl)quinoline

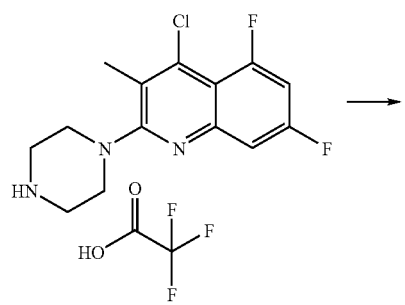

368

-continued

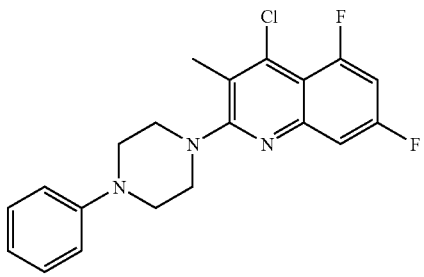

Essentially prepared according to Procedure H using 4-chloro-5,7-difluoro-3-methyl-2-(piperazin-1-yl)quinoline 2,2,2-trifluoroacetate (75.0 mg, 0.18 mmol) and iodobenzene (1.0 eq of triethylamine added to account for TFA salt) in toluene to give 4-chloro-5,7-difluoro-3-methyl-2-(4-phenylpiperazin-1-yl)-quinoline. Mass Spectrum (ESI) m/e=374.2 (M+1).

5,7-Difluoro-3-methyl-N-(5-morpholinopyridin-3-yl)-2-(4-phenylpiperazin-1-yl)quinolin-4-amine Essentially prepared according to Procedure H using 4-chloro-5,7-difluoro-3-methyl-2-(4-phenylpiperazin-1-yl)quinoline (40.0 mg, 0.11 mmol) and 5-morpholinopyridin-3-amine in toluene to give 5,7-difluoro-3-methyl-N-(5-morpholinopyridin-3-yl)-2-(4-phenylpiperazin-1-yl)quinolin-4-amine. $^1$H NMR (CDCl$_3$) δ ppm 7.94 (1H, d, J=2.5 Hz), 7.72 (1H, d, J=2.2 Hz), 7.28-7.36 (3H, m), 7.01 (2H, dd, J=8.8, 1.0 Hz), 6.87-6.96 (2H, m), 6.81 (1H, ddd, J=13.8, 8.8, 2.6 Hz), 6.61 (1H, t, J=2.3 Hz), 3.81-3.88 (4H, m), 3.48-3.57 (4H, m), 3.29-3.45 (4H, m), 3.18 (4H, dd, J=5.8, 4.0 Hz), 2.12 (3H, s). Mass Spectrum (ESI) m/e=517.3 (M+1).

Example 224

Preparation of 2-(5,7-Difluoro-3-methyl-4-(5-morpholinopyridin-3-ylamino)quinolin-2-ylamino)acetic acid, ammonia salt Methyl 2-(4-bromo-5,7-difluoro-3-methylquinolin-2-ylamino)acetate

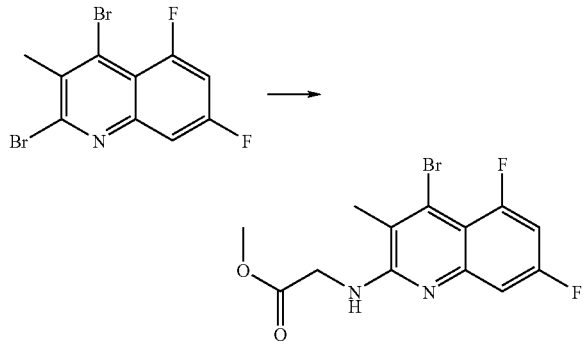

2-Isobutyrylcyclohexanone (0.086 mL, 0.51 mmol), glycine methyl ester hydrochloride (480 mg, 3.9 mmol), 2,4-dibromo-5,7-difluoro-3-methylquinoline (870 mg, 2.6 mmol), copper(I) iodide (24 mg, 0.13 mmol) and cesium carbonate (2.5 g, 7.70 mmol) were slurried in DMF (3.0 mL) and stirred in an oil bath at 70° C. for 2 h. Another aliquot of copper(I) iodide (24 mg, 0.13 mmol) and 2-isobutyryl-cyclohexanone (0.086 mL, 0.51 mmol) were added and heated for an additional 1.5 h. No further progress was observed. The reaction mixture was then diluted with water and extracted with EtOAc (2×100 mL). The combined organic layers were washed with 1N lithium chloride (1×50 mL) and brine (1×50 mL) and dried over magnesium sulfate. The residue was then purified by medium pressure chromatography (silica gel, 0 to 40% EtOAc:hexanes) to give methyl 2-(4-bromo-5,7-difluoro-3-methylquinolin-2-ylamino)acetate. Mass Spectrum (ESI) m/e=347.0 (M+1).

2-(5,7-Difluoro-3-methyl-4-(5-morpholinopyridin-3-ylamino)quinolin-2-ylamino)acetic acid, ammonia salt

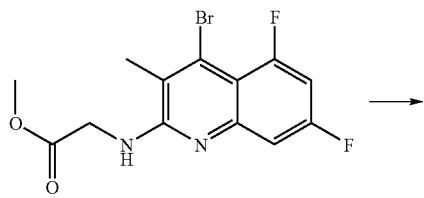

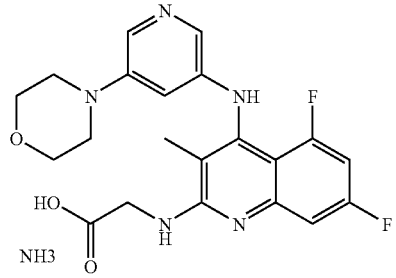

Essentially prepared according to Procedure H using methyl 2-(4-bromo-5,7-difluoro-3-methylquinolin-2-ylamino)acetate (55.0 mg, 0.16 mmol) and 5-morpholinopyridin-3-amine in toluene to give 2-(5,7-difluoro-3-methyl-4-(5-morpholinopyridin-3-ylamino)quinolin-2-ylamino)acetic acid, ammonia salt after eluting the TFA salt though an SCX column eluting with 0 to 2M ammonia in MeOH. $^1$H NMR (CDCl$_3$) δ ppm 7.80 (1H, d, J=2.3 Hz), 7.40 (1H, s), 7.17-7.26 (1H, m), 7.02 (1H, s), 6.78-6.88 (1H, m), 4.32 (2H, s), 3.80 (4H, dd, J=5.8, 4.0 Hz), 3.23-3.29 (4H, m), 2.17 (3H, s). Mass Spectrum (ESI) m/e=430.1 (M+1).

Example 225

Preparation of tert-Butyl 4-(4-(2,5-dimorpholinopyridin-3-ylamino)-5,7-difluoro-3-methylquinolin-2-yl)piperazine-1-carboxylate

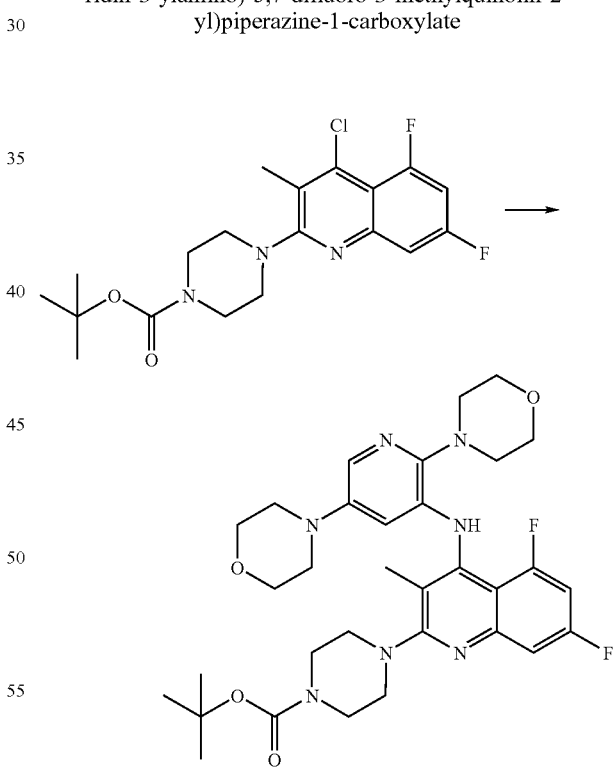

Essentially prepared according to Procedure H using tert-butyl 4-(4-chloro-5,7-difluoro-3-methylquinolin-2-yl)piperazine-1-carboxylate (240.0 mg, 0.60 mmol) and 2,5-dimorpholinopyridin-3-amine in toluene to give tert-butyl 4-(4-(2,5-dimorpholinopyridin-3-ylamino)-5,7-difluoro-3-methylquinolin-2-yl)piperazine-1-carboxylate. $^1$H NMR (CDCl$_3$) δ ppm 7.62 (1H, d, J=2.7 Hz), 7.57 (1H, d, J=11.2 Hz), 7.31 (1H, d, J=7.6 Hz), 6.80 (1H, ddd, J=13.4, 8.8, 2.5

Hz), 6.25 (1H, d, J=2.5 Hz), 3.88-3.94 (4H, m), 3.72-3.83 (4H, m), 3.62 (4H, br. s.), 3.36 (4H, br. s.), 3.15 (4H, br. s.), 2.90-3.04 (4H, m), 2.11 (3H, s), 1.48-1.56 (9H, m). Mass Spectrum (ESI) m/e=626.3 (M+1).

Example 226

Preparation of 1-(3-(5,7-Difluoro-3-methyl-4-(5-morpholinopyridin-3-ylamino)quinolin-2-yl)-4-(methylsulfonyl)phenyl)ethanone 1-(3-Bromo-4-(methylthio)phenyl)ethanone

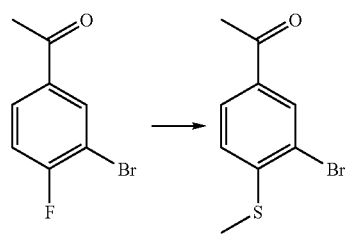

The 1-(3-bromo-4-fluorophenyl)ethanone (2.00 g, 9.20 mmol) and sodium thiomethoxide (0.710 g, 10.1 mmol) was dissolved in dimethylacetamide (4.6 mL) and the slurry was heated at 120° C. in a microwave reactor for 1 h. The reaction mixture was diluted with water (30 mL) and the mixture was extracted with EtOAc (2×100 mL). The combined organic layers were washed with water (1×75 mL) and dried over magnesium sulfate. The crude product was purified by medium pressure chromatography (silica gel, 0 to 75% EtOAc:hexanes) to give 1-(3-bromo-4-(methylthio)phenyl)ethanone. Mass Spectrum (ESI) m/e=245.1 (M+1).

1-(4-(Methylthio)-3-(4,4,5,5-tetramethyl-1,3,2-dioxaborolan-2-yl)phenyl)-ethanone

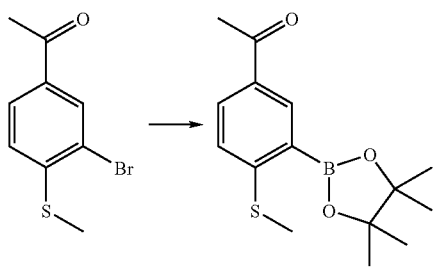 [SMILES: CSc1ccc(C(C)=O)cc1Br ; CSc1ccc(C(C)=O)cc1B1OC(C)(C)C(C)(C)O1]

The PdCl$_2$(dppf)-DCM adduct (260 mg, 0.32 mmol), bis(pinacolato)diboron (600 mg, 2.4 mmol), 1-(3-bromo-4-(methylthio)phenyl)ethanone (520 mg, 2.1 mmol) and potassium acetate (630 mg, 6.4 mmol) were added to dioxane (5.3 mL) and heated in a microwave reactor at 100° C. for 1 h. Another 100 mg of the catalyst was added and the reaction was heated again for 2 h. The reaction mixture was diluted with water and the mixture was extracted with EtOAc (2×50 mL). The combined organic layers were washed with water (1×50 mL) and brine (1×25 mL) and dried over magnesium sulfate. The crude product was purified by medium pressure chromatography (silica gel, 0 to 45% EtOAc:hexanes) to give 1-(4-(methylthio)-3-(4,4,5,5-tetramethyl-1,3,2-dioxaborolan-2-yl)phenyl)-ethanone. Mass Spectrum (ESI) m/e=293.2 (M+1).

1-(3-(4-Chloro-5,7-difluoro-3-methylquinolin-2-yl)-4-(methylthio)phenyl)-ethanone

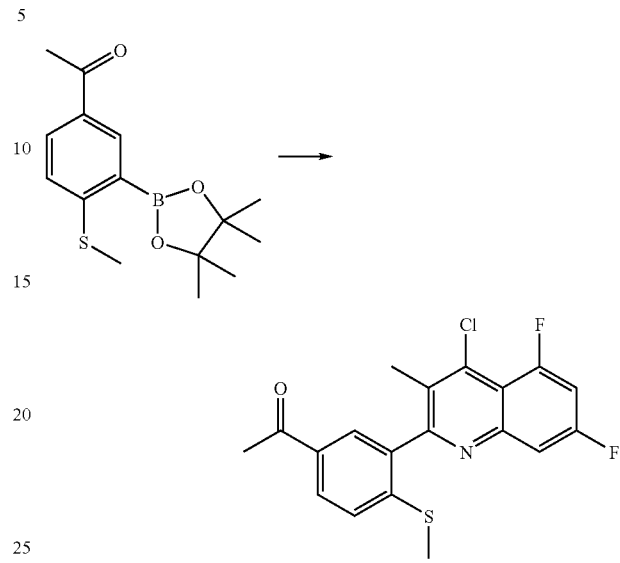

Essentially prepared according to Procedure F using 2,4-dichloro-5,7-difluoro-3-methylquinoline (150 mg, 0.59 mmol) and 1-(4-(methylthio)-3-(4,4,5,5-tetramethyl-1,3,2-dioxaborolan-2-yl)phenyl)ethanone to give 1-(3-(4-chloro-5,7-difluoro-3-methylquinolin-2-yl)-4-(methylthio)phenyl)ethanone. Mass Spectrum (ESI) m/e=378.1 (M+1).

1-(3-(4-Chloro-5,7-difluoro-3-methylquinolin-2-yl)-4-(methylsulfonyl)-phenyl)ethanone

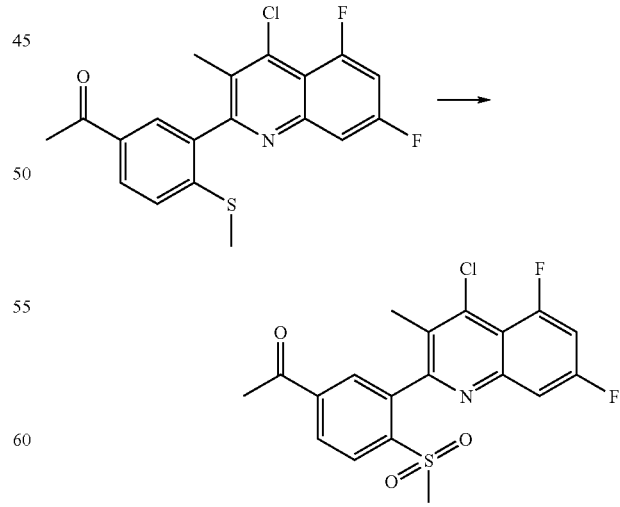

The 1-(3-(4-chloro-5,7-difluoro-3-methylquinolin-2-yl)-4-(methylthio)phenyl)-ethanone (230 mg, 0.61 mmol) was added to a mixture of THF (4.6 mL) and water (1.5 mL). To the milky solution was added Oxone™ (940 mg, 1.5 mmol) and the reaction was stirred for 2.5 days. Another portion of Oxone™ (940 mg, 1.5 mmol) was added along with the same amount of THF and water amounts as initially. The slurry was stirred vigorously overnight. The reaction was then poured into water and stirred vigorously for 10 min. The mixture was filtered and washed with water. The precipitate was dissolved in EtOAc and dried over magnesium sulfate. The crude product was purified by medium pressure chromatography (silica gel, 0 to 100% EtOAc:hexanes) to give 1-(3-(4-chloro-5,7-difluoro-3-methylquinolin-2-yl)-4-(methylsulfonyl)phenyl)ethanone. Mass Spectrum (ESI) m/e=410.0 (M+1).

1-(3-(5,7-Difluoro-3-methyl-4-(5-morpholinopyridin-3-ylamino)quinolin-2-yl)-4-(methylsulfonyl)phenyl)ethanone

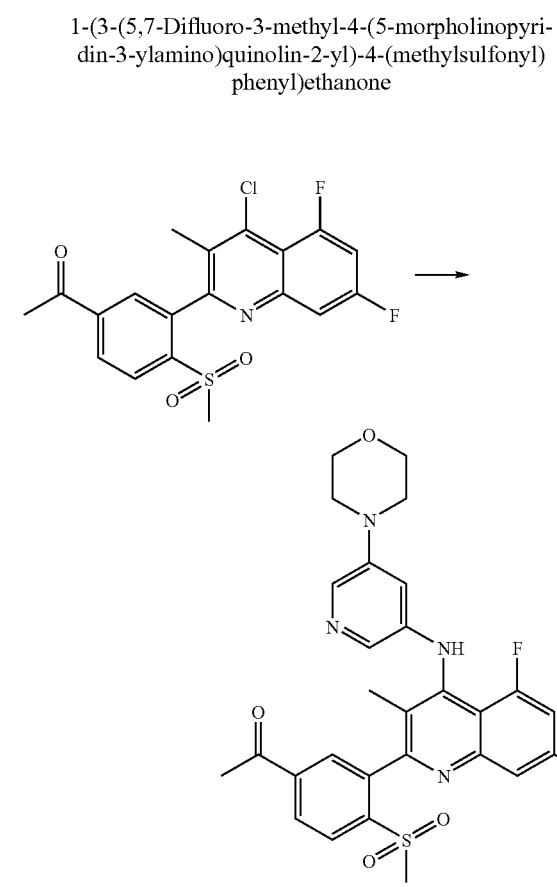

Essentially prepared according to Procedure H using 1-(3-(4-chloro-5,7-difluoro-3-methylquinolin-2-yl)-4-(methylsulfonyl)phenyl)ethanone (150.0 mg, 0.35 mmol) and 5-morpholinopyridin-3-amine in toluene to give 1-(3-(5,7-difluoro-3-methyl-4-(5-morpholinopyridin-3-ylamino)quinolin-2-yl)-4-(methylsulfonyl)-phenyl)ethanone. $^1$H NMR (CDCl$_3$) δ ppm 8.17-8.35 (3H, m), 7.94-8.13 (2H, m), 7.76 (1H, s), 7.54-7.66 (1H, m), 7.17 (1H, ddd, J=13.0, 8.5, 2.4 Hz), 6.73 (1H, s), 3.72-3.88 (4H, m), 3.18-3.33 (4H, m), 3.10 (3H, s), 2.70 (3H, s), 1.96 (3H, s). Mass Spectrum (ESI) m/e=553.2 (M+1).

Example 227

Preparation of (+/−)-1-(3-(5,7-Difluoro-3-methyl-4-(5-morpholinopyridin-3-ylamino)quinolin-2-yl)-4-(methylsulfonyl)phenyl)-ethanol

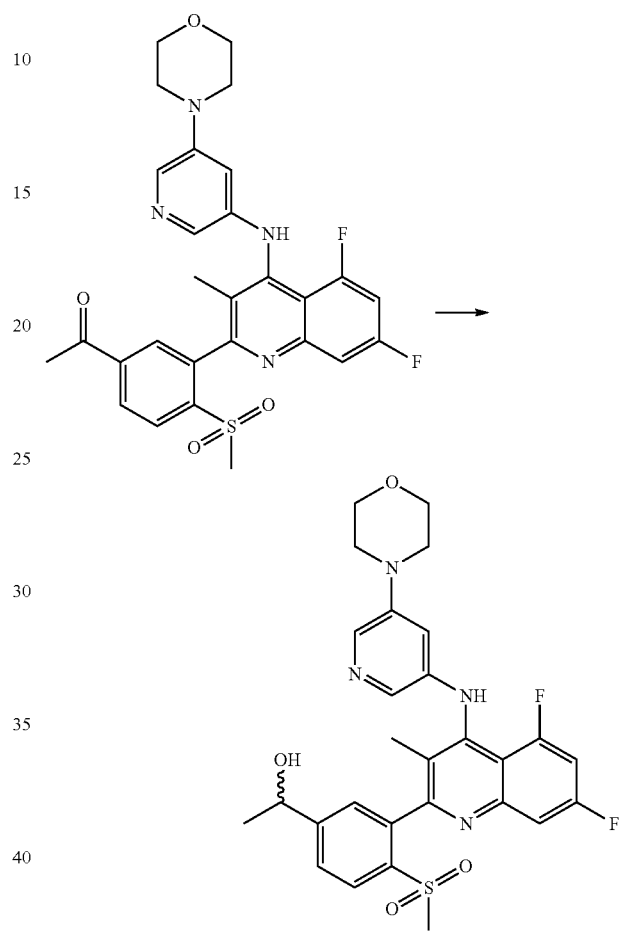

The 1-(3-(5,7-difluoro-3-methyl-4-(5-morpholinopyridin-3-ylamino)quinolin-2-yl)-4-(methylsulfonyl)phenyl)ethanone (40 mg, 0.072 mmol) was dissolved in THF (1.00 mL) and cooled to 0° C. To the solution was added 1M lithium aluminum hydride (0.072 mL, 0.072 mmol) in THF and the reaction mixture was allowed to warm to rt over a period of 1.5 h. The reaction was then worked up via the method found in the Fieser and Fieser (Vol. 1) and the mixture was filtered over a short plug of silica gel and washed with EtOAc. The filtrate was cond to give (+/−)-1-(3-(5,7-difluoro-3-methyl-4-(5-morpholinopyridin-3-ylamino)-quinolin-2-yl)-4-(methylsulfonyl)-phenyl)ethanol. $^1$H NMR (CDCl$_3$) δ ppm 8.14 (1H, dd, J=8.2, 4.1 Hz), 7.93 (1H, t, J=2.4 Hz), 7.75 (1H, dd, J=4.1, 2.5 Hz), 7.68 (1H, ddd, J=18.5, 8.3, 1.6 Hz), 7.42-7.58 (3H, m), 7.09 (1H, ddd, J=13.4, 8.6, 2.5 Hz), 6.63-6.73 (1H, m), 5.06 (1H, q, J=6.7 Hz), 3.78 (4H, t, J=4.8 Hz), 3.20 (4H, q, J=3.9 Hz), 3.12 (3H, d, J=1.6 Hz), 1.91 (3H, d, J=5.3 Hz), 1.57 (3H, d, J=6.7 Hz). Mass Spectrum (ESI) m/e=555.2 (M+1).

Example 228

Preparation of 2-(4-Ethylpiperazin-1-yl)-5,7-difluoro-3-methyl-N-(5-morpholinopyridin-3-yl)quinolin-4-amine

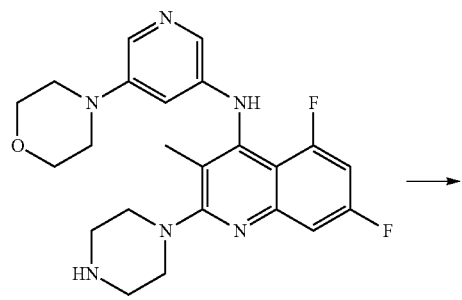

The 5,7-difluoro-3-methyl-N-(5-morpholinopyridin-3-yl)-2-(piperazin-1-yl)-quinolin-4-amine (50 mg, 0.11 mmol) was dissolved in a mixture of dichloroethane (1.3 mL) and MeOH (0.63 mL). The acetaldehyde (6.4 μL, 0.11 mmol) and sodium triacetoxyborohydride (72 mg, 0.34 mmol) were added and the mixture was stirred overnight. A small amount (50 mg) of sodium cyanoborohydride was added to drive the reaction to completion. The reaction was quenched with satd sodium bicarbonate solution and extracted with EtOAc. The organic layer was then dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in $CH_3CN/H_2O$, gradient 10% to 95% over 20 min to provide 2-(4-ethylpiperazin-1-yl)-5,7-difluoro-3-methyl-N-(5-morpholinopyridin-3-yl)quinolin-4-amine. The salt was then free based by eluting through an SCX column with 0 to 2M ammonia in MeOH to give the desired product as the free base. TFA salt: $^1$H NMR ($CDCl_3$) δ ppm 7.86 (2H, dd, J=4.3, 2.2 Hz), 7.61 (1H, d, J=9.2 Hz), 7.36-7.43 (1H, m), 7.20 (1H, t, J=2.0 Hz), 6.89 (1H, ddd, J=13.4, 8.5, 2.3 Hz), 4.24 (2H, d, J=14.7 Hz), 3.86-3.95 (4H, m), 3.77 (2H, t, J=13.2 Hz), 3.63 (2H, d, J=12.3 Hz), 3.26-3.38 (4H, m), 3.15 (4H, q, J=7.2 Hz), 2.13 (3H, s), 1.39 (3H, t, J=7.3 Hz). Mass Spectrum (ESI) m/e=469.3 (M+1).

Example 229

Preparation of 1-(4-(5,7-Difluoro-3-methyl-4-(5-morpholinopyridin-3-ylamino)quinolin-2-yl)piperazin-1-yl)ethanone

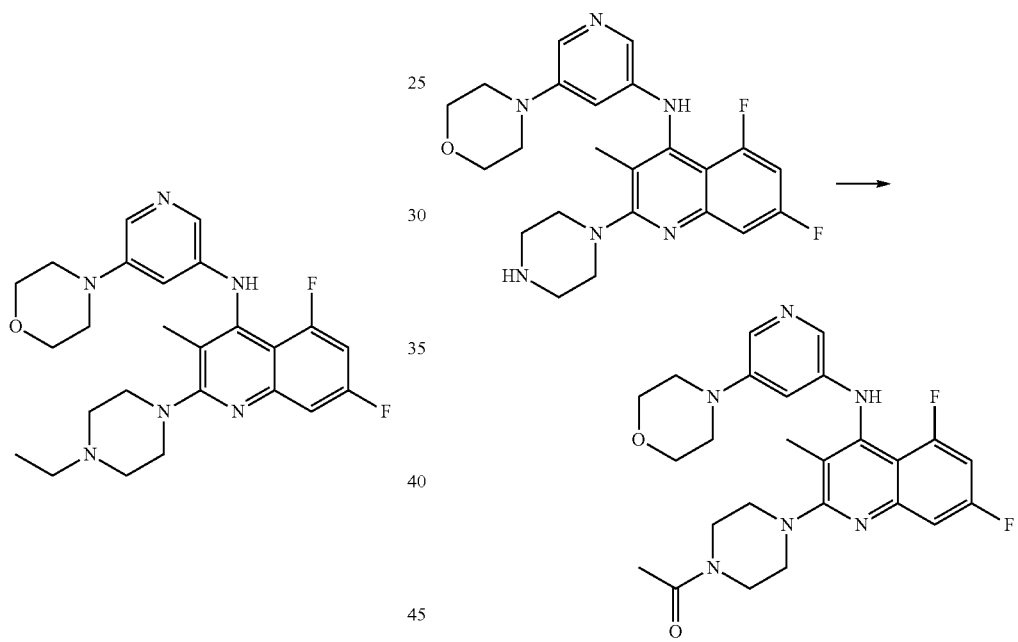

The 5,7-difluoro-3-methyl-N-(5-morpholinopyridin-3-yl)-2-(piperazin-1-yl)-quinolin-4-amine (50 mg, 0.11 mmol) was dissolved in THF (1.1 mL) and the triethylamine (24.0 μL, 0.17 mmol) and acetic anhydride (11.0 μL, 0.11 mmol) were added and the mixture was stirred overnight. The reaction was then quenched with water and extracted with EtOAc. The organic layers were dried over magnesium sulfate and the filtrate was cond. The crude material was purified by reverse-phase preparative HPLC using a Phenomenex Gemini column, 10 micron, C18, 100 Å, 150×30 mm, 0.1% TFA in $CH_3CN/H_2O$, gradient 10% to 95% over 20 min to provide, after treatment with sodium bicarbonate 1-(4-(5,7-difluoro-3-methyl-4-(5-morpholinopyridin-3-ylamino)quinolin-2-yl)piperazin-1-yl)ethanone: $^1$H NMR ($CDCl_3$) δ ppm 8.22 (1H, d, J=7.6 Hz), 7.88 (1H, d, J=2.2 Hz), 7.82 (1H, d, J=1.8 Hz), 7.49 (1H, dd, J=9.6, 1.2 Hz), 7.14-7.23 (1H, m), 6.86 (1H, ddd, J=13.0, 8.4, 2.3 Hz), 3.77-3.95 (6H, m), 3.61-3.76 (4H, m), 3.53-3.61 (2H, m), 3.23-3.37 (4H, m), 2.19 (3H, s), 2.16 (3H, s). Mass Spectrum (ESI) m/e=483.3 (M+1).

Example 230

Preparation of 5,7-Difluoro-3-methyl-2-(4-(methylsulfonyl)-piperazin-1-yl)-N-(5-morpholinopyridin-3-yl)quinolin-4-amine

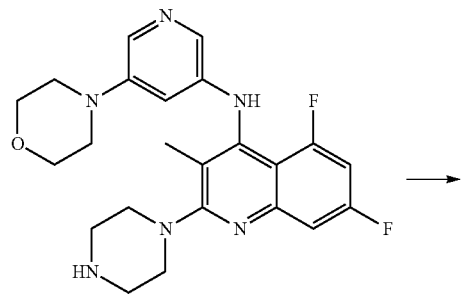

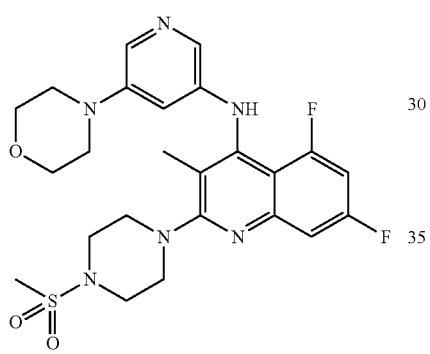

The 5,7-difluoro-3-methyl-N-(5-morpholinopyridin-3-yl)-2-(piperazin-1-yl)-quinolin-4-amine (50 mg, 0.11 mmol) was dissolved in DCM (1.1 mL) and the triethylamine (24.0 μL, 0.170 mmol) and methanesulfonyl chloride (8.8 μL, 0.11 mmol) were added and the mixture was stirred overnight. The reaction was then quenched with water and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH$_3$CN/H$_2$O, gradient 10% to 95% over 20 min to provide 5,7-difluoro-3-methyl-2-(4-(methylsulfonyl)piperazin-1-yl)-N-(5-morpholinopyridin-3-yl)quinolin-4-amine as a TFA salt. The compound was eluted through an SCX column with 0 to 2M ammonia in MeOH to give the free amine. TFA salt: $^1$H NMR (CDCl$_3$) δ ppm 7.84-7.97 (2H, m), 7.81 (1H, d, J=2.2 Hz), 7.46 (1H, ddd, J=9.5, 2.4, 1.2 Hz), 7.10 (1H, t, J=1.9 Hz), 6.85 (1H, ddd, J=13.2, 8.6, 2.5 Hz), 3.79-3.96 (4H, m), 3.60-3.77 (4H, m), 3.36-3.48 (4H, m), 3.22-3.35 (4H, m), 2.84 (3H, s), 2.16 (3H, s). Mass Spectrum (ESI) m/e=519.2 (M+1).

Example 231

Preparation of 4-(4-(3,3-Dimethyl-1-(5-morpholinopyridin-3-yl)ureido)-5,7-difluoro-3-methylquinolin-2-yl)-N,N-dimethylpiperazine-1-carboxamide (1) and 4-(5,7-Difluoro-3-methyl-4-(5-morpholinopyridin-3-ylamino)quinolin-2-yl)-N,N-dimethylpiperazine-1-carboxamide (2)

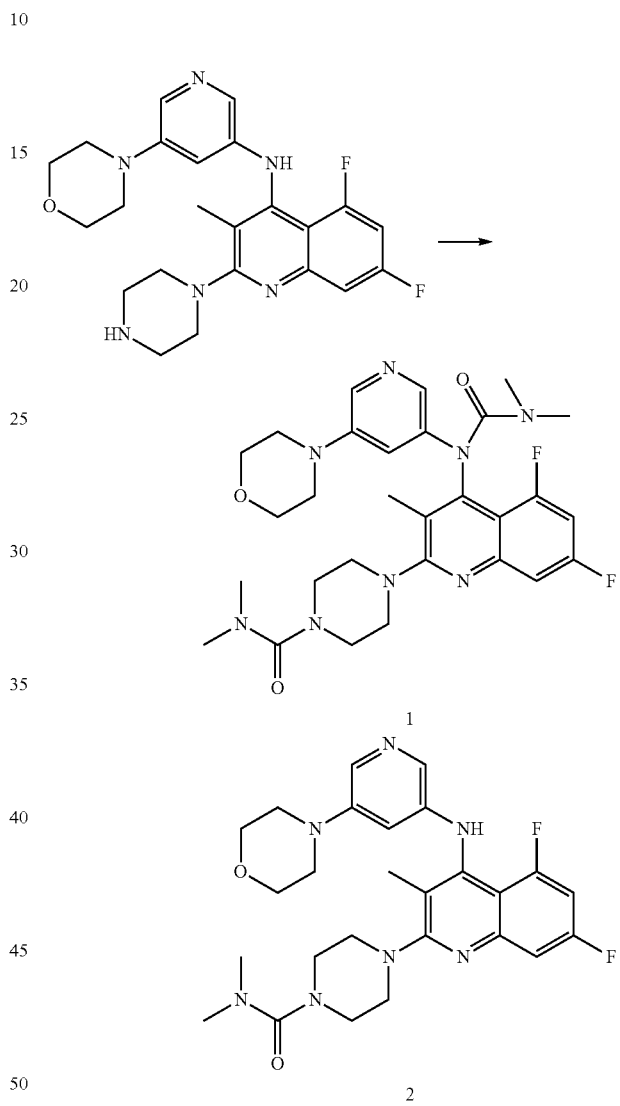

The 5,7-difluoro-3-methyl-N-(5-morpholinopyridin-3-yl)-2-(piperazin-1-yl)-quinolin-4-amine (50 mg, 0.11 mmol) was dissolved in DCM (1.00 mL) and triethylamine (0.024 mL, 0.170 mmol) was added followed by dimethylcarbamyl chloride (10.0 μL, 0.11 mmol) and the reaction was stirred overnight. The reaction was then quenched with water and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH$_3$CN/H$_2$O, gradient 10% to 95% over 20 min to provide 4-(5,7-difluoro-3-methyl-4-(5-morpholinopyridin-3-ylamino)quinolin-2-yl)-N,N-dimethylpiperazine-1-carboxamide and 4-(4-(3,3-dimethyl-1-(5-morpholinopyridin-3-yl)ureido)-5,7-difluoro-3- methylquinolin-2-yl)-N,N-dimethylpiperazine-1-carboxamide The compounds were eluted through an SCX column with 0 to 2M ammonia in MeOH to give the free amine, (1) TFA salt: ¹H NMR (CDCl₃) δ ppm 8.00 (1H, br. s.), 7.58-7.69 (1H, m), 7.42-7.53 (1H, m), 7.12 (1H, br. s.), 6.81 (1H, ddd, J=12.1, 8.6, 2.4 Hz), 3.74-3.84 (4H, m), 3.51-3.61 (4H, m), 3.39-3.51 (4H, m), 3.20-3.28 (4H, m), 3.16 (3H, br. s.), 2.94 (3H, br. s.), 2.90 (6H, s), 2.28 (3H, s). Mass Spectrum (ESI) m/e=583.3 (M+1). (2) TFA salt: ¹H NMR (CDCl₃) δ ppm 9.06 (1H, d, J=5.9 Hz), 7.88 (1H, d, J=2.2 Hz), 7.85 (1H, d, J=1.4 Hz), 7.43-7.58 (2H, m), 6.83 (1H, ddd, J=12.6, 8.3, 2.3 Hz), 3.83-3.99 (4H, m), 3.72 (4H, br. s.), 3.47 (4H, br. s.), 3.26-3.41 (4H, m), 2.91 (6H, s), 2.07 (3H, s). Mass Spectrum (ESI) m/e=512.2 (M+1).

Example 232

Preparation of 5,7-Difluoro-3-methyl-N-(5-morpholinopyridin-3-yl)-N-(2,2,2-trifluoroethyl)-2-(4-(2,2,2-trifluoroethyl)piperazin-1-yl)-quinolin-4-amine (1) and 5,7-Difluoro-3-methyl-N-(5-morpholinopyridin-3-yl)-2-(4-(2,2,2-trifluoroethyl)piperazin-1-yl)quinolin-4-amine (2)

The 5,7-difluoro-3-methyl-N-(5-morpholinopyridin-3-yl)-2-(piperazin-1-yl)-quinolin-4-amine (50 mg, 0.11 mmol) was dissolved in dichloromethane (1.00 mL) and triethylamine (0.024 mL, 0.17 mmol) followed by 2,2,2-trifluoroethyl trifluoromethanesulfonate (0.016 mL, 0.11 mmol) was added. The mixture was stirred for 24 h. Another aliquot of triethylamine (0.024 mL, 0.17 mmol) and 2,2,2-trifluoroethyl trifluoromethanesulfonate (0.016 mL, 0.11 mmol) was added and stirred for an additional 4.5 days. The reaction was then quenched with water and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH₃CN/H₂O, gradient 10% to 95% over 20 min to provide 5,7-difluoro-3-methyl-N-(5-morpholinopyridin-3-yl)-2-(4-(2,2,2-trifluoroethyl)piperazin-1-yl)quinolin-4-amine (2) and 5,7-difluoro-3-methyl-N-(5-morpholinopyridin-3-yl)-N-(2,2,2-trifluoroethyl)-2-(4-(2,2,2-trifluoroethyl)-piperazin-1-yl)quinolin-4-amine (1) as TFA salts. The compounds were eluted through an SCX column with 0 to 2M ammonia in MeOH to give the free amine. (1) TFA salt: ¹H NMR (MeOD) δ ppm 7.76-7.88 (2H, m), 7.34 (1H, d, J=9.6 Hz), 6.81 (1H, br. s.), 6.75 (1H, ddd, J=12.0, 9.1, 2.5 Hz), 5.21 (2H, q, J=7.8 Hz), 3.69-3.80 (4H, m), 3.38-3.49 (4H, m), 3.12-3.22 (4H, m), 3.08 (2H, q, J=9.5 Hz), 2.78-2.95 (4H, m), 2.17 (3H, s). Mass Spectrum (ESI) m/e=605.2 (M+1). (2) TFA salt: ¹H NMR (CDCl₃) δ ppm 9.03 (1H, d, J=5.7 Hz), 7.87 (1H, d, J=2.3 Hz), 7.84 (1H, d, J=1.8 Hz), 7.46-7.57 (2H, m), 6.80 (1H, ddd, J=12.5, 8.4, 2.3 Hz), 3.86-3.98 (4H, m), 3.77 (4H, br. s.), 3.28-3.40 (4H, m), 3.15 (2H, q, J=9.4 Hz), 2.84-3.06 (4H, m), 2.08 (3H, s). Mass Spectrum (ESI) m/e=523.3 (M+1).

Example 233

Preparation of methyl 4-(5,7-Difluoro-3-methyl-4-(5-morpholinopyridin-3-ylamino)quinolin-2-yl)piperazine-1-carboxylate

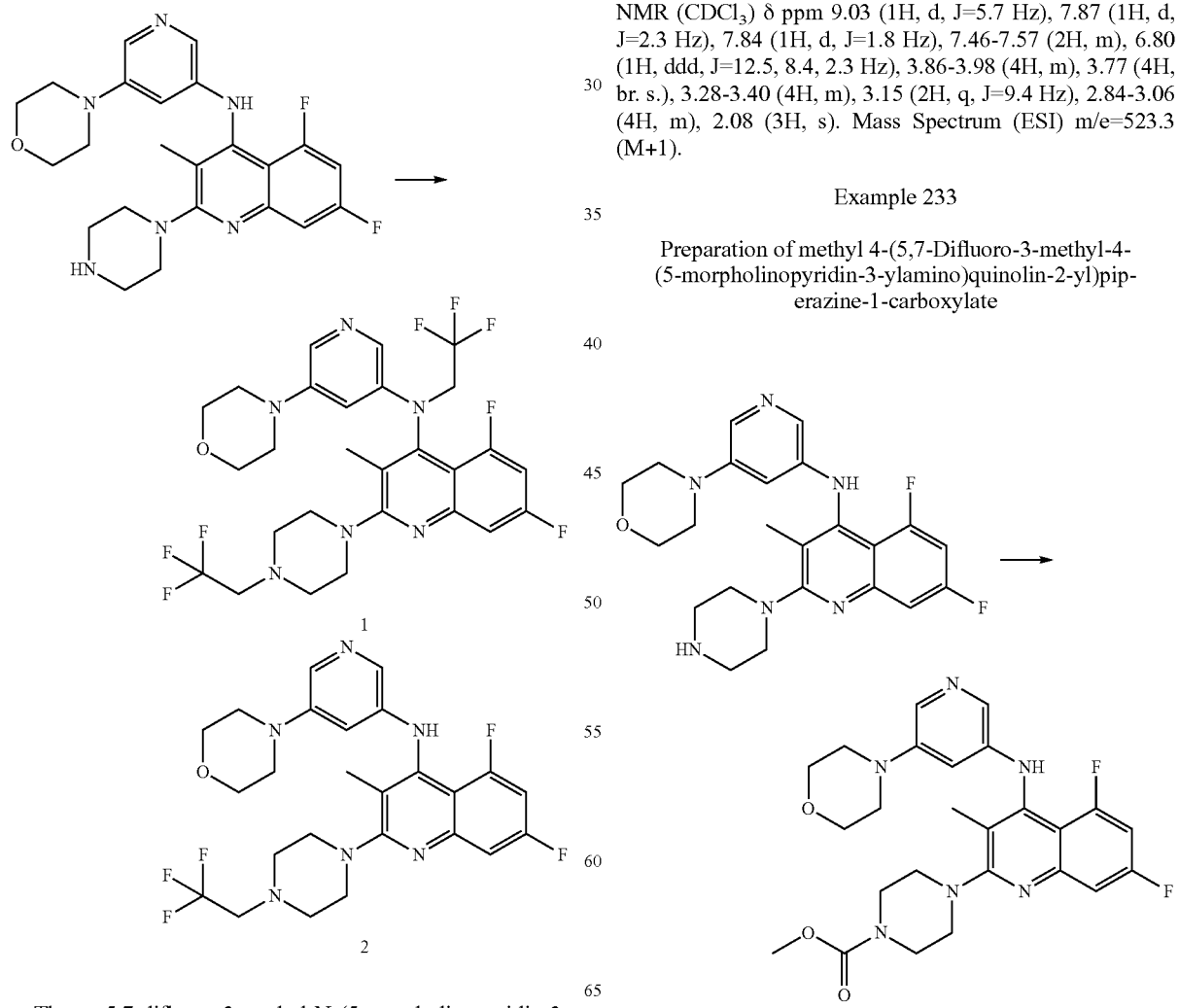

The 5,7-difluoro-3-methyl-N-(5-morpholinopyridin-3-yl)-2-(piperazin-1-yl)-quinolin-4-amine (50 mg, 0.11 mmol) was dissolved in acetone and the potassium carbonate (94 mg, 0.68 mmol) and methyl chloroformate (0.035 mL, 0.45 mmol) were heated in a microwave reactor at 80° C. for 2.5 h. The reaction was then diluted with water and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH$_3$CN/H$_2$O, gradient 10% to 95% over 20 min to provide methyl 4-(5,7-difluoro-3-methyl-4-(5-morpholinopyridin-3-ylamino)quinolin-2-yl)piperazine-1-carboxylate as a TFA salt. The compounds were eluted through an SCX column with 0 to 2M ammonia in MeOH to give the free amine. TFA salt: $^1$H NMR (CDCl$_3$) δ ppm 8.75 (1H, d, J=6.5 Hz), 7.88 (1H, d, J=1.8 Hz), 7.84 (1H, s), 7.53 (1H, d, J=9.2 Hz), 7.34 (1H, s), 6.84 (1H, ddd, J=12.7, 8.4, 2.2 Hz), 3.82-3.93 (4H, m), 3.76 (3H, s), 3.66-3.74 (4H, m), 3.57-3.65 (4H, m), 3.21-3.41 (4H, m), 2.12 (3H, s). Mass Spectrum (ESI) m/e=499.2 (M+1).

Example 234

Preparation of 1-(4-(5,7-Difluoro-3-methyl-4-(5-morpholinopyridin-3-ylamino)quinolin-2-yl)piperazin-1-yl)-2-methylpropan-1-one

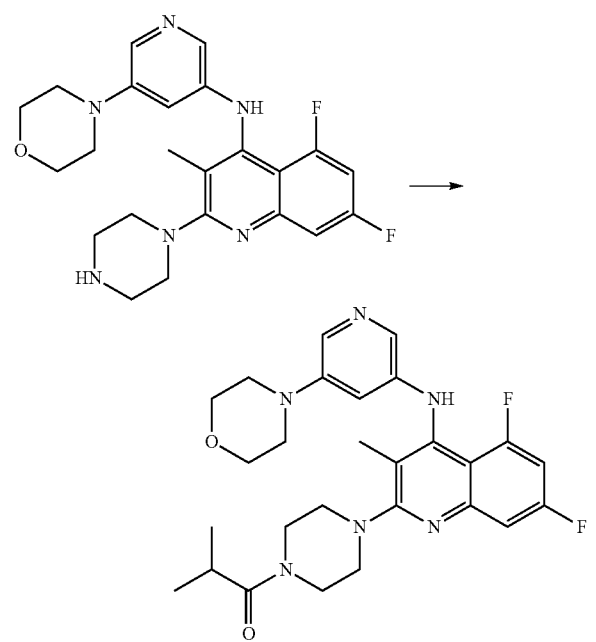

The 5,7-difluoro-3-methyl-N-(5-morpholinopyridin-3-yl)-2-(piperazin-1-yl)-quinolin-4-amine (50 mg, 0.11 mmol) was dissolved in THF (1.1 mL) and the triethylamine (24.0 µL, 0.17 mmol) and isobutyric anhydride (11.0 µL, 0.11 mmol) were added and the mixture was stirred overnight. The reaction was then quenched with water and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH$_3$CN/H$_2$O, gradient 10% to 95% over 20 min to provide 1-(4-(5,7-difluoro-3-methyl-4-(5-morpholinopyridin-3-ylamino)quinolin-2-yl)piperazin-1-yl)-2-methylpropan-1-one as a TFA salt. The compound was eluted through an SCX column with 0 to 2M ammonia in MeOH to give the free amine. TFA salt: $^1$H NMR (CDCl$_3$) δ ppm 8.57 (1H, d, J=6.7 Hz), 7.85 (2H, dd, J=13.3, 2.0 Hz), 7.52 (1H, d, J=9.4 Hz), 7.29 (1H, br. s.), 6.86 (1H, ddd, J=12.9, 8.4, 2.5 Hz), 3.85-3.92 (4H, m), 3.84 (2H, br. s.), 3.75 (2H, br. s.), 3.69 (2H, br. s.), 3.60 (2H, br. s.), 3.24-3.34 (4H, m), 2.86 (1H, spt, J=6.7 Hz), 2.15 (3H, s), 1.17 (6H, d, J=6.8 Hz). Mass Spectrum (ESI) m/e=511.3 (M+1).

Example 235

Preparation of 5,7-Difluoro-3-methyl-N-(5-morpholinopyridin-3-yl)-2-(4-(phenylsulfonyl)piperazin-1-yl)quinolin-4-amine

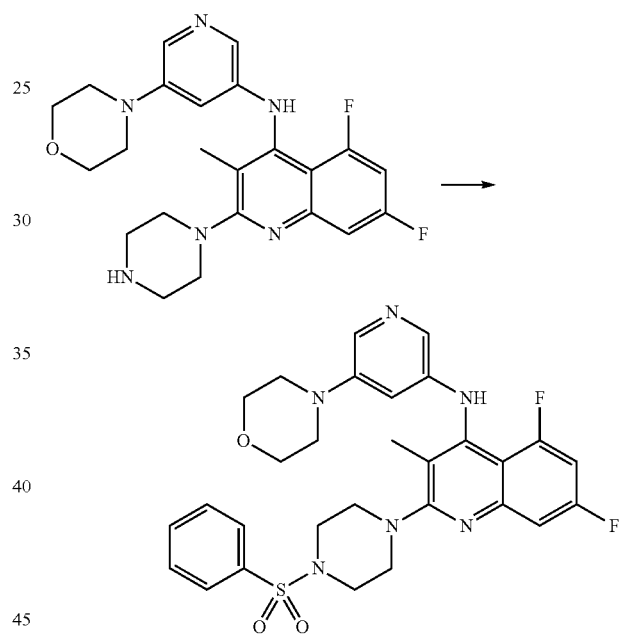

The 5,7-difluoro-3-methyl-N-(5-morpholinopyridin-3-yl)-2-(piperazin-1-yl)-quinolin-4-amine (50 mg, 0.11 mmol) was dissolved in DCM (1.1 mL) and the triethylamine (24.0 µL, 0.17 mmol) and benzenesulfonyl chloride (15.0 µL, 0.11 mmol) were added and the mixture was stirred overnight. The reaction was then quenched with water and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH$_3$CN/H$_2$O, gradient 10% to 95% over 20 min to provide 5,7-difluoro-3-methyl-N-(5-morpholinopyridin-3-yl)-2-(4-(phenylsulfonyl)piperazin-1-yl)quinolin-4-amine as a TFA salt. The compound was eluted through an SCX column with 0 to 2M ammonia in MeOH to give the free amine. TFA salt: $^1$H NMR (CDCl$_3$) δ ppm 7.65-7.77 (3H, m), 7.43-7.60 (4H, m), 7.27-7.30 (1H, m), 7.16-7.25 (1H, m), 6.63-6.78 (2H, m), 3.64-3.78 (4H, m), 3.38 (4H, d, J=4.9 Hz), 3.04-3.21 (8H, m), 2.02 (3H, s). Mass Spectrum (ESI) m/e=581.2 (M+1).

Example 236

Preparation of 5,7-Difluoro-2-(4-isopropylpiperazin-1-yl)-3-methyl-N-(5-morpholinopyridin-3-yl)quinolin-4-amine

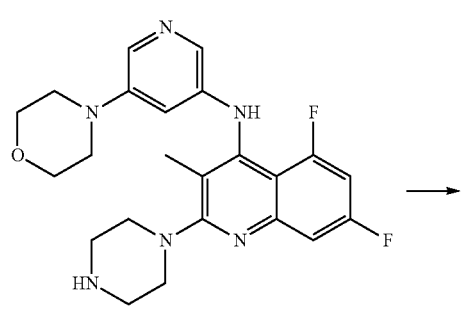

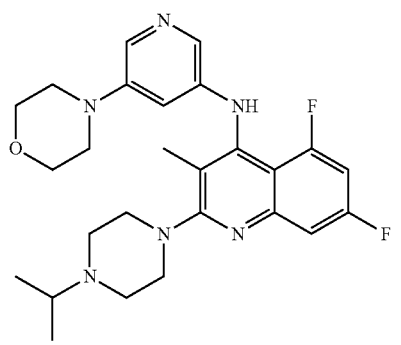

The 5,7-difluoro-3-methyl-N-(5-morpholinopyridin-3-yl)-2-(piperazin-1-yl)-quinolin-4-amine (50 mg, 0.11 mmol) was dissolved in a mixture of dichloroethane (1.3 mL) and MeOH (630 μL). The acetone (8.3 μL, 0.11 mmol) and sodium triacetoxyborohydride (72 mg, 0.34 mmol) were added and the mixture was stirred overnight. A small amount (50 mg) of sodium cyanoborohydride was added to drive the reaction to completion with heating at 80° C. for a short duration. The reaction was quenched with satd sodium bicarbonate solution and extracted with EtOAc. The organic layer was then dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH$_3$CN/H$_2$O, gradient 10% to 95% over 20 min to provide 5,7-difluoro-2-(4-isopropylpiperazin-1-yl)-3-methyl-N-(5-morpholinopyridin-3-yl)quinolin-4-amine as the TFA salt. The compound was eluted through an SCX column with 0 to 2M ammonia in MeOH to give the free amine. TFA salt: $^1$H NMR (CDCl$_3$) δ ppm 7.92 (1H, d, J=2.0 Hz), 7.80 (1H, d, J=2.2 Hz), 7.38 (1H, d, J=9.6 Hz), 7.34 (1H, d, J=9.8 Hz), 7.16 (1H, t, J=2.1 Hz), 6.87 (1H, ddd, J=13.6, 8.6, 2.6 Hz), 4.27 (2H, d, J=14.7 Hz), 3.87-3.98 (4H, m), 3.80 (2H, t, J=13.7 Hz), 3.40-3.57 (3H, m), 3.27-3.38 (4H, m), 3.04-3.27 (2H, m), 2.13 (3H, s), 1.36 (6H, d, J=6.7 Hz). Mass Spectrum (ESI) m/e=483.2 (M+1).

Example 237

Preparation of (4-(5,7-Difluoro-3-methyl-4-(5-morpholinopyridin-3-ylamino)quinolin-2-yl)piperazin-1-yl)(phenyl)methanone

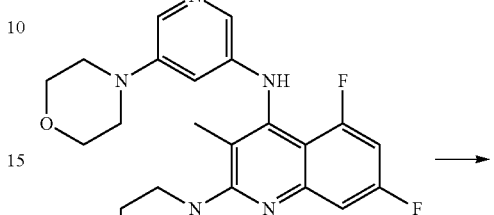

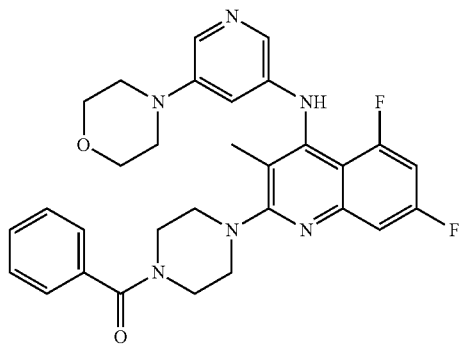

The 5,7-difluoro-3-methyl-N-(5-morpholinopyridin-3-yl)-2-(piperazin-1-yl)-quinolin-4-amine (50 mg, 0.11 mmol) was dissolved in THF (1.1 mL) and the triethylamine (24.0 μL, 0.17 mmol) and benzoyl chloride (13.0 μL, 0.11 mmol) were added and the mixture was stirred overnight. The reaction was then quenched with water and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH$_3$CN/H$_2$O, gradient 10% to 95% over 20 min to provide (4-(5,7-difluoro-3-methyl-4-(5-morpholinopyridin-3-ylamino)quinolin-2-yl)piperazin-1-yl)(phenyl)methanone as a TFA salt. The compound was eluted through an SCX column with 0 to 2M ammonia in MeOH to give the free amine. TFA salt: $^1$H NMR (CDCl$_3$) δ ppm 10.93 (3H, br. s.), 8.48 (1H, d, J=6.3 Hz), 7.84 (1H, d, J=2.3 Hz), 7.78 (1H, d, J=1.8 Hz), 7.35-7.54 (6H, m), 7.17-7.24 (1H, m), 6.84 (1H, ddd, J=12.8, 8.5, 2.5 Hz), 3.88-4.07 (2H, m), 3.79-3.88 (5H, m), 3.47-3.79 (5H, m), 3.21-3.33 (4H, m), 2.12 (3H, s). Mass Spectrum (ESI) m/e=545.2 (M+1).

Example 238

Preparation of 5,7-Difluoro-3-methyl-N-(5-morpholinopyridin-3-yl)-2-(4-(pyridin-3-yl)piperazin-1-yl)quinolin-4-amine

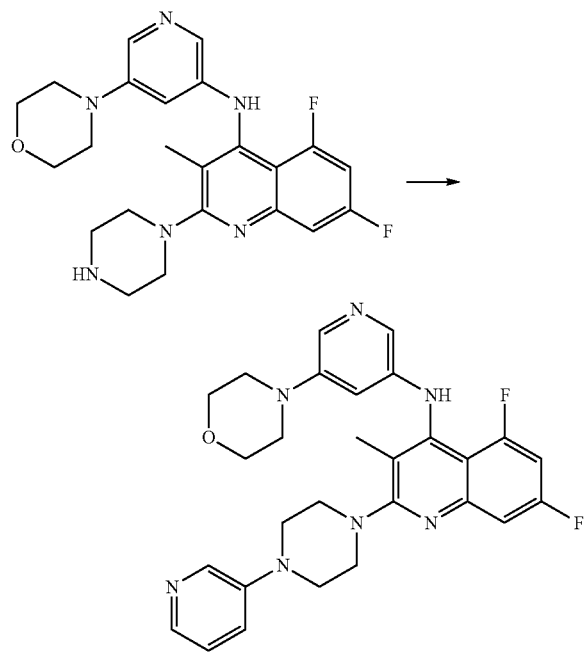

Essentially prepared according to Procedure H using 5,7-difluoro-3-methyl-N-(5-morpholinopyridin-3-yl)-2-(piperazin-1-yl)quinolin-4-amine (50.0 mg, 0.11 mmol) and 3-bromopyridine in toluene to give 5,7-difluoro-3-methyl-N-(5-morpholinopyridin-3-yl)-2-(4-(pyridin-3-yl)piperazin-1-yl)quinolin-4-amine. $^1$H NMR (CDCl$_3$) δ ppm 8.53 (1H, d, J=2.9 Hz), 8.11 (1H, d, J=4.3 Hz), 7.89 (1H, d, J=2.2 Hz), 7.72-7.80 (2H, m), 7.63-7.71 (1H, m), 7.53 (1H, d, J=8.4 Hz), 7.41 (1H, dd, J=9.6, 1.4 Hz), 7.12 (1H, t, J=2.2 Hz), 6.86 (1H, ddd, J=13.3, 8.5, 2.4 Hz), 3.85-3.94 (4H, m), 3.70-3.80 (4H, m), 3.52-3.61 (4H, m), 3.24-3.36 (4H, m), 2.22 (3H, s). Mass Spectrum (ESI) m/e=518.2 (M+1).

Example 239

Preparation of 5,7-Difluoro-3-methyl-N-(5-morpholinopyridin-3-yl)-2-(4-propylpiperazin-1-yl)quinolin-4-amine

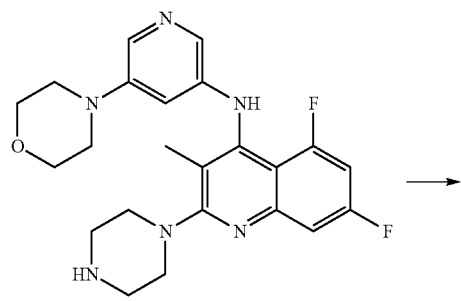

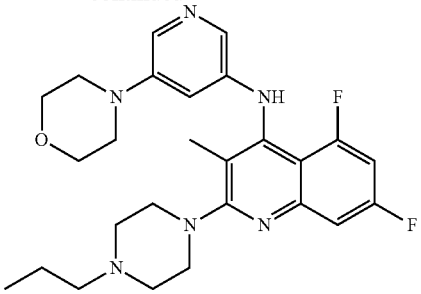

Essentially prepared according to Procedure L using 5,7-difluoro-3-methyl-N-(5-morpholinopyridin-3-yl)-2-(piperazin-1-yl)quinolin-4-amine (50.0 mg, 0.11 mmol) and propionaldehyde to give 5,7-difluoro-3-methyl-N-(5-morpholinopyridin-3-yl)-2-(4-propylpiperazin-1-yl)quinolin-4-amine. TFA salt: $^1$H NMR (CDCl$_3$) δ ppm 11.75 (2H, br. s.), 7.86 (1H, d, J=6.7 Hz), 7.76 (1H, d, J=1.8 Hz), 7.70 (1H, d, J=2.2 Hz), 7.26-7.33 (1H, m), 7.16-7.24 (1H, m), 6.82 (1H, ddd, J=13.1, 8.7, 2.5 Hz), 4.13 (2H, d, J=13.9 Hz), 3.81-3.95 (4H, m), 3.68 (2H, t, J=12.7 Hz), 3.55 (2H, d, J=11.7 Hz), 3.21-3.36 (4H, m), 3.10 (2H, t, J=10.1 Hz), 2.89-3.01 (2H, m), 2.11 (3H, s), 1.70-1.91 (2H, m), 0.98 (3H, t, J=7.4 Hz). Mass Spectrum (ESI) m/e=483.3 (M+1).

Example 240

Preparation of 5,7-Difluoro-2-(4-(isopropylsulfonyl)piperazinyl)-3-methyl-N-(5-morpholinopyridin-3-yl)quinolin-4-amine

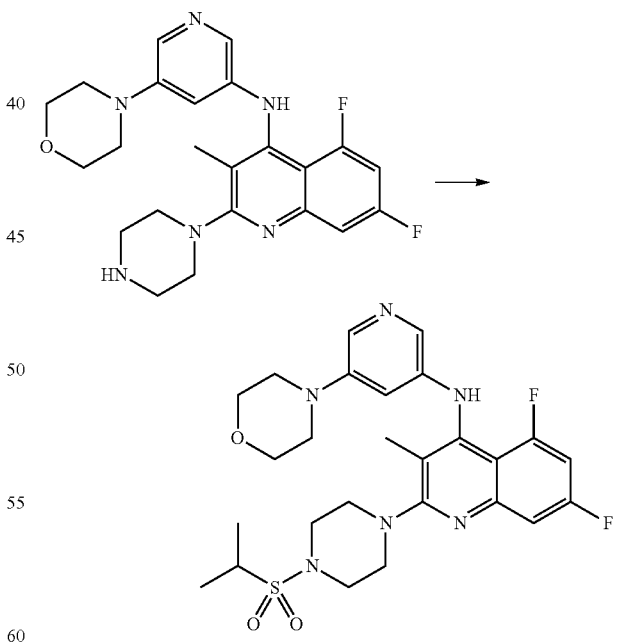

Essentially prepared according to Procedure M using 5,7-difluoro-3-methyl-N-(5-morpholinopyridin-3-yl)-2-(piperazin-1-yl)quinolin-4-amine (50.0 mg, 0.11 mmol) and isopropylsulfonyl chloride to give 5,7-difluoro-2-(4-(isopropylsulfonyl)piperazin-1-yl)-3-methyl-N-(5-morpholinopyridin-3-yl)quinolin-4-amine. TFA salt: $^1$H NMR (CDCl₃) δ ppm 9.29 (3H, br. s.), 8.51 (1H, d, J=7.8 Hz), 7.90 (1H, d, J=2.3 Hz), 7.86 (1H, d, J=2.0 Hz), 7.45-7.57 (1H, m), 7.30-7.40 (1H, m), 6.86 (1H, ddd, J=13.0, 8.4, 2.3 Hz), 3.82-3.98 (4H, m), 3.70 (4H, d, J=5.1 Hz), 3.58 (4H, d, J=4.7 Hz), 3.28-3.38 (4H, m), 3.23 (1H, quin, J=6.8 Hz), 2.10 (3H, s), 1.37 (6H, d, J=6.8 Hz). Mass Spectrum (ESI) m/e=547.3 (M+1).

Example 241

Preparation of 4-(5,7-Difluoro-3-methyl-4-(5-morpholinopyridin-3-ylamino)quinolin-2-yl)-N-methylpiperazine-1-carboxamide

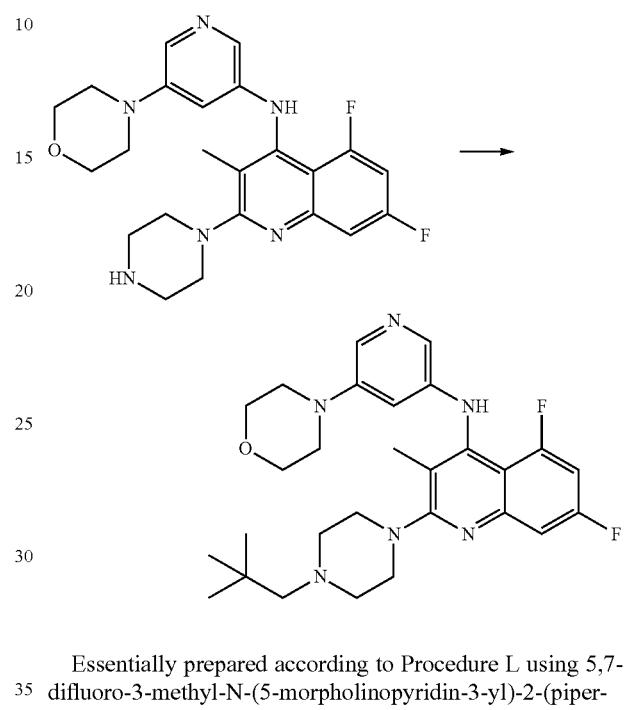

The 5,7-difluoro-3-methyl-N-(5-morpholinopyridin-3-yl)-2-(piperazin-1-yl)-quinolin-4-amine (50 mg, 0.11 mmol) was dissolved in 2.5 mL of THF. The triethylamine (0.095 mL, 0.68 mmol) and triphosgene (8.4 µL, 0.057 mmol) were added and the resulting solution was stirred for 2 h. The diisopropylethylamine (0.041 mL, 0.24 mmol) and 2M methylamine solution in THF (0.063 mL, 0.13 mmol) was added and the reaction mixture was stirred overnight. Duplicate aliquots of the reagents were added and the procedure as above was followed. The reaction was then quenched and extracted with EtOAc. The organic layers were dried over magnesium sulfate and the filtrate was cond. The crude material was purified by reverse-phase preparative HPLC using a Phenomenex Gemini™ column, 10 micron, C18, 100 Å, 150×30 mm, 0.1% TFA in CH₃CN/H₂O, gradient 10% to 95% over 20 min to provide the TFA salt. The compound was eluted through an SCX column with 0 to 2M ammonia in MeOH to give the free amine. TFA salt: ¹H NMR (CDCl₃) δ ppm 7.76 (1H, d, J=2.3 Hz), 7.59 (1H, d, J=2.2 Hz), 7.28-7.32 (1H, m), 6.76 (1H, ddd, J=12.8, 8.7, 2.4 Hz), 6.65-6.71 (1H, m), 3.70-3.81 (4H, m), 3.44-3.56 (4H, m), 3.34-3.38 (4H, m), 3.10-3.18 (4H, m), 2.75 (3H, s), 2.14 (3H, s). Mass Spectrum (ESI) m/e=498.2 (M+1).

Example 242

Preparation of 5,7-Difluoro-3-methyl-N-(5-morpholinopyridin-3-yl)-2-(4-neopentylpiperazin-1-yl)quinolin-4-amine

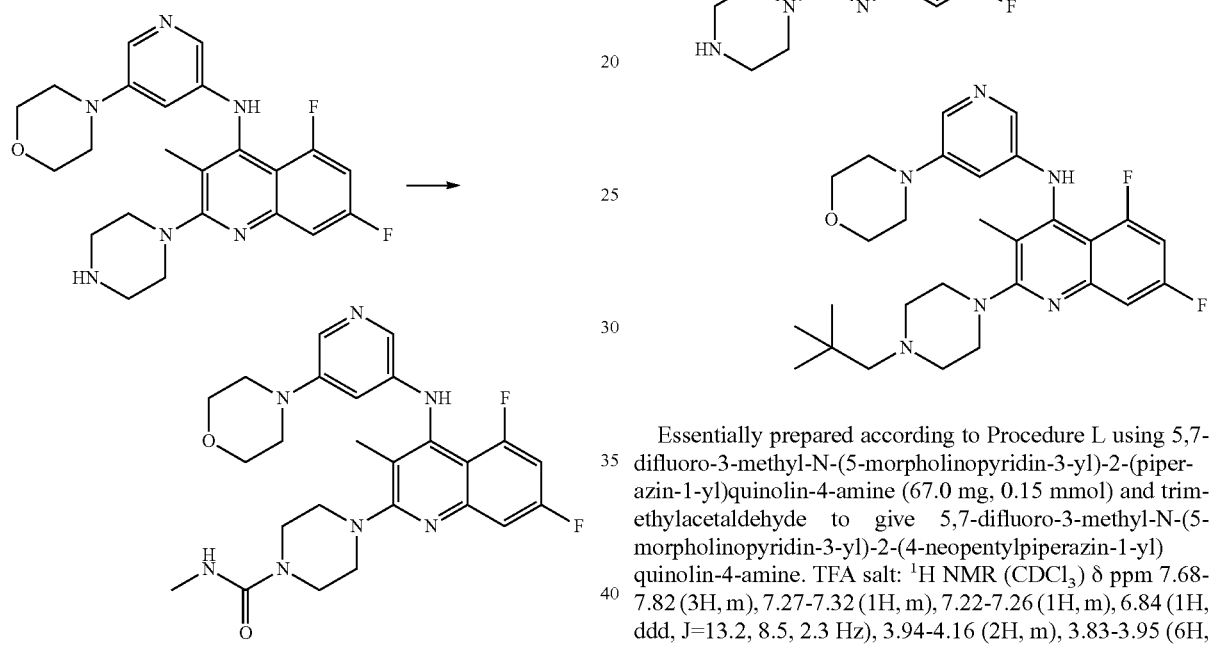

Essentially prepared according to Procedure L using 5,7-difluoro-3-methyl-N-(5-morpholinopyridin-3-yl)-2-(piperazin-1-yl)quinolin-4-amine (67.0 mg, 0.15 mmol) and trimethylacetaldehyde to give 5,7-difluoro-3-methyl-N-(5-morpholinopyridin-3-yl)-2-(4-neopentylpiperazin-1-yl)quinolin-4-amine. TFA salt: ¹H NMR (CDCl₃) δ ppm 7.68-7.82 (3H, m), 7.27-7.32 (1H, m), 7.22-7.26 (1H, m), 6.84 (1H, ddd, J=13.2, 8.5, 2.3 Hz), 3.94-4.16 (2H, m), 3.83-3.95 (6H, m), 3.47-3.82 (2H, m), 3.26-3.39 (5H, m), 3.06-3.26 (1H, m), 2.87 (2H, s), 2.08 (3H, s), 1.15 (9H, s). Mass Spectrum (ESI) m/e=511.3 (M+1).

Example 243

Preparation of 5,7-Difluoro-3-methyl-N-(5-morpholinopyridin-3-yl)-2-(4-(tetrahydro-2H-pyran-4-yl)piperazin-1-yl)quinolin-4-amine

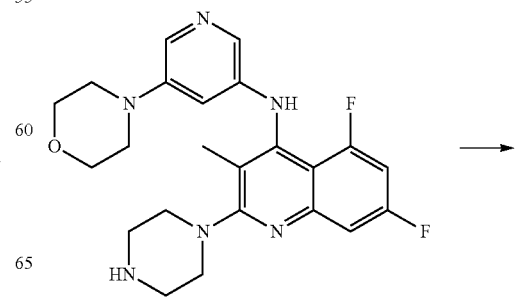

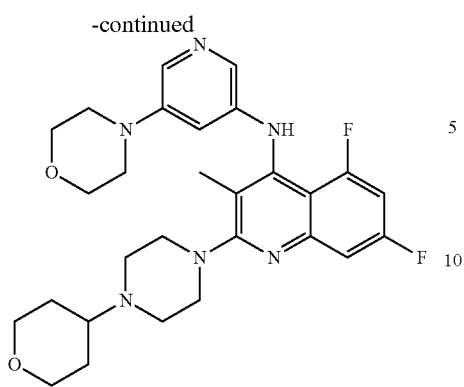

Essentially prepared according to Procedure L using 5,7-difluoro-3-methyl-N-(5-morpholinopyridin-3-yl)-2-(piperazin-1-yl)quinolin-4-amine (67.0 mg, 0.15 mmol) and dihydro-2H-pyran-4(3H)-one to give 5,7-difluoro-3-methyl-N-(5-morpholinopyridin-3-yl)-2-(4-(tetrahydro-2H-pyran-4-yl)piperazin-1-yl)quinolin-4-amine. $^1$H NMR (CDCl$_3$) δ ppm $^1$H NMR 7.93 (1H, d, J=2.5 Hz), 7.69 (1H, d, J=2.2 Hz), 7.30 (1H, ddd, J=10.0, 2.6, 1.3 Hz), 6.87 (1H, d, J=12.7 Hz), 6.79 (1H, ddd, J=13.9, 8.7, 2.4 Hz), 6.58 (1H, t, J=2.3 Hz), 4.07 (2H, dd, J=11.2, 3.9 Hz), 3.80-3.92 (4H, m), 3.46-3.53 (4H, m), 3.41 (2H, td, J=11.7, 1.6 Hz), 3.16 (4H, dd, J=5.7, 3.9 Hz), 2.75-2.93 (4H, m), 2.06 (3H, s), 1.87 (2H, d, J=12.3 Hz), 1.61-1.78 (2H, m). Mass Spectrum (ESI) m/e=525.4 (M+1).

Example 244

Preparation of Methyl 4-(4-(2,5-dimorpholinopyridin-3-ylamino)-5,7-difluoro-3-methylquinolin-2-yl)piperazine-1-carboxylate Methyl 4-(4-chloro-5,7-difluoro-3-methylquinolin-2-yl)piperazine-1-carboxylate

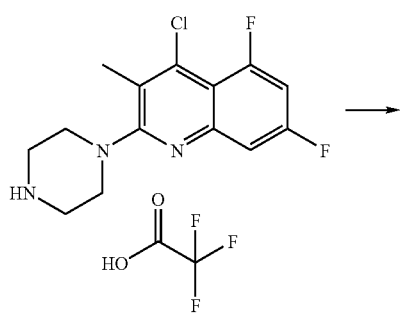

The 4-chloro-5,7-difluoro-3-methyl-2-(piperazin-1-yl)quinoline 2,2,2-trifluoroacetate (150 mg, 0.37 mmol), potassium carbonate (360 mg, 2.60 mmol) and methyl chloroformate (0.11 mL, 1.50 mmol) were added to acetone (3.0 mL). The slurry was heated in a microwave reactor at 80° C. for 3 h. The reaction mixture was cond and the residue was partitioned between water and EtOAc. The aq. layer was extracted with EtOAc (2×50 mL). The combined organic layers were washed with brine (1×30 mL) and dried over magnesium sulfate to give crude methyl 4-(4-chloro-5,7-difluoro-3-methylquinolin-2-yl)piperazine-1-carboxylate. Mass Spectrum (ESI) m/e=356.2 (M+1).

Methyl 4-(4-(2,5-dimorpholinopyridin-3-ylamino)-5,7-difluoro-3-methylquinolin-2-yl)piperazine-1-carboxylate

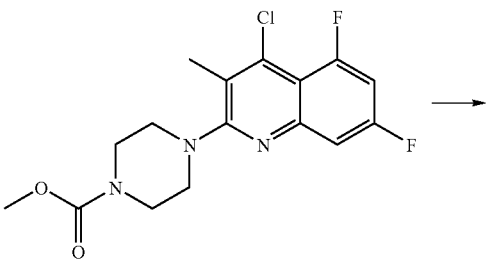

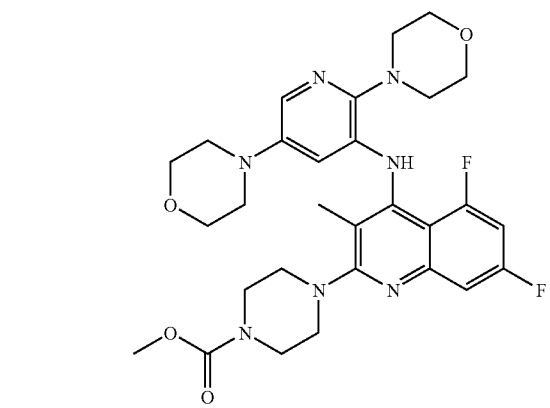

Essentially prepared according to Procedure H using methyl 4-(4-chloro-5,7-difluoro-3-methylquinolin-2-yl)piperazine-1-carboxylate (40.0 mg, 0.11 mmol) and 2,5-dimorpholinopyridin-3-amine in toluene to give methyl 4-(4-(2,5-dimorpholinopyridin-3-ylamino)-5,7-difluoro-3-methylquinolin-2-yl)piperazine-1-carboxylate. TFA salt: $^1$H NMR (CDCl$_3$) δ ppm 11.48 (4H, br. s.), 8.30 (1H, d, J=16.0 Hz), 7.84 (1H, d, J=2.7 Hz), 7.61 (1H, d, J=8.6 Hz), 7.04 (1H, ddd, J=13.8, 8.1, 2.3 Hz), 6.80 (1H, d, J=2.5 Hz), 3.87-3.95 (4H, m), 3.80-3.86 (4H, m), 3.78 (3H, s), 3.73 (4H, br. s.), 3.59 (4H, br. s.), 3.20-3.55 (4H, m), 3.10-3.19 (4H, m), 2.05 (3H, s). Mass Spectrum (ESI) m/e=584.3 (M+1).

Example 245

Preparation of 1-(5,7-Difluoro-3-methyl-4-(5-morpholinopyridin-3-ylamino)quinolin-2-yl)-5,5-dimethylpiperidin-2-one 5,5-Dimethylpiperidin-2-one

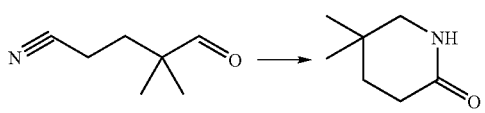

The procedure outlined in *J. Med. Chem.* 1977, pp. 1180 was followed using 4,4-dimethyl-5-oxopentanenitrile (4.00 g, 32.0 mmol) to obtain 5,5-dimethylpiperidin-2-one. Mass Spectrum (ESI) m/e=128.2 (M+1).

1-(4-Chloro-5,7-difluoro-3-methylquinolin-2-yl)-5,5-dimethylpiperidin-2-one

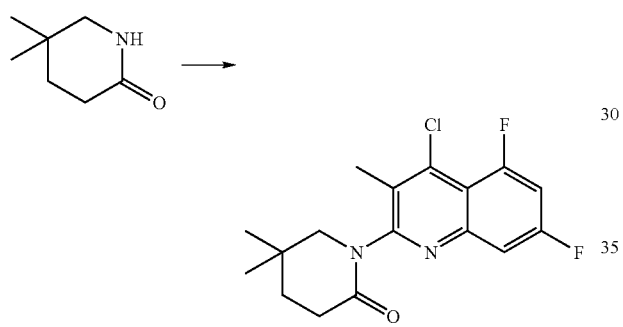

The 4,5-bis(diphenylphosphino)-9,9-dimethylxanthene (273 mg, 0.472 mmol), 2,4-dichloro-5,7-difluoro-3-methylquinoline (XantPhos) (780 mg, 3.20 mmol), 5,5-dimethylpiperidin-2-one (400 mg, 3.20 mmol), cesium carbonate (1.40 g, 4.40 mmol) and $Pd_2(dba)_3$ (140 mg, 0.160 mmol) were slurried in 1,4-dioxane (8.5 mL) and heated in a microwave reactor at 100° C. for 3 h. The reaction was cooled and then diluted with EtOAc and DCM. The slurry was then filtered and the filtrate cond. The residue was purified by medium pressure chromatography (silica gel, 0 to 50% EtOAc:DCM) to give 1-(4-chloro-5,7-difluoro-3-methylquinolin-2-yl)-5,5-dimethylpiperidin-2-one. Mass Spectrum (ESI) m/e=339.1 (M+1).

1-(5,7-Difluoro-3-methyl-4-(5-morpholinopyridin-3-ylamino)quinolin-2-yl)-5,5-dimethylpiperidin-2-one

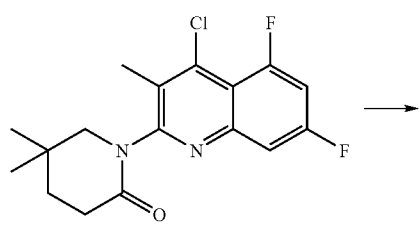

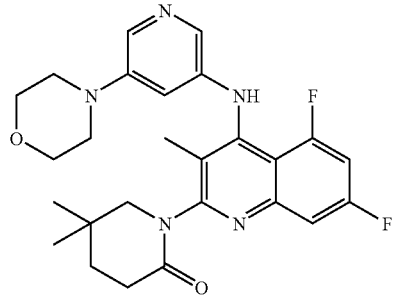

Essentially prepared according to Procedure H using 1-(4-chloro-5,7-difluoro-3-methylquinolin-2-yl)-5,5-dimethylpiperidin-2-one (24.0 mg, 0.071 mmol) and 5-morpholinopyridin-3-amine in toluene to give 1-(5,7-difluoro-3-methyl-4-(5-morpholinopyridin-3-ylamino)quinolin-2-yl)-5,5-dimethylpiperidin-2-one. TFA salt: $^1$H NMR (CDCl$_3$) δ ppm 8.06 (1H, d, J=7.2 Hz), 7.94 (1H, d, J=1.2 Hz), 7.78 (1H, d, J=2.2 Hz), 7.48 (1H, dt, J=9.2, 1.2 Hz), 7.01 (1H, ddd, J=13.1, 8.5, 2.4 Hz), 6.73-6.82 (1H, m), 4.06 (1H, d, J=12.1 Hz), 3.71-3.89 (4H, m), 3.13-3.41 (5H, m), 2.58-2.74 (1H, m), 2.46-2.58 (1H, m), 2.04 (3H, s), 1.82-1.97 (1H, m), 1.70-1.82 (1H, m), 1.22 (6H, d, J=10.8 Hz). Mass Spectrum (ESI) m/e=482.4 (M+1).

Example 246

Preparation of (S)-tert-Butyl 4-(5,7-difluoro-3-methyl-4-(5-morpholinopyridin-3-ylamino)quinolin-2-yl)-2-methylpiperazine-1-carboxylate (S)-tert-Butyl 4-(4-chloro-5,7-difluoro-3-methylquinolin-2-yl)-2-methylpiperazine-1-carboxylate

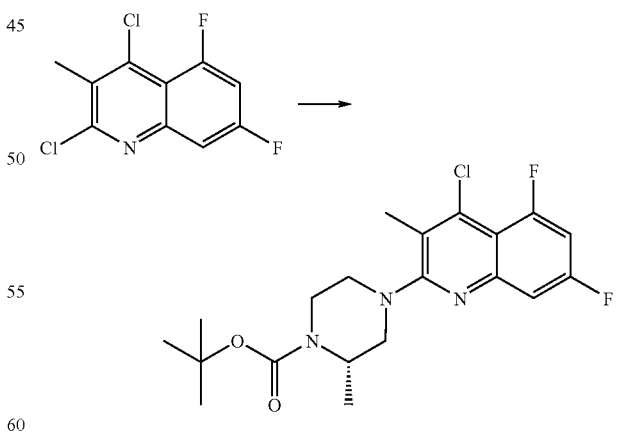

Essentially prepared according to Procedure G using 2,4-dichloro-5,7-difluoro-3-methylquinoline (1.00 g, 4.10 mmol) and (S)-tert-butyl 2-methylpiperazine-1-carboxylate to give (S)-tert-butyl 4-(4-chloro-5,7-difluoro-3-methylquinolin-2-yl)-2-methylpiperazine-1-carboxylate. Mass Spectrum (ESI) m/e=412.3 (M+1).

393

(S)-tert-Butyl 4-(5,7-difluoro-3-methyl-4-(5-morpholinopyridin-3-ylamino)-quinolin-2-yl)-2-methylpiperazine-1-carboxylate

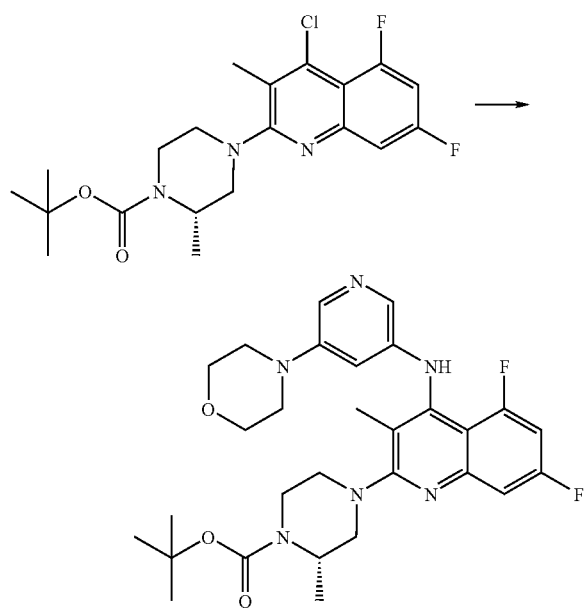 [SMILES: Cc1c(N2CCN(C(=O)OC(C)(C)C)[C@@H](C)C2)nc2cc(F)cc(F)c2c1Cl ; Cc1c(N2CCN(C(=O)OC(C)(C)C)[C@@H](C)C2)nc2cc(F)cc(F)c2c1Nc1cncc(N2CCOCC2)c1]

Essentially prepared according to Procedure H using (S)-tert-butyl 4-(4-chloro-5,7-difluoro-3-methylquinolin-2-yl)-2-methylpiperazine-1-carboxylate (350 mg, 0.85 mmol) and 5-morpholinopyridin-3-amine in toluene to give (S)-tert-butyl 4-(5,7-difluoro-3-methyl-4-(5-morpholinopyridin-3-ylamino)quinolin-2-yl)-2-methylpiperazine-1-carboxylate. $^1$H NMR (CDCl$_3$) δ ppm 7.93 (1H, d, J=2.3 Hz), 7.69 (1H, d, J=2.2 Hz), 7.29 (1H, ddd, J=10.0, 2.5, 1.4 Hz), 6.89 (1H, d, J=13.1 Hz), 6.80 (1H, ddd, J=13.9, 8.6, 2.5 Hz), 6.57 (1H, t, J=2.4 Hz), 4.38 (1H, br. s.), 3.98 (1H, d, J=13.3 Hz), 3.79-3.91 (4H, m), 3.64-3.75 (1H, m), 3.49-3.61 (1H, m), 3.32 (1H, td, J=12.7, 3.1 Hz), 3.16 (4H, dd, J=5.7, 3.9 Hz), 3.10 (1H, dd, J=12.8, 3.8 Hz), 2.92 (1H, td, J=12.5, 3.3 Hz), 2.09 (3H, s), 1.50 (9H, s), 1.29 (3H, d, J=6.7 Hz). Mass Spectrum (ESI) m/e=555.3 (M+1).

Example 247

Preparation of (S)-5,7-Difluoro-3-methyl-2-(3-methylpiperazin-1-yl)-N-(5-morpholinopyridin-3-yl)quinolin-4-amine

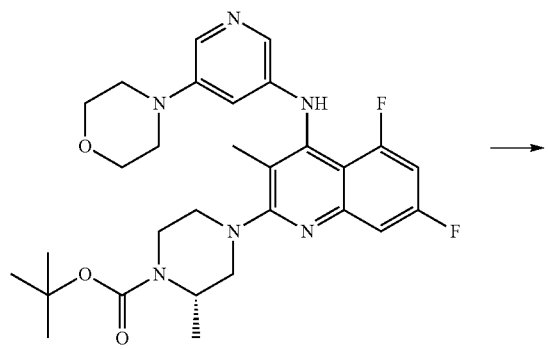

394

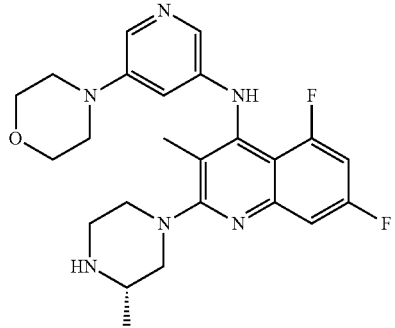

Essentially prepared according to Procedure O using (S)-tert-butyl 4-(5,7-difluoro-3-methyl-4-(5-morpholinopyridin-3-ylamino)quinolin-2-yl)-2-methylpiperazine-1-carboxylate (270 mg, 0.48 mmol) to give (S)-5,7-difluoro-3-methyl-2-(3-methylpiperazin-1-yl)-N-(5-morpholinopyridin-3-yl)quinolin-4-amine. 1H NMR (CDCl$_3$) δ ppm 7.68 (1H, d, J=2.3 Hz), 7.40 (1H, d, J=2.2 Hz), 7.27 (1H, br. s.), 7.20 (1H, ddd, J=9.8, 2.5, 1.2 Hz), 6.69-6.81 (2H, m), 3.67-3.84 (6H, m), 3.41 (1H, ddd, J=9.8, 6.7, 2.5 Hz), 3.25-3.35 (2H, m), 3.15-3.21 (1H, m), 3.07-3.13 (4H, m), 3.02 (1H, dd, J=14.2, 10.5 Hz), 2.04 (3H, s), 1.30 (3H, d). Mass Spectrum (ESI) m/e=455.4 (M+1).

Example 248

Preparation of (S)-Methyl 4-(5,7-difluoro-3-methyl-4-(5-morpholinopyridin-3-ylamino)quinolin-2-yl)-2-methylpiperazine-1-carboxylate

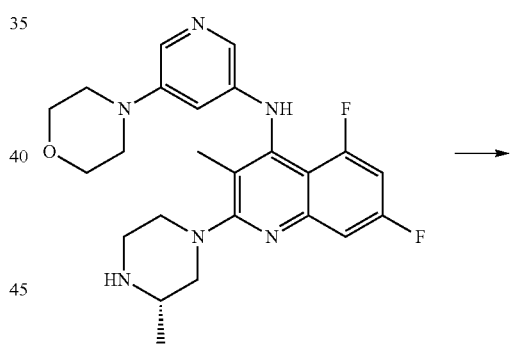

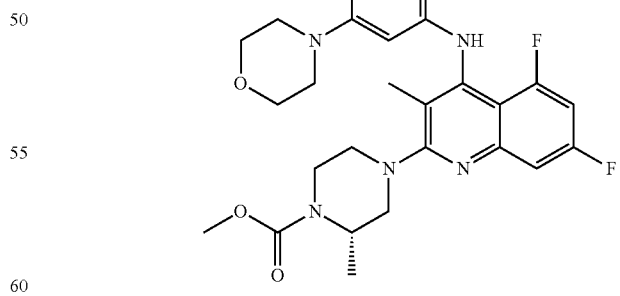

Essentially prepared according to Procedure N using (S)-5,7-difluoro-3-methyl-2-(3-methylpiperazin-1-yl)-N-(5-morpholinopyridin-3-yl)quinolin-4-amine (50 mg, 0.11 mmol) and methyl chloroformate to give (S)-methyl 4-(5,7-difluoro-3-methyl-4-(5-morpholinopyridin-3-ylamino)quinolin-2-yl)-2-methylpiperazine-1-carboxylate. $^1$H NMR (CDCl₃) δ ppm 7.94 (1H, d, J=2.3 Hz), 7.69 (1H, d, J=2.2 Hz), 7.30 (1H, ddd, J=10.0, 2.6, 1.3 Hz), 6.89 (1H, d, J=12.9 Hz), 6.81 (1H, ddd, J=13.9, 8.8, 2.5 Hz), 6.58 (1H, t, J=2.4 Hz), 4.43 (1H, br. s.), 4.03 (1H, d, J=13.5 Hz), 3.86 (4H, dd, J=5.7, 3.9 Hz), 3.76 (3H, s), 3.71 (1H, d, J=9.8 Hz), 3.52-3.64 (1H, m), 3.38 (1H, td, J=12.8, 3.2 Hz), 3.17 (4H, dd, J=5.7, 4.1 Hz), 3.12 (1H, dd, J=12.8, 3.8 Hz), 2.93 (1H, td, J=12.6, 3.4 Hz), 2.10 (3H, s), 1.32 (3H, d, J=6.8 Hz). Mass Spectrum (ESI) m/e=513.3 (M+1).

Example 249

Preparation of (S)-5,7-Difluoro-3-methyl-2-(3-methyl-4-(methylsulfonyl)piperazin-1-yl)-N-(5-morpholinopyridin-3-yl)quinolin-4-amine

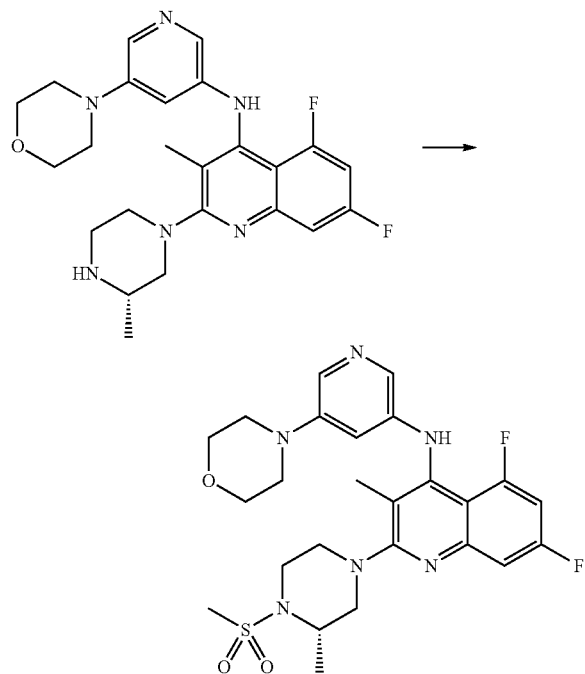

Essentially prepared according to Procedure M using (S)-5,7-difluoro-3-methyl-2-(3-methylpiperazin-1-yl)-N-(5-morpholinopyridin-3-yl)quinolin-4-amine (50 mg, 0.11 mmol) and methylsulfonyl chloride to give (S)-5,7-difluoro-3-methyl-2-(3-methyl-4-(methylsulfonyl)piperazin-1-yl)-N-(5-morpholinopyridin-3-yl)quinolin-4-amine. ¹H NMR (CDCl₃) δ ppm 7.95 (1H, d, J=2.5 Hz), 7.66 (1H, d, J=2.3 Hz), 7.30 (1H, ddd, J=9.9, 2.5, 1.3 Hz), 6.92 (1H, d, J=13.3 Hz), 6.83 (1H, ddd, J=13.9, 8.7, 2.6 Hz), 6.60 (1H, t, J=2.3 Hz), 4.15-4.28 (1H, m), 3.86 (4H, dd, J=5.7, 4.1 Hz), 3.65-3.80 (2H, m), 3.58 (1H, dt, J=12.9, 1.9 Hz), 3.51 (1H, td, J=12.3, 2.9 Hz), 3.22 (1H, dd, J=12.9, 3.5 Hz), 3.13-3.19 (4H, m), 3.06 (1H, td, J=12.3, 3.2 Hz), 2.93 (3H, s), 2.09 (3H, s), 1.41 (3H, d, J=6.8 Hz). Mass Spectrum (ESI) m/e=533.2 (M+1).

Example 250

Preparation of Isopropyl 4-(5,7-difluoro-3-methyl-4-(5-morpholinopyridin-3-ylamino)quinolin-2-yl)piperazine-1-carboxylate

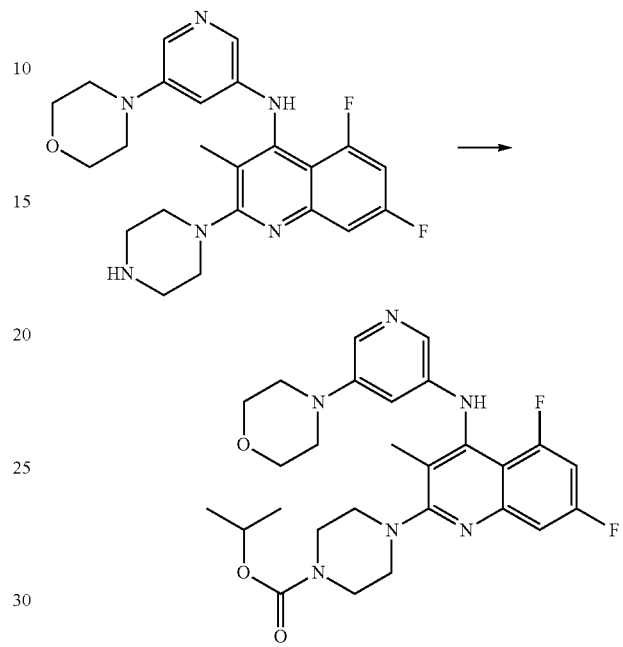

Prepared according to Procedure N using 5,7-difluoro-3-methyl-N-(5-morpholinopyridin-3-yl)-2-(piperazin-1-yl)quinolin-4-amine (50 mg, 0.11 mmol) and isopropyl chloroformate to give isopropyl 4-(5,7-difluoro-3-methyl-4-(5-morpholinopyridin-3-ylamino)quinolin-2-yl)piperazine-1-carboxylate. ¹H NMR (DMSO-d6) δ ppm 1.14-1.22 (m, 6H), 2.09 (br s, 3H), 3.05 (t, J=4.4 Hz, 4H), 3.27-3.31 (m, 4H), 3.54 (br s, 4H), 3.69 (t, J=4.4 Hz, 4H), 4.81 (m, 1H) 6.49 (br s, 1H), 7.13-7.18 (m, 1H), 7.29 (d, J=5.2 Hz, 1H), 7.52 (d, J=1.6 Hz, 1H), 7.78 (d, J=2 Hz, 1H), 8.34 (s, 1H). Mass Spectrum (ESI) m/e=527.3 (M+1).

Example 251

Preparation of Neopentyl 4-(5,7-difluoro-3-methyl-4-(5-morpholinopyridin-3-ylamino)quinolin-2-yl)piperazine-1-carboxylate

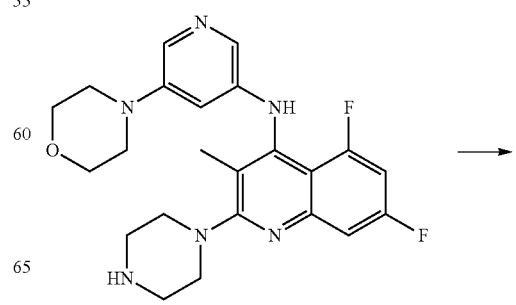

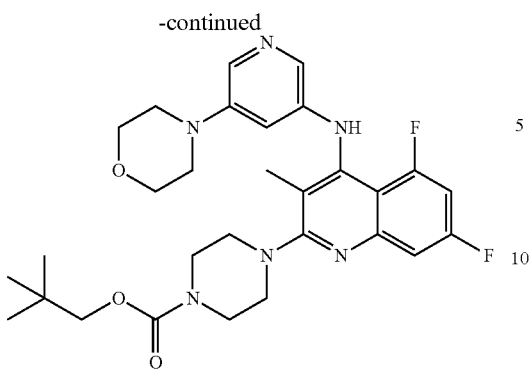

Prepared according to Procedure N using 5,7-difluoro-3-methyl-N-(5-morpholinopyridin-3-yl)-2-(piperazin-1-yl)quinolin-4-amine (50 mg, 0.11 mmol) and neopentyl chloroformate to give neopentyl 4-(5,7-difluoro-3-methyl-4-(5-morpholinopyridin-3-ylamino)quinolin-2-yl)piperazine-1-carboxylate. $^1$H NMR (DMSO-d6) δ ppm 0.93 (br s, 9H), 2.09 (br s, 3H), 3.05 (t, J=4.4 Hz, 4H), 3.29-3.33 (m, 4H), 3.58 (br s, 4H), 3.69 (t, J=4.4 Hz, 4H), 3.74 (s, 2H), 6.50 (s, 1H), 7.14-7.19 (m, 1H), 7.30-7.28 (m, 1H), 7.51 (d, J=2 Hz, 1H), 7.78 (d, J=2.4 Hz, 1H), 8.36 (s, 1H). Mass Spectrum (ESI) m/e=555.3 (M+1).

Example 252

Preparation of ethyl 4-(5,7-Difluoro-3-methyl-4-(5-morpholinopyridin-3-ylamino)quinolin-2-yl)piperazine-1-carboxylate

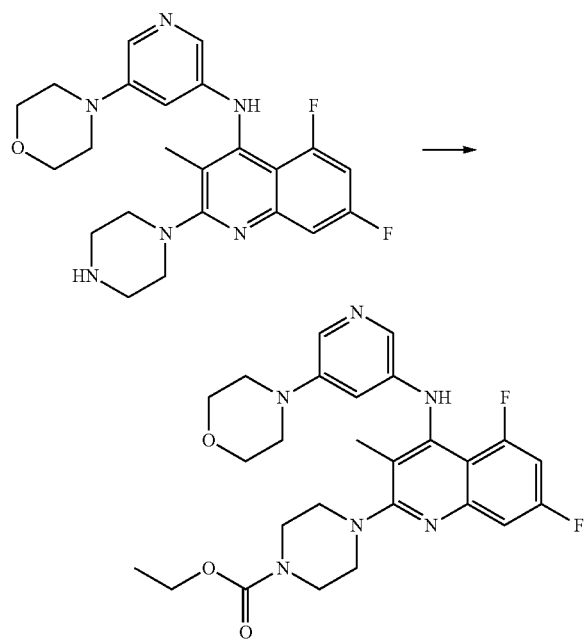

Prepared according to Procedure N using 5,7-difluoro-3-methyl-N-(5-morpholinopyridin-3-yl)-2-(piperazin-1-yl)quinolin-4-amine (50 mg, 0.11 mmol) and ethyl chloroformate to give ethyl 4-(5,7-difluoro-3-methyl-4-(5-morpholinopyridin-3-ylamino)quinolin-2-yl)piperazine-1-carboxylate. $^1$H NMR (DMSO-d6) δ ppm 1.09 (t, J=7.2 Hz, 3H), 2.13 (s, 3H), 3.04-3.06 (m, 4H), 3.27 (s, 4H), 3.55 (s, 4H), 3.68-3.70 (m, 4H), 4.08 (q, J=6.8 Hz, 2H,), 6.49 (m, 1H), 7.14-7.20 (m, 1H), 7.29 (dd, J=9.8 Hz, J=2 Hz, 1H), 7.52 (d, J=1.6 Hz, 1H), 7.78 (d, J=2 Hz, 1H), 8.38 (s, 1H). Mass Spectrum (ESI) m/e=513.1 (M+1).

Example 253

Preparation of 5,7-Difluoro-2-(4-(2-fluorophenylsulfonyl)-piperazin-1-yl)-3-methyl-N-(5-morpholinopyridin-3-yl)quinolin-4-amine

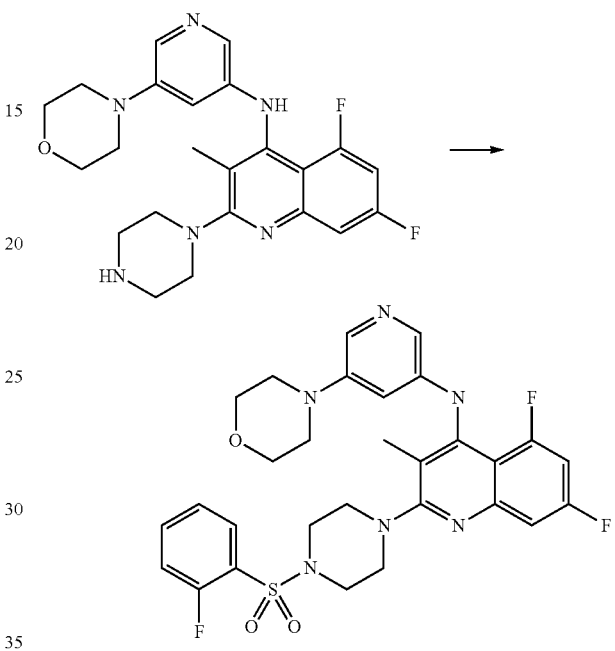

Prepared according to Procedure M using 5,7-difluoro-3-methyl-N-(5-morpholinopyridin-3-yl)-2-(piperazin-1-yl)quinolin-4-amine (50 mg, 0.11 mmol) and 2-fluorobenzene-1-sulfonyl chloride to give 5,7-difluoro-2-(4-(2-fluorophenylsulfonyl)-piperazin-1-yl)-3-methyl-N-(5-morpholinopyridin-3-yl)quinolin-4-amine. $^1$H NMR (DMSO-d6) δ ppm 2.00 (br s, 3H), 3.04 (t, J=4.4 Hz, 4H), 3.26 (br s, 4H), 3.33-3.37 (m, 4H), 3.68 (t, J=4.0 Hz, 4H), 6.48 (s, 1H), 7.14-7.19 (m, 1H), 7.26-7.29 (m, 1H), 7.45-7.54 (m, 3H), 7.77 (d, J=2.4 Hz, 2H), 7.81-7.85 (m, 1H), 8.35 (s, 1H). Mass Spectrum (ESI) m/e=599.4 (M+1).

Example 254

Preparation of 5,7-Difluoro-2-(4-(3-fluorophenylsulfonyl)-piperazin-1-yl)-3-methyl-N-(5-morpholinopyridin-3-yl)quinolin-4-amine

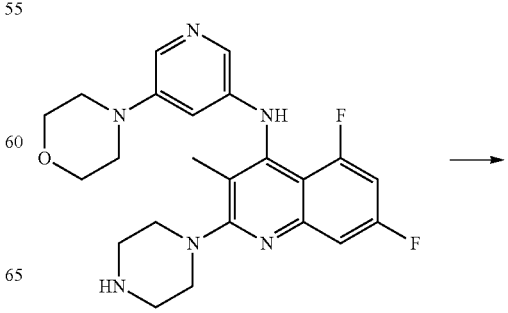

-continued

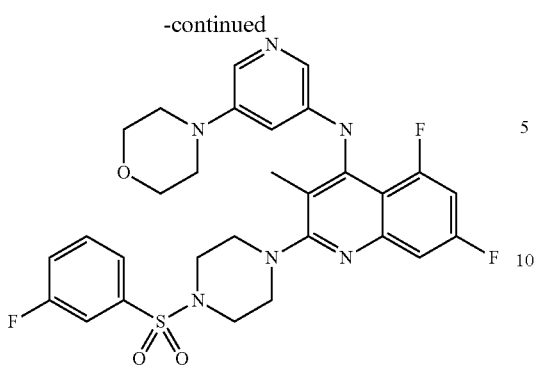

Prepared according to Procedure M using 5,7-difluoro-3-methyl-N-(5-morpholinopyridin-3-yl)-2-(piperazin-1-yl)quinolin-4-amine (50 mg, 0.11 mmol) and 3-fluorobenzene-1-sulfonyl chloride to give 5,7-difluoro-2-(4-(3-fluorophenylsulfonyl)-piperazin-1-yl)-3-methyl-N-(5-morpholinopyridin-3-yl)quinolin-4-amine. $^1$H NMR (DMSO-d6) δ ppm 1.96 (br s, 3H), 3.03 (t, J=4.4 Hz, 4H), 3.14 (br s, 4H), 3.34-3.36 (m, 4H), 3.68 (t, J=4.4 Hz, 4H), 6.47 (s, 1H), 7.13-7.19 (m, 1H), 7.25-7.28 (m, 1H), 7.49 (d, J=2.0 Hz, 1H), 7.60-7.65 (m, 3H), 7.71-7.77 (m, 2H,), 8.36 (s, 1H). Mass Spectrum (ESI) m/e=599.4 (M+1).

Example 255

Preparation of 5,7-Difluoro-2-(4-(4-fluorophenylsulfonyl)-piperazin-1-yl)-3-methyl-N-(5-morpholinopyridin-3-yl)quinolin-4-amine

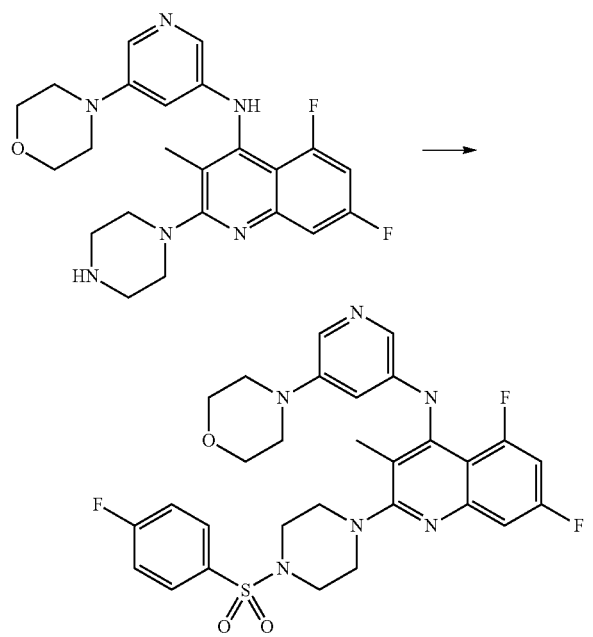

Prepared according to Procedure M using 5,7-difluoro-3-methyl-N-(5-morpholinopyridin-3-yl)-2-(piperazin-1-yl)quinolin-4-amine (50 mg, 0.11 mmol) and 4-fluorobenzene-1-sulfonyl chloride to give 5,7-difluoro-2-(4-(4-fluorophenylsulfonyl)-piperazin-1-yl)-3-methyl-N-(5-morpholinopyridin-3-yl)quinolin-4-amine. $^1$H NMR (DMSO-d6) δ ppm 1.97 (br s, 3H), 3.04 (t, J=4.8 Hz, 4H), 3.11 (br s, 4H), 3.33-3.37 (m, 4H), 3.69 (t, J=4.4 Hz, 4H), 6.48 (s, 1H), 7.13-7.19 (m, 1H), 7.25-7.28 (m, 1H), 7.49-7.54 (m, 3H), 7.77 (d, J=2.0 Hz, 1H), 7.84-7.88 (m, 2H,), 8.34 (s, 1H). Mass Spectrum (ESI) m/e=599.4 (M+1).

Example 256

Preparation of 2-(4-(Ethylsulfonyl)piperazin-1-yl)-5,7-difluoro-3-methyl-N-(5-morpholinopyridin-3-yl)quinolin-4-amine

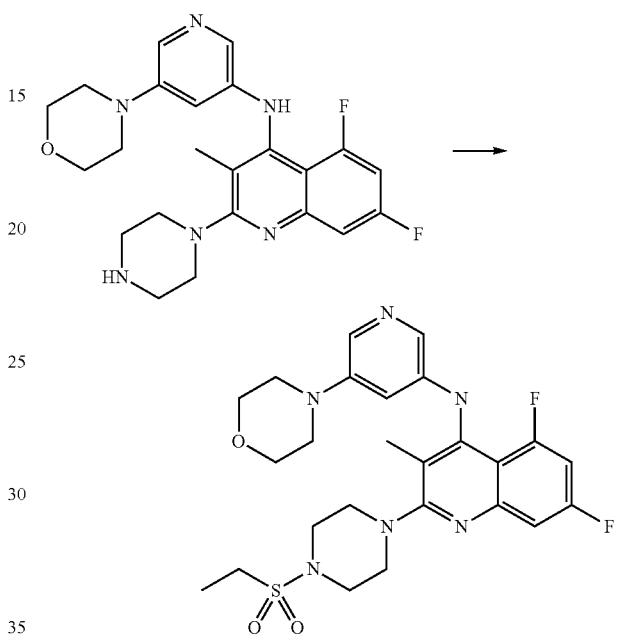

Prepared according to Procedure M using 5,7-difluoro-3-methyl-N-(5-morpholinopyridin-3-yl)-2-(piperazin-1-yl)quinolin-4-amine (50 mg, 0.11 mmol) and ethylsulfonyl chloride to give 2-(4-(ethylsulfonyl)piperazin-1-yl)-5,7-difluoro-3-methyl-N-(5-morpholinopyridin-3-yl)quinolin-4-amine. $^1$H NMR (DMSO-d6) δ ppm 1.15 (t, J=7.2 Hz, 3H), 2.08 (s, 3H), 3.05-3.11 (br s, 4H), 3.13 (q, J=7.2 Hz, 2H), 3.33 (br s, 8H), 3.69 (m, 4H), 6.51 (br s, 1H), 7.10-7.15 (m, 1H), 7.28-7.31 (m, 1H), 7.46 (s, 1H), 7.74 (s, 1H), 8.39 (s, 1H). Mass Spectrum (ESI) m/e=533.4 (M+1).

Example 257

Preparation of 5,7-Difluoro-3-methyl-N-(5-morpholinopyridin-3-yl)-2-(4-(pyridin-3-ylsulfonyl)piperazin-1-yl)quinolin-4-amine

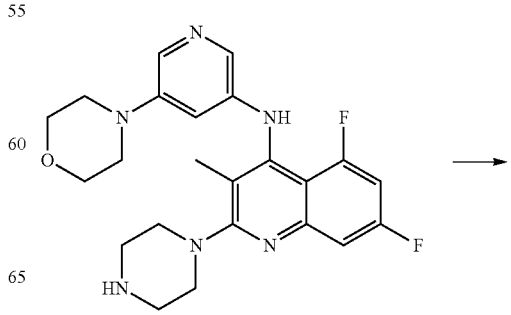

-continued

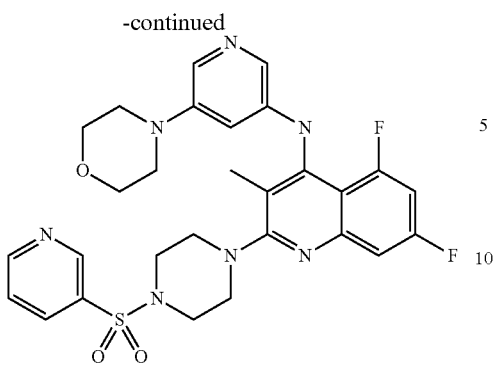

Prepared according to Procedure M using 5,7-difluoro-3-methyl-N-(5-morpholinopyridin-3-yl)-2-(piperazin-1-yl)quinolin-4-amine (50 mg, 0.11 mmol) and pyridine-3-sulfonyl chloride to give 5,7-difluoro-3-methyl-N-(5-morpholinopyridin-3-yl)-2-(4-(pyridin-3-ylsulfonyl)piperazin-1-yl)quinolin-4-amine. ¹H NMR (DMSO-d6) δ ppm 1.98 (d, J=6.0 Hz, 3H), 3.04 (t, J=4.8 Hz, 4H), 3.18 (br s, 4H), 3.33-3.37 (m, 4H), 3.69 (t, J=4.4 Hz, 4H), 6.48 (s, 1H), 7.13-7.19 (m, 1H), 7.25-7.28 (m, 1H), 7.50 (d, J=2.0 Hz, 1H), 7.70-7.77 (m, 1H), 7.77 (d, J=2.0 Hz, 1H,), 8.19-8.22 (m, 1H), 8.34 (s, 1H), 8.90-8.91 (m, 1H), 8.95 (d, J=2.4 Hz, 1H). Mass Spectrum (ESI) m/e=582.4 (M+1).

Example 258

Preparation of Isobutyl 4-(5,7-difluoro-3-methyl-4-(5-morpholinopyridin-3-ylamino)quinolin-2-yl)piperazine-1-carboxylate

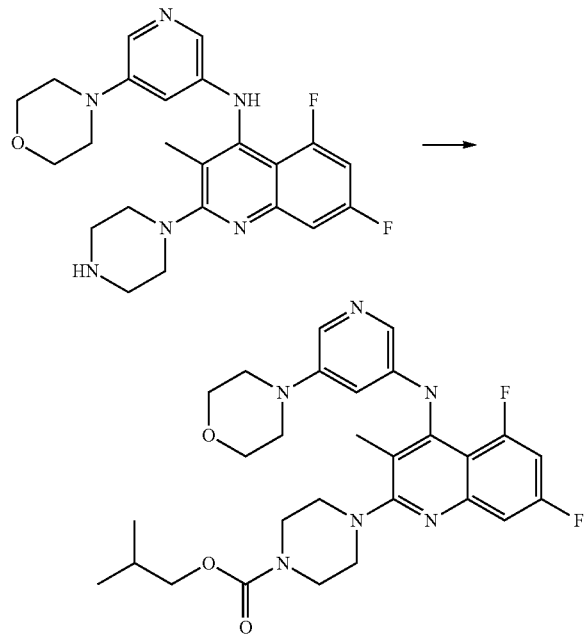

Prepared according to Procedure N using 5,7-difluoro-3-methyl-N-(5-morpholinopyridin-3-yl)-2-(piperazin-1-yl)quinolin-4-amine (50 mg, 0.11 mmol) and isobutyl chloroformate to give isobutyl 4-(5,7-difluoro-3-methyl-4-(5-morpholinopyridin-3-ylamino)quinolin-2-yl)piperazine-1-carboxylate. ¹H NMR (DMSO-d6) δ ppm 0.86-0.92 (m, 6H), 1.86-1.91 (m, 1H), 2.09 (br s, 3H), 3.05 (t, J=4.4 Hz, 4H), 3.28-3.32 (m, 4H), 3.57 (br s, 4H), 3.69 (t, J=4.4 Hz, 4H), 3.83 (d, J=6.4 Hz, 2H), 6.50 (s, 1H), 7.13-7.19 (m, 1H), 7.28-7.32 (m, 1H), 7.517 (s, 1H), 7.78 (d, J=2 Hz, 1H), 8.36 (s, 1H). Mass Spectrum (ESI) m/e=541.4 (M+1).

Example 259

Preparation of (R)-tert-Butyl 4-(5,7-difluoro-3-methyl-4-(5-morpholinopyridin-3-ylamino)quinolin-2-yl)-2-methylpiperazine-1-carboxylate (R)-tert-Butyl 4-(4-chloro-5,7-difluoro-3-methylquinolin-2-yl)-2-methylpiperazine-1-carboxylate

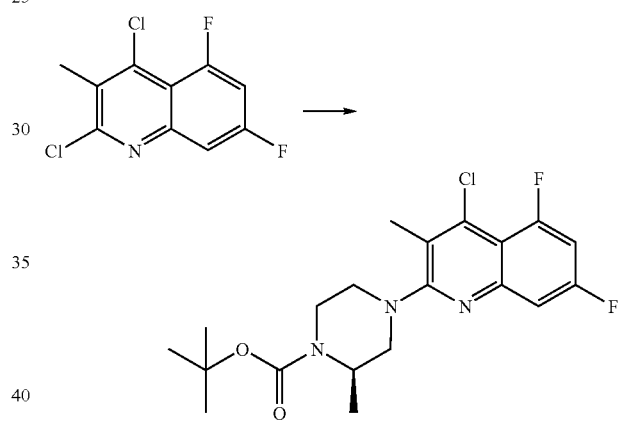

Prepared according to Procedure G using 2,4-dichloro-5,7-difluoro-3-methylquinoline (1.00 g, 4.10 mmol) and (R)-tert-butyl 2-methylpiperazine-1-carboxylate and using DBU as a base to give (R)-tert-butyl 4-(4-chloro-5,7-difluoro-3-methylquinolin-2-yl)-2-methylpiperazine-1-carboxylate. Mass Spectrum (ESI) m/e=412.1 (M+1).

(R)-tert-Butyl 4-(5,7-difluoro-3-methyl-4-(5-morpholinopyridin-3-ylamino)-quinolin-2-yl)-2-methylpiperazine-1-carboxylate

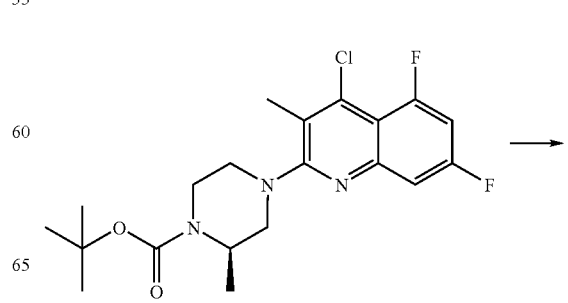

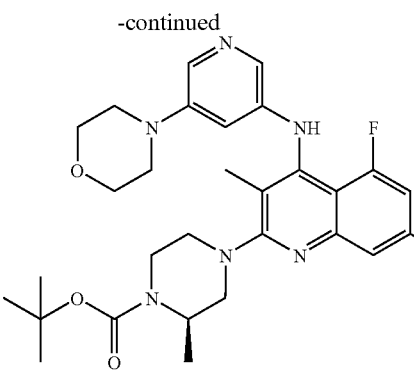

Prepared according to Procedure H using (R)-tert-butyl 4-(4-chloro-5,7-difluoro-3-methylquinolin-2-yl)-2-methylpiperazine-1-carboxylate (230 mg, 0.56 mmol) and 5-morpholinopyridin-3-amine in toluene to give (R)-tert-butyl 4-(5,7-difluoro-3-methyl-4-(5-morpholinopyridin-3-ylamino)quinolin-2-yl)-2-methylpiperazine-1-carboxylate. $^1$H NMR (CDCl$_3$) δ ppm 7.94 (1H, d, J=2.3 Hz), 7.69 (1H, d, J=2.2 Hz), 7.30 (1H, ddd, J=10.0, 2.5, 1.2 Hz), 6.88 (1H, d, J=12.9 Hz), 6.80 (1H, ddd, J=13.9, 8.6, 2.5 Hz), 6.58 (1H, t, J=2.3 Hz), 4.38 (1H, br. s.), 3.98 (1H, d, J=13.1 Hz), 3.85 (4H, dd, J=5.7, 3.9 Hz), 3.70 (1H, d, J=10.2 Hz), 3.56 (1H, dt, J=12.9, 1.8 Hz), 3.32 (1H, td, J=12.7, 3.1 Hz), 3.14-3.21 (4H, m), 3.11 (1H, dd, J=12.8, 3.8 Hz), 2.92 (1H, td, J=12.5, 3.3 Hz), 2.10 (3H, s), 1.50 (9H, s), 1.29 (3H, d, J=6.8 Hz). Mass Spectrum (ESI) m/e=555.7 (M+1).

Example 260

Preparation of (R)-5,7-Difluoro-3-methyl-2-(3-methylpiperazin-1-yl)-N-(5-morpholinopyridin-3-yl)quinolin-4-amine

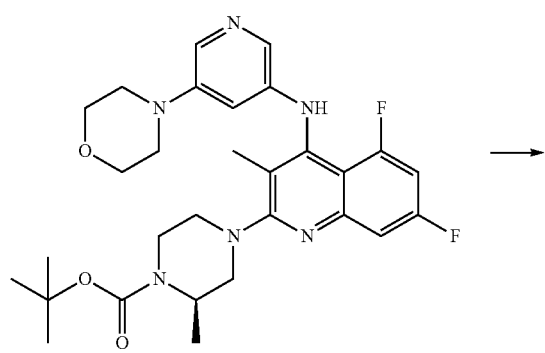

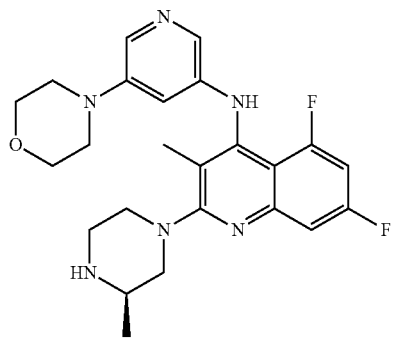

Prepared according to Procedure O using (R)-tert-butyl 4-(5,7-difluoro-3-methyl-4-(5-morpholinopyridin-3-ylamino)quinolin-2-yl)-2-methylpiperazine-1-carboxylate (165 mg, 0.30 mmol) to give (R)-5,7-difluoro-3-methyl-2-(3-methylpiperazin-1-yl)-N-(5-morpholinopyridin-3-yl)quinolin-4-amine. $^1$H NMR (CDCl$_3$) δ ppm 7.91 (1H, d, J=2.5 Hz), 7.70 (1H, d, J=2.2 Hz), 7.27-7.33 (1H, m), 6.88 (1H, d, J=12.7 Hz), 6.76 (1H, ddd, J=13.8, 8.7, 2.5 Hz), 6.55 (1H, t, J=2.3 Hz), 3.76-3.90 (4H, m), 3.65 (2H, d, J=12.3 Hz), 3.11-3.19 (4H, m), 2.89-3.11 (4H, m), 2.62 (1H, dd, J=12.7, 10.2 Hz), 2.10 (1H, br. s.), 2.06 (3H, s), 1.14 (3H, d, J=6.3 Hz). Mass Spectrum (ESI) m/e=455.2 (M+1).

Example 261

Preparation of (R)-Methyl 4-(5,7-difluoro-3-methyl-4-(5-morpholinopyridin-3-ylamino)quinolin-2-yl)-2-methylpiperazine-1-carboxylate

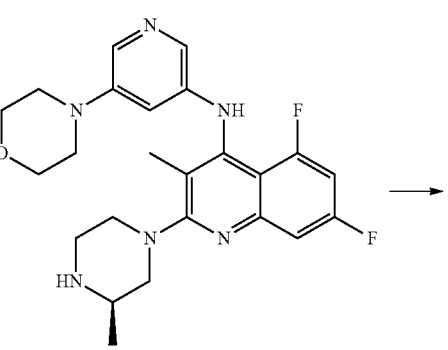

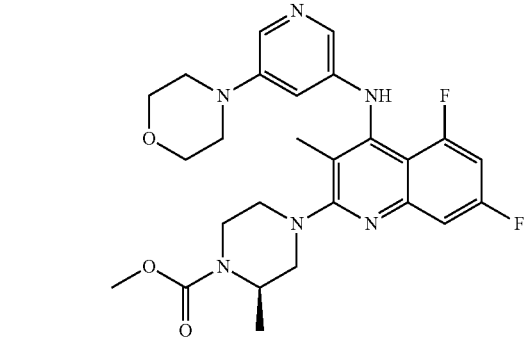

Prepared according to Procedure L using (R)-5,7-difluoro-3-methyl-2-(3-methylpiperazin-1-yl)-N-(5-morpholinopyridin-3-yl)quinolin-4-amine (32 mg, 0.070 mmol) and methyl chloroformate to give (R)-methyl 4-(5,7-difluoro-3-methyl-4-(5-morpholinopyridin-3-ylamino)quinolin-2-yl)-2-methylpiperazine-1-carboxylate. TFA Salt: $^1$H NMR (CDCl$_3$) δ ppm 8.67 (3H, br. s.), 8.29 (1H, d, J=7.8 Hz), 7.92 (1H, d, J=2.2 Hz), 7.85 (1H, d, J=1.4 Hz), 7.54 (1H, dd, J=9.8, 1.4 Hz), 7.19 (1H, s), 6.88 (1H, ddd, J=13.0, 8.4, 2.5 Hz), 4.41-4.59 (1H, m), 4.09 (1H, d, J=13.3 Hz), 3.81-3.93 (5H, m), 3.77 (3H, s), 3.73 (1H, d, J=13.1 Hz), 3.37-3.53 (2H, m), 3.18-3.36 (5H, m), 2.17 (3H, s), 1.31 (3H, d, J=6.8 Hz). Mass Spectrum (ESI) m/e=513.3 (M+1).

Example 262

Preparation of (R)-5,7-Difluoro-3-methyl-2-(3-methyl-4-(methylsulfonyl)piperazin-1-yl)-N-(5-morpholinopyridin-3-yl)quinolin-4-amine

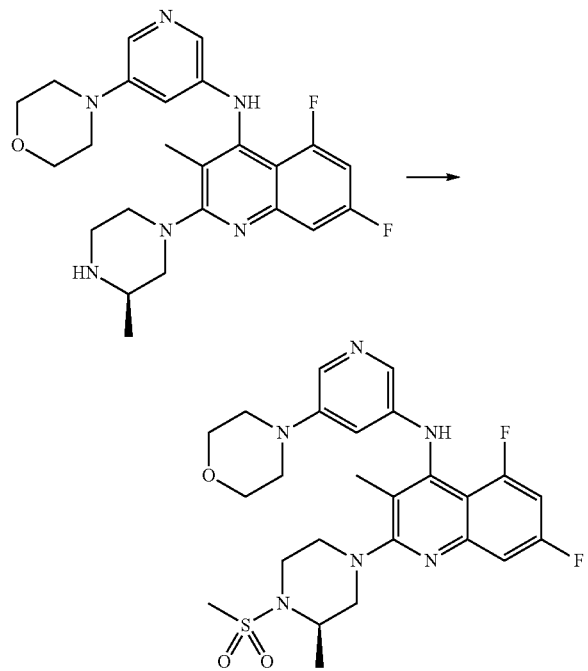

Prepared according to Procedure M using (R)-5,7-difluoro-3-methyl-2-(3-methylpiperazin-1-yl)-N-(5-morpholinopyridin-3-yl)quinolin-4-amine (32 mg, 0.070 mmol) and methylsulfonyl chloride to give (R)-5,7-difluoro-3-methyl-2-(3-methyl-4-(methylsulfonyl)piperazin-1-yl)-N-(5-morpholinopyridin-3-yl)quinolin-4-amine. TFA Salt: $^1$H NMR (CDCl$_3$) δ ppm 7.96 (1H, d, J=2.2 Hz), 7.77 (1H, d, J=1.6 Hz), 7.40-7.50 (2H, m), 6.99 (1H, s), 6.88 (1H, ddd, J=13.4, 8.5, 2.5 Hz), 4.21-4.33 (1H, m), 3.82-3.93 (5H, m), 3.72 (2H, t, J=12.5 Hz), 3.50-3.63 (1H, m), 3.39 (1H, dd, J=13.3, 3.5 Hz), 3.17-3.27 (1H, m), 3.15-3.34 (4H, m), 2.94 (3H, s), 2.19 (3H, s), 1.43 (3H, d, J=6.8 Hz). Mass Spectrum (ESI) m/e=533.2 (M+1).

Example 263

Preparation of Cyclopentyl(4-(5,7-difluoro-3-methyl-4-(5-morpholinopyridin-3-ylamino)quinolin-2-yl)piperazin-1-yl)methanone

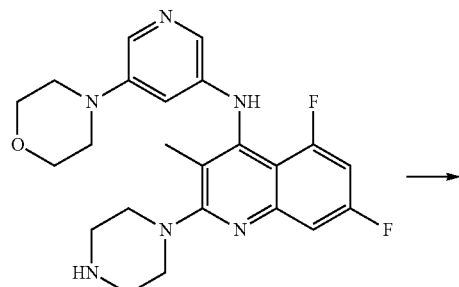

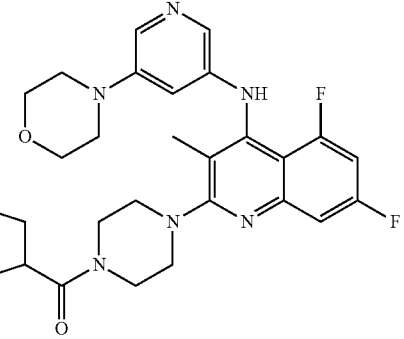

Prepared according to Procedure R using 5,7-difluoro-3-methyl-N-(5-morpholinopyridin-3-yl)-2-(piperazin-1-yl)quinolin-4-amine (40.0 mg, 0.09 mmol) and cyclopentanecarbonyl chloride to give cyclopentyl(4-(5,7-difluoro-3-methyl-4-(5-morpholinopyridin-3-ylamino)quinolin-2-yl)piperazin-1-yl)methanone. $^1$H NMR (DMSO-d6) δ ppm 1.51-1.73 (m, 8H), 2.10 (br s, 3H), 3.00 (m, 1H), 3.00-3.07 (m, 4H), 3.24 (br s, 2H), 3.33 (br s, 4H), 3.65-3.70 (m, 6H), 6.51 (br s, 1H), 7.13-7.19 (m, 1H), 7.27-7.30 (m, 1H), 7.52 (d, J=2.0 Hz, 1H), 7.78 (d, J=2.4 Hz, 1H), 8.37 (s, 1H). Mass Spectrum (ESI) m/e=537.4 (M+1).

Example 264

Preparation of (4-(5,7-Difluoro-3-methyl-4-(5-morpholinopyridin-3-ylamino)quinolin-2-yl)piperazin-1-yl)(tetrahydro-2H-pyran-4-yl)-methanone

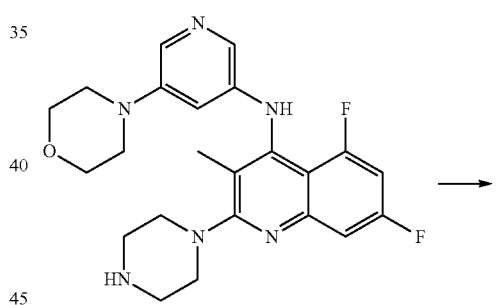

Prepared according to Procedure R using 5,7-difluoro-3-methyl-N-(5-morpholinopyridin-3-yl)-2-(piperazin-1-yl)quinolin-4-amine (40.0 mg, 0.09 mmol) and tetrahydro-2H-pyran-4-carbonyl chloride to give (4-(5,7-difluoro-3-methyl-4-(5-morpholinopyridin-3-ylamino)quinolin-2-yl)piperazin-1-yl)(tetrahydro-2H-pyran-4-yl)methanone. $^1$H NMR (DMSO-d6) δ ppm 1.55-1.67 (m, 4H), 2.10 (br s, 3H), 2.91-2.96 (m, 1H), 3.05 (t, J=4.4 Hz, 4H), 3.24 (br s, 2H), 3.33-3.43

(m, 3H), 3.64 (br s, 2H), 3.69 (t, J=4.0 Hz, 7H), 3.85-3.88 (m, 2H), 6.51 (d, J=2.0 Hz, 1H), 7.13-7.19 (m, 1H), 7.25-7.29 (m, 1H,), 7.52 (d, J=2.0 Hz, 1H), 7.78 (d, J=2.4 Hz, 1H), 8.36 (s, 1H). Mass Spectrum (ESI) m/e=553.4 (M+1).

Example 265

Preparation of 5,7-Difluoro-2-(4-(isobutylsulfonyl)piperazin-1-yl)-3-methyl-N-(5-morpholinopyridin-3-yl)quinolin-4-amine

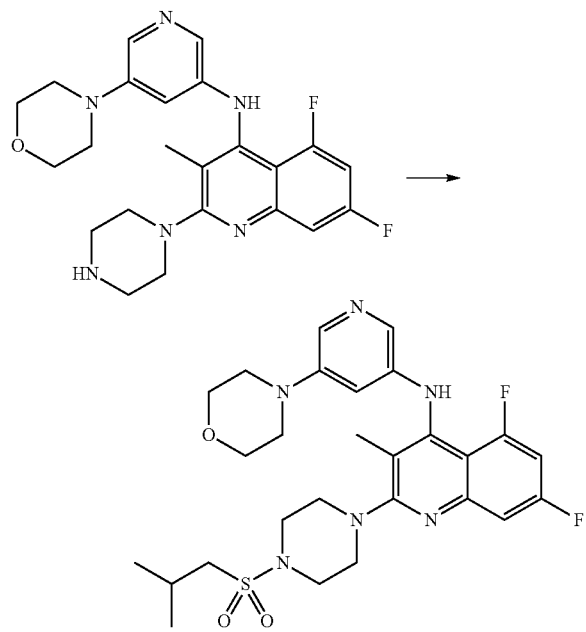

Prepared according to Procedure M using 5,7-difluoro-3-methyl-N-(5-morpholinopyridin-3-yl)-2-(piperazin-1-yl)quinolin-4-amine (50.0 mg, 0.11 mmol) and isobutylsulfonyl chloride to give 5,7-difluoro-2-(4-(isobutylsulfonyl)piperazin-1-yl)-3-methyl-N-(5-morpholinopyridin-3-yl)quinolin-4-amine. $^1$H NMR (DMSO-d6) δ ppm 1.05 (d, J=6.8 Hz, 6H), 2.11 (br s, 3H), 2.12-2.16 (m, 1H) 2.96 (d, J=6.8 Hz, 2H), 3.06 (br s, 4H), 3.33-3.37 (m, 8H), 3.69 (t, J=9.2 Hz, 4H), 6.53 (s, 1H), 7.16-7.20 (m, 1H), 7.29-7.32 (m, 1H), 7.52 (s, 1H), 7.79 (s, 1H,), 8.41 (s, 1H). Mass Spectrum (ESI) m/e=561.4 (M+1).

Example 266

Preparation of 4-(5,7-Difluoro-3-methyl-4-(5-morpholinopyridin-3-ylamino)quinolin-2-yl)-N-isopropylpiperazine-1-carboxamide

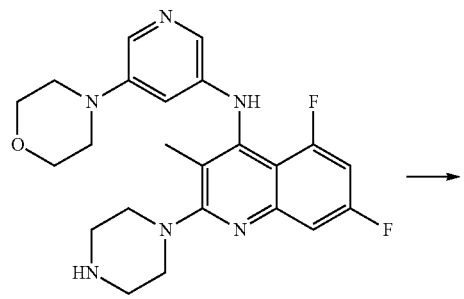

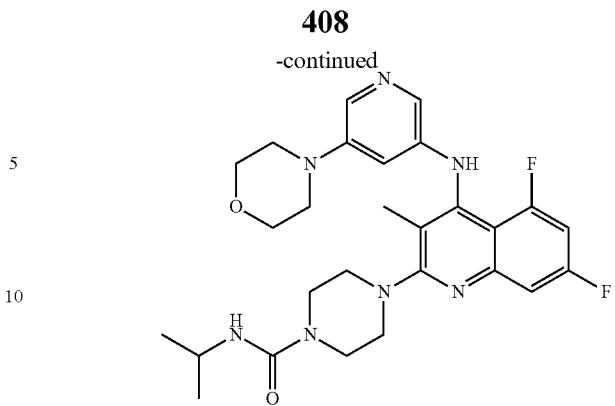

Prepared according to Procedure P using 5,7-difluoro-3-methyl-N-(5-morpholinopyridin-3-yl)-2-(piperazin-1-yl)quinolin-4-amine (50.0 mg, 0.11 mmol) and isopropylisocyanate to give 4-(5,7-difluoro-3-methyl-4-(5-morpholinopyridin-3-ylamino)quinolin-2-yl)-N-isopropylpiperazine-1-carboxamide. $^1$H NMR (DMSO-d6) δ ppm 1.07 (d, J=6.8 Hz, 6H), 2.08 (br s, 3H), 3.04-3.06 (m, 4H), 3.24 (br s, 4H), 3.46-3.50 (m, 4H), 3.68-3.70 (m, 4H), 3.78 (m, 1H), 6.26 (d, J=7.6 Hz, 1H), 6.49 (br s, 1H), 7.12-7.18 (m, 1H), 7.28-7.32 (m, 1H), 7.53 (s, 1H), 7.78 (d, J=2 Hz, 1H), 8.35 (s, 1H). Mass Spectrum (ESI) m/e=526.4 (M+1).

Example 267

Preparation of 2-(4-(cyclopentylsulfonyl)piperazin-1-yl)-5,7-difluoro-3-methyl-N-(5-morpholinopyridin-3-yl)quinolin-4-amine

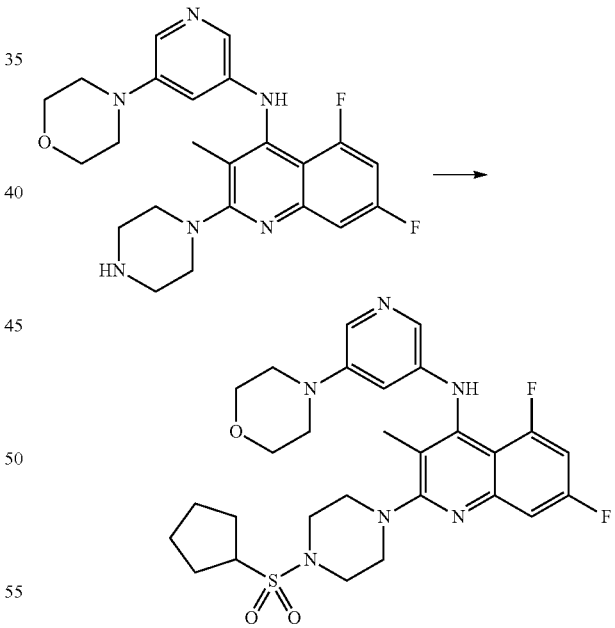

Prepared according to Procedure M using 5,7-difluoro-3-methyl-N-(5-morpholinopyridin-3-yl)-2-(piperazin-1-yl)quinolin-4-amine (50.0 mg, 0.11 mmol) and cyclopentylsulfonyl chloride to give 2-(4-(cyclopentylsulfonyl)piperazin-1-yl)-5,7-difluoro-3-methyl-N-(5-morpholinopyridin-3-yl)quinolin-4-amine. $^1$H NMR (CDCl$_3$) δ ppm 1.54-1.58 (m, 2H), 1.67 (s, 2H), 1.80-1.85 (m, 2H), 1.96-1.99 (m, 2H), 2.08 (s, 3H), 3.05 (t, J=4.4 Hz, 4H), 3.33 (s, 4H), 3.39 (t, J=4.8 Hz, 4H), 3.69 (t, J=3.6 Hz, 5H), 6.51 (s, 1H), 7.15-7.20 (m, 1H), 7.30 (d, J=11.2 Hz, 1H), 7.52 (s, 1H), 7.78 (s, 1H), 8.37 (s, 1H). Mass Spectrum (ESI) m/e=573.1 (M+1).

Example 268

Preparation of (4-(5,7-Difluoro-3-methyl-4-(5-morpholinopyridin-3-ylamino)quinolin-2-yl)piperazin-1-yl)(6-methylpyridin-3-yl)-methanone

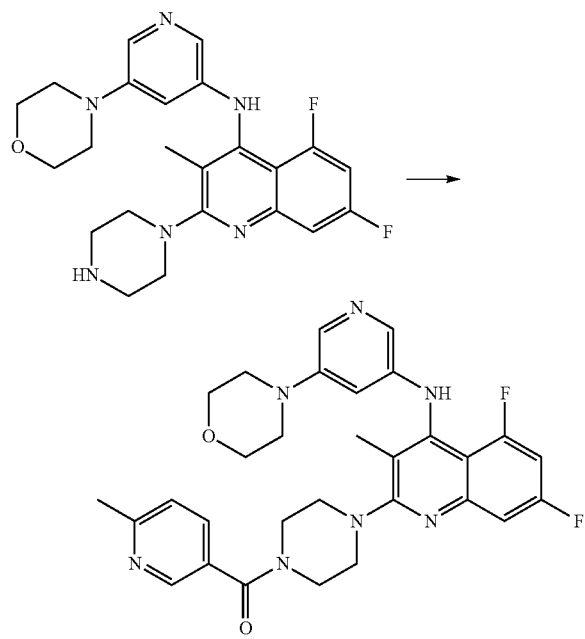

Prepared according to Procedure Q using 5,7-difluoro-3-methyl-N-(5-morpholinopyridin-3-yl)-2-(piperazin-1-yl)quinolin-4-amine (40.0 mg, 0.09 mmol) and 6-methylnicotinic acid to give (4-(5,7-difluoro-3-methyl-4-(5-morpholinopyridin-3-ylamino)quinolin-2-yl)piperazin-1-yl)(6-methylpyridin-3-yl)methanone. $^1$H NMR (DMSO-d6) δ ppm 2.09 (br s, 3H), 2.50-2.52 (m, 4H), 3.03-3.05 (m, 4H), 3.33-3.40 (m, 3H), 3.55 (br s, 2H), 3.67-3.69 (m, 4H), 3.82 (br s, 2H), 6.49 (s, 1H), 7.14-7.20 (m, 1H), 7.30-7.26 (m, 1H), 7.35-7.37 (m, 1H), 7.51 (d, J=2.4 Hz, 1H), 7.78 (br s, 2H), 8.37 (s, 1H), 8.54 (d, J=2.4 Hz, 1H). Mass Spectrum (ESI) m/e=560.4 (M+1).

Example 269

Preparation of (4-(5,7-Difluoro-3-methyl-4-(5-morpholinopyridin-3-ylamino)quinolin-2-yl)piperazin-1-yl)(pyrimidin-2-yl)methanone

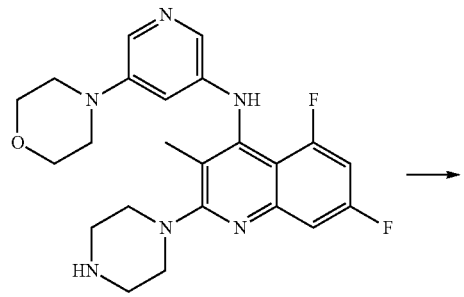

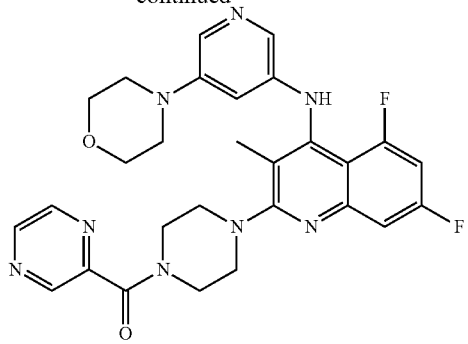

Prepared according to Procedure Q using 5,7-difluoro-3-methyl-N-(5-morpholinopyridin-3-yl)-2-(piperazin-1-yl)quinolin-4-amine (40.0 mg, 0.09 mmol) and pyrimidine-2-carboxylic acid to give (4-(5,7-difluoro-3-methyl-4-(5-morpholinopyridin-3-ylamino)quinolin-2-yl)piperazin-1-yl)(pyrimidin-2-yl)methanone. $^1$H NMR (DMSO-d6) δ ppm 2.09 (br s, 3H), 3.04 (m, 4H), 3.28-3.29 (m, 2H), 3.33-3.40 (m, 4H), 3.68 (m, 4H), 3.86 (m, 2H), 6.50 (s, 1H), 7.14-7.20 (m, 1H), 7.29-7.30 (m, 1H), 7.52 (s, 1H), 7.63 (t, J=4.8 Hz, 1H), 7.78 (br s, 1H), 8.37 (s, 1H), 8.93 (d, J=5.2 Hz, 2H). Mass Spectrum (ESI) m/e=546.9 (M+1).

Example 270

Preparation of (4-(5,7-difluoro-3-methyl-4-(5-morpholinopyridin-3-ylamino)quinolin-2-yl)piperazin-1-yl)(pyrimidin-4-yl)methanone

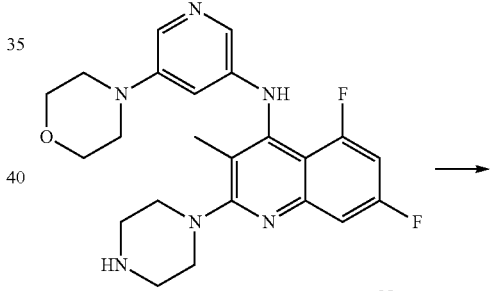

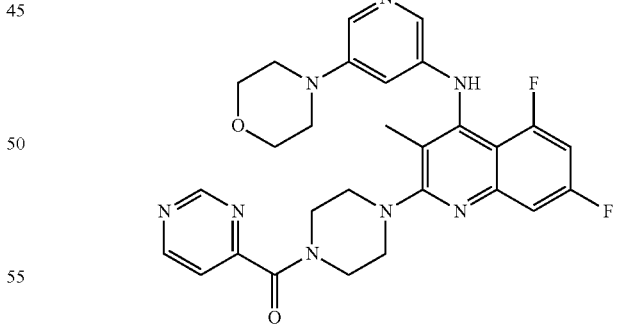

Prepared according to Procedure Q using 5,7-difluoro-3-methyl-N-(5-morpholinopyridin-3-yl)-2-(piperazin-1-yl)quinolin-4-amine (40.0 mg, 0.09 mmol) and pyrimidine-4-carboxylic acid to give (4-(5,7-difluoro-3-methyl-4-(5-morpholinopyridin-3-ylamino)quinolin-2-yl)piperazin-1-yl)(pyrimidin-4-yl)methanone. $^1$H NMR (DMSO-d6) δ ppm 2.10 (br s, 3H), 3.05 (t, J=4.4 Hz, 4H), 3.30-3.35 (m, 2H), 3.36-3.40 (m, 2H), 3.53-3.56 (m, 2H), 3.67-3.69 (m, 4H), 3.84-3.86 (m, 2H), 6.51 (s, 1H), 7.14-7.19 (m, 1H), 7.28-7.31

(m, 1H), 7.51 (s, 1H), 7.74 (d, J=5.2 Hz, 1H), 7.78 (d, J=3.2 Hz, 1H), 8.37 (s, 1H), 9.00 (d, J=5.2 Hz, 1H), 9.28 (s, 1H). Mass Spectrum (ESI) m/e=546.9 (M+1).

Example 271

Preparation of (4-(5,7-Difluoro-3-methyl-4-(5-morpholinopyridin-3-ylamino)quinolin-2-yl)piperazin-1-yl)(5-methylfuran-2-yl)methanone

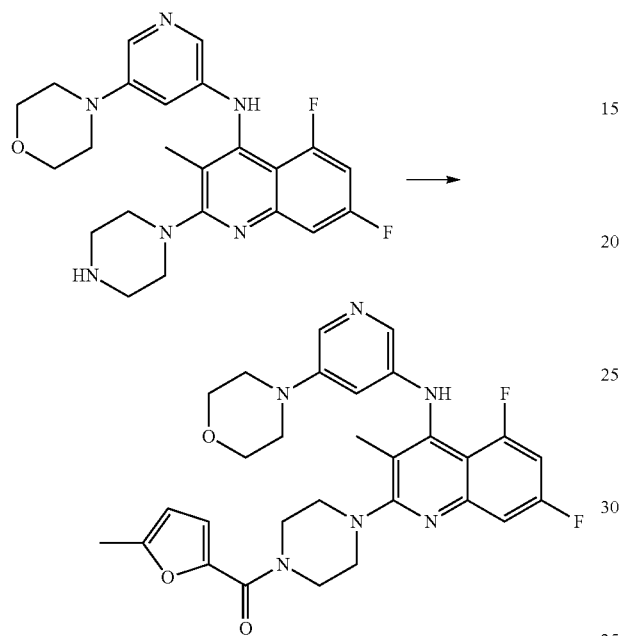

Prepared according to Procedure R using 5,7-difluoro-3-methyl-N-(5-morpholinopyridin-3-yl)-2-(piperazin-1-yl)quinolin-4-amine (50.0 mg, 0.11 mmol) and 5-methylfuran-2-carbonyl chloride to give (4-(5,7-difluoro-3-methyl-4-(5-morpholinopyridin-3-ylamino)quinolin-2-yl)piperazin-1-yl)(5-methylfuran-2-yl)methanone. $^1$H NMR (CDCl$_3$) δ ppm 2.11 (br s, 3H), 2.49 (br s, 3H), 3.06 (t, J=5.6 Hz, 4H), 3.30-3.40 (m, 4H), 3.69 (t, J=5.6 Hz, 4H), 3.86 (br s, 4H), 6.27 (br s, 1H), 6.52 (s, 1H), 6.94 (d, J=3.2 Hz, 1H), 7.16 (s, 1H), 7.28-7.31 (m, 1H), 7.53 (br s, 1H,), 7.79 (br s, 1H), 8.37 (s, 1H). Mass Spectrum (ESI) m/e=549.0 (M+1).

Example 272

Preparation of (4-(5,7-Difluoro-3-methyl-4-(5-morpholinopyridin-3-ylamino)quinolin-2-yl)piperazin-1-yl)(oxazol-5-yl)methanone

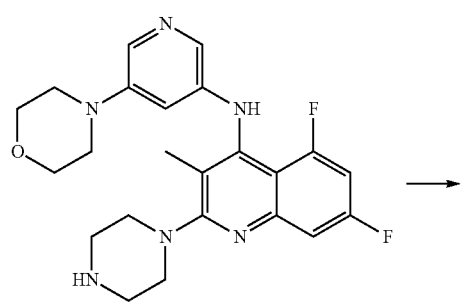

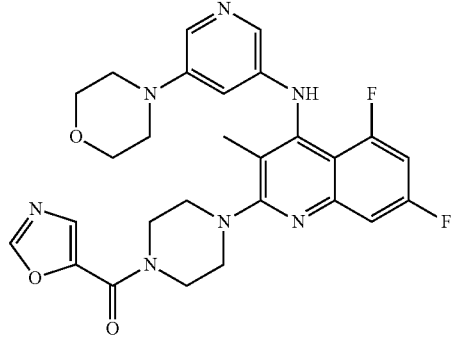

Prepared according to Procedure Q using 5,7-difluoro-3-methyl-N-(5-morpholinopyridin-3-yl)-2-(piperazin-1-yl)quinolin-4-amine (40.0 mg, 0.09 mmol) and oxazole-5-carboxylic acid to give (4-(5,7-difluoro-3-methyl-4-(5-morpholinopyridin-3-ylamino)quinolin-2-yl)piperazin-1-yl)(oxazol-5-yl)methanone. $^1$H NMR (DMSO-d6) δ ppm 2.11 (s, 3H), 3.06 (br s, 4H), 3.33-3.39 (m, 4H), 3.69 (br s, 4H), 3.86 (br s, 4H), 6.52 (s, 1H), 7.15-7.20 (m, 1H), 7.28-7.30 (m, 1H), 7.53 (s, 1H), 7.78 (br s, 2H), 8.38 (s, 1H), 8.59 (s, 1H). Mass Spectrum (ESI) m/e=535.9 (M+1).

Example 273

Preparation of 4-(5,7-Difluoro-3-methyl-4-(5-morpholinopyridin-3-ylamino)quinolin-2-yl)-N-ethylpiperazine-1-carboxamide

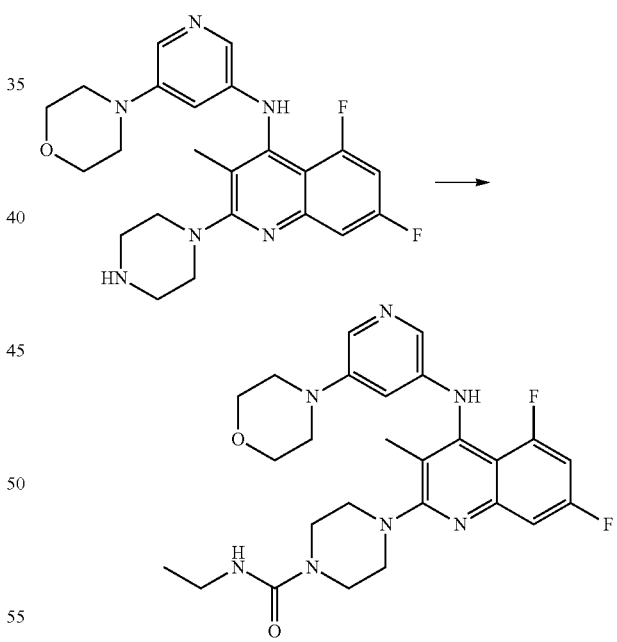

Prepared according to Procedure P using 5,7-difluoro-3-methyl-N-(5-morpholinopyridin-3-yl)-2-(piperazin-1-yl)quinolin-4-amine (50.0 mg, 0.11 mmol) and ethylisocyanate to give 4-(5,7-difluoro-3-methyl-4-(5-morpholinopyridin-3-ylamino)quinolin-2-yl)-N-ethylpiperazine-1-carboxamide. $^1$H NMR (DMSO-d6) δ ppm 1.03 (t, J=6.4 Hz, 3H), 2.08 (br s, 3H), 3.05-3.11 (m, 6H), 3.25 (br s, 4H), 3.44-3.45 (m, 4H), 3.68-3.69 (m, 4H), 6.49 (br s, 1H), 6.59-6.56 (m, 1H), 7.13-7.18 (m, 1H), 7.28-7.30 (m, 1H), 7.53 (s, 1H), 7.78 (s, 1H), 8.36 (s, 1H). Mass Spectrum (ESI) m/e=512.1 (M+1).

Example 274

Preparation of (4-(5,7-Difluoro-3-methyl-4-(5-morpholinopyridin-3-ylamino)quinolin-2-yl)piperazin-1-yl)(1H-imidazol-2-yl)methanone

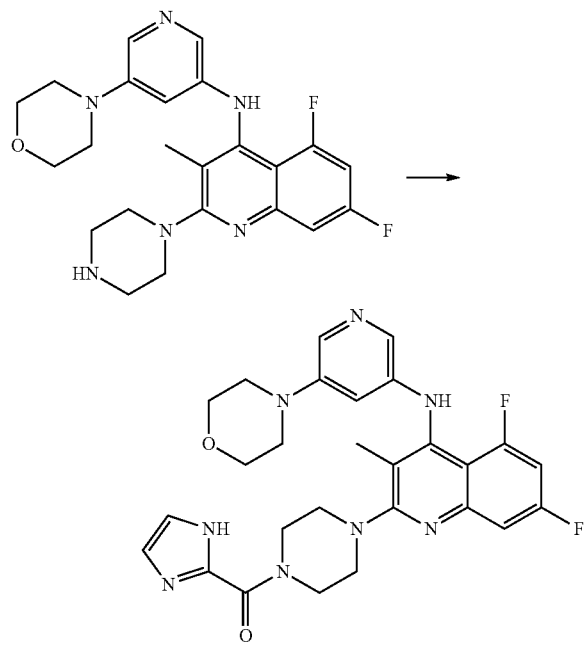

Prepared according to Procedure Q using 5,7-difluoro-3-methyl-N-(5-morpholinopyridin-3-yl)-2-(piperazin-1-yl)quinolin-4-amine (40.0 mg, 0.09 mmol) and 1H-imidazole-2-carboxylic acid to give (4-(5,7-difluoro-3-methyl-4-(5-morpholinopyridin-3-ylamino)quinolin-2-yl)piperazin-1-yl)(1H-imidazol-2-yl)methanone. $^1$H NMR (DMSO-d6) δ ppm 2.13 (br s, 3H), 3.06 (br s, 4H), 3.33-3.39 (m, 4H), 3.69 (br s, 4H), 3.84-3.85 (m, 2H), 4.66-4.69 (m, 2H), 6.50 (br s, 1H), 7.11-7.16 (m, 1H), 7.18-7.20 (m, 1H), 7.28-7.31 (m, 2H), 7.54 (br s, 1H), 7.79 (s, 1H), 8.38 (br s, 1H), 12.96 (s, 1H). Mass Spectrum (ESI) m/e=534.9 (M+1).

Example 275

Preparation of (4-(5,7-Difluoro-3-methyl-4-(5-morpholinopyridin-3-ylamino)quinolin-2-yl)piperazin-1-yl)(oxazol-4-yl)methanone

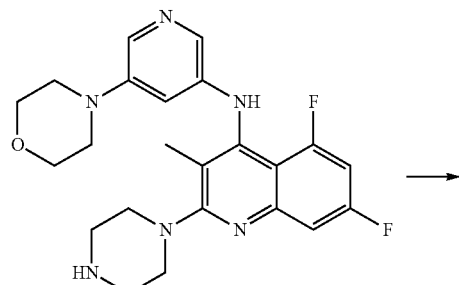

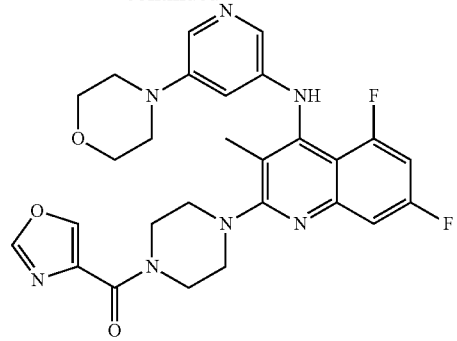

Prepared according to Procedure Q using 5,7-difluoro-3-methyl-N-(5-morpholinopyridin-3-yl)-2-(piperazin-1-yl)quinolin-4-amine (40.0 mg, 0.09 mmol) and oxazole-4-carboxylic acid to give (4-(5,7-difluoro-3-methyl-4-(5-morpholinopyridin-3-ylamino)quinolin-2-yl)piperazin-1-yl)(oxazol-4-yl)methanone. $^1$H NMR (DMSO-d6) δ ppm 2.11 (br s, 3H), 3.05 (t, J=4.4 Hz, 4H), 3.32-3.37 (m, 4H), 3.69 (t, J=4.4 Hz, 4H), 3.80 (br s, 2H), 4.00-4.07 (m, 2H), 6.51 (s, 1H), 7.11-7.16 (m, 1H), 7.27-7.32 (m, 1H), 7.53 (s, 1H), 7.78 (s, 1H), 8.36 (s, 1H), 8.54 (s, 1H), 8.62 (s, 1H). Mass Spectrum (ESI) m/e=536.0 (M+1).

Example 276

Preparation of (4-(5,7-Difluoro-3-methyl-4-(5-morpholinopyridin-3-ylamino)quinolin-2-yl)piperazin-1-yl)(pyridin-3-yl)methanone

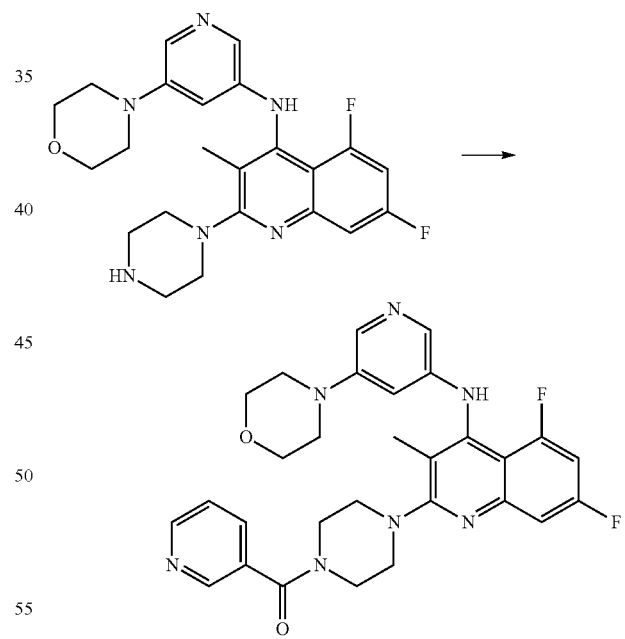

Prepared according to Procedure Q using 5,7-difluoro-3-methyl-N-(5-morpholinopyridin-3-yl)-2-(piperazin-1-yl)quinolin-4-amine (40.0 mg, 0.09 mmol) and nicotinic acid to give (4-(5,7-difluoro-3-methyl-4-(5-morpholinopyridin-3-ylamino)quinolin-2-yl)piperazin-1-yl)(pyridin-3-yl)methanone. $^1$H NMR (DMSO-d6) δ ppm 2.10 (s, 3H), 3.05 (br s, 4H), 3.32-3.40 (br s, 4H), 3.54 (br s, 2H), 3.68 (br s, 4H), 3.84 (br s, 2H), 6.50 (br s, 1H), 7.16 (br s, 1H), 7.28 (br s, 2H), 7.56 (br s, 2H), 7.78 (s, 1H), 7.90 (d, J=7.6 Hz, 1H), 8.36 (s, 1H), 8.67 (s, 2H). Mass Spectrum (ESI) m/e=545.7 (M+1).

Example 277

Preparation of 5,7-Difluoro-2-(4-isobutylpiperazin-1-yl)-3-methyl-N-(5-morpholinopyridin-3-yl)quinolin-4-amine

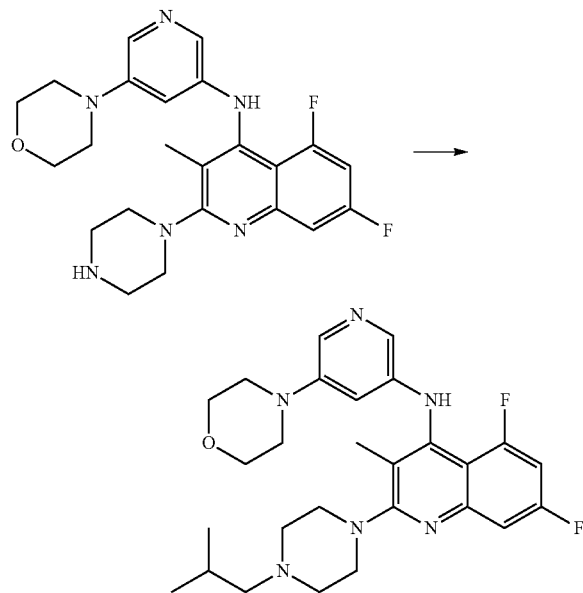 [SMILES: Cc1c(N2CCNCC2)nc2cc(F)cc(F)c2c1Nc1cncc(N2CCOCC2)c1 ; Cc1c(N2CCN(CC(C)C)CC2)nc2cc(F)cc(F)c2c1Nc1cncc(N2CCOCC2)c1]

Prepared according to Procedure L using 5,7-difluoro-3-methyl-N-(5-morpholinopyridin-3-yl)-2-(piperazin-1-yl)quinolin-4-amine (25.0 mg, 0.056 mmol) and 3-methylbutanal to give (4-(5,7-difluoro-3-methyl-4-(5-morpholinopyridin-3-ylamino)quinolin-2-yl)piperazin-1-yl)(pyridin-3-yl)methanone. $^1$H NMR (DMSO-d6) δ ppm 0.89 (d, J=6.4 Hz, 6H), 1.78-1.85 (m, 1H), 2.06 (br s, 3H), 2.11 (d, J=7.6 Hz, 2H), 3.04 (t, J=4.4 Hz, 4H), 3.29-3.32 (m, 8H), 3.69 (t, J=4.4 Hz, 4H), 6.49 (s, 1H), 7.09-7.15 (m, 1H), 7.25-7.27 (m, 1H), 7.51 (s, 1H), 7.77 (d, J=2.0 Hz, 1H), 8.32 (s, 1H). Mass Spectrum (ESI) m/e=497.1 (M+1).

Example 278

Preparation of 5,7-Difluoro-3-methyl-N-(5-morpholinopyridin-3-yl)-2-(4-(3,3,3-trifluoropropyl)piperazin-1-yl)quinolin-4-amine

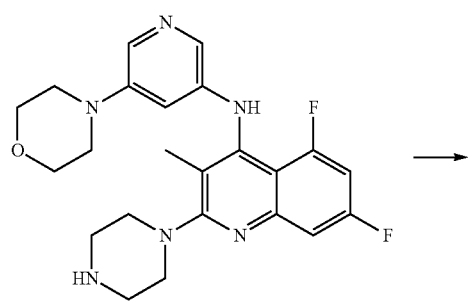

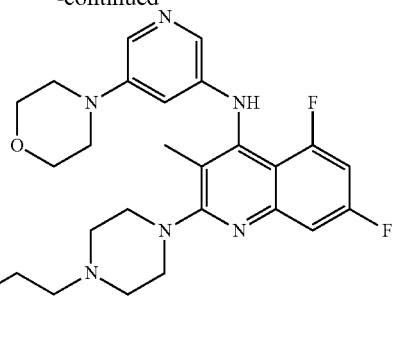

Prepared according to Procedure L using 5,7-difluoro-3-methyl-N-(5-morpholinopyridin-3-yl)-2-(piperazin-1-yl)quinolin-4-amine (25.0 mg, 0.056 mmol) and 3,3,3-trifluoropropanal to give 5,7-difluoro-3-methyl-N-(5-morpholinopyridin-3-yl)-2-(4-(3,3,3-trifluoropropyl)piperazin-1-yl)quinolin-4-amine. $^1$H NMR (DMSO-d6) δ ppm 2.07 (br s, 3H), 2.50 (m(buried), 2H), 2.60 (br s, 6H), 3.04 (br s, 4H), 3.29-3.31 (m, 4H), 3.69 (br s, 4H), 6.49 (s, 1H), 7.10-7.16 (m, 1H), 7.26-7.28 (m, 1H), 7.51 (s, 1H), 7.77 (s, 1H), 8.32 (s, 1H). Mass Spectrum (ESI) m/e=537.1 (M+1).

Example 279

Preparation of 1-(5,7-Difluoro-3-methyl-4-(5-morpholinopyridin-3-ylamino)quinolin-2-yl)-4,4-dimethylpyrrolidin-2-one 1-(4-Chloro-5,7-difluoro-3-methylquinolin-2-yl)-4,4-dimethylpyrrolidin-2-one

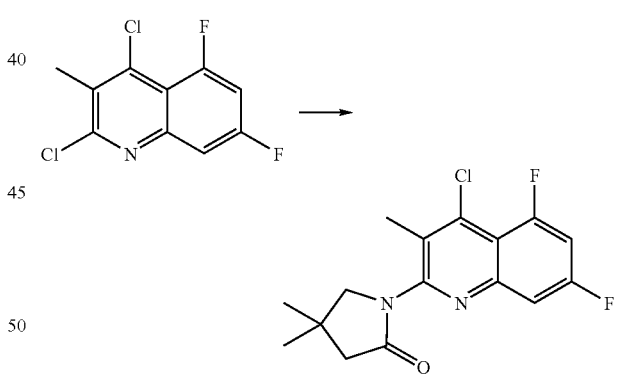

The 2,4-dichloro-5,7-difluoro-3-methylquinoline (1.50 g, 6.20 mmol), (9,9-dimethyl-9H-xanthene-4,5-diyl)bis(diphenylphosphine) (XantPhos) (540 mg, 0.93 mmol), 4,4-dimethylpyrrolidin-2-one (700 mg, 6.20 mmol), cesium carbonate (2.80 g, 8.70 mmol) and Pd$_2$(dba)$_3$ (280 mg, 0.31 mmol) were slurried in 21 mL of dry 1,4-dioxane along with 1.0 g of activated 3 A molecular sieves. The reaction was heated in an oil bath at 100° C. for 1 h. The reaction was then cooled to rt, diluted with EtOAc and filtered over a pad of celite. The filtrate was cond and the residue was purified by medium pressure chromatography (silica gel, 0 to 30% EtOAc:DCM) to give 1-(4-chloro-5,7-difluoro-3-methylquinolin-2-yl)-4,4-dimethylpyrrolidin-2-one. Mass Spectrum (ESI) m/e=325.1 (M+1).

1-(5,7-Difluoro-3-methyl-4-(5-morpholinopyridin-3-ylamino)quinolin-2-yl)-4,4-dimethylpyrrolidin-2-one

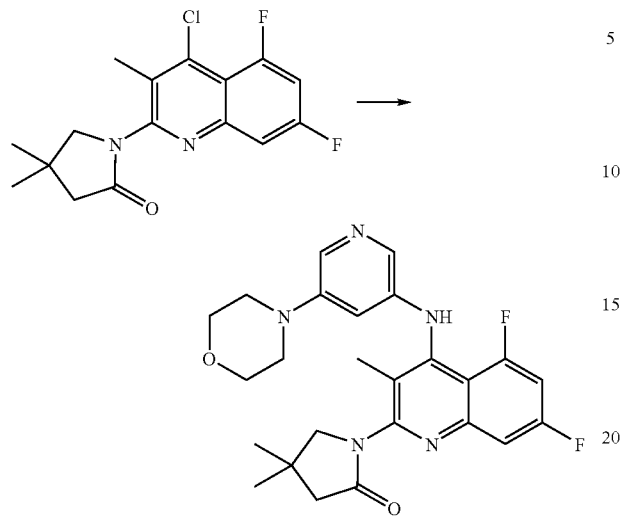

Prepared according to Procedure H using 1-(4-chloro-5,7-difluoro-3-methylquinolin-2-yl)-4,4-dimethylpyrrolidin-2-one (150 mg, 0.46 mmol) and 5-morpholinopyridin-3-amine in toluene to give 1-(5,7-difluoro-3-methyl-4-(5-morpholinopyridin-3-ylamino)quinolin-2-yl)-4,4-dimethylpyrrolidin-2-one. $^1$H NMR (CDCl$_3$) δ ppm 8.11 (1H, d, J=1.8 Hz), 8.02 (1H, d, J=9.2 Hz), 7.83 (1H, d, J=2.2 Hz), 7.45 (1H, dd, J=9.3, 1.1 Hz), 7.02 (1H, ddd, J=13.3, 8.6, 2.5 Hz), 6.82 (1H, t, J=2.2 Hz), 3.91 (2H, br. s.), 3.71-3.85 (4H, m), 3.25-3.39 (4H, m), 2.44 (2H, s), 2.09 (3H, s), 1.34 (6H, s). Mass Spectrum (ESI) m/e=468.3 (M+1).

Example 280

Preparation of 1-(5,7-Difluoro-3-methyl-4-(5-morpholinopyridin-3-ylamino)quinolin-2-yl)azetidin-2-one 1-(4-Chloro-5,7-difluoro-3-methylquinolin-2-yl)azetidin-2-one

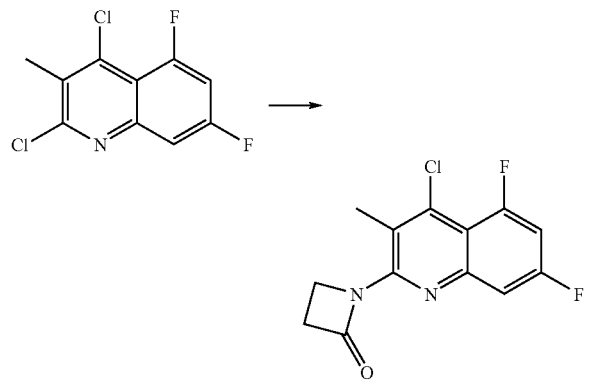

The 2,4-dichloro-5,7-difluoro-3-methylquinoline (1.90 g, 7.70 mmol), (9,9-dimethyl-9H-xanthene-4,5-diyl)bis(diphenylphosphine) (XantPhos) (670 mg, 1.20 mmol), azetidin-2-one (550 mg, 7.70 mmol), cesium carbonate (3.50 g, 11.0 mmol) and Pd$_2$(dba)$_3$ (350 mg, 0.39 mmol) were slurried in 26 mL of dry dioxane along with 1.0 grams of activated 3 A molecular sieves. The reaction was heated in an oil bath at 100° C. for 3 h. The reaction was then cooled to rt, diluted with EtOAc and filtered over a pad of celite. The filtrate was cond and the residue was purified by medium pressure chromatography (silica gel, 0 to 30% EtOAc:DCM) to give 1-(4-chloro-5,7-difluoro-3-methylquinolin-2-yl)azetidin-2-one. Mass Spectrum (ESI) m/e=283.1 (M+1).

1-(5,7-Difluoro-3-methyl-4-(5-morpholinopyridin-3-ylamino)quinolin-2-yl)-azetidin-2-one

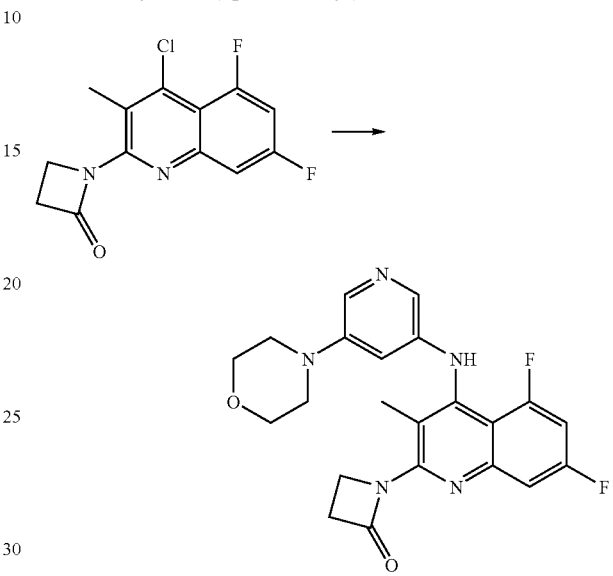

Prepared according to Procedure H except using chloro(2-dicyclohexylphosphino-2',4',6'-tri-i-propyl-1,1'-biphenyl)[2-(2-aminoethyl)phenyl]palladium(II) methyl-t-butylether adduct (X-Phos precatalyst) and cesium carbonate as base with 1-(4-chloro-5,7-difluoro-3-methylquinolin-2-yl)azetidin-2-one (50 mg, 0.18 mmol) and 5-morpholinopyridin-3-amine in toluene to give 1-(5,7-difluoro-3-methyl-4-(5-morpholinopyridin-3-ylamino)quinolin-2-yl)azetidin-2-one.
TFA salt: $^1$H NMR (CDCl$_3$) δ ppm 9.20 (1H, br. s.), 8.11 (1H, d, J=2.0 Hz), 7.94 (1H, d, J=8.6 Hz), 7.87 (1H, d, J=2.3 Hz), 7.44 (1H, ddd, J=9.4, 2.6, 1.3 Hz), 6.98 (1H, ddd, J=13.3, 8.6, 2.5 Hz), 6.75 (1H, t, J=2.2 Hz), 4.05 (2H, t, J=4.7 Hz), 3.78-3.94 (4H, m), 3.22-3.36 (4H, m), 3.17 (2H, t, J=5.0 Hz), 2.25 (3H, s). Mass Spectrum (ESI) m/e=426.2 (M+1).

Example 281

Preparation of (S)-4-(5,7-Difluoro-3-methyl-4-(5-morpholinopyridin-3-ylamino)quinolin-2-yl)-N,2-dimethylpiperazine-1-carboxamide

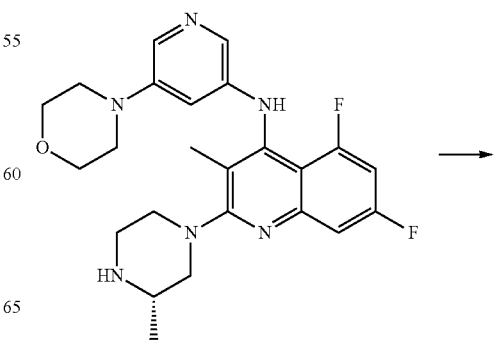

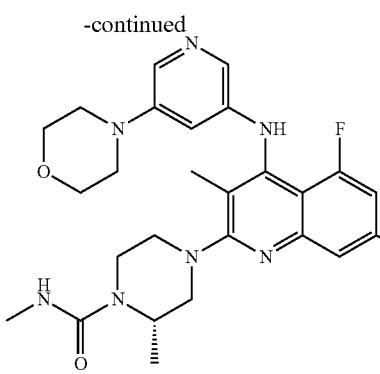

Prepared according to Procedure N using (S)-5,7-difluoro-3-methyl-2-(3-methylpiperazin-1-yl)-N-(5-morpholinopyridin-3-yl)quinolin-4-amine (50.0 mg, 0.11 mmol) and methylisocyanate to give (S)-4-(5,7-difluoro-3-methyl-4-(5-morpholinopyridin-3-ylamino)quinolin-2-yl)-N,2-dimethylpiperazine-1-carboxamide. $^1$H NMR (CDCl$_3$) δ ppm 7.94 (1H, d, J=2.5 Hz), 7.69 (1H, d, J=2.2 Hz), 7.30 (1H, ddd, J=10.0, 2.5, 1.2 Hz), 6.90 (1H, d, J=13.3 Hz), 6.81 (1H, ddd, J=13.8, 8.7, 2.5 Hz), 6.59 (1H, t, J=2.3 Hz), 4.49 (1H, q, J=4.9 Hz), 4.18-4.31 (1H, m), 3.78-3.91 (5H, m), 3.69-3.78 (1H, m), 3.60 (1H, dt, J=12.8, 1.7 Hz), 3.37 (1H, td, J=12.4, 3.1 Hz), 3.09-3.23 (5H, m), 2.96 (1H, td, J=12.4, 3.5 Hz), 2.87 (3H, d, J=4.7 Hz), 2.10 (3H, s), 1.31 (3H, d). Mass Spectrum (ESI) m/e=512.2 (M+1).

Example 282

Preparation of (R)-4-(5,7-Difluoro-3-methyl-4-(5-morpholinopyridin-3-ylamino)quinolin-2-yl)-N,2-dimethylpiperazine-1-carboxamide

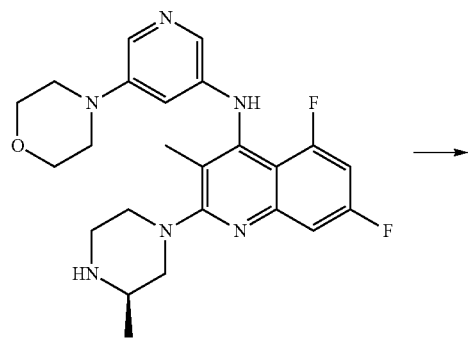

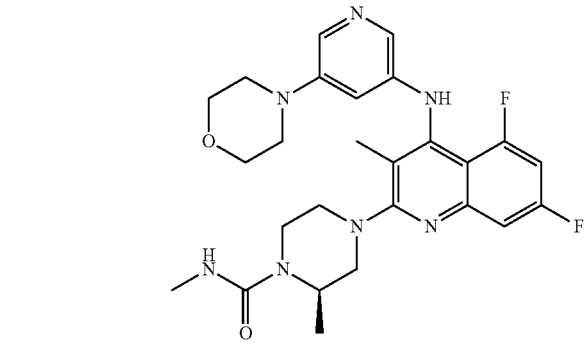

Prepared according to Procedure N using (R)-5,7-difluoro-3-methyl-2-(3-methylpiperazin-1-yl)-N-(5-morpholinopyridin-3-yl)quinolin-4-amine (50.0 mg, 0.11 mmol) and methylisocyanate to give (R)-4-(5,7-difluoro-3-methyl-4-(5-morpholinopyridin-3-ylamino)quinolin-2-yl)-N,2-dimethylpiperazine-1-carboxamide. $^1$H NMR (CDCl$_3$) δ ppm 7.93 (1H, d, J=2.5 Hz), 7.68 (1H, d, J=2.3 Hz), 7.27-7.33 (1H, m), 6.92 (1H, d, J=12.7 Hz), 6.79 (1H, ddd, J=13.8, 8.8, 2.6 Hz), 6.58 (1H, t, J=2.3 Hz), 4.58 (1H, q, J=4.3 Hz), 4.16-4.29 (1H, m), 3.78-3.92 (5H, m), 3.68-3.78 (1H, m), 3.54-3.64 (1H, m), 3.36 (1H, td, J=12.4, 3.3 Hz), 3.11-3.25 (5H, m), 2.95 (1H, td, J=12.4, 3.4 Hz), 2.85 (3H, d, J=4.5 Hz), 2.09 (3H, s), 1.30 (3H, d, J=6.7 Hz). Mass Spectrum (ESI) m/e=512.3 (M+1).

Example 283

Preparation of (R)-5,7-Difluoro-3-methyl-2-(2-methylpiperazin-1-yl)-N-(5-morpholinopyridin-3-yl)quinolin-4-amine (R)-tert-Butyl 4-(4-chloro-5,7-difluoro-3-methylquinolin-2-yl)-3-methylpiperazine-1-carboxylate

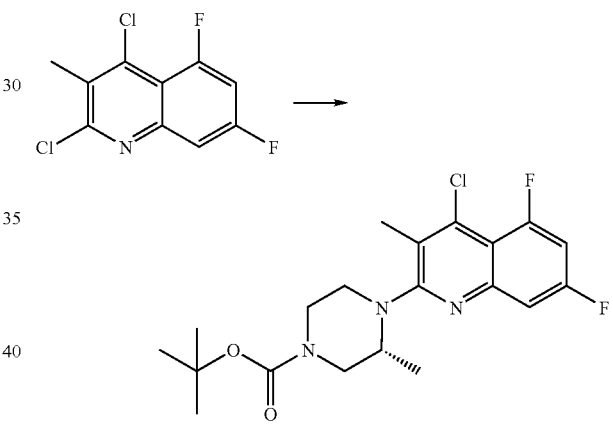

Prepared according to Procedure G using 2,4-dichloro-5,7-difluoro-3-methylquinoline (1.00 g, 4.10 mmol) and (R)-tert-butyl 3-methylpiperazine-1-carboxylate and using DBU (1.0 eq) as a base to give (R)-tert-butyl 4-(4-chloro-5,7-difluoro-3-methylquinolin-2-yl)-3-methylpiperazine-1-carboxylate. Mass Spectrum (ESI) m/e=412.1 (M+1).

(R)-tert-Butyl 4-(5,7-difluoro-3-methyl-4-(5-morpholinopyridin-3-ylamino)-quinolin-2-yl)-3-methylpiperazine-1-carboxylate

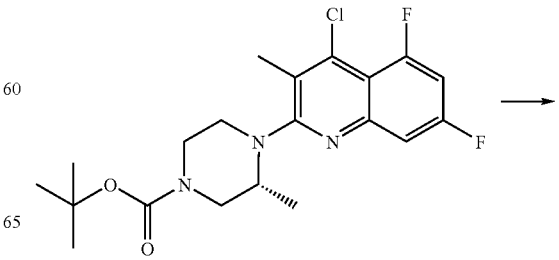

-continued

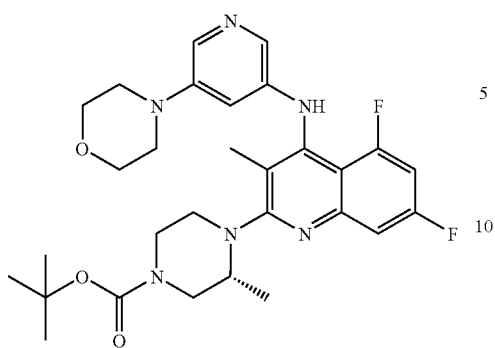

Prepared according to Procedure H using (R)-tert-butyl 4-(4-chloro-5,7-difluoro-3-methylquinolin-2-yl)-3-methylpiperazine-1-carboxylate (31.0 mg, 0.075 mmol) and 5-morpholinopyridin-3-amine in toluene to give (R)-tert-butyl 4-(5,7-difluoro-3-methyl-4-(5-morpholinopyridin-3-ylamino)quinolin-2-yl)-3-methylpiperazine-1-carboxylate. Mass Spectrum (ESI) m/e=555.5 (M+1).

(R)-5,7-Difluoro-3-methyl-2-(2-methylpiperazin-1-yl)-N-(5-morpholinopyridin-3-yl)quinolin-4-amine

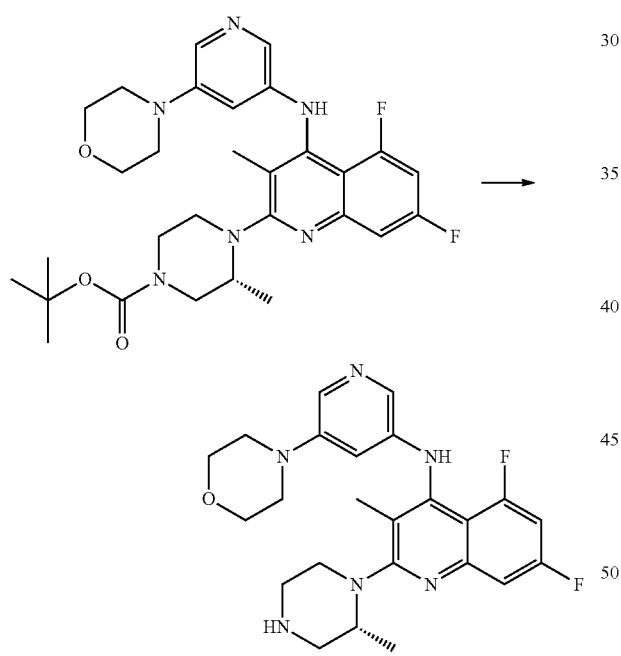

Prepared according to Procedure O using (R)-tert-butyl 4-(5,7-difluoro-3-methyl-4-(5-morpholinopyridin-3-ylamino)quinolin-2-yl)-3-methylpiperazine-1-carboxylate (25 mg, 0.045 mmol) to give (R)-5,7-difluoro-3-methyl-2-(2-methylpiperazin-1-yl)-N-(5-morpholinopyridin-3-yl)quinolin-4-amine. $^1$H NMR (CDCl$_3$) δ ppm 7.93 (1H, d, J=2.5 Hz), 7.65 (1H, d, J=2.2 Hz), 7.33 (1H, dt, J=9.7, 1.2 Hz), 6.99-7.09 (1H, m), 6.87 (1H, ddd, J=13.7, 8.6, 2.5 Hz), 6.61 (1H, t, J=2.3 Hz), 4.06-4.23 (1H, m), 3.78-3.92 (4H, m), 3.50-3.73 (2H, m), 3.32-3.49 (3H, m), 3.08-3.27 (5H, m), 2.07 (3H, s), 1.40 (3H, d, J=6.8 Hz). Mass Spectrum (ESI) m/e=455.2 (M+1).

Example 284

Preparation of (R)-Methyl 4-(5,7-difluoro-3-methyl-4-(5-morpholinopyridin-3-ylamino)quinolin-2-yl)-3-methylpiperazine-1-carboxylate

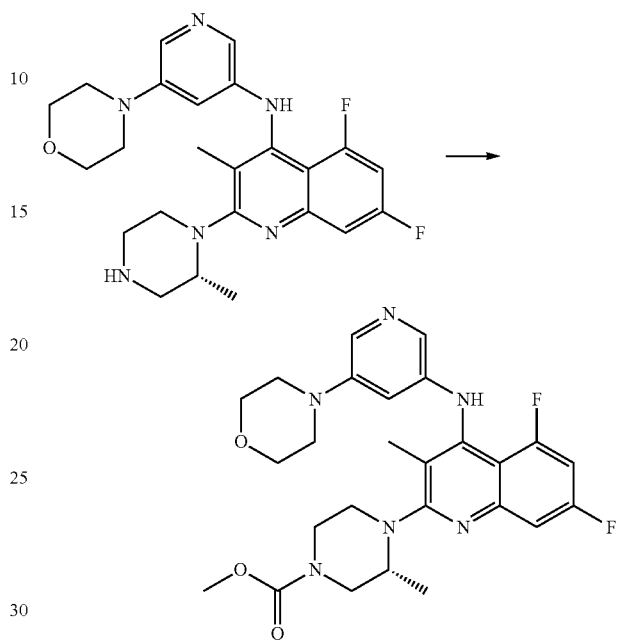

Prepared according to Procedure L using (R)-5,7-difluoro-3-methyl-2-(2-methylpiperazin-1-yl)-N-(5-morpholinopyridin-3-yl)quinolin-4-amine (15.0 mg, 0.033 mmol) and methyl chloroformate to give (R)-methyl 4-(5,7-difluoro-3-methyl-4-(5-morpholinopyridin-3-ylamino)quinolin-2-yl)-3-methylpiperazine-1-carboxylate. TFA Salt: $^1$H NMR (CDCl$_3$) δ ppm 8.11-8.35 (1H, m), 7.91 (1H, br. s.), 7.85 (1H, br. s.), 7.52 (1H, d, J=10.4 Hz), 7.21 (1H, br. s.), 6.84 (1H, ddd, J=12.8, 8.6, 2.6 Hz), 4.03-4.33 (2H, m), 3.96 (1H, br. s.), 3.82-3.91 (4H, m), 3.77 (3H, s), 3.51-3.71 (2H, m), 3.36 (1H, d, J=13.9 Hz), 3.26-3.33 (4H, m), 3.22 (1H, br. s.), 2.13 (3H, s), 1.32 (3H, d, J=6.7 Hz). Mass Spectrum (ESI) m/e=513.3 (M+1).

Example 285

Preparation of (S)-tert-Butyl 1-(5,7-difluoro-3-methyl-4-(5-morpholinopyridin-3-ylamino)quinolin-2-yl)pyrrolidine-2-carboxylate (S)-tert-Butyl 1-(4-chloro-5,7-difluoro-3-methylquinolin-2-yl)pyrrolidine-2-carboxylate

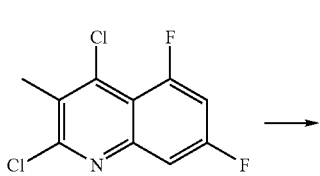

-continued

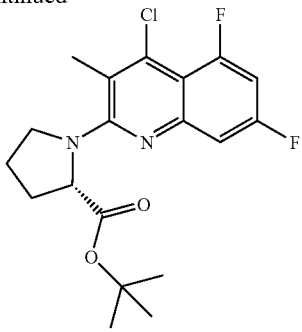

The 2,4-dichloro-5,7-difluoro-3-methylquinoline (300 mg, 1.20 mmol), (S)-tert-butyl pyrrolidine-2-carboxylate (620 mg, 3.60 mmol) and triethylamine (50 µL, 3.60 mmol) were combined in acetonitrile (7.6 mL). The mixture was then heated in a microwave reactor at 140° C. for 90 min. The reaction mixture was then cond to dryness and the residue was diluted with water (~25 mL) and acetic acid (2 mL). This mixture was extracted with DCM (2×75 mL). The combined organic layers were washed with water (50 mL) and brine (50 mL) and dried over magnesium sulfate. The filtrate was cond to obtain (S)-tert-butyl 1-(4-chloro-5,7-difluoro-3-methylquinolin-2-yl)pyrrolidine-2-carboxylate. Mass Spectrum (ESI) m/e=383.2 (M+1).

(S)-tert-Butyl 1-(5,7-difluoro-3-methyl-4-(5-morpholinopyridin-3-ylamino)-quinolin-2-yl)pyrrolidine-2-carboxylate

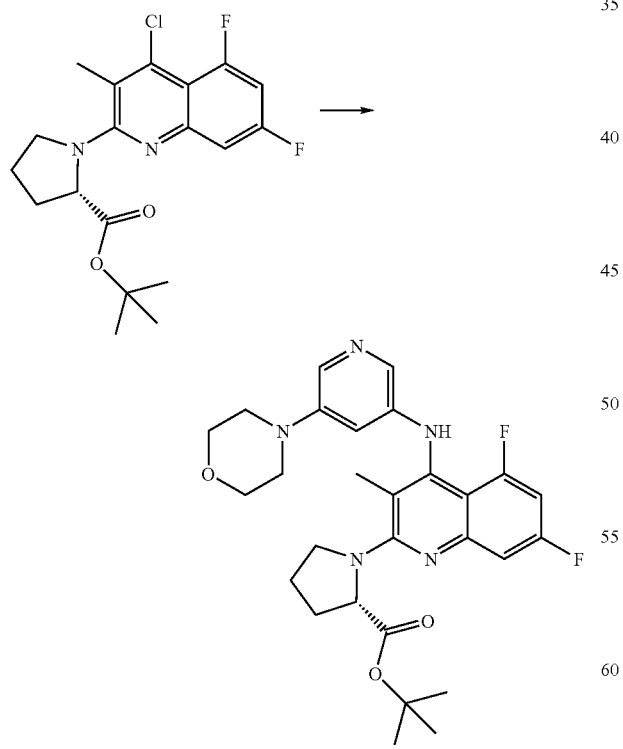

Prepared according to Procedure H using (S)-tert-butyl 1-(4-chloro-5,7-difluoro-3-methylquinolin-2-yl)pyrrolidine-2-carboxylate (260 mg, 0.68 mmol) and 5-morpholinopyridin-3-amine in toluene to give (S)-tert-butyl 1-(5,7-difluoro-3-methyl-4-(5-morpholinopyridin-3-ylamino) quinolin-2-yl)pyrrolidine-2-carboxylate. $^1$H NMR (CDCl$_3$) δ ppm 7.80 (1H, d, J=2.2 Hz), 7.65-7.75 (2H, m), 7.07-7.17 (1H, m), 6.90 (1H, br. s.), 6.60 (1H, ddd, J=13.1, 8.8, 2.5 Hz), 4.71 (1H, t, J=7.0 Hz), 3.83-3.94 (1H, m), 3.77-3.83 (4H, m), 3.67-3.77 (1H, m), 3.15-3.26 (4H, m), 2.28-2.43 (1H, m), 2.21 (3H, s), 2.08-2.19 (1H, m), 1.90-2.06 (2H, m), 1.45 (9H, s). Mass Spectrum (ESI) m/e=526.3 (M+1).

Example 286

Preparation of (S)-1-(5,7-Difluoro-3-methyl-4-(5-morpholinopyridin-3-ylamino)quinolin-2-yl)pyrrolidine-2-carboxylic acid, ammonia salt

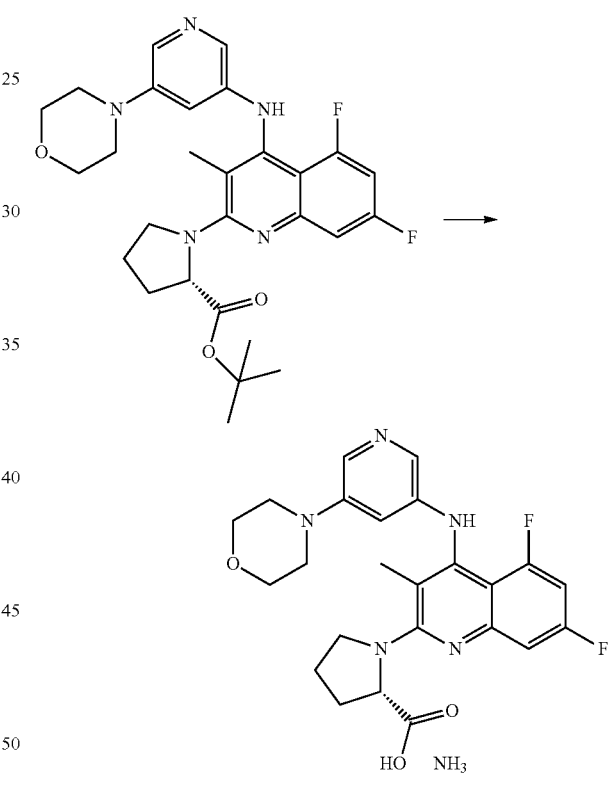

Prepared according to Procedure O using (S)-tert-butyl 1-(5,7-difluoro-3-methyl-4-(5-morpholinopyridin-3-ylamino)quinolin-2-yl)pyrrolidine-2-carboxylate (133 mg, 0.25 mmol) to give (S)-1-(5,7-difluoro-3-methyl-4-(5-morpholinopyridin-3-ylamino)quinolin-2-yl)pyrrolidine-2-carboxylic acid, ammonia salt. $^1$H NMR (DMSO-d6) δ ppm 8.21 (1H, s), 7.73 (1H, d, J=2.5 Hz), 7.58 (1H, d, J=2.2 Hz), 6.87-7.07 (2H, m), 6.51 (1H, s), 4.64 (1H, t, J=7.2 Hz), 3.72-3.83 (1H, m), 3.67-3.72 (4H, m), 3.56-3.67 (1H, m), 2.99-3.13 (4H, m), 2.25-2.38 (1H, m), 2.06 (3H, s), 1.80-2.03 (3H, m). Mass Spectrum (ESI) m/e=470.2 (M+1).

Example 287

Preparation of (S)-1-(5,7-Difluoro-3-methyl-4-(5-morpholinopyridin-3-ylamino)quinolin-2-yl)-N-methylpyrrolidine-2-carboxamide

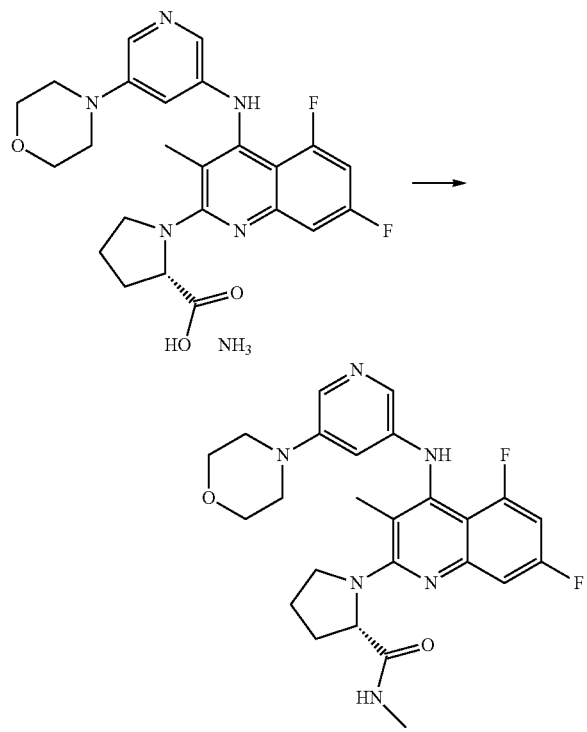

The (S)-1-(5,7-difluoro-3-methyl-4-(5-morpholinopyridin-3-ylamino)quinolin-2-yl)pyrrolidine-2-carboxylic acid (72 mg, 0.15 mmol) was dissolved in DMF (1.0 mL). DIEA (0.13 mL, 0.77 mmol) and 2-(1H-7-azabenzotriazol-1-yl)-1,1,3,3-tetramethyl uronium hexafluorophosphate methanaminium (HATU) (70 mg, 0.18 mmol) were added followed by addition of 2M methyl amine in THF (0.15 mL, 0.31 mmol). The reaction was stirred overnight. The reaction was then diluted with water and extracted with EtOAc (2×50 mL). The combined organic layers were washed with 1M lithium chloride solution (1×20 mL) brine (1×20 mL) and dried over magnesium sulfate. The crude product was then purified by medium pressure chromatography (silica gel, 0 to 7% 2M ammonia in MeOH:DCM) to give impure product. This material was also purified by reverse-phase preparative HPLC using a Phenomenex Gemini column, 10 micron, C18, 100 Å, 150×30 mm, 0.1% TFA in $CH_3CN/H_2O$, gradient 10% to 95% over min to provide the TFA salt of (S)-1-(5,7-difluoro-3-methyl-4-(5-morpholinopyridin-3-ylamino)quinolin-2-yl)-N-methylpyrrolidine-2-carboxamide. The salt was then treated with satd sodium bicarbonate to give the desired product. $^1H$ NMR (Acetonitrile-d3) δ ppm 7.77 (1H, d, J=2.0 Hz), 7.66 (1H, s), 7.61 (1H, d, J=3.1 Hz), 7.16 (1H, d, J=10.0 Hz), 6.96 (1H, br. s.), 6.77-6.89 (1H, m), 6.77 (1H, br. s.), 4.84 (1H, t, J=7.8 Hz), 3.81-3.95 (1H, m), 3.69-3.79 (4H, m), 3.56 (1H, t, J=7.5 Hz), 3.10-3.25 (4H, m), 2.63 (3H, d, J=4.7 Hz), 2.28 (1H, m, J=6.8 Hz), 2.19 (3H, s), 2.00 (1H, m, J=4.5 Hz), 1.74-1.91 (2H, m). Mass Spectrum (ESI) m/e=483.3 (M+1).

Example 288

Preparation of (R)-tert-Butyl 1-(5,7-difluoro-3-methyl-4-(5-morpholinopyridin-3-ylamino)quinolin-2-yl)pyrrolidine-2-carboxylate (R)-tert-Butyl 1-(4-chloro-5,7-difluoro-3-methylquinolin-2-yl)pyrrolidine-2-carboxylate

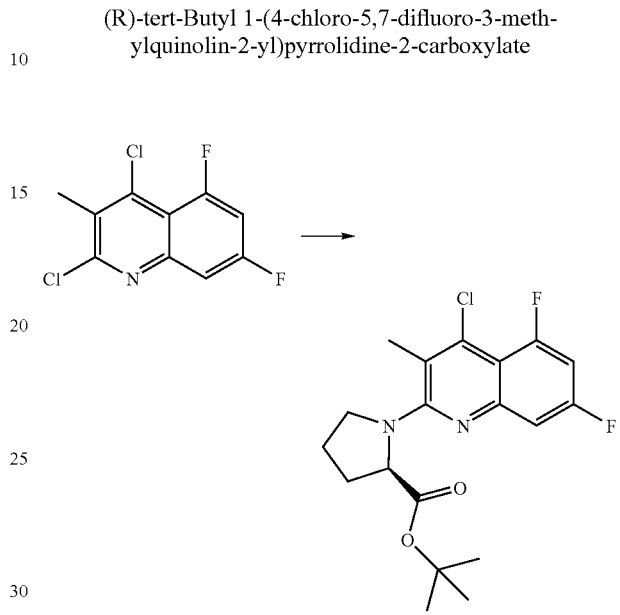

The 2,4-dichloro-5,7-difluoro-3-methylquinoline (450 mg, 1.8 mmol), (R)-tert-butyl pyrrolidine-2-carboxylate (780 mg, 4.50 mmol) and triethylamine (0.63 mL, 4.5 mmol) were combined in acetonitrile (11 mL). The mixture was then heated in a microwave reactor at 140° C. for 90 min. The reaction mixture was then cond to dryness and diluted with water (35 mL) and acetic acid (3 mL) to acidify the solution. This mixture was extracted with EtOAc (1×100 mL) and DCM (1×100 mL). The combined organic layers were washed with water (50 mL) and brine (50 mL) and dried over magnesium sulfate. The filtrate was cond to obtain (R)-tert-butyl 1-(4-chloro-5,7-difluoro-3-methylquinolin-2-yl)pyrrolidine-2-carboxylate. Mass Spectrum (ESI) m/e=383.2 (M+1).

(R)-tert-Butyl 1-(5,7-difluoro-3-methyl-4-(5-morpholinopyridin-3-ylamino)-quinolin-2-yl)pyrrolidine-2-carboxylate

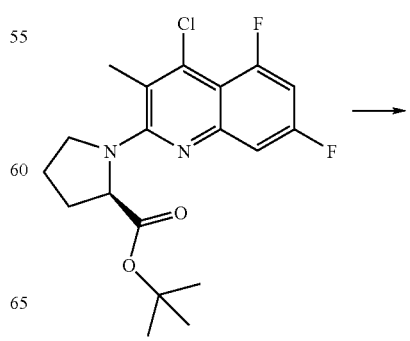

427

-continued

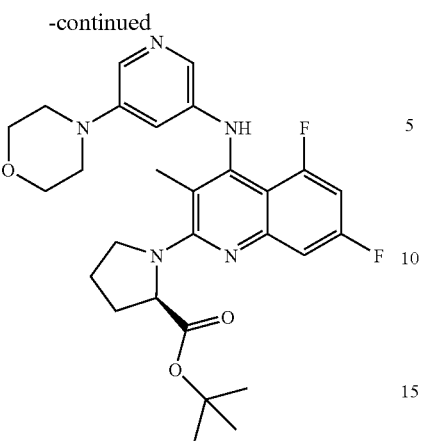

Prepared according to Procedure H using (R)-tert-butyl 1-(4-chloro-5,7-difluoro-3-methylquinolin-2-yl)pyrrolidine-2-carboxylate (350 mg, 0.91 mmol) and 5-morpholinopyridin-3-amine in toluene to give (R)-tert-butyl 1-(5,7-difluoro-3-methyl-4-(5-morpholinopyridin-3-ylamino)quinolin-2-yl)pyrrolidine-2-carboxylate. $^1$H NMR (CDCl$_3$) δ ppm 7.90 (1H, d, J=2.3 Hz), 7.77 (1H, d, J=2.2 Hz), 7.10 (1H, ddd, J=10.3, 2.4, 1.2 Hz), 6.85 (1H, d, J=12.5 Hz), 6.66 (1H, ddd, J=14.0, 8.9, 2.5 Hz), 6.61 (1H, t, J=2.3 Hz), 4.68 (1H, t, J=7.0 Hz), 3.77-3.90 (5H, m), 3.56-3.68 (1H, m), 3.12-3.21 (4H, m), 2.23-2.39 (1H, m), 2.13-2.21 (1H, m), 2.12 (3H, s), 1.90-2.07 (2H, m), 1.44 (9H, s). Mass Spectrum (ESI) m/e=526.3 (M+1).

Example 289

Preparation of (R)-1-(5,7-difluoro-3-methyl-4-(5-morpholinopyridin-3-ylamino)quinolin-2-yl)pyrrolidine-2-carboxylic acid, ammonia salt

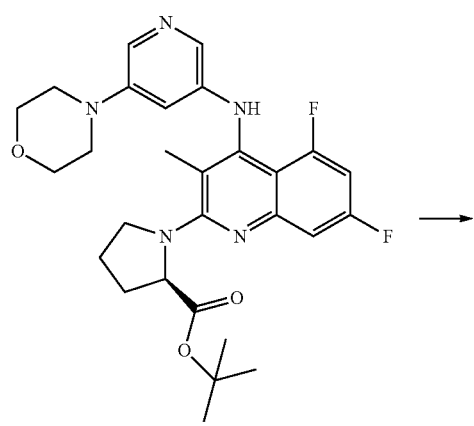

428

-continued

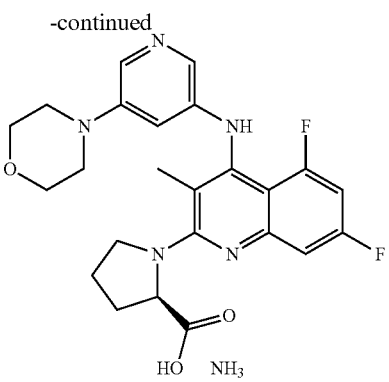

Prepared according to Procedure O using (R)-tert-butyl 1-(5,7-difluoro-3-methyl-4-(5-morpholinopyridin-3-ylamino)quinolin-2-yl)pyrrolidine-2-carboxylate (250 mg, 0.48 mmol) to give (R)-1-(5,7-difluoro-3-methyl-4-(5-morpholinopyridin-3-ylamino)quinolin-2-yl)pyrrolidine-2-carboxylic acid, ammonia salt. $^1$H NMR (DMSO-d6) δ ppm 8.26 (1H, s), 7.75 (1H, d, J=2.5 Hz), 7.57 (1H, d, J=2.0 Hz), 6.92-7.11 (2H, m), 6.52 (1H, s), 4.69 (1H, t, J=7.2 Hz), 3.74-3.86 (2H, m), 3.69 (4H, d, J=5.1 Hz), 3.58-3.67 (1H, m), 3.07 (4H, dd, J=5.5, 3.7 Hz), 2.23-2.39 (1H, m), 2.08 (3H, s), 1.80-2.05 (2H, m). Mass Spectrum (ESI) m/e=470.2 (M+1).

Example 290

Preparation of (R)-1-(5,7-Difluoro-3-methyl-4-(5-morpholinopyridin-3-ylamino)quinolin-2-yl)-N-methylpyrrolidine-2-carboxamide

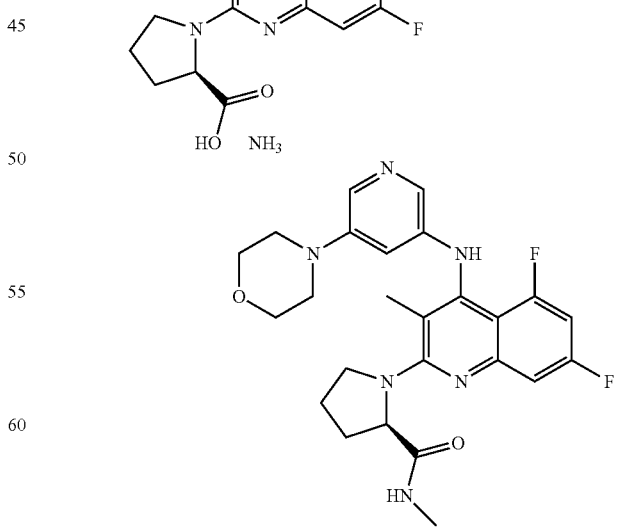

The (R)-1-(5,7-difluoro-3-methyl-4-(5-morpholinopyridin-3-ylamino)quinolin-2-yl)pyrrolidine-2-carboxylic acid, ammonia salt (50 mg, 0.10 mmol) was dissolved in DMF (1.0 mL). The triethylamine (0.029 mL, 0.21 mmol), bromotripyrrolidin-1-ylphosphonium hexafluorophosphate(V) (PyBrop) (120 mg, 0.26 mmol) and 2.0M methylamine in THF (1.0 mL, 2.1 mmol) were added. The reaction was stirred overnight. The reaction was then diluted with water and extracted with ether (3×30 mL). The combined organic layers were washed with 1M lithium chloride solution (1×30 mL) and brine (1×30 mL) and dried over magnesium sulfate. The crude material was purified medium pressure chromatography (silica gel, 0 to 7% 2M ammonia in MeOH:DCM) to give (R)-1-(5,7-difluoro-3-methyl-4-(5-morpholinopyridin-3-ylamino)quinolin-2-yl)-N-methylpyrrolidine-2-carboxamide. $^1$H NMR (CDCl$_3$) δ ppm 7.94 (1H, d, J=2.5 Hz), 7.76 (1H, d, J=2.2 Hz), 7.29 (1H, br. s.), 6.99 (1H, d, J=13.9 Hz), 6.75 (1H, ddd, J=14.0, 8.7, 2.5 Hz), 6.65 (1H, br. s.), 6.62 (1H, br. s.), 5.16 (1H, t, J=7.8 Hz), 3.78-4.01 (5H, m), 3.30-3.44 (1H, m), 3.11-3.29 (4H, m), 2.78 (3H, d, J=5.1 Hz), 2.30-2.44 (1H, m), 2.13-2.29 (1H, m), 2.10 (3H, s), 2.02-2.09 (1H, m), 1.80-1.98 (1H, m). Mass Spectrum (ESI) m/e=483.3 (M+1).

rolidin-1-ylphosphonium hexafluorophosphate(V) (PyBrop) (160 mg, 0.34 mmol) and 2.0M dimethylamine in THF (1.4 mL, 2.8 mmol) were added. The reaction was stirred overnight. The reaction was then diluted with water and extracted with ether (3×30 mL). The combined organic layers were washed with 1M lithium chloride solution (1×30 mL) and brine (1×30 mL) and dried over magnesium sulfate. The crude material was purified by medium pressure chromatography (silica gel, 0 to 8% 2M ammonia in MeOH:DCM) to give (R)-1-(5,7-difluoro-3-methyl-4-(5-morpholinopyridin-3-ylamino)quinolin-2-yl)-N,N-dimethylpyrrolidine-2-carboxamide. $^1$H NMR (CDCl$_3$) δ ppm 7.88 (1H, d, J=2.2 Hz), 7.74 (1H, d, J=1.6 Hz), 6.99 (1H, d, J=11.2 Hz), 6.94 (1H, d, J=10.6 Hz), 6.68 (1H, t, J=2.1 Hz), 6.63 (1H, ddd, J=13.8, 8.9, 2.5 Hz), 5.13-5.29 (1H, m), 3.90-4.05 (1H, m), 3.82-3.90 (4H, m), 3.58-3.69 (1H, m), 3.39 (3H, s), 3.18 (4H, dd, J=5.7, 3.9 Hz), 3.02 (3H, s), 2.17-2.36 (2H, m), 2.14 (3H, s), 1.88-2.11 (2H, m). Mass Spectrum (ESI) m/e=497.2 (M+1).

Example 291

Preparation of (R)-1-(5,7-Difluoro-3-methyl-4-(5-morpholinopyridin-3-ylamino)quinolin-2-yl)-N,N-dimethylpyrrolidine-2-carboxamide

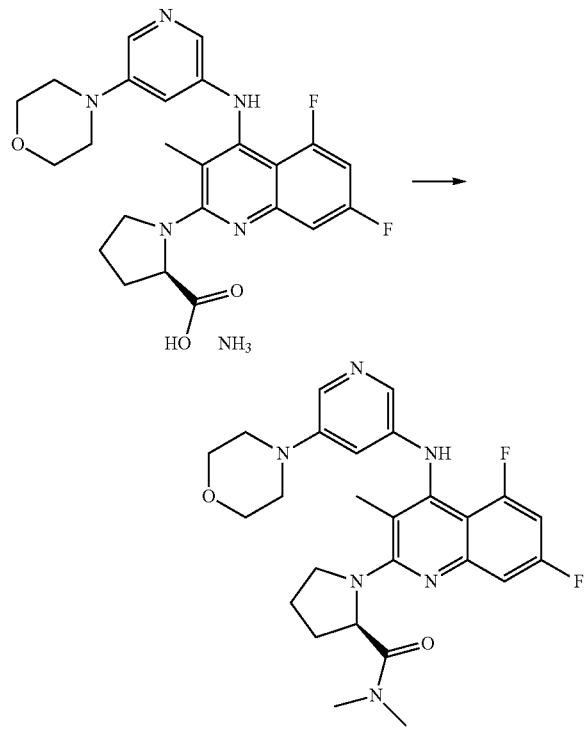

The (R)-1-(5,7-difluoro-3-methyl-4-(5-morpholinopyridin-3-ylamino)quinolin-2-yl)pyrrolidine-2-carboxylic acid, ammonia salt (67 mg, 0.14 mmol) was dissolved in DMF (1.0 mL). The triethylamine (0.038 mL, 0.28 mmol), bromotripyr- Example 292

Preparation of (S)-tert-Butyl 4-(5,7-difluoro-3-methyl-4-(5-morpholinopyridin-3-ylamino)quinolin-2-yl)-3-methylpiperazine-1-carboxylate (S)-tert-Butyl 4-(4-chloro-5,7-difluoro-3-methylquinolin-2-yl)-3-methylpiperazine-1-carboxylate

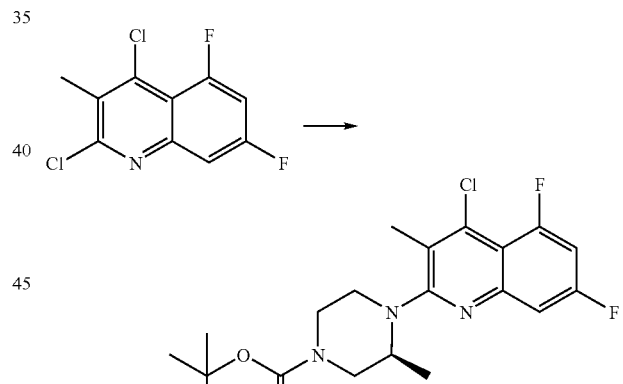

The 2,4-dichloro-5,7-difluoro-3-methylquinoline (150 mg, 0.60 mmol) was slurried in N-methylpyrrolidinone (1.0 mL) and (S)-tert-butyl 3-methylpiperazine-1-carboxylate (110 mg, 0.54 mmol) and cesium carbonate (360 mg, 1.10 mmol) were added and the reaction mixture was heated at 120° C. for 2.5 h in the microwave. The reaction mixture was then diluted with water (15 mL) and the mixture was extracted with ethyl acetate (3×50 mL). The combined layers were combined and washed with water (1×100 mL) and brine (1×30 mL). The organic layer was dried over magnesium sulfate and the residue was purified by medium pressure chromatography (silica gel, 0 to 15% EtOAc:hexanes) to give (S)-tert-butyl 4-(4-chloro-5,7-difluoro-3-methylquinolin-2-yl)-3-methylpiperazine-1-carboxylate. Mass Spectrum (ESI) m/e=412.1 (M+1).

431

(S)-tert-Butyl 4-(5,7-difluoro-3-methyl-4-(5-morpholinopyridin-3-ylamino)-quinolin-2-yl)-3-methylpiperazine-1-carboxylate

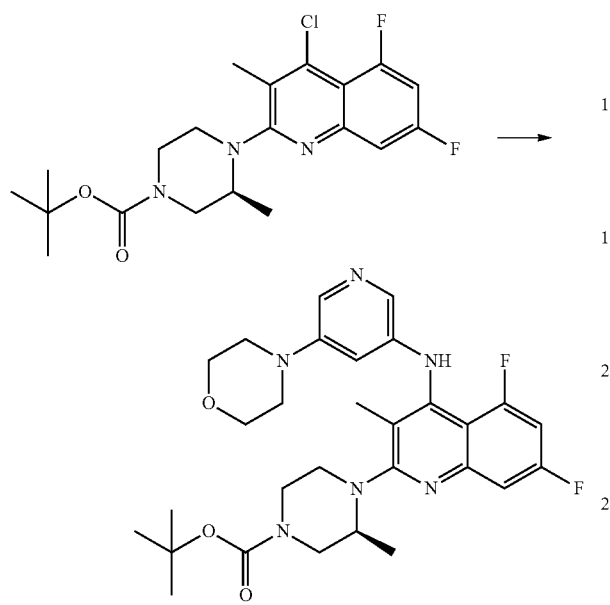

Prepared according to Procedure H using (S)-tert-butyl 4-(4-chloro-5,7-difluoro-3-methylquinolin-2-yl)-3-methylpiperazine-1-carboxylate (52.0 mg, 0.13 mmol) 5-morpholinopyridin-3-amine in toluene to give (S)-tert-butyl 4-(5,7-difluoro-3-methyl-4-(5-morpholinopyridin-3-ylamino)quinolin-2-yl)-3-methylpiperazine-1-carboxylate. $^1$H NMR (CDCl$_3$) δ ppm 7.91 (1H, d, J=2.3 Hz), 7.71 (1H, d, J=2.2 Hz), 7.25-7.33 (1H, m), 6.96 (1H, d, J=12.1 Hz), 6.79 (1H, ddd, J=13.8, 8.8, 2.6 Hz), 6.57 (1H, t, J=2.3 Hz), 4.01 (1H, br. s.), 3.88-3.96 (1H, m), 3.81-3.88 (4H, m), 3.76 (1H, br. s.), 3.34-3.48 (2H, m), 3.25 (2H, br. s.), 3.11-3.18 (4H, m), 2.08 (3H, s), 1.50 (9H, s), 1.17 (3H, d, J=6.5 Hz). Mass Spectrum (ESI) m/e=555.3 (M+1).

Example 293

Preparation of (S)-5,7-Difluoro-3-methyl-2-(2-methylpiperazin-1-yl)-N-(5-morpholinopyridin-3-yl)quinolin-4-amine

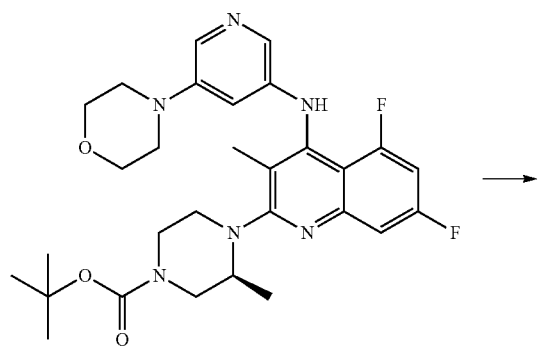

432

-continued

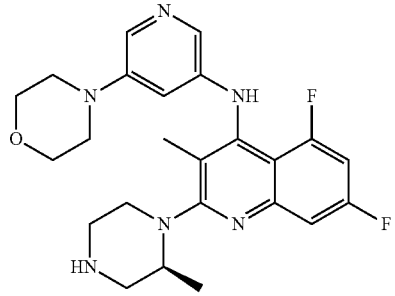

Prepared according to Procedure O using (S)-tert-butyl 4-(5,7-difluoro-3-methyl-4-(5-morpholinopyridin-3-ylamino)quinolin-2-yl)-3-methylpiperazine-1-carboxylate (30.0 mg, 0.054 mmol) to give (S)-5,7-difluoro-3-methyl-2-(2-methylpiperazin-1-yl)-N-(5-morpholinopyridin-3-yl)quinolin-4-amine. $^1$H NMR (CDCl$_3$) δ ppm 7.92 (1H, d, J=2.5 Hz), 7.68 (1H, d, J=2.3 Hz), 7.28-7.34 (1H, m), 6.89 (1H, d, J=13.1 Hz), 6.80 (1H, ddd, J=13.8, 8.8, 2.6 Hz), 6.56 (1H, t, J=2.3 Hz), 3.88-4.00 (1H, m), 3.81-3.88 (4H, m), 3.71 (2H, br. s.), 3.36-3.47 (2H, m), 3.22 (1H, dd, J=12.3, 3.7 Hz), 3.03-3.19 (5H, m), 2.91 (1H, dd, J=12.3, 3.9 Hz), 2.07 (3H, s), 1.27 (3H, d, J=6.7 Hz). Mass Spectrum (ESI) m/e=455.2 (M+1).

Example 294

Preparation of N-(2,5-di-4-morpholinylphenyl)-3-methyl-2-(2-pyridinyl)-1,8-naphthyridin-4-amine-3-methyl-1,8-naphthyridine-2,4-diol

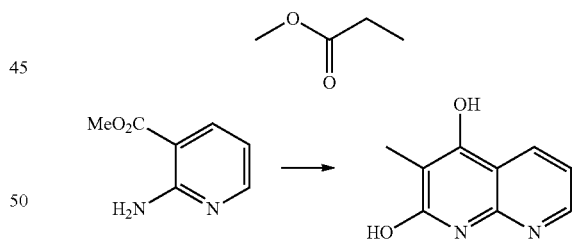

To a stirred solution of methyl 2-aminonicotinate (1.3 g, 8.54 mmol) and methyl propionate (20.08 mL, 214 mmol) in THF (20 mL) was added sodium tert-butoxide (2.053 g, 21.36 mmol) portion wise over 1 min. The reaction was stirred at rt for 40 min and then at 100° C. for 4 h. After this time the reaction was cooled to rt and evaporated in vacuo. The resulting solid was dissolved in water (20 mL) and neutralized to pH 7 with 1.0M aqueous HCl. The resulting solid was filtered and dried under vacuum overnight to give 3-methyl-1,8-naphthyridine-2,4-diol as a tan solid. Mass Spectrum (ESI) m/e=177.2 (M+1).

433

2,4-Dichloro-3-methyl-1,8-naphthyridine

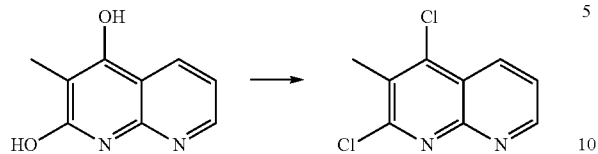

A stirred suspension of 3-methyl-1,8-naphthyridine-2,4-diol (0.82 g, 4.65 mmol) in phosphorus oxychloride (4.34 mL, 46.5 mmol) was heated at 120° C. for 3 h. After this time the reaction was allowed to cool to rt and evaporated in vacuo. The resulting residue was carefully basified to pH>10 with an aqueous solution of $Na_2CO_3$ and the resulting solid was filtered, washed with water and dried under vacuum to give 2,4-dichloro-3-methyl-1,8-naphthyridine. H NMR (400 MHz, CDCl3) δ ppm 9.11 (1H, dd, J=4.3, 2.0 Hz), 8.57 (1H, dd, J=8.4, 2.0 Hz), 7.60 (1H, dd, J=8.3, 4.2 Hz), 2.72 (3H, s).

4-Chloro-3-methyl-2-(pyridin-2-yl)-1,8-naphthyridine

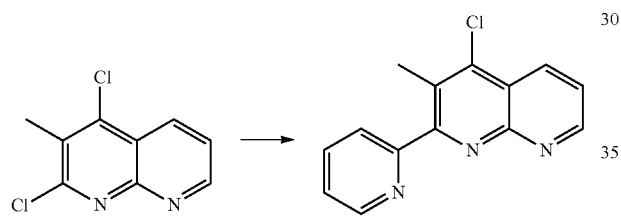

The Stille coupled product was prepared according to Procedure E using 2,4-dichloro-3-methyl-1,8-naphthyridine (540 mg, 2.53 mmol), 2-(1,1,1-tributylstannyl)pyridine (933 µL, 2.53 mmol), Pd(PPh3)4 in toluene (10 mL) and heating at reflux for 14 h. The reaction was allowed to cool to rt and evaporated in vacuo. The resulting residue was triturated with hexanes and the solid was dried under vacuum to give 4-chloro-3-methyl-2-(pyridin-2-yl)-1,8-naphthyridine. 1H NMR (400 MHz, CDCl3) δ ppm 9.14 (1H, dd, J=4.3, 2.0 Hz), 8.72 (1H, ddd, J=4.9, 1.8, 1.0 Hz), 8.65 (1H, dd, J=8.3, 1.9 Hz), 8.09 (1H, dt, J=8.0, 1.1 Hz), 7.90 (1H, td, J=7.7, 1.8 Hz), 7.60 (1H, dd, J=8.3, 4.2 Hz), 7.40 (1H, ddd, J=7.6, 4.8, 1.3 Hz), 2.75 (3H, s)

N-(2,5-Di-4-morpholinylphenyl)-3-methyl-2-(2-pyridinyl)-1,8-naphthyridin-4-amine

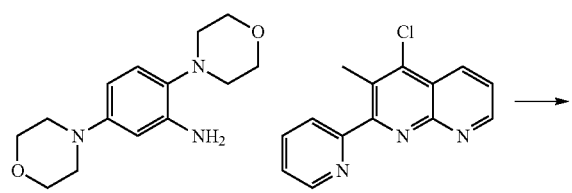

434

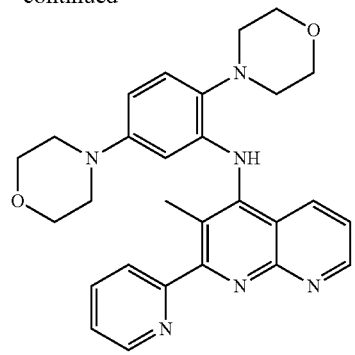

To a stirred solution of 4-chloro-3-methyl-2-(pyridin-2-yl)-1,8-naphthyridine (48.6 mg, 0.19 mmol), 2,5-dimorpholinoaniline (50 mg, 0.19 mmol) and XPhos precatalyst (14 mg, 0.019 mmol) in toluene (4 mL) was added sodium tert-butoxide (36 mg, 0.38 mmol) and the reaction was heated at reflux for 2 h. After this time the reaction was allowed to cool to rt and partitioned between EtOAc (60 mL) and water (20 mL). The separated organic layer was dried over $MgSO_4$, filtered and evaporated in vacuo. Purification by reverse phase HPLC gave N-(2,5-di-4-morpholinylphenyl)-3-methyl-2-(2-pyridinyl)-1,8-naphthyridin-4-amine. H NMR (500 MHz, CDCl3) δ ppm 9.08 (1H, dd, J=3.9, 1.7 Hz), 8.71 (1H, br. s.), 8.26 (1H, dd, J=8.3, 1.7 Hz), 8.16 (1H, d, J=7.8 Hz), 7.88-7.96 (1H, m), 7.39 (2H, dd, J=8.3, 4.2 Hz), 7.11 (1H, d, J=8.8 Hz), 6.45 (1H, dd, J=8.7, 2.6 Hz), 5.99 (1H, d, J=2.7 Hz), 3.90 (4H, t, J=4.4 Hz), 3.66-3.77 (4H, m), 3.05 (4H, br. s.), 2.82-2.93 (4H, m), 2.51 (3H, s). Mass Spectrum (ESI) m/e=483.2 (M+1).

Example 295

Preparation of 3-methyl-N-(5-(4-morpholinyl)-3-pyridinyl)-2-(2-pyridinyl)-1,8-naphthyridin-4-amine

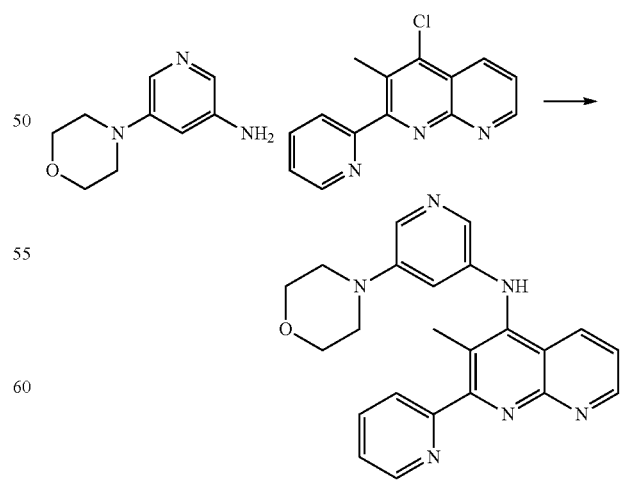

To a stirred solution of 4-chloro-3-methyl-2-(pyridin-2-yl)-1,8-naphthyridine (70 mg, 0.27 mmol), 5-morpholinopyridin-3-amine (49 mg, 0.27 mmol) and XPhos precatalyst (20 mg, 0.027 mmol) in toluene (4 mL) was added sodium tert-butoxide (52 mg, 0.55 mmol) and the reaction was heated at reflux for 2 h. After this time the reaction was allowed to cool to rt and partitioned between EtOAc (60 mL) and water (20 mL). The separated organic layer was dried over MgSO₄, filtered and evaporated in vacuo. Purification by reverse phase HPLC gave 3-methyl-N-(5-(4-morpholinyl)-3-pyridinyl)-2-(2-pyridinyl)-1,8-naphthyridin-4-amine. H NMR (400 MHz, CDCl3) δ ppm 9.03 (1H, dd, J=4.1, 2.0 Hz), 8.69 (1H, ddd, J=4.8, 1.7, 1.1 Hz), 8.20 (1H, dd, J=8.3, 1.9 Hz), 8.08 (1H, dt, J=7.9, 1.1 Hz), 7.84-7.93 (2H, m), 7.78 (1H, d, J=2.3 Hz), 7.31-7.42 (2H, m), 6.51-6.61 (1H, m), 6.37 (1H, t, J=2.4 Hz), 3.74-3.87 (4H, m), 3.00-3.10 (4H, m), 2.47 (3H, s). Mass Spectrum (ESI) m/e=399.2 (M+1).

Example 296

Preparation 4-(5-(5,7-difluoro-3-methyl-2-(pyridin-2-yl)-quinolin-4-yloxy)pyridin-3-yl)morpholine 5-Morpholinopyridin-3-ol

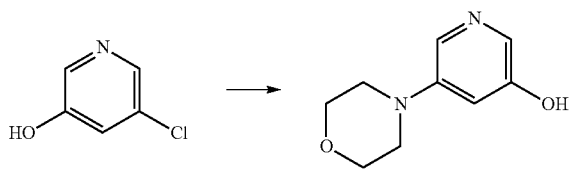 [SMILES: Oc1cncc(Cl)c1 ; Oc1cncc(N2CCOCC2)c1]

A mixture of 5-chloro-3-hydroxypyridine (0.2 g, 1.6 mmol), morpholine (0.7 mL, 8.0 mmol), 2-(dicyclohexylphosphino)-2',4',6',-triisopropyl-biphenyl, (X-Phos) (0.12 g, 0.26 mmol), and tris(dibenzylideneacetone)dipalladium (0) (0.06 g, 0.07 mmol) in dry THF (2.0 mL) was degassed by nitrogen. To this mixture was added 1.0M lithium bis(trimethylsilyl)amide in THF (8.8 mL, 8.8 mmol) dropwise, and the resulting reaction was heated to 60° C. After 20.5 h, the reaction was cooled to rt then concd. The residue was purified on silica gel (0-100% of a premixed solution of 89:9:1 DCM:methanol:ammonium hydroxide in DCM) to afford an off white solid as 5-morpholinopyridin-3-ol. ¹H NMR (500 MHz, DMSO-d₆) δ ppm 9.62 (1H, br. s.), 7.79 (1H, d, J=2.4 Hz), 7.61 (1H, d, J=2.2 Hz), 6.65 (1H, t, J=2.4 Hz), 3.79 (4H, m), 3.16 (4H, m). Mass Spectrum (pos.) m/e: 181.0 (M+H)⁺.

4-(5-(5,7-Difluoro-3-methyl-2-(pyridin-2-yl)quinolin-4-yloxy)pyridin-3-yl)morpholine

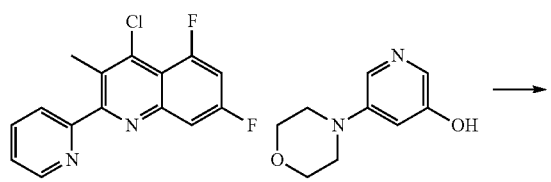

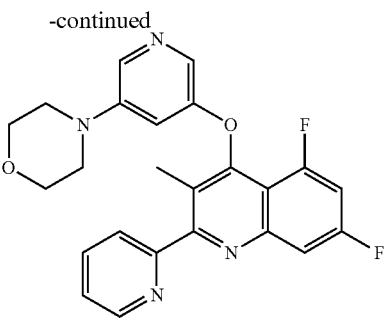

To a vial containing 5-morpholinopyridin-3-ol (67.3 mg, 0.37 mmol) in DMF (3 mL) was added cesium carbonate (0.26 g, 0.8 mmol) in portions. The mixture was stirred at 23° C. for 15 minutes, then 4-chloro-5,7-difluoro-3-methyl-2-(pyridin-2-yl)quinoline (90.7 mg, 0.31 mmol) was added in portions. Upon complete addition, the mixture was warmed to 100° C. After 18 h, the reaction mixture was diluted with water then subsequently extracted five times with EtOAc. The organic extractions were then washed one time with brine and dried over anhydrous magnesium sulfate. After filtration and concentration, the residue was purified on silica gel (0-45% of a premixed solution of 89:9:1 DCM:methanol:ammonium hydroxide in DCM) to afford light yellow film that was further purified with HPLC (10-90% of 0.1% TFA acetonitrile solution in 0.1% TFA water solution.) The desired fractions were concd then diluted with EtOAc. After washing twice with satd aq. sodium bicarbonate solution and once with brine, the solvent was removed under reduced pressure to yield a light yellow solid as 4-(5-(5,7-difluoro-3-methyl-2-(pyridin-2-yl)quinolin-4-yloxy)pyridin-3-yl)morpholine. ¹H NMR (500 MHz, CDCl₃) δ ppm 8.74 (1H, d, J=4.6 Hz), 8.12 (1H, d, J=2.4 Hz), 7.98 (2H, m), 7.68 (1H, dd, J=9.4, 1.3 Hz), 7.59 (1H, d, J=2.2 Hz), 7.43 (1H, sxt, J=4.4 Hz), 7.02 (1H, ddd, J=11.4, 8.9, 2.4 Hz), 6.87 (1H, s), 3.93 (4H, m), 3.29 (4H, m), 2.41 (3H, s). Mass Spectrum (pos.) m/e: 435.1 (M+H)⁺.

Example 297

Preparation of 4-(5,7-difluoro-3-methyl-2-(pyridin-2-yl)quinolin-4-ylamino)-5-(5-methoxypyridin-3-yl)-2-morpholinobenzonitrile 4-Amino-2-chloro-5-iodobenzonitrile

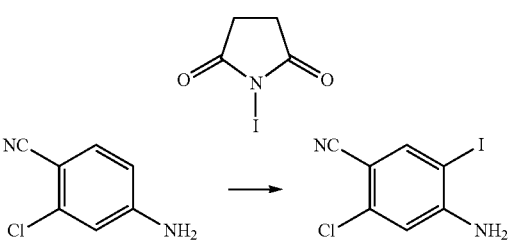

A mixture of 4-amino-2-chlorobenzonitrile (5.0 g, 33 mmol) and N-iodosuccinimide (8.4 g, 37 mmol) in Acetic Acid (35 mL) was stirred at 23° C. After 18 h, the solid was collected by filtration then purified on silica gel (0-20% EtOAc in hexanes) to afford a pale brown solid as 4-amino-2-chloro-5-iodobenzonitrile. ¹H NMR (500 MHz, CDCl₃) δ ppm 7.87 (1H, s), 6.77 (1H, s), 4.72 (2H, br. s.)

4-Amino-5-iodo-2-morpholinobenzonitrile

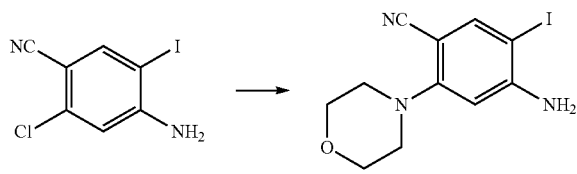 [SMILES: N#Cc1cc(I)c(N)cc1Cl ; N#Cc1cc(I)c(N)cc1N1CCOCC1]

To a flask containing 4-amino-2-chloro-5-iodobenzonitrile (1 g, 3.6 mmol) in DMSO (5.0 mL) was added morpholine (1.0 mL, 11.5 mmol) dropwise. Upon complete addition, the mixture was warmed to 100° C. After 40 h, the reaction mixture was cooled to rt, then an additional 2 mL of morpholine was added to the mixture. The reaction was re-heated to 100° C. and monitored with LC-MS. After 17 h, the reaction was cooled to rt, then 1 g of potassium carbonate was added in portions. The reaction was re-heated to 100° C. and monitored with LC-MS. After 13 days, the reaction was diluted with water then subsequently extracted five times with EtOAc. The organic extractions were then washed one time with brine and dried over anhydrous magnesium sulfate. After filtration and concentration, the residue was purified on silica gel (0-35% EtOAc in hexanes) to afford a pale brown solid as 4-amino-5-iodo-2-morpholinobenzonitrile. $^1$H NMR (500 MHz, CDCl$_3$) δ ppm 7.80 (1H, m), 6.27 (1H, s), 4.57 (2H, br. s.), 3.92 (4H, m), 3.20 (4H, m). Mass Spectrum (pos.) m/e: 330.0 (M+H)$^+$.

4-(5,7-Difluoro-3-methyl-2-(pyridin-2-yl)quinolin-4-ylamino)-5-iodo-2-morpholinobenzonitrile

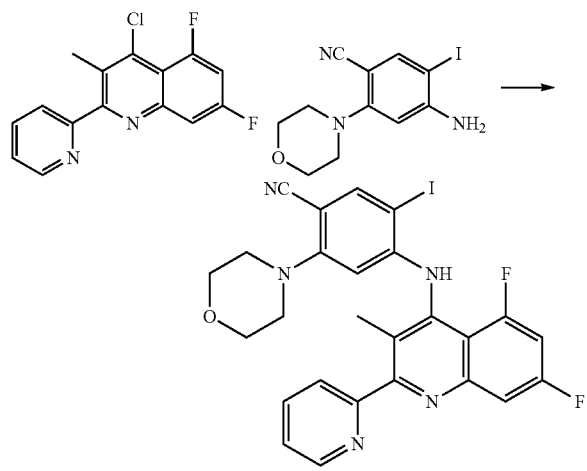

A dry flask containing 4-amino-5-iodo-2-morpholinobenzonitrile (140 mg, 0.42 mmol) in dry DMF (3.0 mL) was cooled to 0° C., then sodium hydride, 60% dispersion in mineral oil (34.7 mg, 0.87 mmol) was added carefully in portions. The mixture was stirred at 0° C. for 15 minutes, then 4-chloro-5,7-difluoro-3-methyl-2-(pyridin-2-yl)quinoline (185 mg, 0.64 mmol) was added in portions. Upon complete addition, the mixture was warmed to 60° C. After 2.5 h, the reaction was cooled to rt then was carefully treated with 10% sodium carbonate solution. The black mixture was subsequently extracted five times with DCM:methanol (90:10). The organic extraction was then washed one time with brine and dried over anhydrous magnesium sulfate. After filtration and concentration, the black residue was treated with methanol and placed on the rotovap. (without vac.) in a 45° C. water bath. After 30 minutes, the solid was filtered and rinsed twice with methanol to afford an off white solid as 4-(5,7-difluoro-3-methyl-2-(pyridin-2-yl)quinolin-4-ylamino)-5-iodo-2-morpholinobenzonitrile. Mass Spectrum (pos.) m/e: 583.9 (M+H)$^+$.

4-(5,7-Difluoro-3-methyl-2-(pyridin-2-yl)quinolin-4-ylamino)-5-(5-methoxypyridin-3-yl)-2-morpholinobenzonitrile

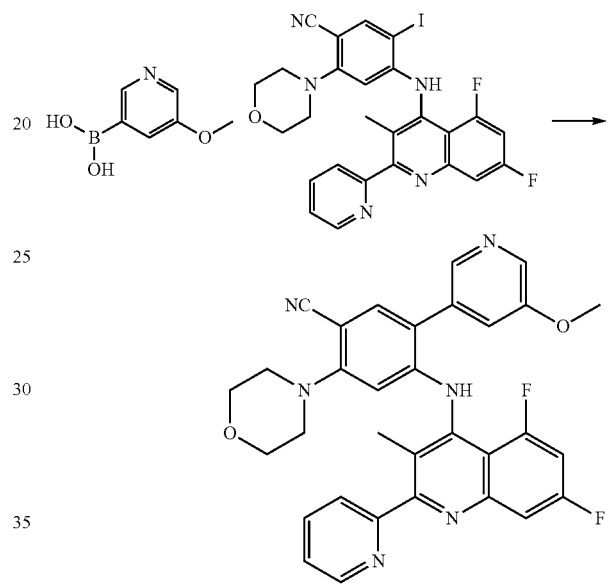

4-(5,7-Difluoro-3-methyl-2-(pyridin-2-yl)quinolin-4-ylamino)-5-iodo-2-morpholinobenzonitrile (65.2 mg, 0.11 mmol), 5-methoxypyridin-3-ylboronic acid (26.6 mg, 0.17 mmol), tricyclohexylphosphine (5.9 mg, 0.021 mmol), and tris(dibenzylideneacetone)dipalladium (0) (9.7 mg, 10.6 µmol) were added to a flask then degassed and backfilled with argon. To the flask, 1,4-dioxane (2.0 mL) and aqueous 1.3M potassium phosphate tribasic (0.26 mL, 0.34 mmol) were added by syringe. The resulting reaction was heated to 90° C. and monitored with TLC and LC-MS. After 19 h, the reaction was cooled to rt then poured into water. After extracting twice with EtOAc and twice with DCM, the combined organic extractions were dried over anhydrous magnesium sulfate. After filtration and concentration, the residue was purified on silica gel (0-50% of a premixed solution of 89:9:1 DCM:methanol:ammonium hydroxide in DCM) to afford a yellow film that was further purified with HPLC (10-90% of 0.1% TFA acetonitrile solution in 0.1% TFA water solution.) The desired fractions were concd then diluted with EtOAc. After washing twice with satd aq. sodium bicarbonate solution and once with brine, the solvent was removed under reduced pressure to yield a yellow solid as 4-(5,7-difluoro-3-methyl-2-(pyridin-2-yl)-quinolin-4-ylamino)-5-(5-methoxypyridin-3-yl)-2-morpholinobenzonitrile. $^1$H NMR (400 MHz, CDCl$_3$) δ ppm 8.73 (1H, m), 8.41 (2H, d, J=2.0 Hz), 7.94 (2H, m), 7.64 (1H, m), 7.47 (3H, m), 7.25 (1H, m), 6.99 (1H, m), 6.87 (1H, m), 6.18 (1H, s), 3.96 (3H, s), 3.85 (4H, m), 3.16 (4H, m), 2.27 (3H, s). Mass Spectrum (pos.) m/e: 565.2 (M+H)$^+$.

Example 298

Preparation of 4-(5,7-difluoro-3-methyl-2-(pyridin-2-yl)-quinolin-4-ylamino)-2-morpholinobenzonitrile 4-Amino-5-iodo-2-morpholinobenzonitrile and 4-amino-2-morpholinobenzonitrile

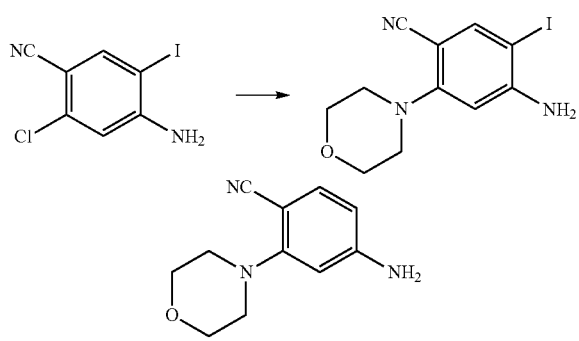

4-Amino-2-chloro-5-iodobenzonitrile (0.60 g, 2.1 mmol) and morpholine (2.0 mL, 23 mmol) were added to a microwave vial and heated in the microwave to 200° C. After 60 minutes, the residue was concd then purified on silica gel (0-40% EtOAc in hexanes) to yield a white solid as 4-amino-5-iodo-2-morpholinobenzonitrile. Mass Spectrum (pos.) m/e: 330.0 (M+H)$^+$. 4-amino-2-morpholinobenzonitrile was also isolated. $^1$H NMR (500 MHz, CDCl$_3$) δ ppm 7.35 (1H, d, J=8.3 Hz), 6.28 (1H, dd, J=8.4, 2.1 Hz), 6.20 (1H, d, J=2.0 Hz), 4.14 (2H, br. s.), 3.95 (4H, m), 3.24 (4H, m). Mass Spectrum (pos.) m/e: 204.1 (M+H)$^+$.

4-(5,7-Difluoro-3-methyl-2-(pyridin-2-yl)quinolin-4-ylamino)-2-morpholinobenzonitrile

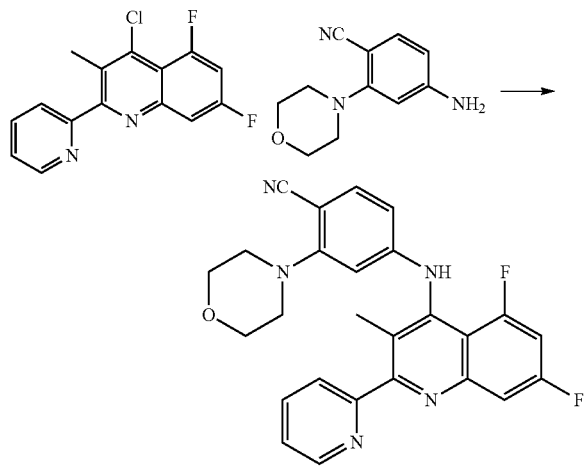

A dry flask containing 4-amino-2-morpholinobenzonitrile (46.5 mg, 0.23 mmol) in dry DMF (2.0 mL) was cooled to 0° C., then potassium tert-butoxide (78.8 mg, 0.70 mmol) was added carefully in portions. The mixture was stirred at 0° C. for 15 minutes, then 4-chloro-5,7-difluoro-3-methyl-2-(pyridin-2-yl)quinoline (74.7 mg, 0.26 mmol) was added in portions. Upon complete addition, the mixture was warmed to 100° C. After 2.5 h, the reaction was cooled to rt then was carefully treated with 10% sodium carbonate solution. The black mixture was subsequently extracted five times with DCM:methanol (90:10). The organic extraction was then washed one time with brine and dried over anhydrous magnesium sulfate. After filtration and concentration, the residue was purified on silica gel (0-45% of a premixed solution of 89:9:1 DCM:methanol:ammonium hydroxide in DCM) to afford a yellow film that was further purified with HPLC (10-90% of 0.1% TFA acetonitrile solution in 0.1% TFA water solution.) The desired fractions were concd then diluted with EtOAc. After washing twice with satd aq. sodium bicarbonate solution and once with brine, the solvent was removed under reduced pressure to yield a light yellow solid as 4-(5,7-difluoro-3-methyl-2-(pyridin-2-yl)quinolin-4-ylamino)-2-morpholinobenzonitrile. $^1$H NMR (500 MHz, CDCl$_3$) δ ppm 8.74 (1H, d, J=4.6 Hz), 7.97 (2H, m), 7.72 (1H, m), 7.47 (1H, d, J=8.3 Hz), 7.44 (1H, m), 7.11 (2H, m), 6.44 (2H, m), 3.96 (4H, m), 3.26 (4H, m), 2.24 (3H, s). Mass Spectrum (pos.) m/e: 458.0 (M+H)$^+$.

Example 299

Preparation of N-(2,5-dimorpholinopyridin-3-yl)-5,7-difluoro-3-methyl-2-(6-morpholinopyridin-3-yl)quinolin-4-amine 4-(5-(4-Chloro-5,7-difluoro-3-methylquinolin-2-yl)pyridin-2-yl)morpholine The Stille coupled product was prepared according to Procedure E using 2,4-dichloro-5,7-difluoro-3-methylquinoline (0.30 g, 1.21 mmol), 4-(5-(tributylstannyl)-pyridin-2-yl)morpholine (0.66 g, 1.45 mmol), palladium tetrakistriphenylphosphine (0.140 g, 0.12 mmol) in toluene (2 mL) to give 4-(5-(4-chloro-5,7-difluoro-3-methylquinolin-2-yl)pyridin-2-yl)morpholine as a white solid. Mass Spectrum (ESI) m/e=376.0 (M+1).

441

N-(2,5-Dimorpholinopyridin-3-yl)-5,7-difluoro-3-methyl-2-(6-morpholinopyridin-3-yl)quinolin-4-amine

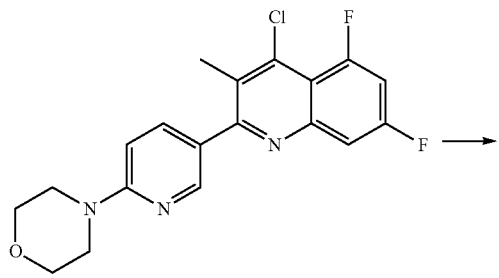

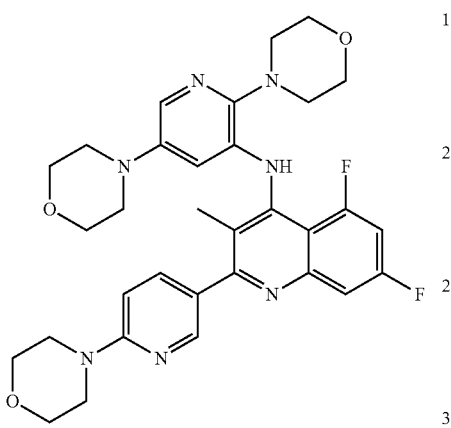

The Buchwald coupled product was prepared according to Procedure S using dicyclohexyl(2',4',6'-triisopropylbiphenyl-2-yl)phosphine (0.020 g, 0.043 mmol), 2,5-dimorpholinopyridin-3-amine (0.084 g, 0.32 mmol), 4-(5-(4-chloro-5,7-difluoro-3-methylquinolin-2-yl)pyridin-2-yl)morpholine (0.1 g, 0.27 mmol), Pd$_2$dba$_3$ (0.010 g, 0.011 mmol) and sodium tert-butoxide (0.079 g, 0.82 mmol) in toluene (2.7 mL) at 120° C. for 1.9 h. The crude product was purified by column chromatography on basic alumina (0 to 50% hexanes/EtOAc) to give the desired product N-(2,5-dimorpholinopyridin-3-yl)-5,7-difluoro-3-methyl-2-(6-morpholinopyridin-3-yl)quinolin-4-amine. 1H NMR (400 MHz, DMSO-d$_6$) δ ppm 8.47 (1H, dd, J=2.4, 0.7 Hz), 7.90 (1H, dd, J=8.8, 2.5 Hz), 7.75 (1H, d, J=5.9 Hz), 7.60 (1H, ddd, J=10.0, 2.5, 1.0 Hz), 7.55 (1H, d, J=2.5 Hz), 7.42 (1H, dd, J=4.0, 2.6 Hz), 6.98 (1H, d, J=8.6 Hz), 6.41 (1H, d, J=2.5 Hz), 3.69-3.78 (6H, m), 3.61-3.69 (6H, m), 3.52-3.61 (4H, m), 3.14 (2H, br. s.), 2.95-3.05 (4H, m), 2.83 (2H, br. s.), 2.12 (3H, s). Mass Spectrum (ESI) m/e=604.3 (M+1).

Example 300

Preparation of N-(2,5-dimorpholinopyridin-3-yl)-5,7-difluoro-3-methyl-2-(6-(piperidin-1-yl)pyridin-3-yl)quinolin-4-amine 4-Chloro-5,7-difluoro-3-methyl-2-(6-(piperidin-1-yl)pyridin-3-yl)quinoline

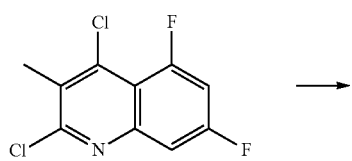

442

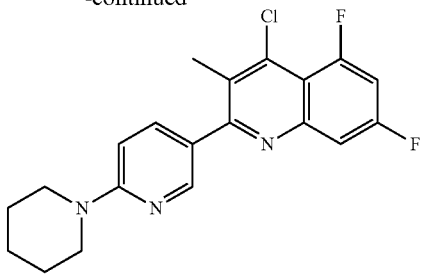

The Suzuki coupled product was prepared according to Procedure F using 2,4-dichloro-5,7-difluoro-3-methylquinoline (0.50 g, 2.02 mmol), 6-(piperidin-1-yl)pyridine-3-boronic acid pinacol ester (0.581 g, 2.02 mmol), palladium tetrakistriphenylphosphine (0.23 g, 0.20 mmol), potassium carbonate (0.56 g, 4.03 mmol) in toluene (4 mL) at 100° C. for 18 h to give 4-chloro-5,7-difluoro-3-methyl-2-(6-(piperidin-1-yl)pyridin-3-yl)quinoline as a yellow solid. Mass Spectrum (ESI) m/e=374.0 (M+1).

N-(2,5-Dimorpholinopyridin-3-yl)-5,7-difluoro-3-methyl-2-(6-(piperidin-1-yl)pyridin-3-yl)quinolin-4-amine The Buchwald coupled product was prepared according to Procedure S using dicyclohexyl(2',4',6'-triisopropylbiphenyl-2-yl)phosphine (0.020 g, 0.043 mmol), 2,5-dimorpholinopyridin-3-amine (0.085 g, 0.32 mmol), 4-chloro-5,7-difluoro-3-methyl-2-(6-(piperidin-1-yl)pyridin-3-yl)quinoline (0.1 g, 0.268 mmol), Pd$_2$dba$_3$ (0.010 g, 0.011 mmol) and sodium tert-butoxide (0.064 g, 0.67 mmol) in toluene (2.7 mL) at 100° C. for 19 h. The crude product was purified by column chromatography on basic alumina (0 to 50% hexanes/EtOAc) to give the desired product N-(2,5-dimorpholinopyridin-3-yl)-5,7-difluoro-3-methyl-2-(6-(piperidin-1-yl)-pyridin-3-yl)quinolin-4-amine. 1H NMR (400 MHz, DMSO-d$_6$) δ ppm 8.44 (1H, dd, J=2.5, 0.4 Hz), 7.84 (1H, dd, J=8.9, 2.4 Hz), 7.74 (1H, d, J=6.3 Hz), 7.59 (1H, m), 7.55 (1H, d, J=2.7 Hz), 7.36-7.44 (1H, m), 6.94 (1H, d, J=9.0 Hz), 6.40 (1H, d, J=2.7 Hz), 3.78-3.59 (12H, m), 3.13 (2H, br. s.), 2.94-3.04 (4H, m), 2.84 (2H, br. s.), 2.13 (3H, s), 1.64 (2H, m), 1.57 (4H, m). Mass Spectrum (ESI) m/e=602.3 (M+1).

Example 301

Preparation of N-(2,5-dimorpholinopyridin-3-yl)-5,7-difluoro-3-methyl-2-(6-(piperazin-1-yl)pyridin-3-yl)quinolin-4-amine 4-Chloro-5,7-difluoro-3-methyl-2-(6-(piperazin-1-yl)pyridin-3-yl)quinoline

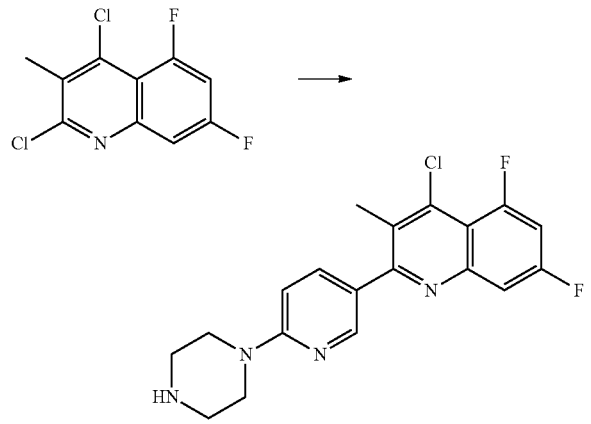

The Suzuki coupled product was prepared according to Procedure F using 2,4-dichloro-5,7-difluoro-3-methylquinoline (0.50 g, 2.02 mmol), 1-(5-(4,4,5,5-tetramethyl-1,3,2-dioxaborolan-2-yl)pyridin-2-yl)piperazine (0.583 g, 2.02 mmol), palladium tetrakistriphenylphosphine (0.23 g, 0.20 mmol), potassium carbonate (0.56 g, 4.03 mmol) in toluene (4 mL) at 100° C. for 18 h to give 4-chloro-5,7-difluoro-3-methyl-2-(6-(piperazin-1-yl)pyridin-3-yl)quinoline as a white solid. Mass Spectrum (ESI) m/e=375.1 (M+1).

N-(2,5-Dimorpholinopyridin-3-yl)-5,7-difluoro-3-methyl-2-(6-(piperazin-1-yl)pyridin-3-yl)quinolin-4-amine

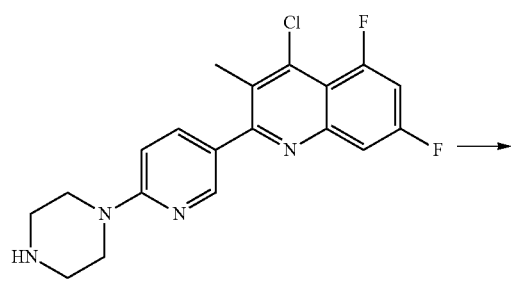

-continued

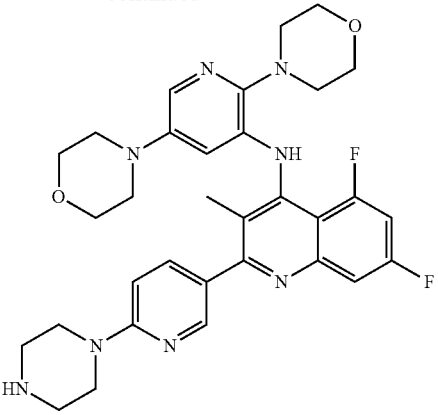

The Buchwald coupled product was prepared according to Procedure S using of dicyclohexyl(2',4',6'-triisopropylbiphenyl-2-yl)phosphine (0.020 g, 0.043 mmol), 2,5-dimorpholinopyridin-3-amine (0.085 g, 0.32 mmol), 4-chloro-5,7-difluoro-3-methyl-2-(6-(piperazin-1-yl)pyridin-3-yl)quinoline (0.1 g, 0.27 mmol), Pd$_2$dba$_3$ (0.009 g, 0.011 mmol) and sodium tert-butoxide (0.064 g, 0.67 mmol) in toluene (3.3 mL) at 100° C. for 2.1 h. The crude product was further purified with HPLC (10-90% of 0.1% TFA acetonitrile solution in 0.1% TFA water solution). The desired fractions were concd then diluted with EtOAc. After washing twice with satd aqueous sodium bicarbonate solution, the solvent was removed under reduced pressure to yield desired product N-(2,5-dimorpholinopyridin-3-yl)-5,7-difluoro-3-methyl-2-(6-(piperazin-1-yl)pyridin-3-yl)quinolin-4-amine. 1H NMR (500 MHz, CD$_2$Cl$_2$) δ ppm 8.50 (1H, d, J=2.2 Hz), 7.89 (1H, dd, J=8.6, 2.4 Hz), 7.63 (1H, d, J=10.0 Hz), 7.61 (1H, d, J=2.7 Hz), 7.51-7.56 (1H, m), 6.99 (1H, ddd, J=13.3, 8.7, 2.4 Hz), 6.81 (1H, d, J=8.8 Hz), 6.34 (1H, d, J=2.4 Hz), 3.85 (4H, m), 3.78-3.83 (4H, m), 3.73-3.78 (4H, m), 3.12-3.21 (4H, m), 2.97-3.05 (4H, m), 2.22 (3H, s). Mass Spectrum (ESI) m/e=603.2 (M+1).

Example 302

Preparation of 5,7-difluoro-3-methyl-N-(5-morpholinopyridin-3-yl)-2-(6-(piperidin-1-yl)pyridin-3-yl)quinolin-4-amine

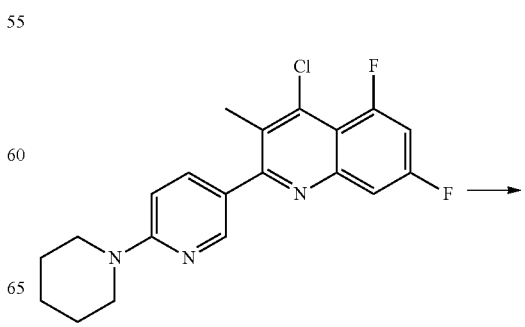

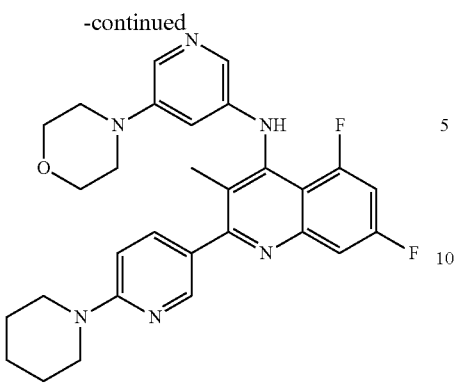

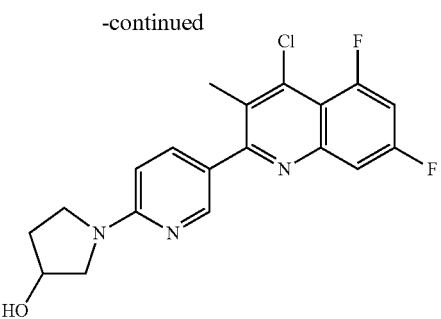

To a stirred solution of 4-chloro-5,7-difluoro-2-(6-fluoropyridin-3-yl)-3-methylquinoline (0.1 g, 0.32 mmol) in DMF (2.5 mL) was added 3-pyrrolidinol (0.029 mL, 0.36 mmol) followed by potassium carbonate (0.090 g, 0.65 mmol). The reaction was stirred at 120° C. and stirring continued for 1.6 h. After which, the reaction mixture was cooled to rt and water was added. The crude reaction mixture was extracted with EtOAc, dried over magnesium sulfate and concd in vacuo. The crude material was purified on silica gel, eluting with 0-30% EtOAc in hexanes to provide 1-(5-(4-chloro-5,7-difluoro-3-methylquinolin-2-yl)pyridin-2-yl)pyrrolidin-3-ol as a yellow solid. Mass Spectrum (ESI) m/e=376.1 (M+1).

The Buchwald coupled product was prepared according to Procedure S using of dicyclohexyl(2',4',6'-triisopropylbiphenyl-2-yl)phosphine (0.020 g, 0.043 mmol), 5-morpholinopyridin-3-amine (0.058 g, 0.32 mmol), 4-chloro-5,7-difluoro-3-methyl-2-(6-(piperidin-1-yl)pyridin-3-yl)quinoline (0.1 g, 0.27 mmol), Pd$_2$dba$_3$ (0.010 g, 0.011 mmol) and sodium tert-butoxide (0.064 g, 0.67 mmol) in toluene (2.7 mL) at 100° C. for 23.3 h. The crude product was further purified with HPLC (10-90% of 0.1% TFA acetonitrile solution in 0.1% TFA water solution). The desired fractions were concd then diluted with EtOAc. After washing twice with satd aq. sodium bicarbonate solution, the solvent was removed under reduced pressure to yield the desired product 5,7-difluoro-3-methyl-N-(5-morpholinopyridin-3-yl)-2-(6-(piperidin-1-yl)pyridin-3-yl)quinolin-4-amine. 1H NMR (500 MHz, DMSO-d$_6$) δ ppm 8.43-8.47 (2H, m), 7.86 (1H, dd, J=8.9, 2.6 Hz), 7.79 (1H, d, J=2.4 Hz), 7.56-7.61 (2H, m), 7.37 (1H, ddd, J=12.5, 9.5, 2.7 Hz), 6.93 (1H, d, J=8.8 Hz), 6.55 (1H, t, J=2.3 Hz), 3.66-3.74 (4H, m), 3.59-3.66 (4H, m), 3.04-3.11 (4H, m), 2.19 (3H, s). Mass Spectrum (ESI) m/e=517.2 (M+1).

1-(5-(4-(2,5-Dimorpholinopyridin-3-ylamino)-5,7-difluoro-3-methylquinolin-2-yl)pyridin-2-yl)pyrrolidin-3-ol

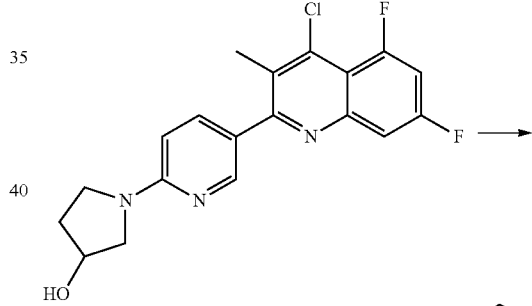

Example 303

Preparation of 1-(5-(4-(2,5-dimorpholinopyridin-3-ylamino)-5,7-difluoro-3-methylquinolin-2-yl)pyridin-2-yl)pyrrolidin-3-ol 1-(5-(4-Chloro-5,7-difluoro-3-methylquinolin-2-yl)pyridin-2-yl)pyrrolidin-3-ol

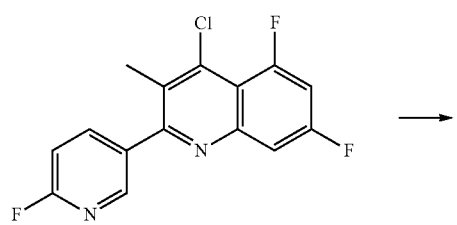

The Buchwald coupled product was prepared according to Procedure S using of dicyclohexyl(2',4',6'-triisopropylbiphenyl-2-yl)phosphine (8.73 mg, 0.018 mmol), 2,5-dimorpholinopyridin-3-amine (0.036 g, 0.14 mmol), 1-(5-(4-chloro-5,7-difluoro-3-methylquinolin-2-yl)pyridin-2-yl)pyrrolidin-3-ol (0.043 g, 0.11 mmol), Pd₂dba₃ (0.004 g, 0.005 mmol) and sodium tert-butoxide (0.027 g, 0.29 mmol) in toluene (1.1 mL) at 100° C. for 2.5 h. The crude product was purified by column chromatography on silica gel (0 to 100% DCM/methanol/ammonium hydroxide (90/9/1)) to give the desired product 1-(5-(4-(2,5-dimorpholinopyridin-3-ylamino)-5,7-difluoro-3-methylquinolin-2-yl)pyridin-2-yl)pyrrolidin-3-ol. 1H NMR (400 MHz, DMSO-d₆) δ ppm 8.43 (1H, d, J=2.2 Hz), 7.85 (1H, dd, J=8.8, 2.5 Hz), 7.74 (1H, d, J=6.1 Hz), 7.60 (1H, m), 7.56 (1H, d, J=2.5 Hz), 7.40 (1H, m), 6.58 (1H, d, J=9.2 Hz), 6.40 (1H, d, J=2.5 Hz), 5.00 (1H, m), 4.43 (1H, br. s.), 3.64-3.78 (8H, m), 3.55 (4H, m), 3.42 (4H, m), 3.00 (4H, d, J=4.9 Hz), 2.14 (3H, s), 1.95 (2H, br. s.). Mass Spectrum (ESI) m/e=604.3 (M+1).

Example 304

Preparation of 5,7-difluoro-3-methyl-N-(5-morpholinopyridin-3-yl)-2-(6-morpholinopyridin-3-yl)quinolin-4-amine 5,7-Difluoro-3-methyl-N-(5-morpholinopyridin-3-yl)-2-(6-morpholinopyridin-3-yl)quinolin-4-amine

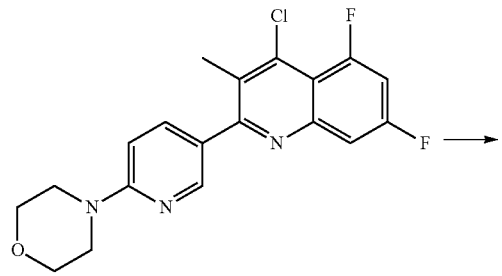

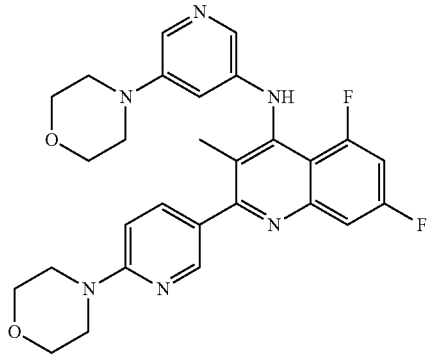

The Buchwald coupled product was prepared according to Procedure S using of dicyclohexyl(2',4',6'-triisopropylbiphenyl-2-yl)phosphine (0.020 g, 0.043 mmol), 5-morpholinopyridin-3-amine (0.057 g, 0.32 mmol), 4-(5-(4-chloro-5,7-difluoro-3-methylquinolin-2-yl)pyridin-2-yl)morpholine (0.1 g, 0.27 mmol), Pd₂dba₃ (0.010 g, 0.011 mmol) and sodium tert-butoxide (0.064 g, 0.67 mmol) in toluene (2.7 mL) at 100° C. for 2.5 h. The crude product was purified by column chromatography on silica gel (0 to 100% DCM/methanol/ammonium hydroxide (90/9/1)) to give the desired product 5,7-difluoro-3-methyl-N-(5-morpholinopyridin-3-yl)-2-(6-morpholinopyridin-3-yl)quinolin-4-amine. 1H NMR (400 MHz, DMSO-d₆) δ ppm 8.47 (1H, dd, J=2.5, 0.6 Hz), 8.45 (1H, d, J=1.6 Hz), 7.92 (1H, dd, J=8.9, 2.4 Hz), 7.79 (1H, d, J=2.5 Hz), 7.57-7.62 (2H, m), 7.35-7.42 (1H, m), 6.96 (1H, d, J=8.6 Hz), 6.56 (1H, t, J=2.3 Hz), 3.71 (8H, dt, J=12.1, 4.8 Hz), 3.53-3.59 (4H, m), 3.05-3.11 (4H, m), 2.18 (3H, s). Mass Spectrum (ESI) m/e=519.2 (M+1).

Example 305

Preparation of 2-(6-(3-(dimethylamino)pyrrolidin-1-yl)pyridin-3-yl)-N-(2,5-dimorpholinopyridin-3-yl)-5,7-difluoro-3-methylquinolin-4-amine 1-(5-(4-Chloro-5,7-difluoro-3-methylquinolin-2-yl)pyridin-2-yl)-N,N-dimethylpyrrolidin-3-amine

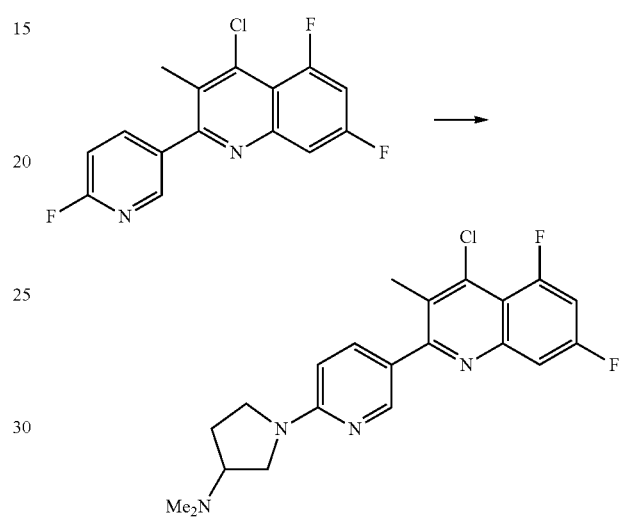

To a stirred solution of 4-chloro-5,7-difluoro-2-(6-fluoropyridin-3-yl)-3-methylquinoline (0.1 g, 0.32 mmol) in DMF (3.0 mL) was added 3-(dimethylamino)-pyrrolidine (0.041 mL, 0.32 mmol) followed by potassium carbonate (0.090 g, 0.65 mmol). The reaction was stirred at 100° C. and stirring continued for 19 h. After which, the reaction mixture was cooled to rt and water was added. The crude mixture was extracted with EtOAc and dried over magnesium sulfate and concd in vacuo. The crude material was purified on silica gel, eluting with 0-30% EtOAc in hexanes to provide 1-(5-(4-chloro-5,7-difluoro-3-methylquinolin-2-yl)pyridin-2-yl)-N,N-dimethylpyrrolidin-3-amine as a white solid. Mass Spectrum (ESI) m/e=403.1 (M+1).

2-(6-(3-(Dimethylamino)pyrrolidin-1-yl)pyridin-3-yl)-N-(2,5-dimorpholinopyridin-3-yl)-5,7-difluoro-3-methylquinolin-4-amine

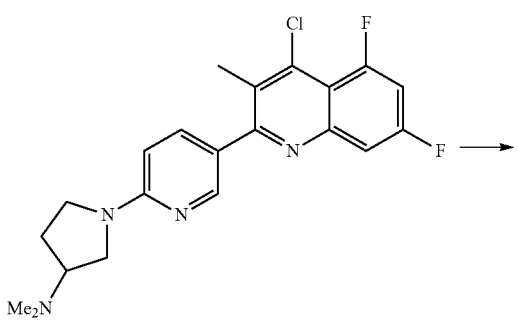

-continued

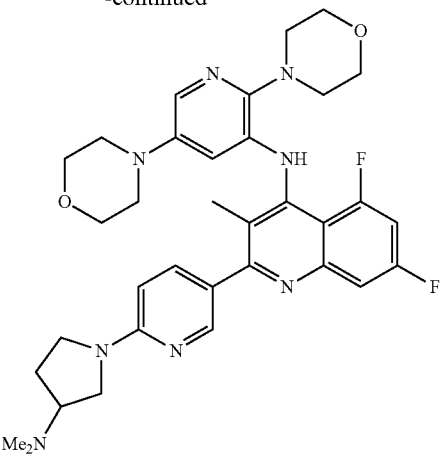

The Buchwald coupled product was prepared according to Procedure S using of dicyclohexyl(2',4',6'-triisopropylbiphenyl-2-yl)phosphine (0.022 g, 0.047 mmol), 2,5-dimorpholinopyridin-3-amine (0.093 g, 0.351 mmol), 1-(5-(4-chloro-5,7-difluoro-3-methylquinolin-2-yl)pyridin-2-yl)-N,N-dimethylpyrrolidin-3-amine (0.118 g, 0.29 mmol), Pd$_2$dba$_3$ (0.011 g, 0.012 mmol) and sodium tert-butoxide (0.070 g, 0.73 mmol) in toluene (2.9 mL) at 100° C. for 2 h. The crude product was purified by column chromatography on silica gel (0 to 100% DCM/methanol/ammonium hydroxide (90/9/1)) to give the desired product 2-(6-(3-(dimethylamino)pyrrolidin-1-yl)pyridin-3-yl)-N-(2,5-dimorpholinopyridin-3-yl)-5,7-difluoro-3-methylquinolin-4-amine. 1H NMR (400 MHz, DMSO-d$_6$) δ ppm 8.42 (1H, d, J=2.0 Hz), 7.85 (1H, dd, J=8.7, 2.4 Hz), 7.74 (1H, d, J=5.9 Hz), 7.59 (1H, m), 7.55 (1H, d, J=2.5 Hz), 7.39 (1H, ddd, J=13.3, 9.3, 2.4 Hz), 6.61 (1H, d, J=8.6 Hz), 6.40 (1H, d, J=2.5 Hz), 3.58-3.82 (10H, m), 3.39 (1H, m), 3.21-3.10 (3H, br. m), 2.95-3.04 (4H, m), 2.90-2.75 (3H, br. m), 2.22 (6H, s), 2.18 (1H, m), 2.13 (3H, s), 1.83 (1H, m). Mass Spectrum (ESI) m/e=631.2 (M+1).

Example 306

Preparation of N-(2,5-dimorpholinopyridin-3-yl)-5,7-difluoro-3-methyl-2-(6-(4-methylpiperazin-1-yl)pyridin-3-yl)quinolin-4-amine 4-Chloro-5,7-difluoro-3-methyl-2-(6-(4-methylpiperazin-1-yl)pyridin-3-yl)quinoline

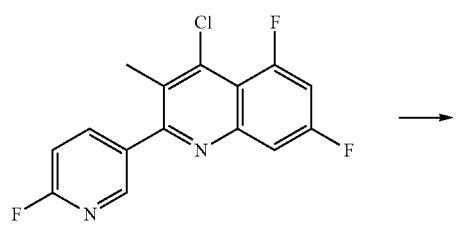

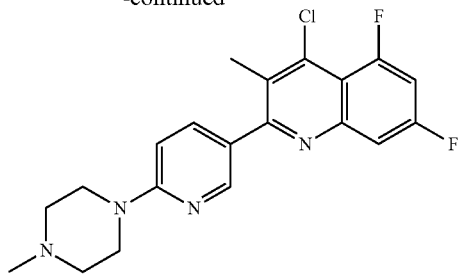

To a stirred solution of 4-chloro-5,7-difluoro-2-(6-fluoropyridin-3-yl)-3-methylquinoline (0.1 g, 0.324 mmol) in dmf (0.025 mL, 0.32 mmol) was added 1-methylpiperazine (0.036 g, 0.356 mmol) followed by potassium carbonate (0.090 g, 0.65 mmol). The reaction was stirred at 80° C. and stirring continued for 19 h. After which, the reaction mixture was cooled to rt and water was added. The crude reaction mixture was extracted with EtOAc, dried over magnesium sulfate and concd in vacuo. The crude material was purified on silica gel, eluting with 0-30% EtOAc in hexanes to provide 4-chloro-5,7-difluoro-3-methyl-2-(6-(4-methylpiperazin-1-yl)pyridin-3-yl)quinoline as a white solid. Mass Spectrum (ESI) m/e=389.1 (M+1).

N-(2,5-Dimorpholinopyridin-3-yl)-5,7-difluoro-3-methyl-2-(6-(4-methylpiperazin-1-yl)pyridin-3-yl)quinolin-4-amine

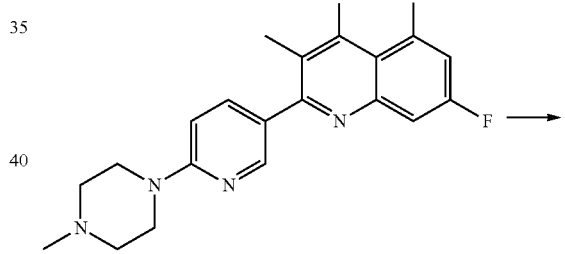

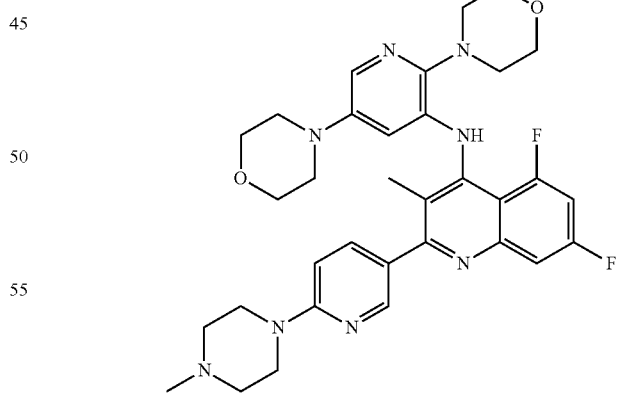

The Buchwald coupled product was prepared according to Procedure S using of dicyclohexyl(2',4',6'-triisopropylbiphenyl-2-yl)phosphine (0.016 g, 0.033 mmol), 2,5-dimorpholinopyridin-3-amine (0.065 g, 0.25 mmol), 4-chloro-5,7-difluoro-3-methyl-2-(6-(4-methylpiperazin-1-yl)pyridin-3-yl)quinoline (0.08 g, 0.21 mmol), Pd$_2$dba$_3$ (0.008 g, 0.008 mmol) and sodium tert-butoxide (0.049 g, 0.51 mmol) in toluene (2.1 mL) at 100° C. for 2 h. The crude product was purified by column chromatography on silica gel (0 to 100% DCM/methanol/ammonium hydroxide (90/9/1)) to give the desired product N-(2,5-dimorpholinopyridin-3-yl)-5,7-difluoro-3-methyl-2-(6-(4-methylpiperazin-1-yl)pyridin-3-yl)quinolin-4-amine. 1H NMR (400 MHz, DMSO-d$_6$) δ ppm 8.50 (1H, d, J=2.3 Hz), 7.96 (1H, dd, J=9.2, 2.5 Hz), 7.83 (1H, d, J=2.7 Hz), 7.69 (2H, m), 7.21 (2H, m), 4.61 (2H, br. d), 3.73 (4H, m), 3.57 (3H, br. d.), 3.46 (4H, br. s.), 3.29 (3H, m), 3.15-3.06 (7H, m), 2.88 (4H, s), 2.04 (3H, s). Mass Spectrum (ESI) m/e=617.3 (M+1).

Example 307

Preparation of 5,7-difluoro-3-methyl-N-(5-morpholinopyridin-3-yl)-2-(6-(piperazin-1-yl)pyridin-3-yl)quinolin-4-amine 5,7-Difluoro-3-methyl-N-(5-morpholinopyridin-3-yl)-2-(6-(piperazin-1-yl)pyridin-3-yl)quinolin-4-amine

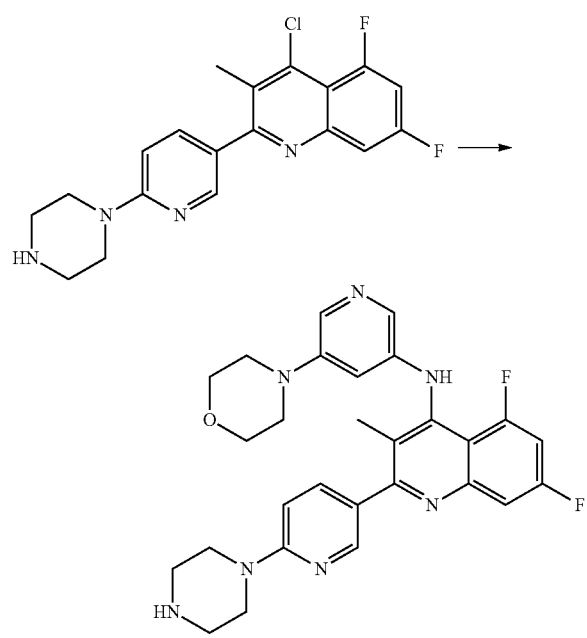

The Buchwald coupled product was prepared according to Procedure S using of dicyclohexyl(2',4',6'-triisopropylbiphenyl-2-yl)phosphine (0.020 g, 0.043 mmol), 5-morpholinopyridin-3-amine (0.057 g, 0.320 mmol), 4-chloro-5,7-difluoro-3-methyl-2-(6-(piperazin-1-yl)pyridin-3-yl)quinoline (0.1 g, 0.27 mmol), Pd$_2$dba$_3$ (0.010 g, 0.011 mmol) and sodium tert-butoxide (0.049 g, 0.51 mmol) in toluene (2.7 mL) at 100° C. for 2.5 h. The crude product was purified by column chromatography on basic alumina (0 to 50% hexanes/EtOAc) to give the desired product 5,7-difluoro-3-methyl-N-(5-morpholinopyridin-3-yl)-2-(6-(piperazin-1-yl)pyridin-3-yl)quinolin-4-amine. 1H NMR (400 MHz, DMSO-d$_6$) δ ppm 8.45 (2H, dd, J=4.9, 2.2 Hz), 7.89 (1H, dd, J=8.9, 2.4 Hz), 7.79 (1H, d, J=2.5 Hz), 7.56-7.60 (2H, m), 7.35-7.41 (1H, m), 6.93 (1H, d, J=8.8 Hz), 6.55 (1H, t, J=2.3 Hz), 3.70 (4H, m), 3.55 (4H, m), 3.08 (4H, m), 2.85 (4H, m), 2.19 (3H, s). Mass Spectrum (ESI) m/e=518.2 (M+1).

Example 308

Preparation of N-(2,5-dimorpholinopyridin-3-yl)-5,7-difluoro-3-methyl-2-(6-(4-methylpiperidin-1-yl)pyridin-3-yl)quinolin-4-amine 4-Chloro-5,7-difluoro-3-methyl-2-(6-(4-methylpiperidin-1-yl)pyridin-3-yl)quinoline

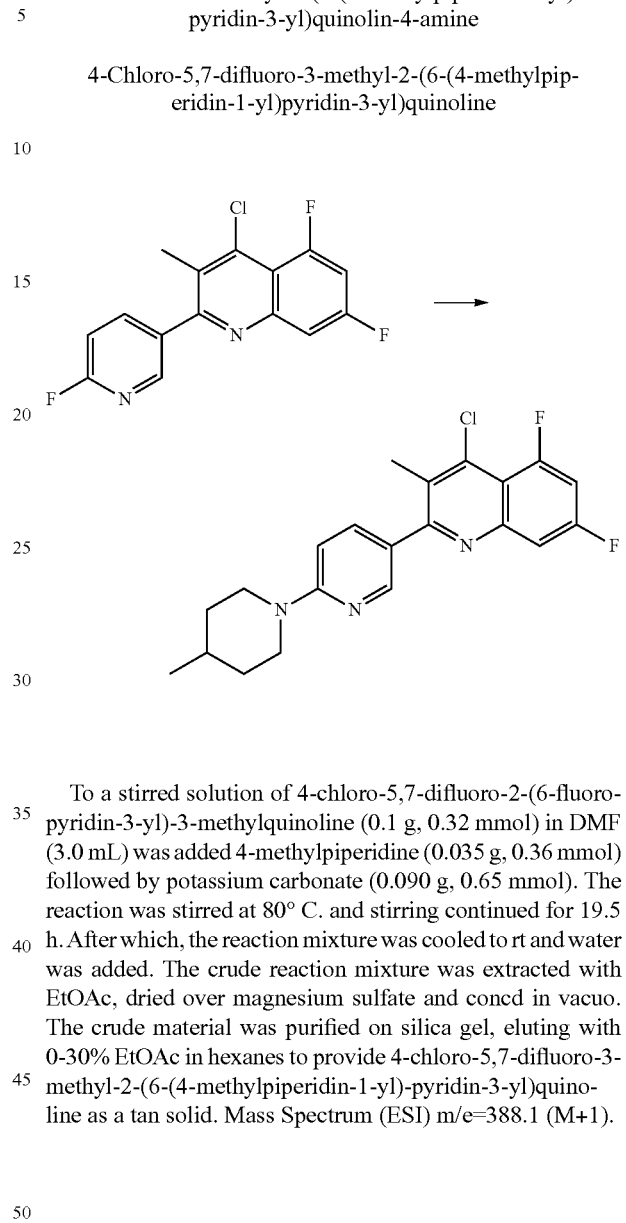

To a stirred solution of 4-chloro-5,7-difluoro-2-(6-fluoropyridin-3-yl)-3-methylquinoline (0.1 g, 0.32 mmol) in DMF (3.0 mL) was added 4-methylpiperidine (0.035 g, 0.36 mmol) followed by potassium carbonate (0.090 g, 0.65 mmol). The reaction was stirred at 80° C. and stirring continued for 19.5 h. After which, the reaction mixture was cooled to rt and water was added. The crude reaction mixture was extracted with EtOAc, dried over magnesium sulfate and concd in vacuo. The crude material was purified on silica gel, eluting with 0-30% EtOAc in hexanes to provide 4-chloro-5,7-difluoro-3-methyl-2-(6-(4-methylpiperidin-1-yl)-pyridin-3-yl)quinoline as a tan solid. Mass Spectrum (ESI) m/e=388.1 (M+1).

N-(2,5-Dimorpholinopyridin-3-yl)-5,7-difluoro-3-methyl-2-(6-(4-methylpiperidin-1-yl)pyridin-3-yl)quinolin-4-amine

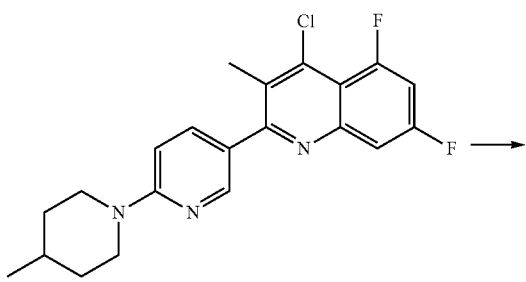

-continued

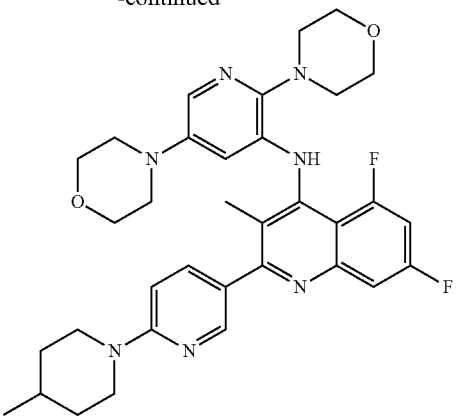

The Buchwald coupled product was prepared according to Procedure S using of dicyclohexyl(2',4',6'-triisopropylbiphenyl-2-yl)phosphine (0.024 g, 0.050 mmol), 2,5-dimorpholinopyridin-3-amine (0.098 g, 0.37 mmol), 4-chloro-5,7-difluoro-3-methyl-2-(6-(4-methylpiperidin-1-yl)pyridin-3-yl)quinoline (0.12 g, 0.31 mmol), Pd₂dba₃ (0.011 g, 0.012 mmol) and sodium tert-butoxide (0.074 g, 0.77 mmol) in toluene (3.1 mL) at 100° C. for 5 h. The crude product was purified by column chromatography on silica gel (0 to 100% DCM/methanol/ammonium hydroxide (90/9/1)) to give the desired product N-(2,5-dimorpholinopyridin-3-yl)-5,7-difluoro-3-methyl-2-(6-(4-methylpiperidin-1-yl)pyridin-3-yl)quinolin-4-amine. 1H NMR (400 MHz, DMSO-$d_6$) δ ppm 8.43 (1H, d, J=2.3 Hz), 7.84 (1H, dd, J=8.9, 2.4 Hz), 7.74 (1H, d, J=5.3 Hz), 7.59 (1H, dd, J=9.8, 1.8 Hz), 7.55 (1H, d, J=2.5 Hz), 7.35-7.45 (1H, m), 6.95 (1H, d, J=9.0 Hz), 6.40 (1H, d, J=2.5 Hz), 4.39 (2H, d, J=13.5 Hz), 3.59-3.80 (8H, m), 3.17 (4H, m), 2.94-3.04 (4H, m), 2.87 (4H, m), 2.13 (3H, s), 1.69 (3H, m), 1.14 (2H, m), 0.94 (3H, d, J=6.3 Hz). Mass Spectrum (ESI) m/e=616.3 (M+1).

Example 309

Preparation of 2-(6-(4,4-difluoropiperidin-1-yl)pyridin-3-yl)-N-(2,5-dimorpholinopyridin-3-yl)-5,7-difluoro-3-methylquinolin-4-amine 4-Chloro-2-(6-(4,4-difluoropiperidin-1-yl)pyridin-3-yl)-5,7-difluoro-3-methylquinoline

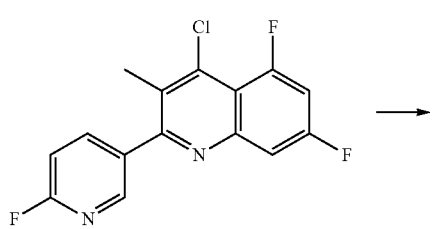

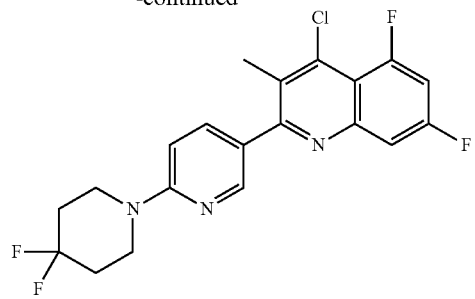

To a stirred solution of 4-chloro-5,7-difluoro-2-(6-fluoropyridin-3-yl)-3-methylquinoline (0.10 g, 0.32 mmol) in DMF (2 mL) was added 4,4-difluoropiperidine hydrochloride (0.056 g, 0.36 mmol) followed by potassium carbonate (0.090 g, 0.65 mmol). The reaction was stirred at 100° C. and stirring continued for 66.5 h. After which, the reaction mixture was cooled to rt and water was added. The crude reaction mixture was extracted with EtOAc and dried over magnesium sulfate and concd in vacuo. The crude material was purified on silica gel, eluting with 0-30% EtOAc in hexanes to provide 4-chloro-2-(6-(4,4-difluoropiperidin-1-yl)pyridin-3-yl)-5,7-difluoro-3-methylquinoline as a brown solid. Mass Spectrum (ESI) m/e=410.0 (M+1).

2-(6-(4,4-difluoropiperidin-1-yl)pyridin-3-yl)-N-(2,5-dimorpholinopyridin-3-yl)-5,7-difluoro-3-methylquinolin-4-amine

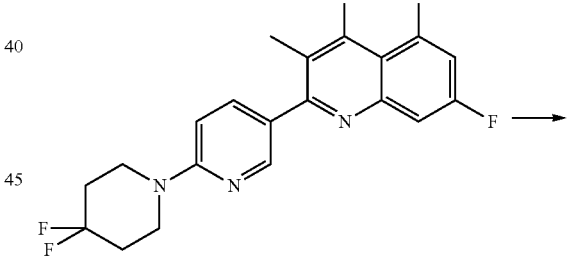

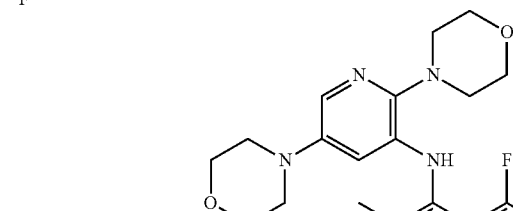

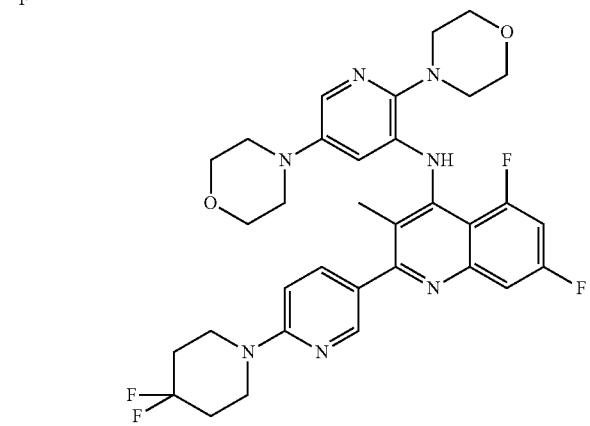

The Buchwald coupled product was prepared according to Procedure S using of dicyclohexyl(2',4',6'-triisopropylbiphenyl-2-yl)phosphine (0.015 g, 0.031 mmol), 2,5-dimorpholinopyridin-3-amine (0.062 g, 0.23 mmol), 4-chloro-2-(6-(4,4-difluoropiperidin-1-yl)pyridin-3-yl)-5,7-difluoro-3-methylquinoline (0.08 g, 0.20 mmol) and Pd₂dba₃ (0.007 g, 0.008 mmol) and sodium tert-butoxide (0.047 g, 0.49 mmol) in toluene (2.0 mL) at 100° C. for 73 h. The crude product was purified by column chromatography on silica gel (0 to 100% DCM/methanol/ammonium hydroxide (90/9/1)) to give the desired product 2-(6-(4,4-difluoropiperidin-1-yl)pyridin-3-yl)-N-(2,5-dimorpholinopyridin-3-yl)-5,7-difluoro-3-methylquinolin-4-amine. 1H NMR (400 MHz, DMSO-d₆) δ ppm 8.47 (1H, d, J=2.2 Hz), 7.90 (1H, dd, J=8.9, 2.4 Hz), 7.76 (1H, d, J=5.9 Hz), 7.57-7.63 (1H, m), 7.55 (1H, d, J=2.7 Hz), 7.38-7.46 (1H, m), 7.10 (1H, d, J=8.8 Hz), 6.41 (1H, d, J=2.3 Hz), 3.80 (4H, m), 3.60-3.77 (8H, m), 3.13 (2H, br. s.), 2.94-3.04 (4H, m), 2.82 (2H, br. s.), 2.13 (3H, s), 2.03 (4H, m). Mass Spectrum (ESI) m/e=638.2 (M+1).

Example 310

Preparation of N-(2,5-dimorpholinopyridin-3-yl)-5,7-difluoro-3-methyl-2-(2-(piperazin-1-yl)pyridin-4-yl)quinolin-4-amine 4-Chloro-5,7-difluoro-3-methyl-2-(2-(piperazin-1-yl)pyridin-4-yl)quinoline

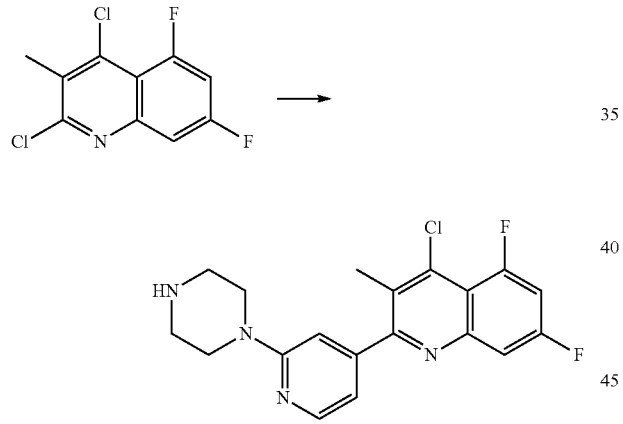

The Suzuki coupled product was prepared according to Procedure F using 2,4-dichloro-5,7-difluoro-3-methylquinoline (0.5 g, 2.0 mmol), 1-(4-(4,4,5,5-tetramethyl-1,3,2-dioxaborolan-2-yl)pyridin-2-yl)piperazine (0.641 g, 2.22 mmol), palladium tetrakistriphenylphosphine (0.23 g, 0.20 mmol), potassium carbonate (0.56 g, 4.0 mmol) in toluene (4.0 mL) at 100° C. for 23 h to give 4-chloro-5,7-difluoro-3-methyl-2-(2-(piperazin-1-yl)pyridin-4-yl)quinoline as a yellow solid. Mass Spectrum (ESI) m/e=375.2 (M+1).

N-(2,5-Dimorpholinopyridin-3-yl)-5,7-difluoro-3-methyl-2-(2-(piperazin-1-yl)pyridin-4-yl)quinolin-4-amine

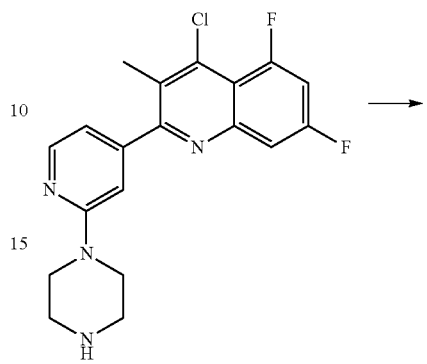

The Buchwald coupled product was prepared according to Procedure S using of dicyclohexyl(2',4',6'-triisopropylbiphenyl-2-yl)phosphine (0.020 g, 0.043 mmol), 2,5-dimorpholinopyridin-3-amine (0.085 g, 0.32 mmol), 4-chloro-5,7-difluoro-3-methyl-2-(2-(piperazin-1-yl)pyridin-4-yl)quinoline (0.1 g, 0.27 mmol) and Pd₂dba₃ (0.010 g, 0.011 mmol) and sodium tert-butoxide (0.064 g, 0.67 mmol) in toluene (2.7 mL) at 100° C. for 2 h. The crude product was purified by column chromatography on silica gel (0 to 100% DCM/methanol/ammonium hydroxide (90/9/1)) to give the desired product N-(2,5-dimorpholinopyridin-3-yl)-5,7-difluoro-3-methyl-2-(2-(piperazin-1-yl)pyridin-4-yl)quinolin-4-amine. 1H NMR (400 MHz, DMSO-d₆) δ ppm 8.25 (1H, d, J=5.1 Hz), 7.81 (1H, d, J=6.3 Hz), 7.62-7.66 (1H, m), 7.55 (1H, d, J=2.5 Hz), 7.46-7.53 (1H, m), 6.91 (1H, s), 6.81 (1H, dd, J=5.0, 1.1 Hz), 6.45 (1H, d, J=2.5 Hz), 3.65 (8H, m), 3.44-3.53 (4H, m), 3.32 (4H, m), 3.00 (4H, br. s.), 2.78-2.88 (4H, m), 1.99 (3H, s). Mass Spectrum (ESI) m/e=603.3 (M+1).

Example 311

Preparation of N-(2,5-dimorpholinopyridin-3-yl)-5,7-difluoro-3-methyl-2-(2-(4-methylpiperazin-1-yl)pyridin-4-yl)quinolin-4-amine 4-Chloro-5,7-difluoro-3-methyl-2-(2-(4-methylpiperazin-1-yl)pyridin-4-yl)quinoline

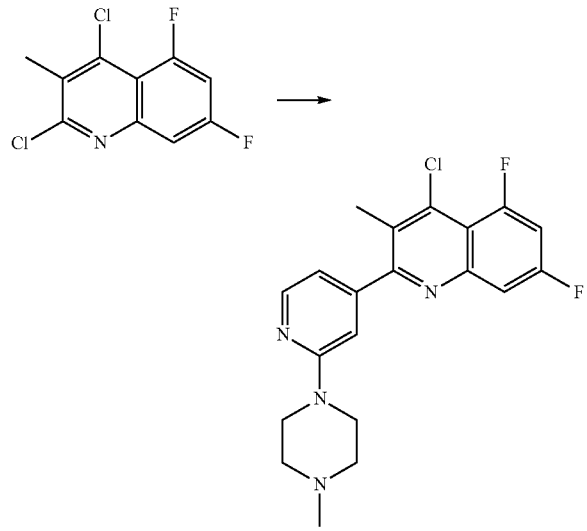

The Suzuki coupled product was prepared according to Procedure F using 2,4-dichloro-5,7-difluoro-3-methylquinoline (0.50 g, 2.0 mmol), 1-methyl-4-(4-(4,4,5,5-tetramethyl-1,3,2-dioxaborolan-2-yl)pyridin-2-yl)piperazine (0.61 g, 2.02 mmol), palladium tetrakistriphenylphosphine (0.23 g, 0.20 mmol), potassium carbonate (0.56 g, 4.0 mmol) in toluene (4.0 mL) at 100° C. for 22 h to give 4-chloro-5,7-difluoro-3-methyl-2-(2-(4-methylpiperazin-1-yl)pyridin-4-yl)quinoline as a light yellow solid. Mass Spectrum (ESI) m/e=389.1 (M+1).

N-(2,5-Dimorpholinopyridin-3-yl)-5,7-difluoro-3-methyl-2-(2-(4-methylpiperazin-1-yl)pyridin-4-yl)quinolin-4-amine

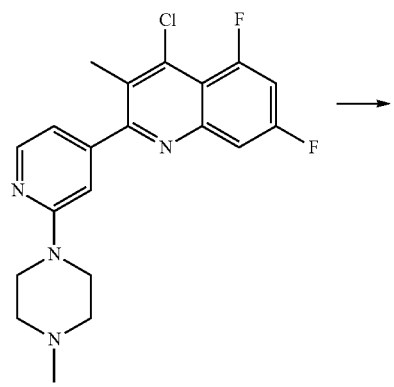

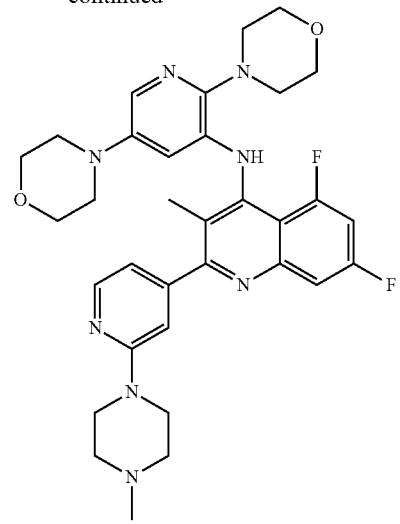

The Buchwald coupled product was prepared according to Procedure S using of dicyclohexyl(2',4',6'-triisopropylbiphenyl-2-yl)phosphine (0.020 g, 0.041 mmol), 2,5-dimorpholinopyridin-3-amine (0.082 g, 0.31 mmol), 4-chloro-5,7-difluoro-3-methyl-2-(2-(4-methylpiperazin-1-yl)pyridin-4-yl)quinoline (0.10 g, 0.26 mmol) and Pd$_2$dba$_3$ (0.009 g, 0.010 mmol) and sodium tert-butoxide (0.072 g, 0.75 mmol) in toluene (2.6 mL) at 100° C. for 1.6 h. The crude product was purified by column chromatography on silica gel (0 to 100% DCM/methanol/ammonium hydroxide (90/9/1)) to give the desired product N-(2,5-dimorpholinopyridin-3-yl)-5,7-difluoro-3-methyl-2-(2-(4-methylpiperazin-1-yl)pyridin-4-yl)quinolin-4-amine. 1H NMR (400 MHz, DMSO-d$_6$) δ ppm 8.25 (1H, d, J=5.5 Hz), 7.80 (1H, d, J=6.3 Hz), 7.62-7.67 (1H, m), 7.55 (1H, d, J=2.5 Hz), 7.49 (1H, ddd, J=13.2, 9.2, 2.6 Hz), 6.93 (1H, s), 6.81 (1H, dd, J=5.0, 1.1 Hz), 6.44 (1H, d, J=2.7 Hz), 3.79-3.61 (8H, m), 3.48-3.56 (4H, m), 3.14 (2H, br. s.), 2.99 (4H, d, J=2.2 Hz), 2.83 (2H, br. s.), 2.36-2.44 (4H, m), 2.22 (3H, s), 1.99 (3H, s). Mass Spectrum (ESI) m/e=617.3 (M+1).

Example 312

Preparation of N-(2,5-dimorpholinopyridin-3-yl)-5,7-difluoro-3-methyl-2-(2-(pyrrolidin-1-yl)pyridin-4-yl)quinolin-4-amine 4-Chloro-5,7-difluoro-3-methyl-2-(2-(pyrrolidin-1-yl)pyridin-4-yl)quinoline

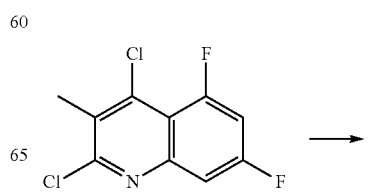

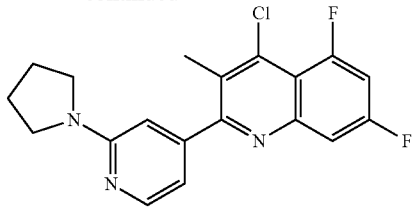

The Suzuki coupled product was prepared according to Procedure F using 2,4-dichloro-5,7-difluoro-3-methylquinoline (0.5 g, 2.0 mmol), 2-(pyrrolidin-1-yl)-4-(4,4,5,5-tetramethyl-1,3,2-dioxaborolan-2-yl)pyridine (0.608 g, 2.22 mmol), palladium tetrakistriphenylphosphine (0.23 g, 0.20 mmol), potassium carbonate (0.56 g, 4.0 mmol) in toluene (4.0 mL) at 100° C. for 18 h to give 4-chloro-5,7-difluoro-3-methyl-2-(2-(pyrrolidin-1-yl)pyridin-4-yl)quinoline as a yellow solid. Mass Spectrum (ESI) m/e=360.0 (M+1).

N-(2,5-Dimorpholinopyridin-3-yl)-5,7-difluoro-3-methyl-2-(2-(pyrrolidin-1-yl)pyridin-4-yl)quinolin-4-amine

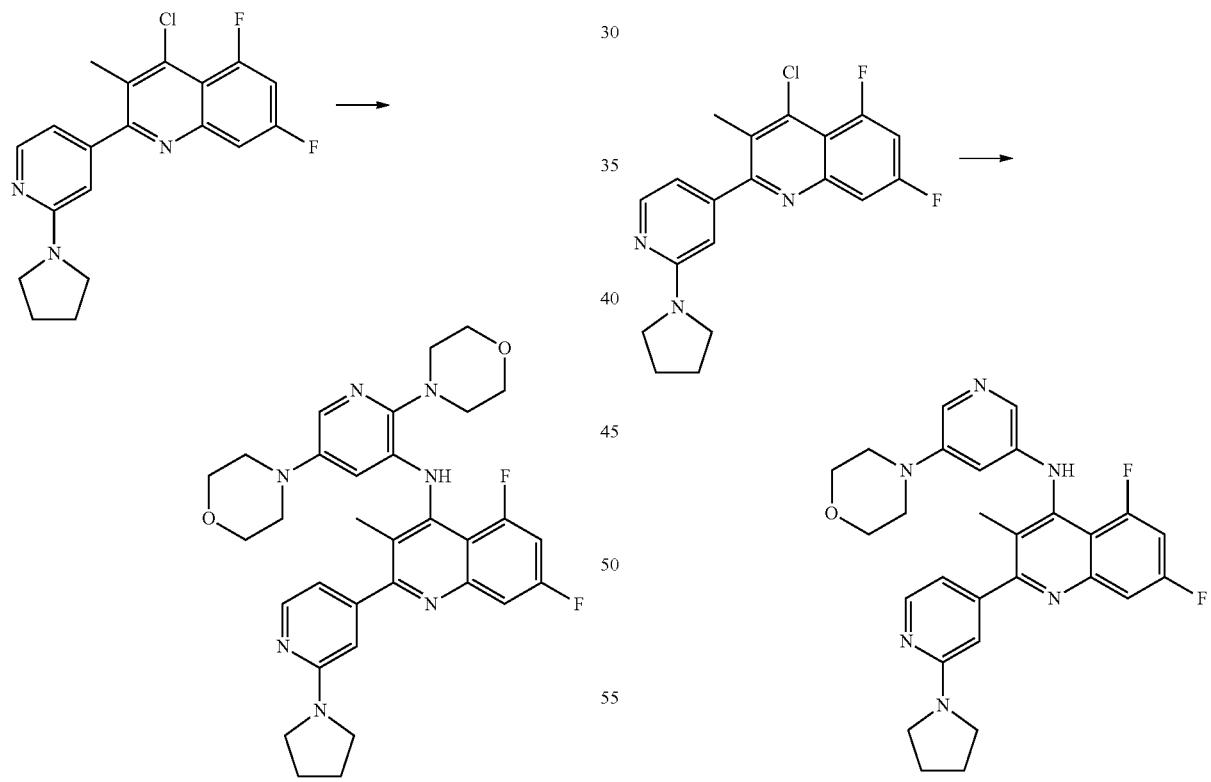

The Buchwald coupled product was prepared according to Procedure S using of dicyclohexyl(2',4',6'-triisopropylbiphenyl-2-yl)phosphine (0.021 g, 0.044 mmol), 2,5-dimorpholinopyridin-3-amine (0.088 g, 0.33 mmol), 4-chloro-5,7-difluoro-3-methyl-2-(2-(pyrrolidin-1-yl)pyridin-4-yl)quinoline (0.1 g, 0.28 mmol) and Pd$_2$dba$_3$ (0.010 g, 0.011 mmol) and sodium tert-butoxide (0.067 g, 0.70 mmol) in toluene (2.8 mL) at 100° C. for 1.0 h. The crude product was purified by column chromatography on silica gel (0 to 100% DCM/methanol/ammonium hydroxide (90/9/1)) to give the desired product N-(2,5-dimorpholinopyridin-3-yl)-5,7-difluoro-3-methyl-2-(2-(pyrrolidin-1-yl)pyridin-4-yl)quinolin-4-amine. 1H NMR (400 MHz, DMSO-d$_6$) δ ppm 8.42 (1H, dd, J=2.3, 0.6 Hz), 7.84 (1H, dd, J=8.8, 2.5 Hz), 7.73 (1H, d, J=5.5 Hz), 7.59 (1H, dd, J=9.9, 1.7 Hz), 7.55 (1H, d, J=2.7 Hz), 7.35-7.43 (1H, m), 6.58 (1H, d, J=8.6 Hz), 6.39 (1H, d, J=2.5 Hz), 3.59-3.81 (8H, m), 3.47 (4H, t, J=6.5 Hz), 3.15 (2H, br. s.), 2.94-3.05 (4H, m), 2.83 (2H, br. s.), 2.13 (3H, s), 1.93-2.04 (4H, m). Mass Spectrum (ESI) m/e=588.2 (M+1).

Example 313

Preparation of 5,7-difluoro-3-methyl-N-(5-morpholinopyridin-3-yl)-2-(2-(pyrrolidin-1-yl)pyridin-4-yl)quinolin-4-amine 5,7-Difluoro-3-methyl-N-(5-morpholinopyridin-3-yl)-2-(2-(pyrrolidin-1-yl)pyridin-4-yl)quinolin-4-amine The Buchwald coupled product was prepared according to Procedure S using of dicyclohexyl(2',4',6'-triisopropylbiphenyl-2-yl)phosphine (0.021 g, 0.044 mmol), 5-morpholinopyridin-3-amine (0.060 g, 0.33 mmol), 4-chloro-5,7-difluoro-3-methyl-2-(2-(pyrrolidin-1-yl)pyridin-4-yl)quinoline (0.10 g, 0.28 mmol) and Pd$_2$dba$_3$ (0.010 g, 0.011 mmol) and sodium tert-butoxide (0.067 g, 0.70 mmol) in toluene (2.8 mL) at 100° C. for 5 h. The crude product was purified by column chromatography on silica gel (0 to 100% DCM/methanol/ammonium hydroxide (90/9/1)). The desired product was further purified with HPLC (10-90% of 0.1% TFA acetonitrile solution in 0.1% TFA water solution). The desired fractions were concd then diluted with EtOAc. After washing twice with satd aqueous sodium bicarbonate solution, the solvent was removed under reduced pressure to yield pure product 5,7-difluoro-3-methyl-N-(5-morpholinopyridin-3-yl)-2-(2-(pyrrolidin-1-yl)pyridin-4-yl)quinolin-4-amine. 1H NMR (500 MHz, DMSO-d$_6$) δ ppm 8.44 (1H, s), 8.43 (1H, d, J=2.0 Hz), 7.86 (1H, dd, J=8.8, 2.4 Hz), 7.79 (1H, d, J=2.4 Hz), 7.56-7.60 (2H, m), 7.34-7.39 (1H, m), 6.57 (1H, d, J=8.6 Hz), 6.54 (1H, t, J=2.3 Hz), 3.68-3.75 (4H, m), 3.47 (4H, t, J=6.5 Hz), 3.06-3.11 (4H, m), 2.19 (3H, s), 1.95-2.01 (4H, m). Mass Spectrum (ESI) m/e=503.1 (M+1).

Example 314

Preparation of N-(2,5-dimorpholinopyridin-3-yl)-5,7-difluoro-3-methyl-2-(6-(pyrrolidin-1-yl)pyridin-3-yl)quinolin-4-amine 4-Chloro-5,7-difluoro-3-methyl-2-(6-(pyrrolidin-1-yl)pyridin-3-yl)quinoline

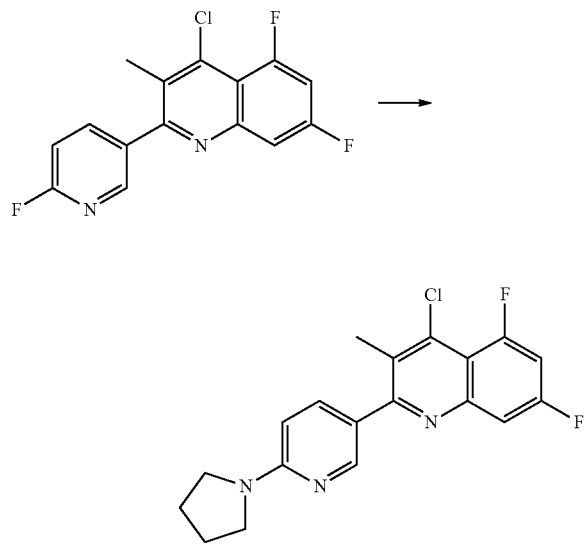

To a stirred solution of 4-chloro-5,7-difluoro-2-(6-fluoropyridin-3-yl)-3-methylquinoline (0.2 g, 0.65 mmol) in DMF (1.3 mL) was added pyrrolidine (0.046 g, 0.65 mmol) followed by potassium carbonate (0.180 g, 1.3 mmol). The reaction was stirred at 100° C. for 22.6 h. After which, the reaction mixture is cooled to rt and water was added. The crude reaction was extracted with EtOAc, dried over magnesium sulfate and concd in vacuo. The crude material was purified on silica gel, eluting with 0-30% EtOAc in hexanes to provide 4-chloro-5,7-difluoro-3-methyl-2-(6-(pyrrolidin-1-yl)pyridin-3-yl)quinoline (0.09 g, 0.250 mmol, 38.6% yield). Mass Spectrum (ESI) m/e=360.0 (M+1).

N-(2,5-dimorpholinopyridin-3-yl)-5,7-difluoro-3-methyl-2-(6-(pyrrolidin-1-yl)pyridin-3-yl)quinolin-4-amine

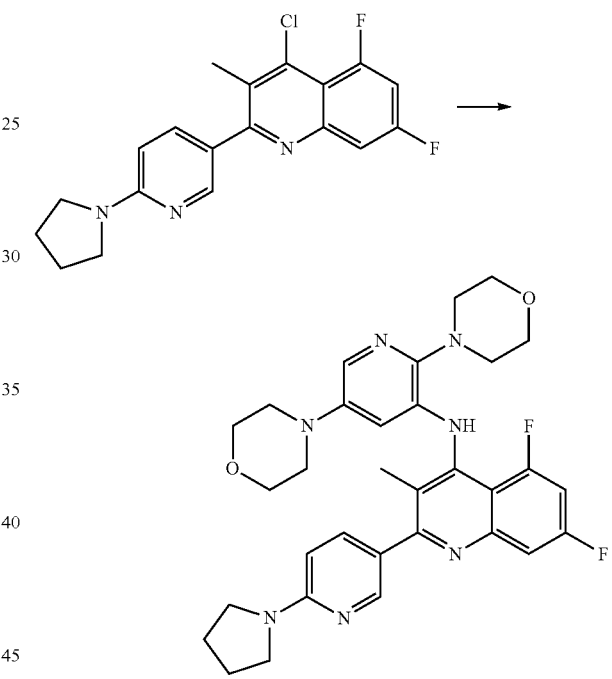

The Buchwald coupled product was prepared according to Procedure S using of dicyclohexyl(2',4',6'-triisopropylbiphenyl-2-yl)phosphine (0.018 g, 0.037 mmol), 2,5-dimorpholinopyridin-3-amine (0.074 g, 0.28 mmol), 4-chloro-5,7-difluoro-3-methyl-2-(6-(pyrrolidin-1-yl)pyridin-3-yl)quinoline (0.084 g, 0.23 mmol) and Pd$_2$dba$_3$ (0.009 g, 0.009 mmol) and sodium tert-butoxide (0.056 g, 0.58 mmol) in toluene (2.3 mL) at 100° C. for 2.5 h. The crude product was purified by column chromatography on alumina (0-60% EtOAc/hexanes) to give the desired product N-(2,5-dimorpholinopyridin-3-yl)-5,7-difluoro-3-methyl-2-(6-(pyrrolidin-1-yl)-pyridin-3-yl)quinolin-4-amine. 1H NMR (400 MHz, DMSO-d$_6$) δ ppm 8.42 (1H, dd, J=2.4, 0.5 Hz), 7.84 (1H, dd, J=8.7, 2.4 Hz), 7.73 (1H, d, J=5.7 Hz), 7.56-7.62 (1H, m), 7.55 (1H, d, J=2.5 Hz), 7.39 (1H, ddd, J=13.2, 9.4, 2.4 Hz), 6.58 (1H, d, J=8.6 Hz), 6.39 (1H, d, J=2.7 Hz), 3.61-3.82 (8H, m), 3.47 (4H, t, J=6.6 Hz), 3.15 (2H, br. s.), 2.94-3.05 (4H, m), 2.84 (2H, br. s.), 2.13 (3H, s), 1.95-2.03 (4H, m). Mass Spectrum (ESI) m/e=588.2 (M+1).

Example 315

Preparation of N-(3-chloro-5-morpholinophenyl)-5,7-difluoro-3-methyl-2-(pyridin-2-yl)quinolin-4-amine N-(3-Chloro-5-morpholinophenyl)-5,7-difluoro-3-methyl-2-(pyridin-2-yl)quinolin-4-amine

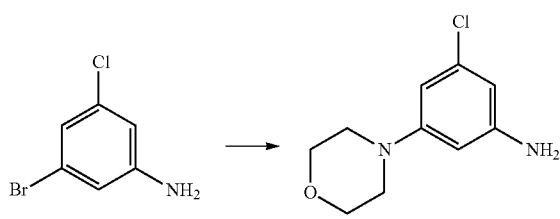 [SMILES: Nc1cc(Cl)cc(Br)c1 ; Nc1cc(Cl)cc(N2CCOCC2)c1]

To a stirred solution of 3-bromo-5-chloroaniline (1.00 g, 4.84 mmol), dicyclohexyl(2',4',6'-triisopropylbiphenyl-2-yl)phosphine (0.185 g, 0.39 mmol), Pd$_2$dba$_3$ (0.177 g, 0.194 mmol) and morpholine (0.464 g, 5.33 mmol) in tetrahydrofuran (9.7 mL) was added LHMDS in THF (19.37 mL, 19.37 mmol). The resulting mixture was heated to 65° C. and stirring continued for 2.3 h. The reaction was cooled to rt and then poured into water (100 mL) and extracted with EtOAc (2×150 mL) and DCM (2×150 mL). The combined organic layers were dried over magnesium sulfate and the crude product was purified on silica gel (0 to 100% DCM in EtOAc) to give 3-chloro-5-morpholinoaniline. Mass Spectrum (ESI) m/e=213.1 (M+1).

N-(3-Chloro-5-morpholinophenyl)-5,7-difluoro-3-methyl-2-(pyridin-2-yl)quinolin-4-amine

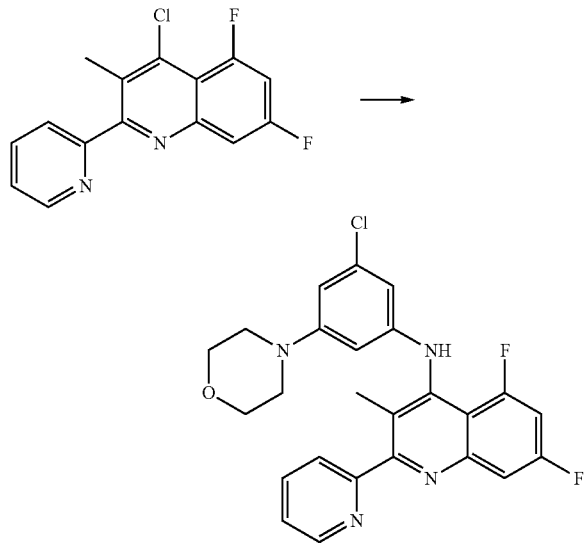

The Buchwald coupled products were prepared according to Procedure S using of dicyclohexyl(2',4',6'-triisopropylbiphenyl-2-yl)phosphine (0.026 g, 0.055 mmol), 3-chloro-5-morpholinoaniline (0.088 g, 0.413 mmol), 4-chloro-5,7-difluoro-3-methyl-2-(pyridin-2-yl)quinoline (0.1 g, 0.344 mmol) and Pd$_2$dba$_3$ (0.013 g, 0.014 mmol) and sodium tert-butoxide (0.063 g, 0.66 mmol) in toluene (3.4 mL) at 100° C. for 45 mins. The crude product was purified by column chromatography on alumina (0 to 50% EtOAc in hexanes) to give the desired product N-(3-chloro-5-morpholinophenyl)-5,7-difluoro-3-methyl-2-(pyridin-2-yl)quinolin-4-amine. 1H NMR (400 MHz, CDCl$_3$) δ ppm 8.72 (1H, ddd, J=4.9, 1.8, 1.0 Hz), 7.89 (1H, td, J=7.4, 1.8 Hz), 7.80-7.85 (1H, m), 7.67 (1H, br. s.), 7.38 (1H, ddd, J=7.5, 4.8, 1.2 Hz), 7.02 (2H, ddd, J=13.7, 8.6, 2.5 Hz), 6.51 (1H, s), 6.36 (1H, s), 6.27 (1H, s), 3.83 (4H, app t, J=4.9 Hz), 3.15 (4H, app t, J=4.9 Hz), 2.17 (3H, s). Mass Spectrum (ESI) m/e=467.2 (M+1).

Example 316

Preparation of 3-(5,7-difluoro-3-methyl-2-(pyridin-2-yl)quinolin-4-ylamino)-5-morpholinobenzonitrile 3-(5,7-Difluoro-3-methyl-2-(pyridin-2-yl)quinolin-4-ylamino)-5-morpholinobenzonitrile

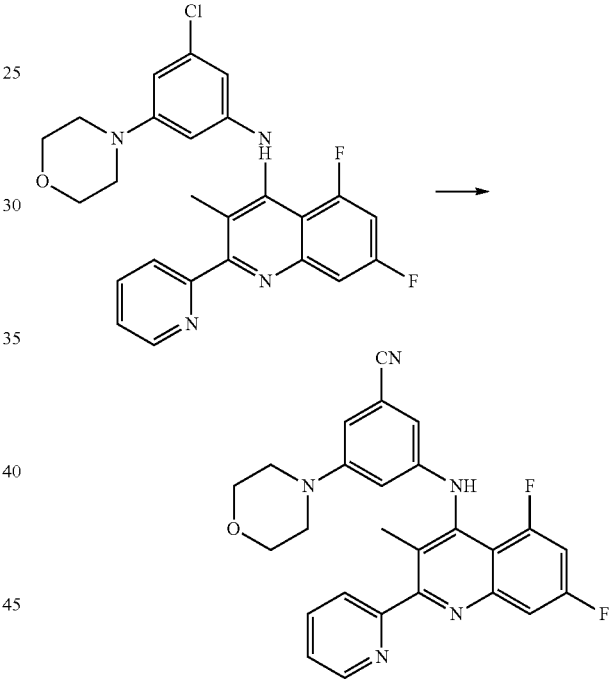

To a stirred solution of N-(3-chloro-5-morpholinophenyl)-5,7-difluoro-3-methyl-2-(pyridin-2-yl)quinolin-4-amine (0.059 g, 0.13 mmol) in 1-methylpyrrolidin-2-one (1.26 mL, 0.13 mmol) was added palladium bis(trifluoroacetate) (0.013 g, 0.038 mmol), 2-(dicyclohexylphosphino)-2',4',6',-triisopropyl-biphenyl (0.036 g, 0.076 mmol) followed by tri-n-butyltin cyanide (0.040 g, 0.13 mmol). The reaction was heated to 160° C. for 36 h. A further 0.3 eq of palladium bis(trifluoroacetate) and 0.6 eq of 2-(dicyclohexylphosphino)-2',4',6',-triisopropyl-biphenyl were added. Heating continued at 160° C. for a further 3 h. After which, the reaction was cooled to 23° C. The crude product was filtered through a plug of alumina eluting with EtOAc. The organics were washed with water, dried over MgSO$_4$ and filtered and evaporated in vacuo. The crude product was purified by column chromatography on alumina (0 to 50% EtOAc/hexane)) to give the desired product 3-(5,7-difluoro-3-methyl-2-(pyridin-2-yl)quinolin-4-ylamino)-5-morpholinobenzonitrile. 1H NMR (400 MHz, DMSO-d$_6$) δ ppm 8.71 (1H, ddd, J=4.9, 1.8, 1.0 Hz), 8.62 (1H, s), 8.02 (1H, td, J=7.6, 1.8 Hz), 7.91 (1H, dt, J=7.8, 1.1 Hz), 7.65-7.70 (1H, m), 7.45-7.54 (2H, m), 6.81 (1H, dd, J=2.1, 1.3 Hz), 6.56 (1H, t, J=2.1 Hz), 6.34 (1H, d, J=1.2 Hz), 3.69 (4H, m), 3.09 (4H, m), 2.19 (3H, s). Mass Spectrum (ESI) m/e=458.2 (M+1).

Procedure S

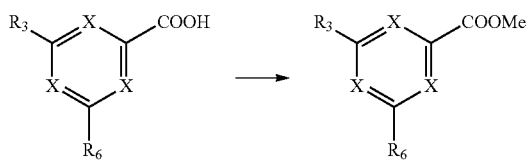

A solution of the substituted benzoic acid (1 eq), potassium carbonate (2 eq), iodomethane (2 eq), and DMF (0.4 M) was stirred at 55° C. under a reflux condenser for 30 minutes, then concd. The crude material was partitioned between EtOAc and water, and the organic layer was washed thrice with brine, dried over magnesium sulfate, and concd to afford the substituted methyl benzoate.

Procedure T

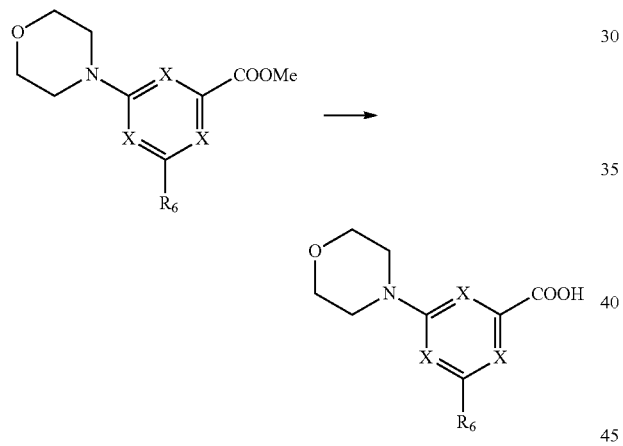

To a stirring solution of substituted methyl benzoate (1 eq) in 3:2 THF:methanol (1 M) was added 1 N aqueous lithium hydroxide (6 eq). The reaction was stirred at 23° C. for 1 hour, then quenched with a slight excess of 1 N HCl and concd to remove the organic solvents. The product was extracted from the remaining aqueous solution with EtOAc, and the combined organics were dried over magnesium sulfate and concd to afford the substituted benzoic acid.

Procedure U

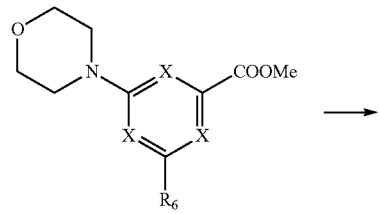

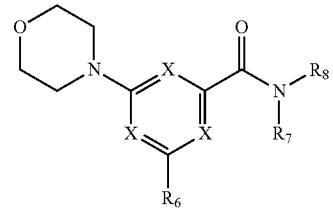

A reaction vessel was charged with substituted aryl acid (1 eq), EDC (2 eq), and DMAP (2 eq). DCM (0.3 M) and alkyl amine (1.3 eq) were then added by syringe, and the reaction was stirred at 23° C. for 1-48 h. Upon completion, the reaction was concd and partitioned between EtOAc and either water or 1 N HCl. The organic phase was dried over magnesium sulfate and concd, affording a crude residue that was purified, if necessary, by column chromatography (silica; eluting with EtOAc in hexanes) or reverse-phase HPLC (70% acetonitrile in water) to afford the substituted aryl amide.

Procedure V

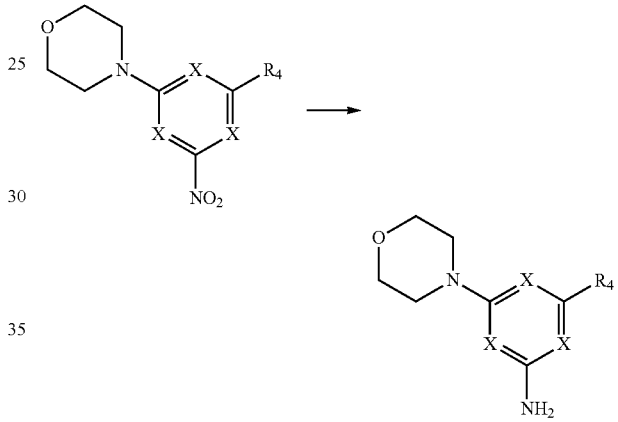

A reaction vessel charged with the substituted nitrobenzene (1 eq), 10% palladium on carbon (0.1 eq), and methanol (0.1-0.2 M) was subjected to three rounds of evacuation and backfilling with hydrogen, then stirred under a hydrogen balloon. Upon completion, the reaction mixture was filtered through Celite and the filtrate was concd, affording the substituted aryl amine.

Procedure W

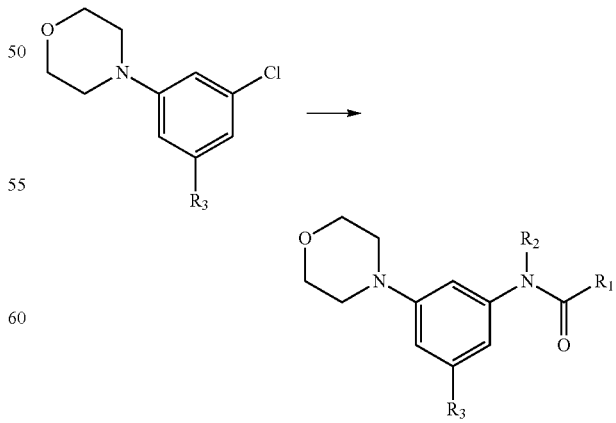

Two screw-cap vials were prepared, one containing palladium (II) acetate (0.05 eq) and tetramethyl tert-butyl XPhos (0.15 eq), the other containing the substituted quinoline (1 eq), amide (1.2 eq), and tripotassium phosphate (1.4 eq). Each vial was subjected to three rounds of evacuation and backfilling with argon. To the first vial was added tert-butanol (0.5 M), and the contents were heated at 110° C. for 90 seconds. The resulting solution was then transferred to the second vial, and that vial was heated at 110° C. for 20 minutes-24 h. Upon completion, the reaction was cooled to 23° C. and partitioned between EtOAc and water. The organic phase was dried over magnesium sulfate and concd, and the resulting crude material was purified either by column chromatography (silica; eluting with EtOAc in hexanes) or by reverse-phase HPLC (0-70% EtOAc in hexanes) to afford the substituted benzamide.

Procedure X

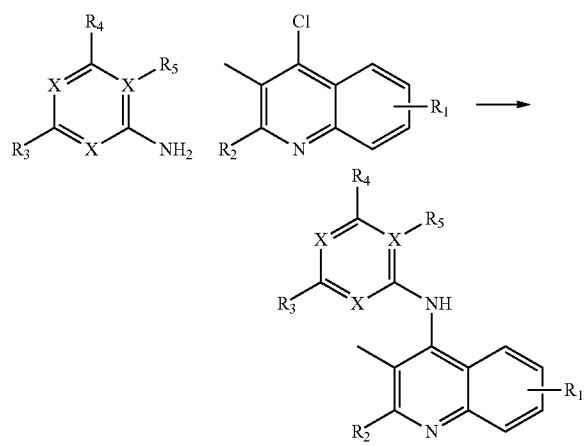

Two screw-cap vials were prepared, one containing palladium (II) acetate (0.05 eq) and XPhos (0.15 eq), the other containing the chloroquinoline (1 eq), aniline (1-1.2 eq), potassium carbonate (2.5 eq), and a small amount of molecular sieves. Each vial was subjected to three rounds of evacuation and backfilling with argon. To the first vial was added tert-butanol (0.1-0.5 M), and the contents were heated at 110° C. for 1 minute. The resulting solution was then transferred to the second vial, and that vial was heated at 110° C. for 20 minutes-18 h. Upon completion, the reaction was cooled to 23° C. and partitioned between EtOAc and water. The organic phase was dried over magnesium sulfate and concd, and the resulting crude material was purified either by column chromatography (silica; eluting with methanol in DCM) or by reverse-phase HPLC (eluting with acetonitrile in water) to afford the substituted amino quinoline.

Procedure Y

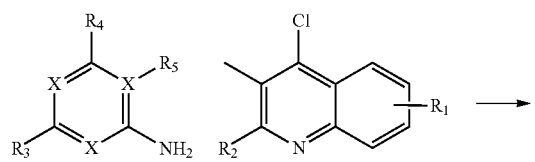

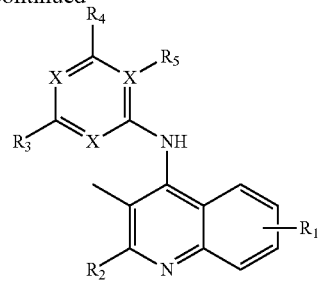

A mixture of substituted chloroquinoline (1 eq), substituted aniline (1 eq), sodium tert-butoxide (1.7), XPhos precatalyst (CAS 1028206-56-5; 0.1 eq) or tris(dibenzylideneacetone)dipalladium (0) (0.1 eq), XPhos (0.1 eq), and toluene (0.1-0.5 M) was stirred at 95-100° C. under nitrogen for 45 minutes-18 h, then filtered through Celite and concd. The crude material was partitioned between EtOAc and water, and the organic phase was dried over magnesium sulfate and concd. Purification by column chromatography or reverse-phase chromatography (0-70% acetonitrile in water) afforded the substituted amino quinoline.

Example 317

Preparation of 3-((7-fluoro-3-methyl-2-(2-pyridinyl)-4-quinolinyl)amino)-N-methyl-5-(4-morpholinyl)benzamide Methyl 3-bromo-5-nitrobenzoate

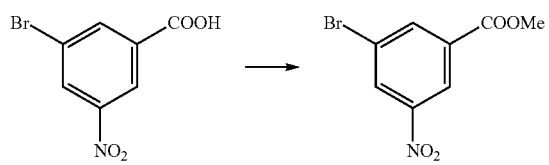 [SMILES: O=C(O)c1cc(Br)cc([N+](=O)[O-])c1 ; COC(=O)c1cc(Br)cc([N+](=O)[O-])c1]

Prepared according to Procedure S using 3-bromo-5-nitrobenzoic acid (5.0 g, 20.32 mmol), potassium carbonate (5.62 g, 40.6 mmol), DMF (55 mL), and methyl iodide (2.54 mL, 40.6 mmol) to afford methyl 3-bromo-5-nitrobenzoate as an orange amorphous solid. Mass Spectrum (ESI) m/e=261.1 (M+1).

Methyl 3-morpholino-5-nitrobenzoate

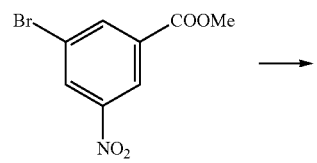

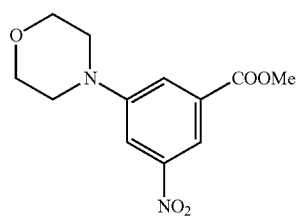

A mixture of methyl 3-bromo-5-nitrobenzoate (5 g, 19.23 mmol), morpholine (1.76 mL, 20.19 mmol), tris(dibenzylideneacetone)dipalladium (0) (1.32 g, 1.442 mmol), XPhos (1.38 g, 2.88 mmol), tripotassium phosphate (5.71 g, 26.9 mmol), and toluene (38.5 mL) was stirred overnight at 95° C. under nitrogen. Upon completion, the reaction was cooled to 23° C. and filtered over Celite. The filtrate was concd, and the crude material was purified by column chromatography (silica; 0-30% EtOAc in hexanes) to afford methyl 3-morpholino-5-nitrobenzoate as an orange amorphous solid. Mass Spectrum (ESI) m/e=267.2 (M+1).

3-Morpholino-5-nitrobenzoic acid

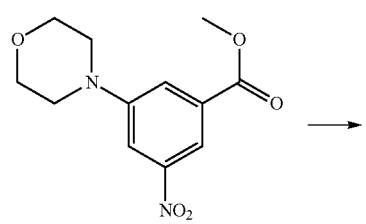

Prepared according to Procedure T using methyl 3-morpholino-5-nitrobenzoate (3.53 g, 13.24 mmol), THF (100 mL), methanol (66 mL), and 1 N aqueous lithium hydroxide (79 mL, 79 mmol). This afforded 3-morpholino-5-nitrobenzoic acid as an orange amorphous solid. Mass Spectrum (ESI) m/e=253.0 (M+1).

N-Methyl-3-morpholino-5-nitrobenzamide

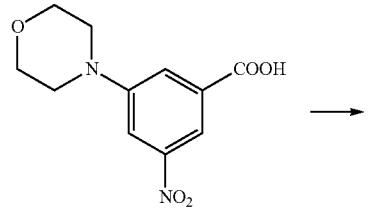

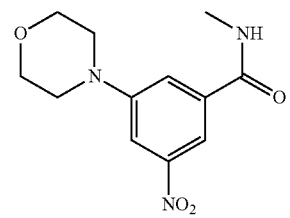

Prepared according to Procedure U using 3-morpholino-5-nitrobenzoic acid (0.8 g, 3.17 mmol), EDC (1.22 g, 6.34 mmol), DMAP (0.78 g, 6.34 mmol), 2.0M methanamine in THF (2.4 mL, 4.76 mmol), and DCM (12 mL). Purification by column chromatography (silica; 0-75% EtOAc in hexanes) afforded N-methyl-3-morpholino-5-nitrobenzamide as a yellow amorphous solid. Mass Spectrum (ESI) m/e=266.2 (M+1).

3-Amino-N-methyl-5-morpholinobenzamide

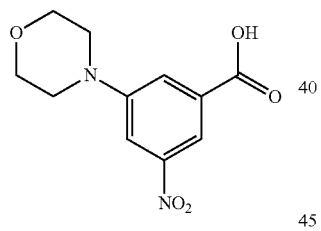

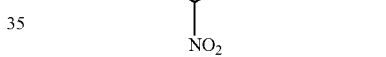

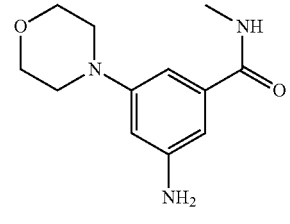

Prepared according to Procedure V using N-methyl-3-morpholino-5-nitrobenzamide (0.183 g, 0.690 mmol), 10% palladium on carbon (0.011 g, 0.103 mmol), and methanol (3 mL) to afford 3-amino-N-methyl-5-morpholinobenzamide as a beige amorphous solid. Mass Spectrum (ESI) m/e=236.2 (M+1).

3-((7-Fluoro-3-methyl-2-(2-pyridinyl)-4-quinolinyl) amino)-N-methyl-5-(4-morpholinyl)benzamide

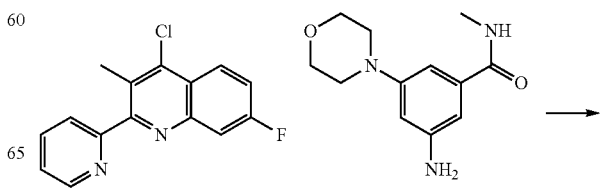

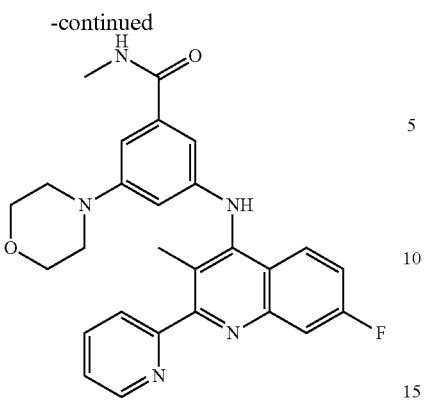

Prepared according to Procedure X using palladium (II) acetate (2.1 mg, 9.17 µmol), XPhos (0.013 g, 0.028 mmol), 4-chloro-7-fluoro-3-methyl-2-(pyridin-2-yl)quinoline (0.050 g, 0.183 mmol), 3-amino-N-methyl-5-morpholinobenzamide (0.043 g, 0.183 mmol), potassium carbonate (0.063 g, 0.458 mmol), and tert-butanol (1 mL). Purification using column chromatography (silica; 0-5% methanol in DCM) afforded 3-((7-fluoro-3-methyl-2-(2-pyridinyl)-4-quinolinyl)amino)-N-methyl-5-(4-morpholinyl)benzamide as a yellow amorphous solid. $^1$H NMR (400 MHz, CHLOROFORM-d) δ ppm 8.70-8.76 (1H, m), 7.80-7.95 (3H, m), 7.72-7.79 (1H, m), 7.35-7.44 (1H, m), 7.14-7.23 (1H, m), 6.88-6.96 (1H, m), 6.53-6.59 (1H, m), 6.36-6.43 (1H, m), 6.21-6.32 (1H, m), 6.15 (1H, br. s.), 3.76-3.84 (4H, m), 3.07-3.14 (4H, m), 2.93 (3H, d, J=4.7 Hz), 2.33 (3H, s). Mass Spectrum (ESI) m/e=472.1 (M+1).

Example 318

Preparation of N-(3-((7-fluoro-3-methyl-2-(2-pyridinyl)-4-quinolinyl)amino)-5-(4-morpholinyl)phenyl)acetamide 4-(3-chloro-5-nitrophenyl)morpholine

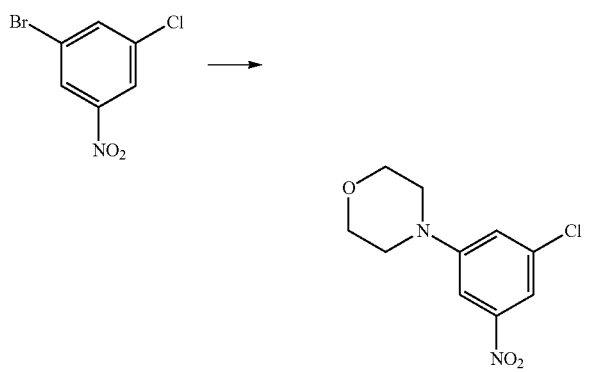

A mixture of 1-bromo-3-chloro-5-nitrobenzene (4.5 g, 19.03 mmol), morpholine (1.7 mL, 19.03 mmol), sodium tert-butoxide (3.11 g, 32.4 mmol), tris(dibenzylideneacetone) dipalladium (0) (0.87 g, 0.952 mmol), XPhos (0.91 g, 1.903 mmol), and toluene (40 mL) was stirred at 100° C. under nitrogen for 2 h, then filtered through Celite and concd. The resulting residue was partitioned between EtOAc and water, and the organic phase was washed with satd aqueous sodium bicarbonate and brine, dried over magnesium sulfate, and concd. Purification by column chromatography (silica; 0-25% EtOAc in hexanes) afforded 4-(3-chloro-5-nitrophenyl)morpholine as a yellow amorphous solid. Mass Spectrum (ESI) m/e=243.0 (M+1).

N-(3-Morpholino-5-nitrophenyl)acetamide

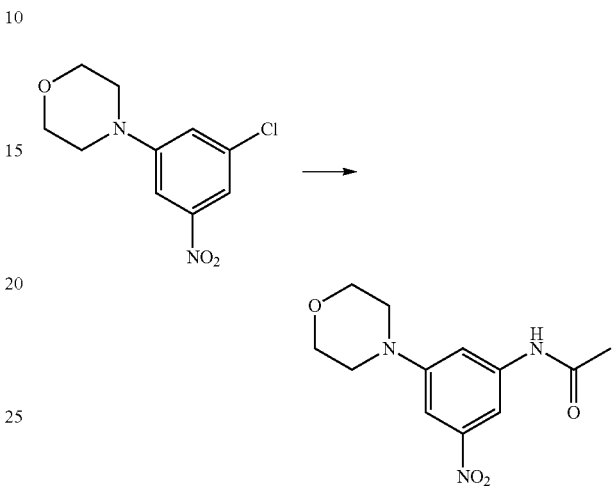

Prepared according to Procedure V using palladium (II) acetate (0.013 g, 0.057 mmol), tetramethyl t-butyl XPhos (0.082 g, 0.170 mmol), 4-(3-chloro-5-nitrophenyl)morpholine (0.275 g, 1.133 mmol), acetamide (0.080 g, 1.360 mmol), tripotassium phosphate (0.337 g, 1.587 mmol), and tert-butanol (2.5 mL) to afford N-(3-morpholino-5-nitrophenyl)acetamide. No purification was performed. Mass Spectrum (ESI) m/e=266.1 (M+1).

N-(3-Amino-5-morpholinophenyl)acetamide

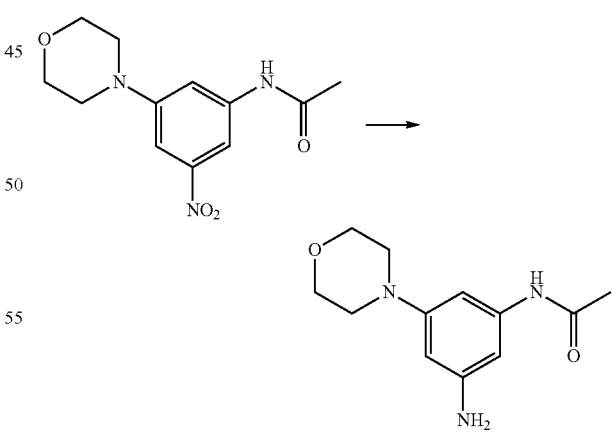

Prepared according to Procedure V by stirring N-(3-morpholino-5-nitrophenyl)-acetamide (0.014 g, 0.051 mmol), 10% palladium on carbon (5.5 mg, 5.13 µmol), and methanol (1 mL) at 23° C. to afford N-(3-amino-5-morpholinophenyl) acetamide as a tan amorphous solid. Mass Spectrum (ESI) m/e=236.1 (M+1).

473

N-(3-((7-fluoro-3-methyl-2-(2-pyridinyl)-4-quinolinyl)amino)-5-(4-morpholinyl)phenyl)acetamide

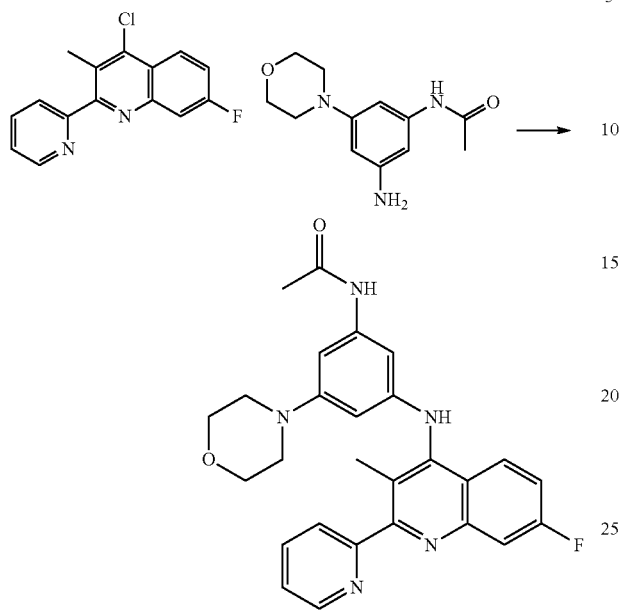

Prepared according to Procedure X using palladium (II) acetate (2.1 mg, 9.17 µmol), XPhos (0.013 g, 0.028 mmol), 4-chloro-7-fluoro-3-methyl-2-(pyridin-2-yl)quinoline (0.050 g, 0.183 mmol), N-(3-amino-5-morpholinophenyl)acetamide (0.043 g, 0.183 mmol), potassium carbonate (0.063 g, 0.458 mmol), and tert-butanol (0.5 mL). Purification by column chromatography (silica; 0-5% methanol in DCM) afforded N-(3-((7-fluoro-3-methyl-2-(2-pyridinyl)-4-quinolinyl)amino)-5-(4-morpholinyl)phenyl)acetamide as a yellow amorphous solid. $^1$H NMR (400 MHz, DMSO-d$_6$) δ ppm 9.59 (1H, s), 8.68-8.71 (1H, m), 8.43 (1H, s), 8.08 (1H, dd, J=9.3, 6.2 Hz), 7.98 (1H, dd, J=7.7, 1.9 Hz), 7.83-7.87 (1H, m), 7.68-7.76 (1H, m), 7.44-7.51 (2H, m), 6.80-6.83 (1H, m), 6.34-6.36 (1H, m), 6.11 (1H, t, J=2.1 Hz), 5.76 (1H, s), 3.67-3.73 (4H, m), 2.96-3.01 (4H, m), 2.20 (3H, s), 1.93 (3H, s). Mass Spectrum (ESI) m/e=472.1 (M+1).

Example 319

Preparation of (3-chloro-5-(4-morpholinyl)phenyl) (7-fluoro-3-methyl-2-(2-pyridinyl)-4-quinolinyl) methanol

7-Fluoro-3-methyl-2-(pyridin-2-yl)-4-vinylquinoline

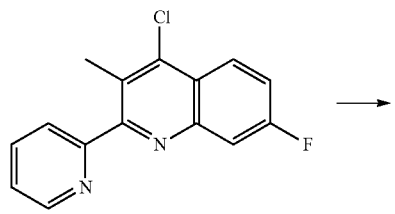

474

-continued

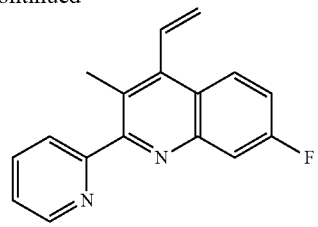

A solution of 4-chloro-7-fluoro-3-methyl-2-(pyridin-2-yl) quinoline (2.67 g, 9.79 mmol), bis(tri-tert-butylphosphine) palladium (0) (0.600 g, 1.175 mmol), vinyl tributyl tin (3.26 mL, 10.28 mmol), cesium fluoride (1.49 g, 9.79 mmol), and dioxane (20 mL) was stirred at 105° C. under nitrogen for 30 minutes, then concd. The resulting residue was partitioned between EtOAc and water, and the organic phase was dried over magnesium sulfate and concd. This afforded a crude material that was purified by column chromatography (silica; 0-60% EtOAc in hexanes) to yield 7-fluoro-3-methyl-2-(pyridin-2-yl)-4-vinylquinoline as a white amorphous solid. Mass Spectrum (ESI) m/e=265.2 (M+1).

7-Fluoro-3-methyl-2-(pyridin-2-yl)quinoline-4-carbaldehyde

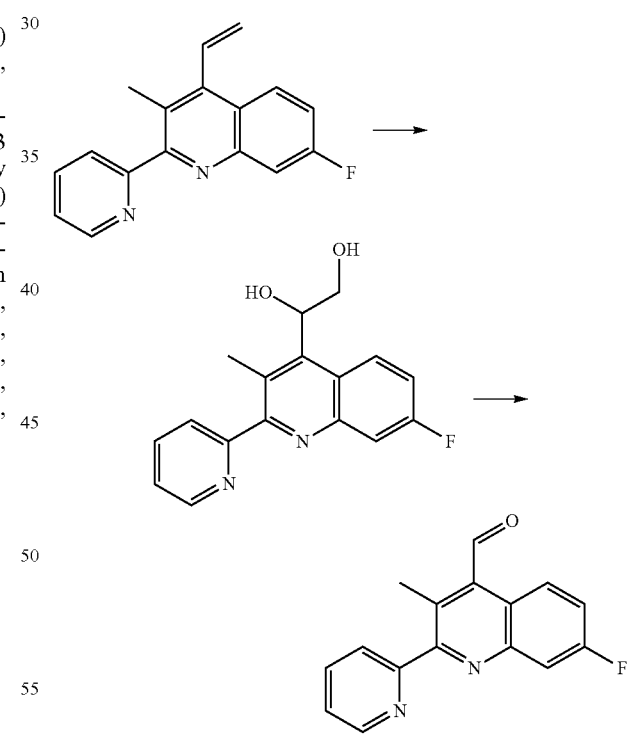

To a solution of 7-fluoro-3-methyl-2-(pyridin-2-yl)-4-vinylquinoline (1.53 g, 5.79 mmol) in acetone (30 mL) and water (7.50 mL) were added N-methylmorpholine-N-oxide (2.034 g, 17.37 mmol) and osmium tetroxide (0.074 g, 0.289 mmol). The reaction was stirred at 23° C. for 18 h. Upon completion, 10% aqueous sodium thiosulfate was added and the reaction was stirred for an additional 10 minutes. The reaction mixture was then concd, and the dihydroxylated product was extracted with EtOAc (twice) and DCM (twice).

The combined organics were dried over magnesium sulfate and concd, and the resulting residue was resolubilized in 30 mL 4:1 acetone:water and 3 mL dioxane. To this solution sodium periodate (3.10 g, 14.47 mmol) was added, and stirring continued at 23° C. for 2 h. Upon completion, the organic solvents were removed under vacuum, and the afforded crude material was partitioned between EtOAc and water. The organic phase was dried over magnesium sulfate and concd, and purification by column chromatography (silica; 0-70% EtOAc in hexanes) yielded 7-fluoro-3-methyl-2-(pyridin-2-yl)quinoline-4-carbaldehyde as a white amorphous solid. Mass Spectrum (ESI) m/e=367.1 (M+1).

4-(3-Bromo-5-chlorophenyl)morpholine

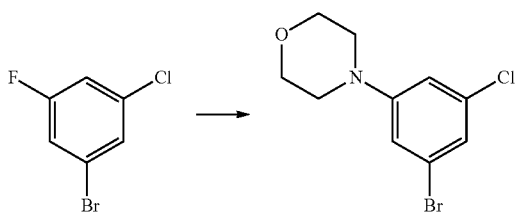 [SMILES: Fc1cc(Cl)cc(Br)c1 ; Clc1cc(Br)cc(N2CCOCC2)c1]

A solution of 1-bromo-3-chloro-5-fluorobenzene (5.05 g, 24.11 mmol), morpholine (3.15 mL, 36.2 mmol), potassium carbonate (6.66 g, 48.2 mmol), and DMF (45 mL) was stirred at 60° C. for 48 h, then at 110° C. for 24 h. The reaction mixture was concd, and the resulting residue was partitioned between EtOAc and water. The organic phase was dried over magnesium sulfate and concd, affording a crude material that was purified by column chromatography (silica; 0-10% EtOAc in hexanes) to yield 4-(3-bromo-5-chlorophenyl)morpholine as a white amorphous solid. Mass Spectrum (ESI) m/e=276.0 (M+1).

(3-Chloro-5-(4-morpholinyl)phenyl)(7-fluoro-3-methyl-2-(2-pyridinyl)-4-quinolinyl)methanol

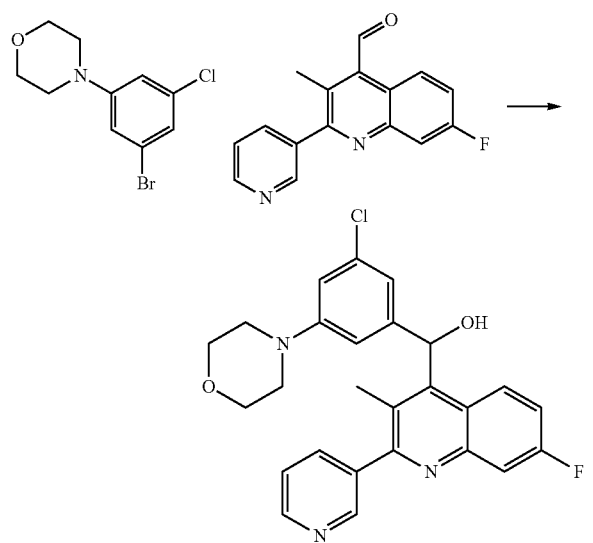

An oven-dried conical flask was charged with 4-(3-bromo-5-chlorophenyl)-morpholine (0.384 g, 1.390 mmol) and 1.0 mL THF. While this solution was stirring at −78° C. under nitrogen, 2.5M butyllithium hexanes (0.556 mL, 1.390 mmol) was added via syringe. This solution was stirred at −78° C. for 30 minutes. After this time a solution of 7-fluoro-3-methyl-2-(pyridin-2-yl)quinoline-4-carbaldehyde (0.074 g, 0.278 mmol) in 2.0 mL THF was added, and the reaction continued at −78° C. for 45 minutes. Upon completion, the reaction was quenched with satd aqueous ammonium chloride and concd. The resulting material was partitioned between EtOAc and water, and the organic phase was dried over magnesium sulfate and concd. The afforded crude product was purified by column chromatography (silica; 0-50% EtOAc in hexanes) to yield (3-chloro-5-(4-morpholinyl)phenyl)(7-fluoro-3-methyl-2-(2-pyridinyl)-4-quinolinyl)methanol as a white amorphous solid. $^1$H NMR (400 MHz, DMSO-d$_6$) δ ppm 8.70 (1H, d), 8.35 (1H, m), 8.01 (1H, t), 7.83 (1H, s), 7.71 (1H, d), 7.51 (1H, m), 7.42 (1H, m), 6.97 (1H, s), 6.83 (1H, s), 6.64 (1H, d, J=4.5 Hz), 6.55 (1H, d), 6.51 (1H, s), 3.69 (4H, t, J=4.8 Hz), 3.08 (4H, d, J=3.9 Hz), 2.46 (3H, s). Mass Spectrum (ESI) m/e=464.0 (M+1).

Example 320

Preparation of 3-((7-fluoro-3-methyl-2-(2-pyridinyl)-4-quinolinyl)(hydroxy)methyl)-5-(4-morpholinyl)benzonitrile

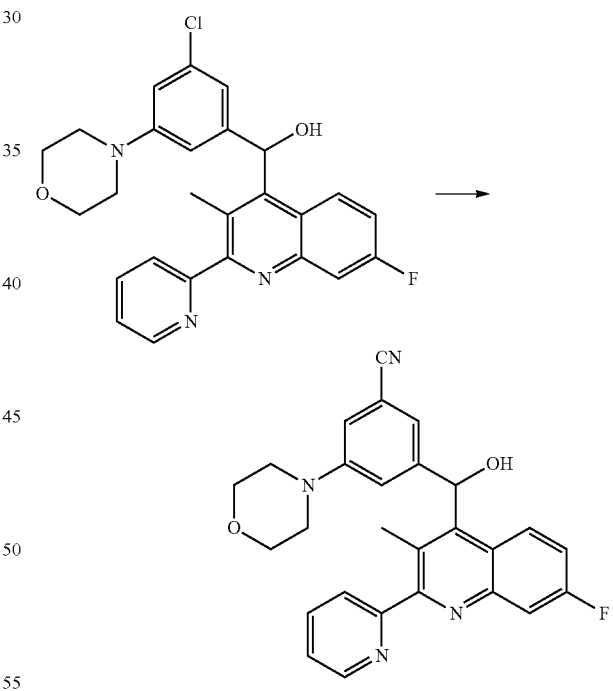

A solution of (3-chloro-5-morpholinophenyl)(7-fluoro-3-methyl-2-(pyridin-2-yl)-quinolin-4-yl)methanol (0.050 g, 0.108 mmol), tributyltin cyanide (0.034 g, 0.108 mmol), XPhos precatalyst (CAS 1028206-56-5; 0.014 g, 0.022 mmol), and NMP (1.0 mL) was heated in a microwave at 150° C. for 2 h. Upon completion, the reaction mixture was partitioned between EtOAc and water, and the organic phase was dried over magnesium sulfate and concd. This afforded a crude material that was purified by column chromatography (silica; 0-100% EtOAc in hexanes) to yield 3-((7-fluoro-3-methyl-2-(pyridin-2-yl)quinolin-4-yl)(hydroxy)methyl)-5- morpholinobenzonitrile as an amorphous beige solid. $^1$H NMR (400 MHz, DMSO-$d_6$) δ ppm 8.70 (1H, d), 8.31 (1H, m), 8.01 (1H, d, J=1.8 Hz), 7.83 (1H, d, J=7.8 Hz), 7.72 (1H, d), 7.51 (1H, m), 7.41 (1H, m), 7.33 (1H, s), 7.24 (1H, s), 6.85 (1H, s), 6.75 (1H, d, J=4.3 Hz), 6.59 (1H, d), 3.71 (4H, t, J=4.8 Hz), 3.14 (4H, q, J=4.4 Hz), 2.46 (3H, s). Mass Spectrum (ESI) m/e=455.0 (M+1).

Example 321

Preparation of 3-((7-fluoro-3-methyl-2-(2-pyridinyl)-4-quinolinyl)amino)-N,N-dimethyl-5-(4-morpholinyl)benzamide N,N-Dimethyl-3-morpholino-5-nitrobenzamide

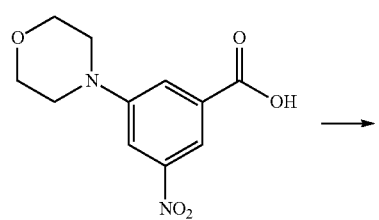

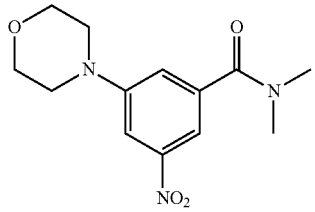

To a solution of 3-morpholino-5-nitrobenzoic acid (0.500 g, 1.982 mmol) in DCM (5.0 mL) were added oxalyl chloride (0.23 mL, 2.58 mmol) and 1 drop DMF. The mixture was stirred under nitrogen (vessel vented with a needle) at 23° C. for 45 minutes, then concd under vacuum. The resulting residue was taken up in 4 mL DCM and added dropwise to a stirring solution of 2.0M dimethylamine in THF (1.289 mL, 2.58 mmol) and triethylamine (0.414 mL, 2.97 mmol). The reaction was stirred under nitrogen for 15 minutes, then diluted with 1N HCl. The organic phase was washed with 1M sodium hydroxide and brine, then dried over magnesium sulfate and concd. This afforded N,N-dimethyl-3-morpholino-5-nitrobenzamide as an orange amorphous solid. Mass Spectrum (ESI) m/e=280.2 (M+1).

3-Amino-N,N-dimethyl-5-morpholinobenzamide

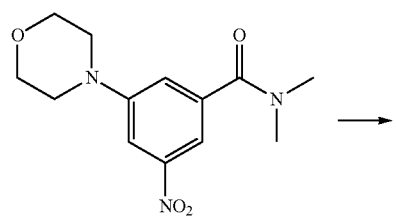

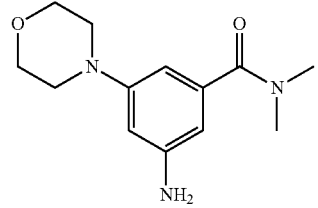

Prepared according to Procedure V by stirring N,N-dimethyl-3-morpholino-5-nitrobenzamide (0.480 g, 1.719 mmol), 10% palladium on carbon (0.366 g, 0.344 mmol), and methanol (30 mL) for 2 h to afford -amino-N,N-dimethyl-5-morpholinobenzamide as a white amorphous solid. Mass Spectrum (ESI) m/e=250.2 (M+1).

3-((7-Fluoro-3-methyl-2-(2-pyridinyl)-4-quinolinyl) amino)-N,N-dimethyl-5-(4-morpholinyl)benzamide

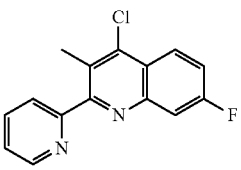 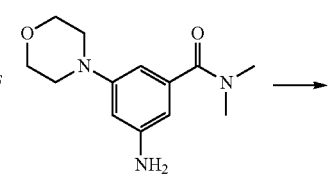

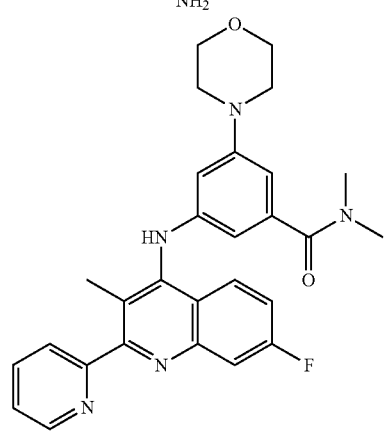

Prepared according to Procedure Y using 3-amino-N,N-dimethyl-5-morpholinobenzamide (0.046 g, 0.183 mmol), 4-chloro-7-fluoro-3-methyl-2-(pyridin-2-yl)-quinoline (0.050 g, 0.183 mmol), sodium tert-butoxide (0.035 g, 0.367 mmol), XPhos (8.7 mg, 0.018 mmol), XPhos precatalyst (CAS 1028206-56-5; 0.012 g, 0.018 mmol), and toluene (1.0 mL) to afford 3-((7-fluoro-3-methyl-2-(2-pyridinyl)-4-quinolinyl)amino)-N,N-dimethyl-5-(4-morpholinyl)benzamide as a yellow amorphous solid. $^1$H NMR (400 MHz, DMSO-$d_6$) δ ppm 8.66-8.71 (1H, m), 8.60 (1H, s), 8.09 (1H, dd, J=9.4, 6.3 Hz), 7.99 (1H, td, J=7.7, 1.8 Hz), 7.87 (1H, dt, J=7.8, 1.2 Hz), 7.71-7.77 (1H, m), 7.45-7.52 (2H, m), 6.41-6.46 (1H, m), 6.35-6.41 (1H, m), 5.95-5.98 (1H, m), 3.68-3.73 (4H, m), 3.04-3.11 (4H, m), 2.82-2.91 (6H, m), 2.21 (3H, s). Mass Spectrum (ESI) m/e=486.2 (M+1).

Example 322

Preparation of 4-(3-chloro-5-(4-morpholinyl)benzyl)-7-fluoro-3-methyl-2-(2-pyridinyl)quinoline

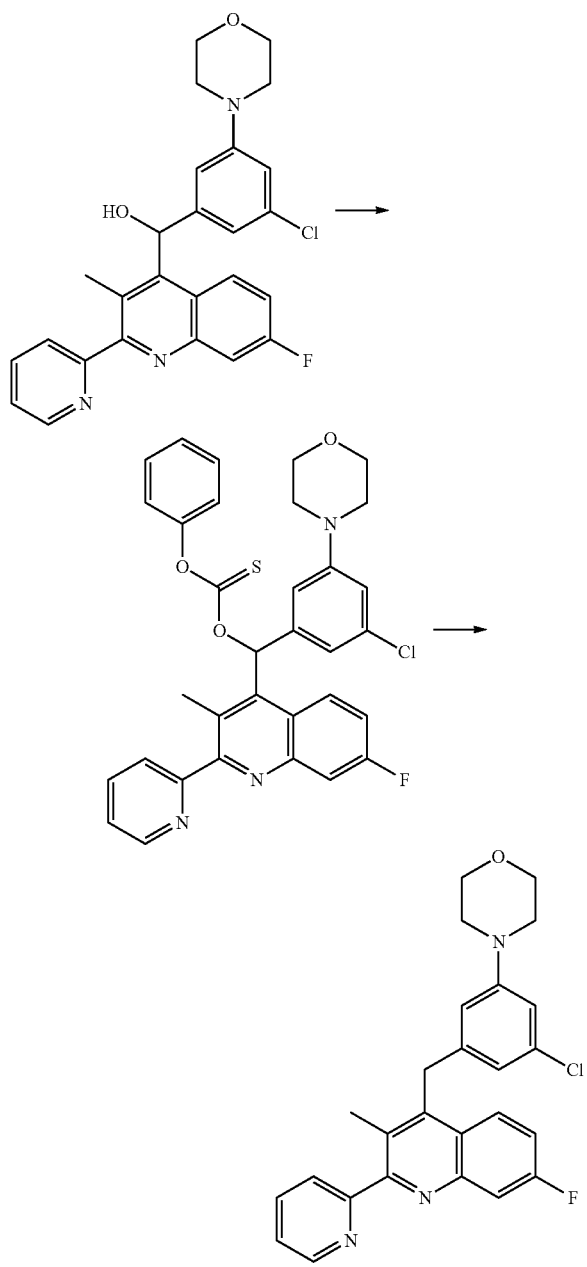

A screw-cap vial containing (3-chloro-5-morpholinophenyl)(7-fluoro-3-methyl-2-(pyridin-2-yl)quinolin-4-yl)methanol (0.025 g, 0.054 mmol), DMAP (0.020 g, 0.162 mmol), O-phenyl carbonochloridothioate (0.014 g, 0.081 mmol), and DCM (1.0 mL) was subjected to three rounds of evacuation and backfilling with argon, and the reaction was then stirred at 23° C. under argon for 18 h. Upon completion, the reaction mixture was diluted with DCM and washed with satd aqueous sodium bicarbonate and brine. The organic phase was dried over magnesium sulfate and concd, affording the intermediate as a pink amorphous solid. To the screw-cap vial containing this solid was added AIBN (2.65 mg, 0.016 mmol). The vial was subjected to three rounds of evacuation and backfilling with argon, then toluene (1.0 mL) and tributyltin hydride (0.037 mL, 0.140 mmol) were added via syringe. The reaction was stirred at 100° C. under argon for 5 minutes, then concd. The resulting crude material was purified by column chromatography (silica; 0-50% EtOAc in hexanes), to afford 4-(3-chloro-5-((7-fluoro-3-methyl-2-(pyridin-2-yl)quinolin-4-yl)methyl)phenyl)morpholine as a white amorphous solid. $^1$H NMR (400 MHz, CHLOROFORM-d) δ ppm 8.75 (1H, d), 7.93 (2H, s), 7.84 (2H, m), 7.41 (1H, t), 7.33 (1H, t), 6.71 (1H, s), 6.53 (1H, s), 6.50 (1H, s), 4.49 (2H, s), 3.74-3.85 (4H, m), 3.01-3.11 (4H, m), 2.46 (3H, s). Mass Spectrum (ESI) m/e=448.0 (M+1).

Example 323

Preparation of N-(3-((dimethylamino)methyl)-5-(4-morpholinyl)phenyl)-7-fluoro-3-methyl-2-(2-pyridinyl)-4-quinolinamine

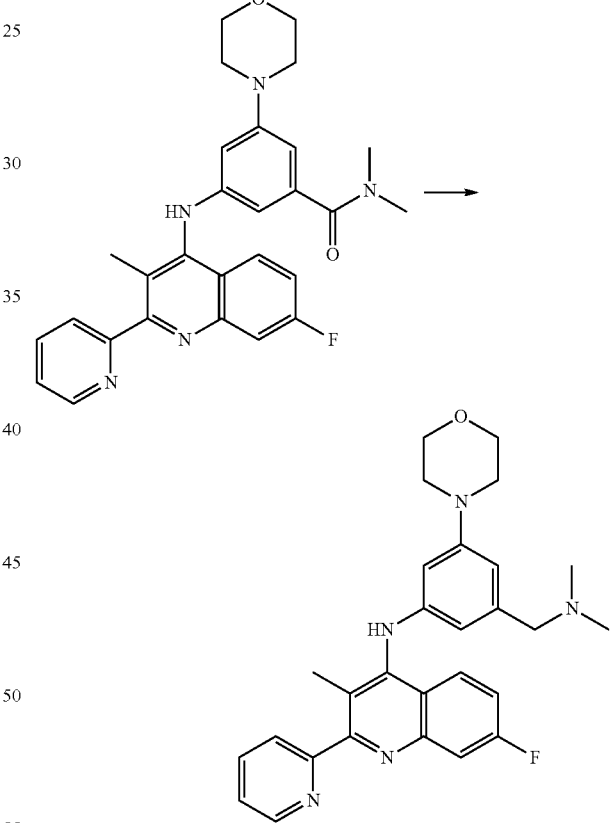

To a stirring solution of 3-(7-fluoro-3-methyl-2-(pyridin-2-yl)quinolin-4-ylamino)-N,N-dimethyl-5-morpholinobenzamide (0.074 g, 0.152 mmol) in THF (1.5 mL) was added 1M borane:THF complex (0.76 mL, 0.762 mmol). The reaction was stirred at 60° C. for 18 h, then cooled to 23° C., quenched with 0.7 mL concd HCl, and concd. To the resulting residue, 5 mL water was added as the reaction was stirred at 90° C. for one hour. The reaction was then basified with 1M sodium hydroxide, and the product was extracted twice with EtOAc. The combined organics were dried over magnesium sulfate and concd, affording a crude material that was purified by reverse-phase HPLC (0-70% acetonitrile in water). This yielded N-(3-((dimethylamino)methyl)-5-(4-morpholinyl)phenyl)-7-fluoro-3-methyl-2-(2-pyridinyl)-4-quinolinamine as a yellow amorphous solid. $^1$H NMR (400 MHz, DMSO-d$_6$) δ ppm 8.65-8.72 (1H, m), 8.47 (1H, s), 8.08 (1H, dd, J=9.2, 6.3 Hz), 7.96-8.01 (1H, m), 7.83-7.87 (1H, m), 7.69-7.73 (1H, m), 7.42-7.50 (2H, m), 6.38 (1H, s), 6.27-6.30 (1H, m), 6.09-6.11 (1H, m), 3.69 (4H, dd, J=5.6, 4.0 Hz), 3.23 (1H, br. s.), 2.99-3.05 (4H, m), 2.18 (3H, s), 2.10 (5H, br. s.). Mass Spectrum (ESI) m/e=472.2 (M+1).

Example 324

Preparation of 7-fluoro-3-methyl-N-(3-(5-methyl-1,3,4-oxadiazol-2-yl)-5-(4-morpholinyl)phenyl)-2-(2-pyridinyl)-4-quinolinamine N'-acetyl-3-morpholino-5-nitrobenzohydrazide

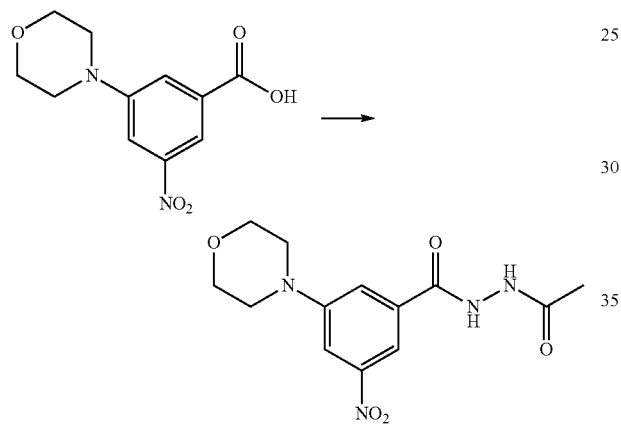

A screw-cap vial was charged with 3-morpholino-5-nitrobenzoic acid (0.250 g, 0.991 mmol), sodium bicarbonate (0.250 g, 2.97 mmol), EDC (0.285 g, 1.487 mmol), 1-hydroxy-7-azabenzotriazole (0.202 g, 1.487 mmol), acetic hydrazide (0.088 g, 1.189 mmol), and DMF (2.0 mL). The orange solution was stirred at 23° C. for 18 h, then partitioned between EtOAc and water. The organic phase was washed with brine, dried over magnesium sulfate, and concd., affording N'-acetyl-3-morpholino-5-nitrobenzohydrazide as an orange oil. Mass Spectrum (ESI) m/e=309.2 (M+1).

4-(3-(5-Methyl-1,3,4-oxadiazol-2-yl)-5-nitrophenyl)morpholine

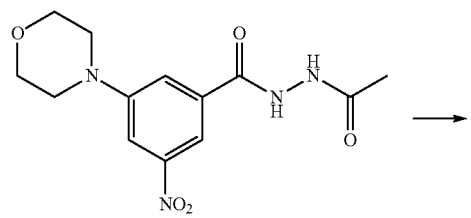

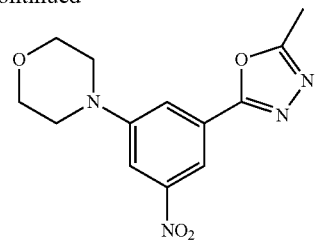

A 10 mL microwave vessel equipt with a stirbar was charged with N'-acetyl-3-morpholino-5-nitrobenzohydrazide (0.250 g, 0.811 mmol), Burgess reagent (0.97 g, 4.05 mmol), and dichloroethane (4 mL). The red solution was heated in a microwave at 120° C. for 20 minutes, then concd. The resulting residue was partitioned between EtOAc and water, and the organic layer washed with 1 N HCl, 1 N sodium hydroxide, and brine, then dried over magnesium sulfate and concd. This afforded a crude material that was purified by column chromatography (silica; 0-75% EtOAc in hexanes), providing 4-(3-(5-methyl-1,3,4-oxadiazol-2-yl)-5-nitrophenyl)morpholine as a yellow amorphous solid. Mass Spectrum (ESI) m/e=291.1 (M+1).

3-(5-Methyl-1,3,4-oxadiazol-2-yl)-5-morpholinoaniline

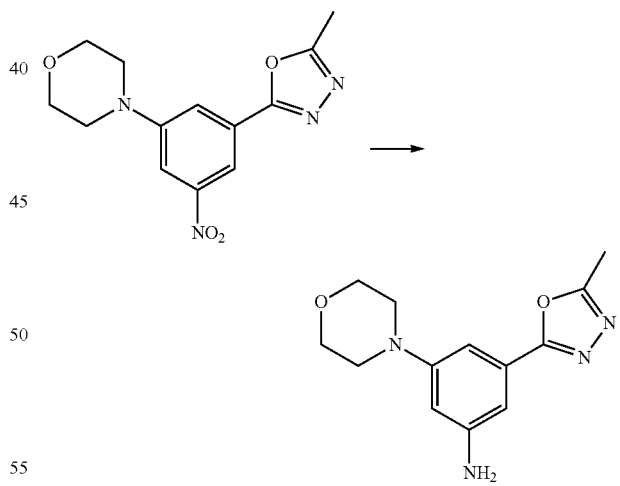

Prepared according to Procedure V by stirring a mixture of 4-(3-(5-methyl-1,3,4-oxadiazol-2-yl)-5-nitrophenyl)morpholine (0.16 g, 0.565 mmol), 10% palladium on carbon (0.120 g, 0.113 mmol), and methanol (5.7 mL) at 23° C. for 15 minutes. This afforded 3-(5-methyl-1,3,4-oxadiazol-2-yl)-5-morpholinoaniline as a yellow amorphous solid. Mass Spectrum (ESI) m/e=261.1 (M+1).

483

7-Fluoro-3-methyl-N-(3-(5-methyl-1,3,4-oxadiazol-2-yl)-5-(4-morpholinyl)-phenyl)-2-(2-pyridinyl)-4-quinolinamine

484

Example 325

Preparation of N-(3-((7-fluoro-3-methyl-2-(2-pyridinyl)-4-quinolinyl)(hydroxy)methyl)-5-(4-morpholinyl)phenyl)acetamide

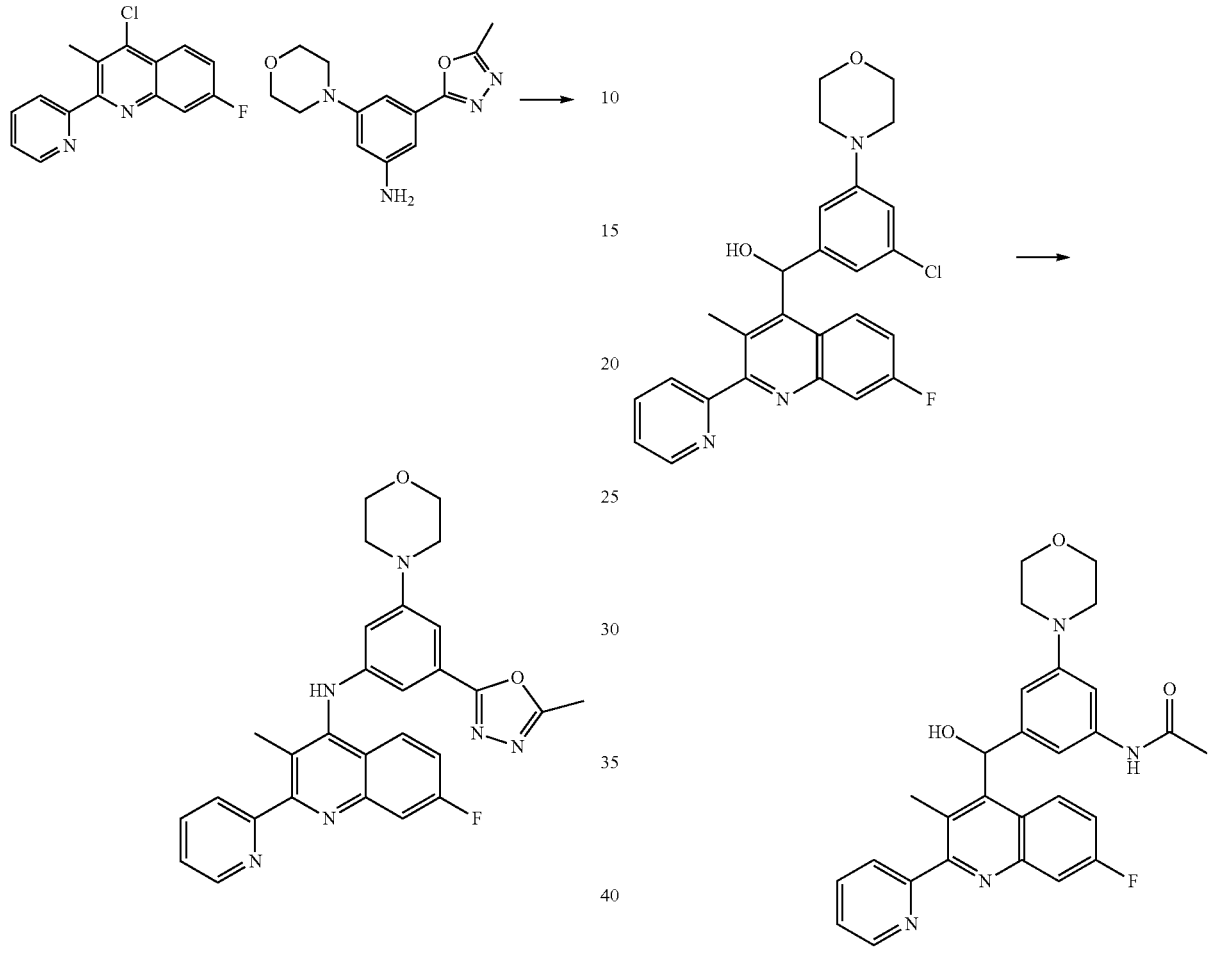

Prepared according to Procedure N using 3-(5-methyl-1,3,4-oxadiazol-2-yl)-5-morpholinoaniline (0.034 g, 0.131 mmol), 4-chloro-7-fluoro-3-methyl-2-(pyridin-2-yl)quinoline (0.036 g, 0.131 mmol), sodium tert-butoxide (0.031 g, 0.327 mmol), XPhos precatalyst (CAS 1028206-56-5; 8.79 mg, 0.013 mmol), XPhos (6.23 mg, 0.013 mmol), and toluene (0.7 mL) to afford 7-fluoro-3-methyl-N-(3-(5-methyl-1,3,4-oxadiazol-2-yl)-5-(4-morpholinyl)phenyl)-2-(2-pyridinyl)-4-quinolinamine as a yellow amorphous solid. $^1$H NMR (400 MHz, DMSO-d$_6$) δ ppm 8.79 (1H, s), 8.68-8.71 (1H, m), 8.07-8.15 (1H, m), 8.00 (1H, dd, J=7.6, 2.0 Hz), 7.88-7.91 (1H, m), 7.77 (1H, dd, J=10.3, 2.6 Hz), 7.48-7.54 (2H, m), 6.96 (1H, t, J=1.9 Hz), 6.72 (1H, t, J=1.7 Hz), 6.51 (1H, t, J=2.2 Hz), 3.70-3.74 (4H, m), 3.07-3.14 (4H, m), 2.52 (3H, s), 2.23 (3H, s). Mass Spectrum (ESI) m/e=497.1 (M+1).

Prepared according to Procedure W by stirring palladium (II) acetate (1.5 mg, 6.70 μmol), tetramethyl tert-butyl XPhos (9.7 mg, 0.020 mmol), (3-chloro-5-morpholinophenyl)(7-fluoro-3-methyl-2-(pyridin-2-yl)quinolin-4-yl)methanol (0.031 g, 0.067 mmol), tripotassium phosphate (0.020 g, 0.094 mmol), acetamide (4.8 mg, 0.080 mmol), and tert-butanol (0.9 mL) at 110° C. for 1 hour. Purification by reverse-phase HPLC afforded N-(3-((7-fluoro-3-methyl-2-(pyridin-2-yl)quinolin-4-yl)(hydroxy)methyl)-5-morpholinophenyl)acetamide as a white amorphous solid. $^1$H NMR (400 MHz, DMSO-d$_6$) δ ppm 9.67 (1H, s), 8.70 (1H, d), 8.39 (1H, m), 8.02 (1H, t), 7.80 (1H, d), 7.70 (1H, d), 7.52 (1H, m), 7.39 (1H, t), 7.32 (1H, s), 6.87 (1H, s), 6.60 (1H, s), 6.52 (1H, d), 6.48 (1H, s), 3.72 (4H, t, J=4.7 Hz), 3.03 (4H, d, J=3.3 Hz), 2.47 (3H, s), 1.91 (3H, s). Mass Spectrum (ESI) m/e=467.2 (M+1).

Example 326

Preparation of 3-((7-fluoro-3-methyl-2-(2-pyridinyl)-4-quinolinyl)amino)-5-(4-morpholinyl)benzoic acid Methyl 3-amino-5-morpholinobenzoate

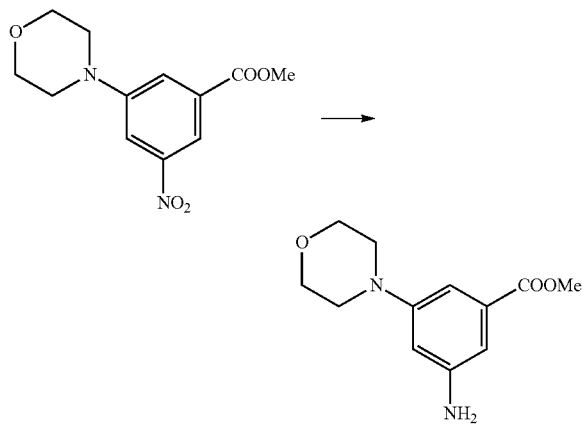

Prepared according to Procedure V by stirring methyl 3-morpholino-5-nitrobenzoate (0.503 g, 1.889 mmol), 10% palladium on carbon (0.201 g, 0.189 mmol), and methanol (25 mL) at 23° C. for 7 h. This afforded methyl 3-amino-5-morpholinobenzoate as a brown amorphous solid. Mass Spectrum (ESI) m/e=237.2 (M+1).

Methyl 3-(7-fluoro-3-methyl-2-(pyridin-2-yl)quinolin-4-ylamino)-5-morpholinobenzoate

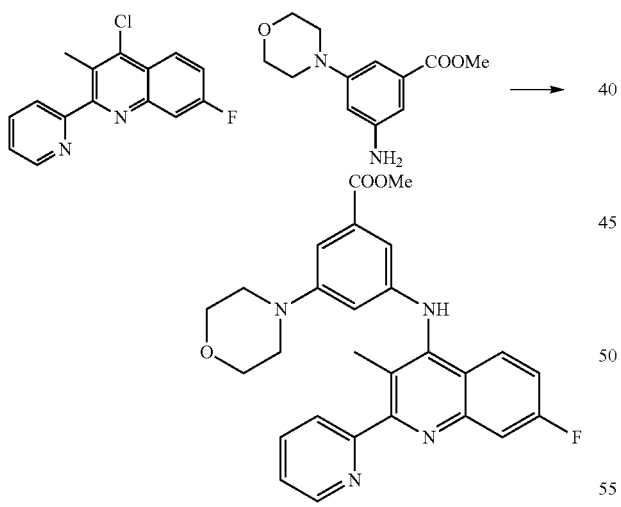

Prepared according to Procedure Y using 4-chloro-7-fluoro-3-methyl-2-(pyridin-2-yl)quinoline (0.300 g, 1.100 mmol), methyl 3-amino-5-morpholinobenzoate (0.260 g, 1.100 mmol), XPhos precatalyst (CAS 1028206-56-5; 0.074 g, 0.110 mmol), XPhos (0.052 g, 0.110 mmol), sodium tert-butoxide (0.26 g, 2.75 mmol), and toluene (2.2 mL). Purification by column chromatography (silica; 0-90% EtOAc in hexanes) afforded methyl 3-(7-fluoro-3-methyl-2-(pyridin-2-yl)quinolin-4-ylamino)-5-morpholinobenzoate as a yellow amorphous solid. Mass Spectrum (ESI) m/e=473.2 (M+1).

3-((7-Fluoro-3-methyl-2-(2-pyridinyl)-4-quinolinyl)amino)-5-(4-morpholinyl)benzoic acid

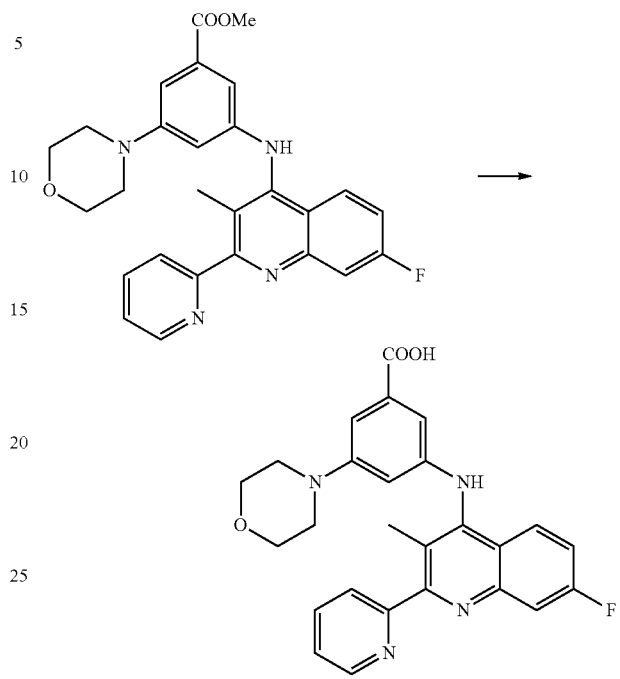

Prepared according to Procedure T using methyl 3-(7-fluoro-3-methyl-2-(pyridin-2-yl)quinolin-4-ylamino)-5-morpholinobenzoate (0.233 g, 0.493 mmol), methanol (2 mL), THF (3 mL), and 1 N aqueous lithium hydroxide (4.9 mL, 4.93 mmol). (Extraction was performed with 20% 2-propanol in chloroform rather than EtOAc). This afforded 3-((7-fluoro-3-methyl-2-(2-pyridinyl)-4-quinolinyl)-amino)-5-(4-morpholinyl)benzoic acid as an orange amorphous solid. $^1$H NMR (400 MHz, DMSO-$d_6$) δ ppm 8.72-8.76 (1H, m), 8.13 (1H, m), 8.01-8.06 (1H, m), 7.89 (1H, dt, J=7.8, 1.2 Hz), 7.74-7.82 (1H, m), 7.49-7.56 (2H, m), 7.05 (1H, br. s.), 6.79 (1H, br. s.), 6.65 (1H, br. s.), 3.66-3.75 (4H, m), 3.06-3.11 (4H, m), 2.17 (3H, s). Mass Spectrum (ESI) m/e=459.0 (M+1).

Example 327

Preparation of 1-(3-((7-fluoro-3-methyl-2-(2-pyridinyl)-4-quinolinyl)amino)-5-(4-morpholinyl)phenyl)-2-pyrrolidinone 1-(3-morpholino-5-nitrophenyl)pyrrolidin-2-one

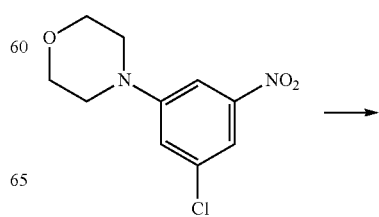

487
-continued

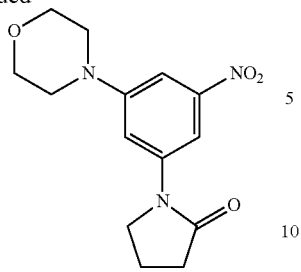

Prepared according to Procedure W using palladium (II) acetate (4.63 mg, 0.021 mmol), tetramethyl t-butyl XPhos (0.030 g, 0.062 mmol), 4-(3-chloro-5-nitrophenyl)morpholine (0.100 g, 0.412 mmol), tripotassium phosphate (0.122 g, 0.577 mmol), 2-pyrrolidinone (0.044 mL, 0.577 mmol), and tert-butanol (1 mL). Purification by column chromatography (silica; 0-50% EtOAc in hexanes) afforded 1-(3-morpholino-5-nitrophenyl)pyrrolidin-2-one as an orange amorphous solid. Mass Spectrum (ESI) m/e=292.2 (M+1).

1-(3-Amino-5-morpholinophenyl)pyrrolidin-2-one

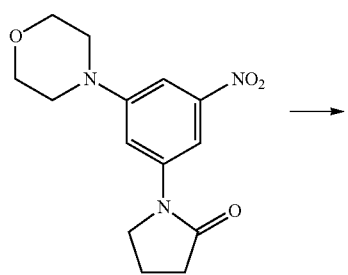

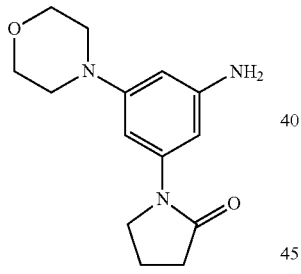

Prepared according to Procedure V by stirring 1-(3-morpholino-5-nitrophenyl)-pyrrolidin-2-one (0.056 g, 0.192 mmol), 10% palladium on carbon (0.041 g, 0.038 mmol), and methanol (4 mL) at 23° C. for 15 minutes. This afforded 1-(3-amino-5-morpholinophenyl)pyrrolidin-2-one as a tan amorphous solid. Mass Spectrum (ESI) m/e=262.2 (M+1).

1-(3-((7-Fluoro-3-methyl-2-(2-pyridinyl)-4-quinolinyl)amino)-5-(4-morpholinyl)phenyl)-2-pyrrolidinone

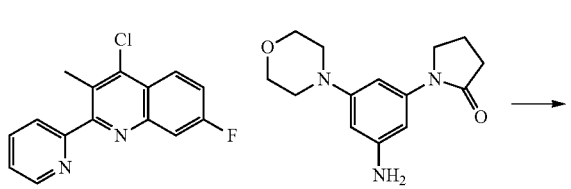

488
-continued

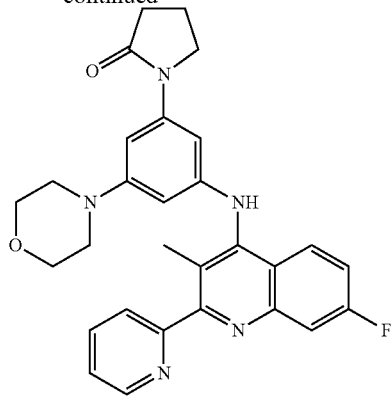

Prepared according to Procedure Y using 4-chloro-7-fluoro-3-methyl-2-(pyridin-2-yl)quinoline (0.047 g, 0.172 mmol), 1-(3-amino-5-morpholinophenyl)pyrrolidin-2-one (0.045 g, 0.172 mmol), XPhos precatalyst (CAS 1028206-56-5; 0.012 g, 0.017 mmol), XPhos (8.21 mg, 0.017 mmol), sodium tert-butoxide (0.041 g, 0.431 mmol), and toluene (1 mL). This afforded 1-(3-((7-fluoro-3-methyl-2-(2-pyridinyl)-4-quinolinyl)amino)-5-(4-morpholinyl)phenyl)-2-pyrrolidinone as a yellow film. $^1$H NMR (400 MHz, CHLOROFORM-d) δ ppm 8.73-8.77 (1H, m), 7.81-7.93 (3H, m), 7.73-7.78 (1H, m), 7.36-7.41 (1H, m), 7.15-7.22 (1H, m), 6.89-6.92 (1H, m), 6.55-6.61 (1H, m), 6.16 (1H, br. s.), 6.04-6.07 (1H, m), 3.76-3.81 (4H, m), 3.73 (2H, t, J=7.0 Hz), 3.02-3.09 (4H, m), 2.58 (2H, t, J=8.0 Hz), 2.36 (3H, s), 2.11 (2H, quin, J=7.6 Hz). Mass Spectrum (ESI) m/e=498.0 (M+1).

Example 328

Preparation of 7-fluoro-3-methyl-2-(pyridin-2-yl)quinolin-4-amine 7-fluoro-N-(4-methoxybenzyl)-3-methyl-2-(pyridin-2-yl)quinolin-4-amine

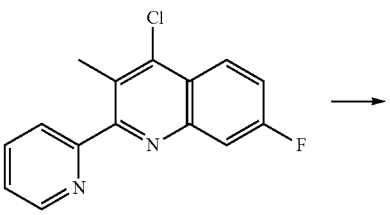

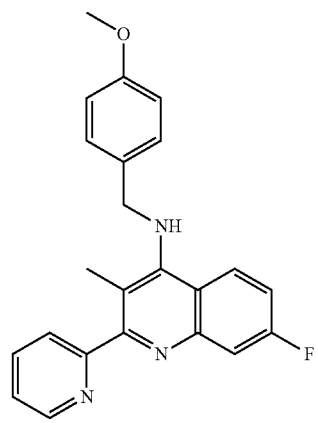

489

A mixture of 4-chloro-7-fluoro-3-methyl-2-(pyridin-2-yl)quinoline (2.0 g, 7.33 mmol), sodium tert-butoxide (1.41 g, 14.67 mmol), tris(dibenzylideneacetone)-dipalladium (0) (0.504 g, 0.550 mmol), XPhos (0.52 g, 1.100 mmol), 4-methoxybenzylamine (0.95 mL, 7.33 mmol), and toluene (15 mL) was stirred at 110° C. under nitrogen for 3 h. Upon completion, the reaction was cooled to 23° C. and concd. The resulting crude residue was taken up in EtOAc, filtered through Celite, and washed with water and brine. The organic phase was dried over magnesium sulfate and concd, affording a crude material that was purified by column chromatography (silica; 0-50% EtOAc in hexanes) to yield 7-fluoro-N-(4-methoxybenzyl)-3-methyl-2-(pyridin-2-yl)quinolin-4-amine as an orange oil. Mass Spectrum (ESI) m/e=374.2 (M+1).

7-Fluoro-3-methyl-2-(pyridin-2-yl)quinolin-4-amine

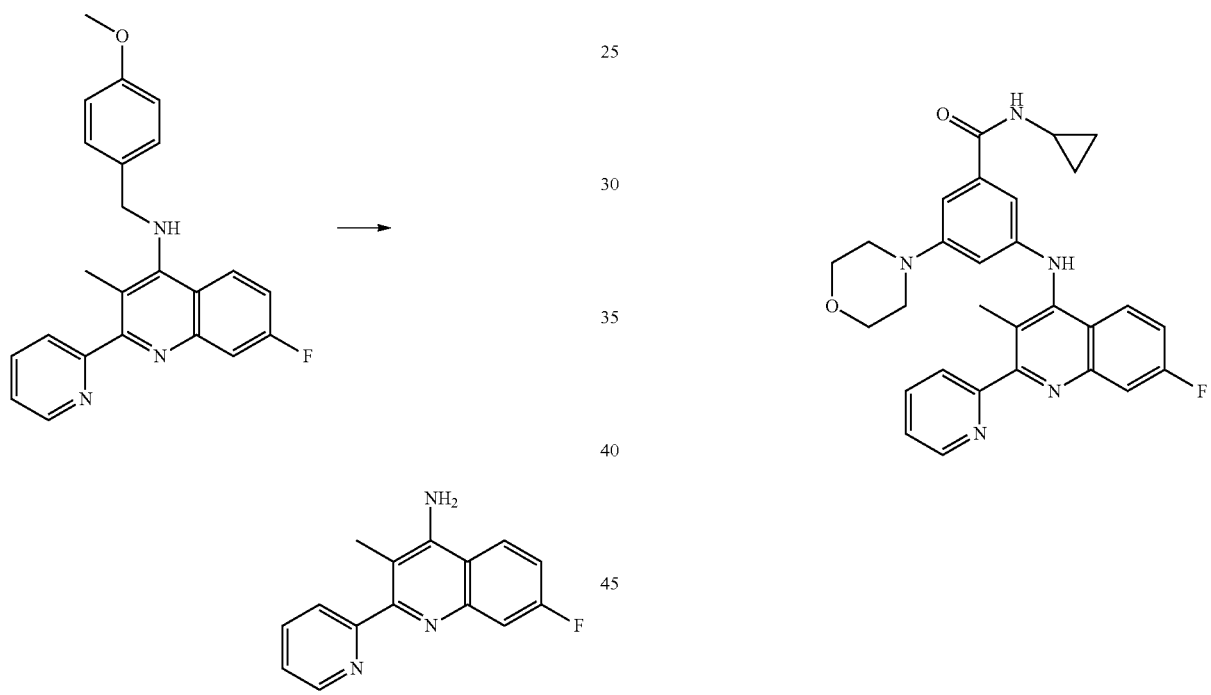

A solution of 7-fluoro-N-(4-methoxybenzyl)-3-methyl-2-(pyridin-2-yl)quinolin-4-amine (0.900 g, 2.410 mmol), trifluoroacetic acid (2.8 mL, 36.2 mmol), and DCM (4 mL) was stirred at 23° C. for 1 hour. Upon completion, the reaction was concd, and the resulting residue was partitioned between EtOAc and 1 N HCl. The aqueous layer was then basified, and the product extracted twice with EtOAc. The combined organics were dried over magnesium sulfate and concd, affording 7-fluoro-3-methyl-2-(pyridin-2-yl)quinolin-4-amine as a beige amorphous solid. Mass Spectrum (ESI) m/e=254.2 (M+1).

490

Example 329

Preparation of N-cyclopropyl-3-((7-fluoro-3-methyl-2-(2-pyridinyl)-4-quinolinyl)amino)-5-(4-morpholinyl)benzamide Prepared according to Procedure U by stirring 3-(7-fluoro-3-methyl-2-(pyridin-2-yl)quinolin-4-ylamino)-5-morpholinobenzoic acid (0.030 g, 0.065 mmol), DMAP (0.016 g, 0.131 mmol), EDC (0.025 g, 0.131 mmol), cyclopropylamine (6.46 μL, 0.092 mmol), and DCM (0.6 mL) at 23° C. for 1 hour. Purification by reverse-phase HPLC afforded N-cyclopropyl-3-((7-fluoro-3-methyl-2-(2-pyridinyl)-4-quinolinyl)amino)-5-(4-morpholinyl)benzamide as a yellow amorphous solid. $^1$H NMR (400 MHz, DMSO-$d_6$) δ ppm 8.68-8.71 (1H, m), 8.61 (1H, s), 8.24 (1H, d, J=4.3 Hz), 8.08 (1H, dd, J=9.3, 6.2 Hz), 7.99 (1H, dd, J=7.6, 1.8 Hz), 7.85-7.89 (1H, m), 7.74 (1H, dd, J=10.4, 2.7 Hz), 7.45-7.51 (2H, m), 6.82-6.84 (1H, m), 6.59-6.61 (1H, m), 6.44 (1H, t, J=2.2 Hz), 3.68-3.74 (4H, m), 3.04-3.09 (4H, m), 2.76 (1H, m), 2.18 (3H, s), 0.60-0.69 (2H, m), 0.51 (2H, dd, J=4.2, 2.2 Hz). Mass Spectrum (ESI) m/e=498.0 (M+1).

Example 330

Preparation of N-ethyl-3-((7-fluoro-3-methyl-2-(2-pyridinyl)-4-quinolinyl)amino)-5-(4-morpholinyl)benzamide

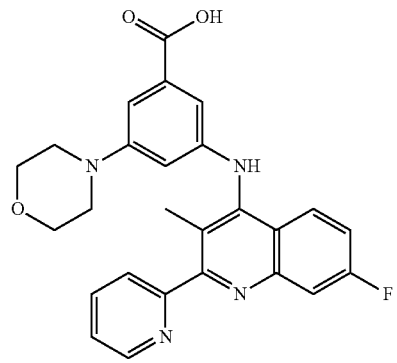

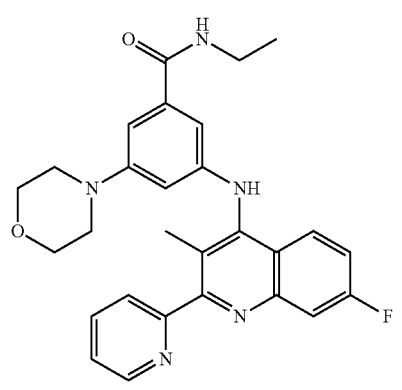

Prepared according to Procedure U by stirring 3-(7-fluoro-3-methyl-2-(pyridin-2-yl)quinolin-4-ylamino)-5-morpholinobenzoic acid (0.025 g, 0.055 mmol), DMAP (0.013 g, 0.109 mmol), EDC (0.021 g, 0.109 mmol), 2M ethanamine THF (0.035 mL, 0.071 mmol), and DCM (0.6 mL) at 23° C. for 1 hour. Purification by reverse-phase HPLC afforded N-ethyl-3-((7-fluoro-3-methyl-2-(2-pyridinyl)-4-quinolinyl)amino)-5-(4-morpholinyl)benzamide as a yellow amorphous solid. $^1$H NMR (400 MHz, DMSO-$d_6$) δ ppm 8.67-8.71 (1H, m), 8.61 (1H, s), 8.27 (1H, m), 8.09 (1H, dd, J=9.3, 6.2 Hz), 7.97-8.02 (1H, m), 7.84-7.91 (1H, m), 7.71-7.77 (1H, m), 7.45-7.52 (2H, m), 6.86-6.89 (1H, m), 6.59-6.62 (1H, m), 6.44-6.48 (1H, m), 3.69-3.75 (4H, m), 3.17-3.25 (2H, m), 3.05-3.11 (4H, m), 2.16-2.20 (3H, m), 1.04-1.10 (3H, m). Mass Spectrum (ESI) m/e=486.2 (M+1).

Example 331

Preparation of 3-((7-fluoro-3-methyl-2-(2-pyridinyl)-4-quinolinyl)amino)-5-(4-morpholinyl)benzamide

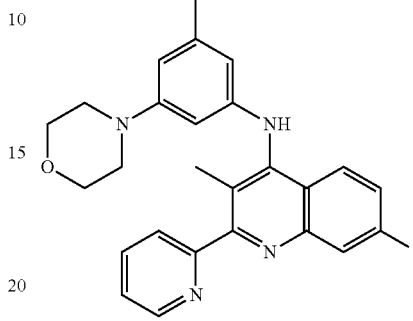

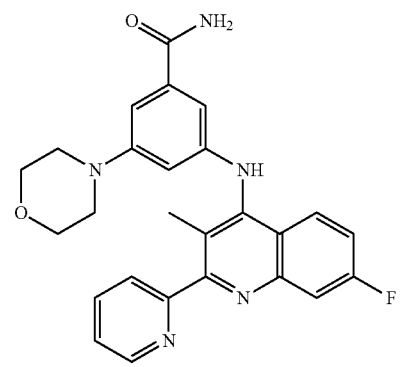

Prepared according to Procedure U by stirring 3-(7-fluoro-3-methyl-2-(pyridin-2-yl)quinolin-4-ylamino)-5-morpholinobenzoic acid (0.014 g, 0.031 mmol), DMAP (7.46 mg, 0.061 mmol), EDC (0.023 g, 0.122 mmol), 0.5M ammonia in dioxane (0.092 mL, 0.046 mmol), and DCM (0.3 mL) at 23° C. for 48 h. Reverse-phase HPLC afforded 3-((7-fluoro-3-methyl-2-(2-pyridinyl)-4-quinolinyl)amino)-5-(4-morpholinyl)benzamide as a yellow amorphous solid. $^1$H NMR (400 MHz, Methanol) δ ppm 8.72 (1H, br. s.), 7.98-8.27 (2H, m), 7.82 (1H, d, J=7.2 Hz), 7.67 (1H, d, J=9.6 Hz), 7.59 (1H, d, J=3.9 Hz), 7.39 (1H, m), 7.08 (1H, br. s.), 6.77 (1H, br. s.), 6.66 (1H, br. s.), 3.70-3.94 (4H, m), 3.03-3.25 (5H, m), 2.01-2.24 (3H, m). Mass Spectrum (ESI) m/e=457.2 (M+1).

Example 332

Preparation of N-(3-((7-fluoro-3-methyl-2-(2-oxo-1-pyrrolidinyl)-4-quinolinyl)amino)-5-(4-morpholinyl)phenyl)acetamide 1-(4-Chloro-7-fluoro-3-methylquinolin-2-yl)pyrrolidin-2-one

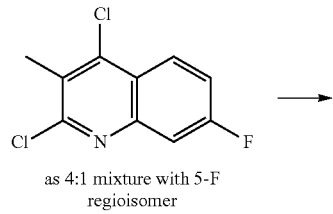

as 4:1 mixture with 5-F regioisomer

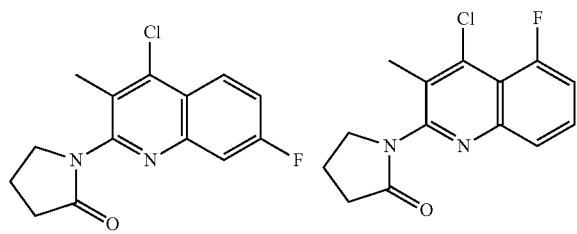

Prepared according to Procedure F using 2,4-dichloro-7-fluoro-3-methylquinoline (2 g, 8.69 mmol), 2-pyrrolidinone (0.73 mL, 9.56 mmol), cesium carbonate (4 g, 12.17 mmol), tris(dibenzylideneacetone)dipalladium (0) (0.40 g, 0.435 mmol), XantPhos (0.76 g, 1.304 mmol), and dioxane (17 mL). Purification by column chromatography (silica; 0-40% EtOAc in hexanes) afforded (in order of elution) 1-(4-chloro-7-fluoro-3-methylquinolin-2-yl)pyrrolidin-2-one and 1-(4-chloro-5-fluoro-3-methylquinolin-2-yl)pyrrolidin-2-one as white amorphous solids. Mass Spectra (ESI) m/e=279.0 (M+1); 279.0 (M+1).

N-(3-((7-Fluoro-3-methyl-2-(2-oxo-1-pyrrolidinyl)-4-quinolinyl)amino)-5-(4-morpholinyl)phenyl)acetamide

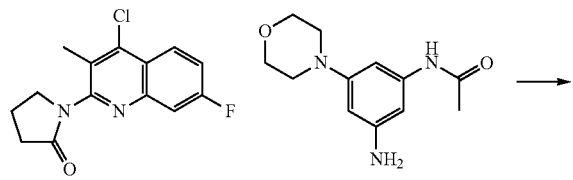

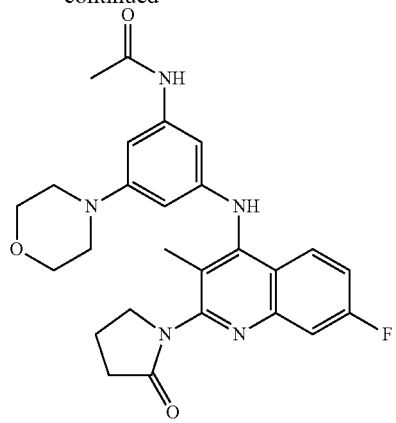

Prepared according to Procedure X by stirring palladium (II) acetate (0.3 mg, 1.417 µmol), XPhos (2.0 mg, 4.25 µmol), 1-(4-chloro-7-fluoro-3-methylquinolin-2-yl)pyrrolidin-2-one (0.020 g, 0.071 mmol), N-(3-amino-5-morpholinophenyl)-acetamide (0.020 g, 0.085 mmol), potassium carbonate (0.024 g, 0.177 mmol), and tert-butanol (0.5 mL) at 110° C. for 30 minutes. Purification by reverse-phase HPLC (0-70% acetonitrile in water) afforded N-(3-((7-fluoro-3-methyl-2-(2-oxo-1-pyrrolidinyl)-4-quinolinyl)amino)-5-(4-morpholinyl)phenyl)acetamide as a yellow amorphous solid. $^1$H NMR (500 MHz, CHLOROFORM-d) δ ppm 7.80 (1H, dd, J=8.8, 7.3 Hz), 7.51-7.61 (1H, m), 7.45 (1H, br. s.), 7.08-7.19 (1H, m), 6.79-6.99 (1H, m), 6.37 (1H, br. s.), 6.25 (1H, br. s.), 6.05 (1H, br. s.), 4.13 (2H, d, J=7.1 Hz), 3.77 (4H, t, J=4.9 Hz), 3.08 (4H, t, J=4.9 Hz), 2.63 (2H, t, J=8.1 Hz), 2.23-2.36 (2H, m), 2.13 (3H, s), 2.06-2.10 (3H, m). Mass Spectrum (ESI) m/e=478.2 (M+1).

Example 333

Preparation of N-(3-((2-(4,4-dimethyl-2-oxo-1-pyrrolidinyl)-7-fluoro-3-methyl-4-quinolinyl)amino)-5-(4-morpholinyl)phenyl)acetamide 1-(4-Chloro-7-fluoro-3-methylquinolin-2-yl)-4,4-dimethylpyrrolidin-2-one

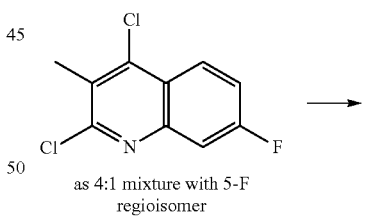

as 4:1 mixture with 5-F regioisomer

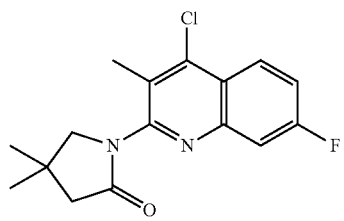

Prepared according to Procedure F using 2,4-dichloro-7-fluoro-3-methylquinoline (0.300 g, 1.304 mmol), 4,4-dimethyl-2-pyrrolidinone (0.162 mL, 1.434 mmol), cesium carbonate (0.600 g, 1.826 mmol), tris(dibenzylideneacetone)dipalladium (0) (0.060 g, 0.065 mmol), XantPhos (0.113 g, 0.196 mmol), and dioxane (2.6 mL). Purification by column chromatography (silica; 0-20% EtOAc in hexanes) afforded 1-(4-chloro-7-fluoro-3-methylquinolin-2-yl)-4,4-dimethylpyrrolidin-2-one as a white amorphous solid. Mass Spectrum (ESI) m/e=307.0 (M+1).

N-(3-((2-(4,4-dimethyl-2-oxo-1-pyrrolidinyl)-7-fluoro-3-methyl-4-quinolinyl)amino)-5-(4-morpholinyl)phenyl)acetamide

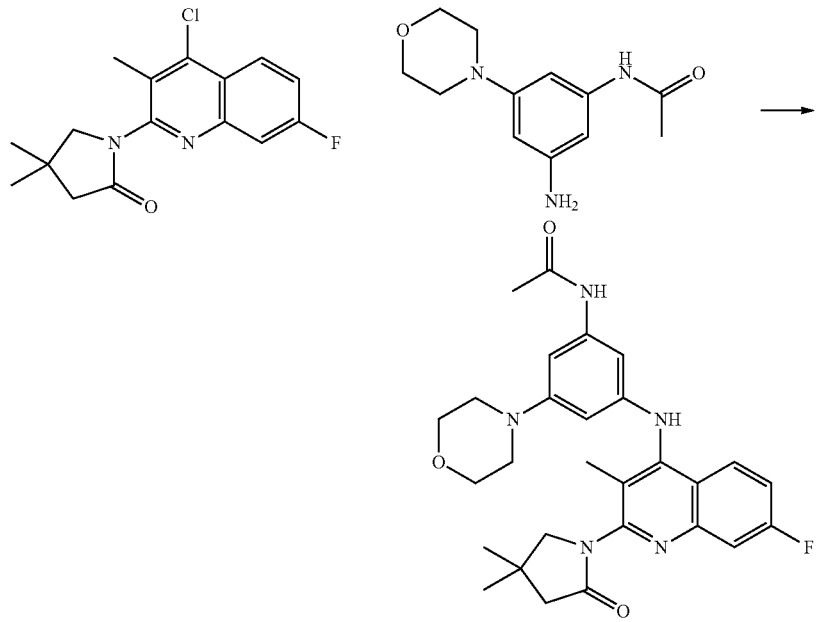

Prepared according to Procedure X by stirring palladium (II) acetate (0.4 mg, 1.743 μmol), XPhos (2.5 mg, 5.23 μmol), 1-(4-chloro-7-fluoro-3-methylquinolin-2-yl)-4,4-dimethylpyrrolidin-2-one (0.018 g, 0.058 mmol), N-(3-amino-5-morpholinophenyl)acetamide (0.0164 g, 0.070 mmol), potassium carbonate (0.020 g, 0.145 mmol), and tert-butanol (0.5 mL) at 110° C. for 30 minutes. Purification by reverse-phase HPLC (0-70% acetonitrile in water) afforded N-(3-((2-(4,4-dimethyl-2-oxo-1-pyrrolidinyl)-7-fluoro-3-methyl-4-quinolinyl)amino)-5-(4-morpholinyl)phenyl)acetamide as a yellow amorphous solid. $^1$H NMR (500 MHz, CHLOROFORM-d) δ ppm 7.79 (1H, br. s.), 7.55 (2H, d, J=9.0 Hz), 7.13 (1H, t). 6.88 (1H, br. s.), 6.39 (1H, br. s.), 6.34 (1H, br. s.), 6.06 (1H, br. s.), 3.88 (2H, br. s.), 3.70-3.81 (4H, m), 2.98-3.15 (4H, m), 2.46 (2H, s), 2.13 (3H, br. s.), 2.09 (3H, s), 1.33 (6H, s). Mass Spectrum (ESI) m/e=506.2 (M+1).

Example 334

Preparation of N-(3-((5,7-difluoro-3-methyl-2-(2-pyridinyl)-4-quinolinyl)amino)-5-(4-morpholinyl)phenyl)acetamide

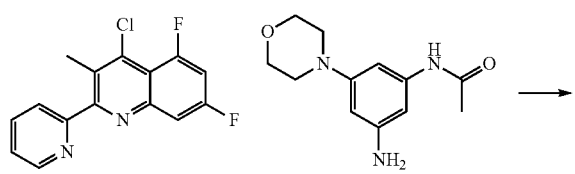

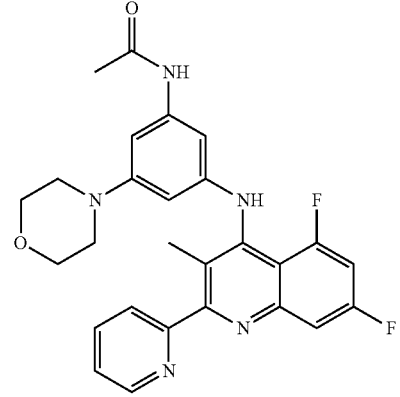

Prepared according to Procedure X by stirring palladium (II) acetate (1.5 mg, 6.88 μmol), XPhos (9.9 mg, 0.021 mmol), 4-chloro-5,7-difluoro-3-methyl-2-(pyridin-2-yl)quinoline (0.040 g, 0.138 mmol), N-(3-amino-5-morpholinophenyl)acetamide (0.034 g, 0.144 mmol), potassium carbonate (0.048 g, 0.344 mmol), and tert-butanol at 110° C. for 2 h. Purification by reverse-phase HPLC (0-70% acetonitrile in water) afforded N-(3-((5,7-difluoro-3-methyl-2-(2-pyridinyl)-4-quinolinyl)amino)-5-(4-morpholinyl)phenyl)acetamide as a yellow amorphous solid. $^1$H NMR (400 MHz, CHLOROFORM-d) δ ppm 8.69 (1H, dq, J=4.8, 1.0 Hz), 7.80-7.95 (3H, m), 7.59 (1H, ddt, J=9.6, 2.2, 1.0, 1.0 Hz), 7.37-7.44 (1H, m), 7.12-7.22 (2H, m), 7.01 (1H, ddd, J=13.8, 8.5, 2.5 Hz), 6.31-6.36 (1H, m), 6.23 (1H, t, J=2.2 Hz), 3.81-3.87 (4H, m), 3.15-3.22 (4H, m), 2.12 (3H, s), 2.10 (3H, s). Mass Spectrum (ESI) m/e=490.0 (M+1).

Example 335

Preparation of N-(3-((7-fluoro-3-methyl-2-(2-pyridinyl)-4-quinolinyl)amino)-5-(4-morpholinyl)phenyl)cyclopropanecarboxamide 4-(3,5-dinitrophenyl)morpholine

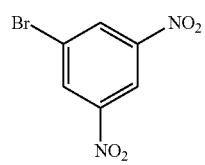
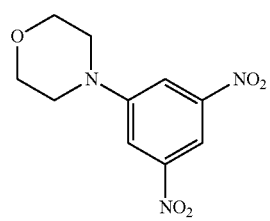

A mixture of 1-bromo-3,5-dinitrobenzene (2.84 g, 11.50 mmol), XPhos (0.493 g, 1.035 mmol), palladium (II) acetate (0.077 g, 0.345 mmol), potassium carbonate (2.225 g, 16.10 mmol), tert-butanol (23.0 mL), and morpholine (1.20 mL, 13.80 mmol) was stirred at 95° C. under nitrogen for 3 h. Upon completion, the reaction was partitioned between EtOAc and water. The organic layer was dried over magnesium sulfate and concd, and the crude material was purified by column chromatography (silica; 0-25% EtOAc in hexanes) to afford 4-(3,5-dinitrophenyl)morpholine as an orange amorphous solid. Mass Spectrum (ESI) m/e=254.2 (M+1).

5-Morpholinobenzene-1,3-diamine

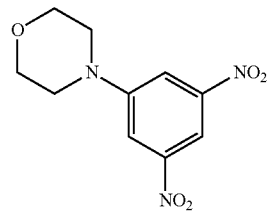
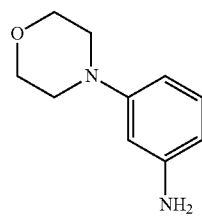

Prepared according to Procedure V by stirring 4-(3,5-dinitrophenyl)morpholine (0.213 g, 0.841 mmol), 10% palladium on carbon (0.179 g, 0.168 mmol), and ethanol (8 mL) for 2 h. This afforded 5-morpholinobenzene-1,3-diamine as a brown solid. Mass Spectrum (ESI) m/e=194.2 (M+1).

N-(3-Amino-5-morpholinophenyl)cyclopropanecarboxamide

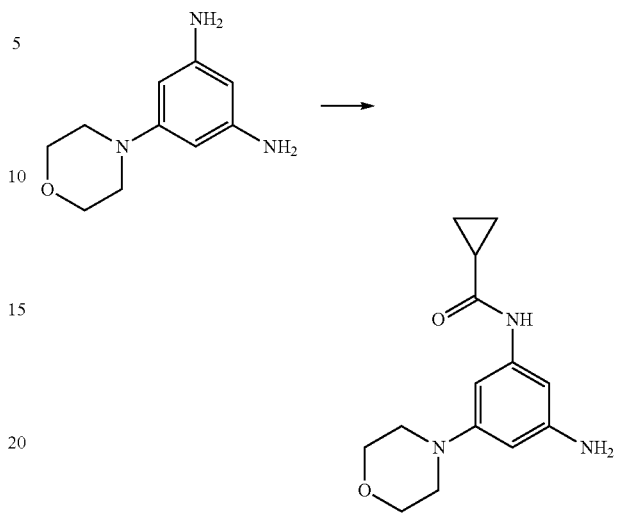

A solution of 5-morpholinobenzene-1,3-diamine (0.074 g, 0.383 mmol), triethylamine (0.080 mL, 0.574 mmol), cyclopropanecarbonyl chloride (0.035 mL, 0.383 mmol), and DCM (2 mL) was stirred at 23° C. for 3 h, then concd. The concentrate was partitioned between EtOAc and water, and the products were extracted twice with 25% 2-propanol in chloroform. The combined organics were dried over magnesium sulfate and concd, affording N-(3-amino-5-morpholinophenyl)cyclopropanecarboxamide as a brown amorphous solid. Mass Spectrum (ESI) m/e=262.2 (M+1).

N-(3-((7-Fluoro-3-methyl-2-(2-pyridinyl)-4-quinolinyl)amino)-5-(4-morpholinyl)phenyl)cyclopropanecarboxamide

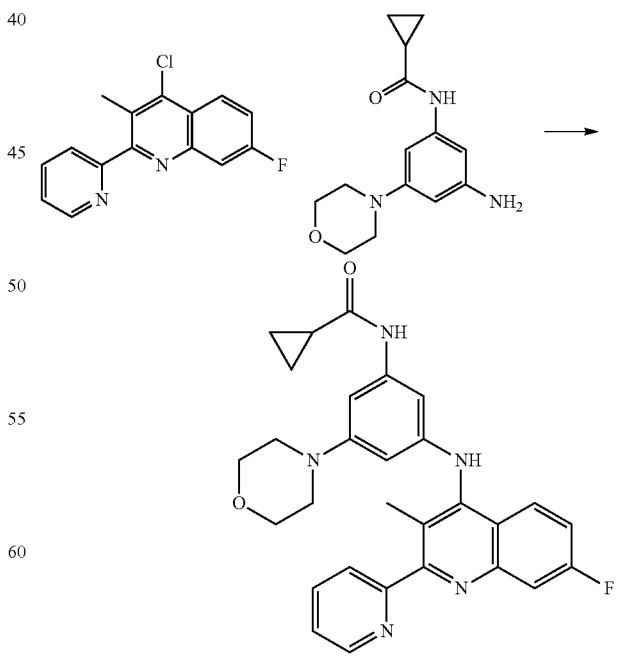

Prepared according to Procedure X by stirring palladium (II) acetate (1.1 mg, 4.78 μmol), XPhos (6.8 mg, 0.014 mmol), 4-chloro-7-fluoro-3-methyl-2-(pyridin-2-yl)quinoline (0.026 g, 0.096 mmol), N-(3-amino-5-morpholinophenyl)cyclopropanecarboxamide (0.025 g, 0.096 mmol), potassium carbonate (0.033 g, 0.239 mmol), and tert-butanol (1 mL) at 110° C. for 1 hour. Purification by column chromatography (silica; 0-10% methanol in DCM) afforded N-(3-((7-fluoro-3-methyl-2-(2-pyridinyl)-4-quinolinyl)amino)-5-(4-morpholinyl)phenyl)cyclopropanecarboxamide as a yellow amorphous solid. $^1$H NMR (400 MHz, CHLOROFORM-d) δ ppm 8.68 (1H, d, J=4.3 Hz), 8.26 (1H, br. s.), 7.86 (2H, td, J=7.7, 1.7 Hz), 7.74 (1H, d, J=7.0 Hz), 7.62 (1H, dd, J=10.0, 2.0 Hz), 7.33-7.42 (1H, m), 7.24 (1H, br. s.), 7.14-7.21 (1H, m), 6.15 (2H, br. s.), 6.02 (1H, br. s.), 3.69-3.87 (4H, m), 3.05-3.20 (4H, m), 2.29 (3H, s), 1.27 (1H, t, J=7.1 Hz), 0.92-0.99 (2H, m), 0.57-0.73 (2H, m). Mass Spectrum (ESI) m/e=498.2 (M+1).

Example 336

Preparation of N-(3-((7-fluoro-3-methyl-2-(2-pyridinyl)-4-quinolinyl)amino)-5-(4-morpholinyl)phenyl)-2-methylpropanamide N-(3-Morpholino-5-nitrophenyl)isobutyramide

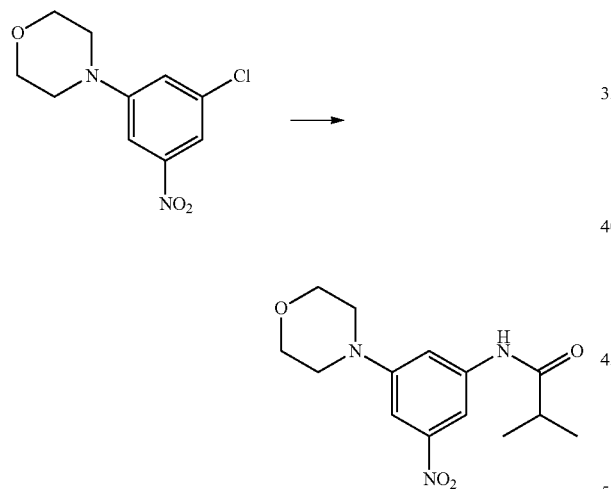

Prepared according to Procedure W by stirring palladium (II) acetate (0.028 g, 0.124 mmol), tetramethyl tert-butyl XPhos (0.178 g, 0.371 mmol), 4-(3-chloro-5-nitrophenyl)morpholine (0.300 g, 1.236 mmol), isobutyramide (0.129 g, 1.484 mmol), potassium phosphate (0.367 g, 1.731 mmol), and tert-butanol (3 mL) at 110° C. for 4 h. Purification by column chromatography (silica; 0-30% EtOAc in hexanes) afforded N-(3-morpholino-5-nitrophenyl)isobutyramide as an orange amorphous solid. Mass Spectrum (ESI) m/e=293.9 (M+1).

N-(3-Amino-5-morpholinophenyl)isobutyramide

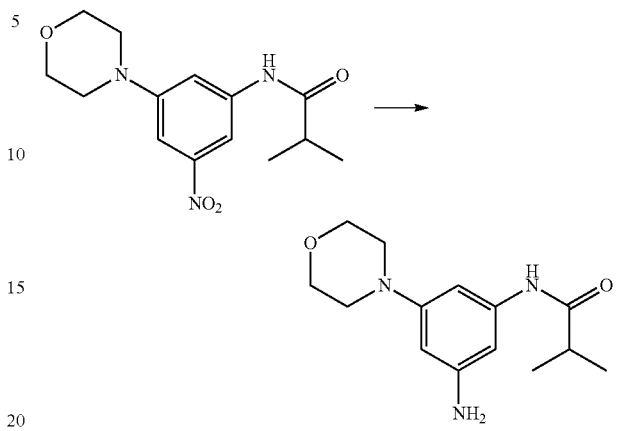

Prepared according to Procedure V by stirring N-(3-morpholino-5-nitrophenyl)-isobutyramide (0.298 g, 1.016 mmol), 10% palladium on carbon (0.216 g, 0.203 mmol), and methanol (3 mL) for 30 minutes to afford N-(3-amino-5-morpholinophenyl)isobutyramide as a beige amorphous solid. Mass Spectrum (ESI) m/e=264.2 (M+1).

N-(3-((7-fluoro-3-methyl-2-(2-pyridinyl)-4-quinolinyl)amino)-5-(4-morpholinyl)phenyl)-2-methylpropanamide

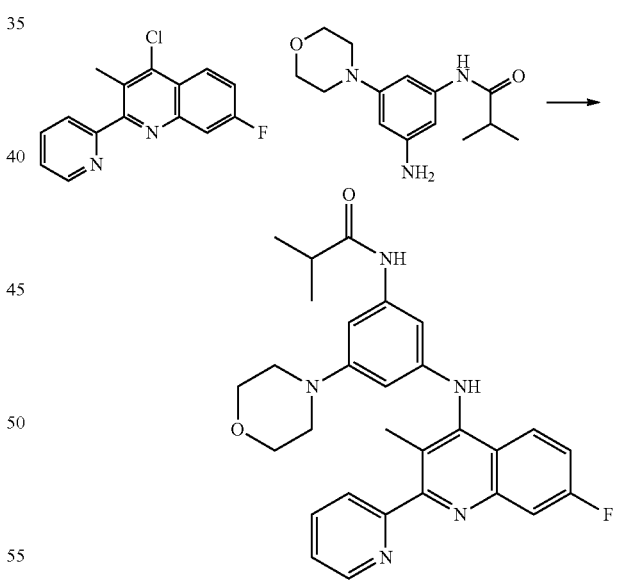

Prepared according to Procedure X by stirring palladium (II) acetate (2.325 mg, 10.36 μmol), XPhos (0.015 g, 0.031 mmol), 4-chloro-7-fluoro-3-methyl-2-(pyridin-2-yl)quinoline (0.056 g, 0.207 mmol), N-(3-amino-5-morpholinophenyl)-isobutyramide (0.060 g, 0.228 mmol), potassium carbonate (0.072 g, 0.518 mmol), and tert-butanol (1 mL) at 110° C. for 20 minutes. Purification by reverse-phase HPLC (0-70% acetonitrile in water) afforded N-(3-((7-fluoro-3-methyl-2-(2-pyridinyl)-4-quinolinyl)amino)-5-(4-morpholinyl)phenyl)-2-methylpropanamide as a yellow amorphous solid.

1H NMR (400 MHz, CHLOROFORM-d) δ ppm 8.74 (1H, d, J=4.5 Hz), 7.92 (2H, d, J=6.8 Hz), 7.86 (1H, s), 7.78 (1H, d), 7.42 (1H, t), 7.18 (2H, m), 6.35 (1H, br. s.), 6.11 (1H, s), 3.74-3.84 (4H, m), 3.05-3.17 (4H, m), 2.32 (3H, s), 1.20 (3H, s), 1.18 (3H, s). Mass Spectrum (ESI) m/e=499.8 (M+1).

Example 337

Preparation of N-(3-((2-(3,5-difluorophenyl)-3-methyl-1,8-naphthyridin-4-yl)amino)-5-(4-morpholinyl)phenyl)acetamide 3-methyl-1,8-naphthyridine-2,4-diol

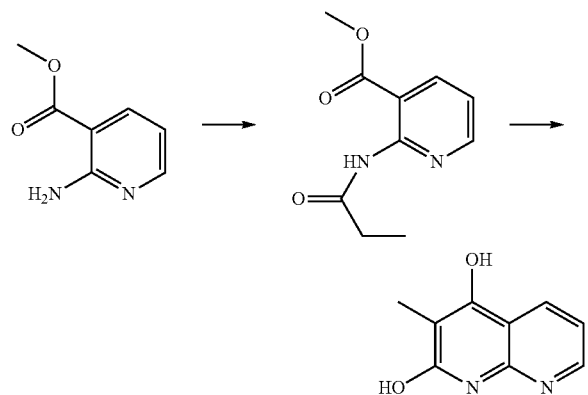

To a stirring solution of methyl 2-aminonicotinate (1.3 g, 8.54 mmol) and methyl propionate (20.08 mL, 214 mmol) in THF (20 mL) was slowly added sodium tert-butoxide (2.05 g, 21.36 mmol). The reaction was stirred at 23° C. for 40 minutes to afford the desired intermediate, then heated at 100° C. for 4 h. Upon completion, the reaction was cooled to 23° C. and concd. The resulting solid was dissolved in water (20 mL) and neutralized to pH 7 with 1.0M aqueous HCl. This afforded a precipitate that was isolated by filtration and dried under vacuum overnight to yield 3-methyl-1,8-naphthyridine-2,4-diol as a tan amorphous solid. Mass Spectrum (ESI) m/e=177.2 (M+1).

2,4-Dichloro-3-methyl-1,8-naphthyridine

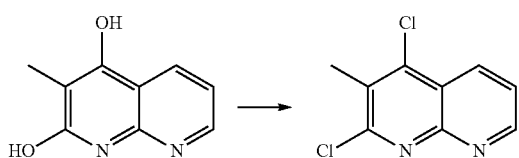

Prepared according to Procedure D by stirring 3-methyl-1,8-naphthyridine-2,4-diol (0.82 g, 4.65 mmol) in phosphorus oxychloride (4.34 mL, 46.5 mmol) at 120° C. for 3 h. No purification was necessary to cleanly afford 2,4-dichloro-3-methyl-1,8-naphthyridine. Mass Spectrum (ESI) m/e=213.0 (M+1).

4-Chloro-2-(3,5-difluorophenyl)-3-methyl-1,8-naphthyridine

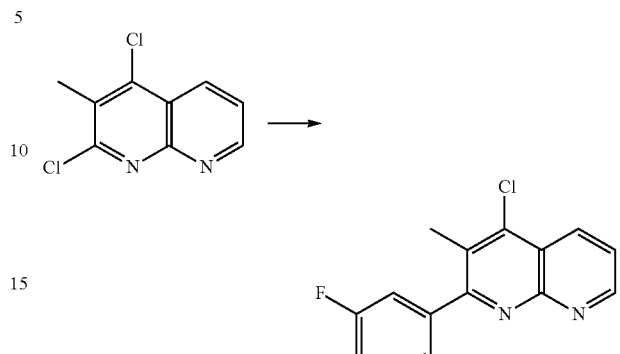

Prepared according to Procedure G by stirring 2,4-dichloro-3-methyl-1,8-naphthyridine (0.4 g, 1.877 mmol), 3,5-difluorophenylboronic acid (0.445 g, 2.82 mmol), tetrakis(triphenylphosphine)palladium (0) (0.217 g, 0.188 mmol), potassium carbonate (0.519 g, 3.75 mmol), and toluene (6 mL) at 95° C. under nitrogen for 18 h. Purification by column chromatography (silica; 0-25% EtOAc in hexanes) afforded 4-chloro-2-(3,5-difluorophenyl)-3-methyl-1,8-naphthyridine as a yellow amorphous solid. Mass Spectrum (ESI) m/e=291.0 (M+1).

N-(3-((2-(3,5-Difluorophenyl)-3-methyl-1,8-naphthyridin-4-yl)amino)-5-(4-morpholinyl)phenyl)acetamide

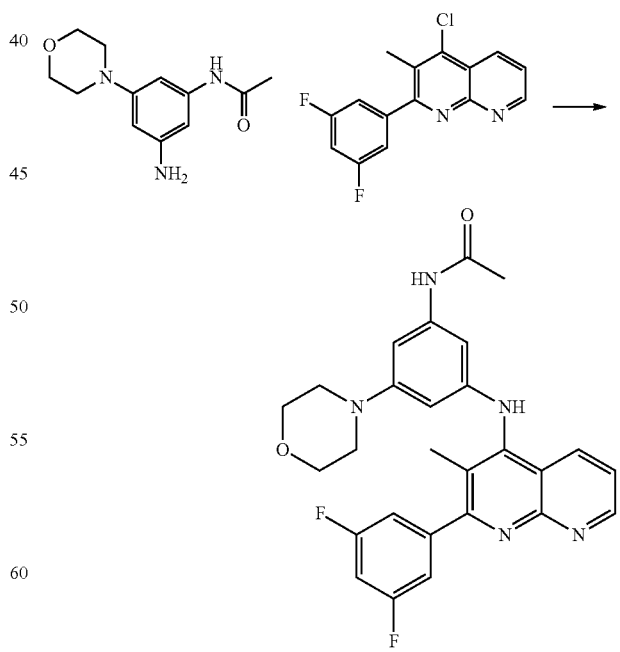

Prepared according to Procedure X by stirring N-(3-amino-5-morpholinophenyl)-acetamide (48.6 mg, 0.206 mmol), 4-chloro-2-(3,5-difluorophenyl)-3-methyl-1,8-naphthyridine (50 mg, 0.172 mmol), palladium (II) acetate (3.9 mg, 0.017 mmol), XPhos (16.4 mg, 0.034 mmol), potassium carbonate (60 mg, 0.43 mmol), and 1 mL tert-butanol at 85° C. for 24 h. Purification by reverse-phase HPLC afforded N-(3-((2-(3,5-difluorophenyl)-3-methyl-1,8-naphthyridin-4-yl)amino)-5-(4-morpholinyl)phenyl)acetamide. $^1$H NMR (400 MHz, CHLOROFORM-d) δ ppm 8.84 (1H, dd, J=4.1, 2.0 Hz), 8.21-8.28 (2H, m), 7.23-7.27 (1H, m), 7.10-7.14 (1H, m), 7.04-7.10 (2H, m), 6.85-6.91 (1H, m), 6.45-6.50 (1H, m), 6.14-6.21 (2H, m), 3.77-3.86 (4H, m), 3.09-3.15 (4H, m), 2.33 (3H, s), 1.99 (3H, s). Mass Spectrum (ESI) m/e=490.0 (M+1).

Example 338

Preparation of N-(3-((7-fluoro-2-(5-fluoro-3-pyridinyl)-3-methyl-4-quinolinyl)amino)-5-(4-morpholinyl)phenyl)acetamide 4-Chloro-7-fluoro-2-(5-fluoropyridin-3-yl)-3-methylquinoline

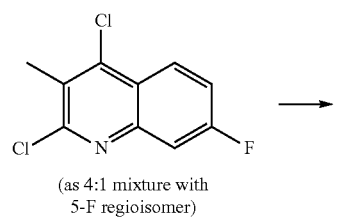

(as 4:1 mixture with 5-F regioisomer)

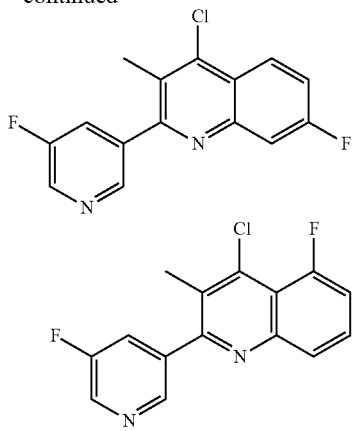

A mixture of 2,4-dichloro-7-fluoro-3-methylquinoline (0.650 g, 2.83 mmol), 5-fluoropyridine-3-boronic acid (0.518 g, 3.67 mmol), dichloro 1,1'-bis(diphenylphosphino)ferrocene palladium (II) (0.346 g, 0.424 mmol), potassium carbonate (0.781 g, 5.65 mmol), and toluene (6 mL) was stirred at 105° C. under nitrogen for 48 h, then cooled to 23° C., filtered through Celite, and concd. The resulting crude material was purified by column chromatography (silica; 0-10% EtOAc in hexanes) to afford (in order of elution) 4-chloro-7-fluoro-2-(5-fluoropyridin-3-yl)-3-methylquinoline and 4-chloro-5-fluoro-2-(5-fluoropyridin-3-yl)-3-methylquinoline as amorphous white solids. Mass Spectra (ESI) m/e=291.1 (M+1); 291.0 (M+1).

N-(3-((7-fluoro-2-(5-fluoro-3-pyridinyl)-3-methyl-4-quinolinyl)amino)-5-(4-morpholinyl)phenyl)acetamide

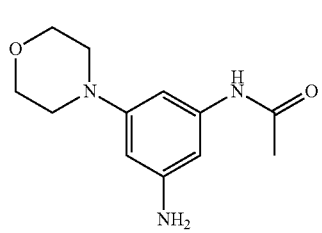 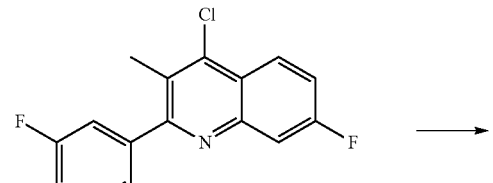

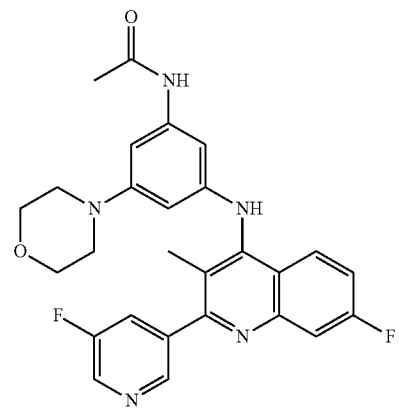

Prepared according to Procedure X by stirring palladium (II) acetate (1.545 mg, 6.88 µmol), XPhos (9.84 mg, 0.021 mmol), 4-chloro-7-fluoro-2-(5-fluoropyridin-3-yl)-3-methylquinoline (0.040 g, 0.138 mmol), N-(3-amino-5-morpholinophenyl)acetamide (0.032 g, 0.138 mmol), potassium carbonate (0.048 g, 0.344 mmol), and tert-butanol (1 mL) at 110° C. for 20 minutes. Purification by column chromatography (silica; 0-4% methanol in DCM) afforded N-(3-((7-fluoro-2-(5-fluoro-3-pyridinyl)-3-methyl-4-quinolinyl)amino)-5-(4-morpholinyl)phenyl)acetamide as a yellow amorphous solid. $^1$H NMR (400 MHz, DMSO-$d_6$) δ ppm 9.63 (1H, s), 8.65-8.79 (3H, m), 8.18 (1H, m), 8.02 (1H, m), 7.73 (1H, m), 7.50 (1H, m), 6.70 (1H, s), 6.55 (1H, s), 6.23 (1H, s), 3.66-3.78 (4H, m), 2.94-3.06 (4H, m), 2.14 (3H, s), 1.96 (3H, s). Mass Spectrum (ESI) m/e=490.1 (M+1).

Biological Assays

Recombinant Expression of PI3Ks

Full length p110 subunits of PI3k α, β and δ, N-terminally labeled with polyHis tag, were coexpressed with p85 with Baculo virus expression vectors in sf9 insect cells. P110/p85 heterodimers were purified by sequential Ni-NTA, Q-HP, Superdex-100 chromatography. Purified α, β and δ isozymes were stored at –20° C. in 20 mM Tris, pH 8, 0.2M NaCl, 50% glycerol, 5 mM DTT, 2 mM Na cholate. Truncated PI3Kγ, residues 114-1102, N-terminally labeled with polyHis tag, was expressed with Baculo virus in Hi5 insect cells. The γ isozyme was purified by sequential Ni-NTA, Superdex-200, Q-HP chromatography. The γ isozyme was stored frozen at –80° C. in $NaH_2PO_4$, pH 8, 0.2M NaCl, 1% ethylene glycol, 2 mM β-mercaptoethanol.

|  | Alpha | Beta | Delta | gamma |
|---|---|---|---|---|
| 50 mM Tris | pH 8 | pH 7.5 | pH 7.5 | pH 8 |
| MgC12 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 h | 2 h | 2 h | 1 h |
| [Enzyme] | 15 nM | 40 nM | 15 nM | 50 nM |

In Vitro PI3K Enzyme Assays

A PI3K Alphascreen® assay (PerkinElmer, Waltham, Mass.) was used to measure the activity of a panel of four phosphoinositide 3-kinases: PI3Kα, PI3Kβ, PI3Kγ, and PI3Kδ. Enzyme reaction buffer was prepared using sterile water (Baxter, Deerfield, Ill.) and 50 mM Tris HCl pH 7, 14 mM $MgCl_2$, 2 mM sodium cholate, and 100 mM NaCl. 2 mM DTT was added fresh the day of the experiment. The Alphascreen buffer was made using sterile water and 10 mM Tris HCl pH 7.5, 150 mM NaCl, 0.10% Tween 20, and 30 mM EDTA. 1 mM DTT was added fresh the day of the experiment. Compound source plates used for this assay were 384-well Greiner clear polypropylene plates containing test compounds at 5 mM and diluted 1:2 over 22 concentrations. Columns 23 and 24 contained only DMSO as these wells comprised the positive and negative controls, respectively. Source plates were replicated by transferring 0.5 uL per well into 384-well Optiplates (PerkinElmer, Waltham, Mass.).

Each PI3K isoform was diluted in enzyme reaction buffer to 2× working stocks. PI3Kα was diluted to 1.6 nM, PI3Kβ was diluted to 0.8 nM, PI3Kγ was diluted to 15 nM, and PI3Kδ was diluted to 1.6 nM. PI(4,5)P2 (Echelon Biosciences, Salt Lake City, Utah) was diluted to 10 µM and ATP was diluted to 20 µM. This 2× stock was used in the assays for PI3Kα and PI3Kβ. For assay of PI3Kγ and PI3Kδ, PI(4,5)P2 was diluted to 10 µM and ATP was diluted to 8 µM to prepare a similar 2× working stock. Alphascreen reaction solutions were made using beads from the anti-GST Alphascreen kit (PerkinElmer, Waltham, Mass.). Two 4× working stocks of the Alphascreen reagents were made in Alphascreen reaction buffer. In one stock, biotinylated-$IP_4$ (Echelon Biosciences, Salt Lake City, Utah) was diluted to 40 nM and streptavadin-donor beads were diluted to 80 µg/mL. In the second stock, $PIP_3$-binding protein (Echelon Biosciences, Salt Lake City, Utah) was diluted to 40 nM and anti-GST-acceptor beads were diluted to 80 µg/mL. As a negative control, a reference inhibitor at a concentration >>Ki (40 uM) was included in column 24 as a negative (100% inhibition) control.

Using a 384-well Multidrop (Titertek, Huntsville, Ala.), 10 µL/well of 2× enzyme stock was added to columns 1-24 of the assay plates for each isoform. 10 µL/well of the appropriate substrate 2× stock (containing 20 µM ATP for the PI3Kα and β assays and containing 8 µM ATP for the PI3Kγ and δ assays) was then added to Columns 1-24 of all plates. Plates were then incubated at room temperature for 20 minutes. In the dark, 10 µL/well of the donor bead solution was added to columns 1-24 of the plates to quench the enzyme reaction. The plates were incubated at room temperature for 30 minutes. Still in the dark, 10 µL/well of the acceptor bead solution was added to columns 1-24 of the plates. The plates were then incubated in the dark for 1.5 hours. The plates were read on an Envision multimode Plate Reader (PerkinElmer, Waltham, Mass.) using a 680 nm excitation filter and a 520-620 nm emission filter.

Alternative In Vitro Enzyme Assays

Assays were performed in 25 µL with the above final concentrations of components in white polyproplyene plates (Costar 3355). Phospatidyl inositol phosphoacceptor, PtdIns (4,5)P2 P4508, was from Echelon Biosciences. The ATPase activity of the alpha and gamma isozymes was not greatly stimulated by PtdIns(4,5)P2 under these conditions and was therefore omitted from the assay of these isozymes. Test compounds were dissolved in dimethyl sulfoxide and diluted with three-fold serial dilutions. The compound in DMSO (1 µL) was added per test well, and the inhibition relative to reactions containing no compound, with and without enzyme was determined. After assay incubation at rt, the reaction was stopped and residual ATP determined by addition of an equal volume of a commercial ATP bioluminescence kit (Perkin Elmer EasyLite) according to the manufacturer's instructions, and detected using a AnalystGT luminometer.

Human B Cells Proliferation Stimulate by Anti-IgM

Isolate Human B CELLS:

Isolate PBMCs from Leukopac or from human fresh blood. Isolate human B cells by using Miltenyi protocol and B cell isolation kit II.—human B cells were Purified by using AutoMacs.column.

Activation of Human B Cells

Use 96 well Flat bottom plate, plate 50000/well purified B cells in B cell proliferation medium (DMEM+5% FCS, 10 mM Hepes, 50 µM 2-mercaptoethanol); 150 µL medium contain 250 ng/mL CD40L-LZ recombinant protein (Amgen) and 2 µg/mL anti-Human IgM antibody (Jackson ImmunoReseach Lab. #109-006-129), mixed with 50 µL B cell medium containing PI3K inhibitors and incubate 72 h at 37° C. incubator. After 72 h, pulse labeling B cells with 0.5-1 uCi/well $^3$H thymidine for overnight ~18 h, and harvest cell using TOM harvester.

Human B Cells Proliferation Stimulate by IL-4
Isolate Human B Cells:
  Isolate human PBMCs from Leukopac or from human fresh blood. Isolate human B cells using Miltenyi protocol—B cell isolation kit. Human B cells were Purified by AutoMacs.column.
Activation of Human B Cells
  Use 96-well flat bottom plate, plate 50000/well purified B cells in B cell proliferation medium (DMEM+5% FCS, 50 µM 2-mercaptoethanol, 10 mM Hepes). The medium (150 µL) contain 250 ng/mL CD40L-LZ recombinant protein (Amgen) and 10 ng/mL IL-4 (R&D system #204-IL-025), mixed with 50 150 µL B cell medium containing compounds and incubate 72 h at 37° C. incubator. After 72 h, pulse labeling B cells with 0.5-1 uCi/well 3H thymidine for overnight ~18 h, and harvest cell using TOM harvester.
Specific T Antigen (Tetanus Toxoid) Induced Human PBMC Proliferation Assays
  Human PBMC are prepared from frozen stocks or they are purified from fresh human blood using a Ficoll gradient. Use 96 well round-bottom plate and plate $2\times10^5$ PBMC/well with culture medium (RPMI1640+10% FCS, 50 uM 2-Mercaptoethanol, 10 mM Hepes). For $IC_{50}$ determinations, PI3K inhibitors was tested from 10 µM to 0.001 µM, in half log increments and in triplicate. Tetanus toxoid, T cell specific antigen (University of Massachusetts Lab) was added at 1 µg/mL and incubated 6 days at 37° C. incubator. Supernatants are collected after 6 days for IL2 ELISA assay, then cells are pulsed with $^3$H-thymidine for ~18 h to measure proliferation.
GFP Assays for Detecting Inhibition of Class Ia and Class III PI3K
  AKT1 (PKBa) is regulated by Class Ia PI3K activated by mitogenic factors (IGF-1, PDGF, insulin, thrombin, NGF, etc.). In response to mitogenic stimuli, AKT1 translocates from the cytosol to the plasma membrane
  Forkhead (FKHRL1) is a substrate for AKT1. It is cytoplasmic when phosphorylated by AKT (survival/growth). Inhibition of AKT (stasis/apoptosis)-forkhead translocation to the nucleus
  FYVE domains bind to PI(3)P. the majority is generated by constitutive action of PI3K Class III
AKT Membrane Ruffling Assay (CHO-1R-AKT1-EGFP Cells/GE Healthcare)
  Wash cells with assay buffer. Treat with compounds in assay buffer 1 h. Add 10 ng/mL insulin. Fix after 10 min at room temp and image
Forkhead Translocation Assay (MDA MB468 Forkhead-DiversaGFP Cells)
  Treat cells with compound in growth medium 1 h. Fix and image.
Class III PI(3)P Assay (U2OS EGFP-2xFYVE Cells/GE Healthcare)
  Wash cells with assay buffer. Treat with compounds in assay buffer 1 h. Fix and image.
Control for all 3 Assays is 10 uM Wortmannin:
AKT is cytoplasmic
Forkhead is nuclear
PI(3)P depleted from endosomes
Biomarker Assay: B-Cell Receptor Stimulation of CD69 or B7.2 (CD86) Expression
  Heparinized human whole blood was stimulated with 10 µg/mL anti-IgD (Southern Biotech, #9030-01). 90 µL of the stimulated blood was then aliquoted per well of a 96-well plate and treated with 100 µL of various concentrations of blocking compound (from 10-0.0003 µM) diluted in IMDM+10% FBS (Gibco). Samples were incubated together for 4 h (for CD69 expression) to 6 h (for B7.2 expression) at 37° C. Treated blood (50 µL) was transferred to a 96-well, deep well plate (Nunc) for antibody staining with 10 µL each of CD45-PerCP (BD Biosciences, #347464), CD19-FITC (BD Biosciences, #340719), and CD69-PE (BD Biosciences, #341652). The second 50 µL of the treated blood was transferred to a second 96-well, deep well plate for antibody staining with 100 µL each of CD19-FITC (BD Biosciences, #340719) and CD86-PeCy5 (BD Biosciences, #555666). All stains were performed for 15-30 minutes in the dark at rt. The blood was then lysed and fixed using 450 µL of FACS lysing solution (BD Biosciences, #349202) for 15 minutes at rt. Samples were then washed 2× in PBS+2% FBS before FACS analysis. Samples were gated on either CD45/CD19 double positive cells for CD69 staining, or CD19 positive cells for CD86 staining
Gamma Counterscreen: Stimulation of Human Monocytes for Phospho-AKT Expression
  A human monocyte cell line, THP-1, was maintained in RPMI+10% FBS (Gibco). One day before stimulation, cells were counted using trypan blue exclusion on a hemocytometer and suspended at a concentration of $1\times10^6$ cells per mL of media. 100 µL of cells plus media ($1\times10^5$ cells) was then aliquoted per well of 4-96-well, deep well dishes (Nunc) to test eight different compounds. Cells were rested overnight before treatment with various concentrations (from 10-0.0003 µM) of blocking compound. The compound diluted in media (12 µL) was added to the cells for 10 minutes at 37° C. Human MCP-1 (12 µL, R&D Diagnostics, #279-MC) was diluted in media and added to each well at a final concentration of 50 ng/mL. Stimulation lasted for 2 minutes at rt. Pre-warmed FACS Phosflow Lyse/Fix buffer (1 mL of 37° C.) (BD Biosciences, #558049) was added to each well. Plates were then incubated at 37° C. for an additional 10-15 minutes. Plates were spun at 1500 rpm for 10 minutes, supernatant was aspirated off, and 1 mL of ice cold 90% MeOH was added to each well with vigorous shaking. Plates were then incubated either overnight at −70° C. or on ice for 30 minutes before antibody staining Plates were spun and washed 2× in PBS+2% FBS (Gibco). Wash was aspirated and cells were suspended in remaining buffer. Rabbit pAKT (50 µL, Cell Signaling, #4058L) at 1:100, was added to each sample for 1 h at rt with shaking. Cells were washed and spun at 1500 rpm for 10 minutes. Supernatant was aspirated and cells were suspended in remaining buffer. Secondary antibody, goat anti-rabbit Alexa 647 (50 µL, Invitrogen, #A21245) at 1:500, was added for 30 minutes at rt with shaking. Cells were then washed 1× in buffer and suspended in 150 µL of buffer for FACS analysis. Cells need to be dispersed very well by pipetting before running on flow cytometer. Cells were run on an LSR II (Becton Dickinson) and gated on forward and side scatter to determine expression levels of pAKT in the monocyte population.
Gamma Counterscreen Stimulation of Monocytes for Phospho-AKT Expression in Mouse Bone Marrow
  Mouse femurs were dissected from five female BALB/c mice (Charles River Labs.) and collected into RPMI+10% FBS media (Gibco). Mouse bone marrow was removed by cutting the ends of the femur and by flushing with 1 mL of media using a 25 gauge needle. Bone marrow was then dispersed in media using a 21 gauge needle. Media volume was increased to 20 mL and cells were counted using trypan blue exclusion on a hemocytometer. The cell suspension was then increased to $7.5\times10^6$ cells per 1 mL of media and 100 µL ($7.5\times10^5$ cells) was aliquoted per well into 4-96-well, deep well dishes (Nunc) to test eight different compounds. Cells were rested at 37° C. for 2 h before treatment with various concentrations (from 10-0.0003 µM) of blocking compound.

Compound diluted in media (12 µL) was added to bone marrow cells for 10 minutes at 37° C. Mouse MCP-1 (12 µL, R&D Diagnostics, #479-JE) was diluted in media and added to each well at a final concentration of 50 ng/mL. Stimulation lasted for 2 minutes at rt. 1 mL of 37° C. pre-warmed FACS Phosflow Lyse/Fix buffer (BD Biosciences, #558049) was added to each well. Plates were then incubated at 37° C. for an additional 10-15 minutes. Plates were spun at 1500 rpm for 10 minutes. Supernatant was aspirated off and 1 mL of ice cold 90% MeOH was added to each well with vigorous shaking. Plates were then incubated either overnight at −70° C. or on ice for 30 minutes before antibody staining. Plates were spun and washed 2× in PBS+2% FBS (Gibco). Wash was aspirated and cells were suspended in remaining buffer. Fc block (2 µL, BD Pharmingen, #553140) was then added per well for 10 minutes at rt. After block, 50 µL of primary antibodies diluted in buffer; CD11b-Alexa488 (BD Biosciences, #557672) at 1:50, CD64-PE (BD Biosciences, #558455) at 1:50, and rabbit pAKT (Cell Signaling, #4058L) at 1:100, were added to each sample for 1 h at RT with shaking. Wash buffer was added to cells and spun at 1500 rpm for 10 minutes. Supernatant was aspirated and cells were suspended in remaining buffer. Secondary antibody; goat anti-rabbit Alexa 647 (50 µL, Invitrogen, #A21245) at 1:500, was added for 30 minutes at rt with shaking. Cells were then washed 1× in buffer and suspended in 100 µL of buffer for FACS analysis. Cells were run on an LSR II (Becton Dickinson) and gated on CD11b/CD64 double positive cells to determine expression levels of pAKT in the monocyte population.

pAKT In Vivo Assay

Vehicle and compounds are administered p.o. (0.2 mL) by gavage (Oral Gavage Needles Popper & Sons, New Hyde Park, N.Y.) to mice (Transgenic Line 3751, female, 10-12 wks Amgen Inc, Thousand Oaks, Calif.) 15 min prior to the injection i.v (0.2 mls) of anti-IgM FITC (50 ug/mouse) (Jackson Immuno Research, West Grove, Pa.). After 45 min the mice are sacrificed within a $CO_2$ chamber. Blood is drawn via cardiac puncture (0.3 mL) (1 cc 25 g Syringes, Sherwood, St. Louis, Mo.) and transferred into a 15 mL conical vial (Nalge/Nunc International, Denmark). Blood is immediately fixed with 6.0 mL of BD Phosflow Lyse/Fix Buffer (BD Bioscience, San Jose, Calif.), inverted 3×'s and placed in 37° C. water bath. Half of the spleen is removed and transferred to an eppendorf tube containing 0.5 mL of PBS (Invitrogen Corp, Grand Island, N.Y.). The spleen is crushed using a tissue grinder (Pellet Pestle, Kimble/Kontes, Vineland, N.J.) and immediately fixed with 6.0 mL of BD Phosflow Lyse/Fix buffer, inverted 3×'s and placed in 37° C. water bath. Once tissues have been collected the mouse is cervically-dislocated and carcass to disposed. After 15 min, the 15 mL conical vials are removed from the 37° C. water bath and placed on ice until tissues are further processed. Crushed spleens are filtered through a 70 µm cell strainer (BD Bioscience, Bedford, Mass.) into another 15 mL conical vial and washed with 9 mL of PBS. Splenocytes and blood are spun @ 2,000 rpms for 10 min (cold) and buffer is aspirated. Cells are resuspended in 2.0 mL of cold (−20° C.) 90% methyl alcohol (Mallinckrodt Chemicals, Phillipsburg, N.J.). Methanol is slowly added while conical vial is rapidly vortexed. Tissues are then stored at −20° C. until cells can be stained for FACS analysis.

Multi-Dose TNP Immunization

Blood was collected by retro-orbital eye bleeds from 7-8 week old BALB/c female mice (Charles River Labs.) at day 0 before immunization. Blood was allowed to clot for 30 minutes and spun at 10,000 rpm in serum microtainer tubes (Becton Dickinson) for 10 minutes. Sera were collected, aliquoted in Matrix tubes (Matrix Tech. Corp.) and stored at −70° C. until ELISA was performed. Mice were given compound orally before immunization and at subsequent time periods based on the life of the molecule. Mice were then immunized with either 50 µg of TNP-LPS (Biosearch Tech., #T-5065), 50 µg of TNP-Ficoll (Biosearch Tech., #F-1300), or 100 µg of TNP-KLH (Biosearch Tech., #T-5060) plus 1% alum (Brenntag, #3501) in PBS. TNP-KLH plus alum solution was prepared by gently inverting the mixture 3-5 times every 10 minutes for 1 hour before immunization. On day 5, post-last treatment, mice were $CO_2$ sacrificed and cardiac punctured. Blood was allowed to clot for 30 minutes and spun at 10,000 rpm in serum microtainer tubes for 10 minutes. Sera were collected, aliquoted in Matrix tubes, and stored at −70° C. until further analysis was performed. TNP-specific IgG1, IgG2a, IgG3 and IgM levels in the sera were then measured via ELISA. TNP-BSA (Biosearch Tech., #T-5050) was used to capture the TNP-specific antibodies. TNP-BSA (10 µg/mL) was used to coat 384-well ELISA plates (Corning Costar) overnight. Plates were then washed and blocked for 1 h using 10% BSA ELISA Block solution (KPL). After blocking, ELISA plates were washed and sera samples/standards were serially diluted and allowed to bind to the plates for 1 h. Plates were washed and Ig-HRP conjugated secondary antibodies (goat anti-mouse IgG1, Southern Biotech #1070-05, goat anti-mouse IgG2a, Southern Biotech #1080-05, goat anti-mouse IgM, Southern Biotech #1020-05, goat anti-mouse IgG3, Southern Biotech #1100-05) were diluted at 1:5000 and incubated on the plates for 1 h. TMB peroxidase solution (SureBlue Reserve TMB from KPL) was used to visualize the antibodies. Plates were washed and samples were allowed to develop in the TMB solution approximately 5-20 minutes depending on the Ig analyzed. The reaction was stopped with 2M sulfuric acid and plates were read at an OD of 450 nm.

The following compounds showed the associated activity from the above PI3Kδ Alphascreen® assay:

| Compound | Ki (µM) |
| --- | --- |
| (1R)-1-(3-(5,7-difluoro-3-methyl-4-((5-(4-morpholinyl)-3-pyridinyl)amino)-2-quinolinyl)-4-(methylsulfonyl)phenyl)-ethanol | 0.001572 |
| 1-(3-(5,7-difluoro-3-methyl-4-((5-(4-morpholinyl)-3-pyridinyl)-amino)-2-quinolinyl)-4-(methylsulfonyl)phenyl)ethanone | 0.002176 |
| 1-(5-(4-((2,5-di-4-morpholinyl-3-pyridinyl)amino)-5,7-difluoro-3-methyl-2-quinolinyl)-2-pyridinyl)-3-pyrrolidinol | 0.036272 |
| 1-(5,7-difluoro-3-methyl-4-((5-(4-morpholinyl)-3-pyridinyl)-amino)-2-quinolinyl)-2-piperidinone | 0.203443 |
| 1-(5,7-difluoro-3-methyl-4-((5-(4-morpholinyl)-3-pyridinyl)-amino)-2-quinolinyl)-5,5-dimethyl-2-piperidinone | 0.038589 |
| 1-(5,7-difluoro-3-methyl-4-((5-(4-morpholinyl)-3-pyridinyl)-amino)-2-quinolinyl)-4,4-dimethyl-2-pyrrolidinone | 0.021398 |

-continued

| Compound | Ki (μM) |
|---|---|
| 1-(5,7-difluoro-3-methyl-4-((5-(4-morpholinyl)-3-pyridinyl)-amino)-2-quinolinyl)-2-azetidinone | 0.027163 |
| 1-(5,7-difluoro-3-methyl-4-((5-(4-morpholinyl)-3-pyridinyl)-amino)-2-quinolinyl)-L-proline | 0.00937 |
| 1-(5,7-difluoro-3-methyl-4-((5-(4-morpholinyl)-3-pyridinyl)-amino)-2-quinolinyl)-D-proline | 0.059878 |
| 1-(5,7-difluoro-3-methyl-4-((5-(4-morpholinyl)-3-pyridinyl)-amino)-2-quinolinyl)-N-methyl-D-prolinamide | 0.010387 |
| 1-(5,7-difluoro-3-methyl-4-((5-(4-morpholinyl)-3-pyridinyl)-amino)-2-quinolinyl)-N,N-dimethyl-D-prolinamide | 0.010341 |
| 1-methylethyl 4-(5,7-difluoro-3-methyl-4-((5-(4-morpholinyl)-3-pyridinyl)amino)-2-quinolinyl)-1-piperazinecarboxylate | 0.038794 |
| 2-(2,3-dimethylphenyl)-N-(2,5-di-4-morpholinyl-3-pyridinyl)-5,7-difluoro-3-methyl-4-quinolinamine | 0.012912 |
| 2-(2,4-bis(trifluoromethyl)phenyl)-N-(2,5-di-4-morpholinyl-3-pyridinyl)-5,7-difluoro-3-methyl-4-quinolinamine | 0.344364 |
| 2-(2,4-dimethylphenyl)-N-(2,5-di-4-morpholinyl-3-pyridinyl)-5,7-difluoro-3-methyl-4-quinolinamine | 0.026825 |
| 2-(3,4-dimethylphenyl)-N-(2,5-di-4-morpholinyl-3-pyridinyl)-5,7-difluoro-3-methyl-4-quinolinamine | 0.101441 |
| 2-(3,5-difluorophenyl)-N-(2,5-di-4-morpholinylphenyl)-3-methyl-1,8-naphthyridin-4-amine | 0.5815 |
| 2-(4-(2,2-dimethylpropyl)-1-piperazinyl)-5,7-difluoro-3-methyl-N-(5-(4-morpholinyl)-3-pyridinyl)-4-quinolinamine | 0.09878 |
| 2-(4-(cyclopentylcarbonyl)-1-piperazinyl)-5,7-difluoro-3-methyl-N-(5-(4-morpholinyl)-3-pyridinyl)-4-quinolinamine | 0.041954 |
| 2-(4-(cyclopentylsulfonyl)-1-piperazinyl)-5,7-difluoro-3-methyl-N-(5-(4-morpholinyl)-3-pyridinyl)-4-quinolinamine | 0.050988 |
| 2-(4-(ethylsulfonyl)-1-piperazinyl)-5,7-difluoro-3-methyl-N-(5-(4-morpholinyl)-3-pyridinyl)-4-quinolinamine | 0.088363 |
| 2-(4-acetyl-1-piperazinyl)-5,7-difluoro-3-methyl-N-(5-(4-morpholinyl)-3-pyridinyl)-4-quinolinamine | 0.033579 |
| 2-(4-chloro-2-pyridinyl)-N-(2,5-di-4-morpholinyl-3-pyridinyl)-5,7-difluoro-3-methyl-4-quinolinamine | 0.004374 |
| 2-(4-cyclohexyl-1-piperazinyl)-5,7-difluoro-3-methyl-N-(5-(4-morpholinyl)-3-pyridinyl)-4-quinolinamine | 0.028399 |
| 2-(4-ethyl-1-piperazinyl)-5,7-difluoro-3-methyl-N-(5-(4-morpholinyl)-3-pyridinyl)-4-quinolinamine | 0.015271 |
| 2-(5-chloro-3-pyridinyl)-N-(2,5-di-4-morpholinyl-3-pyridinyl)-5,7-difluoro-3-methyl-4-quinolinamine | 0.011207 |
| 2-(6-((3R)-3-(dimethylamino)-1-pyrrolidinyl)-3-pyridinyl)-N-(2,5-di-4-morpholinyl-3-pyridinyl)-5,7-difluoro-3-methyl-4-quinolinamine | 0.028371 |
| 2-(6-(4,4-difluoro-1-piperidinyl)-3-pyridinyl)-N-(2,5-di-4-morpholinyl-3-pyridinyl)-5,7-difluoro-3-methyl-4-quinolinamine | 0.043498 |
| 2-(6-(cyclopropylmethoxy)-3-pyridinyl)-N-(2,5-di-4-morpholinyl-3-pyridinyl)-5,7-difluoro-3-methyl-4-quinolinamine | 0.04764 |
| 2-(6-(dimethylamino)-3-pyridinyl)-5,7-difluoro-3-methyl-N-(5-(4-morpholinyl)-3-pyridinyl)-4-quinolinamine | 0.180248 |
| 2-(6-(dimethylamino)-3-pyridinyl)-N-(2,5-di-4-morpholinyl-3-pyridinyl)-5,7-difluoro-3-methyl-4-quinolinamine | 0.02436 |
| 2-(6-ethoxy-3-pyridinyl)-5,7-difluoro-3-methyl-N-(5-(4-morpholinyl)-3-pyridinyl)-4-quinolinamine | 0.290851 |
| 2,2-dimethylpropyl 4-(5,7-difluoro-3-methyl-4-((5-(4-morpholinyl)-3-pyridinyl)amino)-2-quinolinyl)-1-piperazinecarboxylate | 0.09904 |
| 2-methylpropyl 4-(5,7-difluoro-3-methyl-4-((5-(4-morpholinyl)-3-pyridinyl)amino)-2-quinolinyl)-1-piperazinecarboxylate | 0.108285 |
| 3-((5,7-difluoro-3-methyl-2-(2-pyridinyl)-4-quinolinyl)amino)-5-(4-morpholinyl)benzonitrile | 0.007971 |
| 3-(4-((2,5-di-4-morpholinyl-3-pyridinyl)amino)-7-fluoro-3-methyl-2-quinolinyl)-4-(methylsulfonyl)phenol | 0.017461 |
| 3-methyl-2-(4-methyl-2-pyridinyl)-4-((5-(4-morpholinyl)-3-pyridinyl)amino)-8-quinolinecarbonitrile | 0.057302 |
| 3-methyl-N-(5-(4-morpholinyl)-3-pyridinyl)-2-(2-pyridinyl)-1,8-naphthyridin-4-amine | 0.7160 |
| 4-((2,5-di-4-morpholinyl-3-pyridinyl)amino)-3-methyl-2-(2-pyridinyl)-8-quinolinecarbonitrile | 0.054359 |
| 4-((5,7-difluoro-3-methyl-2-(2-pyridinyl)-4-quinolinyl)amino)-5-(5-methoxy-3-pyridinyl)-2-(4-morpholinyl)benzonitrile | 0.00787 |
| 4-((5,7-difluoro-3-methyl-2-(2-pyridinyl)-4-quinolinyl)amino)-2-(4-morpholinyl)benzonitrile | 0.484139 |
| 4-((5'-methoxy-5-(4-morpholinyl)-2,3'-bipyridin-3-yl)amino)-3-methyl-2-(4-methyl-2-pyridinyl)-8-quinolinecarbonitrile | 0.232579 |
| 4-(3-((5,7-difluoro-3-methyl-2-(2-pyridinyl)-4-quinolinyl)-amino)-5-(4-morpholinyl)-2-pyridinyl)benzonitrile | 0.005509 |

| Compound | Ki (μM) |
|---|---|
| 4-(3-((5,7-difluoro-3-methyl-2-(2-pyridinyl)-4-quinolinyl)-amino)-5-(4-morpholinyl)-2-pyridinyl)phenol | 0.000285 |
| 4-(4-((2,5-di-4-morpholinyl-3-pyridinyl)amino)-5,7-difluoro-3-methyl-2-quinolinyl)-1-ethyl-2-piperazinone | 0.001286 |
| 4-(4-((2,5-di-4-morpholinyl-3-pyridinyl)amino)-5,7-difluoro-3-methyl-2-quinolinyl)-1-propyl-2-piperazinone | 0.001835 |
| 4-(4-((2,5-di-4-morpholinyl-3-pyridinyl)amino)-5,7-difluoro-3-methyl-2-quinolinyl)-1-(1-methylethyl)-2-piperazinone | 0.002375 |
| 4-(4-((dimethylcarbamoyl)(5-(4-morpholinyl)-3-pyridinyl)-amino)-5,7-difluoro-3-methyl-2-quinolinyl)-N,N-dimethyl-1-piperazinecarboxamide | 0.081596 |
| 4-(5,7-difluoro-3-methyl-4-((5-(4-morpholinyl)-3-pyridinyl)-amino)-2-quinolinyl)-1-ethyl-2-piperazinone | 0.013171 |
| 4-(5,7-difluoro-3-methyl-4-((5-(4-morpholinyl)-3-pyridinyl)-amino)-2-quinolinyl)-1-propyl-2-piperazinone | 0.009184 |
| 4-(5,7-difluoro-3-methyl-4-((5-(4-morpholinyl)-3-pyridinyl)-amino)-2-quinolinyl)-1-(1-methylethyl)-2-piperazinone | 0.02402 |
| 4-(5,7-difluoro-3-methyl-4-((5-(4-morpholinyl)-3-pyridinyl)-amino)-2-quinolinyl)-N,N-dimethyl-1-piperazinecarboxamide | 0.072505 |
| 4-(5,7-difluoro-3-methyl-4-((5-(4-morpholinyl)-3-pyridinyl)-amino)-2-quinolinyl)-N-methyl-1-piperazinecarboxamide | 0.016469 |
| 4-(5,7-difluoro-3-methyl-4-((5-(4-morpholinyl)-3-pyridinyl)-amino)-2-quinolinyl)-N-(1-methylethyl)-1-piperazinecarboxamide | 0.050567 |
| 4-(5,7-difluoro-3-methyl-4-((5-(4-morpholinyl)-3-pyridinyl)-amino)-2-quinolinyl)-N-ethyl-1-piperazinecarboxamide | 0.02475 |
| 5,7-difluoro-2-(2-methoxy-4-pyridinyl)-3-methyl-N-(5-(4-morpholinyl)-3-pyridinyl)-4-quinolinamine | 0.149717 |
| 5,7-difluoro-2-(4-((2-fluorophenyl)sulfonyl)-1-piperazinyl)-3-methyl-N-(5-(4-morpholinyl)-3-pyridinyl)-4-quinolinamine | 0.06637 |
| 5,7-difluoro-2-(4-((3-fluorophenyl)sulfonyl)-1-piperazinyl)-3-methyl-N-(5-(4-morpholinyl)-3-pyridinyl)-4-quinolinamine | 0.061104 |
| 5,7-difluoro-2-(4-(1H-imidazol-2-ylcarbonyl)-1-piperazinyl)-3-methyl-N-(5-(4-morpholinyl)-3-pyridinyl)-4-quinolinamine | 0.054359 |
| 5,7-difluoro-2-(5-fluoro-2-(methylsulfonyl)phenyl)-3-methyl-N-(5-(4-morpholinyl)-3-pyridinyl)-4-quinolinamine | 0.002914 |
| 5,7-difluoro-2-(5-methoxy-3-pyridinyl)-3-methyl-N-(5-(4-morpholinyl)-3-pyridinyl)-4-quinolinamine | 0.037391 |
| 5,7-difluoro-3-methyl-2-((2R)-2-methyl-1-piperazinyl)-N-(5-(4-morpholinyl)-3-pyridinyl)-4-quinolinamine | 0.015903 |
| 5,7-difluoro-3-methyl-2-((2S)-2-methyl-1-piperazinyl)-N-(5-(4-morpholinyl)-3-pyridinyl)-4-quinolinamine | 0.078067 |
| 5,7-difluoro-3-methyl-2-((3R)-3-methyl-1-piperazinyl)-N-(5-(4-morpholinyl)-3-pyridinyl)-4-quinolinamine | 0.044266 |
| 5,7-difluoro-3-methyl-2-((3R)-3-methyl-4-(methylsulfonyl)-1-piperazinyl)-N-(5-(4-morpholinyl)-3-pyridinyl)-4-quinolinamine | 0.243933 |
| 5,7-difluoro-3-methyl-2-((3S)-3-methyl-1-piperazinyl)-N-(5-(4-morpholinyl)-3-pyridinyl)-4-quinolinamine | 0.020633 |
| 5,7-difluoro-3-methyl-2-(2-((S)-methylsulfinyl)phenyl)-N-(5-(4-morpholinyl)-3-pyridinyl)-4-quinolinamine | 0.00389 |
| 5,7-difluoro-3-methyl-2-(2-(methylsulfonyl)-5-(trifluoromethoxy)phenyl)-N-(5-(4-morpholinyl)-3-pyridinyl)-4-quinolinamine | 0.004182 |
| 5,7-difluoro-3-methyl-2-(2-(methylsulfonyl)phenyl)-N-(5-(4-morpholinyl)-3-pyridinyl)-4-quinolinamine | 0.003242 |
| 5,7-difluoro-3-methyl-2-(2-pyridinyl)-N-(5-(tetrahydro-2H-pyran-4-yl)-3-pyridinyl)-4-quinolinamine | 0.209149 |
| 5,7-difluoro-3-methyl-2-(4-((1-methylethyl)sulfonyl)-1-piperazinyl)-N-(5-(4-morpholinyl)-3-pyridinyl)-4-quinolinamine | 0.053428 |
| 5,7-difluoro-3-methyl-2-(4-((2-methylpropyl)sulfonyl)-1-piperazinyl)-N-(5-(4-morpholinyl)-3-pyridinyl)-4-quinolinamine | 0.071297 |
| 5,7-difluoro-3-methyl-2-(4-((5-methyl-2-furanyl)carbonyl)-1-piperazinyl)-N-(5-(4-morpholinyl)-3-pyridinyl)-4-quinolinamine | 0.078247 |
| 5,7-difluoro-3-methyl-2-(4-((6-methyl-3-pyridinyl)carbonyl)-1-piperazinyl)-N-(5-(4-morpholinyl)-3-pyridinyl)-4-quinolinamine | 0.180331 |
| 5,7-difluoro-3-methyl-2-(4-(1-methylethyl)-1-piperazinyl)-N-(5-(4-morpholinyl)-3-pyridinyl)-4-quinolinamine | 0.011349 |
| 5,7-difluoro-3-methyl-2-(4-(2-methylpropanoyl)-1-piperazinyl)-N-(5-(4-morpholinyl)-3-pyridinyl)-4-quinolinamine | 0.033256 |
| 5,7-difluoro-3-methyl-2-(4-(methylsulfonyl)-1-piperazinyl)-N-(5-(4-morpholinyl)-3-pyridinyl)-4-quinolinamine | 0.045475 |
| 5,7-difluoro-3-methyl-2-(4-methyl-1-piperazinyl)-N-(5-(4-morpholinyl)-3-pyridinyl)-4-quinolinamine | 0.035173 |
| 5,7-difluoro-3-methyl-2-(4-methyl-2-pyridinyl)-N-(2-(methylsulfonyl)-5-(4-morpholinyl)phenyl)-4-quinolinamine | 0.000821 |
| 5,7-difluoro-3-methyl-2-(4-methyl-2-pyridinyl)-N-(5-(4-morpholinyl)-3-pyridinyl)-4-quinolinamine | 0.019203 |

| Compound | Ki (μM) |
|---|---|
| 5,7-difluoro-3-methyl-2-(4-morpholinyl)-N-(5-(4-morpholinyl)-3-pyridinyl)-4-quinolinamine | 0.055656 |
| 5,7-difluoro-3-methyl-2-(5-methyl-2-(methylsulfonyl)phenyl)-N-(5-(4-morpholinyl)-3-pyridinyl)-4-quinolinamine | 0.001349 |
| 5,7-difluoro-3-methyl-2-(5-methyl-2-pyridinyl)-N-(5-(4-morpholinyl)-3-pyridinyl)-4-quinolinamine | 0.019052 |
| 5,7-difluoro-3-methyl-2-(6-methyl-3-pyridinyl)-N-(5-(4-morpholinyl)-3-pyridinyl)-4-quinolinamine | 0.019106 |
| 5,7-difluoro-3-methyl-4-((5-(4-morpholinyl)-3-pyridinyl)oxy)-2-(2-pyridinyl)quinoline | 0.051924 |
| 5,7-difluoro-3-methyl-N-(2-(4-(methylsulfonyl)phenyl)-5-(4-morpholinyl)-3-pyridinyl)-2-(2-pyridinyl)-4-quinolinamine | 0.002152 |
| 5,7-difluoro-3-methyl-N-(2-(methylsulfonyl)-5-(4-morpholinyl)-phenyl)-2-(2-(methylsulfonyl)phenyl)-4-quinolinamine | 0.000827 |
| 5,7-difluoro-3-methyl-N-(5-((3R)-3-methyl-4-morpholinyl)-2-(4-morpholinyl)-3-pyridinyl)-2-(3-pyridinyl)-4-quinolinamine | 0.069546 |
| 5,7-difluoro-3-methyl-N-(5-((3S)-3-methyl-4-morpholinyl)-2-(4-morpholinyl)-3-pyridinyl)-2-(3-pyridinyl)-4-quinolinamine | 0.021383 |
| 5,7-difluoro-3-methyl-N-(5-(4-morpholinyl)-3-pyridinyl)-2-(1-piperazinyl)-4-quinolinamine | 0.087071 |
| 5,7-difluoro-3-methyl-N-(5-(4-morpholinyl)-3-pyridinyl)-2-(2-(1-pyrrolidinyl)-4-pyridinyl)-4-quinolinamine | 0.314608 |
| 5,7-difluoro-3-methyl-N-(5-(4-morpholinyl)-3-pyridinyl)-2-(4-(1,3-oxazol-5-ylcarbonyl)-1-piperazinyl)-4-quinolinamine | 0.048003 |
| 5,7-difluoro-3-methyl-N-(5-(4-morpholinyl)-3-pyridinyl)-2-(4-(1,3-oxazol-4-ylcarbonyl)-1-piperazinyl)-4-quinolinamine | 0.014544 |
| 5,7-difluoro-3-methyl-N-(5-(4-morpholinyl)-3-pyridinyl)-2-(4-(2,2,2-trifluoroethyl)-1-piperazinyl)-4-quinolinamine | 0.040726 |
| 5,7-difluoro-3-methyl-N-(5-(4-morpholinyl)-3-pyridinyl)-2-(4-(2-pyrimidinylcarbonyl)-1-piperazinyl)-4-quinolinamine | 0.645015 |
| 5,7-difluoro-3-methyl-N-(5-(4-morpholinyl)-3-pyridinyl)-2-(4-(3-pyridinyl)-1-piperazinyl)-4-quinolinamine | 0.011783 |
| 5,7-difluoro-3-methyl-N-(5-(4-morpholinyl)-3-pyridinyl)-2-(4-(3-pyridinylsulfonyl)-1-piperazinyl)-4-quinolinamine | 0.067526 |
| 5,7-difluoro-3-methyl-N-(5-(4-morpholinyl)-3-pyridinyl)-2-(4-(3-pyridinylcarbonyl)-1-piperazinyl)-4-quinolinamine | 0.342586 |
| 5,7-difluoro-3-methyl-N-(5-(4-morpholinyl)-3-pyridinyl)-2-(4-(4-pyrimidinylcarbonyl)-1-piperazinyl)-4-quinolinamine | 0.099122 |
| 5,7-difluoro-3-methyl-N-(5-(4-morpholinyl)-3-pyridinyl)-2-(4-(phenylsulfonyl)-1-piperazinyl)-4-quinolinamine | 0.033425 |
| 5,7-difluoro-3-methyl-N-(5-(4-morpholinyl)-3-pyridinyl)-2-(4-(phenylcarbonyl)-1-piperazinyl)-4-quinolinamine | 0.087896 |
| 5,7-difluoro-3-methyl-N-(5-(4-morpholinyl)-3-pyridinyl)-2-(4-(tetrahydro-2H-pyran-4-ylcarbonyl)-1-piperazinyl)-4-quinolinamine | 0.05574 |
| 5,7-difluoro-3-methyl-N-(5-(4-morpholinyl)-3-pyridinyl)-2-(4-phenyl-1-piperazinyl)-4-quinolinamine | 0.078105 |
| 5,7-difluoro-3-methyl-N-(5-(4-morpholinyl)-3-pyridinyl)-2-(4-propyl-1-piperazinyl)-4-quinolinamine | 0.013517 |
| 5,7-difluoro-3-methyl-N-(5-(4-morpholinyl)-3-pyridinyl)-2-(6-(1-piperidinyl)-3-pyridinyl)-4-quinolinamine | 0.517251 |
| 5,7-difluoro-3-methyl-N-(5-(4-morpholinyl)-3-pyridinyl)-2-(6-(1-piperazinyl)-3-pyridinyl)-4-quinolinamine | 0.432086 |
| 5,7-difluoro-3-methyl-N-(5-(4-morpholinyl)-3-pyridinyl)-2-(6-(4-morpholinyl)-3-pyridinyl)-4-quinolinamine | 0.444498 |
| 5,7-difluoro-3-methyl-N-(5-(4-morpholinyl)-3-pyridinyl)-N-(2,2,2-trifluoroethyl)-2-(4-(2,2,2-trifluoroethyl)-1-piperazinyl)-4-quinolinamine | 0.493253 |
| 5,7-difluoro-N-(2-(2-methoxyphenyl)-5-(4-morpholinyl)-3-pyridinyl)-3-methyl-2-(2-pyridinyl)-4-quinolinamine | 0.008527 |
| 5,7-difluoro-N-(2-(4-methoxy-2,6-dimethylphenyl)-5-(4-morpholinyl)-3-pyridinyl)-3-methyl-2-(2-pyridinyl)-4-quinolinamine | 0.000972 |
| 5,7-difluoro-N-(2-(4-methoxyphenyl)-5-(4-morpholinyl)-3-pyridinyl)-3-methyl-2-(4-methyl-2-pyridinyl)-4-quinolinamine | 0.005983 |
| 5,7-difluoro-N-(2-(5-methoxy-3-pyridinyl)-5-(4-morpholinyl)-phenyl)-3-methyl-2-(2-pyridinyl)-4-quinolinamine | 0.000627 |
| 5,7-difluoro-N-(2-(6-methoxy-3-pyridinyl)-5-(4-morpholinyl)-phenyl)-3-methyl-2-(2-(methylsulfonyl)phenyl)-4-quinolinamine | 0.002725 |
| 5,7-difluoro-N-(2-(6-methoxy-3-pyridinyl)-5-(4-morpholinyl)-phenyl)-3-methyl-2-(4-methyl-2-pyridinyl)-4-quinolinamine | 0.003594 |
| 5,7-difluoro-N-(2-(6-methoxy-3-pyridinyl)-5-(4-morpholinyl)-phenyl)-3-methyl-2-(2-pyridinyl)-4-quinolinamine | 0.003193 |
| 5,7-difluoro-N-(4'-methoxy-4-(4-morpholinyl)-2-biphenylyl)-3-methyl-2-(2-pyridinyl)-4-quinolinamine | 0.038541 |
| 5-fluoro-3-methyl-N-(2-(methylsulfonyl)-5-(4-morpholinyl)-phenyl)-2-(2-pyridinyl)-4-quinolinamine | 0.000485 |

-continued

| Compound | Ki (μM) |
|---|---|
| 7-fluoro-2-(2-fluoro-5-nitrophenyl)-3-methyl-N-(5-(4-morpholinyl)-3-pyridinyl)-4-quinolinamine | 0.047451 |
| 8-chloro-3-methyl-2-(4-methyl-2-pyridinyl)-N-(5-(4-morpholinyl)-3-pyridinyl)-4-quinolinamine | 0.002393 |
| 8-chloro-3-methyl-N-(5-(4-morpholinyl)-3-pyridinyl)-2-(2-pyridinyl)-4-quinolinamine | 0.007445 |
| 8-chloro-N-(2,5-di-4-morpholinyl-3-pyridinyl)-3-methyl-2-(4-methyl-2-pyridinyl)-4-quinolinamine | 0.009488 |
| 8-chloro-N-(2,5-di-4-morpholinyl-3-pyridinyl)-5,7-difluoro-3-methyl-2-(2-pyridinyl)-4-quinolinamine | 0.002854 |
| 8-chloro-N-(2,5-di-4-morpholinyl-3-pyridinyl)-5-fluoro-3-methyl-2-(2-pyridinyl)-4-quinolinamine | 0.002571 |
| 8-chloro-N-(2,5-di-4-morpholinyl-3-pyridinyl)-7-fluoro-3-methyl-2-(2-pyridinyl)-4-quinolinamine | 0.022644 |
| ethyl 4-(5,7-difluoro-3-methyl-4-((5-(4-morpholinyl)-3-pyridinyl)amino)-2-quinolinyl)-1-piperazinecarboxylate | 0.045527 |
| methyl (2R)-4-(5,7-difluoro-3-methyl-4-((5-(4-morpholinyl)-3-pyridinyl)amino)-2-quinolinyl)-2-methyl-1-piperazinecarboxylate | 0.184659 |
| methyl (2S)-4-(5,7-difluoro-3-methyl-4-((5-(4-morpholinyl)-3-pyridinyl)amino)-2-quinolinyl)-2-methyl-1-piperazinecarboxylate | 0.015006 |
| methyl (3R)-4-(5,7-difluoro-3-methyl-4-((5-(4-morpholinyl)-3-pyridinyl)amino)-2-quinolinyl)-3-methyl-1-piperazinecarboxylate | 0.031752 |
| methyl 4-(4-((2,5-di-4-morpholinyl-3-pyridinyl)amino)-5,7-difluoro-3-methyl-2-quinolinyl)-1-piperazinecarboxylate | 0.007019 |
| methyl 4-(5,7-difluoro-3-methyl-4-((5-(4-morpholinyl)-3-pyridinyl)amino)-2-quinolinyl)-1-piperazinecarboxylate | 0.009229 |
| N-(2-(3-(difluoromethoxy)phenyl)-5-(4-morpholinyl)-3-pyridinyl)-5,7-difluoro-3-methyl-2-(2-pyridinyl)-4-quinolinamine | 0.002262 |
| N-(2-(3,6-dihydro-2H-pyran-4-yl)-5-(4-morpholinyl)phenyl)-5,7-difluoro-3-methyl-2-(2-pyridinyl)-4-quinolinamine | 0.007652 |
| N-(2-(4-(difluoromethoxy)phenyl)-5-(4-morpholinyl)-3-pyridinyl)-5,7-difluoro-3-methyl-2-(2-pyridinyl)-4-quinolinamine | 0.001247 |
| N-(2,5-di-3,6-dihydro-2H-pyran-4-yl-3-pyridinyl)-5,7-difluoro-3-methyl-2-(2-pyridinyl)-4-quinolinamine | 0.003075 |
| N-(2,5-di-4-morpholinyl-3-pyridinyl)-2-(4-ethenyl-2-pyridinyl)-5,7-difluoro-3-methyl-4-quinolinamine | 0.118869 |
| N-(2,5-di-4-morpholinyl-3-pyridinyl)-2-(6-ethoxy-3-pyridinyl)-5,7-difluoro-3-methyl-4-quinolinamine | 0.025549 |
| N-(2,5-di-4-morpholinyl-3-pyridinyl)-5,7-difluoro-2-(2-fluorophenyl)-3-methyl-4-quinolinamine | 0.006219 |
| N-(2,5-di-4-morpholinyl-3-pyridinyl)-5,7-difluoro-2-(2-methoxy-4-pyridinyl)-3-methyl-4-quinolinamine | 0.033402 |
| N-(2,5-di-4-morpholinyl-3-pyridinyl)-5,7-difluoro-2-(6-fluoro-3-pyridinyl)-3-methyl-4-quinolinamine | 0.01853 |
| N-(2,5-di-4-morpholinyl-3-pyridinyl)-5,7-difluoro-2-(6-methoxy-3-pyridinyl)-3-methyl-4-quinolinamine | 0.033163 |
| N-(2,5-di-4-morpholinyl-3-pyridinyl)-5,7-difluoro-3-methyl-2-(1-methyl-1H-indol-4-yl)-4-quinolinamine | 0.016051 |
| N-(2,5-di-4-morpholinyl-3-pyridinyl)-5,7-difluoro-3-methyl-2-(1-methyl-1H-indazol-4-yl)-4-quinolinamine | 0.008604 |
| N-(2,5-di-4-morpholinyl-3-pyridinyl)-5,7-difluoro-3-methyl-2-(2-pyrazinyl)-4-quinolinamine | 0.007954 |
| N-(2,5-di-4-morpholinyl-3-pyridinyl)-5,7-difluoro-3-methyl-2-(2-methyl-4-(trifluoromethyl)phenyl)-4-quinolinamine | 0.248439 |
| N-(2,5-di-4-morpholinyl-3-pyridinyl)-5,7-difluoro-3-methyl-2-(2-methyl-4-pyridinyl)-4-quinolinamine | 0.026485 |
| N-(2,5-di-4-morpholinyl-3-pyridinyl)-5,7-difluoro-3-methyl-2-(2-methyl-3-pyridinyl)-4-quinolinamine | 0.001712 |
| N-(2,5-di-4-morpholinyl-3-pyridinyl)-5,7-difluoro-3-methyl-2-(2-(1-piperazinyl)-4-pyridinyl)-4-quinolinamine | 0.034711 |
| N-(2,5-di-4-morpholinyl-3-pyridinyl)-5,7-difluoro-3-methyl-2-(2-(4-methyl-1-piperazinyl)-4-pyridinyl)-4-quinolinamine | 0.014972 |
| N-(2,5-di-4-morpholinyl-3-pyridinyl)-5,7-difluoro-3-methyl-2-(2-(1-pyrrolidinyl)-4-pyridinyl)-4-quinolinamine | 0.040698 |
| N-(2,5-di-4-morpholinyl-3-pyridinyl)-5,7-difluoro-3-methyl-2-(2-((S)-methylsulfinyl)phenyl)-4-quinolinamine | 0.050976 |
| N-(2,5-di-4-morpholinyl-3-pyridinyl)-5,7-difluoro-3-methyl-2-(3-pyridinyl)-4-quinolinamine | 0.008427 |
| N-(2,5-di-4-morpholinyl-3-pyridinyl)-5,7-difluoro-3-methyl-2-(4-methyl-2-pyridinyl)-4-quinolinamine | 0.236809 |
| N-(2,5-di-4-morpholinyl-3-pyridinyl)-5,7-difluoro-3-methyl-2-(4-phenyl-2-pyridinyl)-4-quinolinamine | 0.047914 |

-continued

| Compound | Ki (μM) |
|---|---|
| N-(2,5-di-4-morpholinyl-3-pyridinyl)-5,7-difluoro-3-methyl-2-(4-methyl-3-pyridinyl)-4-quinolinamine | 0.001613 |
| N-(2,5-di-4-morpholinyl-3-pyridinyl)-5,7-difluoro-3-methyl-2-(4-methyl-1-piperazinyl)-4-quinolinamine | 0.011989 |
| N-(2,5-di-4-morpholinyl-3-pyridinyl)-5,7-difluoro-3-methyl-2-(5-methyl-2-(methylsulfonyl)phenyl)-4-quinolinamine | 0.008216 |
| N-(2,5-di-4-morpholinyl-3-pyridinyl)-5,7-difluoro-3-methyl-2-(5-methyl-3-pyridinyl)-4-quinolinamine | 0.008924 |
| N-(2,5-di-4-morpholinyl-3-pyridinyl)-5,7-difluoro-3-methyl-2-(5-(methylsulfanyl)-3-pyridinyl)-4-quinolinamine | 0.011313 |
| N-(2,5-di-4-morpholinyl-3-pyridinyl)-5,7-difluoro-3-methyl-2-(5-(methylsulfonyl)-3-pyridinyl)-4-quinolinamine | 0.083818 |
| N-(2,5-di-4-morpholinyl-3-pyridinyl)-5,7-difluoro-3-methyl-2-(6-methyl-3-pyridinyl)-4-quinolinamine | 0.017958 |
| N-(2,5-di-4-morpholinyl-3-pyridinyl)-5,7-difluoro-3-methyl-2-(6-(4-morpholinyl)-3-pyridinyl)-4-quinolinamine | 0.067541 |
| N-(2,5-di-4-morpholinyl-3-pyridinyl)-5,7-difluoro-3-methyl-2-(6-(trifluoromethyl)-3-pyridinyl)-4-quinolinamine | 0.023167 |
| N-(2,5-di-4-morpholinyl-3-pyridinyl)-5,7-difluoro-3-methyl-2-(6-(1-piperidinyl)-3-pyridinyl)-4-quinolinamine | 0.044002 |
| N-(2,5-di-4-morpholinyl-3-pyridinyl)-5,7-difluoro-3-methyl-2-(6-(1-piperazinyl)-3-pyridinyl)-4-quinolinamine | 0.056334 |
| N-(2,5-di-4-morpholinyl-3-pyridinyl)-5,7-difluoro-3-methyl-2-(6-(4-methyl-1-piperazinyl)-3-pyridinyl)-4-quinolinamine | 0.295372 |
| N-(2,5-di-4-morpholinyl-3-pyridinyl)-5,7-difluoro-3-methyl-2-(6-(4-methyl-1-piperidinyl)-3-pyridinyl)-4-quinolinamine | 0.133712 |
| N-(2,5-di-4-morpholinyl-3-pyridinyl)-5,7-difluoro-3-methyl-2-(6-(1-pyrrolidinyl)-3-pyridinyl)-4-quinolinamine | 0.04676 |
| N-(2,5-di-4-morpholinyl-3-pyridinyl)-6,8-difluoro-3-methyl-2-(2-pyridinyl)-4-quinolinamine | 0.344602 |
| N-(2,5-di-4-morpholinyl-3-pyridinyl)-7-fluoro-2-(2-fluoro-5-nitrophenyl)-3-methyl-4-quinolinamine | 0.011225 |
| N-(2,5-di-4-morpholinyl-3-pyridinyl)-7-fluoro-3-(1-methylethyl)-2-(4-methyl-2-pyridinyl)-4-quinolinamine | 0.01427 |
| N-(2,5-di-4-morpholinyl-3-pyridinyl)-7-fluoro-3-methyl-2-(2-(methylsulfonyl)-5-nitrophenyl)-4-quinolinamine | 0.008254 |
| N-(2,5-di-4-morpholinyl-3-pyridinyl)-7-fluoro-3-methyl-2-(4-methyl-2-pyridinyl)-4-quinolinamine | 0.035108 |
| N-(2,5-di-4-morpholinylphenyl)-3-methyl-2-(2-pyridinyl)-1,7-naphthyridin-4-amine | 0.8765 |
| N-(2,5-di-4-morpholinylphenyl)-3-methyl-2-(2-pyridinyl)-1,8-naphthyridin-4-amine | 0.5820 |
| N-(2-chloro-5-(4-morpholinyl)-3-pyridinyl)-5,7-difluoro-3-methyl-2-(2-pyridinyl)-4-quinolinamine | 0.004257 |
| N-(5-(2-amino-4-pyrimidinyl)-3-pyridinyl)-5,7-difluoro-3-methyl-2-(4-methyl-2-pyridinyl)-4-quinolinamine | 0.005344 |
| N-(5-(3,6-dihydro-2H-pyran-4-yl)-3-pyridinyl)-5,7-difluoro-3-methyl-2-(2-(methylsulfonyl)phenyl)-4-quinolinamine | 0.00178 |
| N-(5-(3,6-dihydro-2H-pyran-4-yl)-3-pyridinyl)-5,7-difluoro-3-methyl-2-(4-morpholinyl)-4-quinolinamine | 0.068344 |
| N-(5-(3,6-dihydro-2H-pyran-4-yl)-3-pyridinyl)-5,7-difluoro-3-methyl-2-(4-methyl-2-pyridinyl)-4-quinolinamine | 0.014357 |
| N-(5,7-difluoro-3-methyl-2-(2-(methylsulfonyl)phenyl)-4-quinolinyl)-6'-methoxy-5-(4-morpholinyl)-2,3'-bipyridin-3-amine | 0.001764 |
| N-(5,7-difluoro-3-methyl-2-(2-pyridinyl)-4-quinolinyl)-2,2,2-trifluoro-N-(5'-methoxy-5-(4-morpholinyl)-2,3'-bipyridin-3-yl)-acetamide | 0.226866 |
| N-(5,7-difluoro-3-methyl-2-(2-pyridinyl)-4-quinolinyl)-2'-methoxy-5-(4-morpholinyl)-2,3'-bipyridin-3-amine | 0.121214 |
| N-(5,7-difluoro-3-methyl-2-(2-pyridinyl)-4-quinolinyl)-2'-methoxy-5-(4-morpholinyl)-2,4'-bipyridin-3-amine | 0.007931 |
| N-(5,7-difluoro-3-methyl-2-(2-pyridinyl)-4-quinolinyl)-3'-methoxy-5-(4-morpholinyl)-2,4'-bipyridin-3-amine | 0.007683 |
| N-(5,7-difluoro-3-methyl-2-(2-pyridinyl)-4-quinolinyl)-5'-fluoro-2'-methoxy-5-(4-morpholinyl)-2,4'-bipyridin-3-amine | 0.023523 |
| N-(5,7-difluoro-3-methyl-2-(2-pyridinyl)-4-quinolinyl)-5'-methoxy-5-(4-morpholinyl)-2,3'-bipyridin-3-amine | 0.000512 |
| N-(5,7-difluoro-3-methyl-2-(2-pyridinyl)-4-quinolinyl)-6'-ethoxy-5-(4-morpholinyl)-2,3'-bipyridin-3-amine | 0.002617 |
| N-(5,7-difluoro-3-methyl-2-(2-pyridinyl)-4-quinolinyl)-6'-methoxy-5-(4-morpholinyl)-2,3'-bipyridin-3-amine | 0.001536 |
| N-(5,7-difluoro-3-methyl-2-(3-pyridinyl)-4-quinolinyl)-2,2,2-trifluoro-N-(5-(4-morpholinyl)-3-pyridinyl)acetamide | 0.047279 |
| N-(5,7-difluoro-3-methyl-2-(4-methyl-2-pyridinyl)-4-quinolinyl)-6'-methoxy-5-(4-morpholinyl)-2,3'-bipyridin-3-amine | 0.00318 |

-continued

| Compound | Ki (μM) |
|---|---|
| N-(5,7-difluoro-3-methyl-4-((5-(4-morpholinyl)-3-pyridinyl)-amino)-2-quinolinyl)glycine | 0.131362 |
| N-(8-chloro-3-methyl-2-(4-methyl-2-pyridinyl)-4-quinolinyl)-5'-methoxy-5-(4-morpholinyl)-2,3'-bipyridin-3-amine | 0.009005 |
| tert-butyl (2R)-4-(5,7-difluoro-3-methyl-4-((5-(4-morpholinyl)-3-pyridinyl)amino)-2-quinolinyl)-2-methyl-1-piperazinecarboxylate | 0.832472 |
| tert-butyl (2S)-4-(5,7-difluoro-3-methyl-4-((5-(4-morpholinyl)-3-pyridinyl)amino)-2-quinolinyl)-2-methyl-1-piperazinecarboxylate | 0.112091 |
| tert-butyl (3S)-4-(5,7-difluoro-3-methyl-4-((5-(4-morpholinyl)-3-pyridinyl)amino)-2-quinolinyl)-3-methyl-1-piperazinecarboxylate | 0.358484 |
| tert-butyl 1-(5,7-difluoro-3-methyl-4-((5-(4-morpholinyl)-3-pyridinyl)amino)-2-quinolinyl)-L-prolinate | 0.002217 |
| tert-butyl 1-(5,7-difluoro-3-methyl-4-((5-(4-morpholinyl)-3-pyridinyl)amino)-2-quinolinyl)-D-prolinate | 0.018012 |
| tert-butyl 4-(4-((2,5-di-4-morpholinyl-3-pyridinyl)amino)-5,7-difluoro-3-methyl-2-quinolinyl)-1-piperazinecarboxylate | 0.034086 |
| tert-butyl 4-(5,7-difluoro-3-methyl-4-((5-(4-morpholinyl)-3-pyridinyl)amino)-2-quinolinyl)-1-piperazinecarboxylate | 0.353121 |

For the treatment of PI3Kδ-mediated-diseases, such as rheumatoid arthritis, ankylosing spondylitis, osteoarthritis, psoriatic arthritis, psoriasis, inflammatory diseases, and autoimmune diseases, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, rheumatoid arthritis, ankylosing spondylitis, osteoarthritis, psoriatic arthritis, psoriasis, inflammatory diseases, and autoimmune diseases and the like.

The dosage regimen for treating PI3Kδ-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aq. or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/ or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051

(Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$)-alkyloxy)ethyl, for example, methoxyethyl, ethoxyethyl, propoxyethyl, isopropoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethylformamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

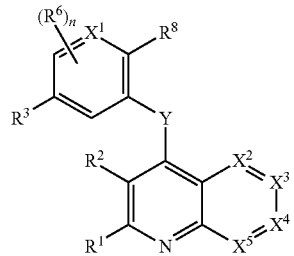

or any pharmaceutically-acceptable salt thereof, wherein:
$X^1$ is C—H or N;
$X^2$ is C($R^4$) or N;
$X^3$ is C($R^5$) or N;
$X^4$ is C($R^5$) or N;
$X^5$ is C($R^4$) or N; wherein no more than two of $X^2$, $X^3$, $X^4$ and $X^5$ are N;
Y is $NR^7$, $CR^aR^a$ or O;
n is 0, 1, 2 or 3;

$R^1$ is a direct-bonded, $C_{1-4}$alk-linked, $OC_{1-2}$alk-linked, $C_{1-2}$alkO-linked, $N(R^a)$-linked or O-linked saturated, partially-saturated or unsaturated 3-, 4-, 5-, 6- or 7-membered monocyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups, and wherein the ring is additionally substituted by 0 or 1 directly bonded, $SO_2$ linked, C(=O) linked or $CH_2$ linked group selected from phenyl, pyridyl, pyrimidyl, morpholino, piperazinyl, piperadinyl, pyrrolidinyl, cyclopentyl, cyclohexyl all of which are further substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^2$ is selected from halo, unsubstituted $C_{1-6}$alk, $C_{1-4}$haloalk, cyano, and nitro;

$R^3$ is selected from a saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$;

$R^4$ is, independently, in each instance, H, halo, nitro, cyano, $C_{1-4}$alk, $OC_{1-4}$alk, $OC_{1-4}$haloalk, $NHC_{1-4}$alk, $N(C_{1-4}$alk)$C_{1-4}$alk, C(=O)$NH_2$, C(=O)$NHC_{1-4}$alk, C(=O)$N(C_{1-4}$alk)$C_{1-4}$alk, $N(H)C(=O)C_{1-4}$alk, $N(C_{1-4}$alk)C(=O)$C_{1-4}$alk, $C_{1-4}$haloalk or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —OC$_{1-4}$alk, —$NH_2$, —$NHC_{1-4}$alk, —$N(C_{1-4}$alk)$C_{1-4}$alk;

$R^5$ is, independently, in each instance, H, halo, nitro, cyano, $C_{1-4}$alk, $OC_{1-4}$alk, $OC_{1-4}$haloalk, $NHC_{1-4}$alk, $N(C_{1-4}$alk$)C_{1-4}$alk or $C_{1-4}$haloalk;

$R^6$ is selected from halo, cyano, OH, $OC_{1-4}$alk, $C_{1-4}$alk, $C_{1-3}$haloalk, $OC_{1-4}$alk, $NH_2$, $NHC_{1-4}$alk, $N(C_{1-4}$alk$)C_{1-4}$alk, —C(=O)OR$^a$, —C(=O)N(R$^a$)R$^a$, —N(R$^a$)C(=O)R$^b$ and a 5- or 6-membered saturated or partially saturated heterocyclic ring containing 1, 2 or 3 heteroatoms selected from N, O and S, wherein the ring is substituted by 0, 1, 2 or 3 substituents selected from halo, cyano, OH, oxo, $OC_{1-4}$alk, $C_{1-4}$alk, $C_{1-3}$haloalk, $OC_{1-4}$alk, $NH_2$, $NHC_{1-4}$alk and $N(C_{1-4}$alk$)C_{1-4}$alk;

$R^7$ is H, $C_{1-6}$alk, —C(=O)N(R$^a$)R$^a$, —C(=O)R$^b$ or $C_{1-4}$haloalk;

$R^8$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or $R^8$ is selected from H, halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$;

$R^a$ is independently, at each instance, H or R$^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OC$_{1-4}$alk, —NH$_2$, —NHC$_{1-4}$alk, —N(C$_{1-4}$alk)C$_{1-4}$alk.

2. A pharmaceutical composition comprising a compound according to claim 1 and a pharmaceutically-acceptable diluent or carrier.

3. A compound according to claim 1, wherein:
$X^2$ is C(R$^4$);
$X^3$ is C(R$^5$);
$X^4$ is C(R$^5$); and
$X^5$ is C(R$^4$).

4. A compound according to claim 1, wherein $R^1$ is phenyl or pyridine, both of which are substituted by 0, 1, 2 or 3 substituents independently selected from halo, $C_{1-6}$alk and $C_{1-4}$haloalk.

5. A compound according to claim 1, wherein $R^3$ is selected from saturated 6-membered monocyclic ring containing 1 or 2 atoms selected from N, O and S, but containing no more than one O or S.

6. A compound according to claim 1, wherein $R^8$ is selected from halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

7. A compound according to claim 1, wherein $R^8$ is selected from saturated 5-, 6- or 7-membered monocyclic ring containing 1 or 2 atoms selected from N, O and S, but containing no more than one O or S, wherein the ring is substituted by 0, 1, 2 or 3 substituents independently selected from halo, $C_{1-6}$alk and $C_{1-4}$haloalk.

8. A compound according to claim 1, wherein $R^1$ is a direct-bonded unsaturated 5-, 6- or 7-membered monocyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups.

* * * * *